US011975057B2

(12) United States Patent
Kousoulas et al.

(10) Patent No.: US 11,975,057 B2
(45) Date of Patent: May 7, 2024

(54) COMPOSITIONS COMPRISING HERPES SIMPLEX VIRUS-I FOR USE IN METHODS OF TREATING AND PREVENTING CANCER

(71) Applicants: Konstantin G. Kousoulas, Baton Rouge, LA (US); Vladimir N. Chouljenko, Saint Gabriel, LA (US); James Michael Mathis, Geismer, LA (US)

(72) Inventors: Konstantin G. Kousoulas, Baton Rouge, LA (US); Vladimir N. Chouljenko, Saint Gabriel, LA (US); James Michael Mathis, Geismer, LA (US)

(73) Assignee: Board of Supervisors of Louisiana State University Agriculture and Mechanical College, Baton Rouge, LA (US)

( * ) Notice: Subject to any disclaimer, the term of this patent is extended or adjusted under 35 U.S.C. 154(b) by 582 days.

(21) Appl. No.: 17/264,420

(22) PCT Filed: Aug. 1, 2019

(86) PCT No.: PCT/US2019/044749

§ 371 (c)(1),
(2) Date: Jan. 29, 2021

(87) PCT Pub. No.: WO2020/028719

PCT Pub. Date: Feb. 6, 2020

(65) Prior Publication Data

US 2021/0315984 A1 Oct. 14, 2021

Related U.S. Application Data

(60) Provisional application No. 62/713,269, filed on Aug. 1, 2018, provisional application No. 62/713,183, filed on Aug. 1, 2018.

(51) Int. Cl.

| | |
|---|---|
| ***A61K 39/00*** | (2006.01) |
| ***C12N 7/00*** | (2006.01) |
| *A61K 51/00* | (2006.01) |

(52) U.S. Cl.

CPC ............ *A61K 39/0011* (2013.01); *C12N 7/00* (2013.01); *A61K 2039/585* (2013.01); *A61K 51/00* (2013.01); *C12N 2710/16634* (2013.01); *C12N 2710/16651* (2013.01)

(58) Field of Classification Search

CPC ........ A61K 2039/585; A61K 2039/876; A61K 35/763; A61K 39/0011; A61K 2039/892; A61K 51/00; A61P 35/00; A61P 37/00

See application file for complete search history.

(56) References Cited

U.S. PATENT DOCUMENTS

| | | | |
|---|---|---|---|
| 10,130,703 | B2 | 11/2018 | Kousoulas |
| 10,596,253 | B2 | 2/2020 | Kousoulas |
| 11,229,697 | B2 | 1/2022 | Kousoulas |
| 2008/0299182 | A1 | 12/2008 | Zhang et al. |
| 2017/0319639 | A1 | 11/2017 | Jia |
| 2020/0345836 | A1 | 11/2020 | Kousoulas |
| 2022/0241401 | A1 | 8/2022 | Kousoulas |

FOREIGN PATENT DOCUMENTS

| | | | |
|---|---|---|---|
| WO | 2008141151 | A2 | 11/2008 |
| WO | 2011119925 | | 9/2011 |
| WO | 2015172033 | A1 | 11/2015 |
| WO | 2018175715 | | 9/2018 |
| WO | 2020028719 | A2 | 2/2020 |

OTHER PUBLICATIONS

Li et al. Cancer Gene Therapy, 2013, vol. 20, pp. 478-485.*
European Patent Office, Office Action for European Patent Application No. 19 844 889.6-1112, dated Jan. 10, 2023.
Wolfe D et al: "Engineering Herpes Simplex Viral Vectors for Therapeutic Gene Transfer", Gene and Cell Therapy: Therapeutic Mechanisms and Strategies pp. 103-130, XP009115260, Jan. 1, 2004.
Li H et al: "HSV-NIS, an oncolytic herpes simplex virus type 1 encoding human sodium iodide symporter for preclinical prostate cancer radiovirotherapy", Cancer Gene Therapy, vol. 20, No. 8, pp. 478-485, XP055872997, New York, ISSN: 0929-1903, DOI: 10.1038/cgt.2013.43, Retrieved from the Internet: URL:https://www.ncbi.nlmnih.gov/pmc/articles/PMC3747331/pdf/cgt201343a.pdf, Aug. 1, 2013.
Uche Ifeanyi Kingsley et al: "Novel Oncolytic Herpes Simplex Virus 1 VC2 Promotes Long-Lasting, Systemic Anti-melanoma Tumor Immune Responses and Increased Survival in an Immunocompetent B16F10-Derived Mouse Melanoma Model", Journal of Virology, vol. 95, No. 3, XP055872651, USISSN: 0022-538X, DOI: 10.1128/JVI.01359-20, Retrieved from the Internet: URL: https://journals.asm.org/doi/pdf/10.1128/JVI.01359-20, Jan. 13, 2021.
Stanfield, BA et al, A Single Intramuscular Vaccination of Mice with the HSV-1 VC2 Virus with Mutations in the Glycoprotein K and the Membrane Protein UL20 Confers Full Protection against Lethal Intravaginal Challenge with Virulent HSV-1 and HSV-2 Strains, PLoS One, vol. 9, No. 10, e109890, pp. 1-13; DOI: 10.1371/journal.pone.0109890, Oct. 28, 2014.
USPTO, International Search Report and Written Opinion for PCT/US2019/044749, dated Mar. 9, 2020.

* cited by examiner

*Primary Examiner* — Bao Q Li
(74) *Attorney, Agent, or Firm* — Williams Mullen; David M. Saravitz

(57) ABSTRACT

The present invention provides compositions for treating or preventing cancer and methods of using and making the compositions. The compositions comprise herpes simplex viruses comprising recombinant herpes simplex virus genomes. Further provided are recombinant herpes simplex virus genomes, viruses comprising the recombinant herpes simplex virus genomes, and cancer vaccines and other compositions comprising the viruses.

20 Claims, 30 Drawing Sheets

Specification includes a Sequence Listing.

SEQUENCE LISTING

```
<160> NUMBER OF SEQ ID NOS: 34

<210> SEQ ID NO 1
<211> LENGTH: 151968
<212> TYPE: DNA
<213> ORGANISM: Artificial sequence
<220> FEATURE:
<223> OTHER INFORMATION: synthetic sequence

<400> SEQUENCE: 1

agcccgggcc ccccgcgggc ggggcggcgc gcaaaaaagg cgggcggcgg tccgggcggc      60

gtgcgcgcgc gcggcgggcg ttggggagcg gggggaggag cggggggagg agcgggggga     120

ggagcggggg gaggagcggg gggaggagcg gggggaggag cggggggagg agcgggggga     180

ggagcggggg gaggagcggg gggaggagcg gggggaggag cggggggagg agcgggggga     240

ggagcggggg gaggagcggg gggaggagcg gggggaggag cggggggagg agcgggggga     300

ggagcggaaa acgggccccc cccgaaacac acccccgggg ggtcgcgcgc ggccctttaa     360

agcgcggcgg cgcagcccgg gcccccgcg gccgagacga gcgagttaga caggcaagca     420

ctactcgcct ctgcacgcac atgcttgcct gtcaaactct accaccccgg cacgctctct     480

gtctccatgg cccgccgccg ccgccatcgc ggcccccgcc gcccccggcc gcccgggccc     540

acgggcgccg tcccaaccgc acagtcccag gtaacctcca cgcccaactc ggaacccgcg     600

gtcaggagcg cgcccgcggc cgccccgccg ccgcccccg ccagtgggcc cccgccttct     660

tgttcgctgc tgctgcgcca gtggctccac gttcccgagt ccgcgtccga cgacgacgat     720

gacgacgact ggccggacag ccccccgccc gagccggcgc cagaggcccg gcccaccgcc     780

gccgcccccc gcccccggtc cccaccgccc ggcgcgggcc cgggggcgg ggctaacccc     840

tcccaccccc cctcacgccc cttccgcctt ccgccgcgcc tcgccctccg cctgcgcgtc     900

accgcagagc acctggcgcg cctgcgcctg cgacgcgcgg gcggggaggg ggcgccggag     960

cccccgcga cccccgcgac ccccgcgacc cccgcgaccc ccgcgacccc cgcgcgggtg    1020

cgcttctcgc cccacgtccg ggtgcgccac ctggtggtct gggcctcggc cgcccgcctg    1080

gcgcgccgcg gctcgtgggc ccgcgagcgg gccgaccggg ctcggttccg gcgccgggtg    1140
```

-continued

```
gcggaggccg aggcggtcat cgggccgtgc ctggggcccg aggcccgtgc ccgggccctg   1200
gcccgcggag ccggcccggc gaactcggtc taacgttaca cccgaggcgg cctgggtctt   1260
ccgcggagct cccgggagct ccgcaccaag ccgctctccg gagagacgat ggcaggagcc   1320
gcgcatatat acgctgggag ccggcccgcc cccgaggcgg gcccgccctc ggagggcggg   1380
actggccaat cggcggccgc cagcgcggcg gggcccggcc aaccagcgtc cgccgagtct   1440
tcggggcccg gcccactggg cgggagttac cgcccagtgg gccgggccgc ccacttcccg   1500
gtatggtaat taaaaactta caagaggcct tgttccgctt cccggtatgg taattagaaa   1560
ctcattaatg ggcggccccg gccgcccttc ccgcttccgg caattcccgc ggcccttaat   1620
gggcaacccc ggtattcccc gcctcccgcg ccgcgcgtaa ccactcccct ggggttccgg   1680
gttatgctaa ttgctttttt ggcggaacac acggcccctc gcgcattggc ccgcgggtcg   1740
ctcaatgaac ccgcattggt cccctggggt tccgggtatg gtaatgagtt tcttcgggaa   1800
ggcgggaagc cccggggcac cgacgcaggc caagcccctg ttgcgtcggt gggaggggca   1860
tgctaatggg gttctttggg ggacaccggg ttggtccccc aaatcggggg ccgggccgtg   1920
catgctaatg atattctttg gggcgccgg gttggtcccc ggggacgggg ccgccccgcg   1980
gtgggcctgc ctcccctggg acgcgcggcc attgggggaa tcgtcactgc cgcccctttg   2040
gggaggggaa aggcgtgggg tataagttag ccctggcccg acagtctggt cgcatttgca   2100
cctcggcact cggagcgaga cgcagcagcc aggcagactc gggccgcccc ctctccgcat   2160
caccacagaa gccccgccta cgttgcgacc cccagggacc ctccgtccgc gaccctccaa   2220
ccgcatacga cccccatgga gccccgcccc ggagcgagta cccgccggcc tgagggccgc   2280
ccccagcgcg aggtgagggg ccgggcgcca tgtctggggc gccatattgg ggggcgccat   2340
attgggggc gccatgttgg gggacccccg acccttacac tggaaccggc cgccatgttg   2400
ggggaccccc actcatacac gggagccggg cgccatgtta gggggcgtgg aaccccgtga   2460
cactatatat acagggaccg gggcgccat gttaggggc gcggaacccc ctgaccctat   2520
atatacaggg accggggtcg ccctgttggg ggtcgccatg tgacccctg actttatata   2580
tacagacccc ccaacacata cacatggccc ctttgactca gacgcagggc ccggggtcgc   2640
cgtgggaccc cctgactcat acacagagac acgcccccac aacaaacaca cagggaccgg   2700
ggtcgccgtg ttagggggcg tggtccccac tgactcatac gcagggcccc cttactcaca   2760
cgcatctagg ggggtgggga ggagccgccc gccatatttg ggggacgccg tgggaccccc   2820
gactccggtg cgtctggagg gcgggagaag agggaagaag aggggtcggg atccaaagga   2880
cggacccaga ccacctttgg ttgcagaccc ctttctcccc cctcttccga ggccagcagg   2940
ggggcaggac tttgtgaggc gggggggggg agagggggaa ctcgtgggcg ctgattgacg   3000
cgggaaatcc ccccattctt acccgccccc cttttttcc ccttagcccg ccccggatgt   3060
ctgggtgttt ccctgcgacc gagacctgcc ggacagcagc gactctgagg cggagaccga   3120
agtgggggg cggggggacg ccgaccacca tgacgacgac tccgcctccg aggcggacag   3180
cacggacacg gaactgttcg agacggggct gctggggccg cagggcgtgg atgggggc   3240
ggtctcgggg gggagccccc cccgcgagga agaccccggc agttgcgggg gcgcccccc   3300
tcgagaggac ggggggagcg acgagggcga cgtgtgcgcc gtgtgcacgg atgagatcgc   3360
gccccacctg cgctgcgaca ccttcccgtg catgcaccgc ttctgcatcc cgtgcatgaa   3420
aacctggatg caattgcgca acacctgccc gctgtgcaac gccaagctgg tgtacctgat   3480
agtgggcgtg acgcccagcg ggtcgttcag caccatcccg atcgtgaacg acccccagac   3540
```

```
ccgcatggag gccgaggagg ccgtcagggc gggcacggcc gtggacttta tctggacggg   3600
caatcagcgg ttcgccccgc ggtacctgac cctgggggg cacacggtga gggccctgtc    3660
gcccacccac cctgagccca ccacggacga ggatgacgac gacctggacg acggtgaggc   3720
ggggggcgg cgaggaccct gggggaggag gaggaggagg ggggagggag gaataggcgg    3780
gcgggggggc gaggaaaggg cgggcgcgga aagggagggc ctgggagggg gcgtaacctg   3840
atcgcgcccc ccgttgtctc ttgcagcaga ctacgtaccg cccgcccccc gccggacgcc   3900
ccgcgccccc ccacgcagag gcgccgccgc gcccccgtg acgggcgggg cgtctcacgc    3960
agccccccag ccggccgcgg ctcggacagc gccccccctcg gcgcccatcg ggccacacgg  4020
cagcagtaac accaacacca ccaccaacag cagcggcggc ggcggcggct cccgccagtc   4080
gcgagccgcg gcgccgcggg gggcgtctgg cccctccggg ggggttgggg ttggggttgg   4140
ggttgttgaa gcggaggcgg ggcggccgag gggccggacg ggcccccttg tcaacagacc   4200
cgcccccctt gcaaacaaca gagaccccat agtgatcagc gactcccccc cggcctctcc   4260
ccacaggccc cccgcggcgc ccatgccagg ctccgccccc cgccccgggc ccaccgcgtc   4320
ctcggccgcg tcgggacccg cgcgcccccg cgcggccgtg gccccgtgcg tgcgagcgcc   4380
gcctccgggg cccggccccc gcgcccggc ccccgcggac gcgcgccgtg tgccccagtc    4440
gcactcgtcc ctggctcagg ccgcgaacca agaacagagt ctgtgccggg cgcgtgcgac   4500
ggtggcgcgc ggctcggggg ggccgggcgt ggagggtgga cacgggccct cccgcggcgc   4560
cgccccctcc ggcgcccccc cgctcccctc cgccgcctct gtcgagcagg aggcggcggt   4620
gcgtccgagg aagaggcgcg ggtcgggcca ggaaaacccc tccccccagt ccacgcgtcc   4680
ccccctcgcg ccggcagggg ccaagagggc ggcgacgcac cccccctccg actcagggcc   4740
ggggggcgc ggccagggtg ggcccgggac cccccctgacg tcctcggcgg cctccgcctc   4800
ttcctcctct gcctcttcct cctcggcccc gactcccgcg ggggccgcct cttccgccgc   4860
cggggccgcg tcctcctccg cttccgcctc ctcgggcggg gccgtcggtg ccctgggagg   4920
gagacaagag gaaacctccc tcggccccg cgctgcttct gggccgcggg ggccgaggaa    4980
gtgtgcccgg aagacgcgcc acgcggagac ttccggggcc gcccccgcgg gcggcctcac   5040
gcgctacctg cccatctcgg gggtctctag cgtggtcgcc ctgtcgcctt acgtgaacaa   5100
gacgatcacg ggggactgcc tgcccatcct ggacatggag acggggaaca tcggggcgta   5160
cgtggtcctg gtggaccaga cgggaaacat ggcgacccgg ctgcgggccg cggtccccgg   5220
ctggagccgc cgcaccctgc tccccgagac cgcgggtaac cacgtgatgc cccccgagta   5280
cccgacggcc cccgcgtcgg agtggaacag cctctggatg acccccgtgg ggaacatgct   5340
gttcgaccag ggcaccctag tgggcgccct ggacttccgc agcctgcggt ctcggcaccc   5400
gtggtccggg gagcaggggg cgtcgacccg ggacgaggga aaacaataag ggacgccccc   5460
cgtgtttgtg gggagggggg ggtcgggcgc tgggtggtct ctggccgcgc ccactacacc   5520
agccaatccg tgtcggggag gggaaaagtg aaagacacgg gcaccacaca ccagcgggtc   5580
tttagtgttg gccctaataa aaaactcagg ggatttttgc tgtctattgg gaaataaagg   5640
tttacttttg tatcttttcc ctgtctgtgt tggatggatc tcgggggtgc gtgggagtgg   5700
gggtgcgtgg gagtgggggt gcgtgggagt gggggtgcgt gggagtgggg gtgcgtggga   5760
gtgggggtgc gtgggagtgg gggtgcgtgg gagtgggggt gcgtgggagt gggggtgcgt   5820
gggagtgggg gtgccatgtt gggcaggctc tggtgttaac cacagagccg cggcccgggc   5880
```

-continued

```
tgcctgacca ccgatccccg aaagcatcct gccactggca tggagccaga accacagtgg   5940
gttgggtgtg ggtgttaagt ttccgcgagc gcctgcccgc ccggactgac ctggcctctg   6000
gccgccacaa agggcggggg ggggttaact acactatagg gcaacaaagg acgggagggg   6060
tggcggggcg ggacggggcg cccaaaaggg ggtcggccac accacagacg tgggtgttgg   6120
ggggtggggc ggaggggtgg ggggggagac agaaacagga acatagttag aaaacaagaa   6180
tgcggtgcag ccagagaatc acaggagacg aggggatggg cgtgttggtt accaacccac   6240
acccaggcat gctcggtggt atgaaggagg gggggcggtg cttcttagag accgccgggg   6300
gacgtggggt tggtgtgcag aggcacgcgc acccgcgtcg gccaggtggg ccggtacccc   6360
atccccccctc ccccgaccct tcccaccccc gcgtgccaga gatcaccccg gtcccccggc   6420
acccgccact cctccatatc ctcgctttag gaacaacttt aggggggggta cacacgcgcc   6480
gtgcatttcc ttccacaccc cccctccccc gcactccccc ccccccggca gtaagaccca   6540
agcatagaga gccaggcaca aaaacacagg cggggtggga cacatgcctt cttggagtac   6600
gtgggtcatt ggcgtggggg gttacagcga caccggccga ccccctggcg gtcttccagc   6660
cggcccttag ataagggggc agttggtggt cggacgggta agtaacagag tctgactaag   6720
ggtgggaggg ggggaaaaga acgggctggt gtgctgtaac acgagcccac ccgcgagtgg   6780
cgtggccgac cttagcctct ggggcgcccc ctgtcgtttg ggtccccccc ctctattggg   6840
gagaagcagg tgtctaacct acctggaaac gcggcgtctt tgttgaacca caccggggcg   6900
cccttgacga gtgggataac gggggaggaa gggagggagg agggtactgg gggtgaagaa   6960
gggggggggg ggagaagcga gaacaggaaa ggcgacggag cccgacaaaa caccgagaaa   7020
aaaaaaccac agcgcatgcg ccgggccgtt gtggggcccc gggccggggc cccttgggtc   7080
cgccggggcc ccgggccggg ccgccacggg ggccggccgt tggcggtaac cccgattgtt   7140
tatctcaggc cccgggccgg gaacccggaa aagcctccgg ggggcctttt tcgcgtcgcg   7200
tgccggcgag cgggcccgga cggggcccgg accgccgcgg tcgggggccc cctcgtcccg   7260
ggccgtacgc ggccttcgcc ccgtgagggg acagacgaac gaaacattcc ggcgacggaa   7320
cgaaaaacac cccagacggg ttaaagaaac agaaaccgca accccccccca cccccgaaac   7380
ggggaaaaca aaaaacagac cagcggccgg ccggcgctta gggggaggat gtcgccgacg   7440
ccccttggcc gccccggctg caggggggcc cggagagccg cggcacccgg acgcgcccgg   7500
aaagtctttc gcaccacccg cgatcggcac ggccgcgccc ccgcttttat aaaggctcag   7560
atgacgcagc aaaaacaggc cacagcacca cgtgggtagg tgatgtaatt ttattttcct   7620
cgtctgcggc ctaatggatt tccgggcgcg gtgcccctgt ctgcagagca cttaacggat   7680
tgatatctcg cgggcacgcg cgcccttaat ggaccggcgc ggggcggggg gccggatacc   7740
cacacgggcg gggggggggg tgtcgcgggc cgtctgctgg cccgcggcca cataaacaat   7800
gactctgggc ctttctgcct ctgccgcttg tgtgtgcgcg cgccggctct gcggtgtcgg   7860
cggcggctgc ggcggctgcg gcggccgccg tgttcggtct cggtagccgg ccggcgggtg   7920
gactcgcggg gggccggagg gtggaaggca ggggggtgta ggatgggtat caggacttcc   7980
acttcccgtc cttccatccc ccgttcccct cggttgttcc tcgccccccc ccacaccccg   8040
ccgctttccg ttggggttgt tattgttgtc gggatcgtgc gggccggggg tcgccggggc   8100
aggggcgggg gcgggggtgc tcgtcgatcg accgggctca gtgggggcgt ggggtggggg   8160
ggaaaaggcg aagagactgg gggtgggggg gggtgtcggg ggtggctgtt tttttttgtg   8220
ggtgtttttt gtggctgttc ccgtcccccg tcaccccccct ccctccgtcc ccccgtcgcg   8280
```

-continued

```
ggtgtttgtg tttgtttatt ccgacatcgg tttatttaaa taaacacagc cgttctgcgt   8340
gtctgttctt gcgtgtggct gggggcttat atgtggggtc ccgggggcgg gatggggttt   8400
agcggcgggg ggcggcgcgc cggacggggc gctggagata acggccccg gggaacgggg   8460
gaccggggct gggtctcccg aggtgggtgg gtgggcggcg gtggccgggc cgggccgggc   8520
cgggtgggcg gggtttggaa aaacgaggag gaggaggagg agaaggaggg ggggggagac   8580
ggggggaaag caaggacacg gcccgggggg tgggagcgcg ggccgggccg ctcgtaagag   8640
ccgcgacccg gccgccgggg agcgttgtcg ccgtcggtct gccggccccc gtccctccct   8700
tttttgacca accagcgccc ccccccctca ccaccattcc taccaccacc accaccaccg   8760
acacctcccg cacacccccg cccacactcc ccccccccac ccaacccgca ccacgagcac   8820
gggttggggg tagcagggga tcaaaggggg gcaaggccgg cggggcggtt cgggggcggg   8880
ggcgggagac cgagtaggcc ccgcccatcc gcggcccctc ccggcagcca cgccccccag   8940
cgtcgggtgt cacggggaaa gagcaggggg agaggggaga ggggggggaga ggggagaggg   9000
ggggagaggg gagaggggg gagaggggag aggggggggag aggggagagg gggggagagg   9060
ggagaggggg ggagagggga gagggggga gaggggagag ggggggagag gggagagggg   9120
gggagagggg agaggggggg agagggggta tataaaccaa cgaaaagcgc gggaacgggg   9180
atacggggct tgtgtggcac gacgtcgtgg ttgtgttact gggcaaacac ttggggactg   9240
taggtttctg tgggtgccga ccctaggcgc tatggggatt ttgggttggg tcgggcttat   9300
tgccgttggg gttttgtgtg tgcgggggg cttgtcttca accgaatatg ttattcggag   9360
tcgggtggct cgagaggtgg gggatatatt aaaggtgcct tgtgtgccgc tcccgtctga   9420
cgatcttgat tggcgttacg agacccccctc ggctataaac tatgctttga tagacggtat   9480
atttttgcgt tatcactgtc ccggattgga cacggtcttg tgggataggc atgcccagaa   9540
ggcatattgg gttaacccct ttttatttgt ggcgggtttt ttggaggact tgagtcaccc   9600
cgcgtttcct gccaacaccc aggaaacaga aacgcgcttg gccctttata aagagatacg   9660
ccaggcgctg gacagtcgca agcaggccgc cagccacaca cctgtgaagg ctgggtgtgt   9720
gaactttgac tattcgcgca cccgccgctg tgtagggcga caggatttgg gacctaccaa   9780
cggaacgtct ggacggaccc cggttctgcc gccggacgat gaagcgggcc tgcagccgaa   9840
gcccctcacc acgccgccgc ccatcatcgc cacgttggac ccccaccccgc gacgggacgc   9900
cgccgcaaaa agcagacgcc gacgacccca ctcccggcgc atctaatgat gccgcgacgg   9960
aaacccgtcc gggttcgggg ggcgaaccgg ccgcctgtcg ctcgtcaggg ccggcgggcg   10020
ctcctcgccg ccctagaggc tgtcccgctg gtgtgacgtt ttcctcgtcc gcgccccccg   10080
accctcccat ggatttaaca aacggggggg tgtcgcctgt ggcgacctcg gcgcctctgg   10140
actggaccac gtttcggcgt gtgtttctga tcgacgacgc gtggcggccc ctgttggagc   10200
ctgagctggc gaaccccctta accgcccacc tcctgaccga atataatcgt cggtgccaga   10260
ccgaagaggt gctgccgccg cgggaggatg tgttttcgtg gactcgttat tgcacccccg   10320
acgaggtgcg cgtggttatc atcggccagg acccatatca ccaccccggc caggcgcacg   10380
gacttgcgtt tagcgtgcgc gcgaacgtgc cgcctccccc gagtcttcgg aatgtcttgg   10440
cggccgtcaa gaactgttat cccgaggcac ggatgagcgg ccacggttgc ctggaaaagt   10500
gggcgcggga cggcgtcctg ttactaaaca cgaccctgac cgtcaagcgc ggggcggcgg   10560
cgtcccactc tagaatcggt tgggaccgct tcgtgggcgg agttatccgc cggttggccg   10620
```

-continued

```
cgcgccgccc cggcctggtg tttatgctct ggggcgcaca tgcccagaat gccatcaggc  10680
cggaccctcg ggtccattgc gtcctcaagt tttcgcaccc gtcgcccctc tccaaggttc  10740
cgttcggaac atgccagcat ttcctcgtgg cgaatcgata tctcgagacc cggtcgattt  10800
cacccatcga ctggtcggtt tgaaaggcat cgacgtccgg ggttttcgtc tgtgggggct  10860
tttgggtatt tccgatgaat aaagacggtt aatggttaaa cctctggtct catacgggtc  10920
ggtgatgtcg ggcgtcgggg gagagggagt tccctctgcg cttgcgattc tagcctcgtg  10980
gggctggacg ttcgacacgc caaaccacga gtcagggata tcgccagata cgactcccgc  11040
agattccatt cggggggccg ctgtggcctc acctgaccaa cctttacacg gggcccgga  11100
acgggaggcc acagcgccgt ctttctcccc aacgcgcgcg gatgacggcc cgccctgtac  11160
cgacgggccc tacgtgacgt ttgataccct gtttatggtg tcgtcgatcg acgaattagg  11220
gcgtcgccag ctcacggaca ccatccgcaa ggacctgcgg ttgtcgctgg ccaagtttag  11280
cattgcgtgc accaagacct cctcgttttc gggaaacgcc ccgcgccacc acagacgcgg  11340
ggcgttccag cgcggcacgc gggcgccgcg cagcaacaaa agccttcaga tgtttgtgtt  11400
gtgcaaacgc acccacgccg ctcgagtgcg agagcagctt cgggtcgtta ttcagtcccg  11460
caagccgcgc aagtattaca cgcgatcttc ggacgggcgg ctctgccccg ccgtccccgt  11520
gttcgtccac gagttcgtct cgtccgagcc aatgcgcctc caccgagata acgtcatgct  11580
ggcctcgggg gccgagtaac cgcccccccg cgccaccctc actgcccgtc gcgcgtgttt  11640
gatgttaata aataacgcat aaatttggct ggttgtttgt tgtctttaat ggaccgcccg  11700
caggggggt ggcatttcag tgtcgggtga cgagcgcgat ccggccggga tcctaggacc  11760
ccaaaagttt gtctgcgtat tccagggcgg ggctcagttg aatctcccgc agcacctcta  11820
ccagcaggtc cgcggtgggc tggagaaact cggccgtccc ggggcaggcg gtcgtcgggg  11880
gtggaggcgc ggcgcccacc ccgtgtgccg cgcctggcgt ctcctctggg ggcgacccgt  11940
aaatggttgc agtgatgtaa atggtgtccg cggtccagac cacggtcaaa atgccggccg  12000
tggcgctccg ggcgctttcg ccgcgcgagg agctgaccca ggagtcgaac ggatacgcgt  12060
acatatgggc gtcccacccg cgttcgagct tctggttgct gtcccggcct ataaagcggt  12120
aggcacaaaa ttcggcgcga cagtcgataa tcaccaacag cccaatgggg gtgtgttgga  12180
taacaacgcc tccgcgcggc aggcggtcct ggcgctcccg gccccgtacc atgatcgcgc  12240
gggtgccgta ctcaaaaaca tgcaccacct gcgcggcgtc gggcagtgcg ctggtcagcg  12300
aggccctggc gtggcatagg ctatacgcga tggtcgtctg tggattggac atctcgcggt  12360
gggtagtgag tcccccgggc cgggttcggt ggaactgtaa ggggacggcg ggttaatata  12420
caatgaccac gttcggatcg cgcagagccg atagtatgtg cttactaatg acgtcatcgc  12480
gctcgtggcg ctcccggagc ggatttaagt tcatgcgaag gaattcggag gaggtggtgc  12540
gggacatggc cacgtacgcg ctgttgaggc gcaggttgcc gggcgtaaag cagatggcga  12600
ccttgtccag gctaaggccc tgggagcgcg tgatggtcat ggcaagcttg gagctgatgc  12660
cgtagtcggc gtttatggcc atggccagct ccgtagagtc aatggactcg acaaactcgc  12720
tgatgttggt gttgacgacg gacatgaagc cgtgttggtc ccgcaagacc acgtaaggca  12780
ggggggcctc ttccagtaac tcggccacgt tggccgtcgc gtgccgcctc cgcagctcgt  12840
ccgcaaaggc aaacacccgt gcgtacgtgt atcccatgag cgtataattg tccgtctgca  12900
gggcgacgga catcagcccc ccgcgcggcg agccggtcag catctcgcag ccccggaaga  12960
taacgttgtc cacgtacgtg ctaaaggggg cgccttcaaa tgcctcccca aagagctctt  13020
```

ggaggattcg gaatctcccg aggaaggccc gcttcagcag cgcaaactgg gtgtgaacgg 13080
cggcggtggt ctccggttcc ccgggggtgt agtggcagta aaacacgtcg agctgttgtt 13140
cgtccagccc cgcgaaaata acgtcgaggt cgtcgtcggg aaaatcgtcc gggcccccgt 13200
cccgcggccc cagttgctta aaatcaaacg cacgctcgcc gggggcgcct gcgtcggcca 13260
ttaccgacgc ctgcgtcggc accccccgaag atttggggcg cagagacaga atctccgccg 13320
ttagttctcc catgcgggcg taggcgaggg tcctctgggt cgcatccagg cccgggcgct 13380
gcagaaagtt gtaaaaggag ataagcccgc taaatatgag ccgcgacagg aacctgtagg 13440
caaactccac cgaagtctcc ccctgagtct ttacaaagct gtcgtcacgc aacactgcct 13500
cgaaggcccg gaacgtccca ctaaacccaa aaaccagttt tcgcaggcgc gcggttaccg 13560
cgatctggct gttgaggacg taagtgacgt cgttgcgggc cacgaccagc tgctgtttgc 13620
tgtgcacctc gcagcgcatg tgccccgcgt cctggtcctg gctctgcgag tagttggtga 13680
tgcggctggc gttggccgtg agccactttt caatagtcag gccgggctgg tgtgtcagcc 13740
gtcggtattc gtcaaactcc ttgaccgaca cgaacgtaag cacggggagg gtgaacacga 13800
caaactcccc ctcacgggtc accttcaggt aggcgtggag cttggccatg tacgcgctca 13860
cctctttgtg ggaggagaac aaccgcgtcc agccggggag gttggcgggg ttggtgatgt 13920
agttttccgg gacgacgaag cgatccacga actgcatgtg ctcctcggtg atgggtaggc 13980
cgtactccag caccttcatg aggttaccga actcgtgctc gatgcaccgt ttgttgttaa 14040
taaaaatggc ccagctatac gagaggcggg cgtactcccg cagcgtgcgg ttgcagatga 14100
ggtacgtgag cacgttctcg ctctggcgga cggaacaccg cagtttctgg tgctcgaagg 14160
tcgactccag ggacgccgtc tgtgtcggcg agcccacaca caccaacacg ggccgcaggc 14220
gggccgcgta ctggggggtg tggtacaggg cgttaatcat ccaccagcaa tacaccacgg 14280
ccgtgaggag gtgacgccca aggagcccgg cctcgtcgat gacgatcacg ttgctgcggg 14340
taaaggccgg cagcgccccg tgggtggccg gggccaaccg cgtcagggcg ccctcggcca 14400
accccagggt ccgttccagg gcggccaggg cgcgaaactc gttccgcgac tcctcgcccc 14460
cggaggcggc cagggtgcgc ttcgtgaggt ccaaaatcac ctcccagtag tacgtcagat 14520
ctcgtcgctg caggtcctcc agcgaggcgg ggttgctggt cagggtgtac gggtactgcc 14580
ccagttgggc ctggacgtga ttcccgcgaa acccaaattc atgaaagatg gtgttgatgg 14640
gtcggctgag aaaggcgccc gagagtttgg cgtacatgtt ttgggccgca atgcgcgtgg 14700
cgcccgtcac cacacagtcc aagacctcgt tgattgtctg cacgcacgtg ctctttccgg 14760
agccagcgtt gccggtgata agatacaccg cgaacggaaa ctccctgagg ggcaggcctg 14820
cgggggactc taaggccgcc acgtcccgga accactgcag acggggcact tgcgctccgt 14880
cgagctgttg ttgcgagagc tctcggatgc gcttaaggat tggctgcacc ccgtgcatag 14940
acgtaaaatt taaaaaggcc tcggccctcc ctggaacggc tggtcggtcc ccgggttgct 15000
gaaggtgcgg cgggccgggt ctctgtccgt ctagctggcg ctccccgccg gccgccgcca 15060
tgaccgcacc acgctcgcgg gcccccacta cgcgtgcgcg gggggacacg gaagcgctgt 15120
gctcccccga ggacggctgg gtaaaggttc accccacccc cggtacgatg ctgttccgcg 15180
agattctcca cgggcagctg gggtataccg agggccaggg ggtgtacaac gtcgtccggt 15240
ccagcgaggc gaccacccgg cagctgcagg cggcgatctt tcacgcgctc ctcaacgcca 15300
ccacttaccg ggacctcgag gcggactggc tcggccacgt ggcggcccgc ggtctgcagc 15360
cccaacggct ggttcgccgg tacaggaacg cccgggaggc ggatatcgcc ggggtggccg 15420
agcgggtgtt cgacacgtgg cggaacacgc ttaggacgac gctgctggac tttgcccacg 15480
ggttggtcgc ctgctttgcg ccgggcggcc cgagcggccc gtcaagcttc cccaaatata 15540
tcgactggct gacgtgcctg gggctggtcc ccatattacg caagcgacaa gaagggggtg 15600
tgacgcaggg tctgagggcg tttctcaagc agcacccgct gacccgccag ctggccacgg 15660
tcgcggaggc cgcggagcgc gccggccccg ggttttttga gctggcgctg gccttcgact 15720
ccacgcgcgt ggcggactac gaccgcgtgt atatttacta caaccaccgc cggggcgact 15780
ggctcgtgcg agaccccatc agcgggcagc gcggagaatg tctggtgctg tggcctccct 15840
tgtggaccgg ggaccgtctg gtcttcgatt cgcccgtaca gcggctgttt cccgagatcg 15900
tcgcgtgtca ctccctccgg gaacacgcgc acgtctgccg gctgcgcaat accgcgtccg 15960
tcaaggtgct gctggggcgc aagagcgaca gcgagcgcgg ggtggccggc gccgcgcggg 16020
tcgttaacaa ggtgttgggg gaggacgacg agaccaaggc cgggtcggcc gcctcgcgcc 16080
tcgtgcggct tatcatcaac atgaagggca tgcgccacgt aggcgacatt aacgacactg 16140
tgcgtgccta cctcgacgag gccgggggcc acctgataga cgccccggcc gtcgacggta 16200
ccctcccggg attcggcaag ggcggaaaca gccgcgggtc tgcgggccag gaccaggggg 16260
ggcgggcgcc gcagcttcgc caggccttcc gcacggccgt ggttaacaac atcaacggcg 16320
tgttggaggg ctatataaat aacctgtttg gaaccatcga gcgcctgcgc gagaccaacg 16380
cgggcctggc gacccagttg caggagcgcg accgcgagct ccggcgcgca acatcggggg 16440
ccctggagcg ccagcagcgc gcggccgacc tggcggccga gtccgtgacc gggggatgcg 16500
gcagccgccc tgcgggggcg gacctgctcc gggccgacta tgacattatc gacgtcagca 16560
agtccatgga cgacgacacg tacgtcgcca acagttttca gcacccgtac atcccttcgt 16620
acgcccagga cctggagcgc ctgtcgcgcc tctgggagca cgagctggtg cgctgtttca 16680
aaattctgtg tcaccgcaac aaccagggcc aagagacgtc gatctcgtac tccagcgggg 16740
cgatcgccgc attcgtcgcc ccctactttg agtcagtgct tcgggccccc cgggtaggcg 16800
cgcccatcac gggctccgat gtcatcctgg gggaggagga gttatgggat gcggtgttta 16860
agaaaacccg cctgcaaacg tacctgacag acatcgcggc cctgttcgtc gcggacgtcc 16920
agcacgcagc gctgcccccg ccccccctccc cggtcggcgc cgatttccgg cccggcgcgt 16980
ccccgcgggg ccggtccaga tcgcggtcgc ccggaagaac tgcgcgaggc gcgccggacc 17040
agggcggggg catcgggcac cgggatggcc gccgcgacgg ccgacgatga ggggtcggcc 17100
gccaccatcc tcaagcaggc catcgccggg gaccgcagcc tggtcgaggc ggccgaggcg 17160
attagccagc agacgctgct ccgcctggcc tgcgaggtgc gccaggtcgg cgaccgccag 17220
ccgcggttta ccgccaccag catcgcgcgc gtcgacgtcg cgcctgggtg ccggttgcgg 17280
ttcgttctgg acgggagtcc cgaggacgcc tatgtgacgt cggaggatta ctttaagcgc 17340
tgctgcggcc agtccagtta tcgcggcttc gcggtggcgg tcctgacggc caacgaggac 17400
cacgtgcaca gcctggccgt gcccccccctc gttctgctgc accggttctc cctgttcaac 17460
cccagggacc tcctggactt tgagcttgcc tgtctgctga tgtacctgga gaactgcccc 17520
cgaagccacg ccaccccgtc gacctttgcc aaggttctgg cgtggctcgg ggtcgcgggt 17580
cgccgcacgt ccccattcga acgcgttcgc tgccttttcc tccgcagttg ccactgggtc 17640
ctaaacacac tcatgttcat ggtgcacgta aaaccgttcg acgacgagtt cgtcctgccc 17700
cactggtaca tggcccggta cctgctggcc aacaacccgc cccccgttct ctcggccctg 17760
ttctgtgcca ccccgacaag ctcctcattc cggctgccgg ggccgccccc ccgctccgac 17820
tgcgtggcct ataaccccgc cgggatcatg gggagctgct gggcgtcgga ggaggtgcgc 17880
gcgcctctgg tctattggtg gctttcggag accccaaaac gacagacgtc gtcgctgttt 17940
tatcagtttt gttgaatttt aggaaataaa cccggttttg tttctgtggc ctcccgacgg 18000
atgcgcgtgt ccttactccg tcttggtggg tgggtggctg tgtatggcgt cccatctgtg 18060
cggggagggg ggcaagtcgg cacgtattcg gacagactca agcacacacg ggggagcgct 18120
cttgtctcag ggcaatgttt ttattggtca aactcaggca aacagaaacg acatcttgtc 18180
gtcaaaggga tacacaaact tccccccctc gccccatact cccgccagca ccccggtaaa 18240
caccaactca atctcgcgca ggatttcgcg caggtgatga gcgcagtcca cgggggggag 18300
cacaaggggc cgcgggtata gatcgacggg gacgccgacc gactccccgc ctccgggaca 18360
gacacgcacg acgcgccgcc agtagtgctc tgcgtccagc aaggcgccgc cgcggaaggc 18420
agtggggggc aaggggtcgc tggcctcaaa gggggacacc cgaacgctcc agtactccgc 18480
gtccaaccgt ttattaaacg cgtccaagat aaggcggtcg caggcgtcct ccataaggcc 18540
ccgggccgtg agtgcgtcct cctccggcac gcctgccgtt gtcaggccca ggacccgtcg 18600
cagcgtgtcg cgtacgaccc cggccgccgt ggtgtacgcg ggcccgcgga gaggaaatcc 18660
cccaagatgg tcagtgttgt cgcgggagtt ccagaaccac actcccgcct ggctccaggc 18720
gactgcgtgg gtgtagacgc cctcgagggc caagcacagt gggtgccgca gccggaggcc 18780
gttggcccta agcacggctc ccacggccgt ctcgatggcc cgccgggcgt cctcgatcac 18840
cccggaagcc gcatccgcgt cttgggggtc cacgttaaag acaccccaga acgcaccccc 18900
atcgcccccg cagaccgcga acttcaccga gctggccgtc tcctcgatct gcaggcagac 18960
ggcggccatt accccaccca ggagctgccg cagcgcaggg caggcgttgc acgtgtccgg 19020
gaccaggcgc tccaagacgg ccccggccca gggctctgag ggagcggcca ccaccagcgc 19080
gtccagtctt gctaggcccg tccggccgtg gggtccgcc agcccgctcc ccccgaggtc 19140
ggccagggcc gccaggagct gggcgcgaag tccggggaag caaaaccgcg ccgtccagac 19200
gggcccgacg gccgcgggcg ggtctaacag ttggatgatt ttagtggcgg gatgccaccg 19260
cgccaccgcc tcccgcactg cgggcaggag gcatccggct gccgccgagg ccacgccggg 19320
ccaggctcgc ggggggagga cgaccctgac ccccaccgcg ggccaggccc ccaggagcgc 19380
ggcgtaagcg gccgcggccc cgcgcaccag gtcccgtgcc gactcggccg tggccggcac 19440
ggtgaacgtg ggccaacccg gaaaccccag gacggcaaag tacgggacgg gtcccccccg 19500
gacctcaaac tcgggcccca gaaaggcaaa gacgggggcc agggccccgg gggcggcgtg 19560
gaccgtggta tgccactgcc ggaaaagggc gacgagcgcc ggcgcggaga acttctcgcc 19620
ggcgcttaca aagtagtcgt aatcgcgggg cagcagcacc cgtgccgtga ctcgttgtgg 19680
gtgcccgcgt ggccgcaggc ccacctcgca cacctcgacc aggtccccga acgcgccctc 19740
cttcttgatc ggcggaaacg caagagtctg gtattcgcgc gcaaatagcg cggttccggt 19800
ggtgatgtta acggtcagcg aagcggtgga cgcgcactgg ggggtgtcgc gaatggccgc 19860
caggcgcgcc cacgccagcc gcgcgtcggg atgctcggca acgcgcgccg ccagggccat 19920
agggtcgatg tcaatgttgg cctccgcgac caggagagcg gcgcgagggg cggcgggcgg 19980
gccccacgac gctctctcaa ctttcaccac cagtcccgtg cgtgggtccg agccgatacg 20040
cagcggggcg aacagggcca ccggcccggt ctggcgctcc agggccgcca ggacgcacgc 20100

-continued

```
gtacagcgcc cgccacagag tcgggttctc caggggctcc agcggggagg cggccggcgt  20160
cgtcgcggcg cgggcggccg ccacgacggc ctggacggag acgtccgcgg agccgtagaa  20220
atcccgcagc tccgtcgcgg tgacggagac ctccgcaaag cgcgcgcgac cctcccctgc  20280
ggcgttgcga catacaaaat acaccagggc gtggaagtac tcgcgagcgc ggggggggcag  20340
ccataccgcg taaagggtaa tggcgctgac gctctcctcc acccacacga tatctgcggt  20400
gtccatcgca cggcccctaa ggatcacggg cggtctgtgg gtcccatgct gccgtgcctg  20460
gccgggcccg gtgggttgcg gaaaccggtg acgggggggg gggcggtttt tggggttggg  20520
gtgggaaacg gcccgggtcc gggggccaac ttggcccctc ggtgcgttcc ggcaacagcg  20580
ccgccggtcc gcggacgacc acgtaccgaa cgagtgcggt cccgagactt atagggtgct  20640
aaagttcacc gccccctgca tcatgggcca ggcctcggtg gggagctccg acagcgccgc  20700
ctccaggatg atgtcagcgt tggggttggc gctggatgag tgcgtgcgca aacagcgccc  20760
ccacgcgggc acgcgtagct tgaagcgcgc gcccgcaaac tcccgcttgt gggccataag  20820
cagggcgtac agctgcctgt gggtccggca ggcgctgtgg tcgatgtggt gggcgtccaa  20880
caaccccacg attgtctgtt tggtgaggtt tttaacgcgc cccgccccgg gaaacgtctg  20940
cgtgcttttg gccatctgca cgccaaacag ttcgccccag attatcttga acagcgccac  21000
cgcgtggtcc gtctcactaa cggaccgcgc gggggacagc cgcttagggc gtcggcgacg  21060
cgcttgacgg cttcctccga gagcagaagt ccgtcggtta cgttacagtg gcccagttcg  21120
aacaccagct gcatgtagcg gtcgtagtgg ggggtcagca ggtccagcac gtcatcgggg  21180
ccgaaggtcc tcccagatcc cccggccgcc gagtcccaat gcaggcgcgc ggccatggtg  21240
ctgcacaggc acaacagctc ccagacaggg gttacgttca gggtgggggg cagggccacg  21300
agctccagct ctccggtgac gttgatcgtg gggatgacgc ccgtggcgta gtggtcatag  21360
atccgccgaa atatggcgct gctgcgggtg gccatgggaa cgcggagaca ggcctccagc  21420
aacgccaggt aaataaaccg cgtgcgtccc atcaggctgt tgaggttgcg catgagcgcg  21480
acaatttccg ccggcgcgac atcggaccgg aggtattttt cgacgaaaag acccacctcc  21540
tccgtctcgg cggcctgggc cggcagcgac gcctcgggat cccggcaccg cagctcccgt  21600
agatcgcgct gggccctgag ggcgtcgaaa tgtacgcccc gcaaaaacag acagaagtcc  21660
tttggggtca gggtatcgtc gtgtccccag aagcgcacgc gtatgcagtt tagggtcagc  21720
agcatgtgaa ggatgttaag gctgtccgag agacacgcca gcgtgcatct ctcaaagtag  21780
tgtttgtaac ggaatttgtt gtagatgcgc gacccccgcc ccagcgacgt gtcgcatgcc  21840
gacgcgtcac agcgcccctt gaaccggcga cacagcaggt ttgtgacctg ggagaactgc  21900
gcgggccact ggccgcagga actgaccacg tggttcagga gcatgggcgt aaagacgggc  21960
tccgagcgcg ccccggagcc gtccatgtaa atcagtagct ccccccttgcg gagggtgcgc  22020
acccgtccca gggactggta cacggacacc atgtccggtc cgtagttcat gggtttcacg  22080
taggcgaaca tgccatcaaa gtgcagggga tcgaagctga ggcccacggt tacgaccgtc  22140
gtgtatataa ccacgcggta ttggccccac gtggtcacgt ccccgagggg ggtgagcgag  22200
tgaagcaaca gcacgcggtc cgtaaactga cggcagaacc gggccacgat ctccgcgaag  22260
gagaccgtcg acgaaaaaat gcagatgtta tcgcccccgc caaggcgcgc ttccagctcc  22320
ccaaagaacg tggccccccg ggcgtccgga gaggcgtccg gagacgggcc gctcggcggc  22380
ccgggcgggc gcagggcagc ctgcaggagc tcggtcccca gacgcgggag aaacaggcac  22440
cggcgcgccg aaaacccggg catggcgtac tcgccgacca ccacatgcac gtttttttcg  22500
```

```
ccccggagac cgcacaggaa gtccaccaac tgcgcgttgg cggttgcgtc catggcgatg  22560
atccgaggac atgtgcgcag caggcgtagc attaacgcat ccacgcggcc cagttgctgc  22620
atcgttggcg aatagagctg gcccagcgtc gacataacct cgtccagaac gaggacgtcg  22680
tagttgttca gaaggttggg gcccacgcga tgaaggcttt ccacctggac gataagtcgg  22740
tggaaggggc ggtcgttcat aatgtaattg gtggatgaga agtaggtgac aaagtcgacc  22800
aggcctgact cagcgaaccg cgtcgccagg gtctgggtaa aactccgacg acaggagacg  22860
acgagcacac tcgtgtccgg agagtggatc gcttcccgca gccagcggat cagcgcggta  22920
gtttttcccg accccattgg cgcgcggacc acagtcacgc acctggccgt cggggcgctc  22980
gcgttgggga aggtgacggg tccgtgctgc tgccgctcga tcgttgtttt cgggtgaacc  23040
cggggcaccc attcggccaa atcccccccg tataacatcc gcgctagcga tacgctcgac  23100
gtgtactgtt cgcactcgtc gtccccaatg ggacgcccgg cccccagagg atcccccgac  23160
tccgcgcccc ccacgaaagg catgaccggg gcgcggacgg cgtggtgggt ctggtgtgtg  23220
caggtggcga cgtttgtggt ctctgcggtc tgcgtcacgg ggctcctcgt cctggcctct  23280
gtgttccggg cacggtttcc ctgcttttac gccacggcga gctcttatgc cggggttaac  23340
tccacggccg aggtgcgcgg gggtgtagcc gtgcccctca ggttggacac gcagagcctt  23400
gtgggcactt atgtaatcac ggccgtattg ttgttggccg cggccgtgta tgccgtggtc  23460
ggcgccgtga cctcccgcta cgaccgcgcc ctggacgcgg gccgccgtct ggctgcggcc  23520
cgcatggcca tgccgcacgc cacgctgatc gccggaaacg tctgctcttg gttgctgcag  23580
atcaccgtcc tgctgctggc ccatcgcatc agccagctgg cccacctggt ttacgtcctg  23640
cactttgcgt gtctggtgta ttttgcggcc catttttgca ccagggggggt cctgagcggg  23700
acgtatctgc gtcaggtgca cggcctgatg gagctggccc cgacccatca tcgcgtcgtc  23760
ggcccggctc gcgccgtgct gacaaacgcc ttgctgttgg gcgtcttcct gtgcacggcc  23820
gacgccgcgg tatccctgaa taccatcgcc gcgttcaact ttaatttttc ggccccgggc  23880
atgctcatct gcctgaccgt gctgttcgcc attctcgtcg tatcgctgtt gttggtggtc  23940
gagggggtgt tgtgtcacta cgtgcgcgtg ttggtgggcc cccacctggg ggccgttgcc  24000
gccacgggca tcgtcggcct ggcctgcgag cactattaca ccaacggcta ctacgtggtg  24060
gagacgcagt ggccgggggc acagacggga gtgcgcgtcg ccctcgccct ggtcgccgcc  24120
tttgccctcg gcatggccgt gctccgctgc acccgcgcct atctgtatca caggcggcac  24180
cacaccaaat tttttatgcg catgcgcgac acgcgacacc gcgcacattc cgccctcaag  24240
cgcgtacgca gttccatgcg cggatcgcga gacggccgcc acaggcccgc gcccggcagc  24300
ccgcccggga ttcccgaata tgcggaagac ccctacgcga tctcatacgg cggccagctc  24360
gaccggtacg gagattccga cggggagccg atttacgacg aggtggcgga cgaccaaacc  24420
gacgtattgt acgccaagat acaacacccg cggcacctgc ccgacgacga gcccatctat  24480
gacaccgttg gggggtacga ccccgagccc gccgaggacc ccgtgtacag caccgtccgc  24540
cgttggtagc tgtttggttc cgttttaata aaccgtttgt gtttaacccg accgtggtgt  24600
atgtctggtg tgtggcgtcc gatcccgtta ctatcaccgt cccccccct caaccccggc  24660
gattgtgggt tttttaaaaa cgacacgcgt gcgaccgtat acagaacatt attttggttt  24720
ttattcgcta tcggacatgg ggggtggaaa ctgggtggcg gggcaggcgc ctccgggggt  24780
ccgccggtga gtgtggcgcg aggggggggtc cgacgaacgc aggcgcggtc tccccggggc  24840
```

-continued

```
ccgcgtaacc acgcgcatat ccgggggcac gtagaaatta ccttcctctt cggactcgat  24900
atccacgacg tcaaagtcgt gggcggtcag cgagacgacc tccccgtcgt cggtgatgag  24960
gacgttgttt cggcagcagc agggccgggc cccggagaac gagaggccca tagctcggcg  25020
agcgtgtcgt cgaacgccag gcggctgctt cgctggatgg ccttatagat ctccggatcg  25080
atgcggacgg gggtaatgat cagggcgatc ggaacggcct ggttcgggag aatggacgcc  25140
ttgctgggtc ctgcggcccc gagagccccg gcgccgtcct ccaggcggaa cgttacgccc  25200
tcctccgcgc tggtgcggtg cctgccgata aacgtcacca gatgcgggtg gggggggcag  25260
tcggggaagt ggctgtcgag cacgtagccc tgcaccaaga tctgcttaaa gttcgggtgg  25320
cgggggttcg cgaagacggg ctcgcggcgg accagatccc cggagctcca ggacacgggg  25380
gagatggtgt ggcgtccgag gtcgggggcg ccaaacagaa gcacctccga gacaacgccg  25440
ctatttaact ccaccaaggc ccgatccgcg gcggagcacc gccttttttc gcccgaggcg  25500
tgggcctctg accaggcctg gtcttgcgtg acgagagcct cctccgggcc ggggacgcgc  25560
ccgggcgcga agtatcgcac gctgggcttc gggatcgacc ggataaatgc ccggaacgcc  25620
tccggggacc ggtgtgccat caagtcctcg tacgcggagg ccgtggggtc gctggggtcc  25680
atggggtcga aagcgtactt ggcccggcat ttgacctcgt aaaaggccag gggggtcttg  25740
gggactgggg ccaggtagcc gtgaatgtcc cgaggacaga cgagaatatc cagggacgcc  25800
ccgaccatcc ccgtgtgacc gtccatgagg accccacacg tatgcacgtt ctcttcggcg  25860
aggtcgctgg gttcgtggaa gataaagcgc cgcgtgtcgg cgccggcctc gccgccgtcg  25920
tccgcgcggc ccacgcagta gcgaaacagc aggcttcggg ccgtcggctc gttcacccgc  25980
ccgaacatca ccgccgaaga ctgtacatcc ggtcgcaggc tggcgttgtg cttcagccac  26040
tggggcgaga aacacggacc ctgggggccc cagcggaggg tggatgcggt cgtgaggccc  26100
cgccggagca gggcccatag ctggcagtcg gcctggtttt gcgtggccgc ctcgtaaaac  26160
cccatgaggg gccggggcgc cacggcgtcc gcggcggccg ggggggcgcg gcgcgtcagg  26220
cgccataggt gccggccgag tccgcggtcc accataccg cctcctcgag gaccacggcc  26280
agggaacaca gataatccag gcgggcccag aggggaccga tggccagagg ggcgcggacg  26340
ccgcgcagca acccgcgcag gtggcgctcg aacgtctcgg ctagtatatg ggagggcagc  26400
gcgttgggga tcaccgacgc cgaccacata gagtcaaggt ccggggagtc gggatcggcg  26460
tccgggtcgc gggcgtgggt gcccccagga gatagcggaa tgtccggggt cggaggcccg  26520
gaggcgtcag aaagtgccgg cgacgcggcc cggggctttt cgtctgcggt gtcggtggcg  26580
tgctgatcac gtgggggggtt atcgggcgaa tgggagctcg ggtccacagc tgacgtcgtc  26640
tggggtgggg ggggcagggg acggaaggtg gttgtcagcg gaagactgtt agggcggggg  26700
cgcttggggg ggctgtcggg gccacgaggg gtgtcctcgg ccagggccca gggacgctta  26760
gtcacggtgc gtcccggcgg acatgctggg cctaccgtgg actccatttc cgagacgacg  26820
tggggggagc ggtggttgag cgcgccgccg ggtgaacgct gattctcacg acagcgcgtg  26880
ccgcgcgcac gggttggtgt gatacaggcg ggacaccagc accaggagag gcttaagctc  26940
gggaggcagc gccaccgacg acagtatcgc cttgtgtgtg tgctggtaat ttatacaccg  27000
atccgtaaac gcgcgccgaa tcttgggatt gcggaggtgg cgccggatgc cctctgggac  27060
gtcatacgcc aggccgtggg tgttggtctc ggccgagttg acaaacaggg ctgggtgcag  27120
cacgcagcga taggcgagca gggccagggc gaagtccggc gacagctggt tgttgaaata  27180
ctggtaaccg ggaaaccggg tcacgggtac gcccaggctc ggggcgacgt acacgctaac  27240
```

caccaactcc agcagcgtct ggcccagggc gtacaggtca accgctagcc cgacgtcgtg 27300
cttcaggcgg tggttggtaa attcggcccg ttcgttgtta aggtatttca ccaacagctc 27360
cgggggctgg ttatacccgt gacccaccag ggtgtgaaag ttggctgtgg ttagggcggt 27420
gggcatgcca aacatccggg gggacttgag gtccggctcc tggaggcaaa actgcccccg 27480
ggcgatcgtg gagttggagt tgagggtgac gaggctaaag tcggcgagga cggcccgccg 27540
gagcgagacg gcgtccgacc gcagcatgac gaggatgttg gcgcacttga tatccaggtg 27600
gctgatcccg caggtggtgt ttaaaaacac aacggcacgg gccagctccg tgaagcactg 27660
gtggagggcc gtcgagaccg aggggtttgt tgtgcgcagg gacgccagtt ggccgatata 27720
cttaccgagg tccatgtcgt acgcggggaa cactatctgt cgttgttgca gcgagaaccc 27780
gaggggcgcg atgaagccgc ggatgttgtg ggtgcggccg gcgcgtagag cgcactcccc 27840
gaccaacagg gtcgcgatga gctcaacggc aaaccactcc ttttccttta tggtcttaac 27900
ggcaagctta tgttcgcgaa tcagttggac ttcgccgtat cccccagacc ccccgaagct 27960
tcgggccccg gggatctcga gggtcgtgta gtgtagggcg gggttgatgg cgaacacggg 28020
gctgcatagc ttgcggatgc gcgtgagggt gaggatgtgc gagggggacg agggggggtgc 28080
ggttaacgcc gcctgggatc tgcgcagggg cgggcggttc agtttggccg ccgtaccggg 28140
cgcctcgggg gacgcgcggc gatgagacga gcggctcatt cgccatcggg atagtcccgc 28200
gcgaagccgc tcgcggaggc cggatcggtg gcggcacccg tgggaggagc gggagacggc 28260
ggcgttctgg agagaggggc cgctggggcg cccggaggcc ccatgggggt tggagtgtat 28320
gtaggatgcg agccaatcct tgaaggaccg ttggcgtgca ccttggggggc tgaggttagc 28380
tgccacatga ccagcaggtc gctgtctgcg ggactcatcc atccttcggc caggtcgccg 28440
tctccccaca gagaagcgtt ggtcgctgcc tcctcgagtt gctcctcctg gtccgcaaga 28500
cgatcgtcca cggcgtccag gcgctcacca agcgccggat cgaggtaccg tcggtgtgcg 28560
gttagaaagt cacgacgcgc cgcttgctcc tccacgcgaa ttttaacaca ggtcgcgcgc 28620
tgtcgcatca tctctaagcg cgcgcgggac tttagccgcg cctccaattc caagtgggcc 28680
gcctttgcag ccataaaggc gccaacaaac cgaggatctt gggtgctgac gccctcccgg 28740
tgcagctgca gggtctggtc cttgtaaatc tcggctcgga ggtgcgtctc ggccaggcgt 28800
cggcgcaggg ccgcgtgggc ggcatctcgg tccattccgc caccctgcgg gcgacccggg 28860
ggtgctctga tagtctcgcg tgcccaaggc ccgtgatcgg ggtacttcgc cgccgcgacc 28920
cgccacccgg tgtgcgcgat gtttggtcag cagctggcgt ccgacgtcca gcagtacctg 28980
gagcgcctcg agaaacagag gcaacttaag gtgggcgcgg acgaggcgtc ggcgggcctc 29040
acaatgggcg gcgatgccct acgagtgccc tttttagatt tcgcgaccgc gacccccaag 29100
cgccaccaga ccgtggtccc gggcgtcggg acgctccacg actgctgcga gcactcgccg 29160
ctcttctcgg ccgtggcgcg gcggctgctg tttaatagcc tggtgccggc gcaactaaag 29220
gggcgtgatt tcgggggcga ccacacggcc aagctggaat tcctggcccc cgagttggta 29280
cgggcggtgg cgcgactgcg gtttaaggag tgcgcgccgg cggacgtggt gcctcagcgt 29340
aacgcctact atagcgttct gaacacgttt caggccctcc accgctccga agcctttcgc 29400
cagctggtgc actttgtgcg ggactttgcc cagctgctta aaacctcctt ccgggcctcc 29460
agcctcacgg agaccacggg cccccccaaa aaacgggcca aggtggacgt ggccacccac 29520
ggccggacgt acggcacgct ggagctgttc caaaaaatga tccttatgca cgccacctac 29580

-continued

```
tttctggccg ccgtgctcct cggggaccac gcggagcagg tcaacacgtt cctgcgtctc  29640
gtgtttgaga tccccctgtt tagcgacgcg gccgtgcgcc acttccgcca gcgcgccacc  29700
gtgtttctcg tcccccggcg ccacggcaag acctggtttc tggtgcccct catcgcgctg  29760
tcgctggcct cctttcgggg gatcaagatc ggctacacgg cgcacatccg caaggcgacc  29820
gagccggtgt ttgaggagat cgacgcctgc ctgcggggct ggttcggttc ggcccgagtg  29880
gaccacgtta aaggggaaac catctccttc tcgtttccgg acgggtcgcg cagtaccatc  29940
gtgtttgcct ccagccacaa cacaaacgta agtcctcttt tctttcgcat ggctctccca  30000
aggggccccg ggtcgacccg acccacaccc acccacccac atacacacac aaccagacgc  30060
gggaggaaag tctgccccgt gggcactgat ttttattcgg gatcgcttga ggaggcccgg  30120
gcaacggccc gggcaacggt ggggcaactc gtagcaaata ggcgactgat gtacgaagag  30180
aagacacaca ggcgccaccc ggcgctggtc ggggggatgt tgtccgcgcc gcaccgtccc  30240
ccgacgacct cttgcagacg gtccgtgatg caaggacggc ggggggcctg cagcagggtg  30300
accgtatcca cgggatggcc aaagagaagc ggacacaggc tagcatcccc ctggaccgcc  30360
agggtacact gggccatctt ggcccacaga cacggggcga cgcagggaca ggactccgtt  30420
acgacggagg agagccacag tgcgttggcg gaatcgatgt ggggcggcgg ggcgcaggac  30480
tcgcagcccc ccgggtggtt agtgatcctg gccaggagcc atcccagatg gcgggccctg  30540
cttcccggtg gacagagcga ccccaggtcg ctgtccatgg cccagcagta gatctggccg  30600
ctggggaggt gccaccaggc ccccgggccc aaggcgcagc acgcgcccgg ctccgggggg  30660
gtcttcgcgg ggaccagata cgcgccatcc agctcgccga ccactggctc ctccgcgagc  30720
tgttcggtgg ttgggtcggg ggtttcctcc ggggggggtgg ccgcccgtat gcgggcgaac  30780
gtgagggtgc acaggagcgg ggtcaggggg tgcgtcacgc tccggaggtg gacgatcgcg  30840
cagtagcggc gctcgcggtt aaagaaaaag agggcaaaga aggtgttcgg gggcaaccgc  30900
agcgccttgg ggcgcgtcag atacagaaaa atctcgcaga agagggcgcg cccggggtct  30960
gggttaggaa gggccacctg acacagaggc tcggtgagga ccgttagaca ccgaaagatc  31020
ttgagccgct cgtccgcccg aacgacgcgc cacacaaaga cggagttgac aatgcgcgcg  31080
atagagtcga cgtccgtccc caggtcgtcg actctgtcgc gcgtgccgcg agctccggcc  31140
cgggaatccg gccggggcaa ggtcccccggg ggaccaggcg gcgccagggg ccgccggggt  31200
cccagctgcg ccatgccggg ggcgggggga gggcaaaccc cagaggcggg ggccaacggc  31260
gcggggagga gtggatgggc gaggtggccg ggggaaggcg cccgctagcg agaacggccg  31320
ttcccggacg acaccttgcg acaaaaccta aggacagcgg cccgcgcgac ggggtccgag  31380
aggctaaggt aggccgcgat gttaatggtg aacgcaaagc cgccgggaaa gacaactatg  31440
ccacagaggc ggcgattaaa ccccaggcag aggtaggcgt agctttcccc gggcaggtat  31500
tgctcgcaga ccctgcgtgg ggctgtggag gggacggcct ccatgaagcg acatttactc  31560
tgctcgcgtt tactgacgtc accatccatc gccacggcga ttggacgatt gttaagccgc  31620
agcgtgtctc cgcttgtgct gtagtagtca aaaacgtaat ggccgtcgga gtcggcaaag  31680
cgggccggga ggtcgtcgcc gagcgggacg acccgccgcc cccgaccgcc ccgtcccccc  31740
aggtgtgcca ggacggccag ggcatacgcg gtgtgaaaaa aggcgtcggg ggcggtcccc  31800
tcgacggcgc gcatcaggtt ctcgaggaga atggggaagc gcctggtcac ctcccccagc  31860
cacgcgcgtt ggtcggggcc aaagtcatag cgcaggcgct gtgagattcg cgggccgccc  31920
tgaagcgcgg cccggatggc ctggcccagg gcccggaggc acgccagatg tatgcgcgcg  31980
```

gtaaaggcga cctcggcggc gatgtcaaag ggcggcagga cggggcgcgg gtggcgcagg 32040
ggcacctcga gcgcgggaaa gcggagcagc agctccgcct gcccagcggg agacagctgg 32100
tgggggcgca cgacgcgttc tgcggcgcag gcctcggtca gggccgtggc cagcgccgag 32160
gacagcagcg gagggcgggc gcgtcgcccg ccccacgcca ctgagttctc gtaggagacg 32220
acgacgaagc gctgcttggt tccgtagtgg tggcgcagga ccacggagat agaacgacgg 32280
ctccacagcc agtccggccg gtcgccgccg gccagggctt cccatccgcg atccaaccac 32340
tcgaccagcg accgcggctt tgtggtacca ggggtaaggg ttagaacgtc gttcaggatg 32400
tcctcgcccc cggcccgtg gggcgctggg gccacaaagc ggccccgcc gggggctcc 32460
agacccgcca gcaccgcatc tgcgtcagcc gcccccatgg cgccccgct gacggcctgg 32520
tgaaccaggg cgccctggcg gagccccgat gcaacgccac aggccgcacg cccggtccga 32580
gcgcggaccg ggtggcggcg ggtgacgtcc tgcactgccc gctgaaccaa cgcgaggatc 32640
tcctcgttct cctgtgcgat ggacacgtcc tgggccgcgg tcgtgtcgcc gccgggggcc 32700
gtcagctgct cctccgggga gatgggggg tcggacgccc cgacgatggg cgggtctgcg 32760
ggcgccccg cgtggggccg ggccaagggc tgcggacgcg gggacgcgct ttcccccaga 32820
cccatggaca ggtgggccgc ggcctccttc gcggccggcg gggcggcggc gccaagcaga 32880
gcgacgtagc ggcacaaatg ccgacagacg cgcatgatgc gcgtgctgtc ggccgcgtag 32940
cgcgtgttgg gggggacgag ctcgtcgtaa ctaaacagaa tcacgcgggc acagctcgcc 33000
cccgagcccc acgcgaggcg cagcgccgcc acggcgtacg ggtcatagac gccctgcgcg 33060
tcacacacca cgggcaggga gacgaacaac cccccggcgc tggacgcacg cggaaggagg 33120
ccagggtgtg ccggcacgac gggggccaga agctcccca ccgcatccgc gggcacgtag 33180
gcggcaaacg ccgtgcacca cggggtacag tcgccggtgg catgagcccg agtctggatt 33240
tcgacctgga agtttgcggc cgtcccgagt ccggggcggc cgcgcatcag ggcggccaga 33300
gggattcccg cggccgccag gcactcgctg gatatgatga cgtgaaccaa agacgagggc 33360
cgacccgggc cgtggccgag atcgtactgg acctcgttgg ccaagtgcgc gttcatggtt 33420
cggggtgggt gtgggtgtgt aggcgatgcg ggtcccccga gtccgcggga agggcgtggg 33480
tttggcgcgc gtatgcgtat tcgccaacgg aggcgtgcgt gcttatgcgc ggcgcgtttc 33540
ttctgtctcc agggaatccg aggccaggac tttaacctgc tctttgtcga cgaggccaac 33600
tttattcgcc cggatgcggt ccagacgatt atgggctttc tcaaccaggc caactgcaag 33660
attatcttcg tgtcgtccac caacaccggg aaggccagta cgagcttttt gtacaacctc 33720
cgcggggccg ccgacgagct tctcaacgtg gtgacctata tatgcgatga tcacatgccg 33780
agggtggtga cgcacacaaa cgccacggcc tgttcttgtt atatcctcaa caagcccgtt 33840
ttcatcacga tggacggggc ggttcgccgg accgccgatt tgtttctggc cgattccttc 33900
atgcaggaga tcatcggggg ccaggccagg gagaccggcg acgaccggcc cgttctgacc 33960
aagtctgcgg gggagcggtt tctgttgtac cgcccctcga ccaccaccaa cagcggcctc 34020
atggcccccg atttgtacgt gtacgtggat ccccgcgttca cggccaacac ccgagcctcc 34080
gggaccggcg tcgctgtcgt cgggcggtac cgcgacgatt atatcatctt tgccctggag 34140
cactttttc tccgcgcgct cacgggctcg gcccccgccg acatcgcccg ctgcgtcgtc 34200
cacagtctga cgcaggtcct ggccctgcat cccggggcgt ttcgcggcgt ccgggtggcg 34260
gtcgagggaa atagcagcca ggactcggcc gtcgccatcg ccacgcacgt gcacacagag 34320

-continued

```
atgcaccgcc tactggcctc ggagggggcc gacgcgggct cgggccccga gcttctcttc  34380
taccactgcg agcctcccgg gagcgcggtg ctgtacccct ttttcctgct caacaaacag  34440
aagacgcccg cctttgaaca ctttattaaa aagtttaact ccgggggcgt catggcctcc  34500
caggagatcg tttccgcgac ggtgcgcctg cagaccgacc cggtcgagta tctgctcgag  34560
cagctgaata acctcaccga aaccgtctcc cccaacactg acgtccgtac gtattccgga  34620
aaacggaacg gcgcctcgga tgaccttatg gtcgccgtca ttatggccat ctaccttgcg  34680
gcccaggccg gacctccgca cacattcgct cccatcacac gcgtttcgtg agcgcccaat  34740
aaacacaccc aggtatgcta cgcacgacca cggtgtcgcc tgttaagggg ggggaagggg  34800
gtgttggcgg gaagcgtggg aacacggggg attctctcac gaccggcacc agtaccaccc  34860
ccctgtgaac acagaaaccc aacccaaatc ccataaacat acgacacaca ggcatatttt  34920
ggaatttctt gggtttttat ttatttaggt atgctggggt ttctccctgg atgcccaccc  34980
cccacccccc cccgtgggtc tagccgggcc ttagggatag cgtataacgg gggccatgtc  35040
tccggaccgc acaacggccg cgccgtcaaa ggtgcacacc cgaaccacgg gagccagggc  35100
caaggtgtct cctagttggc ccgcgtgggt cagccaggcg acgagcgcct cgtaaagcgg  35160
cagccttcgc tctccatcct gcaccagggc cggggcttcg ggtgaatga gctgggcggc  35220
ctcccgcgtg acactctgca tctgcaggag agcgttcacg tacccgtcct gggcacttag  35280
cgcaaagagc cgggggatta gcgtaaggat gatggtggtt ccctccgtga tcgagtaaac  35340
catgttaagg accagcgatc gcagctcggc gtttacggga ccgagttgtt ggacgtccgc  35400
cagcagcgag aggcgactcc cgttgtagta cagcacgttg aggtctggca gccctccggg  35460
gtttctgggg ctggggttca ggtcccggat gcccctggcc acgagccgcg ccacgatttc  35520
gcgcgccagg ggcgatggaa gcggaacggg aaaccgcaac gtgaggtcca gcgaatccag  35580
gcgcacgtcc gtcgcttggc cctcgaacac gggcgggacg aggctgatgg ggtccccgtt  35640
acagagatct acgggggagg tgttgcgaag gttaacggtg ccggcgtggg tgaggcccac  35700
gtccaggggg caggcgacga ttcgcgtggg aagcacccgg gtgatgaccg cggggaagcg  35760
ccttcggtac gccagcaaca accccaacgt gtcgggactg acgcctccgg agacgaagga  35820
ttcgtgcgcc acgtcggcca gcgtcagttg ccggcggatg gtcggcagga ataccacccg  35880
cccttcgcag cgctgcagcg ccgccgcatc ggggcgcgag atgcccgagg gtatcgcgat  35940
gtcagtttca aagccgtccg ccagcatggc gccgatccac gcggcaggga gtgcagtggt  36000
ggttcgggtg gcgggaggag cgcggtgggg gtcagcggcg tagcagagac gggcgaccaa  36060
cctcgcatag gacgggggt gggtcttagg gggttgggag gcgacaggga ccccagagca  36120
tgcgcgggga ggtctgtcgg gcccagacgc accgagagcg aatccgtcca cggagtcccg  36180
gtctgggttt tatggggccc ggccctcgga atcgcggctt gtcggcgggg acaaaggggg  36240
cggggctagg gggcttgcgg aaacagaaga cgcgtgggat aaaagaatcg cactacccca  36300
aggaagggcg gggcggttta ttacagagcc agtcccttga gcggggatgc gtcatagacg  36360
agatactgcg cgaagtgggt ctcccgcgcg tgggcttccc cgttgcgggc gctgcggagg  36420
agggcggggt cgctggcgca ggtgagcggg taggcctcct gaaacaggcc acacgggtcc  36480
tccacgagtt cgcggcaccc cggggggcgc ttaaactgta cgtcgctggc ggcggtggcc  36540
gtggacaccg ccgaacccgt ctccacgatc aggcgctcca ggcagcgatg tttggcggcg  36600
atgtcggccg acgtaaagaa cttaaagcag gggctgagca ccggcgaggc cccgttgagg  36660
tggtaggccc cgttatagag caggtccccg tacgaaaatc gctgcgacgc ccacgggttg  36720
```

```
gccgtggccg caaaggcccg ggacgggtcg ctctggccgt ggtcgtacat gagggcggtg  36780
acatccccct ccttgtcccc cgcgtaaacg cccccggcgg cgcgtccccg ggggttgcag  36840
ggccggcgga agtagttgac gtcggtcgac acgggggtgg cgataaactc acacacggcg  36900
tcctggccgt ggtccatccc tgcgcgccgc ggcacctggg cgcacccgaa cacggggacg  36960
ggctgggccg gccccaggcg gtttcccgcc acgaccgcgt tccgcaggta cacggctgcc  37020
gcgttgtcca ggagaggggg agccccgcgg cccaggtaaa agttttgggg aaggttgccc  37080
atgtcggtga cggggttgcg gacggttgcc gtggccacga cggcggtgta gcccacgccc  37140
aggtccacgt tcccgcgcgg ctgggtgagc gtgaagttta ccccccgcc agtttcgtgc  37200
cgggccacct ggagctggcc caggaagtac gcctccgacg cgcgctccga gaacagcatg  37260
ttctcagtca caaagcggtc ctgtcggacg acggtgaacc caaacccggg atggaggccc  37320
gtcttgagct gatgatgcaa ggccacggga ctgatcttga agtaccccgc catgagcgcg  37380
taggtcagcg cgttctcccc ggccgcgctc tcgcggacgt gctgcacgac gggctgtcgg  37440
atcgacgaaa agtagttggc ccccagagcc ggggggacca gggggacctg ccgcgacagg  37500
tcgcgcaggg ccggggggaa attgggcgcg ttcgccacgt ggtcggcccc ggcgaacagc  37560
gcgttgacgg gaagggggta aaaatagtcg ccattttgga tggtatggtc cagatgctgg  37620
ggggccatca gcaggattcc ggcgtgcaac gccccgtcga atatgcgcat gttggtggtg  37680
gacgcggtgt tggcgcccgc gtcgggcgcc gccgagcaga gcagcgccgt tgtgcgttcg  37740
gccatgttgt gggccagcac ctgcagcgtg agcatggcgg gcccgtccac taccacgcgc  37800
ccgttgtgaa acatggcgtt gaccgtgttg gccaccagat tggccgggtg cagggggtgc  37860
gcggggtccg tcacggggtc gctggggcac tcctcgccgg gggcgatctc cgggaccacc  37920
atgttctgca gggtggcgta tacgcggtcg aagcgaaccc ccgcggtgca gcagcggccc  37980
cgcgagaagg cgggcaccat cacgtagtag taaatcttgt ggtgcacggt ccagtccgcc  38040
ccccggtgcg gccggtcatc cgcggcgtcc gcggctcggg cctgggtgtt gtgcagcagc  38100
tggccgtcgt tgcggttgaa gtccgcggtc gccacgttac atgccgccgc gtacacgggg  38160
tcgtggcccc ccgcgctaac ccggcagtcg cgatggcggt ccagggccgc gcgccgcatc  38220
agggcgtcac agtcccacac gaggggtggc agcagcgccg ggtctcgcat taggtgattc  38280
agctcggctt gcgcctgccc gcccagctcc gggccggtca gggtaaagtc atcaaccagc  38340
tgggccaggg cctcgacgtg cgccaccagg tcccggtaca cggccatgca ctcctcggga  38400
aggtctcccc cgaggtaggt cacgacgtac gagaccagcg agtagtcgtt cacgaacgcc  38460
gcgcaccgcg tgttgttcca gtagctggtg atgcactgga caacgagccg ggccagggcg  38520
cagaagacgt gctcgctgcc gtgtatggcg gcctgcagca ggtaaaacac cgccgggtag  38580
ttgcggtcgt cgaacgcccc gcgaacggcg gcgatggtgg cgggggccat ggcgtggcgt  38640
cccacccccca gctccaggcc ccgggcgtcc cggaacgccg ccggacatag cgccaggggc  38700
aagttgccgt tcaccacgcg ccaggtggcc tggatctccc ccgggccggc cgggggaacg  38760
tcccccccg gcagctccac gtcggccacc cccacgaaga agtcgaacgc ggggtgcagc  38820
tcaagagcca ggttggcgtt gtcgggctgc ataaactgct ccggggtcat ctggccttcc  38880
gcgacccatc ggacccgccc gtgggccagg cgctgccccc aggcgttcaa aaacagctgc  38940
tgcatgtctg cggcggggcc ggccggggcc gccacgtacg ccccgtacgg attggcggct  39000
tcgacggggt cgcggttaag gcccccgacc gccgcgtcaa cgttcatcag cgaagggtgg  39060
```

-continued

```
cacacggtcc cgatcgcgtg ttccagagac aggcgcagca cctggcggtc cttcccccaa  39120
aaaaacagct ggcggggcgg gaaggcgcgg ggatccgggt ggccgggggc ggggactagg  39180
tccccggcgt gcgcggcaaa ccgttccatg accggattga acaggcccag gggcaggacg  39240
aacgtcaggt ccatggcgcc caccaggggg tagggaacgt tggtggcggc gtagatgcgc  39300
ttctccaggg cctccagaaa gaccagcttc tcgccgatgg acaccagatc cgcgcgcacg  39360
cgcgtcgtct ggggggcgct ctcgagctcg tccagcgtct gccggttcag gtcgagctgc  39420
tcctcctgca tctccagcag gtggcggccc acgtcgtcca gacttcgcac ggccttgccc  39480
atcacgagcg ccgtgaccag gttggccccg ttcaggacca tctcgccgta cgtcaccggc  39540
acgtcggctt cggtgtcctc cactttcagg aaggactgca ggaggcgctg tttgatcggg  39600
gctgtggtga ctagcacccc gtcgaccggc cgcccgcgcg tgtcggcatg cgtcagacgg  39660
ggcacggcca cggagggctg cgtggccgtg gtgaggtcca cgagccaggc ctcgacggcc  39720
tcccggcggt ggcccgcctt gcccaggaaa aagctcgtct cgcagaagct tcgctttagc  39780
tcggcgacca gggtcgcccg ggccaccctg gtggccaggc ggccgttgtc caggtatcgt  39840
tgcatcggca acaacaaagc caggggcggc gccttttcca gcagcacgtg cagcatctgg  39900
tcggccgtgc cgcgctcaaa cgccccgagg acggcctgga cgttgcgagc gagctgttgg  39960
atggcgcgca actggcgatg cgcgctgata cccgtcccgt ccagggcctc cccgtgagc  40020
agggcgatgg cctcggtggc caggctgaag gcggcgttca gggcccggcg gtcgataatc  40080
ttggtcatgt aattgtgtgt gggttgctcg atggggtgcg ggccgtcgcg ggcaatcagc  40140
ggctggtgga cctcgaactg tacgcgcccc tcgttcatgt aggccagctc cggaaacttg  40200
gtacacacgc acgccaccga caacccgagc tccagaaagc gcacgagcga cagggtgttg  40260
caatacgacc ccagcagggc gtcgaactcg acgtcgtaca ggctgtttgc atcggagcgc  40320
acgcgggaaa aaaaatcgaa caggcgtcga tgcgacgcca cctcgatcgt gctaaggagg  40380
gacccggtcg gcaccatggc cgtggcatac cggtatcccg gagggtcgcg gttgggagcg  40440
gccatggggt cgcgtggaga tcggctgtct ctagcgatat tggcccgggg aggctaagat  40500
ccaccccaac gcccggccac ccgtgtacgt gcccgacggc ccaaggtcca ccgaaagaca  40560
cgacggaccc ggacccaaag aggcggggga tgctgtgtga gaggccgggt gtcggtcggg  40620
ggggaaaggc accgggagaa ggctgcggcc tcgttccagg agaacccagt gtccccaaca  40680
gacccgggga cgtgggatcc ccggccttat ataccccccc ccgccccacc cccgttagaa  40740
cgcgacgggt gcattcaaga tggccctggt ccaaaagcgt gccaggaaga aattggcaga  40800
ggcggcaaag ctgtccgccg ccgccaccca catcgaggcc ccggccgcac aggctatccc  40860
cagggcccgt gtgcgcaggg gatcggtggg tggcagcatt tggttggtgg cgataaagtg  40920
gaaaagcccg tccggactga aggtctcgtg ggcggcggcg aacaaggcac acagggccgt  40980
gcctcccaaa aacacggaca tcccccaaaa cacgggcgcc gacaacggca gacgatccct  41040
cttgatgtta acgtacagga ggagcgcccg caccgcccac gtaacgtagt agccgacgat  41100
ggcggccagg atacaggccg gcgccaccac ccttccggtc agcccgtaat acatgcccgc  41160
tgccaccatc tccaacggct tcaggaccaa aaacgaccaa aggaacagaa tcacgcgctt  41220
tgaaaagacc ggctgggtat ggggcggaag acgcgagtat gccgaactga caaaaaaatc  41280
agaggtgccg tacgaggaca atgaaaactg ttcctccagc ggcagttctc cctcctccat  41340
ggtcatgggg tgtgcggtgg aggtggggag accgaaaccg caaagggtcg cttacgtcag  41400
caggatcccg agatcaaaga cacccgggtt cttgcacaaa caccacccgg gttgcatccg  41460
```

```
cggaggcgag tgttttgata aggccgttcc gcgccttgat ataacctttg atgttgacca  41520
caaaacccgg aatttacgcc tacgccccaa tgcccacgca agatgaggta ggtaaccccc  41580
ccgtgggtgt gacgttgcgt ttagttcatt ggaggccaag gggaaaaatg gggtggggag  41640
gaaacggaaa acccagtagg ccgtgtcggg aacacgcccg gggttgtcct caaaaggcag  41700
ggtccatact acggaagccg tcgttgtatt cgagacctgc ctgtgcgacg cacgtcgggg  41760
ttgcctgtgt ccggttcggc ccccaccgcg tgcggcacgc acgaggacga gtccgcgtgc  41820
tttattggcg ttccaagcgt tgccctccag tttctgttgt cggtgttccc ccatacccac  41880
gcccacatcc accgtagggg gcctctgggc cgtgttacgt cgccgcccgc gatggagctt  41940
agctacgcca ccaccatgca ctaccgggac gttgtgtttt acgtcacaac ggaccgaaac  42000
cgggcctact ttgtgtgcgg ggggtgtgtt tattccgtgg ggcggccgtg tgcctcgcag  42060
cccggggaga ttgccaagtt tggtctggtc gttcgaggga caggcccaga cgaccgcgtg  42120
gtcgccaact atgtacgaag cgaactccga caacgcggcc tgcaggacgt gcgtcccatt  42180
ggggaggacg aggtgtttct ggacagcgtg tgtcttctaa acccgaacgt gagctccgag  42240
ctggatgtga ttaacacgaa cgacgtggaa gtgctggacg aatgtctggc cgagtactgc  42300
acctcgctgc gaaccagccc gggtgtgcta atatccgggc tgcgcgtgcg ggcgcaagac  42360
agaatcatcg agttgtttga acacccaacg atagtcaacg tttcctcgca ctttgtgtat  42420
accccgtccc catacgtgtt cgccctggcc caggcgcacc tcccccggct cccgagctcg  42480
ctggaggccc tggtgagcgg cctgtttgac ggcatccccg ccccacgcca gccacttgac  42540
gcccacaacc cgcgcacgga tgtggttatc acgggccgcc gcgccccacg acccatcgcc  42600
gggtcggggg cggggtcggg gggcgcgggc gccaagcggg ccaccgtcag cgagttcgtg  42660
caagtcaaac acattgaccg cgtgggcccc gctggcgttt cgccggcgcc tccgccaaac  42720
aacaccgact cgagttccct ggtgcccggg gcccaggatt ccgcccccgcc cggccccacg  42780
ctaagggagc tgtggtgggt gttttatgcc gcagaccggg cgctggagga gccccgcgcc  42840
gactctggcc tcacccgcga ggaggtacgt gccgtacgtg ggttccggga gcaggcgtgg  42900
aaactgtttg gctccgcggg ggccccgcgg gcgtttatcg gggccgcgtt gggcctgagc  42960
cccctccaaa agctggccgt ttactactat atcatccacc gagagaggcg cctgtccccc  43020
ttccccgcgc tagtccggct cgtaggccgg tacacacagc gccacggcct gtacgtccct  43080
cggcccgacg acccagtctt ggccgatgcc atcaacgggc tggttcgcga cgcgctggcg  43140
gccggaacca cagccgagca gctcctcatg ttcgaccttc tcccccccaaa ggacgtgccg  43200
gtgggaagcg acgtgcaggc cgacagcacc gctctgctgc gctttataga atcgcaacgt  43260
ctcgccgtcc ccgggggggt gatctccccc gagcacgtcg cgtaccttgg tgcgttcctg  43320
agcgtgctgt acgctggccg cgggcgcatg tccgcagcaa cgcacaccgc gcggctgaca  43380
ggggtgacct ccctggtgct agcggtgggt gacgtggacc gtctttccgc gtttgaccgc  43440
ggagcggcgg gcgcggccag ccgcacgcgg gccgccgggt acctggatgt gcttctgacc  43500
gttcgtctcg ctcgctccaa acacggacag tctgtgtaac agaccccaat aaacgtatgt  43560
cgctaccaca cccttgtgtg tcaatggacg cctctccggg ggggaaggga aaacaaagag  43620
gggctggggg agcggcacca ctggggcctg aacaaacaaa caaaccacag acacggttac  43680
agtttattcg gtcgggcgga taaacggccg aagccacgcc ccctttattc gcgtctccaa  43740
aaaaacggga cacttgtccg gagaaccttt aggatgccag ccagggcggc ggtaatcata  43800
```

-continued

```
accacgccca gcgcagaggc ggccagaaac ccgggcgcaa ttgcggccac gggctgcgtg  43860
tcaaaggcta gcaaatgaat gacggttccg tttggaaata gcaacaaggc cgtggacggc  43920
acgtcgctcg aaaacacgct cggggcgccc tccgtcggcc cggcggcgat ttgctgctgt  43980
gtgttgtccg tatccaccag caacacagac atgacctccc cggctggggt gtagcgcata  44040
aacacggccc ccacgagccc caggtcgcgc tggttttggg tgcgcaccag ccgcttggac  44100
tcgatatccc gggtggagcc ttcgcatgtc gcggtgaggt aggttaggaa cagtgggcgt  44160
cggacgtcga cgccggtgag cttgtagccg atcccccggg gcagagggga gtgggtgacg  44220
acgtagctgg cgttgtgggt gatgggtacc aggatccgtg gctcgacgtt ggcagactgc  44280
cccccgcacc gatgtgaggc ctcagggacg aaggcgcgga tcagggcgtt gtagtgtgcc  44340
cagcgcgtca gggtcgaggc gaggccgtgg gtctgctggg ccaggacttc gaccggggtc  44400
tcggatcggg tggcttgagc cagcgcgtcc aggataaaca cgctctcgtc tagatcaaag  44460
cgcagggagg ccgcgcatgg cgaaaagtgg tccggaagcc aaaagagggt tttctggtgg  44520
tcggcccggg ccagcgcggt ccggaggtcg gcgttggtcg ctgcggcgac gtcggacgta  44580
cacagggccg atgctatcag aaggctccgg cgggcgcgtt cccgctgcac cgccgagggg  44640
acgcccgcca agaacggctg ccggaggaca gccgaggcgt aaaatagcgc ccggtggacg  44700
accggggtgg tcagcacgcg gccccctaga aactcggcat acagggcgtc gatgagatgg  44760
gctgcgctgg gcgccactgc gtcgtacgcc gaggggctat ccagcacgaa ggccagctga  44820
tagcccagcg cgtgtaatgc caagctctgt tcgcgctcca gaatctcggc caccaggtgc  44880
tggagccgag cctctagctg caggcgggcc gtgggatcca agactgacac attaaaaaac  44940
acagaatccg cggcacagcc cgcggccccg cgggcggcca acccggcaag cgcgcgcgag  45000
tgggccaaaa agcctagcag gtcggagagg cagaccgcgc cgtttgcgtg ggcggcgttc  45060
acgaaagcaa aacccgacgt cgcgagcagc cccgttaggc gccagaagag agggggggcgc  45120
gggccctgct cggcgcccgc gtcccccgag aaaaactccg cgtatgcccg cgacaggaac  45180
tgggcgtagt tcgtgccctc ctccgggtag ccgcccacgc ggcggagggc gtccagcgcg  45240
gagccgttgt cggcccgcgt cagggaccct aggacaaaga cccgataccg ggggccgccc  45300
gggggcccgg gaagagcccc cggggggttt tcgtccgcgg ggtccccgac ccgatctagc  45360
gtctggcccg cggggaccac catcacttcc accggagggc tgtcgtgcat ggatatcacg  45420
agccccatga attcccgccc gtagcgcgcg cgcaccagcg cggcatcgca cccgagcacc  45480
agctcccccg tcgtccagat gcccacgggc cacgtcgagg ccgacgggga gaaatacacg  45540
tacctacctg gggatctcaa caggccccgg gtggccaacc aggtcgtgga cgcgttgtgc  45600
aggtgcgtga tgtccagctc cgtcgtcggg tgccgccggg ccccaaccgg cggtcggggg  45660
ggcggtgtat cacgcggccc gcttgggtgg ctcgccgtcg ccacgttgtc tccccgcggg  45720
aacgtcaggg cctcggggtc agggacggcc gaaaacgtta cccaggcccg ggaacgcagc  45780
aacacggagg cgactggatt gtacaagaga cccttaaggg gggcgaccga gggggggaggc  45840
tgggcggtcg gctcgaccgt ggtgggggcg ggcaggctcg cgttcggggg ccggccgagc  45900
aggtaggtct tcgggatgta aagcagctgg ccggggtccc gcggaaactc ggccgtggtg  45960
accaatacaa aacaaaagcg ctcctcgtac cagcgaagaa ggggcagaga tgccgtagtc  46020
aggtttagtt cgtccggcgg cgccagaaat ccgcgcggtg gtttttgggg gtcgggggtg  46080
tttggcagcc acagacgccc ggtgttcgtg tcgcgccagt acatgcggtc catgcccagg  46140
ccatccaaaa accatgggtc tgtctgctca gtccagtcgt ggacctgacc ccacgcaacg  46200
```

cccaaaataa taacccccac gaaccataaa ccattcccca tgggggaccc cgtccctaac 46260
ccacggggcc cgtggctatg gcagggcttg ccgccccgac gttggctgcg agccctgggc 46320
cttcacccga acttgggggg tggggtgggg aaaaggaaga aacgcgggcg tattggcccc 46380
aatggggtct cggtggggta tcgacagagt gccagccctg ggaccgaacc ccgcgtttat 46440
gaacaaacga cccaacaccc gtgcgtttta ttctgtcttt ttattgccgt catagcgcgg 46500
gttccttccg gtattgtctc cttccgtgtt tcagttagcc tcccccatct cccgggcaaa 46560
cgtgcgcgcc aggtcgcaga tcgtcggtat ggagccgggg gtggtgacgt gggtctggac 46620
catcccggag gtaagttgca gcagggcgtc ccggcagccg gcgggcgatt ggtcgtaatc 46680
caggataaag acgtgcatgg gacggaggcg tttggccaag acgtccaagg cccaggcaaa 46740
cacgttgtac aggtcgccgt tgggggccag caactcgggg gcccgaaaca gggtaaataa 46800
cgtgtccccg atatggggtc gtgggcccgc gttgctctgg ggctcggcac cctggggcgg 46860
cacggccgtc cccgaaagct gtccccaatc ctcccgccac gacccgccgc cctgcagata 46920
ccgcaccgta ttggcaagca gcccgtaaac gcggcgaatc gcggccagca tagccaggtc 46980
aagccgctcg ccggggcgct ggcgtttggc caggcggtcg atgtgtctgt cctccggaag 47040
ggcccccaac acgatgtttg tgccgggcaa ggtcggcggg atgagggcca cgaacgccag 47100
cacggcctgg ggggtcatgc tgcccataag gtatcgcgcg gccgggtagc acaggagggc 47160
ggcgatggga tggcggtcga agatgagggt gagggccggg ggcggggcat gtgagctccc 47220
agcctccccc ccgatatgag gagccagaac ggcgtcggtc acggcataag gcatgcccat 47280
tgttatctgg gcgcttgtca ttaccaccgc cgcgtccccg gccgatatct caccctggtc 47340
gaggcggtgt tgtgtggtgt agatgttcgc gattgtctcg gaagcccccca gcacctgcca 47400
gtaagtcatc ggctcgggta cgtagacgat atcgtcgcgc gaacccaggg ccaccagcag 47460
ttgcgtggtg gtggttttcc ccatcccgtg aggaccctct atataaaccc gcagtagcgt 47520
gggcattttc tgctccaggc ggacttccgt ggcttcttgc tgccggcgag ggcgcaacgc 47580
cgtacgtcgg ttgctatggc cgcgagaacg cgcagcctgg tcgaacgcag acgcgtattg 47640
atggcagggg tacgaagcca tacgcgcttc tacaaggcgc ttgccgaaga ggtgcgggag 47700
tttcacgcca ccaagatctg cggcacgctg ttgacgctgt taagcgggtc gctgcagggt 47760
cgctcggtgt tcgaggccac acgcgtcacc ttaatatgcg aagtggacct gggaccgcgc 47820
cgccccgact gcatctgcgt gttcgaattc gtgaatgaca agacgctggg cggggtttgt 47880
gtcatcatag aactaaagac atgcaaatat atttcttccg gggacaccgc cagcaaacgc 47940
gagcaacggg ccacggggat gaagcagctg cgccactccc tgaagctcct gcagtccctc 48000
gcgcctccgg gtgacaagat agtgtacctg tgccccgtcc tggtgtttgt cgcccaacgg 48060
acgctccgcg tcagccgcgt gacccggctc gtcccgcaga aggtctccgg taatatcacc 48120
gcagtcgtgc ggatgctcca gagcctgtcc acgtatacgg tccccatgga gcctaggacc 48180
cagcgagccc gtcgccgccg cggcggcgcc gcccgggggt ctgcgagcag accgaaaagg 48240
tcacactctg gggcgcgcga cccgcccgag tcagcggccc gccagttacc acccgccgac 48300
caaacccccg cctccacgga gggcgggggg gtgcttaaga ggatcgcggc gctcttctgc 48360
gtgcccgtgg ccaccaagac caaaccccga gccgcctccg aatgagagtg tttcgttcct 48420
tccccctccc cccgcgtcag acaaacccta accaccgctt aagcggcccc cgcgaggtcc 48480
gaagactcat ttggatccgg cgggagccac ccgacaacag cccccgggtt ttcccacgcc 48540

-continued

```
agacgccggt ccgctgtgcc atcgcgcccc ctcatcccac cccccatctt gtccccaaat  48600
aaaacaaggt ctggtagtta ggacaacgac cgcagttctc gtgtgttatt ttcgctctcc  48660
gcctctcgca gatggacccg tactgcccat ttgacgctct ggacgtctgg gaacacaggc  48720
gcttcatagt cgccgattcc cgaaacttca tcacccccga gttcccccgg gacttttgga  48780
tgtcgcccgt ctttaacctc ccccgggaga cggcggcgga gcaggtggtc gtcctacagg  48840
cccagcgcac agcggctgcc gctgccctgg agaacgccgc catgcaggcg gccgagctcc  48900
ccgtcgatat cgagcgccgg ttacgcccga tcgaacggaa cgtgcacaag atcgcaggcg  48960
ccctggaggc gctggagacg gcggcggccg ccgccgaaga ggcggatgcc gcgcgcgggg  49020
atgagccggc gggtgggggc gacggggggg cgcccccgag tctggccgtc gcggagatgg  49080
aggtccagat cgtgcgcaac gacccgccgc tacgatacga caccaacctc cccgtggatc  49140
tgctacacat ggtgtacgcg ggccgcgggg cgaccggatc gtcgggggtg gtgttcggga  49200
cctggtaccg cactatccag gaccgcacca tcacggactt tcccctgacc acccgcagtg  49260
ccgactttcg ggacggccgt atgtccaaga ccttcatgac ggcgctggta ctgtccctgc  49320
agtcgtgcgg ccggctgtat gtgggccagc gccactattc cgccttcgag tgcgccgtgt  49380
tgtgtctcta cctgctgtac cgaaacacgc acggggccgc cgacgatagc gaccgcgctc  49440
cggtcacgtt cggggatctg ctgggccggc tgccccgcta cctggcgtgc ctggccgcgg  49500
tgatcgggac cgagggcggc cggccacagt accgctaccg cgacgacaag ctccccaaga  49560
cgcagttcgc ggccggcggg ggccgctacg aacacggagc gctggcgtcg cacatcgtga  49620
tcgccacgct gatgcaccac ggggtgctcc cggcggcccc gggggacgtc ccccgggacg  49680
cgagcaccca cgttaacccc gacggcgtgg cgcaccacga cgacataaac cgcgccgccg  49740
ccgcgttcct cagccggggc cacaacctat tcctgtggga ggaccagact ctgctgcggg  49800
caaccgcgaa caccataacg gccctgggcg ttatccagcg gctcctcgcg aacggcaacg  49860
tgtacgcgga ccgcctcaac aaccgcctgc agctgggcat gctgatcccc ggagccgtcc  49920
cttcggaggc catcgcccgt ggggcctccg ggtccgactc gggggccatc aagagcggag  49980
acaacaatct ggaggcgcta tgtgccaatt acgtgcttcc gctgtaccgg gccgacccgg  50040
cggtcgagct gacccagctg tttcccggcc tggccgccct gtgtcttgac gcccaggcgg  50100
ggcggccggt cgggtcgacg cggcgggtgg tggatatgtc atcgggggcc cgccaggcgg  50160
cgctggtgcg cctcaccgcc ctggaactca tcaaccgcac ccgcacaaac cccaccccccg  50220
tgggggaggt tatccacgcc cacgacgccc tggcgatcca atacgaacag ggggcttggcc  50280
tgctggcgca gcaggcacgc attggcttgg gctccaacac caagcgtttc tccgcgttca  50340
acgttagcag cgactacgac atgttgtact ttttatgtct ggggttcatt ccacagtacc  50400
tgtcggcggt ttagtgggtg gtgggcgagg ggggaggggg cattagggag aaagaacaag  50460
agcctccgtt gggttttctt tgtgcctgta ctcaaaaggt catacccccgt aaacggcggg  50520
ctccagtccc ggcccggcgg ttggcgtgaa cgcaacggcg ggagctgggt tagcgtttag  50580
tttagcattc gctctcgcct ttccgcccgc cccccgaccg ttgcgccttt ttttttttc  50640
gtccaccaaa gtctctgtgg gtgcgcgcat ggcagccgat gccccgggag accggatgga  50700
ggagcccctg ccagacaggg ccgtgcccat ttacgtggct gggtttttgg ccctgtatga  50760
cagcggggac tcgggcgagt tggcattgga tccggatacg gtgcgtgcgg ccctgcctcc  50820
ggataaccca ctcccgatta acgtggacca ccgcgctggc tgcgaggtgg ggcgggtgct  50880
ggccgtggtc gacgaccccc gcgggccgtt ttttgtggga ctgatcgcct gcgtgcaact  50940
```

-continued ggagcgcgtc ctcgagacgg ccgccagcgc tgcgattttc gagcgccgcg ggccgccgct 51000
ctcccgggag gagcgcctgt tgtacctgat caccaactac ctgccctcgg tctccctggc 51060
cacaaaacgc ctggggggcg aggcgcaccc cgatcgcacg ctgttcgcgc acgtcgcgct 51120
gtgcgcgatc gggcggcgcc tcggcactat cgtcacctac gacaccggtc tcgacgccgc 51180
catcgcgccc tttcgccacc tgtcgccggc gtctcgcgag gggcgcggc gactggccgc 51240 cgaggccgag ctcgcgctgt ccggacgcac ctgggcgccc ggcgtggagg cgctgaccca 51300
cacgctgctt tccaccgccg ttaacaacat gatgctgcgg gaccgctgga gcctggtggc 51360
cgagcggcgg cggcaggccg ggatcgccgg acacacctac ctccaggcga gcgaaaaatt 51420
caaaatgtgg ggggcggagc ctgtttccgc gccggcgcgc gggtataaga acggggcccc 51480
ggagtccacg gacataccgc ccggctcgat cgctgccgcg ccgcagggtg accggtgccc 51540
aatcgtccgt cagcgcgggg tcgcctcgcc cccggtactg ccccccatga accccgttcc 51600
ggcatcgggc accccggccc ccgcgccgcc cggcgacggg agctacctgt ggatcccggc 51660
ctcccattac aaccagctcg tcgccggcca cgccgcgccc caaccccagc cgcattccgc 51720
gtttggtttc ccggctgcgg cgggggccgt ggcctatggg cctcacggcg cgggtctttc 51780
ccagcattac cctccccacg tcgcccatca gtatcccggg gtgctgttct cgggacccag 51840
cccactcgag gcgcagatag ccgcgttggt gggggccata gccgcggacc gccaggcggg 51900
cggtcagacg gccgcgggag accctggggt ccggggggtcg ggaaagcgtc gccggtacga 51960
ggcggggccg tcggagtcct actgcgacca ggacgaaccg gacgcggact acccgtacta 52020
ccccggggag gctcgaggcg ggccgcgcgg ggtcgactct cggcgcgcgg cccgccagtc 52080
tcccgggacc aacgagacca tcacggcgct gatgggggcg gtgacgtctc tgcagcagga 52140
actggcgcac atgcgggctc ggaccagcgc cccctatgga atgtacacgc cggtggcgca 52200
ctatcgccct caggtggggg agccggaacc aacaacgacc cacccggccc tttgtccccc 52260
ggaggccgtg tatcgccccc caccacacag cgccccctac ggtcctcccc agggtccggc 52320
gtcccatgcc cccactcccc cgtatgcccc agctgcctgc ccgccaggcc cgccaccgcc 52380
cccatgtcct tccacccaga cgcgcgcccc tctaccgacg gagcccgcgt tcccccccgc 52440
cgccaccgga tcccaaccgg aggcatccaa cgcggaggcc ggggcccttg tcaacgccag 52500
cagcgcagca cacgtggacg ttgacacggc ccgcgccgcc gatttgttcg tctctcagat 52560
gatgggggcc cgctgattcg ccccggtctt tggtaccatg ggatgtctta ctgtatatct 52620
ttttaaataa accaggtaat accaaataag acccattggt gtatgttctt tttttattgg 52680
gaggcgcggg taggcgggta gctttacaat gcaaaagcct tcgacgtgga ggaaggcgtg 52740 ggggggaat cggcactgac caagggggtc cgttttgtca cgggaaagga aagaggaaac 52800
aggccgcgga cacccggggg agtttatgtg ttccctttc tttcttccca cacacacaaa 52860
aggcgtacca aacaaacaaa ccaaaagatg cacatgcggt ttaacacccg tggtttttat 52920
ttacaacaaa ccccccgtca caggtcgtcc tcgtcggcgt caccgtcttt gttgggaact 52980
tgggtgtagt tggtgttgcg gcgcttgcgc atgaccatgt cggtgacctt ggcgctgagc 53040
agcgcgctcg tgcccttctt cttggccttg tgttccgtgc gctccatggc agacaccagg 53100
gccatgtacc gtatcatctc ccgggcctcg gctagcttgg cctcgtcaaa gtcgccgccc 53160
tcctcgccct ccccggacgc gtccgggttg gtggggttct tgagctcctt ggtggttagc 53220
gggtacaggg ccttcatggg gttgctctgc agccgcatga cgtagcgaaa ggcgaagaaa 53280

-continued gccgccgcca ggccggccag gaccaacaga cccacggcca gcgccccaaa ggggttggac 53340
atgaaggagg acacgcccga cacggccgat accacgccgc ccacgatgcc catcaccacc 53400
ttgccgaccg cgcgccccag gtcgcccatc ccctcgaaga acgcgcccag gcccgcgaac 53460
atggcggcgt tggcgtcggc gtggatgacc gtgtcgatgt cggcgaagcg caggtcgtgc 53520
agctggttgc ggcgctggac ctccgtgtag tccagcaggc cgctgtcctt gatctcgtgt 53580
cgggtgtaca cctccagggg gacaaactcg tgatcctcca gcatggtgat gttgaggtcg 53640
atgaaggtgc tgacggtggt gatgtcggcg cggctcagct ggtgggagta cgcgtactcc 53700
tcgaagtaca cgtagccccc gccgaaggtg aagtagcgcc ggtgtcccac ggtgcacggc 53760
tcgatcgcat cgcgcgtcag ccgcagctcg ttgttctccc ccagctgccc ctcgaccaac 53820
gggccctggt cttcgtaccg aaagctgacc agggggcggc tgtagcaggc cccgggccgc 53880
gagctgatgc gcatcgagtt ttggacgatc acgttgtccg cggcgaccgg cacgcacgtg 53940
gagacggcca tcacgtcgcc gagcatccgc gcgctcaccc gccggcccac ggtggccgag 54000
gcgatggcgt tggggttcag cttgcgggcc tcgttccaca gggtcagctc gtgattctgc 54060
agctcgcacc acgcgatggc aacgcggccc aacatatcgt tgacatggcg ctgtatgtgg 54120
ttgtacgtaa actgcagccg ggcgaactcg atggaggagg tggtcttgat gcgctccacg 54180
gacgcgttgg cgctggcccc gggcggcggg ggcgtggggt ttgggggctt gcggctctgc 54240
tctcggaggt gttcccgcac gtacagctcc gcgagcgtgt tgctgagaag gggctggtac 54300
gcgatcagaa agcccccatt ggccaggtag tactgcggct ggcccacctt gatgtgcgtc 54360
gcgttgtacc tgcgggcgaa gatgcggtcc atggcgtcgc gggcgtcctt gccgatgcag 54420
tcccccaggt ccacgcgcga gagcgggtac tcggtcaggt tggtggtgaa ggtggtggat 54480
atggcgtcgg aggagaatcg gaaggagccg ccgtactcgg agcgcagcat ctcgtccacc 54540
tcctgccact tggtcatggt gcagaccgac gggcgctttg gcacccagtc ccaggccacg 54600
gtgaacttgg gggtcgtgag caggttccgg gtggtcggcg ccgtggcccg ggccttggtg 54660
gtgaggtcgc gcgcgtagaa gccgtcaacc tgcttgaagc ggtcggcggc gtagctggtg 54720
tgttcggtgt gcgacccctc ccggtagccg taaaacgggg acatgtacac aaagtcgcca 54780
gtcgccagca caaactcgtc gtacgggtac accgagcgcg cgtccacctc ctcgacgatg 54840
cagtttaccg tcgtcccgta ccggtggaac gcctccaccc gcgaggggtt gtacttgagg 54900
tcggtggtgt gccagccccg gctcgtgcgg gtcgcggcgt tggccggttt cagctccatg 54960
tcggtctcgt ggtcgtcccg gtgaaacgcg gtggtctcca ggttgttgcg cacgtacttg 55020
gccgtggacc gacagacccc cttggcgttg atcttgtcga tcacctcctc gaaggggacg 55080
ggggcgcggt cctcaaagat ccccataaac tgggagtagc ggtggccgaa ccacacctgc 55140
gaaacggtga cgtctttgta gtacatggtg gccttgaact tgtacggggc gatgttctcc 55200
ttgaagacca ccgcgatgcc ctccgtgtag ttctgaccct cgggccgggt cgggcagcgg 55260
cgcggctgct cgaactgcac caccgtggcg cccgtggggg gtgggcacac gtaaaagttt 55320
gcatcggtgt tctccgcctt gatgtcccgc aggtgctcgc gcagggtggc gtggcccgcg 55380
gcgacggtcg cgttgtcgcc ggcggggcgc ggcggcggtg ggtttttcgg ttttttgttc 55440
ttcttcggtt tcgtgtcccc cgttggggcg gggccagggg cgggcggcgc cggagtggca 55500
ggtcccccgt tcgccgcctg ggtcgcggcc gcgaccccag gcgtgccggg ggaactcgga 55560
gccgccgacg ccaccaggac ccccagcgtc aaccccaaga gcgcccatac gacgaaccac 55620
cggcaccccc gcgcgggggc gccctggcgc atggcgggac tacgggggcc cgtcgtgccc 55680

```
cccgtcaggt agcctggggg cgaggtgctg gaggaccgag tagaggatcg agaaaacgtc  55740
tcggtcgtag accacgaccg accgggggcc gatacagccg tcgggggcgc tctcgacgat  55800
ggccaccagc ggacagtcgg agtcgtacgt gagatatacg ccgggcgggt aacggtaacg  55860
accttcggag gtcgggcggc tgcagtccgg gcggcgcaac tcgagctccc cgcaccggta  55920
gaccgaggca aagagtgtgg tggcgataat cagctcgcga atatatcgcc aggcggcgcg  55980
ctgagtgggc gttattccgg aaatgccgtc aaaacagtaa aacctctgaa attcgctgac  56040
ggcccaatca gcacccgagc cccccgcccc catgatgaac cgggcgagct cctccttcag  56100
gtgcggcagg agccccacgt tctcgacgct gtaatacagc gcggtgttgg ggggctgggc  56160
gaagctgtgg gtggagtgat caaagagggg cccgttgacg agctcgaaga agcgatgggt  56220
gatgctgggg agcagggccg ggtccacctg gtgtcgcagg agagacgctc gcatgaaccg  56280
gtgcgcgtcg aacacgcccg gcgccgagcg gttgtcgatg accgtgcccg cgcccgccgt  56340
cagggcgcag aagcgcgcgc gcgccgcaaa gccgttggcg accgcggcga acgtcgcggg  56400
cagcacctcg ccgtggacgc tgacccgcag catcttctcg agctccccgc gctgctcgcg  56460
gacgcagcgc cccaggctgg ccaacgaccg cttcgtcagg cggtccgcgt acagccgccg  56520
tcgctcccgc acgtccgcgg ccgcttgcgt ggcgatgtcc ccccacgtct cgggcccctg  56580
ccccccgggc ccgcggcgac ggtcttcgtc ctcgccccccg cccccgggag ctcccaaccc  56640
ccgtgcccct tcctctacgg cgacacggtc cccgtcgtcg tcggggcccg cgccgccctt  56700
gggcgcgtcc gccgcgcccc ccgcccccat gcgcgccagc acgcgacgca gcgcctcctc  56760
gtcgcactgt tcggggctga cgaggcgccg caagagcggc gtcgtcaggt ggtggtcgta  56820
gcacgcgcgg atgagcgcct cgatctgatc gtcgggtgac gtggcctgac cgccgattat  56880
tagggcgtcc accatatcca gcgccgccag gtggctcccg aacgcgcgat cgaaatgctc  56940
cgcccgccgc ccgaacagcg ccagttccac ggccaccgcg gcggtctcct gctgcaactc  57000
gcgccgcgcc agcgcggtca ggttgctggc aaacgcgtcc atggtggtct ggccggcgcg  57060
gtcgccggac gcgagccaga atcgcaattc gctgatggcg tacaggccgg gcgtggtggc  57120
ctgaaacacg tcgtgcgcct ccagcagggc gtcggcctcc ttgcggaccg agtcgttctc  57180
gggcgacggg tggggctgcc cgtcgccccc cgcggtccgg gccagcgcat ggtccaacac  57240
ggagagcgcc cgcgcgcggt cggcgtccga cagcccggcg gcgtggggca ggtaccgccg  57300
cagctcgttg gcgtccagcc gcacctgcgc ctgctgggtg acgtggttac agatacggtc  57360
cgccaggcgg cgggcgatcg tcgccccctg gttcgccgtc acacacagtt cctcgaaaca  57420
gaccgcgcag gggtgggacg ggtcgctaag ctccgggggg acgataaggc ccgaccccac  57480
cgcccccacc ataaactccc gaacgcgctc cagcgcggcg gtggcgccgc gcgagggggt  57540
gatgaggtgg cagtagttta gctgctttag aaagttctcg acgtcgtgca ggaaacacag  57600
ctccatatgg acggtcccgc catacgtatc cagcctgacc cgttggtgat acggacaggg  57660
tcgggccagg cccatggtct ccgtgaaaaa caccgcgacg tctcccgcgg tcgcgaacgt  57720
ctccaggctg cccaggagcc gctcgccctc gcgccacgcg tactctagca gcaactccag  57780
ggtgaccgac agcggggtga gaaaggcccc ggcctgggcc tccaggcccg gcctcagacg  57840
acgccgcagc gcccgcacct gaagcgcgtt cagcttcagt tgggggagct tcccccgtcc  57900
gatgtggggg tcgcaccgcc ggagcagctc tatctgaaac acataggtct gcacctgtcc  57960
gagcagggct aacaactttt gacgggccac ggtgggctcg gacaccgggg cggccatctc  58020
```

gcggcgccga tctgtaccgc ggccggagta tgcggtggac cgaggcggtc cgtacgctac 58080
ccggcgtctg gctgagcccc ggggtccccc tattcggggc ggcctcccgc gggcccgccg 58140
accggcaagc cgggagtcgg cggcgcgtgc gtttctgttc tattcccaga caccgcggag 58200
aggaatcacg gcccgcccag agatatagac acggaacaca aacaagcacg gatgtcgtag 58260
caataattta ttttacacac attccccgcc ccgccctagg ttcccccacc ccccaacccc 58320
tcacagcata tccaacgtca ggtctccctt tttgtcgggg ggcccctccc caaacgggtc 58380
atccccgtgg aacgcccgtt tgcggccggc aaatgccggt cccggggccc ccgggccgcc 58440
gaacggcgtc gcgttgtcgt cctcgcagcc aaaatcccca aagttaaaca cctccccggc 58500
gttgccgagt tggctgacta gggcctcggc ctcgtgcgcc acctccaggg ccgcgtccgt 58560
cgaccactcg ccgttgccgc gctccagggc acgtgcggtc agctccatca tctcctcgct 58620
taggtactcg tcctccagga gcgccagcca gtcctcgatc tgcagctgtt gggtgcgggg 58680
ccccaggctt ttcacggtcg ccacgaacac gctactggcg acggccgccc cgccctcgga 58740
gataatgccc cggagctgct cgcacagcga gctttcgtgc gctccgccgc cgaggctcga 58800
ggccgcgcac acaaacccgg cccggggaca ggccaggacg aacttgcggg tgcggtcaaa 58860
aataaggagc gggcacgcgt ttttgccgcc catcaggctg gcccagttcc cggcctgaaa 58920
cacacggtcg ttgccggcca tgccgtagta tttgctgatg ctcaacccca acacgaccat 58980
ggggcgtgcc gccatgacgg gccgcagcag gttgcagctg gcgaacatgg aggtccacgc 59040
gcccggatgc gcgtccacgg cgtccatcag cgcgcgggcc ccggcctcca ggcccgcccc 59100
gccctgcgcg gaccacgcgg ccgccgcctg cacgctgggg ggacggcggg accccgcgat 59160
gatggccgtg agggtgttga tgaagtacgt cgagtgatcg cagtaccgca gaatctggtt 59220
tgccatgtag tacatcgcca gctcgctcac gttgttgggg gccaggttaa taaagttgat 59280
cgcgccgtag tccagggaaa actttttaat gaacgcgatg gtctcgatgt cctcgcgcga 59340
caggagccgg gcgggaagct ggttgcgttg gagggccgtc cagaaccact gcgggttcgg 59400
ctggttggac cccgggggct tgccgttggg gaagatggcc gcgtggaact gcttcagcag 59460
aaagcccagc ggtccgagga ggatgtccac gcgcttgtcg ggcttctggt aggcgctctg 59520
gaggctggcg acccgcgcct tggcggcctc ggacgcgttg gcgctcgcgc ccgcgaacaa 59580
cacgcggctc ttgacgcgca gctccttggg aaaccccagg gtcacgcggg caacgtcgcc 59640
ctcgaagctg ctctcggcgg gggccgtctg gccggccgtc aggctggggg cgcagatagc 59700
cgcaccctcc gagagcgcga ccgtcagcgt tttggccgac agaaacccgt tgttaaacat 59760
gtccatcacg cgccgccgca gcaccggttg gaattgattg cgaaagttgc gcccctcgac 59820
cgactgcccg gcgaacaccc cgtggcactg gctcagggcc aggtcctggt acacggcgag 59880
gttggatcgc cgcccgagaa gctgaagcag ggggcacggc ccgcacgcgt acgggtccag 59940
cgtcagggac atggcgtggt tggcctcgcc cagaccgtcg cgaaacttga agttcctccc 60000
ctccaccagg ttgcgcatca gctgctccac ctcgcggtcc acgacctgcc tgacgttgtt 60060
caccaccgta tgcagggcct cgcggttggt gatgatggtc tccagccgcc ccatggccgt 60120
ggggaccgcc tggtccacgt actgcagggt ctcgagttcg gccatgacgc gctcggtcgc 60180
cgcgcggtac gtctcctgca tgatggtccg ggcggtctcg gatccgtccg cgcgcttcag 60240
ggccgagaag gcggcgtagt ttcccagcac gtcgcagtcg ctgtacatgc tgttcatggt 60300
cccgaagacg ccgatggctc cgcgggcggc gctggcgaac ttgggatggc gcgcccggag 60360
gcgcatgagc gtcgtgtgta cgcaggcgtg gcgcgtgtcg aaggtgcaca ggttacaggg 60420

```
cacgtcggtc tggttggagt ccgcgacgta tcgaaacacg tccatctcct ggcgcccgac  60480
gatcacgccg ccgtcgcagc gctccaggta aaacagcatc ttggccagca gcgccgggga  60540
aaacccacac agcatggcca ggtgctcgcc ggcaaattcc tgggttccgc cgacgagggg  60600
cgcggtgggc cgaccctcga acccgggcac cacgtgtccc tcgcggtcca cctgtgggtt  60660
ggccgccacg tgggtcccgg gcacgaggaa gaagcggtaa aaggagggtt tgctgtggtc  60720
ctttgggtcc gccgggccgg cgtcgtccac ctcggtgaga tggagggccg agttggtgct  60780
aaataccatg gcccccacga gtcccgcggc gcgcgccagg tacgccccga cggcgttggc  60840
gcgggccgcg gccgtgtcct ggccctcgaa cagcggccac gcggagatgt cggtgggcgg  60900
ctcgtcaaag acggccatcg acacgataga ctcgagggcc agggcggcgt ctccggccat  60960
gacggaggcc aggcgctgtt cgaacccgcc cgcagggccc ttgccgccgc cgtcgcgccc  61020
gccccgcggg gtcttaccct ggctggcttc gaaggccgtg aacgtaatgt cggcggggag  61080
ggcggcgccc tcgtggtttt cgtcaaacgc caggtgggcg gccgcgcggg ccacggcgtc  61140
cacgtttcgg catcgcagtg ccacggcggc gggtcccacg accgcctcga acaggaggcg  61200
gtggaggggg cggttaaaaa acggaagcgg gtaggtaaaa ttctccccga tcgatcggtg  61260
gttggcgttg aacggctctg cgatgacacg gctaaaatcc ggcatgaaca gctgcaacgg  61320
gtacacgggt atgcggtgca cctccgcccc gcctatggtt accttgtccg agcctcccag  61380
gtgcagaaag gtgttgttga tgcacacggc ctccttgaag ccctcggtaa cgaccagata  61440
caggagggcg cggtccgggt ccaggccgag gcgctcacac agcgcctccc ccgtcgtctc  61500
gtgtttgagg tcgccgggcc ggggggtgta gtccgaaaag ccaaaatggc ggcgtgcccg  61560
ctcgcagagt cgcgtcaggt tcggggcctg ggtgctgggg tccaggtgcc ggccgccgtg  61620
aaagacgtac acggacgagc tgtagtgcga gggcgtcagt ttcagggaca ccgcggtacc  61680
cccgagcccc gtcgtgcgag aacccacgac cacggccacg ttggcctcaa agccgctctc  61740
cacggtcagg cccacgacca ggggcgccac ggcgacgtcg gcatcgccgc tgcgcgccga  61800
cagtaacgcc agaagctcga tgccttcgga cggacacgcg cgagcgtaca cgtatcccag  61860
gggcccgggg gggaccttga tggtggttgc cgtcttgggc tttgtctcca tgtccttctg  61920
tcaatcggtc cgcgaacgga ggtaatcccg gcacgacgac ggacgcccga caaggtatgt  61980
ctcccgagcg tcaaaatccg gggggggggg cggcgacggt caaggggagg gttggagacc  62040
ggggttgggg aatgaatccc tacccttcac cgacaacccc ccgggtaatc acggggtgcc  62100
gatgaacccc ggcggccggc aacgcggggt ccctgcgaga ggcacagatg cttacggtca  62160
ggtgctccgg gtcgggtgcg tctggtatgc ggttggtata tgtacacttt acctgggggc  62220
gtgcctggcc gccccagccc ctcccacgcc ctgcgcgtca tcagccggtg ggcgtggccg  62280
ctattataaa aaaagtgaga acgcgaagcg ttcgcacttt gtcctaataa tatatatatt  62340
attaggacaa agtgcgaacg cttcgcgttc tcactttttt tataatagcg gccacgccca  62400
ccggctacgt cacgctcctg tcggccgccg gcggtccata agcccggccg gccgggccga  62460
cgcgaataaa ccgggccgcc ggccggggcg ccgcgcagca gctcgccgcc cggatccgcc  62520
agacaaacaa ggcccttgca catgccggcc cgggcgagcc tgggggtccg gtaattttgc  62580
catcccaccc aagcggcttt ttgggttttt ctcttccccc ctccccacat cccccctctt  62640
taggggttcg ggtggtaaca accgcgatgt tttccggtgg cggcggcccg ctgtcccccg  62700
gaggaaagtc ggcggccagg gcggcgtccg ggtttttttgc gcccgccggc cctcgcggag  62760
```

ccggccgggg acccccgcct tgcttgaggc aaaactttta caacccctac ctcgccccag 62820
tcgggacgca acagaagccg accgggccaa cccagcgcca tacgtactat agcgaatgcg 62880
atgaatttcg attcatcgcc ccgcgggtgc tggacgagga tgcccccccg gagaagcgcg 62940
ccggggtgca cgacggtcac ctcaagcgcg cccccaaggt gtactgcggg ggggacgagc 63000
gcgacgtcct ccgcgtcggg tcgggcggct tctggccgcg gcgctcgcgc ctgtggggcg 63060
gcgtggacca cgccccggcg gggttcaacc ccaccgtcac cgtctttcac gtgtacgaca 63120
tcctggagaa cgtggagcac gcgtacggca tgcgcgcggc ccagttccac gcgcggttta 63180
tggacgccat cacaccgacg gggaccgtca tcacgctcct gggcctgact ccggaaggcc 63240
accgggtggc cgttcacgtt tacggcacgc ggcagtactt ttacatgaac aaggaggagg 63300
tcgacaggca cctacaatgc cgcgccccac gagatctctg cgagcgcatg gccgcggccc 63360
tgcgcgagtc cccgggcgcg tcgttccgcg gcatttccgc ggaccacttc gaggcggagg 63420
tggtggagcg caccgacgtg tactactacg agacgcgccc cgctctgttt taccgcgtct 63480
acgtccgaag cgggcgcgtg ctgtcgtacc tgtgcgacaa cttctgcccg gccatcaaga 63540
agtacgaggg tggggtcgac gccaccaccc ggttcatcct ggacaacccc gggttcgtca 63600
ccttcggctg gtaccgtctc aaaccgggcc ggaacaacac gctagcccag ccgcgggccc 63660
cgatggcctt cgggacatcc agcgacgtcg agtttaactg tacggcggac aacctggcca 63720
tcgagggggg catgagcgac ctaccggcat acaagctcat gtgcttcgat atcgaatgca 63780
aggcgggggg ggaggacgag ctggcctttc cggtggccgg gcacccggag gacctggtca 63840
tccagatatc ctgtctgctc tacgacctgt ccaccaccgc cctggagcac gtcctcctgt 63900
tttcgctcgg ttcctgcgac ctccccgaat cccacctgaa cgagctggcg gccaggggcc 63960
tgcccacgcc cgtggttctg gaattcgaca gcgaattcga gatgctgttg gccttcatga 64020
cccttgtgaa acagtacggc cccgagttcg tgaccgggta caacatcatc aacttcgact 64080
ggcccttctt gctggccaag ctgacggaca tttacaaggt cccccctggac gggtacggcc 64140 gcatgaacgg ccggggcgtg tttcgcgtgt gggacatagg ccagagccac ttccagaagc 64200
gcagcaagat aaaggtgaac ggcatggtga acatcgacat gtacgggatt ataaccgaca 64260
agatcaagct ctcgagctac aagctcaacg ccgtggccga agccgtcctg aaggacaaga 64320
agaaggacct gagctatcgc gacatccccg cctactacgc cgccgggccc gcgcaacgcg 64380
gggtgatcgg cgagtactgc atacaggatt ccctgctggt gggccagctg tttttaagt 64440 ttttgcccca tctggagctc tcggccgtcg cgcgcttggc gggtattaac atcacccgca 64500
ccatctacga cggccagcag atccgcgtct ttacgtgcct gctgcgcctg gccgaccaga 64560
agggctttat tctgccggac acccagggc gatttagggg cgccgggggg gaggcgccca 64620
agcgtccggc cgcagcccgg gaggacgagg agcggccaga ggaggagggg gaggacgagg 64680
acgaacgcga ggagggcggg ggcgagcggg agccggaggg cgcgcgggag accgccggcc 64740
ggcacgtggg gtaccagggg gccagggtcc ttgaccccac ttccgggttt catgtgaacc 64800
ccgtggtggt gttcgacttt gccagcctgt accccagcat catccaggcc cacaacctgt 64860
gcttcagcac gctctccctg agggccgacg cagtggcgca cctggaggcg ggcaaggact 64920
acctggagat cgaggtgggg gggcgacggc tgttcttcgt caaggctcac gtgcgagaga 64980
gcctcctcag catcctcctg cgggactggc tcgccatgcg aaagcagatc cgctcgcgga 65040
ttccccagag cagccccgag gaggccgtgc tcctggacaa gcagcaggcc gccatcaagg 65100
tcgtgtgtaa ctcggtttac gggttcacgg gagtgcagca cggactcctg ccgtgcctgc 65160
acgttgccgc gacggtgacg accatcggcc gcgagatgct gctcgcgacc cgcgagtacg 65220
tccacgcgcg ctgggcggcc ttcgaacagc tcctggccga tttcccggag gcggccgaca 65280
tgcgcgcccc cgggccctat tccatgcgca tcatctacgg ggacacggac tccatctttg 65340
tgctgtgccg cggcctcacg gccgccgggc tgacggccgt gggcgacaag atggcgagcc 65400
acatctcgcg cgcgctgttt ctgtccccca tcaaactcga gtgcgaaaag acgttcacca 65460
agctgctgct gatcgccaag aaaaagtaca tcggcgtcat ctacgggggt aagatgctca 65520
tcaagggcgt ggatctggtg cgcaaaaaca actgcgcgtt tatcaaccgc acctccaggg 65580
ccctggtcga cctgctgttt tacgacgata ccgtatccgg agcggccgcc gcgttagccg 65640
agcgccccgc agaggagtgg ctggcgcgac ccctgcccga gggactgcag gcgttcgggg 65700
ccgtcctcgt agacgcccat cggcgcatca ccgacccgga gagggacatc caggactttg 65760
tcctcaccgc cgaactgagc agacacccgc gcgcgtacac caacaagcgc ctggcccacc 65820
tgacggtgta ttacaagctc atggcccgcc gcgcgcaggt cccgtccatc aaggaccgga 65880
tcccgtacgt gatcgtggcc cagacccgcg aggtagagga gacggtcgcg cggctggccg 65940
ccctccgcga gctcgacgcc gccgccccag gggacgagcc cgcccccccc gcggccctgc 66000
cctccccggc caagcgcccc cgggagacgc cgttgcatgc cgacccccccg ggaggcgcgt 66060
ccaagccccg caagctgctg gtgtccgagc tggccgagga tcccgcatac gccattgccc 66120
acggcgtcgc cctgaacacg gactattact tctcccacct gttgggggcg gcgtgcgtga 66180
cattcaaggc cctgtttggg aataacgcca agatcaccga gagtctgtta aaaaggttta 66240
ttcccgaagt gtggcacccc ccggacgacg tggccgcgcg gctccgggcc gcagggttcg 66300
gggcggtggg tgccggcgct acggcggagg aaactcgtcg aatgttgcat agagcctttg 66360
atactctagc atgagccccc cgtcgaagct gatgtccctc attttacaat aaatgtctgc 66420
ggccgacacg gtcggaatct ccgcgtccgt gggtttctct gcgttgcgcc ggaccacgag 66480
cacaaacgtg ctctgccaca cgtgggcgac gaaccggtac cccgggcacg cggtgagcat 66540
ccggtctatg agccggtagt gcaggtgggc ggacgtgccg ggaaagatga cgtacagcat 66600
gtggcccccg taagtggggt ccgggtaaaa caacagccgc gggtcgcacg ccccgcctcc 66660
gcgcaggatc gtgtggacga aaaaaagctc gggttggcca agaatcccgg ccaagaggtc 66720
ctggaggggg gcgttgtggc ggtcggccaa cacgaccaag gaggccagga aggcgcgatg 66780
ctcgaatatc gtgttgatct gctgcacgaa ggccaggatt agggcctcgc ggctggtggc 66840
ggcgaaccgc ccgtctcccg cgttgcacgc gggacagcaa cccccgatgc ctaggtagta 66900
gcccatcccg gagagggtca ggcagttgtc ggccacggtc tggtccagac agaagggcag 66960
cgagacggga gtggtcttca ccaggggcac cgagagcgag cgcacgatgg cgatctcctc 67020
ggagggcgtc tgggcgaggg cggcgaaaag gccccgatag cgctggcgct cgtgtaaaca 67080
cagctcctgt ttgcgggcgt gaggcggcag gctcttccgg gaggcccgac gcaccacgcc 67140
cagagtcccg ccggccgcag aggagcgcga ccgccggcgc tccttgccgt gatagggccc 67200
gggccgggag ccgcggcgat gggggtcggt gtcatacata ggtacacagg gtgtgctcca 67260
gggacaggag cgagatcgag tggcgtctaa gcagcgcgcc cgcctcacgg acaaatgtgg 67320
cgagcgcggt gggctttggt acaaatacct gatacgtctt gaaggtgtag atgagggcac 67380
gcaacgctat gcagacacgc ccctcgaact cgttcccgca ggccagcttg gccttgtgga 67440
gcagcagctc gtcgggatgg gtggcggggg gatggccgaa cagaacccag gggtcaacct 67500

-continued

```
ccatctccgt aatggcgcac atggggtcac agaacatgtg cttaaagatg gcctcgggcc  67560
ccgcggcccg aagcaggctc acaaaccggc ccccgtcccc gggctgcgtc tcggggtcag  67620
cctcgagctg gtcgacgacg ggtacgatac agtcgaagag gctcgtgttg ttttccgagt  67680
agcggaccac ggaggcccgg agtctgcgca gggccagcca gtaagcacgc accagtaaca  67740
ggttacacag caggcattct ccgccggtgc gcccgcgccc ccggccgtgt ttcagcacgg  67800
tggccatcag agggcccagg tcgaggtcgg gctgggcatc gggttcggta aactgcgcaa  67860
agcgcggagc cacgtcgcgc gtgcgtgccc cgcgatgcgc ttcccaggac tggcggaccg  67920
tggcgcgacg ggcctccgcg gcagcgcgca gctggggccc cgactcccag acggcggggg  67980
tgccggcgag gagcagcagg accagatccg cgtacgccca cgtatccggc gactcctccg  68040
gctcgcggtc cccggcgacc gtctcgaatt ccccgttgcg agcggcggcg cgcgtacagc  68100
agctgtcccc gcccccgcgc cgaccctccg tgcagtccag gagacgggcg caatccttcc  68160
agttcatcag cgcggtggtg agcgacggct gcgtgccgga tcccgccgac cccgcccccct  68220
cctcgccccc ggaggccaag gttccgatga gggcccgggt ggcagactgc gccaggaacg  68280
agtagttgga gtactgcacc ttggcggctc ccggggaggg cgagggcttg ggttgcttct  68340
gggcatgccg cccgggcacc ccgccgtcgg tacggaagca gcagtggaga aaaaagtgcc  68400
ggtggatgtc gtttatggtg agggcaaagc gtgcgaagga gccgaccagg gtcgccttct  68460
tggtgcgcag aaagtggcgg tccatgacgt acacaaactc gaacgcggcc acgaagatgc  68520
tagcggcgca gtggggcgcc cccaggcatt tggcacagag aaacgcgtaa tcggccaccc  68580
actgaggcga gaggcggtag gtttgcttgt acagctcgat ggtgcggcag accagacagg  68640
gccggtccag cgcgaaggtg tcgatggccg ccgcggaaaa gggcccggtg tccaaaagcc  68700
cctccccaca gggatccggg ggcgggttgc ggggtcctcc gcgcccgccc gaaccccctc  68760
cgtcgcccgc ccccccgcgg gcccttgagg gggcggtgac cacgtcggcg gcgacgtcct  68820
cgtcgagcgt accgacgggc ggcacaccta tcacgtgact ggccgtcagg agctcggcgc  68880
agagagcctc gttaagagcc aggaggctgg gatcgaaggc cacatacgcg cgctcgaacg  68940
cccccgcctt ccagctgctg ccgggggact cttcgcacac cgcgacgctc gccaggaccc  69000
cggggggcga agttgccatg gctgggcggg aggggcgcac gcgccagcga actttacggg  69060
acacaatccc cgactgcgcg ctgcggtccc agaccctgga gagtctagac gcgcgctacg  69120
tctcgcgaga cggcgcgcat gacgcggccg tctggttcga ggatatgacc cccgccgagc  69180
tggaggttgt cttcccgact acggacgcca agctgaacta cctgtcgcgg acgcagcggc  69240
tggcctccct cctgacgtac gccgggccta taaaagcgcc cgacgacgcc gccgccccgc  69300
agaccccgga caccgcgtgt gtgcacggcg agctgctcgc ccgcaagcgg gaaagattcg  69360
cggcggtcat taaccggttc ctggacctgc accagattct gcggggctga cgcgcgtgct  69420
gttgggcggg acggttcgcg aaccctttgg tgggtttacg cgggcacgca cgctcccatc  69480
gcgggcgcca tggcgggact gggcaagccc tacaccggcc acccaggtga cgccttcgag  69540
ggtctcgttc agcgaattcg gcttatcgtc ccatctacgt tgcggggcgg ggacggggag  69600
gcgggcccct actctccctc caacctcccc tccaggtgcg cctttcagtt tcatggccat  69660
gacgggtccg acgagtcgtt tcccatcgag tatgtactgc ggcttatgaa cgactgggcc  69720
gaggtcccgt gcaaccctta cctgcgcata cagaacaccg gcgtgtcggt gctgtttcag  69780
gggttttttc atcgcccaca caacgccccc gggggcgcga ttacgccaga gcggaccaat  69840
gtgatcctgg ggtccaccga gacgacgggg ttgtccctcg gcgacctgga caccatcaag  69900
```

gggcggctcg gcctggatgc ccggccgatg atggccagca tgtggatcag ctgctttgtg 69960
cgcatgcccc gcgtgcagct cgcgtttcgg ttcatgggcc ccgaagatgc cggacggacg 70020
agacggatcc tgtgccgcgc cgccgagcag gctattaccc gtcgccgccg aacccggcgg 70080
tcccgggagg cgtacggggc cgaggccggg ctgggggtgg ccggaacggg tttccgggcc 70140
agggggggacg gttttggccc gctccccttg ttaacccaag ggccctcccg cccgtggcac 70200
caggccctgc ggggtcttaa gcacctacgg attggccccc ccgcgctcgt tttggcggcg 70260
ggactcgtcc tgggggccgc tatttggtgg gtggttggtg ctggcgcgcg cctataaaaa 70320
aggacgcacc gccgccctaa tcgccagtgc gttccggacg ccttcgcccc acacagccct 70380
cccgaccgac acccccatat cgcttcccga cctccggtcc cgatggccgt cccgcaattt 70440
caccgcccca gcaccgttac caccgatagc gtccgggcgc ttggcatgcg cgggctcgtc 70500
ttggccacca ataactctca gtttatcatg gataacaacc acccacaccc ccagggcacc 70560
caaggggccg tgcgggagtt tctccgcggt caggcggcgg cactgacgga ccttggtctg 70620
gcccacgcaa acaacacgtt taccccgcag cctatgttcg cgggcgacgc accggccgcc 70680
tggttgcggc ccgcgtttgg cctgcggcgc acctattcac cttttgtcgt tcgagaacct 70740
tcgacgcccg ggaccccgtg aggcccaggg agttccttct ggggtgtttt aatcaataaa 70800
agaccacacc aacgcacgag ccttgcgttt aatgtcgtgt ttattcaagg gagtgggata 70860
gggttcgacg gttcgaaact taacacacca aataatcgag cgcgtctagc ccagtaacat 70920
gcgcacgtga tgtaggctgg tcagcacggc gtcgctgtga tgaagcagcg cccggcgggt 70980
ccgctgtaac tgctgttgta ggcggtaaca ggcgcggatc agcaccgcca gggcgctacg 71040
accggtgcgt tgcacgtagc gtcgcgacag aactgcgttt gccgatacgg gcggggggcc 71100
gaattgtaag cgcgtcacct cttgggagtc atcggcggat aacgcactga atggttcgtt 71160
ggttatgggg gagtgtggtt ccccagggag tgggtcgagc gcctcggcct cggaatccga 71220
gaggaacaac gaggtggcgt cggagtcttc gtcgtcagag acatacaggg tctgaagcag 71280
cgacacgggc ggggggtag cgtcgatgtg tagcgcgagg gaggatgccc acgaagacac 71340
cccagacaag gagctgcccg tgcgtggatt tgtggaagac gcggaagccg ggacggatgg 71400
gcggttttgc ggtgcccgga accgaaccgc cggatactcc ccgggtgcta catgcccgtt 71460
ttggggctgg ggttggggct ggggttgggg ctggggttgg ggctggggtt ggggctgggg 71520
ttggggctgg ggttggggtt ggggttgggg ctggggttgg ggttggggct ggggctgggg 71580
ctggggctgg ggctggggct ggggctgggg ctggggctgg ggctggggct ggggctgggg 71640
ctggggctgg ggctggggct ggggttgggg cgcggacagg cggctgacgg tcaaatgccc 71700
ccgggggcgc gcagatgtgg tgggcgtggc caccggctgc cgtgtagtgg ggcggcggga 71760
aaccgggcct ccgggcgtaa caccgccctc cagcgtcaag tatgtggggg gcgggcctga 71820
cgtcggggggc ggggtgacgg gttggaccgc gggaggcggg ggagagggac ctgcgggaga 71880
ggatgaggtc ggctcggccg ggttgcggcc taaaacaggg gccgtggggt cggcggggtc 71940
ccagggtgaa gggagggatt cccgcgattc ggacagcgac gcgacagcgg ggcgcgtaag 72000
gcgccgctgc ggcccgccta cgggaaccct gggggggtt ggcgcgggac ccgaggttag 72060
cggggggcgg cggttttcgc ccccgggcaa aaccgtgccg gttgcgaccg gggcggaac 72120
gggatcgata gggagagcgg gagaagcctg gccggcggac tggggaccga gcgggagggg 72180
cacaccagac accaaagcgt ggggcgctgg ctctgggggt ttgggagggg ccgggggcg 72240 cgcgaaatcg gtaaccgggg cgaccgtgtc ggggagggca ggcggccgcc aaccctgggt 72300
ggtcgcggaa gcctgggtgg cgcgcgccag ggagcgtgcc cggcggtgtc ggcgcgcgcg 72360
cgacccggac gaagaagcgg tagaagcgcg ggaggaggcg ggggggcggg gggcggtggc 72420
atcggggggc gccggggaac tttgggggga cggcaagcgc cggaagtcgt cgcgggggcc 72480
cacgggcgcc ggccgcgtgc tttcggccgg gacgcccggt cgtgcttcgc gagccgtgac 72540
tgccggccca gggggccgcg gtgcacactg ggacgtgggg acggactgat cggcggtggg 72600
cgaaaggggg tccggggcaa ggagggggcgc ggggccgccg gagtcgtcag acgcgagctc 72660
ctccaggccg tgaatccatg cccacatgcg agggggggacg ggctcgccgg gggtggcgtc 72720
ggtgaatagc gtgggggcca ggcttccggg ccccaacgag ccctccgccc caacaaggtc 72780
cgccgggccg ggggtcgggt tcgggaccga ggggctctgg tcgtcggggg cgcgctggta 72840
caccggatgc cccgggaata gctcccccga caggagggag gcgtcgaacg gccgcccgag 72900
gatagctcgc gcgaggaagg ggtcctcgtc ggtggcgctc gcggcgagga cgtcctcgcc 72960
gcccgccaca aacgggagct cctcggtggc ctcgctgcca acaaaccgca tgtcgggggg 73020
gccggggggg tccgggtttt cccacaacac cgcgaccggg gtcatggaga tgtccacgag 73080
caccaggcac ggcgggcccc gggcgagggg ccgctcggcg atgagcgcgg acaggcgcgg 73140
gagctgtgcc gccagacacg cgttttcgat cgggttaagg tcggcgtgca ggaggcggac 73200
ggcccacgtc tcgatgtcgg acgacacggc atcgcgcaag gcggcgtccg gcccgcgagc 73260
gcgtgagtca aacagcgtga ggcacagctc cagttccgac tcgcgggaaa aggccgtggt 73320
gttgcggagc gccacgacga cgggcgcgcc caggagcact gccgccagca ccaggtccat 73380
ggccgtaacg cgcgccgcgg gggtgcggtg ggtggcggcg gccggcacgg cgacgtgctg 73440
gcccgtgggc cggtagaggg cgttgggggg agcggggggt gacgcctcgc gcccccccga 73500
ggggctcagc gtctgcccag attccagacg cgcggtcaga agggcgtcga aactgtcata 73560
ctctgtgtag tcgtccggaa acatgcaggt ccaaagagcg gccagcgcgg tgcttgggag 73620
acacatgcgc ccgaggacgc tcaccgccgc cagcgcctgg gcgggactca gctttcccag 73680
cgcggcgccg cgctcggttc ccagctcggg gaccgagcgc cagggcgcca gggggtcggt 73740
ttcggacaac ttgccgcggc gccagtctgc cagccgcgtg ccgaacatga ggccccgggt 73800
cggagggcct ccggccgaaa acgctggcag cacgcggatg cgggcgtctg gatgcggggt 73860
caggcgctgc acgaatagca tggaatctgc tgcgttctga aacgcacggg ggagggtgag 73920
atgcatgtac tcgtgttggc ggaccagatc caggcgccaa aaggtgtaaa tgtgttccgg 73980
ggagctggcc accagcgcca ccagcacgtc gttctcgtta aaggaaacgc ggtgcctagt 74040
ggagctctgg ggtccgagcg gcggccccgg ggccgccgcg tcaccccccc attccagctg 74100
ggcccagcga cacccaaact cgcgcgtgag agtggtcgcg acgagggcga cgtagagctc 74160
ggccgccgca tccatcgagg ccccccatct cgcctggcgg tggcgcacaa agcgtccgaa 74220
gagctgaaag ttggcggcct gggcgtcgct gagggccagc tgaagccggt tgatgacggt 74280
gaggacgtac atggccgtga cggtcgaggc cgactccagg gtgtccgtcg gaagcggggg 74340
gcgaatgcat gccgcctcgg gacacatcag cagcgcgccg agcttgtcgg tcacggccgg 74400
gaagcagagc gcgtactgca gtggcgttcc atccgggacc aaaaagctgg gggcgaacgg 74460
cctatccagc gtactggtgg cctcgcgcag caccaggggc cccgggcctc cgctcactcg 74520
caggtacgcc tcgccccggc ggcgcagcat ctgcgggtcg gcctcttggc cgggtggggc 74580
ggacgcccgg gcgcgggcgt ctagggcgcg aagatccacg agcaggggcg cgggcgcggc 74640
cgccgcgccc gcgcccgtct ggcctgtggc cttggcgtac gcgctatata agcccatgcg 74700
gcgttggatg agctcccgcg cgccccggaa ctcctccacc gcccatgggg ccaggtcccc 74760
ggccaccgcg tccaattccg ccaacaggcc ccccagggtg tcaaagttca tctcccaggc 74820
cacccttggc accacctcgt cccgcagccg ggcgctcagg tcggcgtgtt gggccacgcg 74880
ccccccgagc tcctccacgg ccccggcccg ctcggcgctc ttggcgccca ggacgccctg 74940
gtacttggcg ggaaggcgct cgtagtcccg ctgggctcgc agccccgaca cagtgttggt 75000
ggtgtcctgc agggcgcgaa gctgctcgca tgccgcgcga aatccctcgg gcgatttcca 75060
ggcccccccg cgaacgcggc cgaagcgacc ccatacctcg tcccactccg cctcggcctc 75120
ctcgaaagac ctccgcaggg cctcgacgcg gcgacgggtg tcgaagagcg actgcaggcg 75180
cgcgccctgt cgcgtcagga ggcccgggcc gtcgccgctg gccgcgctta gcgggtgcgt 75240
ctcaaaggtg cgctgggcat gttccaacca ggcgaccgcc tgcacgtcga gctcgcgcgc 75300
cttctccgtc tggtccaaca gaatctcgac ctgatccgcg atctcctccg ccgagcgcgc 75360
ctggtccagc gtcttggcca cggtcgccgg gacggcaacc accttcagca gggtcttcag 75420
attggccaga ccctcggcct cgagctgggc ccggcgctcg cgcgcggcca gcacctcccg 75480
caaccccgcc gtgacccgct cggtggcttc ggcgcgctgc tgtttggcgc gcaccacggc 75540
gtccttggta tcggccaggt cctgtcgggt cacgaatgcg acgtagtcgg cgtacgccgt 75600
gtccttcacg gggctctggt ccacgcgctc cagcgccgcc acacacgcca ccagcgcgtc 75660
ctcgctcggg cagggcaggg tgacccctgc ccggacaagc tcggcggccg ccgccgggtc 75720
gttgcgcacc gcggatatct cctccgcggc ggcggccagg tccagcgcca cgcttccgat 75780
cgcgcgccgc gcgtcggccc ggagggcgtc caggcgatcg cggatatcca cgtactcggc 75840
gtagcccttt tgaaaaaacg gcacgtactg gcgcagggcc ggcacgcccc ccaagtcttc 75900
cgacaggtgt aggacggcct cgtggtagtc gataaacccg tcgttcgcct gggcccgctc 75960
cagcagcccc cccgcgagcc gcagaagccg cgccaggggc tcggtgtcca cccgaaacat 76020
gtcggcgtac gtgtcggccg cggccccgaa ggccgcgctc cagtcgatgc ggtgaatggc 76080
tgcgagcggg gggagcatgg ggtggcgctg gttctcgggg gtgtatgggt taaacgcaag 76140
ggccgtctcc agggcaaggg tcaccgcctt ggcgttggtt cccagcgcct gctcggcccg 76200
ctttcggaag tcccgggggt tgtagccgtg cgtgcccgcc agcgcctgca ggcgacggag 76260
ctcgaccacg tcaaactcgg caccgctttc cacgcggtcc agcacggcct ccacgtcggc 76320
ggcccagcgc tcgtggctac tgcgggcgcg ctgggccgcc atcttctctc tgaggtcggc 76380
ggtggcggcc tcaagttcgt cggcgcggcg tcgcgtggcg ccgatgacct ttcccagctc 76440
ctgcagggcg cgcccgctgg gggagtggtc cccggccgtc ccttcggcgt gcaacaggcc 76500
cccgaacctg ccctcgtggc ccgcgaggct ttcccgcgcg ccggtggtcg cgcgcgtcgc 76560
ggcctggatc agggaggcat gctctccctc cggttggttg gcggcccggc gcacctggac 76620
gacaaggtcg gcggcagccg accctaaggt cgtgagctgg gcgatggccc cccgcgcgtc 76680
cagggccaac cgagtcgcct tgacgtatcc cgcggcgctg tcggccatgg ccgctaggaa 76740
ggccaggggg gaggccgggt cgctggcggc cgcgcccagg gccgtcactg cgtcgaccag 76800
gacgcggtgc gcccgcacgg ccgcatccac cgtcgacgcg gggtctgccg tcgcgacggc 76860
ggcgctgccg gcgttgatgg cgttcgagac ggcgtgggct atgatcgggg cgtgatcggc 76920
gaagaactgc aagagaaacg gagtctcggg ggcgttggcg aacaggttct tcagcaccac 76980

-continued cacgaagctg ggatgcaagc cggacagagc cgtcgccgtg tccggagtcg ggtgctccag 77040
ggcatctcgg tactgcccca gcagccccca catgtccgcc cgcagcgccg ccgtaacctc 77100
cgggggcgcc ccccgaacgg cctcggggag gtccgaccag cccgccggca gggaggcccg 77160
cagggtcgtc aggacggccg gacaggcctt tagccccaca aagtcaggga ggggccgcag 77220
gaccccctgg agtttgtgca agaacttctc ccgggcgtcg cgggccacct tcgcccgctc 77280
ccgcgctccc tcgagcattg cctccaggga gcgcgcgcgc tcccgcaaac gggcacgcgc 77340
atcgggggcg agctctgccg tcagcttggc ggcatccatg gcccgcgcct gccgcagcgc 77400
ttcctcggcc atgcgcgtgg cctctggcga cagcccgccg tcgtcggggt agggcgacgc 77460
gccgggcgca ggaacaaagg ccgcgtcgct gtccagctgc tggcccaggg ccgcatctag 77520
ggcgtcgaag cgccgcagct cggccagacc cgagctgcgg cgcgcctgct ggtcgttaat 77580
gtcgcggatg ctgcgcgcca gctcgtccag cggcttgcgt tctatcagcc cttggttggc 77640
ggcgtccgtc aggacggaga gccaggccgc caggtcctcg gggcgtcca gcgtctggcc 77700
ccgctgtatc agatcccgca acaggatggc cgtggggctg gtcgcgatcg gggcggggc 77760
gggaatggcg gcgctctgcg cgatgtcccg cgtgtgctgg tcgaagacag gcagggactc 77820
tagcagctgg accacgggca cgacggcggc cgaagccacg tgaaaccggc ggtcgttgtt 77880
gtcgctggcc tgcagagcct tggcgctgta tacggccccc cggtaaaagt actccttaac 77940
cgcgccctcg atcgcccgac gggcctgggt ccgcacctcc tccagccgaa cctgaacggc 78000
ctcggggccc aggggggtg ggcgcggagc cccctgcggg gccgccccgg ccggggcggg 78060
cattacgccg aggggcccgg cgtgctgtga gaccgcgtcg accccgcgag cgagggcgtc 78120
gagggcctcg cgcatctggc gatcctccgc ctccacccta atctcttcgc cacgggcaaa 78180
tttggccaga gcctggactc tatacagaag cggttctggg tgcgtcgggg tggcgggggc 78240
aaaaagggtg tccgggtggg cctgcgagcg ctccagaagc cactcgccga ggcgtgtata 78300
cagattggcc ggcggggccg cgcgaagctg cagctccagg tccgcgagtt ccccgtaaaa 78360
ggcgtccgtc tcccgaatga catccctagc cacaaggatc agcttcgcca gcgccaggcg 78420
accgatcaga gagttttcgt ccagcacgtg ctggacgagg ggcagatggg cggccacgtc 78480
ggccaggctc aggcgcgtgg aggccagaaa gtcccccacg gccgttttcc ggggcagcat 78540
gctcagggta aactccagca gggcggcggc cgggccggcc accccggcct gggtgtgcgt 78600
ccgggccccg ttctcgatga gaaaggcgag gacgcgttca aagaaaaaaa taacacagag 78660
ctccagcagc cccggagaag ccggatacgg cgaccgtaag gcgctgatgg tgagccgcga 78720
acacgcggcg acctcgcggg ccagggcggc ggagcacgcg gtgaacttaa ccgccgtggc 78780
ggccacgttt gggtgggcct cgaacagctg ggcaaggtct gcgcccgggg gctcgggtga 78840
gcggcgagtc ttcagcgcct cgagggcctg cgaggacgcc ggaaccgtgg gcccgtcgtc 78900
ctcgcccgcc tcggcgaccg gcggcccggc cgggtcgggg ggtgccgagg cgaggacagg 78960
ctccggaacg gaggcgggga ccgcggcccc gacgggggtt ttgcctttgg gggtggattt 79020
cttcttggtt ttggcagggg gggccgagcg tttcgttttc tcccccgaag tcaggtcttc 79080
gacgctggaa ggcggagtcc aggtgggtcg gcggcgcttg ggaaggccgg ccgagtagcg 79140
tgcccggtgc cgaccaaccg ggacgacgcc catctccagg acccgcatgt cgtcgtcatc 79200
ttcttcggcc gcctctgcgg cggggggctt gggggcggag ggaggcggtg gtgggatcgc 79260
ggagggtggg tcggcggagg ggggatccgt gggtggggta cccttcaggg ccaccgccca 79320
tacatcgtcg ggcgcccgat tcgggcgctt ggcctctggt tttgccgacg gaccggccgt 79380
cccccgggat gtctcggagg ccctgtcgtc gcgacgggcc cgggtcggtg gcggcgactg 79440
ggcggctgtg ggcgggtggg gccccgtgcc ccctacccc tcccgggggc ccacgccgac 79500
gcagggctcc cccaggcccg cgatctcgcc ccgcaggggg tgcgtgatgg ccacgcgccg 79560
ttcgctgaac gcttcgtcct gcaggtaagt ctcgctggcc ccgtaaagat gcagagccgc 79620
ggccgtcaag tccgcaggag ccgcgggttc cgggcccgac ggcacgaaaa acaccatggc 79680
tcccgcccac cgtacgtccg ggcgatcgcg ggtgtaatac gtcaggtatg gatacatgtc 79740
ccccgcccgc actttggcga tgaacgcggg ggtgccctcc ggaaggccgt gcgggtcaaa 79800
aaggtatgcg gtgtcgccgt ccctgaacag ccccatccct agggggccaa tggttaggag 79860
cgtgtacgac agggggcgca gggcccacgg gccggcgaag aacgtgtgtg cggggcattg 79920
tgtctccagc aggcccgccg cgggctcccc gaagaagccc acctcgccgt atacgcgcga 79980
gaagacacag cgcagtccgc cgcgcgcccc tgggtactcg aggaagttgg ggagctcgac 80040
gatcgaacac atgcgcggcg gcccagggcc cgcggtcgcg cgcgtccact cgcccccctc 80100
gaccaaacaa ccctcgatgg cctccgcgga cagaacgtcg cgagggccca catcaaatat 80160
gaggctgaga aaggacagcg acgagcgcat gcacgatacc gaccccccg gctccaggtc 80220
gggcgcgaac tggttccgag caccggtgac cacgatgtcg cgatccccc cgcgttccat 80280
cgtggagtgc ggtggggtgc ccgcgatcat atgtgcccta ctggccagag acccggcctg 80340
tttatggacc ggacccccgg ggttagtgtt gtttccgcca cccatgcccc cgtaccatgg 80400
ccccggttcc cctgattagg ctacgagtcg cggtgatcgc ttcccaaaaa ccgagctgcg 80460
tttgtctgtc ttgatctttc cccccccgc ccgcccgccc gcccgcacac cataacaccg 80520
agaacaacac acgggggtgg gcgtaacata ataaagcttt attggtaact agttaacggc 80580
aagtccgtgg gtggcgcgac ggtgtcctcc gggctcatct cgtcgtcctc gacgggggtg 80640
ttggaatgag gcgcccctc gcggtccgcc tggcgtgggc cgtgcccata ggcctccggc 80700
ttctgtgcgt ccatgggcat aggcgcgggg agactgtttc cggcgtcgcg gacctccagg 80760
tccctgggag actccggtcc ggctaacgga cgaaacgcgg aagcgcgaaa cacgccgtcg 80820
gtgacccgca ggagctcgtt catcagtaac caatccatac tcagcgtaac ggccagcccc 80880
tggcgagaca gatccacgga gtccggaacc gcggtcgtct ggcccagggg gccgaggctg 80940
tagtcccccc aggcccctag gtcgcgacgg ctcgtaagca cgacgcggtc ggccgcgggg 81000
ctttgcgggg gggcgtcctc gggcgcatgc gccattacct ctcggatggc cgcggcgcgc 81060
tggtcggccg agctgaccaa gggcgccacg accacggcgc gctccgtctg caggcccttc 81120
cacgtgtcgt ggagttcctg gacaaactcg gccacgggct cgggtcccgc ggccgcgcgc 81180
gcggcttgat agcaggccga gagacgccgc cagcgcgcta gaaactgacc catgaagcaa 81240
aacccgggga cctggtctcc cgacagcagc ttcgacgccc gggcgtgaat gccggacacg 81300
acggacagaa acccgtgaat ttcgcgccgg accacggcca gcacgttgtc ctcgtgcgac 81360
acctgggccg ccagctcgtc acacacccc aggtgcgccg tggtttcggt gatgacggaa 81420
cgcaggctcg cgagggacgc gaccagcgcg cgcttggcgt cgtgatacat gctgcagtac 81480
tgactcaccg cgtcccccat ggcctcgggg ggccagggcc ccaggcggtc gggcgtgtcc 81540
ccgaccaccg catacaggcg gcgcccgtcg ctctcgaacc gacactcgaa aaaggcggag 81600
agcgtgcgca tgtgcagccg cagcagcacg atggcgtcct ccagttggcg aatcaggggg 81660
tctgcgcgct cggcgaggtc ctgcagcacc ccccgggcgg ccagggcgta catgctaatc 81720

-continued aacaggaggc tggtgcccac ctcggggggc gggggggct gcagctggac caggggccgc 81780
agctgctcga cggcacccct ggagatcacg tacagctccc ggagcagctg ctctatgttg 81840
tcggccatct gcatagtggg gccgaggccg ccccgggcgg ccggttcgag gagggtaatc 81900
agcgcgccca gtttggtgcg atggccctcg accgtgggga gatagcccag cccaaaatcc 81960
cgggcccagg ccaacacacg cagggcgaac tcgaccgggc gtggaaggta ggccgcgcta 82020
cacgtggccc tcaacgcgtc cccgaccacc agggccagaa cgtaggggac gaagcccggg 82080
tcggcgagga cgttggggtg aatgccctcg agggcgggga agcggatctg ggtcgccgcg 82140
gccaggtgga cagagggggc gtggctgggc tgcccgacgg ggagaagcgc ggacagcggc 82200
gtggccgggg tggtgggggt gatgtcccag tgggtctgac catacacgtc gatccagatg 82260
agcgccgtct cgcggagaag gctgggttga ccggaactaa agcggcgctc ggccgtctca 82320
aactccccca cgagcgcccg ccgcaggctc gccagatgtt ccgtcggcac ggccggaccc 82380
atgatacgcg ccagcgtctg gctcagaacg ccccccgaca ggccgaccgc ctcgcagagc 82440
cgcccgtgcg tgtgctcgct ggcgccctgg acccgcctga aagtttttac gtagttggca 82500
tagtacccgt attcccgcgc cagaccaaac acgttcgacc ccgcgagggc aatgcaccca 82560
aagagctgct ggacttcgcc gagtccgtgg ccggcgggcg tccgcgcggg gacgcccgcc 82620
gccagaaacc cctccagggc cgaaaggtag tgcgtgcagt gcgagggcgt gaacccagcg 82680
tcgatcaggg tgttgatcac cacggagggc gaattggtat tctggatcaa cgtccacgtc 82740
tgctgcaaca gagccaacag ccgctgctgg gcgccggcgg agggctgctc cccgagctgc 82800
agcaggctgg agacggcagg ctggaagact gccagtgccg acgaactcag gaacggcacg 82860
tcgggatcaa acacggccac gtccgtccgc acgcgcgcca ttagcgtccc cgggggcgca 82920
caggccgagc gcgggctgac gcggctgagg gccgtcgaca cgcgcacctc ctcgcggctg 82980
cgaaccatct tgttggcctc cagtggcgga atcattatgg ccgggtcgat ctcccgcacg 83040
gtgtgctgaa actgcgccaa caggggcggc gggaccacag ccccccgctc gggggtcgtc 83100
aggtactcgt ccaccagggc caacgtaaag agggcccgtg tgaggggagt gagggtcgcg 83160
tcgtctatgc gctggaggtg cgccgagaac agcgtcaccc gattactcac cagggccaag 83220
aaccggaggc cctcttgcac gaacggggcg gggaagagca ggctgtacgc cggggtggta 83280
aggttcgcgc tgggctgccc caacgggacc ggcgccatct tgagcgacgt ctccccaagg 83340
gcctcgatgg aggtccgcgg gctcatggcc aagcagctct tggtgacggt ttgccagcgg 83400
tctatccact ccacggcgca ctggcggacg cggaccggcc ccagggccgc cgcggtgcgc 83460
aggccggcgg aatccagcgc atgggacgtg tcggagccgg tgaccgcgag gatggtgtcc 83520
ttgatgacct ccatctcccg gaaggcctgg tcgggggcct cggggagagc caccaccaag 83580
cggtgtacga gcaacccggg gaggttctcg gccaagagcg ccgtctccgg aagcccgtgg 83640
gcccggtgga gcgcgcacag gtgttccagc agcggccgcc agcatgcccg cgcgtctgcc 83700
ggggcgatgg ccgttcccga caacagaaac gccgccatgg cggcgcgcag cttggccgtg 83760
gccagaaacg ccgggtcgtc cgcccccgttt gccgtctcgg ccgtgggggt tggcggttgg 83820
cgaaggccgg ctaggctcgc caataggcgc tgcataggtc cgtccgaggg cggaccggcg 83880
ggtgaggtcg tgacgacggg ggcctcggac gggagaccgc ggtctgccat gacgcccggc 83940
tcgcgtgggt gggggacagc gtagaccaac gacgagaccg ggcgggaatg actgtcgtgc 84000
gctgtaggga gcggcgaatt atcgatcccc tgcggccctc caggaacccc gcaggcgttg 84060
cgagtacccc gcgtcttcgc ggggtgttat acggccactt aagtcccggc atcccgttcg 84120
cggacccagg cccgggggat tgtccggatg tgcgggcagc ccggacggcg tgggttgcgg 84180
actttctgcg gggcggccca aatggccctt taaacgtgtg tatacggacg cgccgggcca 84240
gtcggccaac acaacccacc ggaggcggta gccgcgtttg gctgtggggt gggtggttcc 84300
gccttgcgtg agtgtccttt cgaccccccc ctcccccggg tcttgctagg tcgcgatctg 84360
tggtcgcaat gaagaccaat ccgctacccg caaccccttc cgtgtggggc gggagtaccg 84420
tggaactccc ccccaccaca cgcgataccg cggggcaggg cctgcttcgg cgcgtcctgc 84480
gccccccgat ctctcgccgc gacggcccag tgctccccag gggtcggga ccccggaggg 84540
cggccagcac gctgtggttg cttggcctgg acggcacaga cgcgcccct ggggcgctga 84600
cccccaacga cgataccgaa caggccctgg acaagatcct gcggggcacc atgcgcgggg 84660
gggcggccct gatcggctcc ccgcgccatc atctaacccg ccaagtgatc ctgacggatc 84720
tgtgccaacc caacgcggat cgtgccggga cgctgcttct ggcgctgcgg caccccgccg 84780
acctgcctca cctggcccac cagcgcgccc cgccaggccg gcagaccgag cggctgggcg 84840
aggcctgggg ccagctgatg gaggcgaccg ccctggggtc ggggcgagcc gagagcgggt 84900
gcacgcgcgc gggcctcgtg tcgtttaact tcctggtggc ggcgtgtgcc gcctcgtacg 84960
acgcgcgcga cgccgccgat gcggtacggg cccacgtcac ggccaactac cgcgggacgc 85020
gggtgggggc gcgcctggat cgtttttccg agtgtctgcg cgccatggtt cacacgcacg 85080
tcttccccca cgaggtcatg cggtttttcg gggggctggt gtcgtgggtc acccaggacg 85140
agctagcgag cgtcaccgcc gtgtgcgccg ggccccagga ggcggcgcac accggccacc 85200
cgggccggcc ccgctcggcc gtgatcctcc cggcgtgtgc gttcgtggac ctggacgccg 85260
agctggggct ggggggcccg ggcgcggcgt ttctgtacct ggtattcact taccgccagc 85320
gccgggacca ggagctgtgt tgtgtgtacg tgatcaagag ccagctcccc ccgcgcgggt 85380
tggagccggc cctggagcgg ctgtttgggc gcctccggat caccaacacg attcacggca 85440
ccgaggacat gacgcccccg gccccaaacc gaaaccccga cttccccctc gcgggcctgg 85500
ccgccaatcc ccaaaccccg cgttgctcgg ctggccaggt cacgaacccc cagttcgccg 85560
acaggctgta ccgctggcag ccggaccttc gggggcgccc caccgcacgc acctgtacgt 85620
acgccgcctt tgcagagctc ggcatgatgc ccgaggatag tccccgctgc ctgcaccgca 85680
ccgagcgctt tggggcggtc agcgtccccg ttgttattct ggaaggcgtg gtgtggcgcc 85740
ccggcgagtg gcgggcatgc gcgtgagcgt agcaaacgcc ccgcccacac aacgctccgc 85800
ccccaacccc ttccccgctg tcactcgtgg ttcgttgacc cggacgtccg ccaaataaag 85860
ccactgaaac ccgaaacgcg agtgttgtaa cgtcctttgg gcgggaggaa gccacaaaat 85920
gcaaatggga tacatggaag gaacacaccc ccgtgactca ggacatcggc gtgtcctttt 85980
gggtttcact gaaactggcc cgcgccccac ccctgcgcga tgtggataaa aagccagcgc 86040
gggtggttta gggtaccaca ggtgggtgct ttggaaactt gtcggtcgcc gtgctcctgt 86100
gagcttgcgt ccctccccgg tttcctttgc gctcccgcct tccggacctg ctctcgccta 86160
tcttctttgg ctgtcggtgc gattcgtcag gcagcggcct tgtcgaatct cgaccccacc 86220
actcgccgga cccgccgacg tcccctctgg agcccgccga aacccgccgc gtctgttgaa 86280
atggccagcc gcccagccgc atcctctccc gtcgaagcgc gggccccggt tgggggacag 86340
gaggccggcg gccccagcgc agccacccag ggggaggccg ccggggcccc tctcgcccac 86400
ggccaccacg tgtactgcca gcgagtcaat ggcgtgatgg tgctttccga caagacgccc 86460

-continued

```
gggtccgcgt cctaccgcat cagcgatagc aactttgtcc aatgtggttc caactgcacc  86520
atgattatcg acggagacgt ggtgcgcggg cgcccccagg acccgggggc cgcggcatcc  86580
cccgctccct tcgttgcggt gacaaacatc ggagccggca gcgacggcgg gaccgccgtc  86640
gttgcattcg ggggaacccc acgtcgctcg gcggggacgt ctaccggtac ccagacggcc  86700
gacgtcccag ccgaggccct tgggggcccc cctcctcctc cccgcttcac cctgggtggc  86760
ggctgttgct cctgtcgcga cacacggcgc cgctctgcgg tattcggggg ggaggggat  86820
cccgtcggcc ccgcggagtt cgtctcggac gaccggtcgt ccgattccga ctcggatgac  86880
tcggaggaca ccgactcgga gacgctgtca cacgcctcct cggacgtgtc cggcggggcc  86940
acgtacgacg acgcccttga ctccgattcg tcatcggatg actccctgca gatagatggc  87000
cccgtgtgtc gcccgtggag caatgacacc gcgcccctgg atgtttgccc cgggaccccc  87060
ggcccgggcg ccgacgccgg tggtccctca gcggtagacc cacacgcgcc gacgacaggg  87120
gccggcgctg gtcttgcggc cgatcccgcc gtggcccggg acgacgcgga ggggctttcg  87180
gacccccggc cacgtctggg aacgggcacg gcctaccccg tccccctgga actcacgccc  87240
gagaacgcgg aggccgtggc gcgctttctg ggagatgccg tgaaccgcga acccgcgctc  87300
atgctggagt acttttgccg gtgcgcccgc gaggaaacca agcgtgtccc ccccaggaca  87360
ttctgcagcc cccctcgcct cacggaggac gactttgggc ttctcaacta cgcgctcgtg  87420
gagatgcagc gcctgtgtct ggacgttcct ccggtcccgc cgaacgcata catgccctat  87480
tatctcaggg agtatgtgac gcggctggtc aacgggttca agccgctggt gagccggtcc  87540
gctcgccttt accgcatcct gggggttctg gtgcacctgc ggatccggac ccgggaggcc  87600
tcctttgagg agtggctgcg atccaaggaa gtggccctgg actttggcct gacggaaagg  87660
cttcgcgagc acgaagccca gctggtgatc ctggcccagg ttctggacca ttacgactgt  87720
ctgatccaca gcacaccgca cacgctggtc gagcgggggc tgcaatcggc cctgaagtat  87780
gaggagtttt acctaaagcg ctttggcggg cactacatgg agtccgtctt ccagatgtac  87840
acccgcatcg ccggcttttt ggcctgccgg gccacgcgcg gcatgcgcca catcgccctg  87900
gggcgagagg ggtcgtggtg ggaaatgttc aagttctttt tccaccgcct ctacgaccac  87960
cagatcgtac cgtcgacccc cgccatgctg aacctgggga cccgcaacta ctacacctcc  88020
agctgctacc tggtaaaccc ccaggccacc acaaacaagg cgaccctgcg ggccatcacc  88080
agcaacgtca gtgccatcct cgcccgcaac gggggcatcg ggctatgcgt gcaggcgttt  88140
aacgactccg gccccgggac cgccagcgtc atgcccgccc tcaaggtcct cgactcgctg  88200
gtggcggcgc acaacaaaga gagcgcgcgt ccgaccggcg cgtgcgtgta cctggagccg  88260
tggcacaccg acgtgcgggc cgtgctccgg atgaaggggg tcctcgccgg cgaagaggcc  88320
cagcgctgcg acaatatctt cagcgccctc tggatgccag acctgttttt caagcgcctg  88380
attcgccacc tggacggcga gaagaacgtc acatggaccc tgttcgaccg ggacaccagc  88440
atgtcgctcg ccgactttca cggggaggag ttcgagaagc tctaccagca cctcgaggtc  88500
atggggttcg gcgagcagat acccatccag gagctggcct atggcattgt gcgcagtgcg  88560
gccacgaccg ggagcccctt cgtcatgttc aaagacgcgg tgaaccgcca ctacatctac  88620
gacacccagg gggcggccat cgccggctcc aacctctgca ccgagatcgt ccatccggcc  88680
tccaagcgat ccagtggggt ctgtaatctg ggaagcgtga atctggcccg atgcgtctcc  88740
aggcagacgt ttgactttgg gcggctccgc gacgccgtgc aggcgtgcgt gctgatggtg  88800
aacatcatga tcgacagcac gctacaaccc acgccccagt gcacccgcgg caacgacaac  88860
```

-continued

```
ctgcggtcca tgggaatcgg catgcagggc ctgcacacgg cctgcctgaa gctggggctg  88920
gatctggagt ctgccgaatt tcaggacctg aacaaacaca tcgccgaggt gatgctgctg  88980
tcggcgatga agaccagcaa cgcgctgtgc gttcgcgggg cccgtccctt caaccacttt  89040
aagcgcagca tgtatcgcgc cggccgcttt cactgggagc gctttccgga cgcccggccg  89100
cggtacgagg gcgagtggga gatgctacgc cagagcatga tgaaacacgg cctgcgcaac  89160
agccagtttg tcgcgctgat gcccaccgcc gcctcggcgc agatctcgga cgtcagcgag  89220
ggctttgccc ccctgttcac caacctgttt agcaaggtga cccgggacgg cgagacgctg  89280
cgccccaaca cgctcctgct aaaggaactg gaacgcacgt ttagcgggaa gcgcctcctg  89340
gaggtgatgg acagtctcga cgccaagcag tggtccgtgg cgcaggcgct cccgtgcctg  89400
gagcccaccc accccctccg gcgattcaag accgcgtttg actacgacca gaagttgctg  89460
atcgacctgt gtgcggaccg cgccccctac gtcgaccata gccaatccat gaccctgtat  89520
gtcacggaga aggcggacgg gaccctccca gcctccaccc tggtccgcct tctggtccac  89580
gcatataagc gcggactaaa aacagggatg tactactgca aggttcgcaa ggcgaccaac  89640
agcggggtct ttggcggcga cgacaacatt gtctgcacga gctgcgcgct gtgaccgaca  89700
aaccccctcc gcgccaggcc cgccgccact gtcgtcgccg tcccacgcgc tcccccgctg  89760
ccatggattc cgcggcccca gccctctccc ccgctctgac ggcccatacg ggccagagcg  89820
cgccggcgga cctggcgatc cagattccaa agtgccccga ccccgagagg tacttctaca  89880
cctcccagtg tcccgacatt aaccacctgc gctccctcag catccttaac cgctggctgg  89940
aaaccgagct tgttttcgtg ggggacgagg aggacgtctc caagctttcc gagggcgagc  90000
tcagctttta ccgcttcctc ttcgctttcc tgtcggccgc cgacgacctg gttacggaaa  90060
acctgggcgg cctctccggc ctgtttgagc agaaggacat tctccactac tacgtggagc  90120
aggaatgcat cgaagtcgta cactcgcgcg tgtacaacat catccagctg gtgctttttc  90180
acaacaacga ccaggcgcgc cgcgagtacg tggccggcac catcaaccac ccggccatcc  90240
gcgccaaggt ggactggttg gaagcgcggg tgcgggaatg cgcctccgtt ccggaaaagt  90300
tcattctcat gatcctcatc gagggcatct tttttgccgc ctcgtttgcc gccatcgcct  90360
accttcgcac caacaacctt ctgcgggtca cctgccagtc aaacgacctc atcagccggg  90420
acgaggccgt gcacacgacg gcctcgtgtt acatctacaa caactacctc ggcgggcacg  90480
ccaagccccc gcccgaccgc gtgtacgggc tgttccgcca ggcggtcgag atcgagatcg  90540
gatttatccg atcccaggcg ccgacggaca gccatatcct gagcccggcg gcgctggcgg  90600
ccatcgaaaa ctacgtgcga ttcagcgcgg atcgcctgtt gggccttatc cacatgaagc  90660
cactgttttc cgccccaccc cccgacgcca gctttccgct gagcctcatg tccaccgaca  90720
aacacaccaa ttttttcgag tgtcgcagca cctcctacgc cggggcggtc gtcaacgatc  90780
tgtgagggtc gcggcgcgct tctacccgtg tttgcccata ataaacctct gaaccaaact  90840
ttgggtctca ttgtgattct tgtcagggac gcgggggtgg gagaggataa aaggcggcgc  90900
aaaaagcagt aaccaggtcc ggccagattc tgagggcata ggataccata attttattgg  90960
tgggtcgttt gttcggggac aagcgcgctc gtctgacgtt tgggctactc gtcccagaat  91020
ttggccagga cgtccttgta gaacgcgggt gggggggcct gggtccgcag ctgctccaga  91080
aacctgtcgg cgatatcagg ggccgtgata tgccgggtca cgatagatcg cgccaggttt  91140
tcgtcgcgga tgtcctggta gataggcagg cgtttcagaa gagtccacgg cccccgctcc  91200
```

-continued

```
ttggggccga taagcgatat gacgtactta atgtagcggt gttccaccag ctcggtgatg  91260
gtcatgggat cggggagcca gtccagggac tctggggcgt cgtggatgac gtggcgtcgc  91320
cggctggcca cataactgcg gtgctcttcc agcagctgcg cgttcgggac ctggacgagc  91380
tcgggcgggg tgagtatctc cgaggaggac gacctggggc cggggtggcc cccggtaacg  91440
tcccggggat ccagggggag gtcctcgtcg tcttcgtatc cgccggcgat ctgttgggtt  91500
agaatttcgg tccacgagac gcgcgtctcg gtgccgccgg tggccggcgg cagagggggc  91560
ctggtttccg tggagcgcga gctggtgtgt tcccggcgga tggcccgccg ggtctgagag  91620
cgactcgggg gggtccagtg acattcgcgc agcacatcct ccacggaggc gtaggtgtta  91680
ttgggatgga ggtcggtgtg gcagcggaca aagagggcca ggaactgggg gtagctcatc  91740
ttaaagtact tcagtatatc gcgacagttg atcgtgggaa tgtagcaggc gctaatatcc  91800
aacacaatat cgcagcccat caacaggagg tcagtgtccg tggtgtacac gtacgcgacc  91860
gtgttggtgt gatagaggtt ggcgcaggca tcgtccgcct ccagctgacc cgagttaatg  91920
taggcgtacc ccagggcccg gagaacgcga atacagaaca gatgcgccag acgcagggcc  91980
ggcttcgagg gcgcggcgga cggcagcgcg gctccggacc cggccgtccc ccgggtcccc  92040
gaggccagag aggtgccgcg tcggcgcatg ttggaaaagg cagagctggg tctggagtcg  92100
gtgatggggg aaggcggtgg agaggcgtcc acgtcactgg cctcctcgtc cgtccggcac  92160
tgggccgtcg tgcgggccag gatggccttg gctccaaaca caaccggctc catacaattg  92220
accccgcgat cggtaacgaa gatggggaaa agggactttt gggtaaacac ctttaataag  92280
cgacagaggc agtgtagcgt aatggcctcg cggtcgtaac tggggtatcg gcgctgatat  92340
ttgaccacca acgtgtacat gacgttccac aggtccacgg caatgggggt gaagtacccg  92400
gccggggccc caaggccccg gcgcttgacc agatggtgtg tgtgggcaaa cttcatcatc  92460
ccgaacaaac ccatgtcagg tcgattgtaa ctgcggatcg gcctaactaa ggcgtggttg  92520
gtgcgacggt ccgggacacc cgagcctgtc tctctgtgta tggtgaccca gacaacaaca  92580
ccgacacaag aggacaataa tccgttaggg gacgctcttt ataatttcga tggcccaact  92640
ccacgcggat tggtgcagca ccctgcatgc gccggtgcgg gccaaccttc cccccgctca  92700
ttgcctcttc caaaagggtg tggcctaacg agctgggggc gtatttaatc aggctagcgc  92760
ggcgggcctg ccgtagtttc tggctcggtg agcgacggtc cggttgcttg ggtcccctgg  92820
ctgccatcaa aaccccaccc tcgcagcggc atacgccccc tccgcgtccc gcacccgaga  92880
ccccggcccg gctgccctca ccaccgaagc ccacctcgtc actgtggggt gttcccagcc  92940
cgcgttggga tgacggattc ccctggcggt gtggcccccg cctcccacgt ggaggacgcg  93000
tcggacgcgt ccctcgggca gccggaggag ggggcgccct gccaggtggt cctgcagggc  93060
gccgagctta atggaatcct acaggcgttt gccccgctgc gcacgagcct tctggactcg  93120
cttctggtta tgggagaccg gggcatcctt atccataaca cgatctttgg ggagcaggtg  93180
ttcctgcccc tggaacactc gcaattcagt cggtatcgct ggcgcggacc cacggcggcg  93240
ttcctgtctc tcgtggacca gaagcgctcc ctcctgagcg tgtttcgcgc caaccagtac  93300
ccggacctac gtcgggtgga gttggcgatc acgggccagg ccccgtttcg cacgctggtt  93360
cagcgcatat ggacgacgac gtccgacggc gaggccgttg agctagccag cgagacgctg  93420
atgaagcgcg aactgacgag ctttgtggtg ctggttcccc agggaacccc cgacgttcag  93480
ttgcgcctga cgaggccgca gctcaccaag gtccttaacg cgaccggggc cgatagtgcc  93540
acgcccacca cgttcgagct cggggttaac ggcaaatttt ccgtgttcac cacgagtacc  93600
```

```
tgcgtcacat ttgctgcccg cgaggagggc gtgtcgtcca gcaccagcac ccaggtccag  93660
atcctgtcca acgcgctcac caaggcgggc caggcggccg ccaacgccaa gacggtgtac  93720
ggggaaaata cccatcgtac cttctctgtg gtcgtcgacg attgcagcat gcgggcggtg  93780
ctccggcgac tgcaggtcgc cgggggcacc ctcaagttct tcctcacgac cccgtcccc  93840
agtctgtgcg tcaccgccac cggtcccaac gcggtatcgg cggtatttct cctgaaaccc  93900
cagaagattt gcctggactg gctgggtcat agccaggggt ctccttccgc cgggagctcg  93960
gcctcccggg cctctgggag cgagccaaca gacagccagg actccgcgtc ggacgcggtc  94020
agccacggcg atccggaaga cctcgatggc gctgcccggg cgggagaggc gggggcctcg  94080
tacgcctgtc cgatgccgtc gtcgaccacg cgggtcactc ccacgaccaa gcgggggcgc  94140
tcggggggcg aggatgcgca cgcggacacg gccctaaaga aacctaagac ggggtcgccc  94200
accgcacccc cgcccgcaga tccagtcccc ctggacacgg aggacgactc cgatgcggcg  94260
gacgggacgg cggcccgtcc cgccgctcca gacgcccgaa gcggaagccg ttacgcgtgt  94320
tactttcgcg acctcccgac cggagaagca agccccggcg ccttctccgc cttccggggg  94380
ggcccccaaa ccccgtctgg ttttggattc ccctgacggg gcggggcctt agcggccgcc  94440
caaccctcgc aacatcccgg ggttaatgta aataaacttg gtattgccca acactctccc  94500
gcgtgtcgcg tgtggttcat gtgtgtgcct ggcgccccca ccctcgggtt cgtgtatttc  94560
ctttccctgt ccttataaaa gccgtatgtg gggcgctgac ggaaccaccc cgcgtgccat  94620
cacggccaag gcgcgggatg ctccgcaacg acagccaccg ggccgcgtcc ccggaggacg  94680
gccagggacg ggtcgacgac ggacggccac acctcgcgtg cgtgggggcc ctggcgcggg  94740
ggttcatgca tatctggctt caggccgcca cgctgggttt tgcgggatcg gtcgttatgt  94800
cgcgcgggcc gtacgcgaat gccgcgtctg gggcgttcgc cgtcgggtgc gccgtgctgg  94860
gctttatgcg cgcgccccct cccctcgcgc ggcccaccgc gcggatatac gcctggctca  94920
aactggcggc cggtggagcg gcccttgttc tgtggagtct cggggagccc ggcacgcagc  94980
cgggggccct ggccccgggc ccggccaccc agtgcctggc gctgggcgcc gcctatgcgg  95040
cgctcctggt gctcgccgat gacgtctatc cgctctttct cctcgccccg gggcccctgt  95100
tcgtcggcac cctggggatg gtcgtcggcg ggctgacgat cggaggcagc gcgcgctact  95160
ggtggatcgg tgggcccgcc gcggccgccc tggccgcggc ggtgttggcg ggcccggggg  95220
cgaccaccgc cagggactgc ttctccaggg cgtgccccga ccaccgccgc gtctgcgtca  95280
tcgtcgcagg cgagtctgtt tcccgccgcc ccccggagga cccagagcga cccggggacc  95340
cagggccacc gtcccccccg acaccccaac gatcccaggg gccgccggcc gatgaggtcg  95400
caccggccgg ggtagcgcgg cccgaaaacg tctgggtgcc cgtggtcacc tttctgggggg  95460
ctggcgcgct cgccgtcaag acggtgcgag aacatgcccg gggaacgccg ggcccgggcc  95520
tgccgctgtg gccccaggtg tttctcggag gccatgtggc ggtggccctg acggagctgt  95580
gtcaggcgct tgcgccctgg gaccttacgg acccgctgct gtttgttcac gccggactgc  95640
aggtcatcaa cctcgggttg gtgtttcggt tttccgaggt tgtcgtgtat gcggcgctag  95700
ggggtgccgt gtggatttcg ttggcgcagg tgctggggct ccggcgtcgc ctgcacagga  95760
aggaccccgg ggacggggcc cggttggcgg cgacgcttcg gggcctcttc ttctccgtgt  95820
acgcgctggg gtttggggtg ggggcgctgc tgtgccctcc ggggtcaacg ggcgggcggt  95880
cgggcgattg atatattttt caataaaagg cattagtccc gaagaccgcc ggtgtgtgat  95940
```

-continued

```
gatttcgcca taacacccaa accccggatg gggcccgggt ataaattccg gaaggggaca  96000
cgggctacct tcactaccga gggcgcttgg tcgggaggcc gcatcgaacg cacaccccca  96060
tccggtggtc cgtgtggagg tcgtttttca gtgcccggtc tcgctttgcc gggaacgcta  96120
gccgatccct cgcgaggggg aggcgtcggg catggccccg gggcgggtgg gccttgccgt  96180
ggtcctgtgg agcctggtgt ggctcggggc gggggtgtcc gggggctcgg aaactgcctc  96240
caccgggccc acgatcaccg cgggagcggt gacgaacgcg agcgaggccc ccacatcggg  96300
gtcccccggg tcagccgcca gcccggaggt cacccccaca tcgaccccaa accccaacaa  96360
tgtcacacaa aaccaaacca cccccaccga gccggccagc cccccaacaa cccccaagcc  96420
cacctccaca cccaaaagcc cccccacgtc cacccccgac cccaaaccca agaacaacac  96480
cacccccgcc aagtcggacc gccccactaa accccccggg cccgtgtggt gcgaccgccg  96540
cgatttattg gcccggtacg gctcgcgggt gcagatccga tgccggtttc ggaattccac  96600
ccgcatggag ttccgcctcc agatatggcg ttactccatg ggtccgtccc ccccaatcgc  96660
tccggctccc gacctagagg aggtcctgac gaacatcacc gccccacccg gggactcct   96720
ggtgtacgac agcgccccca acctaacgga cccccacgtg ctctgggcgg agggggccgg  96780
cccgggcgcc gaccctccgt tgtattctgt caccgggccg ctgccgaccc agcggctgat  96840
tatcggcgag gtgacgcccg cgacccaggg aatgtattac ttggcctggg gccggatgga  96900
cagcccgcac gagtacggga cgtgggtgcg cgtccgcatg ttccgccccc cgtctctgac  96960
cctccagccc cacgcggtga tggagggtca gccgttcaag gcgacgtgca cggccgccgc  97020
ctactacccg cgtaaccccg tggagtttgt ctggttcgag gacgaccacc aggtgtttaa  97080
cccgggccag atcgacacgc agacgcacga gcaccccgac gggttcacca cagtctctac  97140
cgtgacctcc gaggctgtcg gcggccaggt ccccccgcgg accttcacct gccagatgac  97200
gtggcaccgc gactccgtga cgttctcgcg acgcaatgcc accgggctgg ccctggtgct  97260
gccgcggcca accatcacca tggaatttgg ggtccggcat gtggtctgca cggccggctg  97320
cgtccccgag ggcgtgacgt ttgcctggtt cctgggggac gacccctcac cggcggctaa  97380
gtcggccgtt acggcccagg agtcgtgcga ccgccccggg ctggctacgg tccggtccac  97440
cctgcccatt tcgtacgact acagcgagta catctgtcgg ttgaccggat atccggccgg  97500
gattcccgtt ctagagcacc acggcagtca ccagccccca cccagggacc ccaccgagcg  97560
gcaggtgatc gaggcgatcg agtgggtggg gattggaatc ggggttctcg cggcgggggt  97620
cctggtcgta acggcaatcg tgtacgtcgt ccgcacatca cagtcgcggc agcgtcatcg  97680
gcggtaacgc gagacccccc cgttaccttt ttaatatcta tatagtttgg tccccctcta  97740
tcccgcccac cgctgggcgc tataaagccg ccaccctctc ttccctcagg tcatccttgg  97800
tcgatcccga acgacacacg gcgtggagca aaacgcctcc ccctgagccg ctttcctacc  97860
agcgcaacgg catgcctctg cgggcatcgg aacacgccta ccggcccctg ggccccggga  97920
cacccccat gcgggctcgg ctccccgccg cggcctgggt tggcgtcggg accatcatcg   97980
ggggagttgt gatcattgcc gcgttggtcc tcgtgccctc gcgggcctcg tgggcacttt  98040
ccccatgcga cagcggatgg cacgagttca acctcgggtg catatcctgg gatccgaccc  98100
ccatggagca cgagcaggcg gtcggcggct gtagcgcccc ggcgaccctg atcccccgcg  98160
cggctgccaa acagctggcc gccgtcgcac gcgtccagtc ggcaagatcc tcgggctact  98220
ggtgggtgag cggagacggc attcgggcct gcctgcggct cgtcgacggc gtcggcggta  98280
ttgaccagtt ttgcgaggag cccgcccttc gcatatgcta ctatccccgc agtcccgggg  98340
```

gctttgttca gtttgtaact tcgacccgca acgcgctggg gctgccgtga ggcgcgtgta 98400
ctgcggtctg tctcgtctcc tcttctcccc ttccctcccc ctccgcatcc caggatcaca 98460
ccggccaacg agggttgggg ggtccggcac ggacccaaaa taataaacac acaatcacgt 98520
gcgataaaaa gaacacgcgg tcccctgtgg tgtttttggt tatttttatt aaatctcgtc 98580
gtcaaacagg gggaaagggg cgtggtctag cgacggcagc acgggtggag gcgttcaccg 98640
gctccggcgt ccttcgcgtt taagcttggt caggagggcg ctcagggcgg cgacgttggt 98700
cgggccgtcg ttggtcaggg cgttggctcg atggcgggcg aggacgggcg aggggctcaa 98760
cggcgggggc gggggcccgg tgcggcccgg gggggaaaat agggcggatc ccccccagtc 98820
gtacagggga ttttccgcct caatgtacgg ggaggccggc gctgcattcg ccgtgttcgc 98880
gcagacgttt tcgtagaccc gcatccatgg tatttcctcg tagacacgcc ccccgtcctc 98940
gctcacagtc tcgtatattg actcgtcgtc ctcgtagggg gcgtgccgtt cgcgggccga 99000
ggcggcgtgg gtggctttgc ggcgggcgtc gtcgtcgtcg tcggccgtca gatacgtggc 99060
ttccatctgg tcgggttctc cctccggggc gggtccccac ccccgtggcc gatcgaggct 99120
ccccagagac gcgcgccgga cgaggagggg gcacgtcgcc gccggcggtc gcctgtcggg 99180
tcccgcgacg ttacgggccg ggaggcgcgg gggcacctcc cccatgtgcg tgtaatacgt 99240
ggccggctgt gcggccgcag cggggggctc ggcgaccggg tcgtccgcat ccggaagcgg 99300
gggcgccgcg ccgtccgcgc ggcgcctccg gaaccgccgg gtggccgcgg gggtcgagtg 99360
taggcgaggt cgggggaggg gcgggggctc gttgtcgcgc cgcgcccgct gaatcttttc 99420
ccgacaggtc ccaccccccg cgcgatgccc ccccgggccg cgggccatgt cgtccggggg 99480
aggccccgcg gaccacgtcg tccggcgaga cgccacgagc cgcaggatgg actcgtagtg 99540
gagcgacggc gccccgctgc ggagcagatc cgcggccagg gcggccccga accaagcctt 99600
gatgctcaac tccatccggg cccagctggg ggcggtcatc gtggggaaca ggggggcggt 99660
ggtccgacag aaacgctcct ggctgtccac cgcggcccgc agatactcgt tgttcaggct 99720
gtcggtggcc cagacgccgt acccggtgag ggtcgcgttg atgatatact gggcgtggtg 99780
atggacgatc gacagaacct ccaccgtgga tacgacggta tccacggtcc cgtacgtacc 99840
gccgctccgc ttgccggtct gccacaggtt ggctaggcgc gtcaggtggc ccaggacgtc 99900
gctgaccgcc gccctgagcg ccatgcactg catggagccg gtcgtgccgc tgggaccccg 99960
gtccagatgg cgcgcgaacg tttccgcggg cgcctccggg ctgccgccga gcgggaggaa 100020
ccggcgattg gagggactca gccggtggca tacgtgcttg tctgtcgtcc acagcatcca 100080
ggacgcccac cggtacagca cggagacgta ggccaggagc tcgttgagcc gcagtgcggt 100140
gtcggtgctg gggcggcttg ggtccgccgg gcgcataaag aacatgtact gctgaatccg 100200
atggagggcg tcgcgcaggc cggccacggt ggcggcgtac ttggccgccg cggccccgct 100260
cttgaacggg gtgcgcgcca gcagctttgg cgccagggtg ggccgcagca gcacgtgaag 100320
gctggggtcg cagtcgccca cggggtcctc ggggacgtcc aggccgctgg gcaccaccgt 100380
ctgcaggtac ttccagtact gcgtgaggat ggcgcggctc aactggccgc cggtgagctc 100440
cacctcgccc agcgcctggg tggcggccga agcgtagtgc cggatgtact cgtagtgcgg 100500
gtcgctggcg agcccgtcca cgatcaaact ctcgggaacc gtgttgtgtt gccgcgcggc 100560
caaccggacg ctgcgatcgg tgcaggtcag aaacgccggc tgcgcgtcgt cggagcgctg 100620
ccgcaaggcg cccacggccg cgctaaggag cccctccggg gtggggagca gacacccgcc 100680
gaagatgcgc cgctcgggaa cgcccgcgtt gtcgccgcgg atcaggttgg caggcgtcag 100740
gcaccgcgcc agccgcaggg agctcgcgcc gcgcgtccgg cgctgcatgg tgacgcccgt 100800
tcggtcggga cccgccggtc ggagttatgc cgcgtccagg gccatcgggg cgctttttat 100860
cgggaggagc ttatgggcgt ggcgggcctc ccagcccggt cgcgcgcctc cccgacacgt 100920
gcgcccgcag ggcggcggcc ccctcgtctc ccatcagcag tttcctaaac tgggacatga 100980
tgtccaccac gcggacccgc gggcccaaca cggacccgcc gcttacgggg gcggggggga 101040
agggctccag gtccttgaga agaaaggcgg ggtctgccgt cccggacacg gggcccgggg 101100
gcgctgagga ggcggggcgc agatccacgt gctccgcggc cgcgcggacg tccgcccaga 101160
acttggcggg ggtggtgcgc gcgtacaggg gctgggtcgc tcggaggacg cacgcgtagc 101220 gcagggggt gtacgtgccc acctcggggg ccgtgaatcc cccgtcaaac gcggccagtg 101280
tcacgcacgc caccacggtg tcggcaaagc ccagcagccg ctgcaggacg agcccggcgg 101340
ccagaatggc gcgcgtggcc gccgcgtcgt cccggcgccg gtgcgcgtcc ccgcacgccc 101400
gggcgtactt taaggtcacg gtcgccaggg ccgtgtgcag cgcgtacacc gcagcgccca 101460
gcacggcgtt gagcccgctg ttggcgagca gccggcgcgc tgcggtgtcg cccagcgcct 101520
cgtgctcggc ccccacgacc gcggggcttc ccaggggcag ggcgcgaaac agctcctccc 101580
gcgccacgtc cgcaaaggcg gggtggtgca cgtgcgggtg caggcgcgcc cccacgacca 101640
ccgagagcca ctggaccgtc tgctccgcca tcaccgccag cacatccagc acgcgcccca 101700
ggaaggcggc ctcccgcgtc aaaacgcacc ggacggcgtc gggattgaag cgggcgagca 101760
gggccccggt ggccaggtac gtcatgcggc cggcatagcg ggcggccacg cgacagtcgc 101820
ggtccagcag cgcgcgcacc ccgggccagt acagcaggga ccccagcgag ctgcgaaaca 101880
ccgcggcgtc ggggccggat tgggggggaca ctaacccccc cgcgctcagt aacggcacgg 101940
ccgcggcccc gacgggacgc aacgccgtga ggctcgcgaa ctgccgcctc agctcggcag 102000
ccctgtcgtc caggtccgac ccgcgcgcct ctgcgtgaag gcgcgtcccg cacacccacc 102060
cgttgatggc cagccgcacg acggcatccg ccaaaaagct catcgcctgg gcggggctgg 102120
tttttgttcg acgatccgtc aggtcaagaa tcccatcgcc cgtgatatac caggccaacg 102180
cctcgccctg ctgcagggtt tggcggaaaa acaccgcggg gttgtcgggg gaggcgaagt 102240
gcatgacccc cacgcgcgat aacccgaacg cgctatccgg acacgggtaa aacccggccg 102300
gatgccccag ggctagggcg gagcgcacgg actcgtccca cacggcaacc tgaggggcca 102360
gtcgatccaa cgggaatgcc gcccggagct ccgggcccgg cacgcgtccc tccagaacct 102420
ccaccttggg cggggaacgg gccccgccgc cgtcctccgg cccgacgtct tccgggtagt 102480
cgtcctcctc gtactgcagc tcctctagga acagcggcga cggcgccacc cgcgaaccgc 102540
cgacccgccc caaaatagcc cgcgcgtcga cgggacccag gtatcccccc tgccgggcct 102600
gcggaggacc gcggggaacc tcatcatcat cgtccaggcg accgcgcacc gactggctac 102660
gggccgcatc gggcccgggg cgctgccggg acgctcggcg atgggatgtg ggcggggctt 102720
ccgacgcgcg ccgtcgtcgg gctcgcgggc cttcccgtcg acggcgcacg ggcggctcgt 102780
cgcccgccat ctcctccaga gcctctagct cgctgtcgtc atccccgcgg aacaccgcac 102840
gcaggtaccc catgaacccc accccatcgc ccgctggctc gtccgccacg ggcgaggcgc 102900
gggggcgggt ggatgcgcgc ctcctacgcc ccgcgggttc gcgagccgac atggtggcga 102960
tagacgcggg ttatcggatg tccgctaccc cccaaaaaag aaaaagaccc cacagcgcgg 103020
atggaggccg gggtaggtgc cgccggaccc cctcgcgatg ggaatggacg ggagcgacgg 103080
ggccggcgca aaaaacgcag tatctcccgc gaaggctacc cgccgcccca gcccccggcc 103140
aaatgcggaa acggtcccgc gctctcgcct ttatacgcgg gccgccctgc gacacaatca 103200
cccgtccgtg gtttcgaatc tacacgacag gcccgcagac gcggctaaca cacacgccgg 103260
caacccagac cccagtgggt tggttgcgcg gtcccgtctc ctggctagtt cttttcccca 103320
ccaccaaata atcagacgac aaccgcaggt ttttgtaatg tatgtgctcg tgtttattgt 103380
ggatacgaac cggggacggg aggggaaaac ccagacgggg gatgcgggtc cggtcgcgcc 103440
ccctacccac cgtactcgtc aattccaagg gcatcggtaa acatctgctc aaactcgaag 103500
tcggccatat ccagagcgcc gtagggggcg gagtcgtggg gggtaaatcc cggacccggg 103560
gaatccccgt cccccaacat gtccagatcg aaatcgtcta gcgcgtcggc atgcgccatc 103620
gccacgtcct cgccgtctaa gtggagctcg tcccccaggc tgacatcggt cggggggggcc 103680
gtcgacagtc tgcgcgtgtg tcccgcgggg agaaaggaca ggcgcggagc cgccagcccc 103740
gcctcttcgg gggcgtcgtc gtccgggaga tcgagcaggc cctcgatggt agacccgtaa 103800
ttgtttttcg tacgcgcgcg gctgtacgcg tgttcccgca tgaccgcctc ggagggcgag 103860
gtcgtgaagc tggaatacga gtccaacttc gcccgaatca acaccataaa tgcgggcctg 103920
gttgccatgc agggtgggag gggtcgtcaa cggcgcccct ggctcctccg tagccgcgct 103980
gcgcaccagc gggaggttaa ggtgctcgcg aatgtggttt agctcccgca gccggcgggc 104040
ctcgattggc actccccgga cggtgagcgc tccgttgacg aacatgaagg gctggaacag 104100
acccgccaac tgacgccagc tctccaggtc gcaacagagg cagtcaaaca ggtcgggccg 104160
catcatctgc tcggcgtacg cggcccatag gatctcgcgg gtcaaaaata gatacaaatg 104220
caaaaacaga acacgcgcca gacgagcggt ctctcggtag tacctgtccg cgatcgtggc 104280
gcgcagcatt tctcccaggt cgcgatcgcg tccgcgcatg tgcgcctggc ggtgcagctg 104340
ccggacgctg gcgcgcaggt accggtacag ggccgagcag aagttggcca acacggttcg 104400
atagctctcc tcccgcgccc gtagctcggc gtggaagaaa cgagagagcg cttcgtagta 104460
gagcccgagg ccgtcgcggg tggccggaag cgtcgggaag gccacgtcgc cgtgggcgcg 104520
aatgtcgatt tgggcgcgtt cggggacgta cgcgtccccc cattccacca catcgctggg 104580
cagcgttgat aggaatttac actcccggta caggtcggcg ttggtcggta acgccgaaaa 104640
caaatcctcg ttccaggtat cgagcatggt acatagcgcg gggcccgcgc taaagcccaa 104700
gtcgtcgagg agacggttaa agagggcggc gggggggacg ggcatgggcg gggagggcat 104760
gagctgggcc tggctcaggc gccccgttgc gtacagcgga ggggccgccg gggtgttttt 104820
gggacccccg gccgggcggg ggggtggtgg cgaagcgccg tccgcgtcca tgtcggcaaa 104880
cagctcgtcg accaagaggt ccattgggtg gggttgatac gggaaagacg atatcgggct 104940
tttgatgcga tcgtccccgc ccgcccagag agtgtgggac gcccgacggc gcgggaagag 105000
aaaaaccccc aaacgcgtta gaggaccgga cggaccttat ggggggaagt gggcagcggg 105060
aaccccgtcc gttcccgagg aatgacagcc cgtggtcgcc accccgcatt taagcaaccc 105120
gcacgggccg ccccgtacct cgtgacttcc ccccacattg gctcctgtca cgtgaaggcg 105180
aaccgagggc ggctgtccaa cccacccccc gccacccagt cacggtcccc gtcggattgg 105240
gaaacaaagg cacgcaacgc caacaccgaa tgaacccctg ttggtgcttt attgtctggg 105300
tacggaagtt tttcactcga cgggccgtct ggggcgagaa gcggagcggg ctggggctcg 105360
aggtcgctcg gtggggcgcg acgccgcaga acgccctcga gtcgccgtgg ccgcgtcgac 105420

-continued gtcctgcacc acgtctggat tcaccaactc gttggcgcgc tgaagcaggt ttttgccctc 105480
gcagaccgtc acgcggatgg tggtgatgcc aaggagttcg ttgaggtctt cgtctgtgcg 105540
cggacgcgac atgtcccaga gctggaccgc cgccatccgg gcatgcatgg ccgccaggcg 105600
cccgaccgcg gcgcagaaga cgcgcttgtt aaagccggcc acccgggggg tccatggcgc 105660
gtcggggttt ggggggcgg tgctaaagtg cagctttctg gccagcccct gcgcgggtgt 105720
cttggatcgg gttggcgccg tcgacgcggg ggcgtctggg agtgcggcgg attctggctg 105780
ggccgatttc ctgccgcggg tggtctccgc cgccggggcc gcgggggcct tagtcgccac 105840
ccgctgggtt cggggggccc ggggggcggt ggtgggtgtg cgtccggccc ctccggaccc 105900
agcgggcggc ggaggcgccc gcgcaggccc cgggccggac aaaaccgccc cggaaacggg 105960
acgccgcgtc cgggggacct ccgggtgttc gtcgtcttcg gatgacgagc cccgtagag 106020 ggcataatcc gactcgtcgt actggacgaa acggacctcg cccctcgggc gcgcgcgtgt 106080
ctgtagggcg ccacggcggg aggtggcagg cggactatcg ggactcgcca tacatgaaga 106140
cggggtgtag tacagatcct cgtactcatc gcgcggaacc tcccgcggac ccgacttcac 106200
ggagcggcga gaggtcatgg ttccacgaac acgctagggt cggatgcgcg gacaattagg 106260
cctgggttcg gacggcgggg ggtggtgcag gtgtggagag gtcgagcgat aggggcggcc 106320
cgggagagaa gagagggtcc gcaaaaccca ctggggatgc gtgagtggcc ctctgtgggc 106380
ggtgggggag agtcttatag gaagtgcata taaccacaac ccatgggtct aaccaatccc 106440
caggggccaa gaaacagaca cgccccaaac ggtctcggtt tccgcgaaga aggggaagtc 106500
ctgggacacc ctccaccccc acccctcacc ccacacaggg cgggttcagg cgtgcccggc 106560
agccagtagc ctctggcaga tctgacagac gtgtgcgata atacacacgc ccatcgaggc 106620
catgcctaca taaaagggca ccagggcccc cggggcagac atttggccag cgttttgggt 106680
ctcgcaccgc gcgcccccga tcccatcgcg cccgccctcc tcgccgggcg gctccccgtg 106740
cgggcccgcg tctcccgccg ctaaggcgac gagcaagaca aacaacaggc ccgcccgaca 106800
gacccttctg ggggggccca tcgtccctaa caggaagatg agtcagtggg gatccggggc 106860
gatccttgtc cagccggaca gcttgggtcg ggggtacgat ggcgactggc acacggccgt 106920
cgctactcgc gggggcggag tcgtgcaact gaacctggtc aacaggcgcg cggtggcttt 106980
tatgccgaag gtcagcgggg actccggatg ggccgtcggg cgcgtctctc tggacctgcg 107040
aatggctatg ccggctgact tttgtgcgat tattcacgcc cccgcgctat ccagcccagg 107100
gcaccacgta atactgggtc ttatcgactc ggggtaccgc ggaaccgtta tggccgtggt 107160
cgtagcgcct aaaaggacgc gggaatttgc ccccgggacc ctgcgggtcg acgtgacgtt 107220
cctggacatc ctggcgaccc ccccggccct caccaagccg atttccctgc ggcagttccc 107280
gcaactggcg cccccccctc caaccggggc cgggatacgc gcagatcctt ggttggaggg 107340
ggcgctcggg gacccaagcg tgactccggc cctaccggcg cgacgccgag ggcggtccct 107400
cgtctatgcc ggcgagctga cgccggttca gacggaacac ggggacggcg tacgagaagc 107460
catcgccttc cttccaaaac gcgaggagga tgccggtttc gacattgtcg tccgtcgccc 107520
ggtcaccgtc ccggcaaacg gcaccacggt cgtgcagcca tccctccgca tgctccacgc 107580
ggacgccggg cccgcggcct gttatgtgtt ggggcggtcg tcgctcaacg cccgcggcct 107640
cctggtcgtt cctacgcgct ggctccccgg gcacgtatgt gcgtttgttg tttacaacct 107700
tacgggggtt cctgtgaccc tcgaggccgg cgccaaggtc gcccagctcc tggttgcggg 107760
ggcggacgct cttccttgga tccccccgga caactttcac gggaccaaag cgcttcgaaa 107820

-continued

```
ctaccccagg ggtgttccgg actcaaccgc cgaacccagg aacccgccgc tcttggtgtt 107880
tacgaacgag tttgacgcgg aggccccccc gagcgagcgc gggaccgggg gttttggctc 107940
taccggtatt tagcccatag cttggggttc gttccgggca ataaaaaacg tttgtatctc 108000
atctttcctg tgtgtagttg tttctgttgg aggcctgtgg gtctatcaca cccgcccctc 108060
catcccacaa acacagaaca cacgggttgg atgaaaacac gcatttattg acccaaaaca 108120
cacggagctg ctcgagatgg gccagggcga ggtgcggttg gggaggctgt aggtctggga 108180
acggacacgc ggggacacga ttccggtttg gggtccggga gggcgtcgcc gtttcgggcg 108240
gcaggcgcca gcgtaacctc cgggggcggc gtgtgggggt gccccaagga gggcgcctcg 108300
gtcaccccaa gcccccccaa gcgggttccc ccggcaaccc cgaaggcgga gaggccaagg 108360
gcccgttcgg cgatggccac atcctccatg accacgtcgc tctcggccat gctccgaata 108420
gcctgggaga cgagcacatc cgcggacttg tcagccgccc ccacggacat gtacatctgc 108480
aggatggtgg ccatacacgt gtccgccagg cgccgcatct tgtcctgatg ggccgccacg 108540
gccccgtcga tcgtgggggc ctcgagcccg gggtggtggc gcgccagtcg ttctaggttc 108600
accatgcagg cgtggtacgt gcgggccaag gcgcgggcct tcacgaggcg tcgggtgtcg 108660
tccagggacc ccagggcgtc atcgagcgtg atgggggcgg gaagtagcgc gttaacgacc 108720
accagggcct cctgcagccg cggctccgcc tccgagggcg gaacggccgc gcggatcatc 108780
tcatattgtt cctcggggcg cgctccccag ccacatatag ccccgagaag agaagccatc 108840
gcgggcgggt actggccctt gggcgcgcgg acgcaatggg gcaggaagac gggaaccgcg 108900
gggagaggcg ggcggccggg actcccgtgg aggtgaccgc gctttatgct accgacgggt 108960
gcgttattac ctcttcgatc gccctcctca caaactctct actgggggcc gagccggttt 109020
atatattcag ctacgacgca tacacgcacg atggccgtgc cgacgggccc acggagcaag 109080
acaggttcga agagagtcgg gcgctctacc aagcgtcggg cgggctaaat ggcgactcct 109140
tccgagtaac cttttgttta ttggggacgg aagtgggtgg gacccaccag gcccgcgggc 109200
gaacccgacc catgttcgtc tgtcgcttcg agcgagcgga cgacgtcgcc gcgctacagg 109260
acgccctggc gcacgggacc ccgctacaac cggaccacat cgccgccacc ctggacgcgg 109320
aggccacgtt cgcgctgcat gcgaacatga tcctggctct caccgtggcc atcaacaacg 109380
ccagcccccg caccggacgc gacgccgccg cggcgcagta tgatcagggc gcgtccctac 109440
gctcgctcgt ggggcgcacg tccctgggac aacgcggcct taccacgcta tacgtccacc 109500
acgaggcgcg cgtgctggcc gcgtaccgca gggcgtatta tggaagcgcg cagagtccct 109560
tctggtttct tagcaaattc gggccggacg aaaaaagcct ggtgctcacc actcggtact 109620
acctgcttca ggcccagcgt ctggggggcg cgggggccac gtacgacctg caggccatca 109680
aggacatctg cgccacctac gcgattcccc acgccccccg ccccgacacc gtcagcgccg 109740
cgtccctgac ctcgtttgcc gccatcacgc ggttctgttg cacgagccag tacgcccgcg 109800
gggccgcggc ggccgggttt ccgctttacg tggagcgccg tattgcggcc gacgtccgcg 109860
agaccagtgc gctggagaag ttcataaccc acgatcgcag ttgcctgcgc gtgtccgacc 109920
gtgaattcat tacgtacatt tacctggccc attttgagtg tttcagcccc ccgcgcctag 109980
ccacgcatct tcgggccgtg acgacccacg accccaaccc cgcggccaac acggagcagc 110040
cctcgcccct gggcagggag gccgtggaac aattttttg ccacgtgcgc gcccaactga 110100
atatcgggga gtacgtcaaa cacaacgtga ccccccggga gaccgtcctg gatggcgata 110160
```

cggccaaggc ctacctgcgc gctcgcacgt acgcgcccgg ggccctgacg cccgcccccg 110220
cgtattgcgg ggccgtggac tccgccacca aaatgatggg gcgtttggcg gacgccgaaa 110280
agctcctggt cccccgcggg tggcccgcgt ttgcgcccgc cagtcccggg gaggatacgg 110340
cgggcggcac gccgccccca cagacctgcg gaatcgtcaa gcgcctcctg agactggccg 110400
ccacggaaca acaggacacc acgcccccgg cgatcgcggc gcttatccgt aatgcggcgg 110460
tgcagactcc cctgcccgtc taccggatat ccatggtccc cacgggacag gcatttgccg 110520
cgctggcctg ggacgactgg gcccgcataa cgcgggacgc tcgcctggcc gaagcggtcg 110580
tgtccgccga agcggcggcg caccccgacc acggcgcgct gggcaggcgg ctcacggatc 110640
gcatccgcgc ccagggcccc gtgatgcccc ctggcggcct ggatgccggg gggcagatgt 110700
acgtgaatcg caacgagata ttcaacggcg cgctggcaat cacaaacatc atcctggatc 110760
tcgacatcgc cctgaaggag cccgtcccct ttcgccggct ccacgaggcc ctgggccact 110820
ttaggcgcgg ggctctggct gcggttcagc tcctgtttcc cgcggcccgc gtggaccccg 110880
acgcatatcc ctgttatttt ttcaaaagcg catgtcggcc cggcccggcg tccgtgggtt 110940
ccggcagcgg actcggcgac gacggggact ggtttccctg ctacgacgac gccggtgatg 111000
aggagtgggc ggaggacccg ggcgccatgg acacatccca cgatccccccg gacgacgagg 111060
ttgcctactt tgacctgtgc cacgaagtcg gccccacggc ggaacctcgc gaaacggatt 111120
cgcccgtgtg ttcctgcacc gacaagatcg gactgcgggt gtgcatgccc gtccccgccc 111180
cgtacgtcgt ccacggttct ctaacgatgc ggggggtggc acgggtcatc cagcaggcgg 111240
tgctgttgga ccgagatttt gtggaggcca tcgggagcta cgtaaaaaac ttcctgttga 111300
tcgatacggg ggtgtacgcc cacggccaca gcctgcgctt gccgtatttt gccaaaatcg 111360
cccccgacgg gcctgcgtgc ggaaggctgc tgccagtgtt tgtgatcccc cccgcctgca 111420
aagacgttcc ggcgtttgtc gccgcgcacg ccgacccgcg gcgcttccat tttcacgccc 111480
cgcccaccta tctcgcttcc ccccgggaga tccgtgtcct gcacagcctg ggtggggact 111540
atgtgagctt ctttgaaagg aaggcgtccc gcaacgcgct ggaacacttt gggcgacgcg 111600
agaccctgac ggaggtcctg ggtcggtaca acgtacagcc ggatgcgggg gggaccgtcg 111660
aggggttcgc atcggaactg ctggggcgga tagtcgcgtg catcgaaacc cactttcccg 111720
aacacgccgg cgaatatcag gccgtatccg tccggcgggc cgtcagtaag gacgactggg 111780
tcctcctaca gctagtcccc gttcgcggta ccctgcagca aagcctgtcg tgtctgcgct 111840
ttaagcacgg ccgggcgagt cgcgccacgg cgcggacatt cgtcgcgctg agcgtcgggg 111900
ccaacaaccg cctgtgcgtg tccttgtgtc agcagtgctt tgccgccaaa tgcgacagca 111960
accgcctgca cacgctgttt accattgacg ccggtacgcc atgctcgccg tccgttccct 112020
gcagcacctc tcaaccgtcg tcttgataac ggcgtacggc ctcgtgctcg tgtggtacac 112080
cgtcttcggt cacccccca acgggggctg gcgcaaccac gcccatatct gctacgccaa 112140
tcttatcgcg ggtagggtcg tgcccttcca ggtcccaccc gacgccatga atcgtcggat 112200
catgaacgtc cacgaggcag ttaactgtct ggagacccta tggtacacac gggtgcgtct 112260
ggtggtcgta gggtggttcc tgtatctggc gttcgtcgcc ctccaccaac gccgatgtat 112320
gtttggtgtc gtgagtcccg cccacaagat ggtggccccg gccacctacc tcttgaacta 112380
cgcaggccgc atcgtatcga gcgtgttcct gcagtacccc tacacgaaaa ttacccgcct 112440
gctctgcgag ctgtcggtcc agcggcaaaa cctggttcag ttgtttgaga cggacccggt 112500
caccttcttg taccaccgcc ccgccatcgg ggtcatcgta ggctgcgagt tgatgctacg 112560
ctttgtggcc gtgggtctca tcgtcggcac cgctttcata tcccgggggg catgtgcaat 112620
cacatacccc ctgtttctga ccatcaccac ctggtgtttt gtctccacca tcggcctgac 112680
agagctgtat tgtattctgc ggcggggccc ggccccccaag aacgcagaca aggccgccgc 112740
cccggggcga tccaaggggc tgtcgggcgt ctgcgggcgc tgctgttcca tcatcctctc 112800
gggcatcgca gtgcgattgt gttatatcgc cgtggtggcc ggggtggtgc tcgtggcgct 112860
tcactacgag caggagatcc agaggcgcct gtttgatgta tgacgtcaca tccaggccgg 112920
cggaaaccgg aacggcatat gcaaattgga aactgtcctg tcttggggcc cacccacccg 112980
acgcgtcata tgcaaatgaa aatcggtccc ccgaggccac gtgtagcctg gatcccaacg 113040
accccgccca tgggtcccaa ttggccgtcc cgttaccaag accaacccag ccagcatatc 113100
cacccccgcc cgggtccccg cggaagcgga acggtgtatg tgatatgcta attaaataca 113160
tgccacgtac ttatggtgtc tgattggtcc ttgtctgtgc cggaggtggg gcgggggccc 113220
cgcccggggg gcggaacgag gaggggtttg ggagagccgg ccccggcacc acgggtataa 113280
ggacatccac cacccggccg gtggtggtgt gcagccgtgt tccaaccacg gtcacgcttc 113340
ggtgcctctc cccgattcgg gcccggtcgc tcgctaccgg tgcgccacca ccagaggcca 113400
tatccgacac cccagccccg acggcagccg acagcccggt catggcgact gacattgata 113460
tgctaattga cctcggcctg gacctctccg acagcgatct ggacgaggac ccacccgagc 113520
cggcggagag ccgccgcgac gacctggaat cggacagcag cggggagtgt tcctcgtcgg 113580
acgaggacat ggaagacccc cacggagagg acggaccgga gccgatactc gacgccgctc 113640
gcccggcggt ccgcccgtct cgtccagaag accccggcgt acccagcacc cagacgcctc 113700
gtccgacgga gcggcagggc cccaacgatc ctcaaccagc gccccacagt gtgtggtcgc 113760
gcctcggggc ccggcgaccg tcttgctccc ccgagcagca cgggggcaag gtggcccgcc 113820
tccaaccccc accgaccaaa gcccagcctg cccgcggcgg acgccgcggg cgtcgcaggg 113880
gtcggggtcg cggtggtccc ggggccgccg atggtttgtc ggacccccgc cggcgtgccc 113940
ccagaaccaa tcgcaacccg gggggacccc gccccggggc ggggtggacg gacggccccg 114000
gcgcccccca tggcgaggcg tggcgcggaa gtgagcagcc cgacccaccc ggaggcccgc 114060
ggacacgggg cgtgcgccaa gcaccccccc cgctaatgac gctggcgatt gcccccccgc 114120
ccgcggaccc ccgcgccccg gccccggagc gaaaggcgcc cgccgccgac accatcgacg 114180
ccaccacgcg gttggtcctg cgctccatct ccgagcgcgc ggcggtcgac cgcatcagcg 114240
agagctttgg ccgcagcgca caggtcatgc acgacccctt tgggggggcag ccgtttcccg 114300 ccgcgaatag cccctgggcc ccggtgttgg cgggccaagg agggcccttt gacgccgaga 114360
ccagacgggt ctcctgggaa accttggtcg cccacggccc gagcctctat cgcacttttg 114420
ccggcaatcc tcgggccgca tcgaccgcca aggccatgcg cgactgcgtg ctgcgccaag 114480
aaaatttcat cgaggcgctg gcctccgccg acgagacgct ggcgtggtgc aagatgtgca 114540
tccaccacaa cctgccgctg cgcccccagg accccattat cgggacggcc gcggctgtgc 114600
tggataacct cgccacgcgc ctgcggccct ttctccagtg ctacctgaag gcgcgaggcc 114660
tgtgcggcct ggacgaactg tgttcgcggc ggcgtctggc ggacattaag gacattgcat 114720
ccttcgtgtt tgtcattctg gccaggctcg ccaaccgcgt cgagcgtggc gtcgcggaga 114780
tcgactacgc gacccttggt gtcggggtcg gagagaagat gcatttctac ctccccgggg 114840
cctgcatggc gggcctgatc gaaatcctag acacacaccg ccaggagtgt tcgagtcgtg 114900
tctgcgagtt gacggccagt cacatcgtcg cccccccgta cgtgcacggc aaatattttt 114960
attgcaactc cctgttttag gtacaataaa aacaaaacat ttcaaacaaa tcgccccacg 115020
tgttgtcctt ctttgctcat ggccggcggg gcgtgggtca cggcagatgg cgggggtggg 115080
cccggcgtac ggcctgggtg ggcggaggga actaacccaa cgtataaatc cgtccccgct 115140
ccaaggccgg tgtcatagtg cccttaggag cttcccgccc gggcgcatcc cccctttgc 115200
actatgacag cgaccccct caccaacctg ttcttacggg ccccggacat aacccacgtg 115260
gcccccctt actgcctcaa cgccacctgg caggccgaaa cggccataca caccagcaaa 115320
acggactccg cttgcgtggc cgtgcggagt tacctggtcc gcgcctcctg tgagaccagc 115380
ggcacaatcc actgcttttt ctttgcggta tacaaggaca cccaccacac ccctccgctg 115440
attaccgagc tccgcaactt tgcggacctg gttaaccacc cgccggtcct acgcgaactg 115500
gaggataagc gcggggtgcg gctgcggtgt gcgcggccgt ttagcgtcgg gacgattaag 115560
gacgtctctg ggtccggcgc gtcctcggcg ggagagtaca cgataaacgg gatcgtgtac 115620
cactgccact gtcggtatcc gttctcaaaa acatgctgga tgggggcctc cgcggcccta 115680
cagcacctgc gctccatcag ctccagcggc atggccgccc gcgcggcaga gcatcgacgc 115740
gtcaagatta aaattaaggc gtgatctcca accccccat gaatgtgtgt aacccccaa 115800
aaaaataaac agccgtaacc caatcaaacc aggcgtggtg tgagtttgtg gacccaaagc 115860
cctcagagac aacgcgacag gccagtatgg accgtgatac ttttatttat taactcacag 115920
gggcgcttac cgccacagga ataccagaat aatgaccacc actatcgcga ccaccccaaa 115980
tacagcatgg cgccccacca cgccacaaca gccctgtcgc cggtatgggg catgatcaga 116040
cgagccgcga gccgcgcgtt gggccctgta cagctcgcgc gaattgaccc taggaggccg 116100
ccacgcgccc gagttttgcg ttcgtcgctg gtcgtcgggc gccaaagccc cggacggctg 116160
ttcggtcgaa cgaacggcca cgacagtggc ataggttggg gggtggtccg acatagcctc 116220
ggtgtacgtc gggaggcccg acaagaggtc ccttgagatg tcgggtgggg ccacaagcct 116280
ggtttccgga agaaacaggg gggttgccaa taacccgcca gggccaaaac tccggcgctg 116340
cgcacgtcgt tcggcgcggc gccgggcgcg ccgagcggct cgctgggcgg cttggcgtga 116400
gcggccccgc tccgacgcct cgccctctcc ggaggaggtt ggcggaattg gcacggacga 116460
caggggccca gcagagtacg gtggaggtgg gtccgtgggg gtgtccagat caataacgac 116520
aaacggcccc tcgttcctac cagacaagct atcgtagggg ggcgggggat cagcaaacgc 116580
gttccccgcg ctccatagac ccgcgtcggg ttgcgccgcc tccgaagcca tggatgcgcc 116640
ccaaagccac gactcccgcg cgctaggtcc ttggggtaag ggaaaaggcc ctactcccca 116700
tccaagccag ccaagttaac gggctacgcc ttcggggatg ggactggcac cccggcggat 116760
tttgttgggc tggtacgcgt tgcccaaccg agggccgcgt ccacgggacg cgccttttat 116820
aaccccgggg gtcattccca acgatcacat gcaatctaac tggctcccct ctcccccct 116880
ctcccctctc cccccctctc ccctctcccc ccctctcccc tctccccccc tctcccctct 116940
ccccccctct cccctctccc cccctctccc ctctcccccc ctctcccctc tcccccccctc 117000
tcccctctcc cccccctctcc cctctccccc cctctcccct ctcccccccct gctctttccc 117060
cgtgacaccc gacgctgggg ggcgtggctg ccgggagggg ccgcggatgg gcggggccta 117120
ctcggtctcc cgcccccgcc cccgaaccgc cccgccggcc ttgccccccct ttgatcccct 117180
gctaccccca acccgtgctc gtggtgcggg ttgggtgggg ggggggagtg tgggcggggg 117240
tgtgcgggag gtgtcggtgg tggtggtggt ggtaggaatg gtggtgaggg ggggggcgc 117300 tggttggtca aaaaagggag ggacgggggc cggcagaccg acggcgacaa cgctccccgg 117360
cggccgggtc gcggctctta cgagcggccc ggcccgcgct cccacccccc gggccgtgtc 117420
cttgctttcc ccccgtctcc cccccctcc ttctcctcct cctcctcctc gtttttccaa 117480
accccgccca cccggcccgg cccggcccgg ccaccgccgc ccacccaccc acctcgggag 117540
acccagcccc ggtcccccgt tccccggggg ccgttatctc cagcgccccg tccggcgcgc 117600
cgccccccgc cgctaaaccc catcccgccc ccgggacccc acatataagc ccccagccac 117660
acgcaagaac agacacgcag aacggctgtg tttatttaaa taaaccgatg tcggaataaa 117720
caaacacaaa cacccgcgac ggggggacgg agggaggggg gtgacggggg acgggaacag 117780
ccacaaaaaa cacccacaaa aaaaaacagc cacccccgac accccccccc acccccagtc 117840
tcttcgcctt ttccccccca ccccacgccc ccactgagcc cggtcgatcg acgagcaccc 117900
ccgcccccgc ccctgccccg gcgacccccg gcccgcacga tcccgacaac aataacaacc 117960
ccaacggaaa gcggcggggt gtgggggggg gcgaggaaca accgagggga acgggggatg 118020
gaaggacggg aagtggaagt cctgataccc atcctacacc cccctgcctt ccaccctccg 118080
gcccccgcg agtccacccg ccggccggct accgagaccg aacacggcgg ccgccgcagc 118140
cgccgcagcc gccgccgaca ccgcagagcc ggcgcgcgca cacacaagcg gcagaggcag 118200
aaaggcccag agtcattgtt tatgtggccg cgggccagca gacggcccgc gacacccccc 118260
cccccgcccg tgtgggtatc cggcccccg ccccgcgccg gtccattaag ggcgcgcgtg 118320
cccgcgagat atcaatccgt taagtgctct gcagacaggg gcaccgcgcc cggaaatcca 118380
ttaggccgca gacgaggaaa ataaaattac atcacctacc cacgtggtgc tgtggcctgt 118440
ttttgctgcg tcatctgagc ctttataaaa gcgggggcgc ggccgtgccg atcgcgggtg 118500
gtgcgaaaga ctttccgggc gcgtccgggt gccgcggctc tccgggcccc cctgcagccg 118560
gggcggccaa ggggcgtcgg cgacatcctc cccctaagcg ccggccggcc gctggtctgt 118620
tttttgtttt ccccgtttcg gggtgggggg gggttgcggt ttctgtttct ttaacccgtc 118680
tggggtgttt ttcgttccgt cgccggaatg tttcgttcgt ctgtcccctc acggggcgaa 118740
ggccgcgtac ggcccgggac gagggggccc ccgaccgcgg cggtccgggc cccgtccggg 118800
cccgctcgcc ggcacgcgac gcgaaaaagg ccccccggag gcttttccgg gttcccggcc 118860
cggggcctga gataaacaat cggggttacc gccaacggcc ggcccccgtg gcggcccggc 118920
ccggggcccc ggcggaccca aggggccccg gcccggggcc ccacaacggc ccggcgcatg 118980
cgctgtggtt ttttttctc ggtgttttgt cgggctccgt cgcctttcct gttctcgctt 119040
ctcccccccc cccttcttc acccccagta ccctcctccc tcccttcctc ccccgttatc 119100
ccactcgtca agggcgcccc ggtgtggttc aacaaagacg ccgcgtttcc aggtaggtta 119160
gacacctgct tctccccaat agaggggggg gacccaaacg acagggggcg ccccagaggc 119220
taaggtcggc cacgccactc gcgggtgggc tcgtgttaca gcacaccagc ccgttctttt 119280
cccccctcc cacccttagt cagactctgt tacttacccg tccgaccacc aactgccccc 119340
ttatctaagg gccggctgga agaccgccag ggggtcggcc ggtgtcgctg taacccccca 119400
cgccaatgac ccacgtactc caagaaggca tgtgtcccac cccgcctgtg tttttgtgcc 119460
tggctctcta tgcttgggtc ttactgccgg gggggggga gtgcggggga gggggggtgt 119520
ggaaggaaat gcacggcgcg tgtgtacccc ccctaaagtt gttcctaaag cgaggatatg 119580
gaggagtggc gggtgccggg ggaccggggt gatctctggc acgcgggggt gggaagggtc 119640

-continued

```
gggggagggg ggatggggta ccggcccacc tggccgacgc gggtgcgcgt gcctctgcac 119700
accaacccca cgtcccccgg cggtctctaa gaagcaccgc ccccctcct tcataccacc 119760
gagcatgcct gggtgtgggt tggtaaccaa cacgcccatc ccctcgtctc ctgtgattct 119820
ctggctgcac cgcattcttg ttttctaact atgttcctgt ttctgtctcc ccccccaccc 119880
ctccgcccca ccccccaaca cccacgtctg tggtgtggcc gaccccctt tgggcgcccc 119940
gtcccgcccc gccacccctc ccgtcctttg ttgccctata gtgtagttaa cccccccccg 120000
ccctttgtgg cggccagagg ccaggtcagt ccgggcgggc aggcgctcgc ggaaacttaa 120060
cacccacacc caacccactg tggttctggc tccatgccag tggcaggatg ctttcgggga 120120
tcggtggtca ggcagcccgg gccgcggctc tgtggttaac accagagcct gcccaacatg 120180
gcacccccac tcccacgcac ccccactccc acgcaccccc actcccacgc acccccactc 120240
ccacgcaccc ccactcccac gcacccccac tcccacgcac ccccactccc acgcaccccc 120300
actcccacgc acccccactc ccacgcaccc ccgagatcca tccaacacag acagggaaaa 120360
gatacaaaag taaaccttta tttcccaata gacagcaaaa atcccctgag ttttttatta 120420
gggccaacac taaagacccg ctggtgtgtg gtgcccgtgt ctttcacttt tcccctcccc 120480
gacacggatt ggctggtgta gtgggcgcgg ccagagacca cccagcgccc gacccccccc 120540
tccccacaaa cacgggggc gtcccttatt gttttccctc gtcccgggtc gacgccccct 120600
gctccccgga ccacgggtgc cgagaccgca ggctgcggaa gtccagggcg cccactaggg 120660
tgccctggtc gaacagcatg ttccccacgg gggtcatcca gaggctgttc cactccgacg 120720
cgggggccgt cgggtactcg gggggcatca cgtggttacc cgcggtctcg gggagcaggg 120780
tgcggcggct ccagccgggg accgcggccc gcagccgggt cgccatgttt cccgtctggt 120840
ccaccaggac cacgtacgcc ccgatgttcc ccgtctccat gtccaggatg ggcaggcagt 120900
cccccgtgat cgtcttgttc acgtaaggcg acagggcgac cacgctagag acccccgaga 120960
tgggcaggta gcgcgtgagg ccgcccgcgg gggcggcccc ggaagtctcc gcgtggcgcg 121020
tcttccgggc acacttcctc ggcccccgcg gcccagaagc agcgcggggg ccgagggagg 121080
tttcctcttg tctccctccc agggcaccga cggccccgcc cgaggaggcg gaagcggagg 121140
aggacgcggc cccggcggcg gaagaggcgg cccccgcggg agtcggggcc gaggaggaag 121200
aggcagagga ggaagaggcg gaggccgccg aggacgtcag gggggtcccg ggcccaccct 121260
ggccgcgccc ccccggccct gagtcggagg gggggtgcgt cgccgccctc ttggcccctg 121320
ccggcgcgag ggggggacgc gtggactggg gggaggggtt ttcctggccc gacccgcgcc 121380
tcttcctcgg acgcaccgcc gcctcctgct cgacagaggc ggcggagggg agcgggggg 121440
cgccggaggg ggcggcgccg cgggagggcc cgtgtccacc ctccacgccc ggcccccccg 121500
agccgcgcgc caccgtcgca cgcgcccggc acagactctg ttcttggttc gcggcctgag 121560
ccagggacga gtgcgactgg ggcacacggc gcgcgtccgc gggggccggg gcgcgggggc 121620
cgggccccgg aggcggcgct cgcacgcacg gggccacggc cgcgcggggg cgcgcgggtc 121680
ccgacgcggc cgaggacgcg gtgggcccgg ggcggggggc ggagcctggc atgggcgccg 121740
cggggggcct gtggggagag gccgggggggg agtcgctgat cactatgggg tctctgttgt 121800
ttgcaagggg ggcgggtctg ttgacaaggg ggcccgtccg gcccctcggc cgccccgcct 121860
ccgcttcaac aaccccaacc ccaaccccaa cccccccgga ggggccagac gccccccgcg 121920
gcgccgcggc tcgcgactgg cgggagccgc cgccgccgcc gctgctgttg gtggtggtgt 121980
tggtgttact gctgccgtgt ggcccgatgg gcgccgaggg gggcgctgtc cgagccgcgg 122040
```

ccggctgggg ggctgcgtga gacgccccgc ccgtcacggg gggcgcggcg gcgcctctgc 122100
gtgggggggc gcggggcgtc cggcgggggg cgggcggtac gtagtctgct gcaagagaca 122160
acggggggcg cgatcaggtt acgcccccctc ccaggccctc cctttccgcg cccgcccttt 122220
cctcgccccc ccgcccgcct attcctccct cccccctcct cctcctcctc ccccagggtc 122280
ctcgccgccc ccccgcctca ccgtcgtcca ggtcgtcgtc atcctcgtcc gtggtgggct 122340
cagggtgggt gggcgacagg gccctcaccg tgtgcccccc cagggtcagg taccgcgggg 122400
cgaaccgctg attgcccgtc cagataaagt ccacggccgt gcccgccctg acggcctcct 122460
cggcctccat gcgggtctgg gggtcgttca cgatcgggat ggtgctgaac gacccgctgg 122520
gcgtcacgcc cactatcagg tacaccagct tggcgttgca cagcgggcag gtgttgcgca 122580
attgcatcca ggttttcatg cacgggatgc agaagcggtg catgcacggg aaggtgtcgc 122640
agcgcaggtg gggcgcgatc tcatccgtgc acacggcgca cacgtcgccc tcgtcgctcc 122700
ccccgtcctc tcgagggggg gcgcccccgc aactgccggg gtcttcctcg cggggggggc 122760
tccccccga gaccgccccc ccatccacgc cctgcggccc cagcagcccc gtctcgaaca 122820
gttccgtgtc cgtgctgtcc gcctcggagg cggagtcgtc gtcatggtgg tcggcgtccc 122880
cccgcccccc cacttcggtc tccgcctcag agtcgctgct gtccggcagg tctcggtcgc 122940
agggaaacac ccagacatcc ggggcgggct aaggggaaaa aaagggggc gggtaagaat 123000
ggggggattt cccgcgtcaa tcagcgccca cgagttcccc ctctcccccc ccccgcctca 123060
caaagtcctg cccccctgct ggcctcggaa gagggggag aaaggggtct gcaaccaaag 123120
gtggtctggg tccgtccttt ggatcccgac ccctcttctt ccctcttctc ccgccctcca 123180
gacgcaccgg agtcgggggt cccacggcgt cccccaaata tggcgggcgg ctcctcccca 123240
ccccctaga tgcgtgtgag taagggggcc ctgcgtatga gtcagtgggg accacgcccc 123300
ctaacacggc gacccggtc cctgtgtgtt tgttgtgggg gcgtgtctct gtgtatgagt 123360
cagggggtcc cacggcgacc ccgggccctg cgtctgagtc aaaggggcca tgtgtatgtg 123420
ttggggggtc tgtatatata aagtcagggg gtcacatggc gacccccaac agggcgaccc 123480
cggtccctgt atatataggg tcagggggtt ccgcgccccc taacatggcg cccccggtcc 123540
ctgtatatat agtgtcacgg ggttccacgc cccctaacat ggcgcccggc tcccgtgtat 123600
gagtgggggt cccccaacat ggcggccggt tccagtgtaa gggtcggggg tcccccaaca 123660
tggcgccccc caatatggcg ccccccaata tggcgcccca gacatggcgc ccggcccctc 123720
acctcgcgct gggggcggcc ctcaggccgg cgggtactcg ctccggggcg gggctccatg 123780
ggggtcgtat gcggttggag ggtcgcggac ggagggtccc tgggggtcgc aacgtaggcg 123840
gggcttctgt ggtgatgcgg agagggggcg gcccgagtct gcctggctgc tgcgtctcgc 123900
tccgagtgcc gaggtgcaaa tgcgaccaga ctgtcgggcc agggctaact tataccccac 123960
gcctttcccc tccccaaagg ggcggcagtg acgattcccc caatggccgc gcgtcccagg 124020
ggaggcaggc ccaccgcggg gcggccccgt ccccggggac caacccggcg cccccaaaga 124080
atatcattag catgcacggc ccggccccg atttggggga ccaacccggt gtcccccaaa 124140
gaaccccatt agcatgcccc tcccaccgac gcaacagggg cttggcctgc gtcggtgccc 124200
cggggcttcc cgccttcccg aagaaactca ttaccatacc cggaacccca ggggaccaat 124260
gcgggttcat tgagcgaccc gcgggccaat gcgcgagggg ccgtgtgttc cgccaaaaaa 124320
gcaattagca taacccggaa ccccagggga gtggttacgc gcggcgcggg aggcggggaa 124380

-continued taccggggtt gcccattaag ggccgcggga attgccggaa gcgggaaggg cggccggggc 124440
cgcccattaa tgagtttcta attaccatac cgggaagcgg aacaaggcct cttgtaagtt 124500
tttaattacc ataccgggaa gtgggcggcc cggcccactg ggcggtaact cccgcccagt 124560
gggccgggcc ccgaagactc ggcggacgct ggttggccgg gccccgccgc gctggcggcc 124620
gccgattggc cagtcccgcc ctccgagggc gggcccgcct cgggggcggg ccggctccca 124680
gcgtatatat gcgcggctcc tgccatcgtc tctccggaga gcggcttggt gcggagctcc 124740
cgggagctcc gcggaagacc caggccgcct cgggtgtaac gttagaccga gttcgccggg 124800
ccggctccgc gggccagggc ccgggcacgg gcctcgggcc ccaggcacgg cccgatgacc 124860
gcctcggcct ccgccacccg gcgccggaac cgagcccggt cggcccgctc gcgggcccac 124920
gagccgcggc gcgccaggcg ggcggccgag gcccagacca ccaggtggcg cacccggacg 124980
tggggcgaga agcgcacccg cgcgggggtc gcgggggtcg cgggggtcgc gggggtcgcg 125040
ggggtcgcgg ggggctccgg cgccccctcc ccgcccgcgc gtcgcaggcg caggcgcgcc 125100
aggtgctctg cggtgacgcg caggcggagg gcgaggcgcg gcggaaggcg gaaggggcgt 125160
gagggggggt gggaggggtt agccccgccc cccgggcccg cgccgggcgg tggggaccgg 125220
gggcgggggg cggcggcggt gggccgggcc tctggcgccg gctcgggcgg ggggctgtcc 125280
ggccagtcgt cgtcatcgtc gtcgtcggac gcggactcgg gaacgtggag ccactggcgc 125340
agcagcagcg aacaagaagg cgggggccca ctggcggggg gcggcggcgg ggcggccgcg 125400
ggcgcgctcc tgaccgcggg ttccgagttg ggcgtggagg ttacctggga ctgtgcggtt 125460
gggacggcgc ccgtgggccc gggcggccgg gggcggcggg ggccgcgatg gcggcggcgg 125520
cgggccatgg agacagagag cgtgccgggg tggtagagtt tgacaggcaa gcatgtgcgt 125580
gcagaggcga gtagtgcttg cctgtctaac tcgctcgtct cggccgcggg gggcccgggc 125640
tgcgccgccg cgctttaaag ggccgcgcgc gaccccgggg gggtgtgttt cggggggggc 125700
ccgttttccg ctcctccccc cgctcctccc cccgctcctc cccccgctcc tccccccgct 125760 cctcccccog ctcctccccc cgctcctccc cccgctcctc cccccgctcc tccccccgct 125820 cctcccccog ctcctccccc cgctcctccc cccgctcctc cccccgctcc tccccccgct 125880 cctcccccog ctcctccccc cgctcctccc cccgctcctc cccccgctcc ccaacgcccg 125940
ccgcgcgcgc gcacgccgcc cggaccgccg cccgcctttt ttgcgcgccg ccccgcccgc 126000
ggggggcccg ggctgccaca ggtgtaacaa caccaacaga acaccaacag cacggcgcac 126060
cggcgactcc ggttcctcat ccacacgtca cacgtcacgt catccaccac acctgcccac 126120
caacacaact cacagcgaca actcaccgcg caacaactcc tgttcctcat ccacacgtca 126180
ccgcgcaccc cccgctcctc cagacgtccc ccagcgcaac acgccgctcc tgtcacacac 126240
caccgcccca gccctcccca gccccagccc tccccagccc cagccctccc cggccccagc 126300
cctccccggc cccagccctc cccggcccca gccctccccg gccccagccc tccccggccc 126360
cagccctccc cggccccagc cctccccggc cgcgtcccgc gctccctcgg gggggttcgg 126420
gcatctctac ctcagtgccg ccaatctcag gtcagagatc caaaccctcc gggggcgccc 126480
gcgcaccacc accgcccctc gccccctccc gcccctcgcc ccctcccgcc cctcgccccc 126540
tcccgcccct cgccccctcc cgcccctcgc cccctcccgc ccctcgcccc ctcccgcccc 126600 tcgcccccte ccgcccctcg ccccctcccg cccctcgccc cctcccgccc ctcgccccct 126660
cccgcccctc gccccctccc gcccctcgcc ccctcccgcc cctcgccccc tcccgcccct 126720
cgccccctcc cgcccctcgc cccctcccgc ccctcgcccc ctcccgcccc tcgcccccte 126780

```
ccgcccctcg ccccctcccg cccctcgccc cctcccgccc ctcgaaataa acaacgctac 126840
tgcaaaacta aatcaggtcg ttgtcgttta ttgcgtcttc gggtttcgca agcgccccgc 126900
cccgtcccgg cccgttacag caccccgtcc ccctcgaacg cgccgccgtc gtcgtcgtcc 126960
caggcgcctt cccagtccac aacttcccgt cgcggggcg tggccaagcc cgcctccgcc 127020
cccagcacct ccacggcccc cgccgccgcc agcacggtgc cgctgcggcc cgtggccgag 127080
gcccagcgaa tcccgggcaa cgccggcggc agggcccccg ggccgtcgtc gtcgtcgtcg 127140
ccgccgcgca gcaccagcgg gggggcgtcg tcgtcgggct ccagcagggc gcgggcgcaa 127200
aagtccctcc gcggcccgcg ccaccgggcc gggccggcgc gcaccgcctc gcgccccagc 127260
gccacgtaca cgggccgcag cggcgcgccc aggccccagc gcgcgcaggc gcggtgcgag 127320
tgggcctcct cctcgcagaa gtccggcgcg ccgggcgcca tggcgtcggt ggtccccgag 127380
gccgccgccc ggccgtccag cgccggcagc acggcccggc ggtactcgcg cggggacatg 127440
ggcaccggcg tgtccgggcc gaagcgcgtg cgcacgcggt agcgcacgtt gccgccgcgg 127500
cacaggcgca gcggcggcgc gtcggggtac aggcgcgcgt gcgcggcctc cacgcgcgcg 127560
aagacccccg ggccgaacac gcggcccggg gccagcaccg tgcggcgcag gtcccgcgcc 127620
gccggccagc gcacggcgca ctgcacggcg ggcagcaggt cgcacgccag gtaggcgtgc 127680
tgccgcgaca ccgcgggccc gtcggcgggc cagtcgcagg cgcgcacggt gttgaccacg 127740
atgagccgcc ggtcgccggc gctggcgagc agccccagaa actccacggc cccggcgaag 127800
gccaggtccc gcgtggacag cagcagcacg ccctgcgcgc ccagcgccga cacgtcgggg 127860
gcgccggtcc agttgcccgc ccaggcggcc gtgtccggcc cgcacagccg gttggccagg 127920
gccgccagca ggcaggacag cccgccgcgc tcggcggacc actccggcgg ccccccgag 127980
gccccgccgc cggccaggtc ctcgcccggc agcggcgagt acagcaccac cacgcgcacg 128040
tcctcggggt cggggatctg gcgcatccag gccgccatgc ggcgcagcgg gcccgaggcg 128100
cgcagggggc caaagaggcg gcccccggcg gccccgtggg ggtgggggtt atcgtcgtcg 128160
tcgccgccgc cgcacgcggc ctgggcggcg gcggcgggcc cggcgcaccg cgcggcgatc 128220
gaggccaggg cccgcgggtc aaacatgagg gccggtcgcc aggggacggg gaacagcggg 128280
tggtccgtga gctcggccac ggcgcgcggg gagcagtagg cctccagggc ggcggccgcg 128340
ggcgccgccg tgtggctggg ccccgggggc tgccgccgcc agccgcccag ggggtcgggg 128400
ccctcggcgg gccggcgcga cagcgccacg gggcgcgggc gggcctgcgc cgcggcggcc 128460
cggggcgccg cgggctgggc gggggcgggc tcgggccccg ggggcgtgga ggggggcgcg 128520
gggagggggg cgcgggcgtc cgagccgggg gcgtccgcgc cgctcttctt cgtcttcggg 128580
ggtcgcgggc cgccgcctcc gggcggccgg gccgggccgg gactcttgcg cttgcgcccc 128640
tcccgcggcg cggcggaggc ggcggcggcc gccagcgcgt cggcggcgtc cggtgcgctg 128700
gcggccgccg ccagcagggg gcgcaggctc tggttctcaa acagcaggtc cgcggcggcg 128760
gcggccgcgg agctcggcag gcgcgggtcc cgcggcagcg cggggcccag ggccccggcg 128820
accaggctca cggcgcgcac ggcggccacg gcggcctcgc tgccgccggc cacgcgcagg 128880
tccccgcgca ggcgcatgag caccagcgcg tcgcgcacga accgcagctc gcgcagccac 128940
gcgcgcaggc ggggcgcgtc ggcgtgcggc ggcggcgggg aagcggggcc cgcgggtccc 129000
tccggccgcg gggggctggc gggccgggcc ccggccagcc ccgggacggc cgccaggtcg 129060
ccgtcgaagc cctcggccag cgcctccagg atcccgcggc aggcggccag gcactccacg 129120
```

gccacgcggc cggcctgggc gcggcgcccg gcgtcgtcgt cggcgtcggc gtggcgggcg 129180
gcgtcggggt cgtcgccccc cgcgggggag gcgggcgcgg cggacagccg ccccagggcg 129240
gcgaggatcc ccgcggcgcc gtacccggcg ggcaccgcgc gctcgcccgg tgcggcggcg 129300
gcggcgacga cggcggcggc gaccccctcg tcatctgcgc cggcgccggg gctccccgcg 129360
gcccccgtca gcgccgcgtt ctcgcgcgcc aacaggggcg cgtaggcgcg gcgcaggctg 129420
gtcagcagga agcccttctg cgcgcggtcg tatcggcggc tcatggccac ggcggccgcc 129480
gcgtgcgcca ggccccagcc gaagcggccg gccgccatgg cgtagcccag gtggggcacg 129540
gcccgcgcca cgctgccggt gatgaaggag ctgctgttgc gcgcggcgcc cgagatccgg 129600
aagcaggcct ggtccagcgc cacgtccccg gggaccacgc gcgggttctg gagccacccc 129660
atggcctccg cgtccggggt gtacagcagc cgcgtgatca gggcgtactg ctgcgcggcg 129720
tcgcccagct cgggcgccca cacggccgcc ggggcgcccg aggcctcgaa ccggcgtcgc 129780
gcctcctccg cctcgggcgc cccccagagg cccgggcggc tgtcgcccag gccgccgtac 129840
agcacccgcc ccgggggcgg gggcccggcg ccgggccacg gctccccgct gacgtacccg 129900
tcgcgatagc gcgcgtagaa ggcgccggag gccgcgtcgg cgtccagctc gacccgccgg 129960
ggctgcccgg ccgtgaagcg gcccgtggcg tcgcggccgg ccaccgccgc gcgggcccgg 130020
cggcgctcga tgcggcccgc ggaggccgcg ggggtcctcg ccgccgcccg gggcttgggc 130080
gcggcctcgg agaggggggg tggcccgggc gggggcggcg tccgcccggg ggcttccggc 130140
gccgcgctcg acggaccccg cccgacggcc cgcgcctcgc gtgcgcggtc ggccgcgtcg 130200
ttgccgtcgt cgtcctcgtc ctcgtcggac gacgaggacg aagaggatgc ggacgacgag 130260
gacgaggacc cggagtccga cgaggtcgat gacgccgatg gccgccgccg gccgtgacga 130320
cgtctccgcg gcggctgggc cggcgggcgc ggcgacaggc ggtccgtggg gtccggatac 130380
gcgccgcgta gcggggcctc ccgtgcgcgg ccccgggccg gggcccggtc gccggcggcg 130440
tcggctgcgt cgtcgtactc gtccccgtca tcgtcgtcgg ctcgaaaggc gggggtccgg 130500
ggcggcgagg ccgcggggtc gggcgtcggg atcgtccgga cggcctcctc taccatggag 130560
gccagcaggg ccagctgtcg cggcgagacg gcgtccccgg cgtcctcgcc ggcgtcggtg 130620
cccgccgcgg gggccctccc gtcccgccgg gcgtcgtcga ggtcgtgggg gtggtcgggg 130680
tcgtggtcgg ggtcgtcccc gccctcctcc gtctccgcgc cccacccgag ggccccccgc 130740
tcgtcgcggt ctgggctcgg ggtgggcggc ggcccgtcgg tggggcccgg ggagccgggg 130800
cgctgcttgt tctccgacgc catcgccgat gcggggcgat cctccgggga tacggctgcg 130860
acggcggacg tagcacggta ggtcacctac ggactctcga tggggagggg gcgagaccca 130920
cggaccccga cgacccccgc cgtcgacgcg gaactagcgc ggaccggtcg atgcttgggt 130980
gggaaaaagg acagggacgg ccgatccccc tcccgcgctt cgtccgcgta tcggcgtccc 131040
ggcgcggcga gcgtctgacg gtctgtctct ggcggtcccg cgtcgggtcg tggatccgtg 131100
tcggcagccg cgctccgtgt ggacgatcgg ggcgtcctcg ggctcatata gtcccagggg 131160
ccggcgggaa ggaggagcag cggaggccgc cggccccccg ccccccaggc gggcccgccc 131220
cgaacggaat tccattatgc acgaccccgc cccgacgccg gcacgccggg ggcccgtggc 131280
cgcggcccgt tggtcgaacc cccggccccg cccatccgcg ccatctgcca tgggcggggc 131340
gcgagggcgg gtgggcccgc gccccgcccc gcatggcatc tcattaccgc ccgatccggt 131400
ggtttccgct tccgttccgc atgctaacga ggaacgggcc gggggcgggg cccgggcccc 131460
gacttcccgg ttcggcggta atgagatacg agccccgcgc gcccgttggc cgtccccggg 131520
cccccggtcc cgcccgccgg acgttgggac caacgggacg gcgggcggcc caagggccgc 131580
ccgccttgcc gcccccccat tggccggcgg gcgggaccgc cccaaggggg cggggccgcc 131640
gggtaaaaga agtgagaacg cgaagcgttc gcacttcgtc ccaatatata tatattatta 131700
gggcgaagtg cgagcactgg cgccgtgccc gactccgcgc cggccccggg ggcgggcccg 131760
ggcggcgggg ggcgggtctc tccggcgcac ataaaggccc ggcgcgaccg acgcccgcag 131820
acggcgccgg ccacgaacga cgggagcggc tgcggagcac gcggaccggg agcgggactc 131880
gcagagggcc gtcggagcgg acggcgtcgg catcgcgacg ccccggctcg ggatcgggat 131940
cgcatcggaa agggacacgc ggaaagaccc acccacccca cccacgaaac acaggggacg 132000
caccccgggg gcctccgacg acagaaaccc accggtccgc ctttgtgcac gggtaagcac 132060
cttgggtggg cggaggaggg ggggacgcgg gggcggagga ggggggacgc gggggcggag 132120
gagggggggac gcgggggcgg aggagggggg acgcgggggc ggaggagggg ggacgcgggg 132180
gcggaggagg gggctcaccc gcgttcgtgc cttcccgcag gaggaacgtc ctcgtcgggg 132240
cgaccggcgg cgaccgttgc gtggaccgct tcctgctcgt cgggcggggg gaagccactg 132300
tggtcctccg ggacgttttc tggatggccg acatttcccc aggcgctttt gcgccttgtg 132360
taaaagcgcg gcgtcccgct ctccgatccc cgcccctggg cacgcgcaag cgcaagcgcc 132420
cttcccgccc cctctcatcg gagtctgagg tagaatccga tacagccttg gagtctgagg 132480
tcgaatccga gacagcatcg gattcgaccg agtctgggga ccaggatgaa gcccccccgca 132540
tcggtggccg tagggccccc cggaggcttg gggggcggtt ttttctggac atgtcggcgg 132600
aatccaccac ggggacggaa acggatgcgt cggtgtcgga cgaccccgac gacacgtccg 132660
actggtctta tgacgacatt cccccacgac ccaagcgggc ccgggtaaac ctgcggctca 132720
cgagctctcc cgatcggcgg gatggggtta tttttcctaa gatggggcgg gtccggtcta 132780
cccgggaaac gcagccccgg gcccccaccc cgtcggcccc aagcccaaat gcaatgctac 132840
ggcgctcggt gcgccaggcc cagaggcgga gcagcgcacg atggaccccc gacctgggct 132900
acatgcgcca gtgtatcaat cagctgtttc gggtcctgcg ggtcgcccgg gacccccacg 132960
gcagtgccaa ccgcctgcgc cacctgatac gcgactgtta cctgatggga tactgccgag 133020
cccgtctggc cccgcgcacg tggtgccgtt tgctgcaggt gtccggcgga acctggggca 133080
tgcacctgcg caacaccata cgggaggtgg aggctcgatt cgacgccacc gcggaacccg 133140
tgtgcaagct tccttgtttg gagaccagac ggtacggccc ggagtgtgat cttagtaatc 133200
tcgagattca tctcagcgcg acaagcgatg atgaaatctc cgatgccacc gatctggagg 133260
ccgccggttc ggaccacacg ctcgcgtccc agtccgacac ggaggatgcc ccctccccccg 133320
ttacgctgga aaccccagaa ccccgcgggt ccctcgctgt gcgtctggag gatgagtttg 133380
gggagtttga ctggaccccc caggagggct cccagccctg gctgtctgcg gtcgtggccg 133440
ataccagctc cgtggaacgc ccgggcccat ccgattctgg ggcgggtcgc gccgcagaag 133500
accgcaagtg tctggacggc tgccggaaaa tgcgcttctc caccgcctgc ccctatccgt 133560
gcagcgacac gtttctccgg ccgtgagtcc ggtcgccccg accccccttgt atgtccccaa 133620
ataaaagacc aaaatcaaag cgtttgtccc agcgtcttaa tggcgggaag ggcggagaga 133680
aacagaccac gcgtacatgg ggggtgtttg ggggtttatt gacatcgggg ctacagggtg 133740
gtaaccggat agcagatgtg aggaagtctg ggccgttcgc cgcgaacggc gatcagaggg 133800
tccgtttctt gcggaccacg gcccggtgat gtgggttgct cgtctgggat ctcgggcatg 133860

-continued cccatacacg cacaacacgg acgccgcacc ggatgggacg tcgtaagggg gcctggggta 133920
gctgggtggg gtttgtgcag agcaatcagg gaccgcagcc agcgcataca atcgcgctcc 133980
cgtccgtttg tcccgggcag taccacgccg tactggtatt cgtaccggct gagcagggtc 134040
tccagggggt ggttgggggc cgcggggaac ggggtccacg ccacggtcca ctcgggcaaa 134100
aaccgagtcg gcacggccca cggttctccc acccacgcgt ctggggtctt gatggcgata 134160
aatcttaccc cgagccggat tttttgggcg tattcgagaa acggcacaca cagatccgcc 134220
gcgcctacca cccacaagtg gtagaggcga ggggggctgg gttggtctcg gtgcagcagt 134280
cggaagcacg ccacggcgtc cacgacctcg gtgctctcca aggggctgtc ctccgcaaac 134340
aggcccgtgg tggtgtttgg ggggcagcga caggacctag tgcgcacgat cgggcgggtg 134400
ggtttgggta agtccatcag cggctcggcc aaccgtcgaa ggttggccgg acgaacgacg 134460
accggggtac ccaggggttc tgatgccaaa atgcggcact gcctaaacag gaagctccac 134520
agggccgggc ttgcgtcgac ggaagtccgg ggcagggcgt tgttctggtc aaggagggtc 134580
attacgttga cgacaacaac gcccatgttg gtatattaca ggcccgtgtc cgatttgggg 134640
cacttgcaga tttgtaaggc cacgcacggc ggggagacag gccgacgcgg gggctgctct 134700
aaaaatttaa gggccctacg gtccacagac ccgccttccc gggggggccc ttggagcgac 134760
cggcagcgga ggcgtccggg ggaggggagg gtgatttacg ggggggtagg tcagggggtg 134820
ggtcgtcaaa ctgccgctcc ttaaaacccc ggggcccgtc gttcggggtg ctcgttggtt 134880
ggcactcacg gtgcggcgaa tggcctgtcg taagttttgt cgcgtttacg gggacaggg 134940 caggaggaag gaggaggccg tcccgccgga gacaaagccg tcccgggtgt ttcctcatgg 135000
ccccttttat accccagccg aggacgcgtg cctggactcc ccgcccccgg agacccccaa 135060
accttcccac accacaccac ccggcgatgc cgagcgcctg tgtcatctgc aggagatcct 135120
ggcccagatg tacggaaacc aggactaccc catagaggac gaccccagcg cggatgccgc 135180
ggacgatgtc gacgaggacg ccccggacga cgtggcctat ccggaggaat acgcagagga 135240
gctttttctg cccggggacg cgcccggtcc ccttatcggg gccaacgacc acatccctcc 135300
cccgtgtggc gcatctcccc ccggtatacg acgacgcagc cgggatgaga ttggggccac 135360
gggatttacc gcggaagaac tggacgccat ggacagggag gcggctcgag ccatcagccg 135420
cggcggcaag cccccctcga ccatggccaa gctggtgact ggcatgggct ttacgatcca 135480
cggagcgctc accccaggat cggaggggtg tgtctttgac agcagccacc cagattaccc 135540
ccaacgggta atcgtgaagg cggggtggta cacgagcacg agccacgagg cgcgactgct 135600
gaggcgactg gaccaccccg cgatcctgcc cctcctggac ctgcatgtcg tctccggggt 135660
cacgtgtctg gtcctcccca agtaccaggc cgacctgtat acctatctga gtaggcgcct 135720
gaacccgctg ggacgcccgc agatcgcagc ggtctcccgg cagctcctaa gcgccgttga 135780
ctacattcac cgccagggca ttatccaccg cgacattaag accgaaaata tttttattaa 135840
cacccccgag gacatttgcc tgggggactt tggtgccgcg tgcttcgtgc agggttcccg 135900
atcaagcccc ttcccctacg gaatcgccgg aaccatcgac accaacgccc ccgaggtcct 135960
ggccggggat ccgtatacca ccaccgtcga catttggagc gccggtctgg tgatcttcga 136020
gactgccgtc cacaacgcgt ccttgttctc ggcccccgc ggccccaaaa ggggcccgtg 136080
cgacagtcag atcacccgca tcatccgaca ggcccaggtc cacgttgacg agttttcccc 136140
gcatccagaa tcgcgcctca cctcgcgcta ccgctcccgc gcggccggga acaatcgccc 136200
gccgtacacc cgaccggcct ggacccgcta ctacaagatg gacatagacg tcgaatatct 136260
ggtttgcaaa gccctcacct tcgacggcgc gcttcgcccc agcgccgcag agctgctttg 136320
tttgccgctg tttcaacaga aatgaccgcc cccagggggc ggtgctgttt gcgggttggc 136380
acaaaaagac cccgacccgc gtctgtggtg tttttggcat catgtcgccg ggcgccatgc 136440
gtgccgttgt tcccattatc ccattccttt tggttcttgt cggtgtatcg gggttcccca 136500
ccaacgtctc ctccaccacc caaccccaac tccagaccac cggtcgtccc tcgcatgaag 136560
cccccaacat gacccagacc ggcaccaccg actctcccac cgccatcagc cttaccacgc 136620
ccgaccacac accccccatg ccaagtatcg gactggagga ggaggaagag gaggaggggg 136680
ccggggacgg cgaacatctt gagggggggag atgggacccg tgacacccta ccccagtccc 136740
cgggcccagc cttcccgttg gctgaggacg tcgagaagga caaacccaac cgtcccgtag 136800
tcccatcccc cgatcccaac aactcccccg cgcgccccga gaccagtcgc ccgaagacac 136860
cccccaccat tatcgggccg ctggcaactc gccccacgac ccgactcacc tcaaagggac 136920
gacccttggt tccgacgcct caacataccc cgctgttctc gttcctcact gcctcccccg 136980
ccctggacac cctcttcgtc gtcagcaccg tcatccacac cttatcgttt ttgtgtattg 137040
gtgcgatggc gacacacctg tgtggcggtt ggtccagacg cgggcgacgc acacacccta 137100
gcgtgcgtta cgtgtgcctg ccgtccgaac gcgggtaggg tatggggcgg gggatgggga 137160
gagcccacac gcggaaagca agaacaataa aggcggtggt atctagttga tatgcatctc 137220
tgggtgtttt tggggtgtgg cggacgcggg gcggtcattg gacggggtgc agttaaatac 137280
atgcccggga cccatgaagc atgcgcgact tccgggcctc ggaacccacc cgaaacggcc 137340
aacggacgtc tgagccaggc ctggctatcc ggagaaacag cacacgactt ggcgttctgt 137400
gtgtcgcgat gtctctgcgc gcagtctggc atctggggct tttgggaagc ctcgtggggg 137460
ctgttcttgc cgccacccat cggggacctg cggccaacac aacggacccc ttaacgcacg 137520
ccccagtgtc ccctcacccc agccccctgg ggggctttgc cgtccccctc gtagtcggtg 137580
ggctgtgcgc cgtagtcctg ggggcggcgt gtctgcttga gctcctgcgt cgtacgtgcc 137640
gcgggtgggg gcgttaccat ccctacatgg acccagttgt cgtataattt cccccccccc 137700
ccccettctc cgcatgggtg atgtcgggtc caaactcccg acaccaccag ctggcatggt 137760
ataaatcacc ggtgcgcccc ccaaaccatg tccggcaggg ggatgggggg gcgaatgcgg 137820
agggcaccca acaacaccgg gctaaccagg aaatccgtgg ccccggcccc caataaagat 137880
cgcggtagcc cggccgtgtg acactatcgt ccataccgac cacaccgacg aatcccctaa 137940
gggggagggg ccattttacg aggaggaggg gtataacaaa gtctgtcttt aaaaagcagg 138000
ggttagggag ttgttcggtc ataagcttca gcgcgaacga ccaactaccc cgatcatcag 138060
ttatccttaa ggtctctttt gtgtggtgcg ttccggtatg gggggggctg ccgccaggtt 138120
gggggccgtg attttgtttg tcgtcatagt gggcctccat ggggtccgcg gcaaatatgc 138180
cttggcggat gcctctctca agatggccga ccccaatcgc tttcgcggca aagaccttcc 138240
ggtcctggac cagctgaccg accctccggg ggtccggcgc gtgtaccaca tccaggcggg 138300
cctaccggac ccgttccagc cccccagcct cccgatcacg gtttactacg ccgtgttgga 138360
gcgcgcctgc cgcagcgtgc tcctaaacgc accgtcggag gccccccaga ttgtccgcgg 138420
ggcctccgaa gacgtccgga aacaacccta caacctgacc atcgcttggt ttcggatggg 138480
aggcaactgt gctatcccca tcacggtcat ggagtacacc gaatgctcct acaacaagtc 138540
tctgggggcc tgtcccatcc gaacgcagcc ccgctggaac tactatgaca gcttcagcgc 138600

-continued cgtcagcgag gataacctgg ggttcctgat gcacgccccc gcgtttgaga ccgccggcac 138660
gtacctgcgg ctcgtgaaga taaacgactg gacggagatt acacagttta tcctggagca 138720
ccgagccaag ggctcctgta agtacgccct cccgctgcgc atccccccgt cagcctgcct 138780
gtccccccag gcctaccagc agggggtgac ggtggacagc atcgggatgc tgccccgctt 138840
catccccgag aaccagcgca ccgtcgccgt atacagcttg aagatcgccg ggtggcacgg 138900
gcccaaggcc ccatacacga gcaccctgct gcccccggag ctgtccgaga cccccaacgc 138960
cacgcagcca gaactcgccc cggaagaccc cgaggattcg gccctcttgg aggaccccgt 139020
ggggacggtg gcgccgcaaa tcccaccaaa ctggcacata ccgtcgatcc aggacgccgc 139080
gacgccttac catcccccgg ccaccccgaa caacatgggc ctgatcgccg gcgcggtggg 139140
cggcagtctc ctggcagccc tggtcatttg cggaattgtg tactggatgc gccgccgcac 139200
tcaaaaagcc ccaaagcgca tacgcctccc ccacatccgg gaagacgacc agccgtcctc 139260
gcaccagccc ttgttttact agatacccc ccttaatggg tgcgggggg tcaggtctgc 139320
ggggttggga tgggacctta actccatata aagcgagtct ggaagggggg aaaggcggac 139380
agtcgataag tcggtagcgg gggacgcgca cctgttccgc ctgtcgcacc cacagctttt 139440
tttgcgaacc gtcccgttcc gggatgccgt gccgcccgtt gcagggcctg gtgctcgtgg 139500
gcctctgggt ctgtgccacc agcctggttg tccgtggccc cacggtcagt ctggtatcaa 139560
actcatttgt ggacgccggg gccttggggc ccgacggcgt agtggaggaa gacctgctta 139620
ttctcgggga gcttcgcttt gtgggggacc aggtccccca caccacctac tacgatgggg 139680
tcgtagagct gtggcactac cccatgggac acaaatgccc acgggtcgtg catgtcgtca 139740
cggtgaccgc gtgcccacgt cgccccgccg tggctttcgc cctgtgtcgc gcgaccgaca 139800
gcactcacag ccccgcatat cccaccctgg agctgaatct ggcccaacag ccgcttttgc 139860
gggtccggag ggcgacgcgt gactatgccg gggtgtacgt gttacgcgta tgggtcgggg 139920
acgcaccaaa cgccagcctg tttgtcctgg ggatggccat agccgccgaa gggactctgg 139980
cgtacaacgg ctcggcccat ggctcctgcg acccgaaact gcttccgtat tcggccccgc 140040
gtctggcccc ggcgagcgta taccaacccg cccctaaccc ggcctccacc ccctcgacca 140100
ccacctccac cccctcgacc accacctcca ccccctcgac caccatcccc gctccccaag 140160
catcgaccac acccttcccc acgggagacc caaaacccca acctcacggg gtcaaccacg 140220
aacccccatc gaatgccacg cgagcgaccc gcgactcgcg atacgcgcta acggtgaccc 140280
agataatcca gatagccatc cccgcgtcca ttatagccct ggtgtttctg gggagctgta 140340
tttgctttat acacagatgt caacgccgct accgacgctc ccgccgcccg atttacaacc 140400
cccagatacc cactggcatc tcatgcgcgg tgaacgaagc ggccatggcc cgcctcggag 140460
ccgagctcaa atcgcatccg agcacccccc ccaaatcccg gcgccggtcg tcacgcacac 140520
caatgccctc cctgacggcc atcgccgaag agtcggagcc cgcgggggcg gctgggcttc 140580
cgacgccccc cgtggacccc acgacatcca ccccaacgcc tcccctgttg gtataggtcc 140640
acggccactg gccgggggca ccacataacc gaccgcagtc actgagttgg gaataaaccg 140700
gtattattta cctatatacg tgtatgtcca tttcttcccc cccccccccg gaaaccaaag 140760
aaggaaacaa agaatggatg ggaggagttc aggaagccgg ggagagggcc cgcggcgcat 140820
ttaaggcgtt gttgtgttga ctttggctct tctggcgggt tggtgcggtg ctgtttgttg 140880
ggctcccatt ttacccgaag atcggctgct atccccggga catggatcgc ggggcggtgg 140940
tggggtttct tctcggtgtt tgtgttgtat cgtgcttggc gggaacgccc aaaacgtcct 141000
ggagacgggt gagtgtcggc gaggacgttt cgttgcttcc agctccgggg cctacggggc 141060
gcggcccgac ccagaaacta ctatgggccg tggaacccct ggatgggtgc ggccccttac 141120
acccgtcgtg ggtctcgctg atgccccca agcaggtgcc cgagacggtc gtggatgcgg 141180
cgtgcatgcg cgctccggtc ccgctggcga tggcgtacgc ccccccggcc ccatctgcga 141240
ccgggggtct acggacggac ttcgtgtggc aggagcgcgc ggccgtggtt aaccggagtc 141300
tggttattta cggggtccga gagacggaca gcggcctgta taccctgtct gtgggcgaca 141360
taaaggaccc ggctcgccaa gtggcctcgg tggtcctggt ggtgcaaccg gccccagttc 141420
cgaccccacc cccgacccca gccgattacg acgaggatga caatgacgag ggcgagggcg 141480
aggacgaaag tctagccggc actcccgcca gcgggacccc ccggctcccg cctccccccg 141540
cccccccgag gtcttggccc agcgccccccg aagtctcaca cgtgcgtggg gtgaccgtgc 141600
gtatggagac tccggaagct atcctgtttt cccccgggga ggcgtttagc acgaacgtct 141660
ccatccatgc catcgcccac gacgaccaga cctacaccat ggacgtcgtc tggttgaggt 141720
tcgacgtgcc gacctcgtgt gccgagatgc gaatatacga atcgtgtctg tatcacccgc 141780
agctcccaga gtgtctgtcc ccggccgacg ctccgtgcgc cgcgagtacg tggacgtctc 141840
gcctggccgt ccgcagctac gcggggtgtt ccagaacaaa ccccccgccg cgctgttcgg 141900
ccgaggctca catggagccc ttcccggggc tggcgtggca ggcggcctcc gtcaatctgg 141960
agttccggga cgcgtcccca caacactccg gcctgtatct gtgcgtggtg tacgtcaacg 142020
accatattca cgcatggggc cacattacca tcagcaccgc ggcgcagtac cggaacgcgg 142080
tggtggaaca gcccctccca cagcgcggcg cggatttggc cgagcccacc cacccgcacg 142140
tcggggcccc tccccacgcg cccccaaccc acggcgccct gcggttaggg gcggtgatgg 142200
gggccgccct gctgctgtct gcgctggggt tgtcggtgtg ggcgtgtatg acctgttggc 142260
gcaggcgtgc ctggcgggcg gttaaaagca gggcctcggg taaggggccc acgtacattc 142320
gcgtggccga cagcgagctg tacgcggact ggagctcgga cagcgaggga gaacgcgacc 142380
aggtcccgtg gctggccccc ccggagagac ccgactctcc ctccaccaat ggatccggct 142440
ttgagatctt atcaccaacg gctccgtctg tataccccg tagcgatggg catcaatctc 142500
gccgccagct cacaaccttt ggatccggaa ggcccgatcg ccgttactcc caggcctccg 142560
attcgtccgt cttctggtaa ggcgccccat cccgaggccc cacgtcggtc gccgaactgg 142620
gcgaccgccg gcgaggtgga cgtcggagac gagctaatcg cgatttccga cgaacgcgga 142680
cccccccgac atgaccgccc gcccctcgcc acgtcgaccg cgccctcgcc acacccgcga 142740
cccccgggct acacggccgt tgtctccccg atggccctcc aggctgtcga cgccccctcc 142800
ctgtttgtcg cctggctggc cgctcggtgg ctccgggggg cttccggcct gggggccgtc 142860
ctgtgtggga ttgcgtggta tgtgacgtca attgcccgag gcgcataaag ggccggtggt 142920
ccgcctagcc gcagcaaatt aaaaatcgtg agtcactgcg accgcaactt cccacccgga 142980
gctttcttcc ggcctcgatg acgtcccggc tctccgatcc caactcctca gcgcgatccg 143040
acatgtccgt gccgctttat cccacggcct cgccagtttc ggtcgaagcc tactactcgg 143100
aaagcgaaga cgaggcggcc aacgacttcc tcgtacgcat gggccgccaa cagtcggtat 143160
taaggcgtcg acgcagacgc acccgctgcg tcggcatggt gatcgcctgt ctcctcgtgg 143220
ccgttctgtc gggcggattt ggggcgctcc tgatgtggct gctccgctaa aagaccgcat 143280
cgacacgcgc gtccttcttg tcgtctctct tccccccat caccccgcaa tttgcaccca 143340
gcctttaact acattaaatt gggttcgatt ggcaatgttg tctcccggtt gatttttggg 143400
tgggtgggga gtgggtgggt ggggagtggg tgggtgggga gtgggtgggt ggggagtggg 143460
tgggtgggga gtgggtgggt ggggagtggg tgggtgggga gtgggtgggt ggggagtggg 143520
tgggtgggga gtgggtgggt ggggagtggc aaggaagaaa caagcccgac caccagacag 143580
aaaatgtaac catacccaaa ccgactctgg gggctgtttg tggggtcgga accataggat 143640
gaacaaacca ccccgtacct cccgcaccct tgggtgcggg tggctcatcg gcatctgtcc 143700
ggtatgggtt gttccccacc cacttgcgtt cggacgtctt agaatcatgg cggttttcta 143760
tgccgacatc ggttttctcc cccgcaataa gacacgatgc gataaaatct gtttgtgaaa 143820
tttattaagg gtacaaattg ccctagcaca ggggtggggt tagggccggg tccccacacc 143880
caaacgcacc aaacagatgc aggcagtggg tcgagtacag ccccgcgtac gaacacgtcg 143940
atgcgtgtgt cagacagcac cagaaagcac aggccatcaa caggtcgtgc atatgtcggt 144000
gggtttggac gcggggggcc atggtggtga taaagttaat ggccgccgtc cgccagggcc 144060
acaggggcga cgtctcttgg ttggcccgga gccactgggt gtggaccagc cgcgcgtggc 144120
ggcccaacat ggcccctgta gccgggggcg ggggatcgcg cacgtttgca gcgcacatgc 144180
gagacacctc gaccacggtt cggaagaagg cccggtggtc cgcgggcaac atcaccaggt 144240
gcgcaagcgc ccgggcgtcc agagggtaga gccctgagtc atccgaggtt ggctcatcgc 144300
ccgggtcatg ccgcaagtgc gtgtgggttg ggcttccggt gggcgggacg cgaaccgcgg 144360
tgtggagccc tacgcgggcc cgagcgtacg ctccatcttg tggggagaag ggtctgggc 144420
tcgccagggg ggcatacttg cccgggctat acagacccgc gagccgtacg tggttcgcgg 144480
ggggtgcgtg gggtccgggg ctcccgggga ggccggggct cccggggttg tcgtggatcc 144540
ctggggtcac gcggtaccct ggggtctctg ggagctcgcg gtactctggg ttccctaggt 144600
tctcggggtg gtcgcggaac ccggggctcc cggggaacac gcggtgtcct ggggattgtt 144660
ggcggtcgga cggcttcaga tggcttcgag atcgtagtgt ccgcaccgac tcgtagtaga 144720
cccgaatctc cacattgccc cgccgcttga tcattatcac cccgttgcgg gggtccggag 144780
atcatgcgcg ggtgtcctcg aggtgcgtga acacctctgg ggtgcatgcc ggcggacggc 144840
acgcctttta agtaaacatc tgggtcgccc ggcccaactg gggccggggg ttgggtctgg 144900
ctcatctcga gagccacggg gggaaccacc ctccgcccag aaacttgggc gatggtcgta 144960
cccgggactc aacgggttac cggattacgg ggactgtcgg tcacggtccc gccggttctt 145020
cgatgtgcca cacccaagga tgcgttgggg gcgattttgg gcagcagccc gggagagcgc 145080
agcagaggac gctccgggtc gtgcacggcg gttttggccg cctcccggtc ctcacgcccc 145140
cttttattga tctcatcgcg tacgtcggcg tacgtcctgg gcccaacccg catgttgtcc 145200
aggaaggtgt ccgccatttc cagggcccac gacatgctcc cccgcccgac gagcaggaag 145260
cggtccacgc aacggtcgcc gccggtcgcc ccgacgagca ggaagcggtc cacgcaacgg 145320
tcgccgccgg tcgcctcgac gaggacgttc ctcctgcggg aaggcacgaa cgcgggtgag 145380
ccccctcctc cgcccccgcg tccccccctcc tccgcccccg cgtcccccct cctccgcccc 145440
cgcgtccccc ctcctccgcc cccgcgtccc ccctcctccg cccccgcgtc ccccctcctc 145500
cgcccccgcg tccccccctcc tccacccccg cgtccccccc tcctccgccc acccaaggtg 145560
cttacccgtg cacaaaggcg gaccggtggg tttctgtcgt cggaggcccc cggggtgcgt 145620
cccctgtgtt tcgtgggtgg ggtgggtggg tctttccgcg tgtccctttc cgatgcgatc 145680
ccgatcccga gccggggcgt cgcgatgccg acgccgtccg ctccgacggc cctctgcgag 145740
tcccgctccc ggtccgcgtg ctccgcagcc gctcccgtcg ttcgtggccg gcgccgtctg 145800
cgggcgtcgg tcgcgccggg cctttatgtg cgccggagag acccgccccc cgccgcccgg 145860
gcccgccccc ggggccggcg cggagtcggg cacggcgcca gtgctcgcac ttcgccctaa 145920
taatatatat atattgggac gaagtgcgaa cgcttcgcgt tctcacttct tttacccggc 145980
ggccccgccc ccttggggcg gtcccgcccg ccggccaatg ggggggcggc aaggcgggcg 146040
gcccttgggc cgcccgccgt cccgttggtc ccaacgtccg gcgggcggga ccgggggccc 146100
ggggacggcc aacgggcgcg cggggctcgt atctcattac cgccgaaccg ggaagtcggg 146160
gcccgggccc cgcccccggc ccgttcctcg ttagcatgcg gaacggaagc ggaaaccacc 146220
ggatcgggcg gtaatgagat gccatgcggg gcggggcgcg ggcccacccg ccctcgcgcc 146280
ccgcccatgg cagatggcgc ggatgggcgg ggccgggggt tcgaccaacg ggccgcggcc 146340
acgggccccc ggcgtgccgg cgtcggggcg gggtcgtgca taatggaatt ccgttcgggg 146400
cgggcccgcc tggggggcgg ggggccggcg gcctccgctg ctcctccttc ccgccggccc 146460
ctgggactat atgagcccga ggacgccccg atcgtccaca cggagcgcgg ctgccgacac 146520
ggatccacga cccgacgcgg gaccgccaga gacagaccgt cagacgctcg ccgcgccggg 146580
acgccgatac gcggacgaag cgcgggaggg ggatcggccg tccctgtcct tttcccacc 146640 caagcatcga ccggtccgcg ctagttccgc gtcgacggcg ggggtcgtcg gggtccgtgg 146700
gtctcgcccc ctccccatcg agagtccgta ggtgacctac cgtgctacgt ccgccgtcgc 146760
agccgtatcc ccggaggatc gccccgcatc ggcgatggcg tcggagaaca agcagcgccc 146820
cggctccccg ggccccaccg acgggccgcc gcccaccccg agcccagacc gcgacgagcg 146880
gggggccctc gggtggggcg cggagacgga ggagggcggg gacgaccccg accacgaccc 146940
cgaccacccc cacgacctcg acgacgcccg gcgggacggg agggcccccg cggcgggcac 147000
cgacgccggc gaggacgccg gggacgccgt ctcgccgcga cagctggccc tgctggcctc 147060
catggtagag gaggccgtcc ggacgatccc gacgcccgac cccgcggcct cgccgccccg 147120
gacccccgcc tttcgagccg acgacgatga cggggacgag tacgacgacg cagccgacgc 147180
cgccggcgac cgggccccgg cccggggccg cgcacgggag gccccgctac gcggcgcgta 147240
tccggacccc acggaccgcc tgtcgccgcg cccgccggcc cagccgccgc ggagacgtcg 147300
tcacggccgg cggcggccat cggcgtcatc gacctcgtcg gactccgggt cctcgtcctc 147360
gtcgtccgca tcctcttcgt cctcgtcgtc cgacgaggac gaggacgacg acggcaacga 147420
cgcggccgac cgcgcacgcg aggcgcgggc cgtcgggcgg ggtccgtcga gcgcggcgcc 147480
ggaagccccc gggcggacgc cgcccccgcc cgggccaccc cccctctccg aggccgcgcc 147540
caagccccgg gcggcggcga ggacccccgc ggcctccgcg ggccgcatcg agcgccgccg 147600
ggcccgcgcg gcggtggccg gccgcgacgc cacgggccgc ttcacggccg ggcagccccg 147660
gcgggtcgag ctggacgccg acgcggcctc cggcgccttc tacgcgcgct atcgcgacgg 147720
gtacgtcagc ggggagccgt ggcccggcgc cgggcccccg cccccggggc gggtgctgta 147780
cggcggcctg ggcgacagcc gcccgggcct ctggggggcg cccgaggcgg aggaggcgcg 147840
acgccggttc gaggcctcgg gcgcccccggc ggccgtgtgg gcgcccgagc tgggcgacgc 147900
cgcgcagcag tacgccctga tcacgcggct gctgtacacc ccggacgcgg aggccatggg 147960
gtggctccag aacccgcgcg tggtccccgg ggacgtggcg ctggaccagg cctgcttccg 148020
gatctcgggc gccgcgcgca acagcagctc cttcatcacc ggcagcgtgg cgcgggccgt 148080
gccccacctg ggctacgcca tggcggccgg ccgcttcggc tggggcctgg cgcacgcggc 148140
ggccgccgtg gccatgagcc gccgatacga ccgcgcgcag aagggcttcc tgctgaccag 148200
cctgcgccgc gcctacgcgc ccctgttggc gcgcgagaac gcggcgctga cgggggccgc 148260
ggggagcccc ggcgccggcg cagatgacga gggggtcgcc gccgccgtcg tcgccgccgc 148320
cgccgcaccg ggcgagcgcg cggtgcccgc cgggtacggc gccgcgggga tcctcgccgc 148380
cctggggcgg ctgtccgccg cgcccgcctc ccccgcgggg ggcgacgacc ccgacgccgc 148440
ccgccacgcc gacgccgacg acgacgccgg gcgccgcgcc caggccggcc gcgtggccgt 148500
ggagtgcctg gccgcctgcc gcgggatcct ggaggcgctg gccgagggct tcgacggcga 148560
cctggcggcc gtcccggggc tggccggggc ccggcccgcc agccccccgc ggccggaggg 148620
acccgcgggc cccgcttccc cgccgccgcc gcacgccgac gcgccccgcc tgcgcgcgtg 148680
gctgcgcgag ctgcggttcg tgcgcgacgc gctggtgctc atgcgcctgc gcggggacct 148740
gcgcgtggcc ggcggcagcg aggccgccgt ggccgccgtg cgcgccgtga gcctggtcgc 148800
cggggccctg ggcccccgcgc tgccgcggga cccgcgcctg ccgagctccg cggccgccgc 148860
cgccgcggac ctgctgtttg agaaccagag cctgcgcccc ctgctggcgg cggccgccag 148920
cgcaccggac gccgccgacg cgctggcggc cgccgccgcc tccgccgcgc cgcgggaggg 148980
gcgcaagcgc aagagtcccg gcccggcccg gccgcccgga ggcggcggcc cgcgaccccc 149040
gaagacgaag aagagcggcg cggacgcccc cggctcggac gcccgcgccc ccctccccgc 149100
gcccccctcc acgcccccgg ggcccgagcc cgcccccgcc cagcccgcgg cgccccgggc 149160
cgccgcggcg caggcccgcc cgcgccccgt ggcgctgtcg cgccggcccg ccgagggccc 149220
cgacccccctg ggcggctggc ggcggcagcc cccggggccc agccacacgg cggcgcccgc 149280
ggccgccgcc ctggaggcct actgctcccc gcgcgccgtg gccgagctca cggaccaccc 149340
gctgttcccc gtcccctggc gaccggccct catgtttgac ccgcgggccc tggcctcgat 149400
cgccgcgcgg tgcgccgggc ccgccgccgc cgcccaggcc gcgtgcggcg gcggcgacga 149460
cgacgataac ccccaccccc acggggccgc cgggggccgc ctctttggcc ccctgcgcgc 149520
ctcgggcccg ctgcgccgca tggcggcctg gatgcgccag atccccgacc ccgaggacgt 149580
gcgcgtggtg gtgctgtact cgccgctgcc gggcgaggac ctggccggcg gcggggcctc 149640
ggggggggccg ccggagtggt ccgccgagcg cggcgggctg tcctgcctgc tggcggccct 149700
ggccaaccgg ctgtgcgggc cggacacggc cgcctgggcg ggcaactgga ccggcgcccc 149760
cgacgtgtcg gcgctgggcg cgcagggcgt gctgctgctg tccacgcggg acctggcctt 149820
cgccggggcc gtggagtttc tggggctgct cgccagcgcc ggcgaccggc ggctcatcgt 149880
ggtcaacacc gtgcgcgcct gcgactggcc cgccgacggg cccgcggtgt cgcggcagca 149940
cgcctacctg gcgtgcgacc tgctgcccgc cgtgcagtgc gccgtgcgct ggccggcggc 150000
gcgggacctg cgccgcacgg tgctggcccc gggccgcgtg ttcggcccgg gggtcttcgc 150060
gcgcgtggag gccgcgcacg cgcgcctgta ccccgacgcg ccgccgctgc gcctgtgccg 150120
cggcggcaac gtgcgctacc gcgtgcgcac gcgcttcggc ccggacacgc cggtgcccat 150180
gtccccgcgc gagtaccgcc gggccgtgct gccggcgctg gacggccggg cggcggcctc 150240
ggggaccacc gacgccatgg cgcccggcgc gccggacttc tgcgaggagg aggcccactc 150300
gcaccgcgcc tgcgcgcgct ggggcctggg cgcgccgctg cggcccgtgt acgtggcgct 150360
ggggcgcgag gcggtgcgcg ccggcccggc ccggtggcgc gggccgcgga gggacttttg 150420
cgcccgcgcc ctgctggagc ccgacgacga cgcccccccg ctggtgctgc gcggcggcga 150480
cgacgacgac gacggcccgg gggccctgcc gccggcgttg cccgggattc gctgggcctc 150540
ggccacgggc cgcagcggca ccgtgctggc ggcggcgggg gccgtggagg tgctgggggc 150600
ggaggcgggc ttggccacgc ccccgcgacg ggaagttgtg gactgggaag gcgcctggga 150660
cgacgacgac ggcggcgcgt tcgaggggga cggggtgctg taacgggccg ggacggggcg 150720
gggcgcttgc gaaacccgaa gacgcaataa acgacaacga cctgatttag ttttgcagta 150780
gcgttgttta tttcgagggg cgggaggggg cgaggggcgg gagggggcga ggggcgggag 150840
ggggcgaggg gcgggagggg gcgaggggcg ggagggggcg aggggcggga gggggcgagg 150900
ggcgggaggg ggcgaggggc gggagggggc gaggggcggg agggggcgag gggcgggagg 150960
gggcgagggg cgggaggggg cgaggggcgg gagggggcga ggggcgggag ggggcgaggg 151020
gcgggagggg gcgaggggcg ggagggggcg aggggcggga gggggcgagg ggcgggaggg 151080
ggcgaggggc gggagggggc gaggggcggg agggggcgag gggcggtggt ggtgcgcggg 151140
cgcccccgga gggtttggat ctctgacctg agattggcgg cactgaggta gagatgcccg 151200
aacccccccg agggagcgcg ggacgcggcc ggggagggct ggggccgggg agggctgggg 151260
ccggggaggg ctggggccgg ggagggctgg ggccggggag ggctggggcc ggggagggct 151320
ggggccgggg agggctgggg ctggggaggg ctggggctgg ggagggctgg ggcggtggtg 151380
tgtgacagga gcggcgtgtt gcgctggggg acgtctggag gagcgggggg tgcgcggtga 151440
cgtgtggatg aggaacagga gttgttgcgc ggtgagttgt cgctgtgagt tgtgttggtg 151500
ggcaggtgtg gtggatgacg tgacgtgtga cgtgtggatg aggaaccgga gtcgccggtg 151560
cgccgtgctg ttggtgttct gttggtgttg ttacacctgt ggcagcccgg gcccccccgcg 151620 ggcggggcgg cgcgcaaaaa aggcgggcgg cggtccgggc ggcgtgcgcg cgcgcggcgg 151680
gcgttggggg agcgggggga ggagcggggg gaggagcggg gggaggagcg gggggaggag 151740 cgggggggagg agcgggggga ggagcggggg gaggagcggg gggaggagcg gggggaggag 151800 cgggggggagg agcgggggga ggagcggggg gaggagcggg gggaggagcg gggggaggag 151860 cgggggggagg agcgggggga ggagcggggg gaggagcggg gggaggagcg gaaaacgggc 151920 ccccccccgaa acacaccccc cgggggtcgc gcgcggccct ttaaagcg 151968

<210> SEQ ID NO 2
<211> LENGTH: 612
<212> TYPE: DNA
<213> ORGANISM: Artificial Sequence
<220> FEATURE:
<223> OTHER INFORMATION: Synthetic sequence derived from HSV-1(F)

<400> SEQUENCE: 2
atgaccatgg aggagggaga actgccgctg gaggaacagt tttcattgtc ctcgtacggc 60
acctctgatt tttttgtcag ttcggcatac tcgcgtcttc cgccccatac ccagccggtc 120
ttttcaaagc gcgtgattct gttcctttgg tcgtttttgg tcctgaagcc gttggagatg 180
gtggcagcgg gcatgtatta cgggctgacc ggaagggtgg tggcgccggc ctgtatcctg 240
gccgccatcg tcggctacta cgttacgtgg gcggtgcggg cgctcctcct gtacgttaac 300
atcaagaggg atcgtctgcc gttgtcggcg cccgtgtttt gggggatgtc cgtgtttttg 360
ggaggcacgg ccctgtgtgc cttgttcgcc gccgcccacg agaccttcag tccggacggg 420
cttttccact ttatcgccac caaccaaatg ctgccaccca ccgatcccct gcgcacacgg 480
gccctgggga tagcctgtgc ggccggggcc tcgatgtggg tggcggcggc ggacagcttt 540
gccgcctctg ccaatttctt cctggcacgc ttttggacca gggccatctt gaatgcaccc 600
gtcgcgttct aa 612

<210> SEQ ID NO 3
<211> LENGTH: 203
<212> TYPE: PRT
<213> ORGANISM: Artificial Sequence
<220> FEATURE:
<223> OTHER INFORMATION: Synthetic sequence derived from HSV-1(F)

<400> SEQUENCE: 3

Met Thr Met Glu Glu Gly Glu Leu Pro Leu Glu Glu Gln Phe Ser Leu
1 5 10 15

Ser Ser Tyr Gly Thr Ser Asp Phe Phe Val Ser Ser Ala Tyr Ser Arg
20 25 30

Leu Pro Pro His Thr Gln Pro Val Phe Ser Lys Arg Val Ile Leu Phe
35 40 45

Leu Trp Ser Phe Leu Val Leu Lys Pro Leu Glu Met Val Ala Ala Gly
50 55 60

Met Tyr Tyr Gly Leu Thr Gly Arg Val Val Ala Pro Ala Cys Ile Leu
65 70 75 80

Ala Ala Ile Val Gly Tyr Tyr Val Thr Trp Ala Val Arg Ala Leu Leu
85 90 95

Leu Tyr Val Asn Ile Lys Arg Asp Arg Leu Pro Leu Ser Ala Pro Val
100 105 110

Phe Trp Gly Met Ser Val Phe Leu Gly Gly Thr Ala Leu Cys Ala Leu
115 120 125

Phe Ala Ala Ala His Glu Thr Phe Ser Pro Asp Gly Leu Phe His Phe
130 135 140

Ile Ala Thr Asn Gln Met Leu Pro Pro Thr Asp Pro Leu Arg Thr Arg
145 150 155 160

Ala Leu Gly Ile Ala Cys Ala Ala Gly Ala Ser Met Trp Val Ala Ala
165 170 175

Ala Asp Ser Phe Ala Ala Ser Ala Asn Phe Phe Leu Ala Arg Phe Trp
180 185 190

Thr Arg Ala Ile Leu Asn Ala Pro Val Ala Phe
195 200

<210> SEQ ID NO 4
<211> LENGTH: 903
<212> TYPE: DNA
<213> ORGANISM: Artificial Sequence
<220> FEATURE:
<223> OTHER INFORMATION: Synthetic sequence derived from HSV-1(F)

<400> SEQUENCE: 4
atgctcgccg tccgttccct gcagcacctc tcaaccgtcg tcttgataac ggcgtacggc 60
ctcgtgctcg tgtggtacac cgtcttcggt caccccccca acgggggctg gcgcaaccac 120
gcccatatct gctacgccaa tcttatcgcg ggtagggtcg tgcccttcca ggtcccaccc 180
gacgccatga atcgtcggat catgaacgtc cacgaggcag ttaactgtct ggagacccta 240
tggtacacac gggtgcgtct ggtggtcgta gggtggttcc tgtatctggc gttcgtcgcc 300
ctccaccaac gccgatgtat gtttggtgtc gtgagtcccg cccacaagat ggtggccccg 360
gccacctacc tcttgaacta cgcaggccgc atcgtatcga gcgtgttcct gcagtacccc 420
tacacgaaaa ttacccgcct gctctgcgag ctgtcggtcc agcggcaaaa cctggttcag 480

-continued

```
ttgtttgaga cggacccggt caccttcttg taccaccgcc ccgccatcgg ggtcatcgta    540

ggctgcgagt tgatgctacg ctttgtggcc gtgggtctca tcgtcggcac cgctttcata    600

tcccgggggg catgtgcaat cacataccc ctgtttctga ccatcaccac ctggtgtttt    660

gtctccacca tcggcctgac agagctgtat tgtattctgc ggcggggccc ggcccccaag    720

aacgcagaca aggccgccgc cccggggcga tccaaggggc tgtcgggcgt ctgcgggcgc    780

tgctgttcca tcatcctctc gggcatcgca gtgcgattgt gttatatcgc cgtggtggcc    840

ggggtggtgc tcgtggcgct tcactacgag caggagatcc agaggcgcct gtttgatgta    900

tga                                                                 903
```

<210> SEQ ID NO 5
<211> LENGTH: 300
<212> TYPE: PRT
<213> ORGANISM: Artificial sequence
<220> FEATURE:
<223> OTHER INFORMATION: synthetic sequence

<400> SEQUENCE: 5

```
Met Leu Ala Val Arg Ser Leu Gln His Leu Ser Thr Val Val Leu Ile
1               5                   10                  15

Thr Ala Tyr Gly Leu Val Leu Val Trp Tyr Thr Val Phe Gly His Pro
            20                  25                  30

Pro Asn Gly Gly Trp Arg Asn His Ala His Ile Cys Tyr Ala Asn Leu
        35                  40                  45

Ile Ala Gly Arg Val Val Pro Phe Gln Val Pro Pro Asp Ala Met Asn
    50                  55                  60

Arg Arg Ile Met Asn Val His Glu Ala Val Asn Cys Leu Glu Thr Leu
65                  70                  75                  80

Trp Tyr Thr Arg Val Arg Leu Val Val Val Gly Trp Phe Leu Tyr Leu
                85                  90                  95

Ala Phe Val Ala Leu His Gln Arg Arg Cys Met Phe Gly Val Val Ser
            100                 105                 110

Pro Ala His Lys Met Val Ala Pro Ala Thr Tyr Leu Leu Asn Tyr Ala
        115                 120                 125

Gly Arg Ile Val Ser Ser Val Phe Leu Gln Tyr Pro Tyr Thr Lys Ile
    130                 135                 140

Thr Arg Leu Leu Cys Glu Leu Ser Val Gln Arg Gln Asn Leu Val Gln
145                 150                 155                 160

Leu Phe Glu Thr Asp Pro Val Thr Phe Leu Tyr His Arg Pro Ala Ile
                165                 170                 175

Gly Val Ile Val Gly Cys Glu Leu Met Leu Arg Phe Val Ala Val Gly
            180                 185                 190

Leu Ile Val Gly Thr Ala Phe Ile Ser Arg Gly Ala Cys Ala Ile Thr
        195                 200                 205

Tyr Pro Leu Phe Leu Thr Ile Thr Thr Trp Cys Phe Val Ser Thr Ile
    210                 215                 220

Gly Leu Thr Glu Leu Tyr Cys Ile Leu Arg Arg Gly Pro Ala Pro Lys
225                 230                 235                 240

Asn Ala Asp Lys Ala Ala Ala Pro Gly Arg Ser Lys Gly Leu Ser Gly
                245                 250                 255

Val Cys Gly Arg Cys Cys Ser Ile Ile Leu Ser Gly Ile Ala Val Arg
            260                 265                 270

Leu Cys Tyr Ile Ala Val Val Ala Gly Val Val Leu Val Ala Leu His
        275                 280                 285
```

```
Tyr Glu Gln Glu Ile Gln Arg Arg Leu Phe Asp Val
    290                 295                 300


<210> SEQ ID NO 6
<211> LENGTH: 150432
<212> TYPE: DNA
<213> ORGANISM: Artificial sequence
<220> FEATURE:
<223> OTHER INFORMATION: synthetic sequence

<400> SEQUENCE: 6

agcccgggcc ccccgcgggc ggggcggcgc gcaaaaaagg cgggcggcgg tccgggcggc     60
gtgcgcgcgc gcggcgggcg ttggggagcg gggggaggag cggggggagg agcgggggga    120
ggagcggggg gaggagcggg gggaggagcg gggggaggag cggggggagg agcgggggga    180
ggagcggggg gaggagcggg gggaggagcg gggggaggag cggggggagg agcgggggga    240
ggagcggggg gaggagcggg gggaggagcg gggggaggag cggggggagg agcgggggga    300
ggagcggaaa acgggccccc cccgaaacac accccccggg ggtcgcgcgc ggccctttaa    360
agcgcggcgg cgcagcccgg gcccccccgcg gccgagacga gcgagttaga caggcaagca    420
ctactcgcct ctgcacgcac atgcttgcct gtcaaactct accaccccgg cacgctctct    480
gtctccatgg cccgccgccg ccgccatcgc ggcccccgcc gcccccggcc gcccgggccc    540
acgggcgccg tcccaaccgc acagtcccag gtaacctcca cgcccaactc ggaacccgcg    600
gtcaggagcg cgcccgcggc cgccccgccg ccgccccccg ccagtgggcc cccgccttct    660
tgttcgctgc tgctgcgcca gtggctccac gttcccgagt ccgcgtccga cgacgacgat    720
gacgacgact ggccggacag ccccccgccc gagccggcgc cagaggcccg gcccaccgcc    780
gccgcccccc gcccccggtc cccaccgccc ggcgcgggcc cggggggcgg ggctaacccc    840
tcccaccccc cctcacgccc cttccgcctt ccgccgcgcc tcgccctccg cctgcgcgtc    900
accgcagagc acctggcgcg cctgcgcctg cgacgcgcgg gcggggaggg ggcgccggag    960
ccccccgcga cccccgcgac ccccgcgacc cccgcgaccc ccgcgacccc cgcgcgggtg   1020
cgcttctcgc cccacgtccg ggtgcgccac ctggtggtct gggcctcggc cgcccgcctg   1080
gcgcgccgcg gctcgtgggc ccgcgagcgg gccgaccggg ctcggttccg gcgccgggtg   1140
gcggaggccg aggcggtcat cgggccgtgc ctggggcccg aggcccgtgc ccgggccctg   1200
gcccgcggag ccggcccggc gaactcggtc taacgttaca cccgaggcgg cctgggtctt   1260
ccgcggagct cccgggagct ccgcaccaag ccgctctccg gagagacgat ggcaggagcc   1320
gcgcatatat acgctgggag ccggcccgcc cccgaggcgg gcccgccctc ggagggcggg   1380
actggccaat cggcggccgc cagcgcggcg gggcccggcc aaccagcgtc cgccgagtct   1440
tcggggcccg gcccactggg cgggagttac cgcccagtgg gccgggccgc ccacttcccg   1500
gtatggtaat taaaaactta caagaggcct tgttccgctt cccggtatgg taattagaaa   1560
ctcattaatg ggcggccccg gccgcccttc ccgcttccgg caattcccgc ggcccttaat   1620
gggcaacccc ggtattcccc gcctcccgcg ccgcgcgtaa ccactcccct ggggttccgg   1680
gttatgctaa ttgctttttt ggcggaacac acggcccctc gcgcattggc ccgcgggtcg   1740
ctcaatgaac ccgcattggt cccctggggt tccgggtatg gtaatgagtt tcttcgggaa   1800
ggcgggaagc cccggggcac cgacgcaggc caagcccctg ttgcgtcggt gggaggggca   1860
tgctaatggg gttctttggg ggacaccggg ttggtccccc aaatcggggg ccgggccgtg   1920
catgctaatg atattctttg gggcgccgg gttggtcccc ggggacgggg ccgccccgcg   1980
```

-continued

```
gtgggcctgc ctcccctggg acgcgcggcc attgggggaa tcgtcactgc cgcccctttg   2040
gggaggggaa aggcgtgggg tataagttag ccctggcccg acagtctggt cgcatttgca   2100
cctcggcact cggagcgaga cgcagcagcc aggcagactc gggccgcccc ctctccgcat   2160
caccacagaa gccccgccta cgttgcgacc cccagggacc ctccgtccgc gaccctccaa   2220
ccgcatacga cccccatgga gccccgcccc ggagcgagta cccgccggcc tgagggccgc   2280
ccccagcgcg aggtgagggg ccgggcgcca tgtctggggc gccatattgg ggggcgccat   2340
attgggggc gccatgttgg gggacccccg acccttacac tggaaccggc cgccatgttg   2400
ggggaccccc actcatacac gggagccggg cgccatgtta gggggcgtgg aaccccgtga   2460
cactatatat acagggaccg ggggcgccat gttagggggc gcggaacccc ctgaccctat   2520
atatacaggg accggggtcg ccctgttggg ggtcgccatg tgacccccctg actttatata   2580
tacagacccc ccaacacata cacatggccc ctttgactca gacgcagggc ccggggtcgc   2640
cgtgggaccc cctgactcat acacagagac acgcccccac aacaaacaca cagggaccgg   2700
ggtcgccgtg ttagggggcg tggtccccac tgactcatac gcagggcccc cttactcaca   2760
cgcatctagg ggggtgggga ggagccgccc gccatatttg gggacgccg tgggaccccc   2820
gactccggtg cgtctggagg gcgggagaag agggaagaag aggggtcggg atccaaagga   2880
cggacccaga ccacctttgg ttgcagaccc ctttctcccc cctcttccga ggccagcagg   2940
ggggcaggac tttgtgaggc gggggggggg agagggggaa ctcgtgggcg ctgattgacg   3000
cgggaaatcc ccccattctt acccgccccc cttttttcc ccttagcccg ccccggatgt   3060
ctgggtgttt ccctgcgacc gagacctgcc ggacagcagc gactctgagg cggagaccga   3120
agtgggggg cgggggggacg ccgaccacca tgacgacgac tccgcctccg aggcggacag   3180
cacggacacg gaactgttcg agacggggct gctggggccg cagggcgtgg atgggggggc   3240
ggtctcgggg gggagccccc cccgcgagga agaccccggc agttgcgggg gcgccccccc   3300
tcgagaggac ggggggagcg acgagggcga cgtgtgcgcc gtgtgcacgg atgagatcgc   3360
gccccacctg cgctgcgaca ccttcccgtg catgcaccgc ttctgcatcc cgtgcatgaa   3420
aacctggatg caattgcgca acacctgccc gctgtgcaac gccaagctgg tgtacctgat   3480
agtgggcgtg acgcccagcg ggtcgttcag caccatcccg atcgtgaacg acccccagac   3540
ccgcatggag gccgaggagg ccgtcagggc gggcacggcc gtggacttta tctggacggg   3600
caatcagcgg ttcgccccgc ggtacctgac cctggggggg cacacggtga gggccctgtc   3660
gcccacccac cctgagccca ccacggacga ggatgacgac gacctggacg acggtgaggc   3720
gggggggcgg cgaggaccct gggggaggag gaggaggagg ggggagggag gaataggcgg   3780
gcgggggggc gaggaaaggg cgggcgcgga aagggagggc ctgggagggg gcgtaacctg   3840
atcgcgcccc ccgttgtctc ttgcagcaga ctacgtaccg cccgcccccc gccggacgcc   3900
ccgcgccccc ccacgcagag gcgccgccgc gcccccgtg acgggcgggg cgtctcacgc   3960
agccccccag ccggccgcgg ctcggacagc gcccccctcg gcgcccatcg ggccacacgg   4020
cagcagtaac accaacacca ccaccaacag cagcggcggc ggcggcggct cccgccagtc   4080
gcgagccgcg gcgccgcggg gggcgtctgg cccctccggg ggggttgggg ttggggttgg   4140
ggttgttgaa gcggaggcgg ggcggccgag gggccggacg ggcccccttg tcaacagacc   4200
cgcccccctt gcaaacaaca gagaccccat agtgatcagc gactcccccc cggcctctcc   4260
ccacaggccc cccgcggcgc ccatgccagg ctccgccccc cgccccgggc ccaccgcgtc   4320
```

-continued

```
ctcggccgcg tcgggacccg cgcgcccccg cgcggccgtg gccccgtgcg tgcgagcgcc   4380
gcctccgggg cccggccccc gcgccccggc ccccgcggac gcgcgccgtg tgccccagtc   4440
gcactcgtcc ctggctcagg ccgcgaacca agaacagagt ctgtgccggg cgcgtgcgac   4500
ggtggcgcgc ggctcggggg ggccgggcgt ggagggtgga cacgggccct cccgcggcgc   4560
cgccccctcc ggcgcccccc cgctcccctc cgccgcctct gtcgagcagg aggcggcggt   4620
gcgtccgagg aagaggcgcg ggtcgggcca ggaaaacccc tccccccagt ccacgcgtcc   4680
ccccctcgcg ccggcagggg ccaagagggc ggcgacgcac ccccccctccg actcagggcc   4740
ggggggggcgc ggccagggtg ggcccgggac cccccctgacg tcctcggcgg cctccgcctc   4800
ttcctcctct gcctcttcct cctcggcccc gactcccgcg gggccgcct cttccgccgc   4860
cggggccgcg tcctcctccg cttccgcctc ctcgggcggg gccgtcggtg ccctgggagg   4920
gagacaagag gaaacctccc tcggcccccg cgctgcttct gggccgcggg ggccgaggaa   4980
gtgtgcccgg aagacgcgcc acgcggagac ttccggggcc gcccccgcgg gcggcctcac   5040
gcgctacctg cccatctcgg gggtctctag cgtggtcgcc ctgtcgcctt acgtgaacaa   5100
gacgatcacg gggggactgcc tgcccatcct ggacatggag acggggaaca tcggggcgta   5160
cgtggtcctg gtggaccaga cgggaaacat ggcgacccgg ctgcgggccg cggtccccgg   5220
ctggagccgc cgcaccctgc tccccgagac cgcgggtaac cacgtgatgc cccccgagta   5280
cccgacggcc cccgcgtcgg agtggaacag cctctggatg acccccgtgg ggaacatgct   5340
gttcgaccag ggcaccctag tgggcgccct ggacttccgc agcctgcggt ctcggcaccc   5400
gtggtccggg gagcaggggg cgtcgacccg ggacgaggga aaacaataag ggacgccccc   5460
cgtgtttgtg gggagggggg ggtcgggcgc tgggtggtct ctggccgcgc ccactacacc   5520
agccaatccg tgtcggggag gggaaaagtg aaagacacgg gcaccacaca ccagcgggtc   5580
tttagtgttg gccctaataa aaaactcagg ggatttttgc tgtctattgg gaaataaagg   5640
tttacttttg tatcttttcc ctgtctgtgt tggatggatc tcgggggtgc gtgggagtgg   5700
gggtgcgtgg gagtgggggt gcgtgggagt gggggtgcgt gggagtgggg gtgcgtggga   5760
gtgggggtgc gtgggagtgg gggtgcgtgg gagtgggggt gcgtgggagt gggggtgcgt   5820
gggagtgggg gtgccatgtt gggcaggctc tggtgttaac cacagagccg cggcccgggc   5880
tgcctgacca ccgatccccg aaagcatcct gccactggca tggagccaga accacagtgg   5940
gttgggtgtg ggtgttaagt ttccgcgagc gcctgcccgc ccggactgac ctggcctctg   6000
gccgccacaa agggcggggg ggggttaact acactatagg gcaacaaagg acgggagggg   6060
tggcggggcg ggacggggcg cccaaaaggg ggtcggccac accacagacg tgggtgttgg   6120
ggggtggggc ggaggggtgg ggggggagac agaaacagga acatagttag aaaacaagaa   6180
tgcggtgcag ccagagaatc acaggagacg aggggatggg cgtgttggtt accaacccac   6240
acccaggcat gctcggtggt atgaaggagg gggggcggtg cttcttagag accgccgggg   6300
gacgtggggt tggtgtgcag aggcacgcgc acccgcgtcg gccaggtggg ccggtacccc   6360
atccccccctc ccccgaccct tcccaccccc gcgtgccaga gatcaccccg gtcccccggc   6420
acccgccact cctccatatc ctcgctttag gaacaacttt aggggggggta cacacgcgcc   6480
gtgcatttcc ttccacaccc cccctccccc gcactccccc ccccccggca gtaagaccca   6540
agcatagaga gccaggcaca aaaacacagg cggggtggga cacatgcctt cttggagtac   6600
gtgggtcatt ggcgtggggg gttacagcga caccggccga ccccctggcg gtcttccagc   6660
cggcccttag ataagggggc agttggtggt cggacgggta agtaacagag tctgactaag   6720
```

-continued

```
ggtgggaggg ggggaaaaga acgggctggt gtgctgtaac acgagcccac ccgcgagtgg   6780
cgtggccgac cttagcctct ggggcgcccc ctgtcgtttg ggtccccccc ctctattggg   6840
gagaagcagg tgtctaacct acctggaaac gcggcgtctt tgttgaacca caccggggcg   6900
cccttgacga gtgggataac gggggaggaa gggagggagg agggtactgg gggtgaagaa   6960
gggggggggg ggagaagcga gaacaggaaa ggcgacggag cccgacaaaa caccgagaaa   7020
aaaaaaccac agcgcatgcg ccgggccgtt gtggggcccc gggccggggc cccttgggtc   7080
cgccggggcc ccgggccggg ccgccacggg ggccggccgt tggcggtaac cccgattgtt   7140
tatctcaggc cccgggccgg gaacccggaa aagcctccgg ggggcctttt tcgcgtcgcg   7200
tgccggcgag cgggcccgga cggggcccgg accgccgcgg tcgggggccc cctcgtcccg   7260
ggccgtacgc ggccttcgcc ccgtgagggg acagacgaac gaaacattcc ggcgacggaa   7320
cgaaaaacac cccagacggg ttaaagaaac agaaaccgca accccccca cccccgaaac    7380
ggggaaaaca aaaaacagac cagcggccgg ccggcgctta gggggaggat gtcgccgacg   7440
cccettggcc gccccggctg caggggggcc cggagagccg cggcacccgg acgcgcccgg   7500
aaagtctttc gcaccacccg cgatcggcac ggccgcgccc ccgcttttat aaaggctcag   7560
atgacgcagc aaaaacaggc cacagcacca cgtgggtagg tgatgtaatt ttattttcct   7620
cgtctgcggc ctaatggatt tccgggcgcg gtgcccctgt ctgcagagca cttaacggat   7680
tgatatctcg cgggcacgcg cgcccttaat ggaccggcgc ggggcggggg gccggatacc   7740
cacacgggcg gggggggggg tgtcgcgggc cgtctgctgg cccgcggcca cataaacaat   7800
gactctgggc ctttctgcct ctgccgcttg tgtgtgcgcg cgccggctct gcggtgtcgg   7860
cggcggctgc ggcggctgcg gcggccgccg tgttcggtct cggtagccgg ccggcgggtg   7920
gactcgcggg gggccggagg gtggaaggca ggggggtgta ggatgggtat caggacttcc   7980
acttcccgtc cttccatccc ccgttcccct cggttgttcc tcgccccccc ccacaccccg   8040
ccgctttccg ttggggttgt tattgttgtc gggatcgtgc gggccggggg tcgccggggc   8100
aggggcgggg gcgggggtgc tcgtcgatcg accgggctca gtgggggcgt ggggtggggg   8160
ggaaaaggcg aagagactgg gggtgggggg gggtgtcggg ggtggctgtt tttttttgtg   8220
ggtgtttttt gtggctgttc ccgtccccccg tcacccccct ccctccgtcc ccccgtcgcg  8280
ggtgtttgtg tttgtttatt ccgacatcgg tttatttaaa taaacacagc cgttctgcgt   8340
gtctgttctt gcgtgtggct gggggcttat atgtggggtc ccgggggcgg gatggggttt   8400
agcggcgggg ggcggcgcgc cggacggggc gctggagata acggcccccg gggaacgggg   8460
gaccggggct gggtctcccg aggtgggtgg gtgggcggcg gtggccgggc cgggccgggc   8520
cgggtgggcg gggtttggaa aaacgaggag gaggaggagg agaaggaggg ggggggagac   8580
ggggggaaag caaggacacg gcccgggggg tgggagcgcg ggccgggccg ctcgtaagag   8640
ccgcgacccg gccgccgggg agcgttgtcg ccgtcggtct gccggccccc gtccctccct   8700
tttttgacca accagcgccc cccccctca ccaccattcc taccaccacc accaccaccg    8760
acacctcccg cacaccccg cccacactcc cccccccac ccaacccgca ccacgagcac     8820
gggttggggg tagcagggga tcaaaggggg gcaaggccgg cggggcggtt cgggggcggg   8880
ggcgggagac cgagtaggcc ccgcccatcc gcggcccctc ccggcagcca cgcccccag    8940
cgtcgggtgt cacggggaaa gagcaggggg agaggggaga gggggggaga ggggagaggg   9000
ggggagaggg gagaggggg gagaggggag agggggggag aggggagagg gggggagagg    9060
```

-continued

```
ggagaggggg ggagagggga gagggggggga gaggggagag ggggggagag gggagagggg    9120
gggagagggg agaggggggg agagggggta tataaaccaa cgaaaagcgc gggaacgggg    9180
atacggggct tgtgtggcac gacgtcgtgg ttgtgttact gggcaaacac ttggggactg    9240
taggtttctg tgggtgccga ccctaggcgc tatggggatt ttgggttggg tcgggcttat    9300
tgccgttggg gttttgtgtg tgcggggggg cttgtcttca accgaatatg ttattcggag    9360
tcgggtggct cgagaggtgg gggatatatt aaaggtgcct tgtgtgccgc tcccgtctga    9420
cgatcttgat tggcgttacg agaccccctc ggctataaac tatgctttga tagacggtat    9480
atttttgcgt tatcactgtc ccggattgga cacggtcttg tgggataggc atgcccagaa    9540
ggcatattgg gttaacccct ttttatttgt ggcgggtttt ttggaggact tgagtcaccc    9600
cgcgtttcct gccaacaccc aggaaacaga aacgcgcttg gccctttata aagagatacg    9660
ccaggcgctg gacagtcgca agcaggccgc cagccacaca cctgtgaagg ctgggtgtgt    9720
gaactttgac tattcgcgca cccgccgctg tgtagggcga caggatttgg gacctaccaa    9780
cggaacgtct ggacggaccc cggttctgcc gccggacgat gaagcgggcc tgcagccgaa    9840
gcccctcacc acgccgccgc ccatcatcgc cacgttggac cccaccccgc gacgggacgc    9900
cgccgcaaaa agcagacgcc gacgacccca ctcccggcgc atctaatgat gccgcgacgg    9960
aaacccgtcc gggttcgggg ggcgaaccgg ccgcctgtcg ctcgtcaggg ccggcgggcg   10020
ctcctcgccg ccctagaggc tgtcccgctg gtgtgacgtt ttcctcgtcc gcgccccccg   10080
accctcccat ggatttaaca aacggggggg tgtcgcctgt ggcgacctcg gcgcctctgg   10140
actggaccac gtttcggcgt gtgtttctga tcgacgacgc gtggcggccc ctgttggagc   10200
ctgagctggc gaacccctta accgcccacc tcctgaccga atataatcgt cggtgccaga   10260
ccgaagaggt gctgccgccg cgggaggatg tgttttcgtg gactcgttat tgcacccccg   10320
acgaggtgcg cgtggttatc atcggccagg acccatatca ccaccccggc caggcgcacg   10380
gacttgcgtt tagcgtgcgc gcgaacgtgc cgcctccccc gagtcttcgg aatgtcttgg   10440
cggccgtcaa gaactgttat cccgaggcac ggatgagcgg ccacggttgc ctggaaaagt   10500
gggcgcggga cggcgtcctg ttactaaaca cgaccctgac cgtcaagcgc ggggcggcgg   10560
cgtcccactc tagaatcggt tggaccgct  tcgtgggcgg agttatccgc cggttggccg   10620
cgcgccgccc cggcctggtg tttatgctct ggggcgcaca tgcccagaat gccatcaggc   10680
cggaccctcg ggtccattgc gtcctcaagt tttcgcaccc gtcgcccctc tccaaggttc   10740
cgttcggaac atgccagcat ttcctcgtgg cgaatcgata tctcgagacc cggtcgattt   10800
cacccatcga ctggtcggtt tgaaaggcat cgacgtccgg ggttttcgtc tgtgggggct   10860
tttgggtatt tccgatgaat aaagacggtt aatggttaaa cctctggtct catacgggtc   10920
ggtgatgtcg ggcgtcgggg gagagggagt tccctctgcg cttgcgattc tagcctcgtg   10980
gggctggacg ttcgacacgc caaaccacga gtcagggata tcgccagata cgactcccgc   11040
agattccatt cggggggccg ctgtggcctc acctgaccaa cctttacacg gggcccgga    11100
acgggaggcc acagcgccgt ctttctcccc aacgcgcgcg gatgacggcc cgccctgtac   11160
cgacgggccc tacgtgacgt ttgataccct gtttatggtg tcgtcgatcg acgaattagg   11220
gcgtcgccag ctcacggaca ccatccgcaa ggacctgcgg ttgtcgctgg ccaagtttag   11280
cattgcgtgc accaagacct cctcgttttc gggaaacgcc ccgcgccacc acagacgcgg   11340
ggcgttccag cgcggcacgc gggcgccgcg cagcaacaaa agccttcaga tgtttgtgtt   11400
gtgcaaacgc acccacgccg ctcgagtgcg agagcagctt cgggtcgtta ttcagtcccg   11460
```

caagccgcgc aagtattaca cgcgatcttc ggacgggcgg ctctgccccg ccgtccccgt 11520
gttcgtccac gagttcgtct cgtccgagcc aatgcgcctc caccgagata acgtcatgct 11580
ggcctcgggg gccgagtaac cgcccccccg cgccaccctc actgcccgtc gcgcgtgttt 11640
gatgttaata aataacgcat aaatttggct ggttgtttgt tgtctttaat ggaccgcccg 11700 caggggggt ggcatttcag tgtcgggtga cgagcgcgat ccggccggga tcctaggacc 11760
ccaaaagttt gtctgcgtat tccagggcgg ggctcagttg aatctcccgc agcacctcta 11820
ccagcaggtc cgcggtgggc tggagaaact cggccgtccc ggggcaggcg gtcgtcgggg 11880
gtggaggcgc ggcgcccacc ccgtgtgccg cgcctggcgt ctcctctggg ggcgacccgt 11940
aaatggttgc agtgatgtaa atggtgtccg cggtccagac cacggtcaaa atgccggccg 12000
tggcgctccg ggcgctttcg ccgcgcgagg agctgaccca ggagtcgaac ggatacgcgt 12060
acatatgggc gtcccacccg cgttcgagct tctggttgct gtcccggcct ataaagcggt 12120
aggcacaaaa ttcggcgcga cagtcgataa tcaccaacag cccaatgggg gtgtgttgga 12180
taacaacgcc tccgcgcggc aggcggtcct ggcgctcccg gccccgtacc atgatcgcgc 12240
gggtgccgta ctcaaaaaca tgcaccacct gcgcggcgtc gggcagtgcg ctggtcagcg 12300
aggccctggc gtggcatagg ctatacgcga tggtcgtctg tggattggac atctcgcggt 12360
gggtagtgag tcccccgggc cgggttcggt ggaactgtaa ggggacggcg ggttaatata 12420
caatgaccac gttcggatcg cgcagagccg atagtatgtg cttactaatg acgtcatcgc 12480
gctcgtggcg ctcccggagc ggatttaagt tcatgcgaag gaattcggag gaggtggtgc 12540
gggacatggc cacgtacgcg ctgttgaggc gcaggttgcc gggcgtaaag cagatggcga 12600
ccttgtccag gctaaggccc tgggagcgcg tgatggtcat ggcaagcttg gagctgatgc 12660
cgtagtcggc gtttatggcc atggccagct ccgtagagtc aatggactcg acaaactcgc 12720
tgatgttggt gttgacgacg gacatgaagc cgtgttggtc ccgcaagacc acgtaaggca 12780
ggggggcctc ttccagtaac tcggccacgt tggccgtcgc gtgccgcctc cgcagctcgt 12840
ccgcaaaggc aaacacccgt gcgtacgtgt atcccatgag cgtataattg tccgtctgca 12900
gggcgacgga catcagcccc ccgcgcggcg agccggtcag catctcgcag ccccggaaga 12960
taacgttgtc cacgtacgtg ctaaaggggg cgccttcaaa tgcctcccca aagagctctt 13020
ggaggattcg gaatctcccg aggaaggccc gcttcagcag cgcaaactgg gtgtgaacgg 13080
cggcggtggt ctccggttcc ccgggggtgt agtggcagta aaacacgtcg agctgttgtt 13140
cgtccagccc cgcgaaaata acgtcgaggt cgtcgtcggg aaaatcgtcc gggcccccgt 13200
cccgcggccc cagttgctta aaatcaaacg cacgctcgcc gggggcgcct gcgtcggcca 13260
ttaccgacgc ctgcgtcggc acccccgaag atttggggcg cagagacaga atctccgccg 13320
ttagttctcc catgcgggcg taggcgaggg tcctctgggt cgcatccagg cccgggcgct 13380
gcagaaagtt gtaaaaggag ataagcccgc taaatatgag ccgcgacagg aacctgtagg 13440
caaactccac cgaagtctcc ccctgagtct ttacaaagct gtcgtcacgc aacactgcct 13500
cgaaggcccg gaacgtccca ctaaacccaa aaaccagttt tcgcaggcgc gcggttaccg 13560
cgatctggct gttgaggacg taagtgacgt cgttgcgggc cacgaccagc tgctgtttgc 13620
tgtgcacctc gcagcgcatg tgccccgcgt cctggtcctg gctctgcgag tagttggtga 13680
tgcggctggc gttggccgtg agccactttt caatagtcag gccgggctgg tgtgtcagcc 13740
gtcggtattc gtcaaactcc ttgaccgaca cgaacgtaag cacggggagg gtgaacacga 13800

```
caaactcccc ctcacgggtc accttcaggt aggcgtggag cttggccatg tacgcgctca  13860
cctctttgtg ggaggagaac aaccgcgtcc agccggggag gttggcgggg ttggtgatgt  13920
agttttccgg gacgacgaag cgatccacga actgcatgtg ctcctcggtg atgggtaggc  13980
cgtactccag caccttcatg aggttaccga actcgtgctc gatgcaccgt ttgttgttaa  14040
taaaaatggc ccagctatac gagaggcggg cgtactcccg cagcgtgcgg ttgcagatga  14100
ggtacgtgag cacgttctcg ctctggcgga cggaacaccg cagtttctgg tgctcgaagg  14160
tcgactccag ggacgccgtc tgtgtcggcg agcccacaca caccaacacg ggccgcaggc  14220
gggccgcgta ctgggggtg tggtacaggg cgttaatcat ccaccagcaa tacaccacgg  14280
ccgtgaggag gtgacgccca aggagcccgg cctcgtcgat gacgatcacg ttgctgcggg  14340
taaaggccgg cagcgccccg tgggtggccg gggccaaccg cgtcagggcg ccctcggcca  14400
accccagggt ccgttccagg gcggccaggg cgcgaaactc gttccgcgac tcctcgcccc  14460
cggaggcggc cagggtgcgc ttcgtgaggt ccaaaatcac ctcccagtag tacgtcagat  14520
ctcgtcgctg caggtcctcc agcgaggcgg ggttgctggt cagggtgtac gggtactgcc  14580
ccagttgggc ctggacgtga ttcccgcgaa acccaaattc atgaaagatg gtgttgatgg  14640
gtcggctgag aaaggcgccc gagagtttgg cgtacatgtt ttgggccgca atgcgcgtgg  14700
cgcccgtcac cacacagtcc aagacctcgt tgattgtctg cacgcacgtg ctctttccgg  14760
agccagcgtt gccggtgata agatacaccg cgaacggaaa ctccctgagg ggcaggcctg  14820
cgggggactc taaggccgcc acgtcccgga accactgcag acggggcact tgcgctccgt  14880
cgagctgttg ttgcgagagc tctcggatgc gcttaaggat tggctgcacc ccgtgcatag  14940
acgtaaaatt taaaaaggcc tcggccctcc ctggaacggc tggtcggtcc ccgggttgct  15000
gaaggtgcgg cgggccgggt ctctgtccgt ctagctggcg ctccccgccg gccgccgcca  15060
tgaccgcacc acgctcgcgg gcccccacta cgcgtgcgcg gggggacacg gaagcgctgt  15120
gctcccccga ggacggctgg gtaaaggttc accccacccc cggtacgatg ctgttccgcg  15180
agattctcca cgggcagctg gggtataccg agggccaggg ggtgtacaac gtcgtccggt  15240
ccagcgaggc gaccacccgg cagctgcagg cggcgatctt tcacgcgctc ctcaacgcca  15300
ccacttaccg ggacctcgag gcggactggc tcggccacgt ggcggcccgc ggtctgcagc  15360
cccaacggct ggttcgccgg tacaggaacg cccgggaggc ggatatcgcc ggggtggccg  15420
agcgggtgtt cgacacgtgg cggaacacgc ttaggacgac gctgctggac tttgcccacg  15480
ggttggtcgc ctgctttgcg ccgggcggcc cgagcggccc gtcaagcttc cccaaatata  15540
tcgactggct gacgtgcctg ggctggtcc ccatattacg caagcgacaa gaagggggtg  15600
tgacgcaggg tctgagggcg tttctcaagc agcacccgct gacccgccag ctggccacgg  15660
tcgcggaggc cgcggagcgc gccggccccg ggttttttga gctggcgctg gccttcgact  15720
ccacgcgcgt ggcggactac gaccgcgtgt atatttacta caaccaccgc cggggcgact  15780
ggctcgtgcg agaccccatc agcgggcagc gcggagaatg tctggtgctg tggcctccct  15840
tgtggaccgg ggaccgtctg gtcttcgatt cgcccgtaca gcggctgttt cccgagatcg  15900
tcgcgtgtca ctccctccgg gaacacgcgc acgtctgccg gctgcgcaat accgcgtccg  15960
tcaaggtgct gctggggcgc aagagcgaca gcgagcgcgg ggtggccggc gccgcgcggg  16020
tcgttaacaa ggtgttgggg gaggacgacg agaccaaggc cgggtcggcc gcctcgcgcc  16080
tcgtgcggct tatcatcaac atgaagggca tgcgccacgt aggcgacatt aacgacactg  16140
tgcgtgccta cctcgacgag gccgggggc acctgataga cgccccggcc gtcgacggta  16200
```

```
ccctcccggg attcggcaag ggcggaaaca gccgcgggtc tgcgggccag gaccaggggg  16260
ggcgggcgcc gcagcttcgc caggccttcc gcacggccgt ggttaacaac atcaacggcg  16320
tgttggaggg ctatataaat aacctgtttg gaaccatcga gcgcctgcgc gagaccaacg  16380
cgggcctggc gacccagttg caggagcgcg accgcgagct ccggcgcgca acatcggggg  16440
ccctggagcg ccagcagcgc gcggccgacc tggcggccga gtccgtgacc gggggatgcg  16500
gcagccgccc tgcgggggcg gacctgctcc gggccgacta tgacattatc gacgtcagca  16560
agtccatgga cgacgacacg tacgtcgcca acagttttca gcacccgtac atcccttcgt  16620
acgcccagga cctggagcgc ctgtcgcgcc tctgggagca cgagctggtg cgctgtttca  16680
aaattctgtg tcaccgcaac aaccagggcc aagagacgtc gatctcgtac tccagcgggg  16740
cgatcgccgc attcgtcgcc ccctactttg agtcagtgct tcgggccccc cgggtaggcg  16800
cgcccatcac gggctccgat gtcatcctgg gggaggagga gttatgggat gcggtgttta  16860
agaaaacccg cctgcaaacg tacctgacag acatcgcggc cctgttcgtc gcggacgtcc  16920
agcacgcagc gctgccccg ccccctccc cggtcggcgc cgatttccgg cccggcgcgt  16980
ccccgcgggg ccggtccaga tcgcggtcgc ccggaagaac tgcgcgaggc gcgccggacc  17040
agggcggggg catcgggcac cgggatggcc gccgcgacgg ccgacgatga ggggtcggcc  17100
gccaccatcc tcaagcaggc catcgccggg gaccgcagcc tggtcgaggc ggccgaggcg  17160
attagccagc agacgctgct ccgcctggcc tgcgaggtgc gccaggtcgg cgaccgccag  17220
ccgcggttta ccgccaccag catcgcgcgc gtcgacgtcg cgcctgggtg ccggttgcgg  17280
ttcgttctgg acgggagtcc cgaggacgcc tatgtgacgt cggaggatta ctttaagcgc  17340
tgctgcggcc agtccagtta tcgcggcttc gcggtggcgg tcctgacggc caacgaggac  17400
cacgtgcaca gcctggccgt gcccccctc gttctgctgc accggttctc cctgttcaac  17460
cccagggacc tcctggactt tgagcttgcc tgtctgctga tgtacctgga gaactgcccc  17520
cgaagccacg ccaccccgtc gacctttgcc aaggttctgg cgtggctcgg ggtcgcgggt  17580
cgccgcacgt ccccattcga acgcgttcgc tgccttttcc tccgcagttg ccactgggtc  17640
ctaaacacac tcatgttcat ggtgcacgta aaaccgttcg acgacgagtt cgtcctgccc  17700
cactggtaca tggcccggta cctgctggcc aacaacccgc cccccgttct ctcggccctg  17760
ttctgtgcca ccccgacaag ctcctcattc cggctgccgg ggccgccccc ccgctccgac  17820
tgcgtggcct ataaccccgc cgggatcatg gggagctgct gggcgtcgga ggaggtgcgc  17880
gcgcctctgg tctattggtg gctttcggag accccaaaac gacagacgtc gtcgctgttt  17940
tatcagtttt gttgaatttt aggaaataaa cccggttttg tttctgtggc ctcccgacgg  18000
atgcgcgtgt ccttactccg tcttggtggg tgggtggctg tgtatggcgt cccatctgtg  18060
cggggagggg ggcaagtcgg cacgtattcg gacagactca agcacacacg gggagcgct  18120
cttgtctcag ggcaatgttt ttattggtca aactcaggca aacagaaacg acatcttgtc  18180
gtcaaaggga tacacaaact tcccccccctc gccccatact cccgccagca ccccggtaaa  18240
caccaactca atctcgcgca ggatttcgcg caggtgatga gcgcagtcca cggggggag  18300
cacaaggggc cgcgggtata gatcgacggg gacgccgacc gactccccgc ctccgggaca  18360
gacacgcacg acgcgccgcc agtagtgctc tgcgtccagc aaggcgccgc cgcggaaggc  18420
agtgggggc aaggggtcgc tggcctcaaa gggggacacc cgaacgctcc agtactccgc  18480
gtccaaccgt ttattaaacg cgtccaagat aaggcggtcg caggcgtcct ccataaggcc  18540
```

ccgggccgtg agtgcgtcct cctccggcac gcctgccgtt gtcaggccca ggacccgtcg 18600
cagcgtgtcg cgtacgaccc cggccgccgt ggtgtacgcg ggcccgcgga gaggaaatcc 18660
cccaagatgg tcagtgttgt cgcgggagtt ccagaaccac actcccgcct ggctccaggc 18720
gactgcgtgg gtgtagacgc cctcgagggc caagcacagt gggtgccgca gccggaggcc 18780
gttggcccta agcacggctc ccacggccgt ctcgatggcc cgccgggcgt cctcgatcac 18840
cccggaagcc gcatccgcgt cttgggggtc cacgttaaag acaccccaga acgcaccccc 18900
atcgcccccg cagaccgcga acttcaccga gctggccgtc tcctcgatct gcaggcagac 18960
ggcggccatt accccaccca ggagctgccg cagcgcaggg caggcgttgc acgtgtccgg 19020
gaccaggcgc tccaagacgg ccccggccca gggctctgag ggagcggcca ccaccagcgc 19080
gtccagtctt gctaggcccg tccggccgtg gggtccgcc agcccgctcc ccccgaggtc 19140
ggccagggcc gccaggagct gggcgcgaag tccggggaag caaaaccgcg ccgtccagac 19200
gggcccgacg gccgcgggcg ggtctaacag ttggatgatt ttagtggcgg gatgccaccg 19260
cgccaccgcc tcccgcactg cgggcaggag gcatccggct gccgccgagg ccacgccggg 19320
ccaggctcgc ggggggagga cgaccctgac ccccaccgcg ggccaggccc ccaggagcgc 19380
ggcgtaagcg gccgcggccc cgcgcaccag gtcccgtgcc gactcggccg tggccggcac 19440
ggtgaacgtg ggccaacccg gaaaccccag gacggcaaag tacgggacgg gtcccccccg 19500
gacctcaaac tcgggcccca gaaaggcaaa gacgggggcc agggccccgg gggcggcgtg 19560
gaccgtggta tgccactgcc ggaaaagggc gacgagcgcc ggcgcggaga acttctcgcc 19620
ggcgcttaca aagtagtcgt aatcgcgggg cagcagcacc cgtgccgtga ctcgttgtgg 19680
gtgcccgcgt ggccgcaggc ccacctcgca cacctcgacc aggtccccga acgcgccctc 19740
cttcttgatc ggcggaaacg caagagtctg gtattcgcgc gcaaatagcg cggttccggt 19800
ggtgatgtta acggtcagcg aagcggtgga cgcgcactgg ggggtgtcgc gaatggccgc 19860
caggcgcgcc cacgccagcc gcgcgtcggg atgctcggca acgcgcgccg ccagggccat 19920
agggtcgatg tcaatgttgg cctccgcgac caggagagcg gcgcgagggg cggcgggcgg 19980
gccccacgac gctctctcaa ctttcaccac cagtcccgtg cgtgggtccg agccgatacg 20040
cagcggggcg aacagggcca ccggcccggt ctggcgctcc agggccgcca ggacgcacgc 20100
gtacagcgcc cgccacagag tcgggttctc caggggctcc agcggggagg cggccggcgt 20160
cgtcgcggcg cgggcggccg ccacgacggc ctggacggag acgtccgcgg agccgtagaa 20220
atcccgcagc tccgtcgcgg tgacggagac ctccgcaaag cgcgcgcgac cctcccctgc 20280
ggcgttgcga catacaaaat acaccagggc gtggaagtac tcgcgagcgc ggggggggcag 20340
ccataccgcg taaagggtaa tggcgctgac gctctcctcc acccacacga tatctgcggt 20400
gtccatcgca cggcccctaa ggatcacggg cggtctgtgg gtcccatgct gccgtgcctg 20460
gccgggcccg gtgggttgcg gaaaccggtg acgggggggg gggcggtttt tggggttggg 20520
gtgggaaacg gcccgggtcc gggggccaac ttggcccctc ggtgcgttcc ggcaacagcg 20580
ccgccggtcc gcggacgacc acgtaccgaa cgagtgcggt cccgagactt atagggtgct 20640
aaagttcacc gccccctgca tcatgggcca ggcctcggtg gggagctccg acagcgccgc 20700
ctccaggatg atgtcagcgt tggggttggc gctggatgag tgcgtgcgca aacagcgccc 20760
ccacgcgggc acgcgtagct tgaagcgcgc gcccgcaaac tcccgcttgt gggccataag 20820
cagggcgtac agctgcctgt gggtccggca ggcgctgtgg tcgatgtggt gggcgtccaa 20880
caaccccacg attgtctgtt tggtgaggtt tttaacgcgc cccgccccgg gaaacgtctg 20940
cgtgcttttg gccatctgca cgccaaacag ttcgccccag attatcttga acagcgccac 21000
cgcgtggtcc gtctcactaa cggaccgcgc gggggacagc cgcttagggc gtcggcgacg 21060
cgcttgacgg cttcctccga gagcagaagt ccgtcggtta cgttacagtg gcccagttcg 21120
aacaccagct gcatgtagcg gtcgtagtgg ggggtcagca ggtccagcac gtcatcgggg 21180
ccgaaggtcc tcccagatcc cccggccgcc gagtcccaat gcaggcgcgc ggccatggtg 21240
ctgcacaggc acaacagctc ccagacaggg gttacgttca gggtgggggg cagggccacg 21300
agctccagct ctccggtgac gttgatcgtg gggatgacgc ccgtggcgta gtggtcatag 21360
atccgccgaa atatggcgct gctgcgggtg gccatgggaa cgcggagaca ggcctccagc 21420
aacgccaggt aaataaaccg cgtgcgtccc atcaggctgt tgaggttgcg catgagcgcg 21480
acaatttccg ccggcgcgac atcggaccgg aggtattttt cgacgaaaag acccacctcc 21540
tccgtctcgg cggcctgggc cggcagcgac gcctcgggat cccggcaccg cagctcccgt 21600
agatcgcgct gggccctgag ggcgtcgaaa tgtacgcccc gcaaaaacag acagaagtcc 21660
tttggggtca gggtatcgtc gtgtccccag aagcgcacgc gtatgcagtt tagggtcagc 21720
agcatgtgaa ggatgttaag gctgtccgag agacacgcca gcgtgcatct ctcaaagtag 21780
tgtttgtaac ggaatttgtt gtagatgcgc gacccccgcc ccagcgacgt gtcgcatgcc 21840
gacgcgtcac agcgcccctt gaaccggcga cacagcaggt ttgtgacctg ggagaactgc 21900
gcgggccact ggccgcagga actgaccacg tggttcagga gcatgggcgt aaagacgggc 21960
tccgagcgcg ccccggagcc gtccatgtaa atcagtagct cccccttgcg gagggtgcgc 22020
acccgtccca gggactggta cacggacacc atgtccggtc cgtagttcat gggtttcacg 22080
taggcgaaca tgccatcaaa gtgcagggga tcgaagctga ggcccacggt tacgaccgtc 22140
gtgtatataa ccacgcggta ttggccccac gtggtcacgt ccccgagggg ggtgagcgag 22200
tgaagcaaca gcacgcggtc cgtaaactga cggcagaacc gggccacgat ctccgcgaag 22260
gagaccgtcg acgaaaaaat gcagatgtta tcgcccccgc caaggcgcgc ttccagctcc 22320
ccaaagaacg tggccccccg ggcgtccgga gaggcgtccg gagacgggcc gctcggcggc 22380
ccgggcgggc gcagggcagc ctgcaggagc tcggtcccca gacgcgggag aaacaggcac 22440
cggcgcgccg aaaacccggg catggcgtac tcgccgacca ccacatgcac gtttttttcg 22500
ccccggagac cgcacaggaa gtccaccaac tgcgcgttgg cggttgcgtc catggcgatg 22560
atccgaggac atgtgcgcag caggcgtagc attaacgcat ccacgcggcc cagttgctgc 22620
atcgttggcg aatagagctg gcccagcgtc gacataacct cgtccagaac gaggacgtcg 22680
tagttgttca gaaggttggg gcccacgcga tgaaggcttt ccacctggac gataagtcgg 22740
tggaaggggc ggtcgttcat aatgtaattg gtggatgaga agtaggtgac aaagtcgacc 22800
aggcctgact cagcgaaccg cgtcgccagg gtctgggtaa aactccgacg acaggagacg 22860
acgagcacac tcgtgtccgg agagtggatc gcttcccgca gccagcggat cagcgcggta 22920
gtttttcccg accccattgg cgcgcggacc acagtcacgc acctggccgt cggggcgctc 22980
gcgttgggga aggtgacggg tccgtgctgc tgccgctcga tcgttgtttt cgggtgaacc 23040
cggggcaccc attcggccaa atcccccccg tataacatcc gcgctagcga tacgctcgac 23100
gtgtactgtt cgcactcgtc gtccccaatg ggacgcccgg cccccagagg atcccccgac 23160
tccgcgcccc ccacgaaagg catgaccggg gcgcggacgg cgtggtgggt ctggtgtgtg 23220
caggtggcga cgtttgtggt ctctgcggtc tgcgtcacgg ggctcctcgt cctggcctct 23280

-continued

```
gtgttccggg cacggtttcc ctgcttttac gccacggcga gctcttatgc cggggttaac  23340
tccacggccg aggtgcgcgg gggtgtagcc gtgcccctca ggttggacac gcagagcctt  23400
gtgggcactt atgtaatcac ggccgtattg ttgttggccg cggccgtgta tgccgtggtc  23460
ggcgccgtga cctcccgcta cgaccgcgcc ctggacgcgg gccgccgtct ggctgcggcc  23520
cgcatggcca tgccgcacgc cacgctgatc gccggaaacg tctgctcttg gttgctgcag  23580
atcaccgtcc tgctgctggc ccatcgcatc agccagctgg cccacctggt ttacgtcctg  23640
cactttgcgt gtctggtgta ttttgcggcc catttttgca ccagggggt cctgagcggg  23700
acgtatctgc gtcaggtgca cggcctgatg gagctggccc cgacccatca tcgcgtcgtc  23760
ggcccggctc gcgccgtgct gacaaacgcc ttgctgttgg gcgtcttcct gtgcacggcc  23820
gacgccgcgg tatccctgaa taccatcgcc gcgttcaact ttaattttc ggccccgggc  23880
atgctcatct gcctgaccgt gctgttcgcc attctcgtcg tatcgctgtt gttggtggtc  23940
gagggggtgt tgtgtcacta cgtgcgcgtg ttggtgggcc cccacctggg ggccgttgcc  24000
gccacgggca tcgtcggcct ggcctgcgag cactattaca ccaacggcta ctacgtggtg  24060
gagacgcagt ggccgggggc acagacggga gtgcgcgtcg ccctcgccct ggtcgccgcc  24120
tttgccctcg gcatggccgt gctccgctgc acccgcgcct atctgtatca caggcggcac  24180
cacaccaaat tttttatgcg catgcgcgac acgcgacacc gcgcacattc cgccctcaag  24240
cgcgtacgca gttccatgcg cggatcgcga gacggccgcc acaggcccgc gcccggcagc  24300
ccgcccggga ttcccgaata tgcggaagac ccctacgcga tctcatacgg cggccagctc  24360
gaccggtacg gagattccga cggggagccg atttacgacg aggtggcgga cgaccaaacc  24420
gacgtattgt acgccaagat acaacacccg cggcacctgc ccgacgacga gcccatctat  24480
gacaccgttg gggggtacga ccccgagccc gccgaggacc ccgtgtacag caccgtccgc  24540
cgttggtagc tgtttggttc cgttttaata aaccgtttgt gtttaacccg accgtggtgt  24600
atgtctggtg tgtggcgtcc gatcccgtta ctatcaccgt cccccccct caaccccggc  24660
gattgtgggt tttttaaaaa cgacacgcgt gcgaccgtat acagaacatt attttggttt  24720
ttattcgcta tcggacatgg ggggtggaaa ctgggtggcg gggcaggcgc ctccgggggt  24780
ccgccggtga gtgtggcgcg aggggggtc cgacgaacgc aggcgcggtc tccccggggc  24840
ccgcgtaacc acgcgcatat ccgggggcac gtagaaatta ccttcctctt cggactcgat  24900
atccacgacg tcaaagtcgt gggcggtcag cgagacgacc tccccgtcgt cggtgatgag  24960
gacgttgttt cggcagcagc agggccgggc cccggagaac gagaggccca tagctcggcg  25020
agcgtgtcgt cgaacgccag gcggctgctt cgctggatgg ccttatagat ctccggatcg  25080
atgcggacgg gggtaatgat cagggcgatc ggaacggcct ggttcgggag aatggacgcc  25140
ttgctgggtc ctgcggcccc gagagccccg gcgccgtcct ccaggcggaa cgttacgccc  25200
tcctccgcgc tggtgcggtg cctgccgata aacgtcacca gatgcgggtg gggggggcag  25260
tcggggaagt ggctgtcgag cacgtagccc tgcaccaaga tctgcttaaa gttcgggtgg  25320
cgggggttcg cgaagacggg ctcgcggcgg accagatccc cggagctcca ggacacgggg  25380
gagatggtgt ggcgtccgag gtcgggggcg ccaaacagaa gcacctccga gacaacgccg  25440
ctatttaact ccaccaaggc ccgatccgcg gcggagcacc gcctttttc gcccgaggcg  25500
tgggcctctg accaggcctg gtcttgcgtg acgagagcct cctccgggcc ggggacgcgc  25560
ccgggcgcga agtatcgcac gctgggcttc gggatcgacc ggataaatgc ccggaacgcc  25620
tccggggacc ggtgtgccat caagtcctcg tacgcggagg ccgtggggtc gctggggtcc  25680
```

atggggtcga aagcgtactt ggcccggcat ttgacctcgt aaaaggccag gggggtcttg 25740
gggactgggg ccaggtagcc gtgaatgtcc cgaggacaga cgagaatatc cagggacgcc 25800
ccgaccatcc ccgtgtgacc gtccatgagg accccacacg tatgcacgtt ctcttcggcg 25860
aggtcgctgg gttcgtggaa gataaagcgc cgcgtgtcgg cgccggcctc gccgccgtcg 25920
tccgcgcggc ccacgcagta gcgaaacagc aggcttcggg ccgtcggctc gttcacccgc 25980
ccgaacatca ccgccgaaga ctgtacatcc ggtcgcaggc tggcgttgtg cttcagccac 26040
tggggcgaga aacacggacc ctgggggccc cagcggaggg tggatgcggt cgtgaggccc 26100
cgccggagca gggcccatag ctggcagtcg gcctggtttt gcgtggccgc ctcgtaaaac 26160
cccatgaggg gccggggcgc cacggcgtcc gcggcggccg ggggggcgcg gcgcgtcagg 26220
cgccataggt gccggccgag tccgcggtcc accatacccg cctcctcgag gaccacggcc 26280
agggaacaca gataatccag gcgggcccag aggggaccga tggccagagg ggcgcggacg 26340
ccgcgcagca acccgcgcag gtggcgctcg aacgtctcgg ctagtatatg ggagggcagc 26400
gcgttgggga tcaccgacgc cgaccacata gagtcaaggt ccggggagtc gggatcggcg 26460
tccgggtcgc gggcgtgggt gcccccagga gatagcggaa tgtccggggt cggaggcccg 26520
gaggcgtcag aaagtgccgg cgacgcggcc cggggctttt cgtctgcggt gtcggtggcg 26580
tgctgatcac gtggggggtt atcgggcgaa tgggagctcg ggtccacagc tgacgtcgtc 26640
tggggtgggg ggggcagggg acggaaggtg gttgtcagcg gaagactgtt agggcggggg 26700
cgcttggggg ggctgtcggg gccacgaggg gtgtcctcgg ccagggccca gggacgctta 26760
gtcacggtgc gtcccggcgg acatgctggg cctaccgtgg actccatttc cgagacgacg 26820
tggggggagc ggtggttgag cgcgccgccg ggtgaacgct gattctcacg acagcgcgtg 26880
ccgcgcgcac gggttggtgt gatacaggcg ggacaccagc accaggagag gcttaagctc 26940
gggaggcagc gccaccgacg acagtatcgc cttgtgtgtg tgctggtaat ttatacaccg 27000
atccgtaaac gcgcgccgaa tcttgggatt gcggaggtgg cgccggatgc cctctgggac 27060
gtcatacgcc aggccgtggg tgttggtctc ggccgagttg acaaacaggg ctgggtgcag 27120
cacgcagcga taggcgagca gggccagggc gaagtccggc gacagctggt tgttgaaata 27180
ctggtaaccg ggaaaccggg tcacgggtac gcccaggctc ggggcgacgt acacgctaac 27240
caccaactcc agcagcgtct ggcccagggc gtacaggtca accgctagcc cgacgtcgtg 27300
cttcaggcgg tggttggtaa attcggcccg ttcgttgtta aggtatttca ccaacagctc 27360
cgggggctgg ttatacccgt gacccaccag ggtgtgaaag ttggctgtgg ttagggcggt 27420
gggcatgcca aacatccggg gggacttgag gtccggctcc tggaggcaaa actgcccccg 27480
ggcgatcgtg gagttggagt tgagggtgac gaggctaaag tcggcgagga cggcccgccg 27540
gagcgagacg gcgtccgacc gcagcatgac gaggatgttg gcgcacttga tatccaggtg 27600
gctgatcccg caggtggtgt ttaaaaacac aacggcacgg gccagctccg tgaagcactg 27660
gtggagggcc gtcgagaccg aggggtttgt tgtgcgcagg gacgccagtt ggccgatata 27720
cttaccgagg tccatgtcgt acgcggggaa cactatctgt cgttgttgca gcgagaaccc 27780
gaggggcgcg atgaagccgc ggatgttgtg ggtgcggccg gcgcgtagag cgcactcccc 27840
gaccaacagg gtcgcgatga gctcaacggc aaaccactcc ttttccttta tggtcttaac 27900
ggcaagctta tgttcgcgaa tcagttggac ttcgccgtat cccccagacc ccccgaagct 27960
tcgggccccg gggatctcga gggtcgtgta gtgtagggcg gggttgatgg cgaacacggg 28020

-continued

```
gctgcatagc ttgcggatgc gcgtgagggt gaggatgtgc gagggggacg agggggggtgc  28080
ggttaacgcc gcctgggatc tgcgcagggg cgggcggttc agtttggccg ccgtaccggg  28140
cgcctcgggg gacgcgcggc gatgagacga gcggctcatt cgccatcggg atagtcccgc  28200
gcgaagccgc tcgcggaggc cggatcggtg gcggcacccg tgggaggagc gggagacggc  28260
ggcgttctgg agagaggggc cgctggggcg cccggaggcc ccatgggggt tggagtgtat  28320
gtaggatgcg agccaatcct tgaaggaccg ttggcgtgca ccttgggggc tgaggttagc  28380
tgccacatga ccagcaggtc gctgtctgcg ggactcatcc atccttcggc caggtcgccg  28440
tctccccaca gagaagcgtt ggtcgctgcc tcctcgagtt gctcctcctg gtccgcaaga  28500
cgatcgtcca cggcgtccag gcgctcacca agcgccggat cgaggtaccg tcggtgtgcg  28560
gttagaaagt cacgacgcgc cgcttgctcc tccacgcgaa ttttaacaca ggtcgcgcgc  28620
tgtcgcatca tctctaagcg cgcgcgggac tttagccgcg cctccaattc caagtgggcc  28680
gcctttgcag ccataaaggc gccaacaaac cgaggatctt gggtgctgac gccctcccgg  28740
tgcagctgca gggtctggtc cttgtaaatc tcggctcgga ggtgcgtctc ggccaggcgt  28800
cggcgcaggg ccgcgtgggc ggcatctcgg tccattccgc caccctgcgg gcgacccggg  28860
ggtgctctga tagtctcgcg tgcccaaggc ccgtgatcgg ggtacttcgc cgccgcgacc  28920
cgccacccgg tgtgcgcgat gtttggtcag cagctggcgt ccgacgtcca gcagtacctg  28980
gagcgcctcg agaaacagag gcaacttaag gtgggcgcgg acgaggcgtc ggcgggcctc  29040
acaatgggcg gcgatgccct acgagtgccc tttttagatt tcgcgaccgc gacccccaag  29100
cgccaccaga ccgtggtccc gggcgtcggg acgctccacg actgctgcga gcactcgccg  29160
ctcttctcgg ccgtggcgcg gcggctgctg tttaatagcc tggtgccggc gcaactaaag  29220
gggcgtgatt tcgggggcga ccacacggcc aagctggaat tcctggcccc cgagttggta  29280
cgggcggtgg cgcgactgcg gtttaaggag tgcgcgccgg cggacgtggt gcctcagcgt  29340
aacgcctact atagcgttct gaacacgttt caggccctcc accgctccga agcctttcgc  29400
cagctggtgc actttgtgcg ggactttgcc cagctgctta aaacctcctt ccgggcctcc  29460
agcctcacgg agaccacggg cccccccaaa aaacgggcca aggtggacgt ggccacccac  29520
ggccggacgt acggcacgct ggagctgttc caaaaaatga tccttatgca cgccacctac  29580
tttctggccg ccgtgctcct cggggaccac gcggagcagg tcaacacgtt cctgcgtctc  29640
gtgtttgaga tccccctgtt tagcgacgcg gccgtgcgcc acttccgcca gcgcgccacc  29700
gtgtttctcg tcccccggcg ccacggcaag acctggtttc tggtgcccct catcgcgctg  29760
tcgctggcct cctttcgggg gatcaagatc ggctacacgg cgcacatccg caaggcgacc  29820
gagccggtgt ttgaggagat cgacgcctgc ctgcggggct ggttcggttc ggcccgagtg  29880
gaccacgtta aaggggaaac catctccttc tcgtttccgg acgggtcgcg cagtaccatc  29940
gtgtttgcct ccagccacaa cacaaacgta agtcctcttt tctttcgcat ggctctccca  30000
aggggccccg ggtcgacccg acccacaccc acccacccac atacacacac aaccagacgc  30060
gggaggaaag tctgccccgt gggcactgat ttttattcgg gatcgcttga ggaggcccgg  30120
gcaacggccc gggcaacggt ggggcaactc gtagcaaata ggcgactgat gtacgaagag  30180
aagacacaca ggcgccaccc ggcgctggtc ggggggatgt tgtccgcgcc gcaccgtccc  30240
ccgacgacct cttgcagacg gtccgtgatg caaggacggc gggggcctg cagcagggtg  30300
accgtatcca cgggatggcc aaagagaagc ggacacaggc tagcatcccc ctggaccgcc  30360
agggtacact gggccatctt ggcccacaga cacggggcga cgcagggaca ggactccgtt  30420
```

acgacggagg agagccacag tgcgttggcg gaatcgatgt ggggcggcgg ggcgcaggac 30480
tcgcagcccc ccgggtggtt agtgatcctg gccaggagcc atcccagatg gcgggccctg 30540
cttcccggtg gacagagcga ccccaggtcg ctgtccatgg cccagcagta gatctggccg 30600
ctggggaggt gccaccaggc ccccgggccc aaggcgcagc acgcgcccgg ctccgggggg 30660
gtcttcgcgg ggaccagata cgcgccatcc agctcgccga ccactggctc ctccgcgagc 30720
tgttcggtgg ttgggtcggg ggtttcctcc gggggggtgg ccgcccgtat gcgggcgaac 30780
gtgagggtgc acaggagcgg ggtcaggggg tgcgtcacgc tccggaggtg gacgatcgcg 30840
cagtagcggc gctcgcggtt aaagaaaaag agggcaaaga aggtgttcgg gggcaaccgc 30900
agcgccttgg ggcgcgtcag atacagaaaa atctcgcaga agagggcgcg cccggggtct 30960
gggttaggaa gggccacctg acacagaggc tcggtgagga ccgttagaca ccgaaagatc 31020
ttgagccgct cgtccgcccg aacgacgcgc cacacaaaga cggagttgac aatgcgcgcg 31080
atagagtcga cgtccgtccc caggtcgtcg actctgtcgc gcgtgccgcg agctccggcc 31140
cgggaatccg gccggggcaa ggtccccggg ggaccaggcg gcgccagggg ccgccggggt 31200
cccagctgcg ccatgccggg ggcgggggga gggcaaaccc cagaggcggg ggccaacggc 31260
gcggggagga gtggatgggc gaggtggccg ggggaaggcg cccgctagcg agaacggccg 31320
ttcccggacg acaccttgcg acaaaaccta aggacagcgg cccgcgcgac ggggtccgag 31380
aggctaaggt aggccgcgat gttaatggtg aacgcaaagc cgccgggaaa gacaactatg 31440
ccacagaggc ggcgattaaa ccccaggcag aggtaggcgt agctttcccc gggcaggtat 31500
tgctcgcaga ccctgcgtgg ggctgtggag gggacggcct ccatgaagcg acatttactc 31560
tgctcgcgtt tactgacgtc accatccatc gccacggcga ttggacgatt gttaagccgc 31620
agcgtgtctc cgcttgtgct gtagtagtca aaaacgtaat ggccgtcgga gtcggcaaag 31680
cgggccggga ggtcgtcgcc gagcgggacg acccgccgcc cccgaccgcc ccgtcccccc 31740
aggtgtgcca ggacggccag ggcatacgcg gtgtgaaaaa aggcgtcggg ggcggtcccc 31800
tcgacggcgc gcatcaggtt ctcgaggaga atggggaagc gcctggtcac ctccccccagc 31860
cacgcgcgtt ggtcggggcc aaagtcatag cgcaggcgct gtgagattcg cgggccgccc 31920
tgaagcgcgg cccggatggc ctggcccagg gcccggaggc acgccagatg tatgcgcgcg 31980
gtaaaggcga cctcggcggc gatgtcaaag ggcggcagga cggggcgcgg gtggcgcagg 32040
ggcacctcga gcgcgggaaa gcggagcagc agctccgcct gcccagcggg agacagctgg 32100
tgggggcgca cgacgcgttc tgcggcgcag gcctcggtca gggccgtggc cagcgccgag 32160
gacagcagcg gagggcgggc gcgtcgcccg ccccacgcca ctgagttctc gtaggagacg 32220
acgacgaagc gctgcttggt tccgtagtgg tggcgcagga ccacggagat agaacgacgg 32280
ctccacagcc agtccggccg gtcgccgccg gccagggctt cccatccgcg atccaaccac 32340
tcgaccagcg accgcggctt tgtggtacca ggggtaaggg ttagaacgtc gttcaggatg 32400
tcctcgcccc cgggcccgtg gggcgctggg gccacaaagc ggcccccgcc ggggggctcc 32460
agacccgcca gcaccgcatc tgcgtcagcc gcccccatgg cgccccccgct gacggcctgg 32520
tgaaccaggg cgccctggcg gagccccgat gcaacgccac aggccgcacg cccggtccga 32580
gcgcggaccg ggtggcggcg ggtgacgtcc tgcactgccc gctgaaccaa cgcgaggatc 32640
tcctcgttct cctgtgcgat ggacacgtcc tgggccgcgg tcgtgtcgcc gccgggggcc 32700
gtcagctgct cctccgggga gatggggggg tcggacgccc cgacgatggg cgggtctgcg 32760

-continued

```
ggcgcccccg cgtggggccg ggccaagggc tgcggacgcg gggacgcgct ttcccccaga  32820
cccatggaca ggtgggccgc ggcctccttc gcggccggcg gggcggcggc gccaagcaga  32880
gcgacgtagc ggcacaaatg ccgacagacg cgcatgatgc gcgtgctgtc ggccgcgtag  32940
cgcgtgttgg gggggacgag ctcgtcgtaa ctaaacagaa tcacgcgggc acagctcgcc  33000
cccgagcccc acgcgaggcg cagcgccgcc acggcgtacg ggtcatagac gccctgcgcg  33060
tcacacacca cgggcaggga gacgaacaac cccccggcgc tggacgcacg cggaaggagg  33120
ccagggtgtg ccggcacgac gggggccaga agctccccca ccgcatccgc gggcacgtag  33180
gcggcaaacg ccgtgcacca cggggtacag tcgccggtgg catgagcccg agtctggatt  33240
tcgacctgga agtttgcggc cgtcccgagt ccggggcggc cgcgcatcag ggcggccaga  33300
gggattcccg cggccgccag gcactcgctg gatatgatga cgtgaaccaa agacgagggc  33360
cgacccgggc cgtggccgag atcgtactgg acctcgttgg ccaagtgcgc gttcatggtt  33420
cggggtgggt gtgggtgtgt aggcgatgcg ggtcccccga gtccgcggga agggcgtggg  33480
tttggcgcgc gtatgcgtat tcgccaacgg aggcgtgcgt gcttatgcgc ggcgcgtttc  33540
ttctgtctcc agggaatccg aggccaggac tttaacctgc tctttgtcga cgaggccaac  33600
tttattcgcc cggatgcggt ccagacgatt atgggctttc tcaaccaggc caactgcaag  33660
attatcttcg tgtcgtccac caacaccggg aaggccagta cgagcttttt gtacaacctc  33720
cgcggggccg ccgacgagct tctcaacgtg gtgacctata tatgcgatga tcacatgccg  33780
agggtggtga cgcacacaaa cgccacggcc tgttcttgtt atatcctcaa caagcccgtt  33840
ttcatcacga tggacggggc ggttcgccgg accgccgatt tgtttctggc cgattccttc  33900
atgcaggaga tcatcggggg ccaggccagg gagaccggcg acgaccggcc cgttctgacc  33960
aagtctgcgg gggagcggtt tctgttgtac cgcccctcga ccaccaccaa cagcggcctc  34020
atggcccccg atttgtacgt gtacgtggat cccgcgttca cggccaacac ccgagcctcc  34080
gggaccggcg tcgctgtcgt cgggcggtac cgcgacgatt atatcatctt tgccctggag  34140
cacttttttc tccgcgcgct cacgggctcg gcccccgccg acatcgcccg ctgcgtcgtc  34200
cacagtctga cgcaggtcct ggccctgcat cccggggcgt ttcgcggcgt ccgggtggcg  34260
gtcgagggaa atagcagcca ggactcggcc gtcgccatcg ccacgcacgt gcacacagag  34320
atgcaccgcc tactggcctc ggagggggcc gacgcgggct cgggccccga gcttctcttc  34380
taccactgcg agcctcccgg gagcgcggtg ctgtacccct ttttcctgct caacaaacag  34440
aagacgcccg cctttgaaca ctttattaaa aagtttaact ccgggggcgt catggcctcc  34500
caggagatcg tttccgcgac ggtgcgcctg cagaccgacc cggtcgagta tctgctcgag  34560
cagctgaata acctcaccga aaccgtctcc cccaacactg acgtccgtac gtattccgga  34620
aaacggaacg gcgcctcgga tgaccttatg gtcgccgtca ttatggccat ctaccttgcg  34680
gcccaggccg gacctccgca cacattcgct cccatcacac gcgtttcgtg agcgcccaat  34740
aaacacaccc aggtatgcta cgcacgacca cggtgtcgcc tgttaagggg ggggaagggg  34800
gtgttggcgg gaagcgtggg aacacggggg attctctcac gaccggcacc agtaccaccc  34860
ccctgtgaac acagaaaccc aacccaaatc ccataaacat acgacacaca ggcatatttt  34920
ggaatttctt gggtttttat ttatttaggt atgctggggt ttctccctgg atgcccaccc  34980
cccacccccc cccgtgggtc tagccgggcc ttagggatag cgtataacgg gggccatgtc  35040
tccggaccgc acaacggccg cgccgtcaaa ggtgcacacc cgaaccacgg gagccagggc  35100
caaggtgtct cctagttggc ccgcgtgggt cagccaggcg acgagcgcct cgtaaagcgg  35160
```

cagccttcgc tctccatcct gcaccagggc cggggcttcg gggtgaatga gctgggcggc 35220
ctcccgcgtg acactctgca tctgcaggag agcgttcacg tacccgtcct gggcacttag 35280
cgcaaagagc cgggggatta gcgtaaggat gatggtggtt ccctccgtga tcgagtaaac 35340
catgttaagg accagcgatc gcagctcggc gtttacggga ccgagttgtt ggacgtccgc 35400
cagcagcgag aggcgactcc cgttgtagta cagcacgttg aggtctggca gccctccggg 35460
gtttctgggg ctggggttca ggtcccggat gcccctggcc acgagccgcg ccacgatttc 35520
gcgcgccagg ggcgatggaa gcggaacggg aaaccgcaac gtgaggtcca gcgaatccag 35580
gcgcacgtcc gtcgcttggc cctcgaacac gggcgggacg aggctgatgg ggtccccgtt 35640
acagagatct acgggggagg tgttgcgaag gttaacggtg ccggcgtggg tgaggcccac 35700
gtccaggggg caggcgacga ttcgcgtggg aagcacccgg gtgatgaccg cggggaagcg 35760
ccttcggtac gccagcaaca accccaacgt gtcgggactg acgcctccgg agacgaagga 35820
ttcgtgcgcc acgtcggcca gcgtcagttg ccggcggatg gtcggcagga ataccacccg 35880
cccttcgcag cgctgcagcg ccgccgcatc ggggcgcgag atgcccgagg gtatcgcgat 35940
gtcagtttca aagccgtccg ccagcatggc gccgatccac gcggcaggga gtgcagtggt 36000
ggttcgggtg gcgggaggag cgcggtgggg gtcagcggcg tagcagagac gggcgaccaa 36060
cctcgcatag gacgggggt gggtcttagg gggttgggag gcgacaggga ccccagagca 36120
tgcgcgggga ggtctgtcgg gcccagacgc accgagagcg aatccgtcca cggagtcccg 36180
gtctgggttt tatggggccc ggccctcgga atcgcggctt gtcggcgggg acaaaggggg 36240
cggggctagg gggcttgcgg aaacagaaga cgcgtgggat aaaagaatcg cactacccca 36300
aggaagggcg gggcggttta ttacagagcc agtcccttga gcggggatgc gtcatagacg 36360
agatactgcg cgaagtgggt ctcccgcgcg tgggcttccc cgttgcgggc gctgcggagg 36420
agggcggggt cgctggcgca ggtgagcggg taggcctcct gaaacaggcc acacgggtcc 36480
tccacgagtt cgcggcaccc cggggggcgc ttaaactgta cgtcgctggc ggcggtggcc 36540
gtggacaccg ccgaacccgt ctccacgatc aggcgctcca ggcagcgatg tttggcggcg 36600
atgtcggccg acgtaaagaa cttaaagcag gggctgagca ccggcgaggc cccgttgagg 36660
tggtaggccc cgttatagag caggtccccg tacgaaaatc gctgcgacgc ccacgggttg 36720
gccgtggccg caaaggcccg ggacgggtcg ctctggccgt ggtcgtacat gagggcggtg 36780
acatccccct ccttgtcccc cgcgtaaacg cccccggcgg cgcgtccccg ggggttgcag 36840
ggccggcgga agtagttgac gtcggtcgac acgggggtgg cgataaactc acacacggcg 36900
tcctggccgt ggtccatccc tgcgcgccgc ggcacctggg cgcacccgaa cacggggacg 36960
ggctgggccg gccccaggcg gtttcccgcc acgaccgcgt tccgcaggta cacggctgcc 37020
gcgttgtcca ggagaggggg agccccgcgg cccaggtaaa agttttgggg aaggttgccc 37080
atgtcggtga cggggttgcg gacggttgcc gtggccacga cggcggtgta gcccacgccc 37140
aggtccacgt tcccgcgcgg ctgggtgagc gtgaagttta ccccccgcc agtttcgtgc 37200
cgggccacct ggagctggcc caggaagtac gcctccgacg cgcgctccga gaacagcatg 37260
ttctcagtca caaagcggtc ctgtcggacg acggtgaacc caaacccggg atggaggccc 37320
gtcttgagct gatgatgcaa ggccacggga ctgatcttga agtaccccgc catgagcgcg 37380
taggtcagcg cgttctcccc ggccgcgctc tcgcggacgt gctgcacgac gggctgtcgg 37440
atcgacgaaa agtagttggc ccccagagcc ggggggacca gggggacctg ccgcgacagg 37500

-continued

```
tcgcgcaggg ccggggggaa attgggcgcg ttcgccacgt ggtcggcccc ggcgaacagc  37560
gcgttgacgg gaagggggta aaaatagtcg ccattttgga tggtatggtc cagatgctgg  37620
ggggccatca gcaggattcc ggcgtgcaac gccccgtcga atatgcgcat gttggtggtg  37680
gacgcggtgt tggcgcccgc gtcgggcgcc gccgagcaga gcagcgccgt tgtgcgttcg  37740
gccatgttgt gggccagcac ctgcagcgtg agcatggcgg gcccgtccac taccacgcgc  37800
ccgttgtgaa acatggcgtt gaccgtgttg gccaccagat tggccgggtg caggggggtgc  37860
gcggggtccg tcacggggtc gctggggcac tcctcgccgg gggcgatctc cgggaccacc  37920
atgttctgca gggtggcgta tacgcggtcg aagcgaaccc ccgcggtgca gcagcggccc  37980
cgcgagaagg cgggcaccat cacgtagtag taaatcttgt ggtgcacggt ccagtccgcc  38040
ccccggtgcg gccggtcatc cgcggcgtcc gcggctcggg cctgggtgtt gtgcagcagc  38100
tggccgtcgt tgcggttgaa gtccgcggtc gccacgttac atgccgccgc gtacacgggg  38160
tcgtggcccc ccgcgctaac ccggcagtcg cgatggcggt ccagggccgc gcgccgcatc  38220
agggcgtcac agtcccacac gaggggtggc agcagcgccg ggtctcgcat taggtgattc  38280
agctcggctt gcgcctgccc gcccagctcc gggccggtca gggtaaagtc atcaaccagc  38340
tgggccaggg cctcgacgtg cgccaccagg tcccggtaca cggccatgca ctcctcggga  38400
aggtctcccc cgaggtaggt cacgacgtac gagaccagcg agtagtcgtt cacgaacgcc  38460
gcgcaccgcg tgttgttcca gtagctggtg atgcactgga caacgagccg ggccagggcg  38520
cagaagacgt gctcgctgcc gtgtatggcg gcctgcagca ggtaaaacac cgccgggtag  38580
ttgcggtcgt cgaacgcccc gcgaacggcg gcgatggtgg cgggggccat ggcgtggcgt  38640
cccaccccca gctccaggcc ccgggcgtcc cggaacgccg ccggacatag cgccaggggc  38700
aagttgccgt tcaccacgcg ccaggtggcc tggatctccc ccgggccggc cgggggaacg  38760
tcccccccg gcagctccac gtcggccacc cccacgaaga agtcgaacgc ggggtgcagc  38820
tcaagagcca ggttggcgtt gtcgggctgc ataaactgct ccggggtcat ctggccttcc  38880
gcgacccatc ggacccgccc gtgggccagg cgctgccccc aggcgttcaa aaacagctgc  38940
tgcatgtctg cggcggggcc ggccggggcc gccacgtacg ccccgtacgg attggcggct  39000
tcgacggggt cgcggttaag gcccccgacc gccgcgtcaa cgttcatcag cgaagggtgg  39060
cacacggtcc cgatcgcgtg ttccagagac aggcgcagca cctggcggtc cttcccccaa  39120
aaaaacagct ggcggggcgg gaaggcgcgg ggatccgggt ggccgggggc ggggactagg  39180
tccccggcgt gcgcggcaaa ccgttccatg accggattga acaggcccag gggcaggacg  39240
aacgtcaggt ccatggcgcc caccaggggg tagggaacgt tggtggcggc gtagatgcgc  39300
ttctccaggg cctccagaaa gaccagcttc tcgccgatgg acaccagatc cgcgcgcacg  39360
cgcgtcgtct ggggggcgct ctcgagctcg tccagcgtct gccggttcag gtcgagctgc  39420
tcctcctgca tctccagcag gtggcggccc acgtcgtcca gacttcgcac ggccttgccc  39480
atcacgagcg ccgtgaccag gttggccccg ttcaggacca tctcgccgta cgtcaccggc  39540
acgtcggctt cggtgtcctc cactttcagg aaggactgca ggaggcgctg tttgatcggg  39600
gctgtggtga ctagcacccc gtcgaccggc cgcccgcgcg tgtcggcatg cgtcagacgg  39660
ggcacggcca cggagggctg cgtggccgtg gtgaggtcca cgagccaggc ctcgacggcc  39720
tcccggcggt ggcccgcctt gcccaggaaa aagctcgtct cgcagaagct tcgctttagc  39780
tcggcgacca gggtcgcccg ggccaccctg gtggccaggc ggccgttgtc caggtatcgt  39840
tgcatcggca acaacaaagc caggggcggc gccttttcca gcagcacgtg cagcatctgg  39900
```

tcggccgtgc cgcgctcaaa cgccccgagg acggcctgga cgttgcgagc gagctgttgg 39960
atggcgcgca actggcgatg cgcgctgata cccgtcccgt ccagggcctc ccccgtgagc 40020
agggcgatgg cctcggtggc caggctgaag gcggcgttca gggcccggcg gtcgataatc 40080
ttggtcatgt aattgtgtgt gggttgctcg atggggtgcg ggccgtcgcg ggcaatcagc 40140
ggctggtgga cctcgaactg tacgcgcccc tcgttcatgt aggccagctc cggaaacttg 40200
gtacacacgc acgccaccga caacccgagc tccagaaagc gcacgagcga cagggtgttg 40260
caatacgacc ccagcagggc gtcgaactcg acgtcgtaca ggctgtttgc atcggagcgc 40320
acgcgggaaa aaaaatcgaa caggcgtcga tgcgacgcca cctcgatcgt gctaaggagg 40380
gacccggtcg gcaccatggc cgtggcatac cggtatcccg gagggtcgcg gttgggagcg 40440
gccatggggt cgcgtggaga tcggctgtct ctagcgatat tggcccgggg aggctaagat 40500
ccaccccaac gcccggccac ccgtgtacgt gcccgacggc ccaaggtcca ccgaaagaca 40560
cgacggaccc ggacccaaag aggcggggga tgctgtgtga gaggccgggt gtcggtcggg 40620
ggggaaaggc accgggagaa ggctgcggcc tcgttccagg agaacccagt gtccccaaca 40680
gacccgggga cgtgggatcc ccggccttat ataccccccc ccgccccacc cccgttagaa 40740
cgcgacgggt gcattcaaga tggccctggt ccaaaagcgt gccaggaaga aattggcaga 40800
ggcggcaaag ctgtccgccg ccgccaccca catcgaggcc ccggccgcac aggctatccc 40860
cagggcccgt gtgcgcaggg gatcggtggg tggcagcatt tggttggtgg cgataaagtg 40920
gaaaagcccg tccggactga aggtctcgtg ggcggcggcg aacaaggcac acagggccgt 40980
gcctcccaaa aacacggaca tcccccaaaa cacgggcgcc gacaacggca gacgatccct 41040
cttgatgtta acgtacagga ggagcgcccg caccgcccac gtaacgtagt agccgacgat 41100
ggcggccagg atacaggccg gcgccaccac ccttccggtc agcccgtaat acatgcccgc 41160
tgccaccatc tccaacggct tcaggaccaa aaacgaccaa aggaacagaa tcacgcgctt 41220
tgaaaagacc ggctgggtat ggggcggaag acgcgagtat gccgaactga caaaaaaatc 41280
agaggtgccg tacgaggaca atgaaaactg ttcctccagc ggcagttctc cctcctccat 41340
ggtcatgggg tgtgcggtgg aggtggggag accgaaaccg caaagggtcg cttacgtcag 41400
caggatcccg agatcaaaga cacccgggtt cttgcacaaa caccacccgg gttgcatccg 41460
cggaggcgag tgttttgata aggccgttcc gcgccttgat ataacctttg atgttgacca 41520
caaaacccgg aatttacgcc tacgccccaa tgcccacgca agatgaggta ggtaaccccc 41580
ccgtgggtgt gacgttgcgt ttagttcatt ggaggccaag ggaaaaaatg gggtggggag 41640
gaaacggaaa acccagtagg ccgtgtcggg aacacgcccg gggttgtcct caaaaggcag 41700
ggtccatact acggaagccg tcgttgtatt cgagacctgc ctgtgcgacg cacgtcgggg 41760
ttgcctgtgt ccggttcggc ccccaccgcg tgcggcacgc acgaggacga gtccgcgtgc 41820
tttattggcg ttccaagcgt tgccctccag tttctgttgt cggtgttccc ccatacccac 41880
gcccacatcc accgtagggg gcctctgggc cgtgttacgt cgccgcccgc gatggagctt 41940
agctacgcca ccaccatgca ctaccgggac gttgtgtttt acgtcacaac ggaccgaaac 42000
cgggcctact ttgtgtgcgg ggggtgtgtt tattccgtgg ggcggccgtg tgcctcgcag 42060
cccggggaga ttgccaagtt tggtctggtc gttcgaggga caggcccaga cgaccgcgtg 42120
gtcgccaact atgtacgaag cgaactccga caacgcggcc tgcaggacgt gcgtcccatt 42180
ggggaggacg aggtgtttct ggacagcgtg tgtcttctaa acccgaacgt gagctccgag 42240

-continued

```
ctggatgtga ttaacacgaa cgacgtggaa gtgctggacg aatgtctggc cgagtactgc  42300
acctcgctgc gaaccagccc gggtgtgcta atatccgggc tgcgcgtgcg ggcgcaagac  42360
agaatcatcg agttgtttga acacccaacg atagtcaacg tttcctcgca ctttgtgtat  42420
accccgtccc catacgtgtt cgccctggcc caggcgcacc tcccccggct cccgagctcg  42480
ctggaggccc tggtgagcgg cctgtttgac ggcatccccg ccccacgcca gccacttgac  42540
gcccacaacc cgcgcacgga tgtggttatc acgggccgcc gcgccccacg acccatcgcc  42600
gggtcggggg cggggtcggg gggcgcgggc gccaagcggg ccaccgtcag cgagttcgtg  42660
caagtcaaac acattgaccg cgtgggcccc gctggcgttt cgccggcgcc tccgccaaac  42720
aacaccgact cgagttccct ggtgcccggg gcccaggatt ccgcccccgcc cggccccacg  42780
ctaagggagc tgtggtgggt gttttatgcc gcagaccggg cgctggagga gccccgcgcc  42840
gactctggcc tcacccgcga ggaggtacgt gccgtacgtg ggttccggga gcaggcgtgg  42900
aaactgtttg gctccgcggg ggccccgcgg gcgtttatcg gggccgcgtt gggcctgagc  42960
cccctccaaa agctggccgt ttactactat atcatccacc gagagaggcg cctgtccccc  43020
ttccccgcgc tagtccggct cgtaggccgg tacacacagc gccacggcct gtacgtccct  43080
cggcccgacg acccagtctt ggccgatgcc atcaacgggc tggttcgcga cgcgctggcg  43140
gccggaacca cagccgagca gctcctcatg ttcgaccttc tccccccaaa ggacgtgccg  43200
gtgggaagcg acgtgcaggc cgacagcacc gctctgctgc gctttataga atcgcaacgt  43260
ctcgccgtcc ccgggggggt gatctccccc gagcacgtcg cgtaccttgg tgcgttcctg  43320
agcgtgctgt acgctggccg cgggcgcatg tccgcagcaa cgcacaccgc gcggctgaca  43380
ggggtgacct ccctggtgct agcggtgggt gacgtggacc gtctttccgc gtttgaccgc  43440
ggagcggcgg gcgcggccag ccgcacgcgg gccgccgggt acctggatgt gcttctgacc  43500
gttcgtctcg ctcgctccaa acacggacag tctgtgtaac agaccccaat aaacgtatgt  43560
cgctaccaca cccttgtgtg tcaatggacg cctctccggg ggggaaggga aaacaaagag  43620
gggctggggg agcggcacca ctggggcctg aacaaacaaa caaaccacag acacggttac  43680
agtttattcg gtcgggcgga taaacggccg aagccacgcc ccctttattc gcgtctccaa  43740
aaaaacggga cacttgtccg gagaaccttt aggatgccag ccagggcggc ggtaatcata  43800
accacgccca gcgcagaggc ggccagaaac ccgggcgcaa ttgcggccac gggctgcgtg  43860
tcaaaggcta gcaaatgaat gacggttccg tttggaaata gcaacaaggc cgtggacggc  43920
acgtcgctcg aaaacacgct cggggcgccc tccgtcggcc cggcggcgat ttgctgctgt  43980
gtgttgtccg tatccaccag caacacagac atgacctccc cggctggggt gtagcgcata  44040
aacacggccc ccacgagccc caggtcgcgc tggttttggg tgcgcaccag ccgcttggac  44100
tcgatatccc gggtggagcc ttcgcatgtc gcggtgaggt aggttaggaa cagtgggcgt  44160
cggacgtcga cgccggtgag cttgtagccg atcccccggg gcagagggga gtgggtgacg  44220
acgtagctgg cgttgtgggt gatgggtacc aggatccgtg gctcgacgtt ggcagactgc  44280
cccccgcacc gatgtgaggc ctcagggacg aaggcgcgga tcagggcgtt gtagtgtgcc  44340
cagcgcgtca gggtcgaggc gaggccgtgg gtctgctggg ccaggacttc gaccggggtc  44400
tcggatcggg tggcttgagc cagcgcgtcc aggataaaca cgctctcgtc tagatcaaag  44460
cgcagggagg ccgcgcatgg cgaaaagtgg tccggaagcc aaaagagggt tttctggtgg  44520
tcggcccggg ccagcgcggt ccggaggtcg gcgttggtcg ctgcggcgac gtcggacgta  44580
cacagggccg atgctatcag aaggctccgg cgggcgcgtt cccgctgcac cgccgagggg  44640
```

```
acgcccgcca agaacggctg ccggaggaca gccgaggcgt aaaatagcgc ccggtggacg  44700

accggggtgg tcagcacgcg gcccccctaga aactcggcat acagggcgtc gatgagatgg  44760

gctgcgctgg gcgccactgc gtcgtacgcc gaggggctat ccagcacgaa ggccagctga  44820

tagcccagcg cgtgtaatgc caagctctgt tcgcgctcca gaatctcggc caccaggtgc  44880

tggagccgag cctctagctg caggcgggcc gtgggatcca agactgacac attaaaaaac  44940

acagaatccg cggcacagcc cgcggccccg cgggcggcca acccggcaag cgcgcgcgag  45000

tgggccaaaa agcctagcag gtcggagagg cagaccgcgc cgtttgcgtg ggcggcgttc  45060

acgaaagcaa aacccgacgt cgcgagcagc cccgttaggc gccagaagag aggggggcgc  45120

gggccctgct cggcgcccgc gtcccccgag aaaaactccg cgtatgcccg cgacaggaac  45180

tgggcgtagt tcgtgccctc ctccgggtag ccgcccacgc ggcggagggc gtccagcgcg  45240

gagccgttgt cggcccgcgt cagggaccct aggacaaaga cccgataccg gggccgcccc  45300

gggggcccgg gaagagcccc cgggggggttt tcgtccgcgg ggtccccgac ccgatctagc  45360

gtctggcccg cggggaccac catcacttcc accggagggc tgtcgtgcat ggatatcacg  45420

agccccatga attcccgccc gtagcgcgcg cgcaccagcg cggcatcgca cccgagcacc  45480

agctcccccg tcgtccagat gcccacgggc cacgtcgagg ccgacgggga gaaatacacg  45540

tacctacctg ggatctcaa caggccccgg gtggccaacc aggtcgtgga cgcgttgtgc  45600

aggtgcgtga tgtccagctc cgtcgtcggg tgccgccggg ccccaaccgg cggtcggggg  45660

ggcggtgtat cacgcggccc gcttgggtgg ctcgccgtcg ccacgttgtc tccccgcggg  45720

aacgtcaggg cctcggggtc agggacggcc gaaaacgtta cccaggcccg ggaacgcagc  45780

aacacggagg cgactggatt gtacaagaga cccttaaggg gggcgaccga ggggggaggc  45840

tgggcggtcg gctcgaccgt ggtgggggcg ggcaggctcg cgttcggggg ccggccgagc  45900

aggtaggtct tcgggatgta aagcagctgg ccggggtccc gcggaaactc ggccgtggtg  45960

accaatacaa aacaaaagcg ctcctcgtac cagcgaagaa ggggcagaga tgccgtagtc  46020

aggtttagtt cgtccggcgg cgccagaaat ccgcgcggtg gtttttgggg gtcgggggtg  46080

tttggcagcc acagacgccc ggtgttcgtg tcgcgccagt acatgcggtc catgcccagg  46140

ccatccaaaa accatgggtc tgtctgctca gtccagtcgt ggacctgacc ccacgcaacg  46200

cccaaaataa taaccccccac gaaccataaa ccattcccca tgggggaccc cgtccctaac  46260

ccacggggcc cgtggctatg gcagggcttg ccgccccgac gttggctgcg agccctgggc  46320

cttcacccga acttgggggg tggggtgggg aaaaggaaga aacgcgggcg tattggcccc  46380

aatggggtct cggtggggta tcgacagagt gccagccctg ggaccgaacc ccgcgtttat  46440

gaacaaacga cccaacaccc gtgcgtttta ttctgtcttt ttattgccgt catagcgcgg  46500

gttccttccg gtattgtctc cttccgtgtt tcagttagcc tcccccatct cccgggcaaa  46560

cgtgcgcgcc aggtcgcaga tcgtcggtat ggagccgggg gtggtgacgt gggtctggac  46620

catcccggag gtaagttgca gcagggcgtc ccggcagccg gcgggcgatt ggtcgtaatc  46680

caggataaag acgtgcatgg gacggaggcg tttggccaag acgtccaagg cccaggcaaa  46740

cacgttgtac aggtcgccgt tgggggccag caactcgggg gcccgaaaca gggtaaataa  46800

cgtgtccccg atatggggtc gtgggcccgc gttgctctgg ggctcggcac cctggggcgg  46860

cacggccgtc cccgaaagct gtccccaatc ctcccgccac gacccgccgc cctgcagata  46920

ccgcaccgta ttggcaagca gcccgtaaac gcggcgaatc gcggccagca tagccaggtc  46980
```

aagccgctcg ccggggcgct ggcgtttggc caggcggtcg atgtgtctgt cctccggaag 47040
ggccccccaac acgatgtttg tgccgggcaa ggtcggcggg atgagggcca cgaacgccag 47100
cacggcctgg ggggtcatgc tgcccataag gtatcgcgcg gccgggtagc acaggagggc 47160
ggcgatggga tggcggtcga agatgagggt gagggccggg ggcggggcat gtgagctccc 47220
agcctccccc ccgatatgag gagccagaac ggcgtcggtc acggcataag gcatgcccat 47280
tgttatctgg gcgcttgtca ttaccaccgc cgcgtccccg gccgatatct caccctggtc 47340
gaggcggtgt tgtgtggtgt agatgttcgc gattgtctcg gaagccccca gcacctgcca 47400
gtaagtcatc ggctcgggta cgtagacgat atcgtcgcgc gaacccaggg ccaccagcag 47460
ttgcgtggtg gtggttttcc ccatcccgtg aggaccctct atataaaccc gcagtagcgt 47520
gggcattttc tgctccaggc ggacttccgt ggcttcttgc tgccggcgag ggcgcaacgc 47580
cgtacgtcgg ttgctatggc cgcgagaacg cgcagcctgg tcgaacgcag acgcgtattg 47640
atggcagggg tacgaagcca tacgcgcttc tacaaggcgc ttgccgaaga ggtgcgggag 47700
tttcacgcca ccaagatctg cggcacgctg ttgacgctgt taagcgggtc gctgcagggt 47760
cgctcggtgt tcgaggccac acgcgtcacc ttaatatgcg aagtggacct gggaccgcgc 47820
cgccccgact gcatctgcgt gttcgaattc gtgaatgaca agacgctggg cggggtttgt 47880
gtcatcatag aactaaagac atgcaaatat atttcttccg gggacaccgc cagcaaacgc 47940
gagcaacggg ccacggggat gaagcagctg cgccactccc tgaagctcct gcagtccctc 48000
gcgcctccgg gtgacaagat agtgtacctg tgccccgtcc tggtgtttgt cgcccaacgg 48060
acgctccgcg tcagccgcgt gacccggctc gtcccgcaga aggtctccgg taatatcacc 48120
gcagtcgtgc ggatgctcca gagcctgtcc acgtatacgg tccccatgga gcctaggacc 48180
cagcgagccc gtcgccgccg cggcggcgcc gcccgggggt ctgcgagcag accgaaaagg 48240
tcacactctg gggcgcgcga cccgcccgag tcagcggccc gccagttacc acccgccgac 48300
caaacccccg cctccacgga gggcgggggg gtgcttaaga ggatcgcggc gctcttctgc 48360
gtgcccgtgg ccaccaagac caaaccccga gccgcctccg aatgagagtg tttcgttcct 48420
tccccctccc cccgcgtcag acaaacccta accaccgctt aagcggcccc cgcgaggtcc 48480
gaagactcat ttggatccgg cgggagccac ccgacaacag cccccgggtt ttcccacgcc 48540
agacgccggt ccgctgtgcc atcgcgcccc ctcatcccac cccccatctt gtccccaaat 48600
aaaacaaggt ctggtagtta ggacaacgac cgcagttctc gtgtgttatt ttcgctctcc 48660
gcctctcgca gatggacccg tactgcccat ttgacgctct ggacgtctgg gaacacaggc 48720
gcttcatagt cgccgattcc cgaaacttca tcacccccga gttcccccgg gacttttgga 48780
tgtcgcccgt ctttaacctc ccccgggaga cggcggcgga gcaggtggtc gtcctacagg 48840
cccagcgcac agcggctgcc gctgccctgg agaacgccgc catgcaggcg gccgagctcc 48900
ccgtcgatat cgagcgccgg ttacgcccga tcgaacggaa cgtgcacaag atcgcaggcg 48960
ccctggaggc gctggagacg gcggcggccg ccgccgaaga ggcggatgcc gcgcgcgggg 49020
atgagccggc gggtgggggc gacgggggggg cgcccccgag tctggccgtc gcggagatgg 49080
aggtccagat cgtgcgcaac gacccgccgc tacgatacga caccaacctc cccgtggatc 49140
tgctacacat ggtgtacgcg ggccgcgggg cgaccggatc gtcgggggtg gtgttcggga 49200
cctggtaccg cactatccag gaccgcacca tcacggactt tcccctgacc acccgcagtg 49260
ccgactttcg ggacggccgt atgtccaaga ccttcatgac ggcgctggta ctgtccctgc 49320
agtcgtgcgg ccggctgtat gtgggccagc gccactattc cgccttcgag tgcgccgtgt 49380
tgtgtctcta cctgctgtac cgaaacacgc acggggccgc cgacgatagc gaccgcgctc 49440
cggtcacgtt cggggatctg ctgggccggc tgccccgcta cctggcgtgc ctggccgcgg 49500
tgatcgggac cgagggcggc cggccacagt accgctaccg cgacgacaag ctccccaaga 49560
cgcagttcgc ggccggcggg ggccgctacg aacacggagc gctggcgtcg cacatcgtga 49620
tcgccacgct gatgcaccac ggggtgctcc cggcggcccc gggggacgtc ccccgggacg 49680
cgagcaccca cgttaacccc gacggcgtgg cgcaccacga cgacataaac cgcgccgccg 49740
ccgcgttcct cagccggggc cacaacctat tcctgtggga ggaccagact ctgctgcggg 49800
caaccgcgaa caccataacg gccctgggcg ttatccagcg gctcctcgcg aacggcaacg 49860
tgtacgcgga ccgcctcaac aaccgcctgc agctgggcat gctgatcccc ggagccgtcc 49920
cttcggaggc catcgcccgt ggggcctccg ggtccgactc gggggccatc aagagcggag 49980
acaacaatct ggaggcgcta tgtgccaatt acgtgcttcc gctgtaccgg gccgacccgg 50040
cggtcgagct gacccagctg tttcccggcc tggccgccct gtgtcttgac gcccaggcgg 50100
ggcggccggt cgggtcgacg cggcgggtgg tggatatgtc atcgggggcc cgccaggcgg 50160
cgctggtgcg cctcaccgcc ctggaactca tcaaccgcac ccgcacaaac cccacccccg 50220
tgggggaggt tatccacgcc cacgacgccc tggcgatcca atacgaacag gggcttggcc 50280
tgctggcgca gcaggcacgc attggcttgg gctccaacac caagcgtttc tccgcgttca 50340
acgttagcag cgactacgac atgttgtact ttttatgtct ggggttcatt ccacagtacc 50400
tgtcggcggt ttagtgggtg gtgggcgagg ggggaggggg cattagggag aaagaacaag 50460
agcctccgtt gggttttctt tgtgcctgta ctcaaaaggt catacccgt aaacggcggg 50520
ctccagtccc ggcccggcgg ttggcgtgaa cgcaacggcg ggagctgggt tagcgtttag 50580
tttagcattc gctctcgcct ttccgcccgc cccccgaccg ttgcgccttt tttttttttc 50640
gtccaccaaa gtctctgtgg gtgcgcgcat ggcagccgat gccccgggag accggatgga 50700
ggagcccctg ccagacaggg ccgtgcccat ttacgtggct gggtttttgg ccctgtatga 50760
cagcggggac tcgggcgagt tggcattgga tccggatacg gtgcgtgcgg ccctgcctcc 50820
ggataaccca ctcccgatta acgtggacca ccgcgctggc tgcgaggtgg ggcgggtgct 50880
ggccgtggtc gacgaccccc gcgggccgtt ttttgtggga ctgatcgcct gcgtgcaact 50940
ggagcgcgtc ctcgagacgg ccgccagcgc tgcgattttc gagcgccgcg ggccgccgct 51000
ctcccgggag gagcgcctgt tgtacctgat caccaactac ctgccctcgg tctccctggc 51060
cacaaaacgc ctgggggggcg aggcgcaccc cgatcgcacg ctgttcgcgc acgtcgcgct 51120
gtgcgcgatc gggcggcgcc tcggcactat cgtcacctac gacaccggtc tcgacgccgc 51180
catcgcgccc tttcgccacc tgtcgccggc gtctcgcgag gggggcgcggc gactggccgc 51240
cgaggccgag ctcgcgctgt ccggacgcac ctgggcgccc ggcgtggagg cgctgaccca 51300
cacgctgctt tccaccgccg ttaacaacat gatgctgcgg gaccgctgga gcctggtggc 51360
cgagcggcgg cggcaggccg ggatcgccgg acacacctac ctccaggcga gcgaaaaatt 51420
caaaatgtgg ggggcggagc ctgtttccgc gccggcgcgc gggtataaga acggggcccc 51480
ggagtccacg gacataccgc ccggctcgat cgctgccgcg ccgcagggtg accggtgccc 51540
aatcgtccgt cagcgcgggg tcgcctcgcc cccggtactg ccccccatga accccgttcc 51600
ggcatcgggc accccggccc ccgcgccgcc cggcgacggg agctacctgt ggatcccggc 51660
ctcccattac aaccagctcg tcgccggcca cgccgcgccc caaccccagc cgcattccgc 51720

-continued

```
gtttggtttc ccggctgcgg cgggggccgt ggcctatggg cctcacggcg cgggtctttc  51780
ccagcattac cctccccacg tcgcccatca gtatcccggg gtgctgttct cgggacccag  51840
cccactcgag gcgcagatag ccgcgttggt gggggccata gccgcggacc gccaggcggg  51900
cggtcagacg gccgcgggag accctggggt ccgggggtcg ggaaagcgtc gccggtacga  51960
ggcggggccg tcggagtcct actgcgacca ggacgaaccg gacgcggact acccgtacta  52020
ccccggggag gctcgaggcg ggccgcgcgg ggtcgactct cggcgcgcgg cccgccagtc  52080
tcccgggacc aacgagacca tcacggcgct gatgggggcg gtgacgtctc tgcagcagga  52140
actggcgcac atgcgggctc ggaccagcgc cccctatgga atgtacacgc cggtggcgca  52200
ctatcgccct caggtggggg agccggaacc aacaacgacc cacccggccc tttgtccccc  52260
ggaggccgtg tatcgccccc caccacacag cgccccctac ggtcctcccc agggtccggc  52320
gtcccatgcc cccactcccc cgtatgcccc agctgcctgc ccgccaggcc cgccaccgcc  52380
cccatgtcct tccacccaga cgcgcgcccc tctaccgacg gagcccgcgt tccccccgc  52440
cgccaccgga tcccaaccgg aggcatccaa cgcggaggcc ggggcccttg tcaacgccag  52500
cagcgcagca cacgtggacg ttgacacggc ccgcgccgcc gatttgttcg tctctcagat  52560
gatgggggcc cgctgattcg ccccggtctt tggtaccatg ggatgtctta ctgtatatct  52620
ttttaaataa accaggtaat accaaataag acccattggt gtatgttctt tttttattgg  52680
gaggcgcggg taggcgggta gctttacaat gcaaaagcct tcgacgtgga ggaaggcgtg  52740
ggggggggaat cggcactgac caagggggtc cgttttgtca cgggaaagga aagaggaaac  52800
aggccgcgga cacccggggg agtttatgtg ttcccttttc tttcttccca cacacacaaa  52860
aggcgtacca aacaaacaaa ccaaaagatg cacatgcggt ttaacacccg tggtttttat  52920
ttacaacaaa ccccccgtca caggtcgtcc tcgtcggcgt caccgtcttt gttgggaact  52980
tgggtgtagt tggtgttgcg gcgcttgcgc atgaccatgt cggtgacctt ggcgctgagc  53040
agcgcgctcg tgcccttctt cttggccttg tgttccgtgc gctccatggc agacaccagg  53100
gccatgtacc gtatcatctc ccgggcctcg gctagcttgg cctcgtcaaa gtcgccgccc  53160
tcctcgccct ccccggacgc gtccgggttg gtggggttct tgagctcctt ggtggttagc  53220
gggtacaggg ccttcatggg gttgctctgc agccgcatga cgtagcgaaa ggcgaagaaa  53280
gccgccgcca ggccggccag gaccaacaga cccacggcca gcgccccaaa ggggttggac  53340
atgaaggagg acacgcccga cacggccgat accacgccgc ccacgatgcc catcaccacc  53400
ttgccgaccg cgcgccccag gtcgcccatc ccctcgaaga acgcgcccag gcccgcgaac  53460
atggcggcgt tggcgtcggc gtggatgacc gtgtcgatgt cggcgaagcg caggtcgtgc  53520
agctggttgc ggcgctggac ctccgtgtag tccagcaggc cgctgtcctt gatctcgtgt  53580
cgggtgtaca cctccagggg gacaaactcg tgatcctcca gcatggtgat gttgaggtcg  53640
atgaaggtgc tgacggtggt gatgtcggcg cggctcagct ggtgggagta cgcgtactcc  53700
tcgaagtaca cgtagccccc gccgaaggtg aagtagcgcc ggtgtcccac ggtgcacggc  53760
tcgatcgcat cgcgcgtcag ccgcagctcg ttgttctccc ccagctgccc ctcgaccaac  53820
gggccctggt cttcgtaccg aaagctgacc agggggcggc tgtagcaggc cccgggccgc  53880
gagctgatgc gcatcgagtt ttggacgatc acgttgtccg cggcgaccgg cacgcacgtg  53940
gagacggcca tcacgtcgcc gagcatccgc gcgctcaccc gccggcccac ggtggccgag  54000
gcgatggcgt tggggttcag cttgcgggcc tcgttccaca gggtcagctc gtgattctgc  54060
agctcgcacc acgcgatggc aacgcggccc aacatatcgt tgacatggcg ctgtatgtgg  54120
```

ttgtacgtaa actgcagccg ggcgaactcg atggaggagg tggtcttgat gcgctccacg 54180
gacgcgttgg cgctggcccc gggcggcggg ggcgtggggt ttgggggctt gcggctctgc 54240
tctcggaggt gttcccgcac gtacagctcc gcgagcgtgt tgctgagaag gggctggtac 54300
gcgatcagaa agcccccatt ggccaggtag tactgcggct ggcccacctt gatgtgcgtc 54360
gcgttgtacc tgcgggcgaa gatgcggtcc atggcgtcgc gggcgtcctt gccgatgcag 54420
tcccccaggt ccacgcgcga gagcgggtac tcggtcaggt tggtggtgaa ggtggtggat 54480
atggcgtcgg aggagaatcg gaaggagccg ccgtactcgg agcgcagcat ctcgtccacc 54540
tcctgccact tggtcatggt gcagaccgac gggcgctttg gcacccagtc ccaggccacg 54600
gtgaacttgg gggtcgtgag caggttccgg gtggtcggcg ccgtggcccg ggccttggtg 54660
gtgaggtcgc gcgcgtagaa gccgtcaacc tgcttgaagc ggtcggcggc gtagctggtg 54720
tgttcggtgt gcgacccctc ccggtagccg taaaacgggg acatgtacac aaagtcgcca 54780
gtcgccagca caaactcgtc gtacgggtac accgagcgcg cgtccacctc ctcgacgatg 54840
cagtttaccg tcgtcccgta ccggtggaac gcctccaccc gcgaggggtt gtacttgagg 54900
tcggtggtgt gccagccccg gctcgtgcgg gtcgcggcgt tggccggttt cagctccatg 54960
tcggtctcgt ggtcgtcccg gtgaaacgcg gtggtctcca ggttgttgcg cacgtacttg 55020
gccgtggacc gacagacccc cttggcgttg atcttgtcga tcacctcctc gaaggggacg 55080
ggggcgcggt cctcaaagat ccccataaac tgggagtagc ggtggccgaa ccacacctgc 55140
gaaacggtga cgtctttgta gtacatggtg gccttgaact tgtacggggc gatgttctcc 55200
ttgaagacca ccgcgatgcc ctccgtgtag ttctgaccct cgggccgggt cgggcagcgg 55260
cgcggctgct cgaactgcac caccgtggcg cccgtggggg gtgggcacac gtaaaagttt 55320
gcatcggtgt tctccgcctt gatgtcccgc aggtgctcgc gcagggtggc gtggcccgcg 55380
gcgacggtcg cgttgtcgcc ggcggggcgc ggcggcggtg ggtttttcgg ttttttgttc 55440
ttcttcggtt tcgtgtcccc cgttggggcg gggccagggg cgggcggcgc cggagtggca 55500
ggtcccccgt tcgccgcctg ggtcgcggcc gcgaccccag gcgtgccggg ggaactcgga 55560
gccgccgacg ccaccaggac ccccagcgtc aaccccaaga gcgcccatac gacgaaccac 55620
cggcaccccc gcgcgggggc gccctggcgc atggcgggac tacgggggcc cgtcgtgccc 55680
cccgtcaggt agcctggggg cgaggtgctg gaggaccgag tagaggatcg agaaaacgtc 55740
tcggtcgtag accacgaccg accgggggcc gatacagccg tcgggggcgc tctcgacgat 55800
ggccaccagc ggacagtcgg agtcgtacgt gagatatacg ccgggcgggt aacggtaacg 55860
accttcggag gtcgggcggc tgcagtccgg gcggcgcaac tcgagctccc cgcaccggta 55920
gaccgaggca aagagtgtgg tggcgataat cagctcgcga atatatcgcc aggcggcgcg 55980
ctgagtgggc gttattccgg aaatgccgtc aaaacagtaa aacctctgaa attcgctgac 56040
ggcccaatca gcacccgagc cccccgcccc catgatgaac cgggcgagct cctccttcag 56100
gtgcggcagg agccccacgt tctcgacgct gtaatacagc gcggtgttgg ggggctgggc 56160
gaagctgtgg gtggagtgat caaagagggg cccgttgacg agctcgaaga agcgatgggt 56220
gatgctgggg agcagggccg ggtccacctg gtgtcgcagg agagacgctc gcatgaaccg 56280
gtgcgcgtcg aacacgcccg gcgccgagcg gttgtcgatg accgtgcccg cgcccgccgt 56340
cagggcgcag aagcgcgcgc gcgccgcaaa gccgttggcg accgcggcga acgtcgcggg 56400
cagcacctcg ccgtggacgc tgacccgcag catcttctcg agctccccgc gctgctcgcg 56460

```
gacgcagcgc cccaggctgg ccaacgaccg cttcgtcagg cggtccgcgt acagccgccg  56520
tcgctcccgc acgtccgcgg ccgcttgcgt ggcgatgtcc ccccacgtct cgggcccctg  56580
ccccccgggc ccgcggcgac ggtcttcgtc ctcgcccccg cccccgggag ctcccaaccc  56640
ccgtgcccct tcctctacgg cgacacggtc cccgtcgtcg tcggggcccg cgccgccctt  56700
gggcgcgtcc gccgcgcccc ccgcccccat gcgcgccagc acgcgacgca gcgcctcctc  56760
gtcgcactgt tcggggctga cgaggcgccg caagagcggc gtcgtcaggt ggtggtcgta  56820
gcacgcgcgg atgagcgcct cgatctgatc gtcgggtgac gtggcctgac cgccgattat  56880
tagggcgtcc accatatcca gcgccgccag gtggctcccg aacgcgcgat cgaaatgctc  56940
cgcccgccgc ccgaacagcg ccagttccac ggccaccgcg gcggtctcct gctgcaactc  57000
gcgccgcgcc agcgcggtca ggttgctggc aaacgcgtcc atggtggtct ggccggcgcg  57060
gtcgccggac gcgagccaga atcgcaattc gctgatggcg tacaggccgg gcgtggtggc  57120
ctgaaacacg tcgtgcgcct ccagcagggc gtcggcctcc ttgcggaccg agtcgttctc  57180
gggcgacggg tggggctgcc cgtcgccccc cgcggtccgg gccagcgcat ggtccaacac  57240
ggagagcgcc cgcgcgcggt cggcgtccga cagcccggcg gcgtggggca ggtaccgccg  57300
cagctcgttg gcgtccagcc gcacctgcgc ctgctgggtg acgtggttac agatacggtc  57360
cgccaggcgg cgggcgatcg tcgcccccctg gttcgccgtc acacacagtt cctcgaaaca  57420
gaccgcgcag gggtgggacg ggtcgctaag ctccgggggg acgataaggc ccgaccccac  57480
cgcccccacc ataaactccc gaacgcgctc cagcgcggcg gtggcgccgc gcgagggggt  57540
gatgaggtgg cagtagttta gctgctttag aaagttctcg acgtcgtgca ggaaacacag  57600
ctccatatgg acggtcccgc catacgtatc cagcctgacc cgttggtgat acggacaggg  57660
tcgggccagg cccatggtct ccgtgaaaaa caccgcgacg tctcccgcgg tcgcgaacgt  57720
ctccaggctg cccaggagcc gctcgccctc gcgccacgcg tactctagca gcaactccag  57780
ggtgaccgac agcggggtga gaaaggcccc ggcctgggcc tccaggcccg gcctcagacg  57840
acgccgcagc gcccgcacct gaagcgcgtt cagcttcagt tgggggagct tcccccgtcc  57900
gatgtggggg tcgcaccgcc ggagcagctc tatctgaaac acataggtct gcacctgtcc  57960
gagcagggct aacaactttt gacgggccac ggtgggctcg gacaccgggg cggccatctc  58020
gcggcgccga tctgtaccgc ggccggagta tgcggtggac cgaggcggtc cgtacgctac  58080
ccggcgtctg gctgagcccc ggggtccccc tattcggggc ggcctcccgc gggcccgccg  58140
accggcaagc cgggagtcgg cggcgcgtgc gtttctgttc tattcccaga caccgcggag  58200
aggaatcacg gcccgcccag agatatagac acggaacaca aacaagcacg gatgtcgtag  58260
caataattta ttttacacac attccccgcc ccgccctagg ttcccccacc ccccaacccc  58320
tcacagcata tccaacgtca ggtctccctt tttgtcgggg ggcccctccc caaacgggtc  58380
atccccgtgg aacgcccgtt tgcggccggc aaatgccggt cccggggccc ccgggccgcc  58440
gaacggcgtc gcgttgtcgt cctcgcagcc aaaatcccca aagttaaaca cctccccggc  58500
gttgccgagt tggctgacta gggcctcggc ctcgtgcgcc acctccaggg ccgcgtccgt  58560
cgaccactcg ccgttgccgc gctccagggc acgtgcggtc agctccatca tctcctcgct  58620
taggtactcg tcctccagga gcgccagcca gtcctcgatc tgcagctgtt gggtgcgggg  58680
ccccaggctt ttcacggtcg ccacgaacac gctactggcg acggccgccc cgccctcgga  58740
gataatgccc cggagctgct cgcacagcga gctttcgtgc gctccgccgc cgaggctcga  58800
ggccgcgcac acaaacccgg cccggggaca ggccaggacg aacttgcggg tgcggtcaaa  58860
```

-continued

```
aataaggagc gggcacgcgt ttttgccgcc catcaggctg gcccagttcc cggcctgaaa  58920
cacacggtcg ttgccggcca tgccgtagta tttgctgatg ctcaacccca acacgaccat  58980
ggggcgtgcc gccatgacgg gccgcagcag gttgcagctg gcgaacatgg aggtccacgc  59040
gcccggatgc gcgtccacgg cgtccatcag cgcgcgggcc ccggcctcca ggcccgcccc  59100
gccctgcgcg gaccacgcgg ccgccgcctg cacgctgggg ggacggcggg accccgcgat  59160
gatggccgtg agggtgttga tgaagtacgt cgagtgatcg cagtaccgca gaatctggtt  59220
tgccatgtag tacatcgcca gctcgctcac gttgttgggg gccaggttaa taaagttgat  59280
cgcgccgtag tccagggaaa actttttaat gaacgcgatg gtctcgatgt cctcgcgcga  59340
caggagccgg gcgggaagct ggttgcgttg gagggccgtc cagaaccact gcgggttcgg  59400
ctggttggac cccgggggct tgccgttggg gaagatggcc gcgtggaact gcttcagcag  59460
aaagcccagc ggtccgagga ggatgtccac gcgcttgtcg ggcttctggt aggcgctctg  59520
gaggctggcg acccgcgcct tggcggcctc ggacgcgttg gcgctcgcgc ccgcgaacaa  59580
cacgcggctc ttgacgcgca gctccttggg aaaccccagg gtcacgcggg caacgtcgcc  59640
ctcgaagctg ctctcggcgg gggccgtctg gccggccgtc aggctggggg cgcagatagc  59700
cgcaccctcc gagagcgcga ccgtcagcgt tttggccgac agaaacccgt tgttaaacat  59760
gtccatcacg cgccgccgca gcaccggttg gaattgattg cgaaagttgc gcccctcgac  59820
cgactgcccg gcgaacaccc cgtggcactg gctcagggcc aggtcctggt acacggcgag  59880
gttggatcgc cgcccgagaa gctgaagcag ggggcacggc ccgcacgcgt acgggtccag  59940
cgtcagggac atggcgtggt tggcctcgcc cagaccgtcg cgaaacttga agttcctccc  60000
ctccaccagg ttgcgcatca gctgctccac ctcgcggtcc acgacctgcc tgacgttgtt  60060
caccaccgta tgcagggcct cgcggttggt gatgatggtc tccagccgcc ccatggccgt  60120
ggggaccgcc tggtccacgt actgcagggt ctcgagttcg gccatgacgc gctcggtcgc  60180
cgcgcggtac gtctcctgca tgatggtccg ggcggtctcg gatccgtccg cgcgcttcag  60240
ggccgagaag gcggcgtagt ttcccagcac gtcgcagtcg ctgtacatgc tgttcatggt  60300
cccgaagacg ccgatggctc cgcgggcggc gctggcgaac ttgggatggc gcgcccggag  60360
gcgcatgagc gtcgtgtgta cgcaggcgtg gcgcgtgtcg aaggtgcaca ggttacaggg  60420
cacgtcggtc tggttggagt ccgcgacgta tcgaaacacg tccatctcct ggcgcccgac  60480
gatcacgccg ccgtcgcagc gctccaggta aaacagcatc ttggccagca gcgccgggga  60540
aaacccacac agcatggcca ggtgctcgcc ggcaaattcc tgggttccgc cgacgagggg  60600
cgcggtgggc cgaccctcga acccgggcac cacgtgtccc tcgcggtcca cctgtgggtt  60660
ggccgccacg tgggtcccgg gcacgaggaa gaagcggtaa aaggagggtt tgctgtggtc  60720
ctttgggtcc gccgggccgg cgtcgtccac ctcggtgaga tggagggccg agttggtgct  60780
aaataccatg gcccccacga gtcccgcggc gcgcgccagg tacgccccga cggcgttggc  60840
gcgggccgcg gccgtgtcct ggccctcgaa cagcggccac gcggagatgt cggtgggcgg  60900
ctcgtcaaag acggccatcg acacgataga ctcgagggcc agggcggcgt ctccggccat  60960
gacggaggcc aggcgctgtt cgaacccgcc cgcagggccc ttgccgccgc cgtcgcgccc  61020
gccccgcggg gtcttaccct ggctggcttc gaaggccgtg aacgtaatgt cggcggggag  61080
ggcggcgccc tcgtggtttt cgtcaaacgc caggtgggcg gccgcgcggg ccacggcgtc  61140
cacgtttcgg catcgcagtg ccacggcggc gggtcccacg accgcctcga acaggaggcg  61200
```

-continued gtggaggggg cggttaaaaa acggaagcgg gtaggtaaaa ttctccccga tcgatcggtg 61260
gttggcgttg aacggctctg cgatgacacg gctaaaatcc ggcatgaaca gctgcaacgg 61320
gtacacgggt atgcggtgca cctccgcccc gcctatggtt accttgtccg agcctcccag 61380
gtgcagaaag gtgttgttga tgcacacggc ctccttgaag ccctcggtaa cgaccagata 61440
caggagggcg cggtccgggt ccaggccgag gcgctcacac agcgcctccc ccgtcgtctc 61500
gtgtttgagg tcgccgggcc ggggggtgta gtccgaaaag ccaaaatggc ggcgtgcccg 61560
ctcgcagagt cgcgtcaggt tcggggcctg ggtgctgggg tccaggtgcc ggccgccgtg 61620
aaagacgtac acggacgagc tgtagtgcga gggcgtcagt ttcagggaca ccgcggtacc 61680
cccgagcccc gtcgtgcgag aacccacgac cacggccacg ttggcctcaa agccgctctc 61740
cacggtcagg cccacgacca ggggcgccac ggcgacgtcg gcatcgccgc tgcgcgccga 61800
cagtaacgcc agaagctcga tgccttcgga cggacacgcg cgagcgtaca cgtatcccag 61860
gggcccgggg gggaccttga tggtggttgc cgtcttgggc tttgtctcca tgtccttctg 61920
tcaatcggtc cgcgaacgga ggtaatcccg gcacgacgac ggacgcccga caaggtatgt 61980
ctcccgagcg tcaaaatccg gggggggggg cggcgacggt caaggggagg gttggagacc 62040
ggggttgggg aatgaatccc taccctcac cgacaacccc ccgggtaatc acggggtgcc 62100
gatgaacccc ggcggccggc aacgcggggt ccctgcgaga ggcacagatg cttacggtca 62160
ggtgctccgg gtcgggtgcg tctggtatgc ggttggtata tgtacacttt acctgggggc 62220
gtgcctggcc gccccagccc ctcccacgcc ctgcgcgtca tcagccggtg ggcgtggccg 62280
ctattataaa aaaagtgaga acgcgaagcg ttcgcacttt gtcctaataa tatatatatt 62340
attaggacaa agtgcgaacg cttcgcgttc tcactttttt tataatagcg gccacgccca 62400
ccggctacgt cacgctcctg tcggccgccg gcggtccata agcccggccg gccgggccga 62460
cgcgaataaa ccgggccgcc ggccggggcg ccgcgcagca gctcgccgcc cggatccgcc 62520
agacaaacaa ggcccttgca catgccggcc cgggcgagcc tgggggtccg gtaattttgc 62580
catcccaccc aagcggcttt ttgggttttt ctcttccccc ctccccacat ccccctctt 62640 taggggttcg ggtggtaaca accgcgatgt tttccggtgg cggcggcccg ctgtccccg 62700 gaggaaagtc ggcggccagg gcggcgtccg ggttttttgc gcccgccggc cctcgcggag 62760
ccggccgggg acccccgcct tgcttgaggc aaaactttta caacccctac ctcgccccag 62820
tcgggacgca acagaagccg accgggccaa cccagcgcca tacgtactat agcgaatgcg 62880
atgaatttcg attcatcgcc ccgcgggtgc tggacgagga tgccccccg gagaagcgcg 62940 ccggggtgca cgacggtcac ctcaagcgcg cccccaaggt gtactgcggg ggggacgagc 63000
gcgacgtcct ccgcgtcggg tcgggcggct tctggccgcg gcgctcgcgc ctgtggggcg 63060
gcgtggacca cgcccggcg gggttcaacc ccaccgtcac cgtctttcac gtgtacgaca 63120
tcctggagaa cgtggagcac gcgtacggca tgcgcgcggc ccagttccac gcgcggttta 63180
tggacgccat cacaccgacg gggaccgtca tcacgctcct gggcctgact ccggaaggcc 63240
accgggtggc cgttcacgtt tacggcacgc ggcagtactt ttacatgaac aaggaggagg 63300
tcgacaggca cctacaatgc cgcgccccac gagatctctg cgagcgcatg gccgcggccc 63360
tgcgcgagtc cccgggcgcg tcgttccgcg gcatttccgc ggaccacttc gaggcggagg 63420
tggtggagcg caccgacgtg tactactacg agacgcgccc cgctctgttt taccgcgtct 63480
acgtccgaag cgggcgcgtg ctgtcgtacc tgtgcgacaa cttctgcccg gccatcaaga 63540
agtacgaggg tggggtcgac gccaccaccc ggttcatcct ggacaacccc gggttcgtca 63600
ccttcggctg gtaccgtctc aaaccgggcc ggaacaacac gctagcccag ccgcgggccc 63660
cgatggcctt cgggacatcc agcgacgtcg agtttaactg tacggcggac aacctggcca 63720
tcgagggggg catgagcgac ctaccggcat acaagctcat gtgcttcgat atcgaatgca 63780
aggcgggggg ggaggacgag ctggcctttc cggtggccgg gcacccggag gacctggtca 63840
tccagatatc ctgtctgctc tacgacctgt ccaccaccgc cctggagcac gtcctcctgt 63900
tttcgctcgg ttcctgcgac ctccccgaat cccacctgaa cgagctggcg gccaggggcc 63960
tgcccacgcc cgtggttctg gaattcgaca gcgaattcga gatgctgttg gccttcatga 64020
cccttgtgaa acagtacggc cccgagttcg tgaccgggta caacatcatc aacttcgact 64080
ggcccttctt gctggccaag ctgacggaca tttacaaggt ccccctggac gggtacggcc 64140
gcatgaacgg ccggggcgtg tttcgcgtgt gggacatagg ccagagccac ttccagaagc 64200
gcagcaagat aaaggtgaac ggcatggtga acatcgacat gtacgggatt ataaccgaca 64260
agatcaagct ctcgagctac aagctcaacg ccgtggccga agccgtcctg aaggacaaga 64320
agaaggacct gagctatcgc gacatccccg cctactacgc cgccgggccc gcgcaacgcg 64380
gggtgatcgg cgagtactgc atacaggatt ccctgctggt gggccagctg tttttaagt 64440
ttttgcccca tctggagctc tcggccgtcg cgcgcttggc gggtattaac atcacccgca 64500
ccatctacga cggccagcag atccgcgtct ttacgtgcct gctgcgcctg gccgaccaga 64560
agggctttat tctgccggac acccagggggc gatttagggg cgccgggggg gaggcgccca 64620
agcgtccggc cgcagcccgg gaggacgagg agcggccaga ggaggagggg gaggacgagg 64680
acgaacgcga ggagggcggg ggcgagcggg agccggaggg cgcgcgggag accgccggcc 64740
ggcacgtggg gtaccagggg gccagggtcc ttgaccccac ttccgggttt catgtgaacc 64800
ccgtggtggt gttcgacttt gccagcctgt accccagcat catccaggcc cacaacctgt 64860
gcttcagcac gctctccctg agggccgacg cagtggcgca cctggaggcg ggcaaggact 64920
acctggagat cgaggtgggg gggcgacggc tgttcttcgt caaggctcac gtgcgagaga 64980
gcctcctcag catcctcctg cgggactggc tcgccatgcg aaagcagatc cgctcgcgga 65040
ttccccagag cagccccgag gaggccgtgc tcctggacaa gcagcaggcc gccatcaagg 65100
tcgtgtgtaa ctcggtttac gggttcacgg gagtgcagca cggactcctg ccgtgcctgc 65160
acgttgccgc gacggtgacg accatcggcc gcgagatgct gctcgcgacc cgcgagtacg 65220
tccacgcgcg ctgggcggcc ttcgaacagc tcctggccga tttcccggag gcggccgaca 65280
tgcgcgcccc cgggccctat tccatgcgca tcatctacgg ggacacggac tccatctttg 65340
tgctgtgccg cggcctcacg gccgccgggc tgacggccgt gggcgacaag atggcgagcc 65400
acatctcgcg cgcgctgttt ctgtccccca tcaaactcga gtgcgaaaag acgttcacca 65460
agctgctgct gatcgccaag aaaaagtaca tcggcgtcat ctacgggggt aagatgctca 65520
tcaagggcgt ggatctggtg cgcaaaaaca actgcgcgtt tatcaaccgc acctccaggg 65580
ccctggtcga cctgctgttt tacgacgata ccgtatccgg agcggccgcc gcgttagccg 65640
agcgccccgc agaggagtgg ctggcgcgac ccctgcccga gggactgcag gcgttcgggg 65700
ccgtcctcgt agacgcccat cggcgcatca ccgacccgga gagggacatc caggactttg 65760
tcctcaccgc cgaactgagc agacacccgc gcgcgtacac caacaagcgc ctggcccacc 65820
tgacggtgta ttacaagctc atggcccgcc gcgcgcaggt cccgtccatc aaggaccgga 65880
tcccgtacgt gatcgtggcc cagacccgcg aggtagagga gacggtcgcg cggctggccg 65940
ccctccgcga gctcgacgcc gccgccccag gggacgagcc cgcccccccc gcggccctgc 66000
cctccccggc caagcgcccc cgggagacgc cgttgcatgc cgaccccccg ggaggcgcgt 66060
ccaagccccg caagctgctg gtgtccgagc tggccgagga tcccgcatac gccattgccc 66120
acggcgtcgc cctgaacacg gactattact tctcccacct gttgggggcg gcgtgcgtga 66180
cattcaaggc cctgtttggg aataacgcca agatcaccga gagtctgtta aaaaggttta 66240
ttcccgaagt gtggcacccc ccggacgacg tggccgcgcg gctccgggcc gcagggttcg 66300
gggcggtggg tgccggcgct acggcggagg aaactcgtcg aatgttgcat agagcctttg 66360
atactctagc atgagccccc cgtcgaagct gatgtccctc attttacaat aaatgtctgc 66420
ggccgacacg gtcggaatct ccgcgtccgt gggtttctct gcgttgcgcc ggaccacgag 66480
cacaaacgtg ctctgccaca cgtgggcgac gaaccggtac cccgggcacg cggtgagcat 66540
ccggtctatg agccggtagt gcaggtgggc ggacgtgccg ggaaagatga cgtacagcat 66600
gtggcccccg taagtggggt ccgggtaaaa caacagccgc gggtcgcacg ccccgcctcc 66660
gcgcaggatc gtgtggacga aaaaaagctc gggttggcca agaatcccgg ccaagaggtc 66720
ctggaggggg gcgttgtggc ggtcggccaa cacgaccaag gaggccagga aggcgcgatg 66780
ctcgaatatc gtgttgatct gctgcacgaa ggccaggatt agggcctcgc ggctggtggc 66840
ggcgaaccgc ccgtctcccg cgttgcacgc gggacagcaa cccccgatgc ctaggtagta 66900
gcccatcccg gagagggtca ggcagttgtc ggccacggtc tggtccagac agaagggcag 66960
cgagacggga gtggtcttca ccaggggcac cgagagcgag cgcacgatgg cgatctcctc 67020
ggagggcgtc tgggcgaggg cggcgaaaag gccccgatag cgctggcgct cgtgtaaaca 67080
cagctcctgt ttgcgggcgt gaggcggcag gctcttccgg gaggcccgac gcaccacgcc 67140
cagagtcccg ccggccgcag aggagcgcga ccgccggcgc tccttgccgt gatagggccc 67200
gggccgggag ccgcggcgat gggggtcggt gtcatacata ggtacacagg gtgtgctcca 67260
gggacaggag cgagatcgag tggcgtctaa gcagcgcgcc cgcctcacgg acaaatgtgg 67320
cgagcgcggt gggctttggt acaaatacct gatacgtctt gaaggtgtag atgagggcac 67380
gcaacgctat gcagacacgc ccctcgaact cgttcccgca ggccagcttg gccttgtgga 67440
gcagcagctc gtcgggatgg gtggcggggg gatggccgaa cagaacccag gggtcaacct 67500
ccatctccgt aatggcgcac atggggtcac agaacatgtg cttaaagatg gcctcgggcc 67560
ccgcggcccg aagcaggctc acaaaccggc ccccgtcccc gggctgcgtc tcggggtcag 67620
cctcgagctg gtcgacgacg ggtacgatac agtcgaagag gctcgtgttg ttttccgagt 67680
agcggaccac ggaggcccgg agtctgcgca gggccagcca gtaagcacgc accagtaaca 67740
ggttacacag caggcattct ccgccggtgc gcccgcgccc ccggccgtgt ttcagcacgg 67800
tggccatcag agggcccagg tcgaggtcgg gctgggcatc gggttcggta aactgcgcaa 67860
agcgcggagc cacgtcgcgc gtgcgtgccc cgcgatgcgc ttcccaggac tggcggaccg 67920
tggcgcgacg ggcctccgcg gcagcgcgca gctggggccc cgactcccag acggcggggg 67980
tgccggcgag gagcagcagg accagatccg cgtacgccca cgtatccggc gactcctccg 68040
gctcgcggtc cccggcgacc gtctcgaatt ccccgttgcg agcggcggcg cgcgtacagc 68100
agctgtcccc gcccccgcgc cgaccctccg tgcagtccag gagacgggcg caatccttcc 68160
agttcatcag cgcggtggtg agcgacggct gcgtgccgga tcccgccgac cccgccccct 68220
cctcgccccc ggaggccaag gttccgatga gggcccgggt ggcagactgc gccaggaacg 68280
agtagttgga gtactgcacc ttggcggctc ccggggaggg cgagggcttg ggttgcttct 68340
gggcatgccg cccgggcacc ccgccgtcgg tacggaagca gcagtggaga aaaaagtgcc 68400
ggtggatgtc gtttatggtg agggcaaagc gtgcgaagga gccgaccagg gtcgccttct 68460
tggtgcgcag aaagtggcgg tccatgacgt acacaaactc gaacgcggcc acgaagatgc 68520
tagcggcgca gtggggcgcc cccaggcatt tggcacagag aaacgcgtaa tcggccaccc 68580
actgaggcga gaggcggtag gtttgcttgt acagctcgat ggtgcggcag accagacagg 68640
gccggtccag cgcgaaggtg tcgatggccg ccgcggaaaa gggcccggtg tccaaaagcc 68700
cctccccaca gggatccggg ggcgggttgc ggggtcctcc gcgcccgccc gaaccccctc 68760
cgtcgcccgc ccccccgcgg gcccttgagg gggcggtgac cacgtcggcg gcgacgtcct 68820
cgtcgagcgt accgacgggc ggcacaccta tcacgtgact ggccgtcagg agctcggcgc 68880
agagagcctc gttaagagcc aggaggctgg gatcgaaggc cacatacgcg cgctcgaacg 68940
cccccgcctt ccagctgctg ccgggggact cttcgcacac cgcgacgctc gccaggaccc 69000
cggggggcga agttgccatg gctgggcggg aggggcgcac gcgccagcga actttacggg 69060
acacaatccc cgactgcgcg ctgcggtccc agaccctgga gagtctagac gcgcgctacg 69120
tctcgcgaga cggcgcgcat gacgcggccg tctggttcga ggatatgacc cccgccgagc 69180
tggaggttgt cttcccgact acggacgcca agctgaacta cctgtcgcgg acgcagcggc 69240
tggcctccct cctgacgtac gccgggccta taaaagcgcc cgacgacgcc gccgccccgc 69300
agaccccgga caccgcgtgt gtgcacggcg agctgctcgc ccgcaagcgg gaaagattcg 69360
cggcggtcat taaccggttc ctggacctgc accagattct gcggggctga cgcgcgtgct 69420
gttgggcggg acggttcgcg aaccctttgg tgggtttacg cgggcacgca cgctcccatc 69480
gcgggcgcca tggcgggact gggcaagccc tacaccggcc acccaggtga cgccttcgag 69540
ggtctcgttc agcgaattcg gcttatcgtc ccatctacgt tgcggggcgg ggacggggag 69600
gcgggcccct actctccctc caacctcccc tccaggtgcg cctttcagtt tcatggccat 69660
gacgggtccg acgagtcgtt tcccatcgag tatgtactgc ggcttatgaa cgactgggcc 69720
gaggtcccgt gcaaccctta cctgcgcata cagaacaccg gcgtgtcggt gctgtttcag 69780
gggtttttttc atcgcccaca caacgccccc gggggcgcga ttacgccaga gcggaccaat 69840
gtgatcctgg ggtccaccga gacgacgggg ttgtccctcg gcgacctgga caccatcaag 69900
gggcggctcg gcctggatgc ccggccgatg atggccagca tgtggatcag ctgctttgtg 69960
cgcatgcccc gcgtgcagct cgcgtttcgg ttcatgggcc ccgaagatgc cggacggacg 70020
agacggatcc tgtgccgcgc cgccgagcag gctattaccc gtcgccgccg aacccggcgg 70080
tcccgggagg cgtacggggc cgaggccggg ctgggggtgg ccggaacggg tttccgggcc 70140
aggggggacg gttttggccc gctccccttg ttaacccaag ggccctcccg cccgtggcac 70200
caggccctgc ggggtcttaa gcacctacgg attggccccc ccgcgctcgt tttggcggcg 70260
ggactcgtcc tgggggccgc tatttggtgg gtggttggtg ctggcgcgcg cctataaaaa 70320
aggacgcacc gccgccctaa tcgccagtgc gttccggacg ccttcgcccc acacagccct 70380
cccgaccgac acccccatat cgcttcccga cctccggtcc cgatggccgt cccgcaattt 70440
caccgcccca gcaccgttac caccgatagc gtccgggcgc ttggcatgcg cgggctcgtc 70500
ttggccacca ataactctca gtttatcatg gataacaacc acccacaccc ccagggcacc 70560
caaggggccg tgcgggagtt tctccgcggt caggcggcgg cactgacgga ccttggtctg 70620
gcccacgcaa acaacacgtt taccccgcag cctatgttcg cgggcgacgc accggccgcc 70680

```
tggttgcggc ccgcgtttgg cctgcggcgc acctattcac cttttgtcgt tcgagaacct  70740
tcgacgcccg ggaccccgtg aggcccaggg agttccttct ggggtgtttt aatcaataaa  70800
agaccacacc aacgcacgag ccttgcgttt aatgtcgtgt ttattcaagg gagtgggata  70860
gggttcgacg gttcgaaact taacacacca aataatcgag cgcgtctagc ccagtaacat  70920
gcgcacgtga tgtaggctgg tcagcacggc gtcgctgtga tgaagcagcg cccggcgggt  70980
ccgctgtaac tgctgttgta ggcggtaaca ggcgcggatc agcaccgcca gggcgctacg  71040
accggtgcgt tgcacgtagc gtcgcgacag aactgcgttt gccgatacgg gcgggggcc  71100
gaattgtaag cgcgtcacct cttgggagtc atcggcggat aacgcactga atggttcgtt  71160
ggttatgggg gagtgtggtt ccccagggag tgggtcgagc gcctcggcct cggaatccga  71220
gaggaacaac gaggtggcgt cggagtcttc gtcgtcagag acatacaggg tctgaagcag  71280
cgacacgggc gggggggtag cgtcgatgtg tagcgcgagg gaggatgccc acgaagacac  71340
cccagacaag gagctgcccg tgcgtggatt tgtggaagac gcggaagccg ggacggatgg  71400
gcggttttgc ggtgcccgga accgaaccgc cggatactcc ccgggtgcta catgcccgtt  71460
ttggggctgg ggttggggct ggggttgggg ctggggttgg ggctggggtt ggggctgggg  71520
ttggggctgg ggttggggtt ggggttgggg ctggggttgg ggttggggct ggggctgggg  71580
ctggggctgg ggctggggct ggggctgggg ctggggctgg ggctggggct ggggctgggg  71640
ctggggctgg ggctggggct ggggttgggg cgcggacagg cggctgacgg tcaaatgccc  71700
ccgggggcgc gcagatgtgg tgggcgtggc caccggctgc cgtgtagtgg ggcggcggga  71760
aaccgggcct ccgggcgtaa caccgccctc cagcgtcaag tatgtggggg gcgggcctga  71820
cgtcgggggc ggggtgacgg gttggaccgc gggaggcggg ggagagggac ctgcgggaga  71880
ggatgaggtc ggctcggccg ggttgcggcc taaaacaggg gccgtggggt cggcggggtc  71940
ccagggtgaa gggagggatt cccgcgattc ggacagcgac gcgacagcgg ggcgcgtaag  72000
gcgccgctgc ggcccgccta cgggaaccct gggggggtt ggcgcgggac ccgaggttag  72060
cgggggcgg cggttttcgc ccccgggcaa aaccgtgccg gttgcgaccg ggggcggaac  72120
gggatcgata gggagagcgg gagaagcctg gccggcggac tggggaccga gcgggagggg  72180
cacaccagac accaaagcgt ggggcgctgg ctctgggggt ttgggagggg ccgggggcg  72240
cgcgaaatcg gtaaccgggg cgaccgtgtc ggggagggca ggcggccgcc aaccctgggt  72300
ggtcgcggaa gcctgggtgg cgcgcgccag ggagcgtgcc cggcggtgtc ggcgcgcgcg  72360
cgacccggac gaagaagcgg tagaagcgcg ggaggaggcg ggggggcggg gggcggtggc  72420
atcggggggc gccggggaac tttgggggga cggcaagcgc cggaagtcgt cgcgggggcc  72480
cacgggcgcc ggccgcgtgc tttcggccgg gacgcccggt cgtgcttcgc gagccgtgac  72540
tgccggccca gggggccgcg gtgcacactg ggacgtgggg acggactgat cggcggtggg  72600
cgaaaggggg tccggggcaa ggaggggcgc ggggccgccg gagtcgtcag acgcgagctc  72660
ctccaggccg tgaatccatg cccacatgcg agggggacg ggctcgccgg gggtggcgtc  72720
ggtgaatagc gtgggggcca ggcttccggg ccccaacgag ccctccgccc caacaaggtc  72780
cgccgggccg ggggtcgggt tcgggaccga ggggctctgg tcgtcggggg cgcgctggta  72840
caccggatgc cccgggaata gctcccccga caggagggag gcgtcgaacg gccgcccgag  72900
gatagctcgc gcgaggaagg ggtcctcgtc ggtggcgctc gcggcgagga cgtcctcgcc  72960
gcccgccaca aacgggagct cctcggtggc ctcgctgcca acaaaccgca tgtcgggggg  73020
gccgggggg tccgggtttt cccacaacac cgcgaccggg gtcatggaga tgtccacgag  73080
```

-continued caccaggcac ggcgggcccc gggcgagggg ccgctcggcg atgagcgcgg acaggcgcgg 73140
gagctgtgcc gccagacacg cgttttcgat cgggttaagg tcggcgtgca ggaggcggac 73200
ggcccacgtc tcgatgtcgg acgacacggc atcgcgcaag gcggcgtccg gcccgcgagc 73260
gcgtgagtca aacagcgtga ggcacagctc cagttccgac tcgcgggaaa aggccgtggt 73320
gttgcggagc gccacgacga cgggcgcgcc caggagcact gccgccagca ccaggtccat 73380
ggccgtaacg cgcgccgcgg gggtgcggtg ggtggcggcg gccggcacgg cgacgtgctg 73440
gcccgtgggc cggtagaggg cgttgggggg agcgggggt gacgcctcgc gcccccccga 73500
ggggctcagc gtctgcccag attccagacg cgcggtcaga agggcgtcga aactgtcata 73560
ctctgtgtag tcgtccggaa acatgcaggt ccaaagagcg gccagcgcgg tgcttgggag 73620
acacatgcgc ccgaggacgc tcaccgccgc cagcgcctgg gcgggactca gctttcccag 73680
cgcggcgccg cgctcggttc ccagctcggg gaccgagcgc cagggcgcca gggggtcggt 73740
ttcggacaac ttgccgcggc gccagtctgc cagccgcgtg ccgaacatga ggccccgggt 73800
cggagggcct ccggccgaaa acgctggcag cacgcggatg cgggcgtctg gatgcggggt 73860
caggcgctgc acgaatagca tggaatctgc tgcgttctga aacgcacggg ggagggtgag 73920
atgcatgtac tcgtgttggc ggaccagatc caggcgccaa aaggtgtaaa tgtgttccgg 73980
ggagctggcc accagcgcca ccagcacgtc gttctcgtta aaggaaacgc ggtgcctagt 74040
ggagctctgg ggtccgagcg gcggccccgg ggccgccgcg tcaccccccc attccagctg 74100
ggcccagcga cacccaaact cgcgcgtgag agtggtcgcg acgagggcga cgtagagctc 74160
ggccgccgca tccatcgagg ccccccatct cgcctggcgg tggcgcacaa agcgtccgaa 74220
gagctgaaag ttggcggcct gggcgtcgct gagggccagc tgaagccggt tgatgacggt 74280
gaggacgtac atggccgtga cggtcgaggc cgactccagg gtgtccgtcg gaagcggggg 74340
gcgaatgcat gccgcctcgg gacacatcag cagcgcgccg agcttgtcgg tcacggccgg 74400
gaagcagagc gcgtactgca gtggcgttcc atccgggacc aaaaagctgg gggcgaacgg 74460
cctatccagc gtactggtgg cctcgcgcag caccaggggc cccgggcctc cgctcactcg 74520
caggtacgcc tcgccccggc ggcgcagcat ctgcgggtcg gcctcttggc cgggtggggc 74580
ggacgcccgg gcgcgggcgt ctagggcgcg aagatccacg agcaggggcg cgggcgcggc 74640
cgccgcgccc gcgcccgtct ggcctgtggc cttggcgtac gcgctatata agcccatgcg 74700
gcgttggatg agctcccgcg cgccccggaa ctcctccacc gcccatgggg ccaggtcccc 74760
ggccaccgcg tccaattccg ccaacaggcc ccccagggtg tcaaagttca tctcccaggc 74820
caccccttggc accacctcgt cccgcagccg ggcgctcagg tcggcgtgtt gggccacgcg 74880
ccccccgagc tcctccacgg ccccggcccg ctcggcgctc ttggcgccca ggacgccctg 74940
gtacttggcg ggaaggcgct cgtagtcccg ctgggctcgc agccccgaca cagtgttggt 75000
ggtgtcctgc agggcgcgaa gctgctcgca tgccgcgcga aatccctcgg gcgatttcca 75060
ggccccccccg cgaacgcggc cgaagcgacc ccatacctcg tcccactccg cctcggcctc 75120
ctcgaaagac ctccgcaggg cctcgacgcg gcgacgggtg tcgaagagcg actgcaggcg 75180
cgcgccctgt cgcgtcagga ggcccgggcc gtcgccgctg gccgcgctta gcgggtgcgt 75240
ctcaaaggtg cgctgggcat gttccaacca ggcgaccgcc tgcacgtcga gctcgcgcgc 75300
cttctccgtc tggtccaaca gaatctcgac ctgatccgcg atctcctccg ccgagcgcgc 75360
ctggtccagc gtcttggcca cggtcgccgg gacggcaacc accttcagca gggtcttcag 75420

-continued

```
attggccaga ccctcggcct cgagctgggc ccggcgctcg cgcgcggcca gcacctcccg  75480
caaccccgcc gtgacccgct cggtggcttc ggcgcgctgc tgtttggcgc gcaccacggc  75540
gtccttggta tcggccaggt cctgtcgggt cacgaatgcg acgtagtcgg cgtacgccgt  75600
gtccttcacg gggctctggt ccacgcgctc cagcgccgcc acacacgcca ccagcgcgtc  75660
ctcgctcggg cagggcaggg tgacccctgc ccggacaagc tcggcggccg ccgccgggtc  75720
gttgcgcacc gcggatatct cctccgcggc ggcggccagg tccagcgcca cgcttccgat  75780
cgcgcgccgc gcgtcggccc ggagggcgtc caggcgatcg cggatatcca cgtactcggc  75840
gtagcccttt tgaaaaaacg gcacgtactg gcgcagggcc ggcacgcccc ccaagtcttc  75900
cgacaggtgt aggacggcct cgtggtagtc gataaacccg tcgttcgcct gggcccgctc  75960
cagcagcccc cccgcgagcc gcagaagccg cgccaggggc tcggtgtcca cccgaaacat  76020
gtcggcgtac gtgtcggccg cggccccgaa ggccgcgctc cagtcgatgc ggtgaatggc  76080
tgcgagcggg gggagcatgg ggtggcgctg gttctcgggg gtgtatgggt taaacgcaag  76140
ggccgtctcc agggcaaggg tcaccgcctt ggcgttggtt cccagcgcct gctcggcccg  76200
ctttcggaag tcccgggggt tgtagccgtg cgtgcccgcc agcgcctgca ggcgacggag  76260
ctcgaccacg tcaaactcgg caccgctttc cacgcggtcc agcacggcct ccacgtcggc  76320
ggcccagcgc tcgtggctac tgcgggcgcg ctgggccgcc atcttctctc tgaggtcggc  76380
ggtggcggcc tcaagttcgt cggcgcggcg tcgcgtggcg ccgatgacct ttcccagctc  76440
ctgcagggcg cgcccgctgg gggagtggtc cccggccgtc ccttcggcgt gcaacaggcc  76500
cccgaacctg ccctcgtggc ccgcgaggct ttcccgcgcg ccggtggtcg cgcgcgtcgc  76560
ggcctggatc agggaggcat gctctccctc cggttggttg gcggcccggc gcacctggac  76620
gacaaggtcg gcggcagccg accctaaggt cgtgagctgg gcgatggccc cccgcgcgtc  76680
cagggccaac cgagtcgcct tgacgtatcc cgcggcgctg tcggccatgg ccgctaggaa  76740
ggccaggggg gaggccgggt cgctggcggc cgcgcccagg gccgtcactg cgtcgaccag  76800
gacgcggtgc gcccgcacgg ccgcatccac cgtcgacgcg gggtctgccg tcgcgacggc  76860
ggcgctgccg gcgttgatgg cgttcgagac ggcgtgggct atgatcgggg cgtgatcggc  76920
gaagaactgc aagagaaacg gagtctcggg ggcgttggcg aacaggttct tcagcaccac  76980
cacgaagctg ggatgcaagc cggacagagc cgtcgccgtg tccggagtcg ggtgctccag  77040
ggcatctcgg tactgcccca gcagccccca catgtccgcc cgcagcgccg ccgtaacctc  77100
cgggggcgcc ccccgaacgg cctcggggag gtccgaccag cccgccggca gggaggcccg  77160
cagggtcgtc aggacggccg gacaggcctt tagccccaca aagtcaggga ggggccgcag  77220
gaccccctgg agtttgtgca agaacttctc ccgggcgtcg cgggccacct tcgcccgctc  77280
ccgcgctccc tcgagcattg cctccaggga gcgcgcgcgc tcccgcaaac gggcacgcgc  77340
atcgggggcg agctctgccg tcagcttggc ggcatccatg gcccgcgcct gccgcagcgc  77400
ttcctcggcc atgcgcgtgg cctctggcga cagcccgccg tcgtcggggt agggcgacgc  77460
gccgggcgca ggaacaaagg ccgcgtcgct gtccagctgc tggcccaggg ccgcatctag  77520
ggcgtcgaag cgccgcagct cggccagacc cgagctgcgg cgcgcctgct ggtcgttaat  77580
gtcgcggatg ctgcgcgcca gctcgtccag cggcttgcgt tctatcagcc cttggttggc  77640
ggcgtccgtc aggacggaga gccaggccgc caggtcctcg gggcgtcca gcgtctggcc  77700
ccgctgtatc agatcccgca acaggatggc cgtggggctg gtcgcgatcg gggcggggc  77760
gggaatggcg gcgctctgcg cgatgtcccg cgtgtgctgg tcgaagacag gcagggactc  77820
```

tagcagctgg accacgggca cgacggcggc cgaagccacg tgaaaccggc ggtcgttgtt 77880
gtcgctggcc tgcagagcct tggcgctgta tacggccccc cggtaaaagt actccttaac 77940
cgcgccctcg atcgcccgac gggcctgggt ccgcacctcc tccagccgaa cctgaacggc 78000
ctcggggccc aggggggtg ggcgcggagc cccctgcggg gccgccccgg ccggggcggg 78060
cattacgccg aggggcccgg cgtgctgtga gaccgcgtcg accccgcgag cgagggcgtc 78120
gagggcctcg cgcatctggc gatcctccgc ctccaccta atctcttcgc cacgggcaaa 78180
tttggccaga gcctggactc tatacagaag cggttctggg tgcgtcgggg tggcgggggc 78240
aaaaagggtg tccgggtggg cctgcgagcg ctccagaagc cactcgccga ggcgtgtata 78300
cagattggcc ggcggggccg cgcgaagctg cagctccagg tccgcgagtt ccccgtaaaa 78360
ggcgtccgtc tcccgaatga catccctagc cacaaggatc agcttcgcca gcgccaggcg 78420
accgatcaga gagttttcgt ccagcacgtg ctggacgagg ggcagatggg cggccacgtc 78480
ggccaggctc aggcgcgtgg aggccagaaa gtcccccacg gccgttttcc ggggcagcat 78540
gctcagggta aactccagca gggcggcggc cgggccggcc accccggcct gggtgtgcgt 78600
ccgggccccg ttctcgatga gaaaggcgag gacgcgttca aagaaaaaaa taacacagag 78660
ctccagcagc cccggagaag ccggatacgg cgaccgtaag gcgctgatgg tgagccgcga 78720
acacgcggcg acctcgcggg ccagggcggc ggagcacgcg gtgaacttaa ccgccgtggc 78780
ggccacgttt gggtgggcct cgaacagctg ggcaaggtct gcgcccgggg gctcgggtga 78840
gcggcgagtc ttcagcgcct cgagggcctg cgaggacgcc ggaaccgtgg gcccgtcgtc 78900
ctcgcccgcc tcggcgaccg gcggcccggc cgggtcgggg ggtgccgagg cgaggacagg 78960
ctccggaacg gaggcgggga ccgcggcccc gacgggggtt ttgcctttgg gggtggattt 79020
cttcttggtt ttggcagggg gggccgagcg tttcgttttc tcccccgaag tcaggtcttc 79080
gacgctggaa ggcggagtcc aggtgggtcg gcggcgcttg ggaaggccgg ccgagtagcg 79140
tgcccggtgc cgaccaaccg ggacgacgcc catctccagg acccgcatgt cgtcgtcatc 79200
ttcttcggcc gcctctgcgg cggggggctt gggggcggag ggaggcggtg gtgggatcgc 79260
ggagggtggg tcggcggagg ggggatccgt gggtggggta cccttcaggg ccaccgccca 79320
tacatcgtcg ggcgcccgat tcgggcgctt ggcctctggt tttgccgacg gaccggccgt 79380
cccccgggat gtctcggagg ccctgtcgtc gcgacgggcc cgggtcggtg gcggcgactg 79440
ggcggctgtg ggcgggtggg gccccgtgcc ccctaccccc tcccgggggc ccacgccgac 79500
gcagggctcc cccaggcccg cgatctcgcc ccgcaggggg tgcgtgatgg ccacgcgccg 79560
ttcgctgaac gcttcgtcct gcaggtaagt ctcgctggcc ccgtaaagat gcagagccgc 79620
ggccgtcaag tccgcaggag ccgcgggttc cgggcccgac ggcacgaaaa acaccatggc 79680
tcccgcccac cgtacgtccg ggcgatcgcg ggtgtaatac gtcaggtatg gatacatgtc 79740
ccccgcccgc actttggcga tgaacgcggg ggtgccctcc ggaaggccgt gcgggtcaaa 79800
aaggtatgcg gtgtcgccgt ccctgaacag ccccatccct agggggccaa tggttaggag 79860
cgtgtacgac agggggcgca gggcccacgg gccggcgaag aacgtgtgtg cggggcattg 79920
tgtctccagc aggcccgccg cgggctcccc gaagaagccc acctcgccgt atacgcgcga 79980
gaagacacag cgcagtccgc cgcgcgcccc tgggtactcg aggaagttgg ggagctcgac 80040
gatcgaacac atgcgcggcg gcccagggcc cgcggtcgcg cgcgtccact cgcccccctc 80100
gaccaaacaa ccctcgatgg cctccgcgga cagaacgtcg cgagggccca catcaaatat 80160

```
gaggctgaga aaggacagcg acgagcgcat gcacgatacc gacccccccg gctccaggtc  80220
gggcgcgaac tggttccgag caccggtgac cacgatgtcg cgatcccccc cgcgttccat  80280
cgtggagtgc ggtggggtgc ccgcgatcat atgtgcccta ctggccagag acccggcctg  80340
tttatggacc ggacccccgg ggttagtgtt gtttccgcca cccatgcccc cgtaccatgg  80400
ccccggttcc cctgattagg ctacgagtcg cggtgatcgc ttcccaaaaa ccgagctgcg  80460
tttgtctgtc ttgatctttc cccccccgc ccgcccgccc gcccgcacac cataacaccg  80520
agaacaacac acgggggtgg gcgtaacata ataaagcttt attggtaact agttaacggc  80580
aagtccgtgg gtggcgcgac ggtgtcctcc gggctcatct cgtcgtcctc gacgggggtg  80640
ttggaatgag gcgccccctc gcggtccgcc tggcgtgggc cgtgcccata ggcctccggc  80700
ttctgtgcgt ccatgggcat aggcgcgggg agactgtttc cggcgtcgcg gacctccagg  80760
tccctgggag actccggtcc ggctaacgga cgaaacgcgg aagcgcgaaa cacgccgtcg  80820
gtgacccgca ggagctcgtt catcagtaac caatccatac tcagcgtaac ggccagcccc  80880
tggcgagaca gatccacgga gtccggaacc gcggtcgtct ggcccagggg gccgaggctg  80940
tagtcccccc aggcccctag gtcgcgacgg ctcgtaagca cgacgcggtc ggccgcgggg  81000
ctttgcgggg gggcgtcctc gggcgcatgc gccattacct ctcggatggc cgcggcgcgc  81060
tggtcggccg agctgaccaa gggcgccacg accacggcgc gctccgtctg caggcccttc  81120
cacgtgtcgt ggagttcctg gacaaactcg gccacgggct cgggtcccgc ggccgcgcgc  81180
gcggcttgat agcaggccga gagacgccgc cagcgcgcta gaaactgacc catgaagcaa  81240
aacccgggga cctggtctcc cgacagcagc ttcgacgccc gggcgtgaat gccggacacg  81300
acggacagaa acccgtgaat ttcgcgccgg accacggcca gcacgttgtc ctcgtgcgac  81360
acctgggccg ccagctcgtc acacaccccc aggtgcgccg tggtttcggt gatgacggaa  81420
cgcaggctcg cgagggacgc gaccagcgcg cgcttggcgt cgtgatacat gctgcagtac  81480
tgactcaccg cgtcccccat ggcctcgggg ggccagggcc ccaggcggtc gggcgtgtcc  81540
ccgaccaccg catacaggcg gcgcccgtcg ctctcgaacc gacactcgaa aaaggcggag  81600
agcgtgcgca tgtgcagccg cagcagcacg atggcgtcct ccagttggcg aatcaggggg  81660
tctgcgcgct cggcgaggtc ctgcagcacc ccccgggcgg ccagggcgta catgctaatc  81720
aacaggaggc tggtgcccac ctcggggggc gggggggcct gcagctggac caggggccgc  81780
agctgctcga cggcacccct ggagatcacg tacagctccc ggagcagctg ctctatgttg  81840
tcggccatct gcatagtggg gccgaggccg ccccgggcgg ccggttcgag gagggtaatc  81900
agcgcgccca gtttggtgcg atggccctcg accgtgggga gatagcccag cccaaaatcc  81960
cgggcccagg ccaacacacg cagggcgaac tcgaccgggc gtggaaggta ggccgcgcta  82020
cacgtggccc tcaacgcgtc cccgaccacc agggccagaa cgtaggggac gaagcccggg  82080
tcggcgagga cgttggggtg aatgccctcg agggcgggga agcggatctg ggtcgccgcg  82140
gccaggtgga cagagggggc gtggctgggc tgcccgacgg ggagaagcgc ggacagcggc  82200
gtggccgggg tggtgggggt gatgtcccag tgggtctgac catacacgtc gatccagatg  82260
agcgccgtct cgcggagaag gctgggttga ccggaactaa agcggcgctc ggccgtctca  82320
aactccccca cgagcgcccg ccgcaggctc gccagatgtt ccgtcggcac ggccggaccc  82380
atgatacgcg ccagcgtctg gctcagaacg ccccccgaca ggccgaccgc ctcgcagagc  82440
cgcccgtgcg tgtgctcgct ggcgccctgg acccgcctga aagtttttac gtagttggca  82500
tagtacccgt attcccgcgc cagaccaaac acgttcgacc ccgcgagggc aatgcaccca  82560
```

aagagctgct ggacttcgcc gagtccgtgg ccggcgggcg tccgcgcggg gacgcccgcc 82620
gccagaaacc cctccagggc cgaaaggtag tgcgtgcagt gcgagggcgt gaacccagcg 82680
tcgatcaggg tgttgatcac cacggagggc gaattggtat tctggatcaa cgtccacgtc 82740
tgctgcaaca gagccaacag ccgctgctgg gcgccggcgg agggctgctc cccgagctgc 82800
agcaggctgg agacggcagg ctggaagact gccagtgccg acgaactcag gaacggcacg 82860
tcgggatcaa acacggccac gtccgtccgc acgcgcgcca ttagcgtccc cgggggcgca 82920
caggccgagc gcgggctgac gcggctgagg gccgtcgaca cgcgcacctc ctcgcggctg 82980
cgaaccatct tgttggcctc cagtggcgga atcattatgg ccgggtcgat ctcccgcacg 83040
gtgtgctgaa actgcgccaa caggggcggc gggaccacag ccccccgctc gggggtcgtc 83100
aggtactcgt ccaccagggc caacgtaaag agggcccgtg tgaggggagt gagggtcgcg 83160
tcgtctatgc gctggaggtg cgccgagaac agcgtcaccc gattactcac cagggccaag 83220
aaccggaggc cctcttgcac gaacggggcg gggaagagca ggctgtacgc cggggtggta 83280
aggttcgcgc tgggctgccc caacgggacc ggcgccatct tgagcgacgt ctccccaagg 83340
gcctcgatgg aggtccgcgg gctcatggcc aagcagctct tggtgacggt ttgccagcgg 83400
tctatccact ccacggcgca ctggcggacg cggaccggcc ccagggccgc cgcggtgcgc 83460
aggccggcgg aatccagcgc atgggacgtg tcggagccgg tgaccgcgag gatggtgtcc 83520
ttgatgacct ccatctcccg gaaggcctgg tcgggggcct cggggagagc caccaccaag 83580
cggtgtacga gcaacccggg gaggttctcg gccaagagcg ccgtctccgg aagcccgtgg 83640
gcccggtgga gcgcgcacag gtgttccagc agcggccgcc agcatgcccg cgcgtctgcc 83700
ggggcgatgg ccgttcccga caacagaaac gccgccatgg cggcgcgcag cttggccgtg 83760
gccagaaacg ccgggtcgtc cgccccgttt gccgtctcgg ccgtgggggt tggcggttgg 83820
cgaaggccgg ctaggctcgc caataggcgc tgcataggtc cgtccgaggg cggaccggcg 83880
ggtgaggtcg tgacgacggg ggcctcggac gggagaccgc ggtctgccat gacgcccggc 83940
tcgcgtgggt gggggacagc gtagaccaac gacgagaccg ggcgggaatg actgtcgtgc 84000
gctgtaggga gcggcgaatt atcgatcccc tgcggccctc caggaacccc gcaggcgttg 84060
cgagtacccc gcgtcttcgc ggggtgttat acggccactt aagtcccggc atcccgttcg 84120
cggacccagg cccgggggat tgtccggatg tgcgggcagc ccggacggcg tgggttgcgg 84180
actttctgcg gggcggccca aatggccctt taaacgtgtg tatacggacg cgccgggcca 84240
gtcggccaac acaacccacc ggaggcggta gccgcgtttg gctgtggggt gggtggttcc 84300
gccttgcgtg agtgtccttt cgaccccccc ctcccccggg tcttgctagg tcgcgatctg 84360
tggtcgcaat gaagaccaat ccgctacccg caacccccttc cgtgtggggc gggagtaccg 84420
tggaactccc ccccaccaca cgcgataccg cggggcaggg cctgcttcgg cgcgtcctgc 84480
gccccccgat ctctcgccgc gacggcccag tgctccccag ggggtcggga ccccggaggg 84540
cggccagcac gctgtggttg cttggcctgg acggcacaga cgcgcccccct ggggcgctga 84600
cccccaacga cgataccgaa caggccctgg acaagatcct gcggggcacc atgcgcgggg 84660
gggcggccct gatcggctcc ccgcgccatc atctaacccg ccaagtgatc ctgacggatc 84720
tgtgccaacc caacgcggat cgtgccggga cgctgcttct ggcgctgcgg caccccgccg 84780
acctgcctca cctggcccac cagcgcgccc cgccaggccg gcagaccgag cggctgggcg 84840
aggcctgggg ccagctgatg gaggcgaccg ccctggggtc ggggcgagcc gagagcgggt 84900

-continued

```
gcacgcgcgc gggcctcgtg tcgtttaact tcctggtggc ggcgtgtgcc gcctcgtacg  84960
acgcgcgcga cgccgccgat gcggtacggg cccacgtcac ggccaactac cgcgggacgc  85020
gggtgggggc gcgcctggat cgtttttccg agtgtctgcg cgccatggtt cacacgcacg  85080
tcttcccccca cgaggtcatg cggtttttcg gggggctggt gtcgtgggtc acccaggacg  85140
agctagcgag cgtcaccgcc gtgtgcgccg ggccccagga ggcggcgcac accggccacc  85200
cgggccggcc ccgctcggcc gtgatcctcc cggcgtgtgc gttcgtggac ctggacgccg  85260
agctggggct ggggggcccg ggcgcggcgt ttctgtacct ggtattcact taccgccagc  85320
gccgggacca ggagctgtgt tgtgtgtacg tgatcaagag ccagctcccc ccgcgcgggt  85380
tggagccggc cctggagcgg ctgtttgggc gcctccggat caccaacacg attcacggca  85440
ccgaggacat gacgcccccg gccccaaacc gaaaccccga cttccccctc gcgggcctgg  85500
ccgccaatcc ccaaaccccg cgttgctcgg ctggccaggt cacgaacccc cagttcgccg  85560
acaggctgta ccgctggcag ccggaccttc gggggcgccc caccgcacgc acctgtacgt  85620
acgccgcctt tgcagagctc ggcatgatgc ccgaggatag tccccgctgc ctgcaccgca  85680
ccgagcgctt tggggcggtc agcgtccccg ttgttattct ggaaggcgtg gtgtggcgcc  85740
ccggcgagtg gcgggcatgc gcgtgagcgt agcaaacgcc ccgcccacac aacgctccgc  85800
ccccaacccc ttccccgctg tcactcgtgg ttcgttgacc cggacgtccg ccaaataaag  85860
ccactgaaac ccgaaacgcg agtgttgtaa cgtcctttgg gcgggaggaa gccacaaaat  85920
gcaaatggga tacatggaag gaacacaccc ccgtgactca ggacatcggc gtgtcctttt  85980
gggtttcact gaaactggcc cgcgccccac ccctgcgcga tgtggataaa aagccagcgc  86040
gggtggttta gggtaccaca ggtgggtgct ttggaaactt gtcggtcgcc gtgctcctgt  86100
gagcttgcgt ccctccccgg tttcctttgc gctcccgcct tccggacctg ctctcgccta  86160
tcttctttgg ctgtcggtgc gattcgtcag gcagcggcct tgtcgaatct cgaccccacc  86220
actcgccgga cccgccgacg tcccctctgg agcccgccga aacccgccgc gtctgttgaa  86280
atggccagcc gcccagccgc atcctctccc gtcgaagcgc gggcccccggt tgggggacag  86340
gaggccggcg gccccagcgc agccacccag ggggaggccg ccggggcccc tctcgcccac  86400
ggccaccacg tgtactgcca gcgagtcaat ggcgtgatgg tgctttccga caagacgccc  86460
gggtccgcgt cctaccgcat cagcgatagc aactttgtcc aatgtggttc caactgcacc  86520
atgattatcg acggagacgt ggtgcgcggg cgcccccagg acccgggggc cgcggcatcc  86580
cccgctccct tcgttgcggt gacaaacatc ggagccggca gcgacggcgg gaccgccgtc  86640
gttgcattcg ggggaacccc acgtcgctcg gcggggacgt ctaccggtac ccagacggcc  86700
gacgtcccag ccgaggccct tgggggcccc cctcctcctc cccgcttcac cctgggtggc  86760
ggctgttgct cctgtcgcga cacacggcgc cgctctgcgg tattcggggg ggagggggat  86820
cccgtcggcc ccgcggagtt cgtctcggac gaccggtcgt ccgattccga ctcggatgac  86880
tcggaggaca ccgactcgga gacgctgtca cacgcctcct cggacgtgtc cggcggggcc  86940
acgtacgacg acgcccttga ctccgattcg tcatcggatg actccctgca gatagatggc  87000
cccgtgtgtc gcccgtggag caatgacacc gcgcccctgg atgtttgccc cgggaccccc  87060
ggcccgggcg ccgacgccgg tggtccctca gcggtagacc cacacgcgcc gacgacaggg  87120
gccggcgctg gtcttgcggc cgatcccgcc gtggcccggg acgacgcgga ggggctttcg  87180
gacccccggc cacgtctggg aacgggcacg gcctaccccg tcccccctgga actcacgccc  87240
gagaacgcgg aggccgtggc gcgctttctg ggagatgccg tgaaccgcga acccgcgctc  87300
```

atgctggagt acttttgccg gtgcgcccgc gaggaaacca agcgtgtccc ccccaggaca 87360
ttctgcagcc cccctcgcct cacggaggac gactttgggc ttctcaacta cgcgctcgtg 87420
gagatgcagc gcctgtgtct ggacgttcct ccggtcccgc cgaacgcata catgccctat 87480
tatctcaggg agtatgtgac gcggctggtc aacgggttca agccgctggt gagccggtcc 87540
gctcgccttt accgcatcct gggggttctg gtgcacctgc ggatccggac ccgggaggcc 87600
tcctttgagg agtggctgcg atccaaggaa gtggccctgg actttggcct gacggaaagg 87660
cttcgcgagc acgaagccca gctggtgatc ctggcccagg ttctggacca ttacgactgt 87720
ctgatccaca gcacaccgca cacgctggtc gagcgggggc tgcaatcggc cctgaagtat 87780
gaggagtttt acctaaagcg ctttggcggg cactacatgg agtccgtctt ccagatgtac 87840
acccgcatcg ccggcttttt ggcctgccgg gccacgcgcg gcatgcgcca catcgccctg 87900
gggcgagagg ggtcgtggtg ggaaatgttc aagttctttt tccaccgcct ctacgaccac 87960
cagatcgtac cgtcgacccc cgccatgctg aacctgggga cccgcaacta ctacacctcc 88020
agctgctacc tggtaaaccc ccaggccacc acaaacaagg cgaccctgcg ggccatcacc 88080
agcaacgtca gtgccatcct cgcccgcaac gggggcatcg ggctatgcgt gcaggcgttt 88140
aacgactccg gccccggac cgccagcgtc atgcccgccc tcaaggtcct cgactcgctg 88200
gtggcggcgc acaacaaaga gagcgcgcgt ccgaccggcg cgtgcgtgta cctggagccg 88260
tggcacaccg acgtgcgggc cgtgctccgg atgaaggggg tcctcgccgg cgaagaggcc 88320
cagcgctgcg acaatatctt cagcgccctc tggatgccag acctgttttt caagcgcctg 88380
attcgccacc tggacggcga gaagaacgtc acatggaccc tgttcgaccg ggacaccagc 88440
atgtcgctcg ccgactttca cggggaggag ttcgagaagc tctaccagca cctcgaggtc 88500
atggggttcg gcgagcagat acccatccag gagctggcct atggcattgt gcgcagtgcg 88560
gccacgaccg ggagcccctt cgtcatgttc aaagacgcgg tgaaccgcca ctacatctac 88620
gacacccagg gggcggccat cgccggctcc aacctctgca ccgagatcgt ccatccggcc 88680
tccaagcgat ccagtggggt ctgtaatctg ggaagcgtga atctggcccg atgcgtctcc 88740
aggcagacgt ttgactttgg gcggctccgc gacgccgtgc aggcgtgcgt gctgatggtg 88800
aacatcatga tcgacagcac gctacaaccc acgccccagt gcacccgcgg caacgacaac 88860
ctgcggtcca tgggaatcgg catgcagggc ctgcacacgg cctgcctgaa gctggggctg 88920
gatctggagt ctgccgaatt tcaggacctg aacaaacaca tcgccgaggt gatgctgctg 88980
tcggcgatga agaccagcaa cgcgctgtgc gttcgcgggg cccgtccctt caaccacttt 89040
aagcgcagca tgtatcgcgc cggccgcttt cactgggagc gctttccgga cgcccggccg 89100
cggtacgagg gcgagtggga gatgctacgc cagagcatga tgaaacacgg cctgcgcaac 89160
agccagtttg tcgcgctgat gcccaccgcc gcctcggcgc agatctcgga cgtcagcgag 89220
ggctttgccc ccctgttcac caacctgttt agcaaggtga cccgggacgg cgagacgctg 89280
cgccccaaca cgctcctgct aaaggaactg gaacgcacgt ttagcgggaa gcgcctcctg 89340
gaggtgatgg acagtctcga cgccaagcag tggtccgtgg cgcaggcgct cccgtgcctg 89400
gagcccaccc accccctccg gcgattcaag accgcgtttg actacgacca gaagttgctg 89460
atcgacctgt gtgcggaccg cgccccctac gtcgaccata gccaatccat gaccctgtat 89520
gtcacggaga aggcggacgg gaccctccca gcctccaccc tggtccgcct tctggtccac 89580
gcatataagc gcggactaaa aacagggatg tactactgca aggttcgcaa ggcgaccaac 89640
agcggggtct ttggcggcga cgacaacatt gtctgcacga gctgcgcgct gtgaccgaca 89700
aaccccctcc gcgccaggcc cgccgccact gtcgtcgccg tcccacgcgc tcccccgctg 89760
ccatggattc cgcggcccca gccctctccc ccgctctgac ggcccatacg ggccagagcg 89820
cgccggcgga cctggcgatc cagattccaa agtgccccga ccccgagagg tacttctaca 89880
cctcccagtg tcccgacatt aaccacctgc gctccctcag catccttaac cgctggctgg 89940
aaaccgagct tgttttcgtg ggggacgagg aggacgtctc caagctttcc gagggcgagc 90000
tcagctttta ccgcttcctc ttcgctttcc tgtcggccgc cgacgacctg gttacggaaa 90060
acctgggcgg cctctccggc ctgtttgagc agaaggacat tctccactac tacgtggagc 90120
aggaatgcat cgaagtcgta cactcgcgcg tgtacaacat catccagctg gtgctttttc 90180
acaacaacga ccaggcgcgc cgcgagtacg tggccggcac catcaaccac ccggccatcc 90240
gcgccaaggt ggactggttg gaagcgcggg tgcgggaatg cgcctccgtt ccggaaaagt 90300
tcattctcat gatcctcatc gagggcatct tttttgccgc ctcgtttgcc gccatcgcct 90360
accttcgcac caacaacctt ctgcgggtca cctgccagtc aaacgacctc atcagccggg 90420
acgaggccgt gcacacgacg gcctcgtgtt acatctacaa caactacctc ggcgggcacg 90480
ccaagccccc gcccgaccgc gtgtacgggc tgttccgcca ggcggtcgag atcgagatcg 90540
gatttatccg atcccaggcg ccgacggaca gccatatcct gagcccggcg gcgctggcgg 90600
ccatcgaaaa ctacgtgcga ttcagcgcgg atcgcctgtt gggccttatc cacatgaagc 90660
cactgttttc cgcccccaccc cccgacgcca gctttccgct gagcctcatg tccaccgaca 90720
aacacaccaa ttttttcgag tgtcgcagca cctcctacgc cggggcggtc gtcaacgatc 90780
tgtgagggtc gcggcgcgct tctacccgtg tttgcccata ataaacctct gaaccaaact 90840
ttgggtctca ttgtgattct tgtcagggac gcgggggtgg gagaggataa aaggcggcgc 90900
aaaaagcagt aaccaggtcc ggccagattc tgagggcata ggataccata attttattgg 90960
tgggtcgttt gttcggggac aagcgcgctc gtctgacgtt tgggctactc gtcccagaat 91020
ttggccagga cgtccttgta gaacgcgggt ggggggcct gggtccgcag ctgctccaga 91080
aacctgtcgg cgatatcagg ggccgtgata tgccgggtca cgatagatcg cgccaggttt 91140
tcgtcgcgga tgtcctggta gataggcagg cgtttcagaa gagtccacgg cccccgctcc 91200
ttggggccga taagcgatat gacgtactta atgtagcggt gttccaccag ctcggtgatg 91260
gtcatgggat cggggagcca gtccagggac tctggggcgt cgtggatgac gtggcgtcgc 91320
cggctggcca cataactgcg gtgctcttcc agcagctgcg cgttcgggac ctggacgagc 91380
tcgggcgggg tgagtatctc cgaggaggac gacctggggc cggggtggcc cccggtaacg 91440
tcccggggat ccagggggag gtcctcgtcg tcttcgtatc cgccggcgat ctgttgggtt 91500
agaatttcgg tccacgagac gcgcgtctcg gtgccgccgg tggccggcgg cagagggggc 91560
ctggtttccg tggagcgcga gctggtgtgt tcccggcgga tggcccgccg ggtctgagag 91620
cgactcgggg gggtccagtg acattcgcgc agcacatcct ccacggaggc gtaggtgtta 91680
ttgggatgga ggtcggtgtg gcagcggaca aagagggcca ggaactgggg gtagctcatc 91740
ttaaagtact tcagtatatc gcgacagttg atcgtgggaa tgtagcaggc gctaatatcc 91800
aacacaatat cgcagcccat caacaggagg tcagtgtccg tggtgtacac gtacgcgacc 91860
gtgttggtgt gatagaggtt ggcgcaggca tcgtccgcct ccagctgacc cgagttaatg 91920
taggcgtacc ccagggcccg gagaacgcga atacagaaca gatgcgccag acgcagggcc 91980
ggcttcgagg gcgcggcgga cggcagcgcg gctccggacc cggccgtccc ccgggtcccc 92040
gaggccagag aggtgccgcg tcggcgcatg ttggaaaagg cagagctggg tctggagtcg 92100
gtgatggggg aaggcggtgg agaggcgtcc acgtcactgg cctcctcgtc cgtccggcac 92160
tgggccgtcg tgcgggccag gatggccttg gctccaaaca caaccggctc catacaattg 92220
accccgcgat cggtaacgaa gatggggaaa agggactttt gggtaaacac ctttaataag 92280
cgacagaggc agtgtagcgt aatggcctcg cggtcgtaac tggggtatcg gcgctgatat 92340
ttgaccacca acgtgtacat gacgttccac aggtccacgg caatgggggt gaagtacccg 92400
gccggggccc caaggccccg gcgcttgacc agatggtgtg tgtgggcaaa cttcatcatc 92460
ccgaacaaac ccatgtcagg tcgattgtaa ctgcggatcg gcctaactaa ggcgtggttg 92520
gtgcgacggt ccgggacacc cgagcctgtc tctctgtgta tggtgaccca gacaacaaca 92580
ccgacacaag aggacaataa tccgttaggg gacgctcttt ataatttcga tggcccaact 92640
ccacgcggat tggtgcagca ccctgcatgc gccggtgcgg gccaaccttc cccccgctca 92700
ttgcctcttc caaaagggtg tggcctaacg agctgggggc gtatttaatc aggctagcgc 92760
ggcgggcctg ccgtagtttc tggctcggtg agcgacggtc cggttgcttg ggtcccctgg 92820
ctgccatcaa aaccccaccc tcgcagcggc atacgccccc tccgcgtccc gcacccgaga 92880
ccccggcccg gctgccctca ccaccgaagc ccacctcgtc actgtggggt gttcccagcc 92940
cgcgttggga tgacggattc ccctggcggt gtggccccca cctcccacgt ggaggacgcg 93000
tcggacgcgt ccctcgggca gccggaggag ggggcgccct gccaggtggt cctgcagggc 93060
gccgagctta atggaatcct acaggcgttt gccccgctgc gcacgagcct tctggactcg 93120
cttctggtta tgggagaccg gggcatcctt atccataaca cgatctttgg ggagcaggtg 93180
ttcctgcccc tggaacactc gcaattcagt cggtatcgct ggcgcggacc cacggcggcg 93240
ttcctgtctc tcgtggacca gaagcgctcc ctcctgagcg tgtttcgcgc caaccagtac 93300
ccggacctac gtcgggtgga gttggcgatc acgggccagg ccccgtttcg cacgctggtt 93360
cagcgcatat ggacgacgac gtccgacggc gaggccgttg agctagccag cgagacgctg 93420
atgaagcgcg aactgacgag ctttgtggtg ctggttcccc agggaacccc cgacgttcag 93480
ttgcgcctga cgaggccgca gctcaccaag gtccttaacg cgaccggggc cgatagtgcc 93540
acgcccacca cgttcgagct cggggttaac ggcaaatttt ccgtgttcac cacgagtacc 93600
tgcgtcacat ttgctgcccg cgaggagggc gtgtcgtcca gcaccagcac ccaggtccag 93660
atcctgtcca acgcgctcac caaggcgggc caggcggccg ccaacgccaa gacggtgtac 93720
ggggaaaata cccatcgtac cttctctgtg gtcgtcgacg attgcagcat gcgggcggtg 93780
ctccggcgac tgcaggtcgc cgggggcacc ctcaagttct tcctcacgac ccccgtcccc 93840
agtctgtgcg tcaccgccac cggtcccaac gcggtatcgg cggtatttct cctgaaaccc 93900
cagaagattt gcctggactg gctgggtcat agccaggggt ctccttccgc cgggagctcg 93960
gcctcccggg cctctgggag cgagccaaca gacagccagg actccgcgtc ggacgcggtc 94020
agccacggcg atccggaaga cctcgatggc gctgcccggg cgggagaggc gggggcctcg 94080
tacgcctgtc cgatgccgtc gtcgaccacg cgggtcactc ccacgaccaa gcgggggcgc 94140
tcggggggcg aggatgcgca cgcggacacg gccctaaaga aacctaagac ggggtcgccc 94200
accgcacccc cgcccgcaga tccagtcccc ctggacacgg aggacgactc cgatgcggcg 94260
gacgggacgg cggcccgtcc cgccgctcca gacgcccgaa gcggaagccg ttacgcgtgt 94320
tactttcgcg acctcccgac cggagaagca agccccggcg ccttctccgc cttccggggg 94380

-continued

```
ggcccccaaa ccccgtctgg ttttggattc ccctgacggg gcggggcctt agcggccgcc  94440
caaccctcgc aacatcccgg ggttaatgta aataaacttg gtattgccca acactctccc  94500
gcgtgtcgcg tgtggttcat gtgtgtgcct ggcgccccca ccctcgggtt cgtgtatttc  94560
ctttccctgt ccttataaaa gccgtatgtg gggcgctgac ggaaccaccc cgcgtgccat  94620
cacggccaag gcgcgggatg ctccgcaacg acagccaccg ggccgcgtcc ccggaggacg  94680
gccagggacg ggtcgacgac ggacggccac acctcgcgtg cgtgggggcc ctggcgcggg  94740
ggttcatgca tatctggctt caggccgcca cgctgggttt tgcgggatcg gtcgttatgt  94800
cgcgcgggcc gtacgcgaat gccgcgtctg ggcgttcgc cgtcgggtgc gccgtgctgg  94860
gctttatgcg cgcgcccct cccctcgcgc ggcccaccgc gcggatatac gcctggctca  94920
aactggcggc cggtggagcg gcccttgttc tgtggagtct cggggagccc ggcacgcagc  94980
cgggggccct ggccccgggc ccggccaccc agtgcctggc gctgggcgcc gcctatgcgg  95040
cgctcctggt gctcgccgat gacgtctatc cgctctttct cctcgccccg gggcccctgt  95100
tcgtcggcac cctggggatg gtcgtcggcg ggctgacgat cggaggcagc gcgcgctact  95160
ggtggatcgg tgggcccgcc gcggccgccc tggccgcggc ggtgttggcg ggcccggggg  95220
cgaccaccgc cagggactgc ttctccaggg cgtgccccga ccaccgccgc gtctgcgtca  95280
tcgtcgcagg cgagtctgtt tcccgccgcc ccccggagga cccagagcga cccggggacc  95340
cagggccacc gtcccccccg acaccccaac gatcccaggg gccgccggcc gatgaggtcg  95400
caccggccgg ggtagcgcgg cccgaaaacg tctgggtgcc cgtggtcacc tttctggggg  95460
ctggcgcgct cgccgtcaag acggtgcgag aacatgcccg gggaacgccg ggcccgggcc  95520
tgccgctgtg gccccaggtg tttctcggag gccatgtggc ggtggccctg acggagctgt  95580
gtcaggcgct tgcgccctgg gaccttacgg acccgctgct gtttgttcac gccggactgc  95640
aggtcatcaa cctcgggttg gtgtttcggt tttccgaggt tgtcgtgtat gcggcgctag  95700
ggggtgccgt gtggatttcg ttggcgcagg tgctggggct ccggcgtcgc ctgcacagga  95760
aggaccccgg ggacggggcc cggttggcgg cgacgcttcg gggcctcttc ttctccgtgt  95820
acgcgctggg gtttggggtg ggggcgctgc tgtgccctcc ggggtcaacg ggcgggcggt  95880
cgggcgattg atatattttt caataaaagg cattagtccc gaagaccgcc ggtgtgtgat  95940
gatttcgcca taacacccaa accccggatg gggcccgggt ataaattccg gaaggggaca  96000
cgggctacct tcactaccga gggcgcttgg tcgggaggcc gcatcgaacg cacaccccca  96060
tccggtggtc cgtgtggagg tcgtttttca gtgcccggtc tcgctttgcc gggaacgcta  96120
gccgatccct cgcgaggggg aggcgtcggg ccgcgagacc cccccgttac ctttttaata  96180
tctatatagt ttggtccccc tctatcccgc ccaccgctgg gcgctataaa gccgccaccc  96240
tctcttccct caggtcatcc ttggtcgatc ccgaacgaca cacggcgtgg agcaaaacgc  96300
ctccccctga gccgctttcc taccagcgca acggcatgcc tctgcgggca tcggaacacg  96360
cctaccggcc cctgggcccc gggacacccc ccatgcgggc tcggctcccc gccgcggcct  96420
gggttggcgt cgggaccatc atcgggggag ttgtgatcat tgccgcgttg gtcctcgtgc  96480
cctcgcgggc ctcgtgggca ctttccccat gcgacagcgg atggcacgag ttcaacctcg  96540
ggtgcatatc ctgggatccg acccccatgg agcacgagca ggcggtcggc ggctgtagcg  96600
ccccggcgac cctgatcccc cgcgcggctg ccaaacagct ggccgccgtc gcacgcgtcc  96660
agtcggcaag atcctcgggc tactggtggg tgagcggaga cggcattcgg gcctgcctgc  96720
ggctcgtcga cggcgtcggc ggtattgacc agttttgcga ggagcccgcc cttcgcatat  96780
```

gctactatcc ccgcagtccc gggggctttg ttcagtttgt aacttcgacc cgcaacgcgc 96840
tggggctgcc gtgaggcgcg tgtactgcgg tctgtctcgt ctcctcttct cccctccct 96900
ccccctccgc atcccaggat cacaccggcc aacgagggtt ggggggtccg gcacggaccc 96960
aaaataataa acacacaatc acgtgcgata aaaagaacac gcggtcccct gtggtgtttt 97020
tggttatttt tattaaatct cgtcgtcaaa caggggggaaa ggggcgtggt ctagcgacgg 97080
cagcacgggt ggaggcgttc accggctccg gcgtccttcg cgtttaagct tggtcaggag 97140
ggcgctcagg gcggcgacgt tggtcgggcc gtcgttggtc agggcgttgg ctcgatggcg 97200
ggcgaggacg ggcgaggggc tcaacggcgg gggcgggggc ccggtgcggc ccgggggga 97260
aaatagggcg gatccccccc agtcgtacag gggattttcc gcctcaatgt acggggaggc 97320
cggcgctgca ttcgccgtgt tcgcgcagac gttttcgtag acccgcatcc atggtatttc 97380
ctcgtagaca cgcccccgt cctcgctcac agtctcgtat attgactcgt cgtcctcgta 97440
gggggcgtgc cgttcgcggg ccgaggcggc gtgggtggct ttgcggcggg cgtcgtcgtc 97500
gtcgtcggcc gtcagatacg tggcttccat ctggtcgggt tctccctccg gggcgggtcc 97560
ccacccccgt ggccgatcga ggctccccag agacgcgcgc cggacgagga gggggcacgt 97620
cgccgccggc ggtcgcctgt cgggtcccgc gacgttacgg gccgggaggc gcgggggcac 97680
ctcccccatg tgcgtgtaat acgtggccgg ctgtgcggcc gcagcggggg gctcggcgac 97740
cgggtcgtcc gcatccggaa gcgggggcgc cgcgccgtcc gcgcggcgcc tccggaaccg 97800
ccgggtggcc gcgggggtcg agtgtaggcg aggtcggggg aggggcgggg gctcgttgtc 97860
gcgccgcgcc cgctgaatct tttcccgaca ggtcccaccc cccgcgcgat gccccccgg 97920
gccgcgggcc atgtcgtccg ggggaggccc cgcggaccac gtcgtccggc gagacgccac 97980
gagccgcagg atggactcgt agtggagcga cggcgccccg ctgcggagca gatccgcggc 98040
cagggcggcc ccgaaccaag ccttgatgct caactccatc cgggcccagc tgggggcggt 98100
catcgtgggg aacaggggggg cggtggtccg acagaaacgc tcctggctgt ccaccgcggc 98160
ccgcagatac tcgttgttca ggctgtcggt ggcccagacg ccgtacccgg tgagggtcgc 98220
gttgatgata tactgggcgt ggtgatggac gatcgacaga acctccaccg tggatacgac 98280
ggtatccacg gtcccgtacg taccgccgct ccgcttgccg gtctgccaca ggttggctag 98340
gcgcgtcagg tggcccagga cgtcgctgac cgccgccctg agcgccatgc actgcatgga 98400
gccggtcgtg ccgctgggac cccggtccag atggcgcgcg aacgtttccg cgggcgcctc 98460
cgggctgccg ccgagcggga ggaaccggcg attggaggga ctcagccggt ggcatacgtg 98520
cttgtctgtc gtccacagca tccaggacgc ccaccggtac agcacggaga cgtaggccag 98580
gagctcgttg agccgcagtg cggtgtcggt gctggggcgg cttgggtccg ccgggcgcat 98640
aaagaacatg tactgctgaa tccgatggag ggcgtcgcgc aggccggcca cggtggcggc 98700
gtacttggcc gccgcggccc cgctcttgaa cggggtgcgc gccagcagct ttggcgccag 98760
ggtgggccgc agcagcacgt gaaggctggg gtcgcagtcg cccacggggt cctcggggac 98820
gtccaggccg ctgggcacca ccgtctgcag gtacttccag tactgcgtga ggatggcgcg 98880
gctcaactgg ccgccggtga gctccacctc gcccagcgcc tgggtggcgg ccgaagcgta 98940
gtgccggatg tactcgtagt gcgggtcgct ggcgagcccg tccacgatca aactctcggg 99000
aaccgtgttg tgttgccgcg cggccaaccg gacgctgcga tcggtgcagg tcagaaacgc 99060
cggctgcgcg tcgtcggagc gctgccgcaa ggcgcccacg gccgcgctaa ggagcccctc 99120
cggggtgggg agcagacacc cgccgaagat gcgccgctcg ggaacgcccg cgttgtcgcc 99180
gcggatcagg ttggcaggcg tcaggcaccg cgccagccgc agggagctcg cgccgcgcgt 99240
ccggcgctgc atggtgacgc ccgttcggtc gggacccgcc ggtcggagtt atgccgcgtc 99300
cagggccatc ggggcgcttt ttatcgggag gagcttatgg gcgtggcggg cctcccagcc 99360
cggtcgcgcg cctccccgac acgtgcgccc gcagggcggc ggccccctcg tctcccatca 99420
gcagtttcct aaactgggac atgatgtcca ccacgcggac ccgcgggccc aacacggacc 99480
cgccgcttac gggggcgggg gggaagggct ccaggtcctt gagaagaaag gcggggtctg 99540
ccgtcccgga cacgggggcc cggggcgctg aggaggcggg gcgcagatcc acgtgctccg 99600
cggccgcgcg gacgtccgcc cagaacttgg cgggggtggt gcgcgcgtac aggggctggg 99660
tcgctcggag gacgcacgcg tagcgcaggg gggtgtacgt gcccacctcg ggggccgtga 99720
atcccccgtc aaacgcggcc agtgtcacgc acgccaccac ggtgtcggca aagcccagca 99780
gccgctgcag gacgagcccg gcggccagaa tggcgcgcgt ggccgccgcg tcgtcccggc 99840
gccggtgcgc gtccccgcac gcccgggcgt actttaaggt cacggtcgcc agggccgtgt 99900
gcagcgcgta caccgcagcg cccagcacgg cgttgagccc gctgttggcg agcagccggc 99960
gcgctgcggt gtcgcccagc gcctcgtgct cggcccccac gaccgcgggg cttcccaggg 100020
gcagggcgcg aaacagctcc tcccgcgcca cgtccgcaaa ggcggggtgg tgcacgtgcg 100080
ggtgcaggcg cgcccccacg accaccgaga gccactggac cgtctgctcc gccatcaccg 100140
ccagcacatc cagcacgcgc cccaggaagg cggcctcccg cgtcaaaacg caccggacgg 100200
cgtcgggatt gaagcgggcg agcagggccc cggtggccag gtacgtcatg cggccggcat 100260
agcgggcggc cacgcgacag tcgcggtcca gcagcgcgcg caccccgggc cagtacagca 100320
gggaccccag cgagctgcga aacaccgcgg cgtcggggcc ggattggggg gacactaacc 100380
cccccgcgct cagtaacggc acggccgcgg ccccgacggg acgcaacgcc gtgaggctcg 100440
cgaactgccg cctcagctcg gcagccctgt cgtccaggtc cgacccgcgc gcctctgcgt 100500
gaaggcgcgt cccgcacacc cacccgttga tggccagccg cacgacggca tccgccaaaa 100560
agctcatcgc ctgggcgggg ctggtttttg ttcgacgatc cgtcaggtca agaatcccat 100620
cgcccgtgat ataccaggcc aacgcctcgc cctgctgcag ggtttggcgg aaaaacaccg 100680
cggggttgtc gggggaggcg aagtgcatga cccccacgcg cgataacccg aacgcgctat 100740
ccggacacgg gtaaaacccg gccggatgcc ccagggctag ggcggagcgc acggactcgt 100800
cccacacggc aacctgaggg gccagtcgat ccaacgggaa tgccgcccgg agctccgggc 100860
ccggcacgcg tccctccaga acctccacct tgggcgggga acgggccccg ccgccgtcct 100920
ccggcccgac gtcttccggg tagtcgtcct cctcgtactg cagctcctct aggaacagcg 100980
gcgacggcgc cacccgcgaa ccgccgaccc gccccaaaat agcccgcgcg tcgacgggac 101040
ccaggtatcc cccctgccgg gcctgcggag gaccgcgggg aacctcatca tcatcgtcca 101100
ggcgaccgcg caccgactgg ctacgggccg catcgggccc ggggcgctgc cgggacgctc 101160
ggcgatggga tgtgggcggg gcttccgacg cgcgccgtcg tcgggctcgc gggccttccc 101220
gtcgacggcg cacgggcggc tcgtcgcccg ccatctcctc cagagcctct agctcgctgt 101280
cgtcatcccc gcggaacacc gcacgcaggt accccatgaa ccccacccca tcgcccgctg 101340
gctcgtccgc cacgggcgag gcgcgggggc gggtggatgc gcgcctccta cgccccgcgg 101400
gttcgcgagc cgacatggtg gcgatagacg cgggttatcg gatgtccgct accccccaaa 101460
aaagaaaaag accccacagc gcggatggag gccggggtag gtgccgccgg acccccctcgc 101520 gatgggaatg gacgggagcg acggggccgg cgcaaaaaac gcagtatctc ccgcgaaggc 101580
tacccgccgc cccagccccc ggccaaatgc ggaaacggtc ccgcgctctc gcctttatac 101640
gcgggccgcc ctgcgacaca atcacccgtc cgtggtttcg aatctacacg acaggcccgc 101700
agacgcggct aacacacacg ccggcaaccc agaccccagt gggttggttg cgcggtcccg 101760
tctcctggct agttcttttc cccaccacca aataatcaga cgacaaccgc aggtttttgt 101820
aatgtatgtg ctcgtgttta ttgtggatac gaaccgggga cgggagggga aaacccagac 101880
gggggatgcg ggtccggtcg cgccccctac ccaccgtact cgtcaattcc aagggcatcg 101940
gtaaacatct gctcaaactc gaagtcggcc atatccagag cgccgtaggg ggcggagtcg 102000
tggggggtaa atcccggacc cggggaatcc ccgtccccca acatgtccag atcgaaatcg 102060
tctagcgcgt cggcatgcgc catcgccacg tcctcgccgt ctaagtggag ctcgtccccc 102120
aggctgacat cggtcggggg ggccgtcgac agtctgcgcg tgtgtcccgc ggggagaaag 102180
gacaggcgcg gagccgccag ccccgcctct tcgggggcgt cgtcgtccgg gagatcgagc 102240
aggccctcga tggtagaccc gtaattgttt ttcgtacgcg cgcggctgta cgcgtgttcc 102300
cgcatgaccg cctcggaggg cgaggtcgtg aagctggaat acgagtccaa cttcgcccga 102360
atcaacacca taaatgcggg cctggttgcc atgcagggtg ggaggggtcg tcaacggcgc 102420
ccctggctcc tccgtagccg cgctgcgcac cagcgggagg ttaaggtgct cgcgaatgtg 102480
gtttagctcc cgcagccggc gggcctcgat tggcactccc cggacggtga gcgctccgtt 102540
gacgaacatg aagggctgga acagacccgc caactgacgc cagctctcca ggtcgcaaca 102600
gaggcagtca aacaggtcgg gccgcatcat ctgctcggcg tacgcggccc ataggatctc 102660
gcgggtcaaa aatagataca aatgcaaaaa cagaacacgc gccagacgag cggtctctcg 102720
gtagtacctg tccgcgatcg tggcgcgcag catttctccc aggtcgcgat cgcgtccgcg 102780
catgtgcgcc tggcggtgca gctgccggac gctggcgcgc aggtaccggt acagggccga 102840
gcagaagttg gccaacacgg ttcgatagct ctcctcccgc gcccgtagct cggcgtggaa 102900
gaaacgagag agcgcttcgt agtagagccc gaggccgtcg cgggtggccg gaagcgtcgg 102960
gaaggccacg tcgccgtggg cgcgaatgtc gatttgggcg cgttcgggga cgtacgcgtc 103020
cccccattcc accacatcgc tggcagcgt tgataggaat ttacactccc ggtacaggtc 103080
ggcgttggtc ggtaacgccg aaaacaaatc ctcgttccag gtatcgagca tggtacatag 103140
cgcggggccc gcgctaaagc ccaagtcgtc gaggagacgg ttaaagaggg cggcgggggg 103200
gacgggcatg ggcggggagg gcatgagctg ggcctggctc aggcgccccg ttgcgtacag 103260
cggaggggcc gccggggtgt ttttgggacc cccggccggg cggggggggtg gtggcgaagc 103320
gccgtccgcg tccatgtcgg caaacagctc gtcgaccaag aggtccattg ggtggggttg 103380
atacgggaaa gacgatatcg ggcttttgat gcgatcgtcc ccgcccgccc agagagtgtg 103440
ggacgcccga cggcgcggga agagaaaaac ccccaaacgc gttagaggac cggacggacc 103500
ttatgggggg aagtgggcag cgggaacccc gtccgttccc gaggaatgac agcccgtggt 103560
cgccaccccg catttaagca acccgcacgg gccgccccgt acctcgtgac ttccccccac 103620
attggctcct gtcacgtgaa ggcgaaccga gggcggctgt ccaacccacc ccccgccacc 103680
cagtcacggt ccccgtcgga ttgggaaaca aaggcacgca acgccaacac cgaatgaacc 103740
cctgttggtg ctttattgtc tgggtacgga agtttttcac tcgacgggcc gtctggggcg 103800
agaagcggag cgggctgggg ctcgaggtcg ctcggtgggg cgcgacgccg cagaacgccc 103860
tcgagtcgcc gtggccgcgt cgacgtcctg caccacgtct ggattcacca actcgttggc 103920
gcgctgaagc aggtttttgc cctcgcagac cgtcacgcgg atggtggtga tgccaaggag 103980
ttcgttgagg tcttcgtctg tgcgcggacg cgacatgtcc cagagctgga ccgccgccat 104040
ccgggcatgc atggccgcca ggcgcccgac cgcggcgcag aagacgcgct tgttaaagcc 104100
ggccacccgg ggggtccatg gcgcgtcggg gtttgggggg gcggtgctaa agtgcagctt 104160
tctggccagc ccctgcgcgg gtgtcttgga tcgggttggc gccgtcgacg cgggggcgtc 104220
tgggagtgcg gcggattctg gctgggccga tttcctgccg cgggtggtct ccgccgccgg 104280
ggccgcgggg gccttagtcg ccacccgctg ggttcggggg gcccgggggg cggtggtggg 104340
tgtgcgtccg gcccctccgg acccagcggg cggcggaggc gcccgcgcag gccccgggcc 104400
ggacaaaacc gccccggaaa cgggacgccg cgtccggggg acctccgggt gttcgtcgtc 104460
ttcggatgac gagcccccgt agagggcata atccgactcg tcgtactgga cgaaacggac 104520
ctcgcccctc gggcgcgcgc gtgtctgtag ggcgccacgg cgggaggtgg caggcggact 104580
atcgggactc gccatacatg aagacggggt gtagtacaga tcctcgtact catcgcgcgg 104640
aacctcccgc ggacccgact tcacggagcg gcgagaggtc atggttccac gaacacgcta 104700
gggtcggatg cgcggacaat taggcctggg ttcggacggc ggggggtggt gcaggtgtgg 104760
agaggtcgag cgataggggc ggcccgggag agaagagagg gtccgcaaaa cccactgggg 104820
atgcgtgagt ggccctctgt gggcggtggg ggagagtctt ataggaagtg catataacca 104880
caacccatgg gtctaaccaa tccccagggg ccaagaaaca gacacgcccc aaacggtctc 104940
ggtttccgcg aagaagggga agtcctggga caccctccac ccccacccct caccccacac 105000
agggcgggtt caggcgtgcc cggcagccag tagcctctgg cagatctgac agacgtgtgc 105060
gataatacac acgcccatcg aggccatgcc tacataaaag ggcaccaggg cccccggggc 105120
agacatttgg ccagcgtttt gggtctcgca ccgcgcgccc ccgatcccat cgcgcccgcc 105180
ctcctcgccg ggcggctccc cgtgcgggcc cgcgtctccc gccgctaagg cgacgagcaa 105240
gacaaacaac aggcccgccc gacagaccct tctggggggg cccatcgtcc ctaacaggaa 105300
gatgagtcag tggggatccg gggcgatcct tgtccagccg gacagcttgg gtcgggggta 105360
cgatggcgac tggcacacgg ccgtcgctac tcgcgggggc ggagtcgtgc aactgaacct 105420
ggtcaacagg cgcgcggtgg cttttatgcc gaaggtcagc ggggactccg gatgggccgt 105480
cgggcgcgtc tctctggacc tgcgaatggc tatgccggct gacttttgtg cgattattca 105540
cgcccccgcg ctatccagcc cagggcacca cgtaatactg ggtcttatcg actcggggta 105600
ccgcggaacc gttatggccg tggtcgtagc gcctaaaagg acgcgggaat ttgcccccgg 105660
gaccctgcgg gtcgacgtga cgttcctgga catcctggcg acccccccgg ccctcaccaa 105720
gccgatttcc ctgcggcagt tcccgcaact ggcgcccccc cctccaaccg gggccgggat 105780
acgcgcagat ccttggttgg agggggcgct cggggaccca agcgtgactc cggccctacc 105840
ggcgcgacgc cgagggcggt ccctcgtcta tgccggcgag ctgacgccgg ttcagacgga 105900
acacggggac ggcgtacgag aagccatcgc cttccttcca aaacgcgagg aggatgccgg 105960
tttcgacatt gtcgtccgtc gcccggtcac cgtcccggca aacggcacca cggtcgtgca 106020
gccatccctc cgcatgctcc acgcggacgc cgggcccgcg gcctgttatg tgttggggcg 106080
gtcgtcgctc aacgcccgcg gcctcctggt cgttcctacg cgctggctcc ccgggcacgt 106140
atgtgcgttt gttgtttaca accttacggg ggttcctgtg accctcgagg ccggcgccaa 106200
ggtcgcccag ctcctggttg cgggggcgga cgctcttcct tggatccccc cggacaactt 106260
tcacgggacc aaagcgcttc gaaactaccc caggggtgtt ccggactcaa ccgccgaacc 106320
caggaacccg ccgctcttgg tgtttacgaa cgagtttgac gcggaggccc ccccgagcga 106380
gcgcgggacc gggggttttg gctctaccgg tatttagccc atagcttggg gttcgttccg 106440
ggcaataaaa aacgtttgta tctcatcttt cctgtgtgta gttgtttctg ttggaggcct 106500
gtgggtctat cacacccgcc cctccatccc acaaacacag aacacacggg ttggatgaaa 106560
acacgcattt attgacccaa aacacacgga gctgctcgag atgggccagg gcgaggtgcg 106620
gttggggagg ctgtaggtct gggaacggac acgcggggac acgattccgg tttggggtcc 106680
gggagggcgt cgccgtttcg ggcggcaggc gccagcgtaa cctccggggg cggcgtgtgg 106740
gggtgcccca aggagggcgc ctcggtcacc ccaagccccc ccaagcgggt tcccccggca 106800
accccgaagg cggagaggcc aagggcccgt tcggcgatgg ccacatcctc catgaccacg 106860
tcgctctcgg ccatgctccg aatagcctgg gagacgagca catccgcgga cttgtcagcc 106920
gcccccacgg acatgtacat ctgcaggatg gtggccatac acgtgtccgc caggcgccgc 106980
atcttgtcct gatgggccgc cacggccccg tcgatcgtgg gggcctcgag cccggggtgg 107040
tggcgcgcca gtcgttctag gttcaccatg caggcgtggt acgtgcgggc caaggcgcgg 107100
gccttcacga ggcgtcgggt gtcgtccagg gaccccaggg cgtcatcgag cgtgatgggg 107160
gcgggaagta gcgcgttaac gaccaccagg gcctcctgca gccgcggctc cgcctccgag 107220
ggcggaacgg ccgcgcggat catctcatat tgttcctcgg ggcgcgctcc ccagccacat 107280
atagccccga gaagagaagc catcgcgggc gggtactggc ccttgggcgc gcggacgcaa 107340
tggggcagga agacgggaac cgcggggaga ggcgggcggc cgggactccc gtggaggtga 107400
ccgcgcttta tgctaccgac gggtgcgtta ttacctcttc gatcgccctc ctcacaaact 107460
ctctactggg ggccgagccg gtttatatat tcagctacga cgcatacacg cacgatggcc 107520
gtgccgacgg gcccacggag caagacaggt tcgaagagag tcgggcgctc taccaagcgt 107580
cgggcgggct aaatggcgac tccttccgag taaccttttg tttattgggg acggaagtgg 107640
gtgggaccca ccaggcccgc gggcgaaccc gacccatgtt cgtctgtcgc ttcgagcgag 107700
cggacgacgt cgccgcgcta caggacgccc tggcgcacgg gaccccgcta caaccggacc 107760
acatcgccgc caccctggac gcggaggcca cgttcgcgct gcatgcgaac atgatcctgg 107820
ctctcaccgt ggccatcaac aacgccagcc cccgcaccgg acgcgacgcc gccgcggcgc 107880
agtatgatca gggcgcgtcc ctacgctcgc tcgtggggcg cacgtccctg ggacaacgcg 107940
gccttaccac gctatacgtc caccacgagg cgcgcgtgct ggccgcgtac cgcagggcgt 108000
attatggaag cgcgcagagt cccttctggt ttcttagcaa attcgggccg gacgaaaaaa 108060
gcctggtgct caccactcgg tactacctgc ttcaggccca gcgtctgggg ggcgcggggg 108120
ccacgtacga cctgcaggcc atcaaggaca tctgcgccac ctacgcgatt ccccacgccc 108180
cccgccccga caccgtcagc gccgcgtccc tgacctcgtt tgccgccatc acgcggttct 108240
gttgcacgag ccagtacgcc cgcggggccg cggcggccgg gtttccgctt tacgtggagc 108300
gccgtattgc ggccgacgtc cgcgagacca gtgcgctgga gaagttcata acccacgatc 108360
gcagttgcct gcgcgtgtcc gaccgtgaat tcattacgta catttacctg gcccattttg 108420
agtgtttcag ccccccgcgc ctagccacgc atcttcgggc cgtgacgacc cacgacccca 108480
accccgcggc caacacggag cagccctcgc ccctgggcag ggaggccgtg gaacaatttt 108540
tttgccacgt gcgcgcccaa ctgaatatcg gggagtacgt caaacacaac gtgacccccc 108600
gggagaccgt cctggatggc gatacggcca aggcctacct gcgcgctcgc acgtacgcgc 108660
ccggggccct gacgcccgcc cccgcgtatt gcggggccgt ggactccgcc accaaaatga 108720
tggggcgttt ggcggacgcc gaaaagctcc tggtccccg cgggtggccc gcgtttgcgc 108780
ccgccagtcc cggggaggat acggcgggcg gcacgccgcc cccacagacc tgcggaatcg 108840
tcaagcgcct cctgagactg gccgccacgg aacaacagga caccacgccc ccggcgatcg 108900
cggcgcttat ccgtaatgcg gcggtgcaga ctcccctgcc cgtctaccgg atatccatgg 108960
tccccacggg acaggcattt gccgcgctgg cctgggacga ctgggcccgc ataacgcggg 109020
acgctcgcct ggccgaagcg gtcgtgtccg ccgaagcggc ggcgcacccc gaccacggcg 109080
cgctgggcag gcggctcacg gatcgcatcc gcgcccaggg ccccgtgatg ccccctggcg 109140
gcctggatgc cggggggcag atgtacgtga atcgcaacga gatattcaac ggcgcgctgg 109200
caatcacaaa catcatcctg gatctcgaca tcgccctgaa ggagcccgtc ccctttcgcc 109260
ggctccacga ggccctgggc cactttaggc gcggggctct ggctgcggtt cagctcctgt 109320
ttcccgcggc ccgcgtggac cccgacgcat atccctgtta tttttcaaa agcgcatgtc 109380
ggcccggccc ggcgtccgtg ggttccggca gcggactcgg cgacgacggg gactggtttc 109440
cctgctacga cgacgccggt gatgaggagt gggcggagga cccgggcgcc atggacacat 109500
cccacgatcc cccggacgac gaggttgcct actttgacct gtgccacgaa gtcggcccca 109560
cggcggaacc tcgcgaaacg gattcgcccg tgtgttcctg caccgacaag atcggactgc 109620
gggtgtgcat gcccgtcccc gccccgtacg tcgtccacgg ttctctaacg atgcgggggg 109680
tggcacgggt catccagcag gcggtgctgt tggaccgaga ttttgtggag gccatcggga 109740
gctacgtaaa aaacttcctg ttgatcgata cgggggtgta cgcccacggc cacagcctgc 109800
gcttgccgta ttttgccaaa atcgcccccg acgggcctgc gtgcggaagg ctgctgccag 109860
tgtttgtgat cccccccgcc tgcaaagacg ttccggcgtt tgtcgccgcg cacgccgacc 109920
cgcggcgctt ccattttcac gccccgccca cctatctcgc ttcccccgg gagatccgtg 109980
tcctgcacag cctgggtggg gactatgtga gcttctttga aaggaaggcg tcccgcaacg 110040
cgctggaaca ctttgggcga cgcgagaccc tgacggaggt cctgggtcgg tacaacgtac 110100
agccggatgc gggggggacc gtcgaggggt tcgcatcgga actgctgggg cggatagtcg 110160
cgtgcatcga aacccacttt cccgaacacg ccggcgaata tcaggccgta tccgtccggc 110220
gggccgtcag taaggacgac tgggtcctcc tacagctagt ccccgttcgc ggtaccctgc 110280
agcaaagcct gtcgtgtctg cgctttaagc acggccgggc gagtcgcgcc acggcgcgga 110340
cattcgtcgc gctgagcgtc ggggccaaca accgcctgtg cgtgtccttg tgtcagcagt 110400
gctttgccgc caaatgcgac agcaaccgcc tgcacacgct gtttaccatt gacgccggta 110460
cgccatgctc gccgtccgtt ccctgcagca cctctcaacc gtcgtcttga taacggcgta 110520
cggcctcgtg ctcgtgtggt acaccgtctt cggtcacccc cccaacgggg gctggcgcaa 110580
ccacgcccat atctgctacg ccaatcttat cgcgggtagg gtcgtgccct tccaggtccc 110640
acccgacgcc atgaatcgtc ggatcatgaa cgtccacgag gcagttaact gtctggagac 110700
cctatggtac acacgggtgc gtctggtggt cgtagggtgg ttcctgtatc tggcgttcgt 110760
cgccctccac caacgccgat gtatgtttgg tgtcgtgagt cccgcccaca agatggtggc 110820
cccggccacc tacctcttga actacgcagg ccgcatcgta tcgagcgtgt tcctgcagta 110880
cccctacacg aaaattaccc gcctgctctg cgagctgtcg gtccagcggc aaaacctggt 110940
tcagttgttt gagacggacc cggtcacctt cttgtaccac cgccccgcca tcggggtcat 111000
cgtaggctgc gagttgatgc tacgctttgt ggccgtgggt ctcatcgtcg gcaccgcttt 111060
catatcccgg ggggcatgtg caatcacata cccccctgttt ctgaccatca ccacctggtg 111120
ttttgtctcc accatcggcc tgacagagct gtattgtatt ctgcggcggg gcccggcccc 111180
caagaacgca gacaaggccg ccgccccggg gcgatccaag gggctgtcgg gcgtctgcgg 111240
gcgctgctgt tccatcatcc tctcgggcat cgcagtgcga ttgtgttata tcgccgtggt 111300
ggccggggtg gtgctcgtgg cgcttcacta cgagcaggag atccagaggc gcctgtttga 111360
tgtatgacgt cacatccagg ccggcggaaa ccggaacggc atatgcaaat tggaaactgt 111420
cctgtcttgg ggcccaccca cccgacgcgt catatgcaaa tgaaaatcgg tcccccgagg 111480
ccacgtgtag cctggatccc aacgaccccg cccatgggtc ccaattggcc gtcccgttac 111540
caagaccaac ccagccagca tatccacccc cgcccgggtc cccgcggaag cggaacggtg 111600
tatgtgatat gctaattaaa tacatgccac gtacttatgg tgtctgattg gtccttgtct 111660
gtgccggagg tggggcgggg gccccgcccg gggggcggaa cgaggagggg tttgggagag 111720
ccggccccgg caccacgggt ataaggacat ccaccacccg gccggtggtg gtgtgcagcc 111780
gtgttccaac cacggtcacg cttcggtgcc tctccccgat tcgggcccgg tcgctcgcta 111840
ccggtgcgcc accaccagag gccatatccg acaccccagc cccgacggca gccgacagcc 111900
cggtcatggc gactgacatt gatatgctaa ttgacctcgg cctggacctc tccgacagcg 111960
atctggacga ggacccaccc gagccggcgg agagccgccg cgacgacctg gaatcggaca 112020
gcagcgggga gtgttcctcg tcggacgagg acatggaaga cccccacgga gaggacggac 112080
cggagccgat actcgacgcc gctcgcccgg cggtccgccc gtctcgtcca gaagaccccg 112140
gcgtacccag cacccagacg cctcgtccga cggagcggca gggccccaac gatcctcaac 112200
cagcgcccca cagtgtgtgg tcgcgcctcg gggcccggcg accgtcttgc tcccccgagc 112260
agcacggggg caaggtggcc cgcctccaac ccccaccgac caaagcccag cctgcccgcg 112320
gcggacgccg cgggcgtcgc aggggtcggg gtcgcggtgg tcccggggcc gccgatggtt 112380
tgtcggaccc ccgccggcgt gcccccagaa ccaatcgcaa cccgggggga ccccgccccg 112440
gggcggggtg gacggacggc cccggcgccc cccatggcga ggcgtggcgc ggaagtgagc 112500
agcccgaccc acccggaggc ccgcggacac ggggcgtgcg ccaagcaccc cccccgctaa 112560
tgacgctggc gattgccccc ccgcccgcgg acccccgcgc cccggccccg gagcgaaagg 112620
cgcccgccgc cgacaccatc gacgccacca cgcggttggt cctgcgctcc atctccgagc 112680
gcgcggcggt cgaccgcatc agcgagagct ttggccgcag cgcacaggtc atgcacgacc 112740 cctttgggggg gcagccgttt cccgccgcga atagcccctg ggccccggtg ttggcgggcc 112800
aaggagggcc ctttgacgcc gagaccagac gggtctcctg ggaaaccttg gtcgcccacg 112860
gcccgagcct ctatcgcact tttgccggca atcctcgggc cgcatcgacc gccaaggcca 112920
tgcgcgactg cgtgctgcgc caagaaaatt tcatcgaggc gctggcctcc gccgacgaga 112980
cgctggcgtg gtgcaagatg tgcatccacc acaacctgcc gctgcgcccc caggacccca 113040
ttatcgggac ggccgcggct gtgctggata acctcgccac gcgcctgcgg ccctttctcc 113100
agtgctacct gaaggcgcga ggcctgtgcg gcctggacga actgtgttcg cggcggcgtc 113160
tggcggacat taaggacatt gcatccttcg tgtttgtcat tctggccagg ctcgccaacc 113220
gcgtcgagcg tggcgtcgcg gagatcgact acgcgaccct tggtgtcggg gtcggagaga 113280
agatgcattt ctacctcccc ggggcctgca tggcgggcct gatcgaaatc ctagacacac 113340
accgccagga gtgttcgagt cgtgtctgcg agttgacggc cagtcacatc gtcgcccccc 113400
cgtacgtgca cggcaaatat ttttattgca actccctgtt ttaggtacaa taaaaacaaa 113460
acatttcaaa caaatcgccc cacgtgttgt ccttctttgc tcatggccgg cggggcgtgg 113520
gtcacggcag atggcggggg tgggcccggc gtacggcctg ggtgggcgga gggaactaac 113580
ccaacgtata aatccgtccc cgctccaagg ccggtgtcat agtgccctta ggagcttccc 113640
gcccgggcgc atcccccctt ttgcactatg acagcgaccc ccctcaccaa cctgttctta 113700
cgggccccgg acataaccca cgtggccccc ccttactgcc tcaacgccac ctggcaggcc 113760
gaaacggcca tacacaccag caaaacggac tccgcttgcg tggccgtgcg gagttacctg 113820
gtccgcgcct cctgtgagac cagcggcaca atccactgct tttctttgc ggtatacaag 113880
gacacccacc acacccctcc gctgattacc gagctccgca actttgcgga cctggttaac 113940
cacccgccgg tcctacgcga actggaggat aagcgcgggg tgcggctgcg gtgtgcgcgg 114000
ccgtttagcg tcgggacgat taaggacgtc tctgggtccg gcgcgtcctc ggcgggagag 114060
tacacgataa acgggatcgt gtaccactgc cactgtcggt atccgttctc aaaaacatgc 114120
tggatggggg cctccgcggc cctacagcac ctgcgctcca tcagctccag cggcatggcc 114180
gcccgcgcgg cagagcatcg acgcgtcaag attaaaatta aggcgtgatc tccaaccccc 114240
ccatgaatgt gtgtaacccc ccaaaaaaat aaacagccgt aacccaatca aaccaggcgt 114300
ggtgtgagtt tgtggaccca aagccctcag agacaacgcg acaggccagt atggaccgtg 114360
atacttttat ttattaactc acaggggcgc ttaccgccac aggaatacca gaataatgac 114420
caccactatc gcgaccaccc caaatacagc atggcgcccc accacgccac aacagccctg 114480
tcgccggtat ggggcatgat cagacgagcc gcgagccgcg cgttgggccc tgtacagctc 114540
gcgcgaattg accctaggag gccgccacgc gcccgagttt tgcgttcgtc gctggtcgtc 114600
gggcgccaaa gccccggacg gctgttcggt cgaacgaacg gccacgacag tggcataggt 114660
tggggggtgg tccgacatag cctcggtgta cgtcgggagg cccgacaaga ggtcccttga 114720
gatgtcgggt ggggccacaa gcctggtttc cggaagaaac agggggggttg ccaataaccc 114780
gccagggcca aaactccggc gctgcgcacg tcgttcggcg cggcgccggg cgcgccgagc 114840
ggctcgctgg gcggcttggc gtgagcggcc ccgctccgac gcctcgccct ctccggagga 114900
ggttggcgga attggcacgg acgacagggg cccagcagag tacggtggag gtgggtccgt 114960
gggggtgtcc agatcaataa cgacaaacgg cccctcgttc ctaccagaca agctatcgta 115020
ggggggcggg ggatcagcaa acgcgttccc cgcgctccat agacccgcgt cgggttgcgc 115080
cgcctccgaa gccatggatg cgccccaaag ccacgactcc cgcgcgctag gtccttgggg 115140
taagggaaaa ggccctactc cccatccaag ccagccaagt taacgggcta cgccttcggg 115200
gatgggactg gcaccccggc ggattttgtt gggctggtac gcgttgccca accgagggcc 115260
gcgtccacgg gacgcgcctt ttataacccc gggggtcatt cccaacgatc acatgcaatc 115320
taactggctc ccctctcccc ccctctcccc tctccccccc tctcccctct cccccccctct 115380
cccctctccc cccctctccc ctctcccccc ctctcccctc tcccccccctc tcccctctcc 115440
ccccctctcc cctctccccc cctctcccct ctcccccccct ctcccctctc ccccccctctc 115500
ccctctcccc ccctgctctt tccccgtgac acccgacgct ggggggcgtg gctgccggga 115560
ggggccgcgg atgggcgggg cctactcggt ctcccgcccc cgcccccgaa ccgccccgcc 115620
ggccttgccc ccctttgatc ccctgctacc cccaacccgt gctcgtggtg cgggttgggt 115680
gggggggggg agtgtgggcg ggggtgtgcg ggaggtgtcg gtggtggtgg tggtggtagg 115740
aatggtggtg aggggggggg gcgctggttg gtcaaaaaag ggagggacgg gggccggcag 115800
accgacggcg acaacgctcc ccggcggccg ggtcgcggct cttacgagcg gcccggcccg 115860
cgctcccacc ccccgggccg tgtccttgct ttccccccgt ctcccccccc ctccttctcc 115920
tcctcctcct cctcgttttt ccaaaccccg cccacccggc ccggcccggc ccggccaccg 115980
ccgcccaccc acccacctcg ggagacccag ccccggtccc ccgttccccg ggggccgtta 116040
tctccagcgc cccgtccggc gcgccgcccc ccgccgctaa accccatccc gcccccggga 116100
ccccacatat aagcccccag ccacacgcaa gaacagacac gcagaacggc tgtgtttatt 116160
taaataaacc gatgtcggaa taaacaaaca caaacacccg cgacgggggg acggagggag 116220
gggggtgacg ggggacggga acagccacaa aaaacaccca caaaaaaaaa cagccacccc 116280
cgacaccccc ccccaccccc agtctcttcg ccttttcccc cccaccccac gcccccactg 116340
agcccggtcg atcgacgagc acccccgccc ccgcccctgc cccggcgacc cccggcccgc 116400
acgatcccga caacaataac aaccccaacg gaaagcggcg gggtgtgggg gggggcgagg 116460
aacaaccgag gggaacgggg gatggaagga cgggaagtgg aagtcctgat acccatccta 116520
caccccccctg ccttccaccc tccggccccc cgcgagtcca cccgccggcc ggctaccgag 116580
accgaacacg gcggccgccg cagccgccgc agccgccgcc gacaccgcag agccggcgcg 116640
cgcacacaca agcggcagag gcagaaaggc ccagagtcat tgtttatgtg gccgcgggcc 116700
agcagacggc ccgcgacacc cccccccccg cccgtgtggg tatccggccc cccgccccgc 116760
gccggtccat taagggcgcg cgtgcccgcg agatatcaat ccgttaagtg ctctgcagac 116820
aggggcaccg cgcccggaaa tccattaggc cgcagacgag gaaaataaaa ttacatcacc 116880
tacccacgtg gtgctgtggc ctgtttttgc tgcgtcatct gagcctttat aaaagcgggg 116940
gcgcggccgt gccgatcgcg ggtggtgcga aagactttcc gggcgcgtcc gggtgccgcg 117000
gctctccggg ccccccctgca gccggggcgg ccaaggggcg tcggcgacat cctcccccta 117060
agcgccggcc ggccgctggt ctgtttttttg ttttccccgt ttcgggggtg ggggggggttg 117120
cggtttctgt ttctttaacc cgtctggggt gtttttcgtt ccgtcgccgg aatgtttcgt 117180
tcgtctgtcc cctcacgggg cgaaggccgc gtacggcccg ggacgagggg gcccccgacc 117240
gcggcggtcc gggccccgtc cgggcccgct cgccggcacg cgacgcgaaa aaggcccccc 117300
ggaggctttt ccgggttccc ggcccggggc ctgagataaa caatcggggt taccgccaac 117360
ggccggcccc cgtggcggcc cggcccgggg ccccggcgga cccaaggggc cccggcccgg 117420
ggccccacaa cggcccggcg catgcgctgt ggtttttttt tctcggtgtt ttgtcgggct 117480
ccgtcgcctt tcctgttctc gcttctcccc ccccccccctt cttcaccccc agtaccctcc 117540
tccctccctt cctccccccgt tatcccactc gtcaagggcg ccccggtgtg gttcaacaaa 117600
gacgccgcgt ttccaggtag gttagacacc tgcttctccc caatagaggg gggggaccca 117660
aacgacaggg ggcgccccag aggctaaggt cggccacgcc actcgcgggt gggctcgtgt 117720
tacagcacac cagcccgttc ttttcccccc ctcccaccct tagtcagact ctgttactta 117780
cccgtccgac caccaactgc ccccttatct aagggccggc tggaagaccg ccagggggtc 117840
ggccggtgtc gctgtaaccc cccacgccaa tgacccacgt actccaagaa ggcatgtgtc 117900
ccaccccgcc tgtgtttttg tgcctggctc tctatgcttg ggtcttactg ccgggggggg 117960
gggagtgcgg gggagggggg gtgtggaagg aaatgcacgg cgcgtgtgta cccccccctaa 118020
agttgttcct aaagcgagga tatggaggag tggcgggtgc cgggggaccg gggtgatctc 118080

```
tggcacgcgg gggtgggaag ggtcggggga ggggggatgg ggtaccggcc cacctggccg 118140
acgcgggtgc gcgtgcctct gcacaccaac cccacgtccc ccggcggtct ctaagaagca 118200
ccgccccccc tccttcatac caccgagcat gcctgggtgt gggttggtaa ccaacacgcc 118260
catcccctcg tctcctgtga ttctctggct gcaccgcatt cttgttttct aactatgttc 118320
ctgtttctgt ctcccccccc accccctccgc cccacccccc aacacccacg tctgtggtgt 118380
ggccgacccc cttttgggcg ccccgtcccg ccccgccacc cctcccgtcc tttgttgccc 118440
tatagtgtag ttaacccccc cccgcccttt gtggcggcca gaggccaggt cagtccgggc 118500
gggcaggcgc tcgcggaaac ttaacaccca cacccaaccc actgtggttc tggctccatg 118560
ccagtggcag gatgctttcg gggatcggtg gtcaggcagc ccgggccgcg gctctgtggt 118620
taacaccaga gcctgcccaa catggcaccc ccactcccac gcacccccac tcccacgcac 118680
ccccactccc acgcaccccc actcccacgc acccccactc ccacgcaccc ccactcccac 118740
gcacccccac tcccacgcac ccccactccc acgcaccccc actcccacgc acccccgaga 118800
tccatccaac acagacaggg aaaagataca aaagtaaacc tttatttccc aatagacagc 118860
aaaaatcccc tgagtttttt attagggcca acactaaaga cccgctggtg tgtggtgccc 118920
gtgtctttca cttttcccct ccccgacacg gattggctgg tgtagtgggc gcggccagag 118980
accacccagc gcccgacccc cccctcccca caaacacggg gggcgtccct tattgttttc 119040
cctcgtcccg ggtcgacgcc ccctgctccc cggaccacgg gtgccgagac cgcaggctgc 119100
ggaagtccag ggcgcccact agggtgccct ggtcgaacag catgttcccc acgggggtca 119160
tccagaggct gttccactcc gacgcggggg ccgtcgggta ctcgggggc atcacgtggt 119220
tacccgcggt ctcggggagc agggtgcggc ggctccagcc ggggaccgcg gcccgcagcc 119280
gggtcgccat gtttcccgtc tggtccacca ggaccacgta cgccccgatg ttccccgtct 119340
ccatgtccag gatgggcagg cagtcccccg tgatcgtctt gttcacgtaa ggcgacaggg 119400
cgaccacgct agagaccccc gagatgggca ggtagcgcgt gaggccgccc gcgggggcgg 119460
ccccggaagt ctccgcgtgg cgcgtcttcc gggcacactt cctcggcccc cgcggcccag 119520
aagcagcgcg ggggccgagg gaggtttcct cttgtctccc tcccagggca ccgacggccc 119580
cgcccgagga ggcggaagcg gaggaggacg cggccccggc ggcggaagag gcggcccccg 119640
cgggagtcgg ggccgaggag gaagaggcag aggaggaaga ggcggaggcc gccgaggacg 119700
tcagggggt cccgggccca ccctggccgc gcccccccgg ccctgagtcg gagggggggt 119760
gcgtcgccgc cctcttggcc cctgccggcg cgaggggggg acgcgtggac tgggggggagg 119820
ggttttcctg gcccgacccg cgcctcttcc tcggacgcac cgccgcctcc tgctcgacag 119880
aggcggcgga ggggagcggg ggggcgccgg agggggcggc gccgcgggag ggcccgtgtc 119940
caccctccac gcccggcccc cccgagccgc gcgccaccgt cgcacgcgcc cggcacagac 120000
tctgttcttg gttcgcggcc tgagccaggg acgagtgcga ctggggcaca cggcgcgcgt 120060
ccgcgggggc cggggcgcgg gggccgggcc ccggaggcgg cgctcgcacg cacggggcca 120120
cggccgcgcg ggggcgcgcg ggtcccgacg cggccgagga cgcggtgggc ccggggcggg 120180
gggcggagcc tggcatgggc gccgcggggg gcctgtgggg agaggccggg ggggagtcgc 120240
tgatcactat ggggtctctg ttgtttgcaa ggggggcggg tctgttgaca agggggcccg 120300
tccggcccct cggccgcccc gcctccgctt caacaacccc aaccccaacc ccaacccccc 120360
cggaggggcc agacgccccc cgcggcgccg cggctcgcga ctggcgggag ccgccgccgc 120420
cgccgctgct gttggtggtg gtgttggtgt tactgctgcc gtgtggcccg atgggcgccg 120480
```

-continued agggggggcgc tgtccgagcc gcggccggct ggggggctgc gtgagacgcc ccgcccgtca 120540
cggggggcgc ggcggcgcct ctgcgtgggg gggcgcgggg cgtccggcgg ggggcgggcg 120600
gtacgtagtc tgctgcaaga gacaacgggg ggcgcgatca ggttacgccc cctcccaggc 120660
cctccctttc cgcgcccgcc ctttcctcgc ccccccgccc gcctattcct ccctcccccc 120720
tcctcctcct cctcccccag ggtcctcgcc gcccccccgc ctcaccgtcg tccaggtcgt 120780
cgtcatcctc gtccgtggtg ggctcagggt gggtgggcga cagggccctc accgtgtgcc 120840
cccccagggt caggtaccgc ggggcgaacc gctgattgcc cgtccagata aagtccacgg 120900
ccgtgcccgc cctgacggcc tcctcggcct ccatgcgggt ctgggggtcg ttcacgatcg 120960
ggatggtgct gaacgacccg ctgggcgtca cgcccactat caggtacacc agcttggcgt 121020
tgcacagcgg gcaggtgttg cgcaattgca tccaggtttt catgcacggg atgcagaagc 121080
ggtgcatgca cgggaaggtg tcgcagcgca ggtggggcgc gatctcatcc gtgcacacgg 121140
cgcacacgtc gccctcgtcg ctccccccgt cctctcgagg gggggcgccc ccgcaactgc 121200
cggggtcttc ctcgcggggg gggctccccc ccgagaccgc ccccccatcc acgccctgcg 121260
gccccagcag ccccgtctcg aacagttccg tgtccgtgct gtccgcctcg gaggcggagt 121320
cgtcgtcatg gtggtcggcg tccccccgcc cccccacttc ggtctccgcc tcagagtcgc 121380
tgctgtccgg caggtctcgg tcgcagggaa acacccagac atccggggcg ggctaagggg 121440
aaaaaaaggg gggcgggtaa gaatgggggg atttcccgcg tcaatcagcg cccacgagtt 121500
ccccctctcc ccccccccgc ctcacaaagt cctgcccccc tgctggcctc ggaagagggg 121560
ggagaaaggg gtctgcaacc aaaggtggtc tgggtccgtc ctttggatcc cgacccctct 121620
tcttccctct tctcccgccc tccagacgca ccggagtcgg gggtcccacg gcgtccccca 121680
aatatggcgg gcggctcctc cccacccccc tagatgcgtg tgagtaaggg ggccctgcgt 121740
atgagtcagt ggggaccacg ccccctaaca cggcgacccc ggtccctgtg tgtttgttgt 121800
gggggcgtgt ctctgtgtat gagtcagggg gtcccacggc gaccccgggc cctgcgtctg 121860
agtcaaaggg gccatgtgta tgtgttgggg ggtctgtata tataaagtca gggggtcaca 121920
tggcgacccc caacagggcg accccggtcc ctgtatatat agggtcaggg ggttccgcgc 121980
cccctaacat ggcgcccccg gtccctgtat atatagtgtc acggggttcc acgcccccta 122040
acatggcgcc cggctcccgt gtatgagtgg gggtccccca acatggcggc cggttccagt 122100
gtaagggtcg gggtccccc aacatggcgc cccccaatat ggcgcccccc aatatggcgc 122160
cccagacatg gcgcccggcc cctcacctcg cgctgggggc ggccctcagg ccggcgggta 122220
ctcgctccgg ggcggggctc catgggggtc gtatgcggtt ggagggtcgc ggacggaggg 122280
tccctggggg tcgcaacgta ggcggggctt ctgtggtgat gcggagaggg ggcggcccga 122340
gtctgcctgg ctgctgcgtc tcgctccgag tgccgaggtg caaatgcgac cagactgtcg 122400
ggccagggct aacttatacc ccacgccttt cccctcccca aaggggcggc agtgacgatt 122460
cccccaatgg ccgcgcgtcc caggggaggc aggcccaccg cggggcggcc ccgtccccgg 122520
ggaccaaccc ggcgccccca aagaatatca ttagcatgca cggcccggcc cccgatttgg 122580
gggaccaacc cggtgtcccc caaagaaccc cattagcatg cccctcccac cgacgcaaca 122640
ggggcttggc ctgcgtcggt gccccggggc ttcccgcctt cccgaagaaa ctcattacca 122700
tacccggaac cccaggggac caatgcgggt tcattgagcg acccgcgggc caatgcgcga 122760
ggggccgtgt gttccgccaa aaaagcaatt agcataaccc ggaaccccag gggagtggtt 122820
acgcgcggcg cgggaggcgg ggaataccgg ggttgcccat taagggccgc gggaattgcc 122880
ggaagcggga agggcggccg gggccgccca ttaatgagtt tctaattacc ataccgggaa 122940
gcggaacaag gcctcttgta agtttttaat taccataccg ggaagtgggc ggcccggccc 123000
actgggcggt aactcccgcc cagtgggccg ggccccgaag actcggcgga cgctggttgg 123060
ccgggccccg ccgcgctggc ggccgccgat tggccagtcc cgccctccga gggcgggccc 123120
gcctcggggg cgggccggct cccagcgtat atatgcgcgg ctcctgccat cgtctctccg 123180
gagagcggct tggtgcggag ctcccgggag ctccgcggaa gacccaggcc gcctcgggtg 123240
taacgttaga ccgagttcgc cgggccggct ccgcgggcca gggcccgggc acgggcctcg 123300
ggccccaggc acggcccgat gaccgcctcg gcctccgcca cccggcgccg gaaccgagcc 123360
cggtcggccc gctcgcgggc ccacgagccg cggcgcgcca ggcgggcggc cgaggcccag 123420
accaccaggt ggcgcacccg gacgtggggc gagaagcgca cccgcgcggg ggtcgcgggg 123480
gtcgcggggg tcgcggggt cgcgggggtc gcgggggct ccggcgcccc ctccccgccc 123540
gcgcgtcgca ggcgcaggcg cgccaggtgc tctgcggtga cgcgcaggcg gagggcgagg 123600
cgcggcggaa ggcggaaggg gcgtgagggg gggtgggagg ggttagcccc gccccccggg 123660
cccgcgccgg gcggtgggga ccgggggcgg ggggcggcgg cggtgggccg ggcctctggc 123720
gccggctcgg gcgggggct gtccggccag tcgtcgtcat cgtcgtcgtc ggacgcggac 123780
tcgggaacgt ggagccactg gcgcagcagc agcgaacaag aaggcggggg cccactggcg 123840
gggggcggcg gcggggcggc cgcgggcgcg ctcctgaccg cgggttccga gttgggcgtg 123900
gaggttacct gggactgtgc ggttgggacg gcgcccgtgg gcccgggcgg ccgggggcgg 123960
cgggggccgc gatggcggcg gcggcgggcc atggagacag agagcgtgcc ggggtggtag 124020
agtttgacag gcaagcatgt gcgtgcagag gcgagtagtg cttgcctgtc taactcgctc 124080
gtctcggccg cggggggccc gggctgcgcc gccgcgcttt aaagggccgc gcgcgacccc 124140
cggggggtgt gtttcggggg gggcccgttt tccgctcctc cccccgctcc tccccccgct 124200
cctccccccg ctcctccccc cgctcctccc cccgctcctc cccccgctcc tccccccgct 124260
cctccccccg ctcctccccc cgctcctccc cccgctcctc cccccgctcc tccccccgct 124320
cctccccccg ctcctccccc cgctcctccc cccgctcctc cccccgctcc tccccccgct 124380
cctccccccg ctccccaacg cccgccgcgc gcgcgcacgc cgcccggacc gccgcccgcc 124440
tttttttgcgc gccgccccgc ccgcgggggg cccgggctgc cacaggtgta acaacaccaa 124500
cagaacacca acagcacggc gcaccggcga ctccggttcc tcatccacac gtcacacgtc 124560
acgtcatcca ccacacctgc ccaccaacac aactcacagc gacaactcac cgcgcaacaa 124620
ctcctgttcc tcatccacac gtcaccgcgc accccccgct cctccagacg tcccccagcg 124680
caacacgccg ctcctgtcac acaccaccgc cccagccctc cccagcccca gccctcccca 124740
gccccagccc tccccggccc cagccctccc cggccccagc cctccccggc cccagccctc 124800
cccggcccca gccctccccg gccccagccc tccccggccc cagccctccc cggccgcgtc 124860
ccgcgctccc tcgggggggt tcgggcatct ctacctcagt gccgccaatc tcaggtcaga 124920
gatccaaacc ctccgggggc gcccgcgcac caccaccgcc cctcgccccc tcccgcccct 124980
cgccccctcc cgcccctcgc cccctcccgc ccctcgcccc ctcccgcccc tcgccccctc 125040
ccgcccctcg cccccctcccg cccctcgccc cctcccgccc ctcgccccct cccgcccctc 125100
gccccctccc gcccctcgcc ccctcccgcc cctcgccccc tcccgcccct cgccccctcc 125160
cgcccctcgc cccctcccgc ccctcgcccc ctcccgcccc tcgccccctc ccgcccctcg 125220 cccccctcccg cccctcgccc cctcccgccc ctcgcccccct cccgcccctc gccccctccc 125280
gcccctcgaa ataaacaacg ctactgcaaa actaaatcag gtcgttgtcg tttattgcgt 125340
cttcgggttt cgcaagcgcc ccgccccgtc ccggcccgtt acagcacccc gtccccctcg 125400
aacgcgccgc cgtcgtcgtc gtcccaggcg ccttcccagt ccacaacttc ccgtcgcggg 125460
ggcgtggcca agcccgcctc cgcccccagc acctccacgg cccccgccgc cgccagcacg 125520
gtgccgctgc ggcccgtggc cgaggcccag cgaatcccgg gcaacgccgg cggcagggcc 125580
cccgggccgt cgtcgtcgtc gtcgccgccg cgcagcacca gcgggggggc gtcgtcgtcg 125640
ggctccagca gggcgcgggc gcaaaagtcc ctccgcggcc cgcgccaccg ggccgggccg 125700
gcgcgcaccg cctcgcgccc cagcgccacg tacacgggcc gcagcggcgc gcccaggccc 125760
cagcgcgcgc aggcgcggtg cgagtgggcc tcctcctcgc agaagtccgg cgcgccgggc 125820
gccatggcgt cggtggtccc cgaggccgcc gcccggccgt ccagcgccgg cagcacggcc 125880
cggcggtact cgcgcgggga catgggcacc ggcgtgtccg ggccgaagcg cgtgcgcacg 125940
cggtagcgca cgttgccgcc gcggcacagg cgcagcggcg gcgcgtcggg gtacaggcgc 126000
gcgtgcgcgg cctccacgcg cgcgaagacc cccgggccga acacgcggcc cggggccagc 126060
accgtgcggc gcaggtcccg cgccgccggc cagcgcacgg cgcactgcac ggcgggcagc 126120
aggtcgcacg ccaggtaggc gtgctgccgc gacaccgcgg gcccgtcggc gggccagtcg 126180
caggcgcgca cggtgttgac cacgatgagc cgccggtcgc cggcgctggc gagcagcccc 126240
agaaactcca cggccccggc gaaggccagg tcccgcgtgg acagcagcag cacgccctgc 126300
gcgcccagcg ccgacacgtc gggggcgccg gtccagttgc ccgcccaggc ggccgtgtcc 126360
ggcccgcaca gccggttggc cagggccgcc agcaggcagg acagcccgcc gcgctcggcg 126420
gaccactccg gcggcccccc cgaggccccg ccgccggcca ggtcctcgcc cggcagcggc 126480
gagtacagca ccaccacgcg cacgtcctcg gggtcgggga tctggcgcat ccaggccgcc 126540
atgcggcgca gcgggcccga ggcgcgcagg gggccaaaga ggcggccccc ggcggccccg 126600
tgggggtggg ggttatcgtc gtcgtcgccg ccgccgcacg cggcctgggc ggcggcggcg 126660
ggcccggcgc accgcgcggc gatcgaggcc agggcccgcg ggtcaaacat gagggccggt 126720
cgccagggga cggggaacag cgggtggtcc gtgagctcgg ccacggcgcg cggggagcag 126780
taggcctcca gggcggcggc cgcgggcgcc gccgtgtggc tgggccccgg gggctgccgc 126840
cgccagccgc ccagggggtc ggggccctcg gcgggccggc gcgacagcgc cacggggcgc 126900
gggcgggcct gcgccgcggc ggcccggggc gccgcgggct gggcgggggc gggctcgggc 126960
cccgggggcg tggagggggg cgcggggagg ggggcgcggg cgtccgagcc gggggcgtcc 127020
gcgccgctct tcttcgtctt cgggggtcgc gggccgccgc ctccgggcgg ccgggccggg 127080
ccgggactct tgcgcttgcg cccctcccgc ggcgcggcgg aggcggcggc ggccgccagc 127140
gcgtcggcgg cgtccggtgc gctggcggcc gccgccagca gggggcgcag gctctggttc 127200
tcaaacagca ggtccgcggc ggcggcggcc gcggagctcg gcaggcgcgg gtcccgcggc 127260
agcgcggggc ccagggcccc ggcgaccagg ctcacggcgc gcacggcggc cacggcggcc 127320
tcgctgccgc cggccacgcg caggtccccg cgcaggcgca tgagcaccag cgcgtcgcgc 127380
acgaaccgca gctcgcgcag ccacgcgcgc aggcggggcg cgtcggcgtg cggcggcggc 127440
ggggaagcgg ggcccgcggg tccctccggc cgcgggggc tggcgggccg ggccccggcc 127500
agccccggga cggccgccag gtcgccgtcg aagccctcgg ccagcgcctc caggatcccg 127560
cggcaggcgg ccaggcactc cacggccacg cggccggcct gggcgcggcg cccggcgtcg 127620
tcgtcggcgt cggcgtggcg ggcggcgtcg gggtcgtcgc cccccgcggg ggaggcgggc 127680
gcggcggaca gccgccccag ggcggcgagg atccccgcgg cgccgtaccc ggcgggcacc 127740
gcgcgctcgc ccggtgcggc ggcggcggcg acgacggcgg cggcgacccc ctcgtcatct 127800
gcgccggcgc cggggctccc cgcggccccc gtcagcgccg cgttctcgcg cgccaacagg 127860
ggcgcgtagg cgcggcgcag gctggtcagc aggaagccct tctgcgcgcg gtcgtatcgg 127920
cggctcatgg ccacggcggc cgccgcgtgc gccaggcccc agccgaagcg gccggccgcc 127980
atggcgtagc ccaggtgggg cacggcccgc gccacgctgc cggtgatgaa ggagctgctg 128040
ttgcgcgcgg cgcccgagat ccggaagcag gcctggtcca gcgccacgtc cccggggacc 128100
acgcgcgggt tctggagcca ccccatggcc tccgcgtccg gggtgtacag cagccgcgtg 128160
atcagggcgt actgctgcgc ggcgtcgccc agctcgggcg cccacacggc cgccggggcg 128220
cccgaggcct cgaaccggcg tcgcgcctcc tccgcctcgg gcgcccccca gaggcccggg 128280
cggctgtcgc ccaggccgcc gtacagcacc cgcccccgggg gcgggggccc ggcgccgggc 128340
cacggctccc cgctgacgta cccgtcgcga tagcgcgcgt agaaggcgcc ggaggccgcg 128400
tcggcgtcca gctcgacccg ccggggctgc ccggccgtga agcggcccgt ggcgtcgcgg 128460
ccggccaccg ccgcgcgggc ccggcggcgc tcgatgcggc ccgcggaggc cgcgggggtc 128520
ctcgccgccg cccggggctt gggcgcggcc tcggagaggg ggggtggccc gggcgggggc 128580
ggcgtccgcc cgggggcttc cggcgccgcg ctcgacggac cccgcccgac ggcccgcgcc 128640
tcgcgtgcgc ggtcggccgc gtcgttgccg tcgtcgtcct cgtcctcgtc ggacgacgag 128700
gacgaagagg atgcggacga cgaggacgag gacccggagt ccgacgaggt cgatgacgcc 128760
gatggccgcc gccggccgtg acgacgtctc cgcggcggct gggccggcgg gcgcggcgac 128820
aggcggtccg tggggtccgg atacgcgccg cgtagcgggg cctcccgtgc gcggccccgg 128880
gccggggccc ggtcgccggc ggcgtcggct gcgtcgtcgt actcgtcccc gtcatcgtcg 128940
tcggctcgaa aggcgggggt ccggggcggc gaggccgcgg ggtcgggcgt cgggatcgtc 129000
cggacggcct cctctaccat ggaggccagc agggccagct gtcgcggcga gacggcgtcc 129060
ccggcgtcct cgccggcgtc ggtgcccgcc gcgggggccc tcccgtcccg ccgggcgtcg 129120
tcgaggtcgt gggggtggtc ggggtcgtgg tcggggtcgt ccccgccctc ctccgtctcc 129180
gcgccccacc cgagggcccc ccgctcgtcg cggtctgggc tcggggtggg cggcggcccg 129240
tcggtggggc ccggggagcc ggggcgctgc ttgttctccg acgccatcgc cgatgcgggg 129300
cgatcctccg gggatacggc tgcgacggcg gacgtagcac ggtaggtcac ctacggactc 129360
tcgatgggga gggggcgaga cccacggacc ccgacgaccc ccgccgtcga cgcggaacta 129420
gcgcggaccg gtcgatgctt gggtgggaaa aaggacaggg acggccgatc cccctcccgc 129480
gcttcgtccg cgtatcggcg tcccggcgcg gcgagcgtct gacggtctgt ctctggcggt 129540
cccgcgtcgg gtcgtggatc cgtgtcggca gccgcgctcc gtgtggacga tcggggcgtc 129600
ctcgggctca tatagtccca ggggccggcg ggaaggagga gcagcggagg ccgccggccc 129660
cccgcccccc aggcgggccc gccccgaacg gaattccatt atgcacgacc ccgccccgac 129720
gccggcacgc cgggggcccg tggccgcggc ccgttggtcg aacccccggc cccgcccatc 129780
cgcgccatct gccatgggcg gggcgcgagg gcgggtgggc ccgcgccccg ccccgcatgg 129840
catctcatta ccgcccgatc cggtggtttc cgcttccgtt ccgcatgcta acgaggaacg 129900
ggccgggggc ggggcccggg ccccgacttc ccggttcggc ggtaatgaga tacgagcccc 129960

-continued gcgcgcccgt tggccgtccc cgggcccccg gtcccgcccg ccggacgttg ggaccaacgg 130020
gacggcgggc ggcccaaggg ccgcccgcct tgccgccccc ccattggccg gcgggcggga 130080
ccgccccaag ggggcggggc cgccgggtaa aagaagtgag aacgcgaagc gttcgcactt 130140
cgtcccaata tatatatatt attagggcga agtgcgagca ctggcgccgt gcccgactcc 130200
gcgccggccc cgggggcggg cccgggcggc ggggggcggg tctctccggc gcacataaag 130260
gcccggcgcg accgacgccc gcagacggcg ccggccacga acgacgggag cggctgcgga 130320
gcacgcggac cgggagcggg actcgcagag ggccgtcgga gcggacggcg tcggcatcgc 130380
gacgccccgg ctcgggatcg ggatcgcatc ggaaagggac acgcggaaag acccacccac 130440
cccacccacg aaacacaggg gacgcacccc gggggcctcc gacgacagaa acccaccggt 130500
ccgcctttgt gcacgggtaa gcaccttggg tgggcggagg aggggggggac gcgggggcgg 130560
aggagggggg acgcggggc ggaggagggg ggacgcgggg gcggaggagg ggggacgcgg 130620
gggcggagga ggggggacgc gggggcggag gagggggctc acccgcgttc gtgccttccc 130680
gcaggaggaa cgtcctcgtc ggggcgaccg gcggcgaccg ttgcgtggac cgcttcctgc 130740
tcgtcgggcg gggggaagcc actgtggtcc tccgggacgt tttctggatg gccgacattt 130800
ccccaggcgc ttttgcgcct tgtgtaaaag cgcggcgtcc cgctctccga tccccgcccc 130860
tgggcacgcg caagcgcaag cgcccttccc gccccctctc atcggagtct gaggtagaat 130920
ccgatacagc cttggagtct gaggtcgaat ccgagacagc atcggattcg accgagtctg 130980
gggaccagga tgaagccccc cgcatcggtg gccgtagggc cccccggagg cttgggggc 131040
ggttttttct ggacatgtcg gcggaatcca ccacggggac ggaaacggat gcgtcggtgt 131100
cggacgaccc cgacgacacg tccgactggt cttatgacga cattccccca cgacccaagc 131160
gggcccgggt aaacctgcgg ctcacgagct ctcccgatcg gcgggatggg gttatttttc 131220
ctaagatggg gcgggtccgg tctacccggg aaacgcagcc ccgggccccc accccgtcgg 131280
ccccaagccc aaatgcaatg ctacggcgct cggtgcgcca ggcccagagg cggagcagcg 131340
cacgatggac ccccgacctg ggctacatgc gccagtgtat caatcagctg tttcgggtcc 131400
tgcgggtcgc ccgggacccc cacggcagtg ccaaccgcct gcgccacctg atacgcgact 131460
gttacctgat gggatactgc cgagcccgtc tggccccgcg cacgtggtgc cgtttgctgc 131520
aggtgtccgg cggaacctgg ggcatgcacc tgcgcaacac catacgggag gtggaggctc 131580
gattcgacgc caccgcggaa cccgtgtgca agcttccttg tttggagacc agacggtacg 131640
gcccggagtg tgatcttagt aatctcgaga ttcatctcag cgcgacaagc gatgatgaaa 131700
tctccgatgc caccgatctg gaggccgccg gttcggacca cacgctcgcg tcccagtccg 131760
acacggagga tgccccctcc cccgttacgc tggaaacccc agaaccccgc gggtccctcg 131820
ctgtgcgtct ggaggatgag tttggggagt ttgactggac cccccaggag ggctcccagc 131880
cctggctgtc tgcggtcgtg gccgatacca gctccgtgga acgcccgggc ccatccgatt 131940
ctggggcggg tcgcgccgca gaagaccgca agtgtctgga cggctgccgg aaaatgcgct 132000
tctccaccgc ctgcccctat ccgtgcagcg acacgtttct ccggccgtga gtccggtcgc 132060
cccgaccccc ttgtatgtcc ccaaataaaa gaccaaaatc aaagcgtttg tcccagcgtc 132120
ttaatggcgg gaagggcgga gagaaacaga ccacgcgtac atgggggtg tttgggggtt 132180
tattgacatc ggggctacag ggtggtaacc ggatagcaga tgtgaggaag tctgggccgt 132240
tcgccgcgaa cggcgatcag agggtccgtt tcttgcggac cacggcccgg tgatgtgggt 132300
tgctcgtctg ggatctcggg catgcccata cacgcacaac acggacgccg caccggatgg 132360
gacgtcgtaa gggggcctgg ggtagctggg tggggtttgt gcagagcaat cagggaccgc 132420
agccagcgca tacaatcgcg ctcccgtccg tttgtcccgg gcagtaccac gccgtactgg 132480
tattcgtacc ggctgagcag ggtctccagg gggtggttgg gggccgcggg gaacggggtc 132540
cacgccacgg tccactcggg caaaaaccga gtcggcacgg cccacggttc tcccacccac 132600
gcgtctgggg tcttgatggc gataaatctt accccgagcc ggattttttg ggcgtattcg 132660
agaaacggca cacacagatc cgccgcgcct accacccaca agtggtagag gcgagggggg 132720
ctgggttggt ctcggtgcag cagtcggaag cacgccacgg cgtccacgac ctcggtgctc 132780
tccaaggggc tgtcctccgc aaacaggccc gtggtggtgt ttggggggca gcgacaggac 132840
ctagtgcgca cgatcgggcg ggtgggtttg ggtaagtcca tcagcggctc ggccaaccgt 132900
cgaaggttgg ccggacgaac gacgaccggg gtacccaggg gttctgatgc caaaatgcgg 132960
cactgcctaa acaggaagct ccacagggcc gggcttgcgt cgacggaagt ccggggcagg 133020
gcgttgttct ggtcaaggag ggtcattacg ttgacgacaa caacgcccat gttggtatat 133080
tacaggcccg tgtccgattt ggggcacttg cagatttgta aggccacgca cggcggggag 133140
acaggccgac gcgggggctg ctctaaaaat ttaagggccc tacggtccac agacccgcct 133200
tcccgggggg gcccttggag cgaccggcag cggaggcgtc cgggggaggg gagggtgatt 133260
tacggggggg taggtcaggg ggtgggtcgt caaactgccg ctccttaaaa ccccggggcc 133320
cgtcgttcgg ggtgctcgtt ggttggcact cacggtgcgg cgaatggcct gtcgtaagtt 133380
ttgtcgcgtt tacgggggac agggcaggag gaaggaggag gccgtcccgc cggagacaaa 133440
gccgtcccgg gtgtttcctc atggcccctt ttataccccca gccgaggacg cgtgcctgga 133500
ctccccgccc ccggagaccc ccaaaccttc ccacaccaca ccacccggcg atgccgagcg 133560
cctgtgtcat ctgcaggaga tcctggccca gatgtacgga aaccaggact accccataga 133620
ggacgacccc agcgcggatg ccgcggacga tgtcgacgag gacgccccgg acgacgtggc 133680
ctatccggag gaatacgcag aggagctttt tctgcccggg gacgcgcccg gtccccttat 133740
cggggccaac gaccacatcc ctccccccgtg tggcgcatct ccccccggta tacgacgacg 133800
cagccgggat gagattgggg ccacgggatt taccgcggaa gaactggacg ccatggacag 133860
ggaggcggct cgagccatca gccgcggcgg caagcccccc tcgaccatgg ccaagctggt 133920
gactggcatg ggctttacga tccacggagc gctcacccca ggatcggagg ggtgtgtctt 133980
tgacagcagc cacccagatt acccccaacg ggtaatcgtg aaggcggggt ggtacacgag 134040
cacgagccac gaggcgcgac tgctgaggcg actggaccac cccgcgatcc tgcccctcct 134100
ggacctgcat gtcgtctccg gggtcacgtg tctggtcctc cccaagtacc aggccgacct 134160
gtatacctat ctgagtaggc gcctgaaccc gctgggacgc ccgcagatcg cagcggtctc 134220
ccggcagctc ctaagcgccg ttgactacat tcaccgccag ggcattatcc accgcgacat 134280
taagaccgaa aatattttta ttaacacccc cgaggacatt tgcctggggg actttggtgc 134340
cgcgtgcttc gtgcagggtt cccgatcaag ccccttcccc tacggaatcg ccggaaccat 134400
cgacaccaac gcccccgagg tcctggccgg ggatccgtat accaccaccg tcgacatttg 134460
gagcgccggt ctggtgatct tcgagactgc cgtccacaac gcgtccttgt tctcggcccc 134520
ccgcggcccc aaaagggggcc cgtgcgacag tcagatcacc cgcatcatcc gacaggccca 134580
ggtccacgtt gacgagtttt ccccgcatcc agaatcgcgc ctcacctcgc gctaccgctc 134640
ccgcgcggcc gggaacaatc gcccgccgta cacccgaccg gcctggaccc gctactacaa 134700
gatggacata gacgtcgaat atctggtttg caaagccctc accttcgacg gcgcgcttcg 134760
ccccagcgcc gcagagctgc tttgtttgcc gctgtttcaa cagaaatgac cgcccccagg 134820
gggcggtgct gtttgcgggt tggcacaaaa agaccccgac ccgcgtctgt ggtgtttttg 134880
gcatcatgtc gccgggcgcc atgcgtgccg ttgttcccat tatcccattc cttttggttc 134940
ttgtcggtgt atcgggggtt cccaccaacg tctcctccac cacccaaccc caactccaga 135000
ccaccggtcg tccctcgcat gaagccccca acatgaccca gaccggcacc accgactctc 135060
ccaccgccat cagccttacc acgcccgacc acacaccccc catgccaagt atcggactgg 135120
aggaggagga agaggaggag ggggccgggg acggcgaaca tcttgagggg ggagatggga 135180
cccgtgacac cctaccccag tccccgggcc cagccttccc gttggctgag gacgtcgaga 135240
aggacaaacc caaccgtccc gtagtcccat cccccgatcc caacaactcc cccgcgcgcc 135300
ccgagaccag tcgcccgaag acaccccccca ccattatcgg gccgctggca actcgcccca 135360
cgacccgact cacctcaaag ggacgaccct tggttccgac gcctcaacat accccgctgt 135420
tctcgttcct cactgcctcc cccgccctgg acaccctctt cgtcgtcagc accgtcatcc 135480
acaccttatc gtttttgtgt attggtgcga tggcgacaca cctgtgtggc ggttggtcca 135540
gacgcgggcg acgcacacac cctagcgtgc gttacgtgtg cctgccgtcc gaacgcgggt 135600
agggtatggg gcgggggatg gggagagccc acacgcggaa agcaagaaca ataaaggcgg 135660
tggtatctag ttgatatgca tctctgggtg tttttggggt gtggcggacg cggggcggtc 135720
attggacggg gtgcagttaa atacatgccc gggacccatg aagcatgcgc gacttccggg 135780
cctcggaacc cacccgaaac ggccaacgga cgtctgagcc aggcctggct atccggagaa 135840
acagcacacg acttggcgtt ctgtgtgtcg cgatgtctct gcgcgcagtc tggcatctgg 135900
ggcttttggg aagcctcgtg ggggctgttc ttgccgccac ccatcgggga cctgcggcca 135960
acacaacgga ccccttaacg cacgccccag tgtcccctca ccccagcccc ctggggggct 136020
ttgccgtccc cctcgtagtc ggtgggctgt gcgccgtagt cctgggggcg gcgtgtctgc 136080
ttgagctcct gcgtcgtacg tgccgcgggt gggggcgtta ccatccctac atggacccag 136140
ttgtcgtata atttcccccc cccccccct tctccgcatg ggtgatgtcg ggtccaaact 136200
cccgacacca ccagctggca tggtataaat caccggtgcg ccccccaaac catgtccggc 136260
agggggatgg gggggcgaat gcggagggca cccaacaaca ccgggctaac caggaaatcc 136320
gtggccccgg cccccaataa agatcgcggt agcccggccg tgtgacacta tcgtccatac 136380
cgaccacacc gacgaatccc ctaaggggga ggggccattt tacgaggagg aggggtataa 136440
caaagtctgt ctttaaaaag caggggttag ggagttgttc ggtcataagc ttcagcgcga 136500
acgaccaact accccgatca tcagttatcc ttaaggtctc ttttgtgtgg tgcgttccgg 136560
tatggggggg gctgccgcca ggttgggggc cgtgattttg tttgtcgtca tagtgggcct 136620
ccatggggtc cgcggcaaat atgccttggc ggatgcctct ctcaagatgg ccgaccccaa 136680
tcgctttcgc ggcaaagacc ttccggtcct ggaccagctg accgaccctc cgggggtccg 136740
gcgcgtgtac cacatccagg cgggcctacc ggacccgttc cagcccccca gcctcccgat 136800
cacggtttac tacgccgtgt tggagcgcgc ctgccgcagc gtgctcctaa acgcaccgtc 136860
ggaggccccc cagattgtcc gcggggcctc cgaagacgtc cggaaacaac cctacaacct 136920
gaccatcgct tggtttcgga tgggaggcaa ctgtgctatc cccatcacgg tcatggagta 136980
caccgaatgc tcctacaaca agtctctggg ggcctgtccc atccgaacgc agccccgctg 137040
gaactactat gacagcttca gcgccgtcag cgaggataac ctggggttcc tgatgcacgc 137100
ccccgcgttt gagaccgccg gcacgtacct gcggctcgtg aagataaacg actggacgga 137160
gattacacag tttatcctgg agcaccgagc caagggctcc tgtaagtacg ccctcccgct 137220
gcgcatcccc ccgtcagcct gcctgtcccc ccaggcctac cagcaggggg tgacggtgga 137280
cagcatcggg atgctgcccc gcttcatccc cgagaaccag cgcaccgtcg ccgtatacag 137340
cttgaagatc gccgggtggc acgggcccaa ggccccatac acgagcaccc tgctgccccc 137400
ggagctgtcc gagaccccca acgccacgca gccagaactc gccccggaag accccgagga 137460
ttcggccctc ttggaggacc ccgtggggac ggtggcgccg caaatcccac caaactggca 137520
cataccgtcg atccaggacg ccgcgacgcc ttaccatccc ccggccaccc cgaacaacat 137580
gggcctgatc gccggcgcgg tgggcggcag tctcctggca gccctggtca tttgcggaat 137640
tgtgtactgg atgcgccgcc gcactcaaaa agccccaaag cgcatacgcc tcccccacat 137700
ccgggaagac gaccagccgt cctcgcacca gcccttgttt tactagatac ccccccttaa 137760
tgggtgcggg ggggtcaggt ctgcggggtt gggatgggac cttaactcca tataaagcga 137820
gtctggaagg ggggaaaggc ggacagtcga taagtcggta gcgggggacg cgcacctgtt 137880
ccgcctgtcg cacccacagc tttttttgcg aaccgtcccg ttccgggatg ccgtgccgcc 137940
cgttgcaggg cctggtgctc gtgggcctct gggtctgtgc caccagcctg gttgtccgtg 138000
gccccacggt cagtctggta tcaaactcat ttgtggacgc cggggccttg gggcccgacg 138060
gcgtagtgga ggaagacctg cttattctcg gggagcttcg ctttgtgggg gaccaggtcc 138120
cccacaccac ctactacgat ggggtcgtag agctgtggca ctaccccatg ggacacaaat 138180
gcccacgggt cgtgcatgtc gtcacggtga ccgcgtgccc acgtcgcccc gccgtggctt 138240
tcgccctgtg tcgcgcgacc gacagcactc acagccccgc atatcccacc ctggagctga 138300
atctggccca acagccgctt ttgcgggtcc ggagggcgac gcgtgactat gccggggtgt 138360
acgtgttacg cgtatgggtc ggggacgcac caaacgccag cctgtttgtc ctggggatgg 138420
ccatagccgc cgaagggact ctggcgtaca acggctcggc ccatggctcc tgcgacccga 138480
aactgcttcc gtattcggcc ccgcgtctgg ccccggcgag cgtataccaa cccgccccta 138540
acccggcctc caccccctcg accaccacct ccaccccctc gaccaccacc tccacccccct 138600 cgaccaccat ccccgctccc caagcatcga ccacaccctt ccccacggga gacccaaaac 138660
cccaacctca cggggtcaac cacgaacccc catcgaatgc cacgcgagcg acccgcgact 138720
cgcgatacgc gctaacggtg acccagataa tccagatagc catccccgcg tccattatag 138780
ccctggtgtt tctggggagc tgtatttgct ttatacacag atgtcaacgc cgctaccgac 138840
gctcccgccg cccgatttac aacccccaga tacccactgg catctcatgc gcggtgaacg 138900
aagcggccat ggcccgcctc ggagccgagc tcaaatcgca tccgagcacc ccccccaaat 138960
cccggcgccg gtcgtcacgc acaccaatgc cctccctgac ggccatcgcc gaagagtcgg 139020
agcccgcggg ggcggctggg cttccgacgc cccccgtgga ccccacgaca tccaccccaa 139080
cgcctcccct gttggtatag gtccacggcc actggccggg ggcaccacat aaccgaccgc 139140
agtcactgag ttgggaataa accggtatta tttacctata tacgtgtatg tccatttctt 139200
cccccccccc cccggaaacc aaagaaggaa acaaagaatg gatgggagga gttcaggaag 139260
ccggggagag ggcccgcggc gcatttaagg cgttgttgtg ttgactttgg ctcttctggc 139320
gggttggtgc ggtgctgttt gttgggctcc cattttaccc gaagatcggc tgctatcccc 139380
gggacatgga tcgcggggcg gtggtggggt ttcttctcgg tgtttgtgtt gtatcgtgct 139440
tggcgggaac gcccaaaacg tcctggagac gggtgagtgt cggcgaggac gtttcgttgc 139500
ttccagctcc ggggcctacg gggcgcggcc cgacccagaa actactatgg gccgtggaac 139560
ccctggatgg gtgcggcccc ttacacccgt cgtgggtctc gctgatgccc cccaagcagg 139620
tgcccgagac ggtcgtggat gcggcgtgca tgcgcgctcc ggtcccgctg gcgatggcgt 139680
acgccccccc ggccccatct gcgaccgggg gtctacggac ggacttcgtg tggcaggagc 139740
gcgcggccgt ggttaaccgg agtctggtta tttacggggt ccgagagacg gacagcggcc 139800
tgtataccct gtctgtgggc gacataaagg acccggctcg ccaagtggcc tcggtggtcc 139860
tggtggtgca accggcccca gttccgaccc cacccccgac cccagccgat tacgacgagg 139920
atgacaatga cgagggcgag ggcgaggacg aaagtctagc cggcactccc gccagcggga 139980
ccccccggct cccgcctccc cccgcccccc cgaggtcttg gcccagcgcc cccgaagtct 140040
cacacgtgcg tggggtgacc gtgcgtatgg agactccgga agctatcctg ttttcccccg 140100
gggaggcgtt tagcacgaac gtctccatcc atgccatcgc ccacgacgac cagacctaca 140160
ccatggacgt cgtctggttg aggttcgacg tgccgacctc gtgtgccgag atgcgaatat 140220
acgaatcgtg tctgtatcac ccgcagctcc cagagtgtct gtccccggcc gacgctccgt 140280
gcgccgcgag tacgtggacg tctcgcctgg ccgtccgcag ctacgcgggg tgttccagaa 140340
caaacccccc gccgcgctgt tcggccgagg ctcacatgga gcccttcccg gggctggcgt 140400
ggcaggcggc ctccgtcaat ctggagttcc gggacgcgtc cccacaacac tccggcctgt 140460
atctgtgcgt ggtgtacgtc aacgaccata ttcacgcatg ggggccacatt accatcagca 140520 ccgcggcgca gtaccggaac gcggtggtgg aacagcccct cccacagcgc ggcgcggatt 140580
tggccgagcc cacccacccg cacgtcgggg cccctcccca cgcgccccca acccacggcg 140640
ccctgcggtt aggggcggtg atgggggccg ccctgctgct gtctgcgctg gggttgtcgg 140700
tgtgggcgtg tatgacctgt tggcgcaggc gtgcctggcg ggcggttaaa agcagggcct 140760
cgggtaaggg gcccacgtac attcgcgtgg ccgacagcga gctgtacgcg gactggagct 140820
cggacagcga gggagaacgc gaccaggtcc cgtggctggc ccccccggag agacccgact 140880
ctccctccac caatggatcc ggctttgaga tcttatcacc aacggctccg tctgtatacc 140940
cccgtagcga tgggcatcaa tctcgccgcc agctcacaac ctttggatcc ggaaggcccg 141000
atcgccgtta ctcccaggcc tccgattcgt ccgtcttctg gtaaggcgcc ccatcccgag 141060
gccccacgtc ggtcgccgaa ctgggcgacc gccggcgagg tggacgtcgg agacgagcta 141120
atcgcgattt ccgacgaacg cggacccccc cgacatgacc gcccgcccct cgccacgtcg 141180
accgcgccct cgccacaccc gcgacccccg ggctacacgg ccgttgtctc cccgatggcc 141240
ctccaggctg tcgacgcccc ctccctgttt gtcgcctggc tggccgctcg gtggctccgg 141300
ggggcttccg gcctgggggc cgtcctgtgt gggattgcgt ggtatgtgac gtcaattgcc 141360
cgaggcgcat aaagggccgg tggtccgcct agccgcagca aattaaaaat cgtgagtcac 141420
tgcgaccgca acttcccacc cggagctttc ttccggcctc gatgacgtcc cggctctccg 141480
atcccaactc ctcagcgcga tccgacatgt ccgtgccgct ttatcccacg gcctcgccag 141540
tttcggtcga agcctactac tcggaaagcg aagacgaggc ggccaacgac ttcctcgtac 141600
gcatgggccg ccaacagtcg gtattaaggc gtcgacgcag acgcacccgc tgcgtcggca 141660
tggtgatcgc ctgtctcctc gtggccgttc tgtcgggcgg atttggggcg ctcctgatgt 141720
ggctgctccg ctaaaagacc gcatcgacac gcgcgtcctt cttgtcgtct ctcttccccc 141780

-continued ccatcacccc gcaatttgca cccagccttt aactacatta aattgggttc gattggcaat 141840
gttgtctccc ggttgatttt tgggtgggtg gggagtgggt gggtggggag tgggtgggtg 141900
gggagtgggt gggtggggag tgggtgggtg gggagtgggt gggtggggag tgggtgggtg 141960
gggagtgggt gggtggggag tgggtgggtg gggagtgggt gggtggggag tggcaaggaa 142020
gaaacaagcc cgaccaccag acagaaaatg taaccatacc caaaccgact ctgggggctg 142080
tttgtggggt cggaaccata ggatgaacaa accaccccgt acctcccgca cccttgggtg 142140
cgggtggctc atcggcatct gtccggtatg ggttgttccc cacccacttg cgttcggacg 142200
tcttagaatc atggcggttt tctatgccga catcggtttt ctcccccgca ataagacacg 142260
atgcgataaa atctgtttgt gaaatttatt aagggtacaa attgccctag cacaggggtg 142320
gggttagggc cgggtcccca cacccaaacg caccaaacag atgcaggcag tgggtcgagt 142380
acagccccgc gtacgaacac gtcgatgcgt gtgtcagaca gcaccagaaa gcacaggcca 142440
tcaacaggtc gtgcatatgt cggtgggttt ggacgcgggg ggccatggtg gtgataaagt 142500
taatggccgc cgtccgccag ggccacaggg gcgacgtctc ttggttggcc cggagccact 142560
gggtgtggac cagccgcgcg tggcggccca acatggcccc tgtagccggg ggcgggggat 142620
cgcgcacgtt tgcagcgcac atgcgagaca cctcgaccac ggttcggaag aaggcccggt 142680
ggtccgcggg caacatcacc aggtgcgcaa gcgcccgggc gtccagaggg tagagccctg 142740
agtcatccga ggttggctca tcgcccgggt catgccgcaa gtgcgtgtgg gttgggcttc 142800
cggtgggcgg gacgcgaacc gcggtgtgga gccctacgcg ggcccgagcg tacgctccat 142860
cttgtgggga gaaggggtct gggctcgcca ggggggcata cttgcccggg ctatacagac 142920
ccgcgagccg tacgtggttc gcggggggtg cgtggggtcc ggggctcccg gggaggccgg 142980
ggctcccggg gttgtcgtgg atccctgggg tcacgcggta ccctggggtc tctgggagct 143040
cgcggtactc tgggttccct aggttctcgg ggtggtcgcg gaacccgggg ctcccgggga 143100
acacgcggtg tcctggggat tgttggcggt cggacggctt cagatggctt cgagatcgta 143160
gtgtccgcac cgactcgtag tagacccgaa tctccacatt gccccgccgc ttgatcatta 143220
tcaccccgtt gcgggggtcc ggagatcatg cgcgggtgtc ctcgaggtgc gtgaacacct 143280
ctggggtgca tgccggcgga cggcacgcct tttaagtaaa catctgggtc gcccggccca 143340
actggggccg ggggttgggt ctggctcatc tcgagagcca cggggggaac caccctccgc 143400
ccagaaactt gggcgatggt cgtacccggg actcaacggg ttaccggatt acggggactg 143460
tcggtcacgg tcccgccggt tcttcgatgt gccacaccca aggatgcgtt gggggcgatt 143520
ttgggcagca gcccgggaga gcgcagcaga ggacgctccg ggtcgtgcac ggcggttttg 143580
gccgcctccc ggtcctcacg ccccctttta ttgatctcat cgcgtacgtc ggcgtacgtc 143640
ctgggcccaa cccgcatgtt gtccaggaag gtgtccgcca tttccagggc ccacgacatg 143700
ctcccccgcc cgacgagcag gaagcggtcc acgcaacggt cgccgccggt cgccccgacg 143760
agcaggaagc ggtccacgca acggtcgccg ccggtcgcct cgacgaggac gttcctcctg 143820
cgggaaggca cgaacgcggg tgagccccct cctccgcccc cgcgtccccc ctcctccgcc 143880
cccgcgtccc ccctcctccg cccccgcgtc ccccctcctc cgcccccgcg tccccccctcc 143940 tccgcccccg cgtcccccct cctccgcccc cgcgtccccc ctcctccacc cccgcgtccc 144000
cccctcctcc gcccacccaa ggtgcttacc cgtgcacaaa ggcggaccgg tgggtttctg 144060
tcgtcggagg cccccggggt gcgtcccctg tgtttcgtgg gtggggtggg tgggtctttc 144120
cgcgtgtccc tttccgatgc gatcccgatc ccgagccggg gcgtcgcgat gccgacgccg 144180

-continued tccgctccga cggccctctg cgagtcccgc tcccggtccg cgtgctccgc agccgctccc 144240
gtcgttcgtg gccggcgccg tctgcgggcg tcggtcgcgc cgggccttta tgtgcgccgg 144300
agagacccgc cccccgccgc ccgggcccgc ccccggggcc ggcgcggagt cgggcacggc 144360
gccagtgctc gcacttcgcc ctaataatat atatatattg ggacgaagtg cgaacgcttc 144420
gcgttctcac ttcttttacc cggcggcccc gcccccttgg ggcggtcccg cccgccggcc 144480
aatggggggg cggcaaggcg ggcggccctt gggccgcccg ccgtcccgtt ggtcccaacg 144540
tccggcgggc gggaccgggg gcccggggac ggccaacggg cgcgcggggc tcgtatctca 144600
ttaccgccga accgggaagt cggggcccgg gccccgcccc cggcccgttc ctcgttagca 144660
tgcggaacgg aagcggaaac caccggatcg ggcggtaatg agatgccatg cggggcgggg 144720
cgcgggccca cccgccctcg cgccccgccc atggcagatg gcgcggatgg gcggggccgg 144780
gggttcgacc aacgggccgc ggccacgggc ccccggcgtg ccggcgtcgg ggcggggtcg 144840
tgcataatgg aattccgttc ggggcgggcc cgcctggggg gcggggggcc ggcggcctcc 144900
gctgctcctc cttcccgccg gcccctggga ctatatgagc ccgaggacgc cccgatcgtc 144960
cacacggagc gcggctgccg acacggatcc acgacccgac gcgggaccgc cagagacaga 145020
ccgtcagacg ctcgccgcgc cgggacgccg atacgcggac gaagcgcggg agggggatcg 145080
gccgtccctg tcctttttcc cacccaagca tcgaccggtc cgcgctagtt ccgcgtcgac 145140
ggcgggggtc gtcggggtcc gtgggtctcg ccccctcccc atcgagagtc cgtaggtgac 145200
ctaccgtgct acgtccgccg tcgcagccgt atccccggag gatcgccccg catcggcgat 145260
ggcgtcggag aacaagcagc gccccggctc cccgggcccc accgacgggc cgccgcccac 145320
cccgagccca gaccgcgacg agcggggggc cctcgggtgg ggcgcggaga cggaggaggg 145380
cggggacgac cccgaccacg accccgacca cccccacgac ctcgacgacg cccggcggga 145440
cgggagggcc cccgcggcgg gcaccgacgc cggcgaggac gccggggacg ccgtctcgcc 145500
gcgacagctg gccctgctgg cctccatggt agaggaggcc gtccggacga tcccgacgcc 145560
cgacccccgcg gcctcgccgc cccggacccc cgcctttcga gccgacgacg atgacgggga 145620
cgagtacgac gacgcagccg acgccgccgg cgaccgggcc ccggcccggg gccgcgcacg 145680
ggaggccccg ctacgcggcg cgtatccgga ccccacggac cgcctgtcgc cgcgcccgcc 145740
ggcccagccg ccgcggagac gtcgtcacgg ccggcggcgg ccatcggcgt catcgacctc 145800
gtcggactcc gggtcctcgt cctcgtcgtc cgcatcctct tcgtcctcgt cgtccgacga 145860
ggacgaggac gacgacggca acgacgcggc cgaccgcgca cgcgaggcgc gggccgtcgg 145920
gcggggtccg tcgagcgcgg cgccggaagc ccccgggcgg acgccgcccc cgcccgggcc 145980
acccccccctc tccgaggccg cgcccaagcc ccgggcggcg gcgaggaccc ccgcggcctc 146040
cgcgggccgc atcgagcgcc gccgggcccg cgcggcggtg gccggccgcg acgccacggg 146100
ccgcttcacg gccgggcagc cccggcgggt cgagctggac gccgacgcgg cctccggcgc 146160
cttctacgcg cgctatcgcg acgggtacgt cagcggggag ccgtggcccg gcgccgggcc 146220
cccgcccccg gggcgggtgc tgtacggcgg cctgggcgac agccgcccgg gcctctgggg 146280
ggcgcccgag gcggaggagg cgcgacgccg gttcgaggcc tcgggcgccc cggcggccgt 146340
gtgggcgccc gagctgggcg acgccgcgca gcagtacgcc ctgatcacgc ggctgctgta 146400
caccccggac gcggaggcca tggggtggct ccagaacccg cgcgtggtcc ccggggacgt 146460
ggcgctggac caggcctgct tccggatctc gggcgccgcg cgcaacagca gctccttcat 146520
caccggcagc gtggcgcggg ccgtgcccca cctgggctac gccatggcgg ccggccgctt 146580
cggctggggc ctggcgcacg cggcggccgc cgtggccatg agccgccgat acgaccgcgc 146640
gcagaagggc ttcctgctga ccagcctgcg ccgcgcctac gcgcccctgt tggcgcgcga 146700
gaacgcggcg ctgacggggg ccgcggggag ccccggcgcc ggcgcagatg acgagggggt 146760
cgccgccgcc gtcgtcgccg ccgccgccgc accgggcgag cgcgcggtgc ccgccgggta 146820
cggcgccgcg ggatcctcg ccgccctggg gcggctgtcc gccgcgcccg cctcccccgc 146880
ggggggcgac gaccccgacg ccgcccgcca cgccgacgcc gacgacgacg ccgggcgccg 146940
cgcccaggcc ggccgcgtgg ccgtggagtg cctggccgcc tgccgcggga tcctggaggc 147000
gctggccgag ggcttcgacg gcgacctggc ggccgtcccg gggctggccg gggcccggcc 147060
cgccagcccc ccgcggccgg agggacccgc gggccccgct tccccgccgc cgccgcacgc 147120
cgacgcgccc cgcctgcgcg cgtggctgcg cgagctgcgg ttcgtgcgcg acgcgctggt 147180
gctcatgcgc ctgcgcgggg acctgcgcgt ggccggcggc agcgaggccg ccgtggccgc 147240
cgtgcgcgcc gtgagcctgg tcgccggggc cctgggcccc gcgctgccgc gggacccgcg 147300
cctgccgagc tccgcggccg ccgccgccgc ggacctgctg tttgagaacc agagcctgcg 147360
ccccctgctg gcggcggccg ccagcgcacc ggacgccgcc gacgcgctgg cggccgccgc 147420
cgcctccgcc gcgccgcggg aggggcgcaa gcgcaagagt cccggcccgg cccggccgcc 147480
cggaggcggc ggcccgcgac ccccgaagac gaagaagagc ggcgcggacg cccccggctc 147540
ggacgcccgc gcccccctcc ccgcgccccc ctccacgccc ccggggcccg agcccgcccc 147600
cgcccagccc gcggcgcccc gggccgccgc ggcgcaggcc cgcccgcgcc ccgtggcgct 147660
gtcgcgccgg cccgccgagg gccccgaccc cctgggcggc tggcggcggc agcccccggg 147720
gcccagccac acggcggcgc ccgcggccgc cgccctggag gcctactgct ccccgcgcgc 147780
cgtggccgag ctcacggacc acccgctgtt ccccgtcccc tggcgaccgg ccctcatgtt 147840
tgacccgcgg gccctggcct cgatcgccgc gcggtgcgcc gggcccgccg ccgccgccca 147900
ggccgcgtgc ggcggcggcg acgacgacga taaccccac ccccacgggg ccgccggggg 147960
ccgcctcttt ggccccctgc gcgcctcggg cccgctgcgc cgcatggcgg cctggatgcg 148020
ccagatcccc gaccccgagg acgtgcgcgt ggtggtgctg tactcgccgc tgccgggcga 148080
ggacctggcc ggcggcgggg cctcgggggg gccgccggag tggtccgccg agcgcggcgg 148140
gctgtcctgc ctgctggcgg ccctggccaa ccggctgtgc gggccggaca cggccgcctg 148200
ggcgggcaac tggaccggcg cccccgacgt gtcggcgctg ggcgcgcagg gcgtgctgct 148260
gctgtccacg cgggacctgg ccttcgccgg ggccgtggag tttctggggc tgctcgccag 148320
cgccggcgac cggcggctca tcgtggtcaa caccgtgcgc gcctgcgact ggcccgccga 148380
cgggcccgcg gtgtcgcggc agcacgccta cctggcgtgc gacctgctgc ccgccgtgca 148440
gtgcgccgtg cgctggccgg cggcgcggga cctgcgccgc acggtgctgg ccccgggccg 148500
cgtgttcggc ccgggggtct tcgcgcgcgt ggaggccgcg cacgcgcgcc tgtaccccga 148560
cgcgccgccg ctgcgcctgt gccgcggcgg caacgtgcgc taccgcgtgc gcacgcgctt 148620
cggcccggac acgccggtgc ccatgtcccc gcgcgagtac cgccgggccg tgctgccggc 148680
gctggacggc cgggcggcgg cctcggggac caccgacgcc atggcgcccg gcgcgccgga 148740
cttctgcgag gaggaggccc actcgcaccg cgcctgcgcg cgctggggcc tgggcgcgcc 148800
gctgcggccc gtgtacgtgg cgctggggcg cgaggcggtg cgcgccggcc cggcccggtg 148860
gcgcgggccg cggagggact tttgcgcccg cgccctgctg gagcccgacg acgacgcccc 148920
cccgctggtg ctgcgcggcg gcgacgacga cgacgacggc ccgggggccc tgccgccggc 148980
gttgcccggg attcgctggg cctcggccac gggccgcagc ggcaccgtgc tggcggcggc 149040
gggggccgtg gaggtgctgg gggcggaggc gggcttggcc acgcccccgc gacgggaagt 149100
tgtggactgg gaaggcgcct gggacgacga cgacggcggc gcgttcgagg gggacggggt 149160
gctgtaacgg gccgggacgg ggcggggcgc ttgcgaaacc cgaagacgca ataaacgaca 149220
acgacctgat ttagttttgc agtagcgttg tttatttcga ggggcgggag ggggcgaggg 149280
gcgggagggg gcgaggggcg ggagggggcg aggggcggga gggggcgagg ggcgggaggg 149340
ggcgaggggc gggagggggc gaggggcggg agggggcgag gggcgggagg gggcgagggg 149400
cgggaggggg cgaggggcgg gagggggcga ggggcgggag ggggcgaggg gcgggagggg 149460
gcgaggggcg ggagggggcg aggggcggga gggggcgagg ggcgggaggg ggcgaggggc 149520
gggagggggc gaggggcggg agggggcgag gggcgggagg gggcgagggg cgggaggggg 149580
cgaggggcgg tggtggtgcg cgggcgcccc cggagggttt ggatctctga cctgagattg 149640
gcggcactga ggtagagatg cccgaacccc cccgagggag cgcgggacgc ggccggggag 149700
ggctggggcc ggggagggct ggggccgggg agggctgggg ccggggaggg ctggggccgg 149760
ggagggctgg ggccggggag ggctggggcc ggggagggct ggggctgggg agggctgggg 149820
ctggggaggg ctggggcggt ggtgtgtgac aggagcggcg tgttgcgctg ggggacgtct 149880
ggaggagcgg ggggtgcgcg gtgacgtgtg gatgaggaac aggagttgtt gcgcggtgag 149940
ttgtcgctgt gagttgtgtt ggtgggcagg tgtggtggat gacgtgacgt gtgacgtgtg 150000
gatgaggaac cggagtcgcc ggtgcgccgt gctgttggtg ttctgttggt gttgttacac 150060
ctgtggcagc ccgggccccc cgcgggcggg gcggcgcgca aaaaaggcgg gcggcggtcc 150120
gggcggcgtg cgcgcgcgcg gcgggcgttg ggggagcggg gggaggagcg gggggaggag 150180 cgggggga gg agcgggggga ggagcggggg gaggagcggg gggaggagcg gggggaggag 150240 cgggggga gg agcgggggga ggagcggggg gaggagcggg gggaggagcg gggggaggag 150300 cgggggga gg agcgggggga ggagcggggg gaggagcggg gggaggagcg gggggaggag 150360 cgggggga gg agcggaaaac gggccccccc cgaaacacac cccccggggg tcgcgcgcgg 150420
ccctttaaag cg 150432

<210> SEQ ID NO 7
<211> LENGTH: 153329
<212> TYPE: DNA
<213> ORGANISM: Artificial sequence
<220> FEATURE:
<223> OTHER INFORMATION: synthetic sequence

<400> SEQUENCE: 7
agcccgggcc ccccgcgggc ggggcggcgc gcaaaaaagg cgggcggcgg tccgggcggc 60
gtgcgcgcgc gcggcgggcg ttggggagcg gggggaggag cgggggga gg agcgggggga 120 ggagcggggg gaggagcggg gggaggagcg gggggaggag cgggggga gg agcgggggga 180 ggagcggggg gaggagcggg gggaggagcg gggggaggag cgggggga gg agcgggggga 240 ggagcggggg gaggagcggg gggaggagcg gggggaggag cgggggga gg agcgggggga 300 ggagcggaaa acgggccccc cccgaaacac accccccggg ggtcgcgcgc ggccctttaa 360
agcgcggcgg cgcagcccgg gcccccc gcg gccgagacga gcgagttaga caggcaagca 420
ctactcgcct ctgcacgcac atgcttgcct gtcaaactct accaccccgg cacgctctct 480

-continued

```
gtctccatgg cccgccgccg ccgccatcgc ggcccccgcc gcccccggcc gcccgggccc    540
acgggcgccg tcccaaccgc acagtcccag gtaacctcca cgcccaactc ggaacccgcg    600
gtcaggagcg cgcccgcggc cgccccgccg ccgcccccg ccagtgggcc cccgccttct    660
tgttcgctgc tgctgcgcca gtggctccac gttcccgagt ccgcgtccga cgacgacgat    720
gacgacgact ggccggacag ccccccgccc gagccggcgc cagaggcccg gcccaccgcc    780
gccgcccccc gcccccggtc cccaccgccc ggcgcgggcc cgggggcgg ggctaacccc    840
tcccaccccc cctcacgccc cttccgcctt ccgccgcgcc tcgccctccg cctgcgcgtc    900
accgcagagc acctggcgcg cctgcgcctg cgacgcgcgg gcggggaggg ggcgccggag    960
ccccccgcga cccccgcgac ccccgcgacc cccgcgaccc ccgcgacccc cgcgcgggtg   1020
cgcttctcgc cccacgtccg ggtgcgccac ctggtggtct gggcctcggc cgcccgcctg   1080
gcgcgccgcg gctcgtgggc ccgcgagcgg gccgaccggg ctcggttccg gcgccgggtg   1140
gcggaggccg aggcggtcat cgggccgtgc ctggggcccg aggcccgtgc ccgggccctg   1200
gcccgcggag ccggcccggc gaactcggtc taacgttaca cccgaggcgg cctgggtctt   1260
ccgcggagct cccgggagct ccgcaccaag ccgctctccg gagagacgat ggcaggagcc   1320
gcgcatatat acgctgggag ccggcccgcc cccgaggcgg gcccgccctc ggagggcggg   1380
actggccaat cggcggccgc cagcgcggcg gggcccggcc aaccagcgtc cgccgagtct   1440
tcggggcccg gcccactggg cgggagttac cgcccagtgg gccgggccgc ccacttcccg   1500
gtatggtaat taaaaactta caagaggcct tgttccgctt cccggtatgg taattagaaa   1560
ctcattaatg ggcggccccg gccgcccttc ccgcttccgg caattcccgc ggcccttaat   1620
gggcaacccc ggtattcccc gcctcccgcg ccgcgcgtaa ccactcccct ggggttccgg   1680
gttatgctaa ttgctttttt ggcggaacac acggcccctc gcgcattggc ccgcgggtcg   1740
ctcaatgaac ccgcattggt cccctggggt tccgggtatg gtaatgagtt tcttcgggaa   1800
ggcgggaagc cccggggcac cgacgcaggc caagcccctg ttgcgtcggt gggaggggca   1860
tgctaatggg gttctttggg ggacaccggg ttggtccccc aaatcggggg ccgggccgtg   1920
catgctaatg atattctttg ggggcgccgg gttggtcccc ggggacgggg ccgccccgcg   1980
gtgggcctgc ctcccctggg acgcgcggcc attgggggaa tcgtcactgc cgcccctttg   2040
gggaggggaa aggcgtgggg tataagttag ccctggcccg acagtctggt cgcatttgca   2100
cctcggcact cggagcgaga cgcagcagcc aggcagactc gggccgcccc ctctccgcat   2160
caccacagaa gccccgccta cgttgcgacc cccagggacc ctccgtccgc gaccctccaa   2220
ccgcatacga cccccatgga gccccgcccc ggagcgagta cccgccggcc tgagggccgc   2280
ccccagcgcg aggtgagggg ccgggcgcca tgtctggggc gccatattgg ggggcgccat   2340
attggggggc gccatgttgg gggacccccg acccttacac tggaaccggc cgccatgttg   2400
ggggaccccc actcatacac gggagccggg cgccatgtta gggggcgtgg aaccccgtga   2460
cactatatat acagggaccg ggggcgccat gttagggggc gcggaacccc ctgaccctat   2520
atatacaggg accggggtcg ccctgttggg ggtcgccatg tgacccccctg actttatata   2580
tacagacccc ccaacacata cacatggccc ctttgactca gacgcagggc ccggggtcgc   2640
cgtgggaccc cctgactcat acacagagac acgcccccac aacaaacaca cagggaccgg   2700
ggtcgccgtg ttagggggcg tggtccccac tgactcatac gcagggcccc cttactcaca   2760
cgcatctagg ggggtgggga ggagccgccc gccatatttg ggggacgccg tgggaccccc   2820
gactccggtg cgtctggagg gcgggagaag agggaagaag aggggtcggg atccaaagga   2880
```

-continued

```
cggacccaga ccacctttgg ttgcagaccc ctttctcccc cctcttccga ggccagcagg   2940
ggggcaggac tttgtgaggc gggggggggg agagggggaa ctcgtgggcg ctgattgacg   3000
cgggaaatcc ccccattctt acccgccccc ctttttttcc ccttagcccg ccccggatgt   3060
ctgggtgttt ccctgcgacc gagacctgcc ggacagcagc gactctgagg cggagaccga   3120
agtggggggg cggggggacg ccgaccacca tgacgacgac tccgcctccg aggcggacag   3180
cacggacacg gaactgttcg agacggggct gctggggccg cagggcgtgg atgggggggc   3240
ggtctcgggg gggagccccc cccgcgagga agaccccggc agttgcgggg gcgccccccc   3300
tcgagaggac ggggggagcg acgagggcga cgtgtgcgcc gtgtgcacgg atgagatcgc   3360
gccccacctg cgctgcgaca ccttcccgtg catgcaccgc ttctgcatcc cgtgcatgaa   3420
aacctggatg caattgcgca acacctgccc gctgtgcaac gccaagctgg tgtacctgat   3480
agtgggcgtg acgcccagcg ggtcgttcag caccatcccg atcgtgaacg acccccagac   3540
ccgcatggag gccgaggagg ccgtcagggc gggcacggcc gtggacttta tctggacggg   3600
caatcagcgg ttcgccccgc ggtacctgac cctggggggg cacacggtga gggccctgtc   3660
gcccacccac cctgagccca ccacggacga ggatgacgac gacctggacg acggtgaggc   3720
gggggggcgg cgaggaccct gggggaggag gaggaggagg ggggagggag gaataggcgg   3780
gcgggggggc gaggaaaggg cgggcgcgga aagggagggc ctgggagggg gcgtaacctg   3840
atcgcgcccc ccgttgtctc ttgcagcaga ctacgtaccg cccgcccccc gccggacgcc   3900
ccgcgccccc ccacgcagag gcgccgccgc gccccccgtg acgggcgggg cgtctcacgc   3960
agccccccag ccggccgcgg ctcggacagc gcccccctcg gcgcccatcg ggccacacgg   4020
cagcagtaac accaacacca ccaccaacag cagcggcggc ggcggcggct cccgccagtc   4080
gcgagccgcg gcgccgcggg gggcgtctgg cccctccggg ggggttgggg ttggggttgg   4140
ggttgttgaa gcggaggcgg ggcggccgag gggccggacg ggccccccttg tcaacagacc   4200
cgcccccctt gcaaacaaca gagaccccat agtgatcagc gactcccccc cggcctctcc   4260
ccacaggccc cccgcggcgc ccatgccagg ctccgccccc cgccccgggc ccaccgcgtc   4320
ctcggccgcg tcgggacccg cgcgcccccg cgcggccgtg gccccgtgcg tgcgagcgcc   4380
gcctccgggg cccggccccc gcgccccggc ccccgcggac gcgcgccgtg tgccccagtc   4440
gcactcgtcc ctggctcagg ccgcgaacca agaacagagt ctgtgccggg cgcgtgcgac   4500
ggtggcgcgc ggctcggggg ggccgggcgt ggagggtgga cacgggccct cccgcggcgc   4560
cgccccctcc ggcgcccccc cgctcccctc cgccgcctct gtcgagcagg aggcggcggt   4620
gcgtccgagg aagaggcgcg ggtcgggcca ggaaaacccc tccccccagt ccacgcgtcc   4680
ccccctcgcg ccggcagggg ccaagagggc ggcgacgcac ccccccctccg actcagggcc   4740
gggggggcgc ggccagggtg ggcccgggac ccccctgacg tcctcggcgg cctccgcctc   4800
ttcctcctct gcctcttcct cctcggcccc gactcccgcg gggggccgcct cttccgccgc   4860
cggggccgcg tcctcctccg cttccgcctc ctcgggcggg gccgtcggtg ccctgggagg   4920
gagacaagag gaaacctccc tcggcccccg cgctgcttct gggccgcggg ggccgaggaa   4980
gtgtgcccgg aagacgcgcc acgcggagac ttccggggcc gcccccgcgg gcggcctcac   5040
gcgctacctg cccatctcgg gggtctctag cgtggtcgcc ctgtcgcctt acgtgaacaa   5100
gacgatcacg ggggactgcc tgcccatcct ggacatggag acggggaaca tcggggcgta   5160
cgtggtcctg gtggaccaga cgggaaacat ggcgacccgg ctgcgggccg cggtccccgg   5220
```

```
ctggagccgc cgcaccctgc tccccgagac cgcgggtaac cacgtgatgc cccccgagta   5280
cccgacggcc cccgcgtcgg agtggaacag cctctggatg acccccgtgg ggaacatgct   5340
gttcgaccag ggcaccctag tgggcgccct ggacttccgc agcctgcggt ctcggcaccc   5400
gtggtccggg gagcaggggg cgtcgacccg ggacgaggga aaacaataag ggacgccccc   5460
cgtgtttgtg gggagggggg ggtcgggcgc tgggtggtct ctggccgcgc ccactacacc   5520
agccaatccg tgtcggggag gggaaaagtg aaagacacgg gcaccacaca ccagcgggtc   5580
tttagtgttg gccctaataa aaaactcagg ggatttttgc tgtctattgg gaaataaagg   5640
tttacttttg tatcttttcc ctgtctgtgt tggatggatc tcgggggtgc gtgggagtgg   5700
gggtgcgtgg gagtgggggt gcgtgggagt gggggtgcgt gggagtgggg gtgcgtggga   5760
gtgggggtgc gtgggagtgg gggtgcgtgg gagtgggggt gcgtgggagt gggggtgcgt   5820
gggagtgggg gtgccatgtt gggcaggctc tggtgttaac cacagagccg cggcccgggc   5880
tgcctgacca ccgatccccg aaagcatcct gccactggca tggagccaga accacagtgg   5940
gttgggtgtg ggtgttaagt ttccgcgagc gcctgcccgc ccggactgac ctggcctctg   6000
gccgccacaa agggcggggg ggggttaact acactatagg gcaacaaagg acgggagggg   6060
tggcggggcg ggacggggcg cccaaaaggg ggtcggccac accacagacg tgggtgttgg   6120
ggggtggggc ggaggggtgg ggggggagac agaaacagga acatagttag aaaacaagaa   6180
tgcggtgcag ccagagaatc acaggagacg aggggatggg cgtgttggtt accaacccac   6240
acccaggcat gctcggtggt atgaaggagg gggggcggtg cttcttagag accgccgggg   6300
gacgtggggt tggtgtgcag aggcacgcgc acccgcgtcg gccaggtggg ccggtacccc   6360
atccccccto ccccgaccct tcccaccccc gcgtgccaga gatcaccccg gtcccccggc   6420
acccgccact cctccatatc ctcgctttag gaacaacttt aggggggggta cacacgcgcc   6480
gtgcatttcc ttccacaccc cccctccccc gcactccccc ccccccggca gtaagaccca   6540
agcatagaga gccaggcaca aaaacacagg cggggtggga cacatgcctt cttggagtac   6600
gtgggtcatt ggcgtggggg gttacagcga caccggccga ccccctggcg gtcttccagc   6660
cggcccttag ataagggggc agttggtggt cggacgggta agtaacagag tctgactaag   6720
ggtgggaggg ggggaaaaga acgggctggt gtgctgtaac acgagcccac ccgcgagtgg   6780
cgtggccgac cttagcctct ggggcgcccc ctgtcgtttg ggtccccccc ctctattggg   6840
gagaagcagg tgtctaacct acctggaaac gcggcgtctt tgttgaacca caccggggcg   6900
cccttgacga gtgggataac gggggaggaa gggagggagg agggtactgg gggtgaagaa   6960
gggggggggg ggagaagcga gaacaggaaa ggcgacggag cccgacaaaa caccgagaaa   7020
aaaaaaccac agcgcatgcg ccgggccgtt gtggggcccc gggccggggc cccttgggtc   7080
cgccggggcc ccgggccggg ccgccacggg ggccggccgt tggcggtaac cccgattgtt   7140
tatctcaggc cccgggccgg gaacccggaa aagcctccgg ggggcctttt tcgcgtcgcg   7200
tgccggcgag cgggcccgga cggggcccgg accgccgcgg tcgggggccc cctcgtcccg   7260
ggccgtacgc ggccttcgcc ccgtgagggg acagacgaac gaaacattcc ggcgacggaa   7320
cgaaaaacac cccagacggg ttaaagaaac agaaaccgca accccccccca cccccgaaac   7380
ggggaaaaca aaaaacagac cagcggccgg ccggcgctta gggggaggat gtcgccgacg   7440
cccctggcc gccccggctg caggggggcc cggagagccg cggcacccgg acgcgcccgg   7500
aaagtctttc gcaccacccg cgatcggcac ggccgcgccc ccgcttttat aaaggctcag   7560
atgacgcagc aaaaacaggc cacagcacca cgtgggtagg tgatgtaatt ttattttcct   7620
```

```
cgtctgcggc ctaatggatt tccgggcgcg gtgcccctgt ctgcagagca cttaacggat   7680
tgatatctcg cgggcacgcg cgcccttaat ggaccggcgc ggggcggggg gccggatacc   7740
cacacgggcg gggggggggg tgtcgcgggc cgtctgctgg cccgcggcca cataaacaat   7800
gactctgggc ctttctgcct ctgccgcttg tgtgtgcgcg cgccggctct gcggtgtcgg   7860
cggcggctgc ggcggctgcg gcggccgccg tgttcggtct cggtagccgg ccggcgggtg   7920
gactcgcggg gggccggagg gtggaaggca ggggggtgta ggatgggtat caggacttcc   7980
acttcccgtc cttccatccc ccgttcccct cggttgttcc tcgccccccc ccacaccccg   8040
ccgctttccg ttggggttgt tattgttgtc gggatcgtgc gggccggggg tcgccggggc   8100
aggggcgggg gcgggggtgc tcgtcgatcg accgggctca gtgggggcgt ggggtggggg   8160
ggaaaaggcg aagagactgg gggtgggggg gggtgtcggg ggtggctgtt tttttttgtg   8220
ggtgtttttt gtggctgttc ccgtccccccg tcaccccccct ccctccgtcc ccccgtcgcg   8280
ggtgtttgtg tttgtttatt ccgacatcgg tttatttaaa taaacacagc cgttctgcgt   8340
gtctgttctt gcgtgtggct gggggcttat atgtggggtc ccgggggcgg gatggggttt   8400
agcggcgggg ggcggcgcgc cggacggggc gctggagata acggccccccg gggaacgggg   8460
gaccggggct gggtctcccg aggtgggtgg gtgggcggcg gtggccgggc cgggccgggc   8520
cgggtgggcg gggtttggaa aaacgaggag gaggaggagg agaaggaggg ggggggagac   8580
ggggggaaag caaggacacg gcccgggggg tgggagcgcg ggccgggccg ctcgtaagag   8640
ccgcgacccg gccgccgggg agcgttgtcg ccgtcggtct gccggccccc gtccctccct   8700
tttttgacca accagcgccc cccccctca ccaccattcc taccaccacc accaccaccg   8760
acacctcccg cacacccccg cccacactcc cccccccac ccaacccgca ccacgagcac   8820
gggttggggg tagcagggga tcaaaggggg gcaaggccgg cggggcggtt cgggggcggg   8880
ggcgggagac cgagtaggcc ccgcccatcc gcggcccctc ccggcagcca cgccccccag   8940
cgtcgggtgt cacggggaaa gagcaggggg agaggggaga ggggggagag gggagagggg   9000
ggggagaggg gagaggggga gagaggggag aggggggag aggggagagg gggggagagg   9060
ggagaggggg ggagagggga gagggggga gaggggagag gggggagag gggagagggg   9120
gggagagggg agaggggggg agagggggta tataaaccaa cgaaaagcgc gggaacgggg   9180
atacggggct tgtgtggcac gacgtcgtgg ttgtgttact gggcaaacac ttggggactg   9240
taggtttctg tgggtgccga ccctaggcgc tatggggatt ttgggttggg tcgggcttat   9300
tgccgttggg gttttgtgtg tgcggggggg cttgtcttca accgaatatg ttattcggag   9360
tcgggtggct cgagaggtgg gggatatatt aaaggtgcct tgtgtgccgc tcccgtctga   9420
cgatcttgat tggcgttacg agaccccctc ggctataaac tatgctttga tagacggtat   9480
atttttgcgt tatcactgtc ccggattgga cacggtcttg tgggataggc atgcccagaa   9540
ggcatattgg gttaacccct ttttatttgt ggcgggtttt ttggaggact tgagtcaccc   9600
cgcgtttcct gccaacaccc aggaaacaga aacgcgcttg gccctttata aagagatacg   9660
ccaggcgctg gacagtcgca agcaggccgc cagccacaca cctgtgaagg ctgggtgtgt   9720
gaactttgac tattcgcgca cccgccgctg tgtagggcga caggatttgg gacctaccaa   9780
cggaacgtct ggacggaccc cggttctgcc gccggacgat gaagcgggcc tgcagccgaa   9840
gcccctcacc acgccgccgc ccatcatcgc cacgttggac cccaccccgc gacgggacgc   9900
cgccgcaaaa agcagacgcc gacgacccca ctcccggcgc atctaatgat gccgcgacgg   9960
```

aaacccgtcc gggttcgggg ggcgaaccgg ccgcctgtcg ctcgtcaggg ccggcgggcg 10020
ctcctcgccg ccctagaggc tgtcccgctg gtgtgacgtt ttcctcgtcc gcgccccccg 10080
accctcccat ggatttaaca aacggggggg tgtcgcctgt ggcgacctcg gcgcctctgg 10140
actggaccac gtttcggcgt gtgtttctga tcgacgacgc gtggcggccc ctgttggagc 10200
ctgagctggc gaacccctta accgcccacc tcctgaccga atataatcgt cggtgccaga 10260
ccgaagaggt gctgccgccg cgggaggatg tgttttcgtg gactcgttat tgcacccccg 10320
acgaggtgcg cgtggttatc atcggccagg acccatatca ccaccccggc caggcgcacg 10380
gacttgcgtt tagcgtgcgc gcgaacgtgc cgcctccccc gagtcttcgg aatgtcttgg 10440
cggccgtcaa gaactgttat cccgaggcac ggatgagcgg ccacggttgc ctggaaaagt 10500
gggcgcggga cggcgtcctg ttactaaaca cgaccctgac cgtcaagcgc ggggcggcgg 10560
cgtcccactc tagaatcggt tgggaccgct tcgtgggcgg agttatccgc cggttggccg 10620
cgcgccgccc cggcctggtg tttatgctct ggggcgcaca tgcccagaat gccatcaggc 10680
cggaccctcg ggtccattgc gtcctcaagt tttcgcaccc gtcgcccctc tccaaggttc 10740
cgttcggaac atgccagcat ttcctcgtgg cgaatcgata tctcgagacc cggtcgattt 10800
cacccatcga ctggtcggtt tgaaaggcat cgacgtccgg ggttttcgtc tgtgggggct 10860
tttgggtatt tccgatgaat aaagacggtt aatggttaaa cctctggtct catacgggtc 10920
ggtgatgtcg ggcgtcgggg gagagggagt tccctctgcg cttgcgattc tagcctcgtg 10980
gggctggacg ttcgacacgc caaaccacga gtcagggata tcgccagata cgactcccgc 11040
agattccatt cgggggggccg ctgtggcctc acctgaccaa cctttacacg gggcccggga 11100
acgggaggcc acagcgccgt ctttctcccc aacgcgcgcg gatgacggcc cgccctgtac 11160
cgacgggccc tacgtgacgt ttgataccct gtttatggtg tcgtcgatcg acgaattagg 11220
gcgtcgccag ctcacggaca ccatccgcaa ggacctgcgg ttgtcgctgg ccaagtttag 11280
cattgcgtgc accaagacct cctcgttttc gggaaacgcc ccgcgccacc acagacgcgg 11340
ggcgttccag cgcggcacgc gggcgccgcg cagcaacaaa agccttcaga tgtttgtgtt 11400
gtgcaaacgc acccacgccg ctcgagtgcg agagcagctt cgggtcgtta ttcagtcccg 11460
caagccgcgc aagtattaca cgcgatcttc ggacgggcgg ctctgccccg ccgtccccgt 11520
gttcgtccac gagttcgtct cgtccgagcc aatgcgcctc caccgagata acgtcatgct 11580
ggcctcgggg gccgagtaac cgcccccccg cgccaccctc actgcccgtc gcgcgtgttt 11640
gatgttaata aataacgcat aaatttggct ggttgtttgt tgtctttaat ggaccgcccg 11700 caggggggggt ggcatttcag tgtcgggtga cgagcgcgat ccggccggga tcctaggacc 11760
ccaaaagttt gtctgcgtat tccagggcgg ggctcagttg aatctcccgc agcacctcta 11820
ccagcaggtc cgcggtgggc tggagaaact cggccgtccc ggggcaggcg gtcgtcgggg 11880
gtggaggcgc ggcgcccacc ccgtgtgccg cgcctggcgt ctcctctggg ggcgacccgt 11940
aaatggttgc agtgatgtaa atggtgtccg cggtccagac cacggtcaaa atgccggccg 12000
tggcgctccg ggcgctttcg ccgcgcgagg agctgaccca ggagtcgaac ggatacgcgt 12060
acatatgggc gtcccacccg cgttcgagct tctggttgct gtcccggcct ataaagcggt 12120
aggcacaaaa ttcggcgcga cagtcgataa tcaccaacag cccaatgggg gtgtgttgga 12180
taacaacgcc tccgcgcggc aggcggtcct ggcgctcccg gccccgtacc atgatcgcgc 12240
gggtgccgta ctcaaaaaca tgcaccacct gcgcggcgtc gggcagtgcg ctggtcagcg 12300
aggccctggc gtggcatagg ctatacgcga tggtcgtctg tggattggac atctcgcggt 12360

```
gggtagtgag tcccccgggc cgggttcggt ggaactgtaa ggggacggcg ggttaatata  12420
caatgaccac gttcggatcg cgcagagccg atagtatgtg cttactaatg acgtcatcgc  12480
gctcgtggcg ctcccggagc ggatttaagt tcatgcgaag gaattcggag gaggtggtgc  12540
gggacatggc cacgtacgcg ctgttgaggc gcaggttgcc gggcgtaaag cagatggcga  12600
ccttgtccag gctaaggccc tgggagcgcg tgatggtcat ggcaagcttg gagctgatgc  12660
cgtagtcggc gtttatggcc atggccagct ccgtagagtc aatggactcg acaaactcgc  12720
tgatgttggt gttgacgacg gacatgaagc cgtgttggtc ccgcaagacc acgtaaggca  12780
ggggggcctc ttccagtaac tcggccacgt tggccgtcgc gtgccgcctc cgcagctcgt  12840
ccgcaaaggc aaacacccgt gcgtacgtgt atcccatgag cgtataattg tccgtctgca  12900
gggcgacgga catcagcccc ccgcgcggcg agccggtcag catctcgcag ccccggaaga  12960
taacgttgtc cacgtacgtg ctaaaggggg cgccttcaaa tgcctcccca aagagctctt  13020
ggaggattcg gaatctcccg aggaaggccc gcttcagcag cgcaaactgg gtgtgaacgg  13080
cggcggtggt ctccggttcc ccgggggtgt agtggcagta aaacacgtcg agctgttgtt  13140
cgtccagccc cgcgaaaata acgtcgaggt cgtcgtcggg aaaatcgtcc gggcccccgt  13200
cccgcggccc cagttgctta aaatcaaacg cacgctcgcc gggggcgcct gcgtcggcca  13260
ttaccgacgc ctgcgtcggc acccccgaag atttggggcg cagagacaga atctccgccg  13320
ttagttctcc catgcgggcg taggcgaggg tcctctgggt cgcatccagg cccgggcgct  13380
gcagaaagtt gtaaaaggag ataagcccgc taaatatgag ccgcgacagg aacctgtagg  13440
caaactccac cgaagtctcc ccctgagtct ttacaaagct gtcgtcacgc aacactgcct  13500
cgaaggcccg gaacgtccca ctaaacccaa aaaccagttt tcgcaggcgc gcggttaccg  13560
cgatctggct gttgaggacg taagtgacgt cgttgcgggc cacgaccagc tgctgtttgc  13620
tgtgcacctc gcagcgcatg tgccccgcgt cctggtcctg gctctgcgag tagttggtga  13680
tgcggctggc gttggccgtg agccactttt caatagtcag gccgggctgg tgtgtcagcc  13740
gtcggtattc gtcaaactcc ttgaccgaca cgaacgtaag cacggggagg gtgaacacga  13800
caaactcccc ctcacgggtc accttcaggt aggcgtggag cttggccatg tacgcgctca  13860
cctctttgtg ggaggagaac aaccgcgtcc agccggggag gttggcgggg ttggtgatgt  13920
agttttccgg gacgacgaag cgatccacga actgcatgtg ctcctcggtg atgggtaggc  13980
cgtactccag caccttcatg aggttaccga actcgtgctc gatgcaccgt ttgttgttaa  14040
taaaaatggc ccagctatac gagaggcggg cgtactcccg cagcgtgcgg ttgcagatga  14100
ggtacgtgag cacgttctcg ctctggcgga cggaacaccg cagtttctgg tgctcgaagg  14160
tcgactccag ggacgccgtc tgtgtcggcg agcccacaca caccaacacg ggccgcaggc  14220
gggccgcgta ctggggggtg tggtacaggg cgttaatcat ccaccagcaa tacaccacgg  14280
ccgtgaggag gtgacgccca aggagcccgg cctcgtcgat gacgatcacg ttgctgcggg  14340
taaaggccgg cagcgccccg tgggtggccg gggccaaccg cgtcagggcg ccctcggcca  14400
accccagggt ccgttccagg gcggccaggg cgcgaaactc gttccgcgac tcctcgcccc  14460
cggaggcggc cagggtgcgc ttcgtgaggt ccaaaatcac ctcccagtag tacgtcagat  14520
ctcgtcgctg caggtcctcc agcgaggcgg ggttgctggt cagggtgtac gggtactgcc  14580
ccagttgggc ctggacgtga ttcccgcgaa acccaaattc atgaaagatg gtgttgatgg  14640
gtcggctgag aaaggcgccc gagagtttgg cgtacatgtt ttgggccgca atgcgcgtgg  14700
```

```
cgcccgtcac cacacagtcc aagacctcgt tgattgtctg cacgcacgtg ctctttccgg  14760
agccagcgtt gccggtgata agatacaccg cgaacggaaa ctccctgagg ggcaggcctg  14820
cgggggactc taaggccgcc acgtcccgga accactgcag acggggcact tgcgctccgt  14880
cgagctgttg ttgcgagagc tctcggatgc gcttaaggat tggctgcacc ccgtgcatag  14940
acgtaaaatt taaaaaggcc tcggccctcc ctggaacggc tggtcggtcc ccgggttgct  15000
gaaggtgcgg cgggccgggt ctctgtccgt ctagctggcg ctccccgccg gccgccgcca  15060
tgaccgcacc acgctcgcgg gcccccacta cgcgtgcgcg gggggacacg gaagcgctgt  15120
gctcccccga ggacggctgg gtaaaggttc accccacccc cggtacgatg ctgttccgcg  15180
agattctcca cgggcagctg gggtataccg agggccaggg ggtgtacaac gtcgtccggt  15240
ccagcgaggc gaccacccgg cagctgcagg cggcgatctt tcacgcgctc ctcaacgcca  15300
ccacttaccg ggacctcgag gcggactggc tcggccacgt ggcggcccgc ggtctgcagc  15360
cccaacggct ggttcgccgg tacaggaacg cccgggaggc ggatatcgcc ggggtggccg  15420
agcgggtgtt cgacacgtgg cggaacacgc ttaggacgac gctgctggac tttgcccacg  15480
ggttggtcgc ctgctttgcg ccgggcggcc cgagcggccc gtcaagcttc cccaaatata  15540
tcgactggct gacgtgcctg ggctggtcc ccatattacg caagcgacaa gaagggggtg  15600
tgacgcaggg tctgagggcg tttctcaagc agcacccgct gacccgccag ctggccacgg  15660
tcgcggaggc cgcggagcgc gccggccccg ggttttttga gctggcgctg gccttcgact  15720
ccacgcgcgt ggcggactac gaccgcgtgt atatttacta caaccaccgc cggggcgact  15780
ggctcgtgcg agaccccatc agcgggcagc gcggagaatg tctggtgctg tggcctccct  15840
tgtggaccgg ggaccgtctg gtcttcgatt cgcccgtaca gcggctgttt cccgagatcg  15900
tcgcgtgtca ctccctccgg gaacacgcgc acgtctgccg gctgcgcaat accgcgtccg  15960
tcaaggtgct gctggggcgc aagagcgaca gcgagcgcgg ggtggccggc gccgcgcggg  16020
tcgttaacaa ggtgttgggg gaggacgacg agaccaaggc cgggtcggcc gcctcgcgcc  16080
tcgtgcggct tatcatcaac atgaagggca tgcgccacgt aggcgacatt aacgacactg  16140
tgcgtgccta cctcgacgag gccgggggc acctgataga cgccccggcc gtcgacggta  16200
ccctcccggg attcggcaag ggcggaaaca gccgcgggtc tgcgggccag gaccaggggg  16260
ggcgggcgcc gcagcttcgc caggccttcc gcacggccgt ggttaacaac atcaacggcg  16320
tgttggaggg ctatataaat aacctgtttg gaaccatcga gcgcctgcgc gagaccaacg  16380
cgggcctggc gacccagttg caggagcgcg accgcgagct ccggcgcgca acatcggggg  16440
ccctggagcg ccagcagcgc gcggccgacc tggcggccga gtccgtgacc gggggatgcg  16500
gcagccgccc tgcgggggcg gacctgctcc gggccgacta tgacattatc gacgtcagca  16560
agtccatgga cgacgacacg tacgtcgcca acagttttca gcacccgtac atcccttcgt  16620
acgcccagga cctggagcgc ctgtcgcgcc tctgggagca cgagctggtg cgctgtttca  16680
aaattctgtg tcaccgcaac aaccagggcc aagagacgtc gatctcgtac tccagcgggg  16740
cgatcgccgc attcgtcgcc ccctactttg agtcagtgct tcgggccccc cgggtaggcg  16800
cgcccatcac gggctccgat gtcatcctgg gggaggagga gttatgggat gcggtgttta  16860
agaaaacccg cctgcaaacg tacctgacag acatcgcggc cctgttcgtc gcggacgtcc  16920
agcacgcagc gctgcccccg ccccccctccc cggtcggcgc cgatttccgg cccggcgcgt  16980
ccccgcgggg ccggtccaga tcgcggtcgc ccggaagaac tgcgcgaggc gcgccggacc  17040
agggcggggg catcgggcac cgggatggcc gccgcgacgg ccgacgatga ggggtcggcc  17100
```

gccaccatcc tcaagcaggc catcgccggg gaccgcagcc tggtcgaggc ggccgaggcg 17160
attagccagc agacgctgct ccgcctggcc tgcgaggtgc gccaggtcgg cgaccgccag 17220
ccgcggttta ccgccaccag catcgcgcgc gtcgacgtcg cgcctgggtg ccggttgcgg 17280
ttcgttctgg acgggagtcc cgaggacgcc tatgtgacgt cggaggatta ctttaagcgc 17340
tgctgcggcc agtccagtta tcgcggcttc gcggtggcgg tcctgacggc caacgaggac 17400
cacgtgcaca gcctggccgt gcccccccctc gttctgctgc accggttctc cctgttcaac 17460
cccagggacc tcctggactt tgagcttgcc tgtctgctga tgtacctgga gaactgcccc 17520
cgaagccacg ccaccccgtc gacctttgcc aaggttctgg cgtggctcgg ggtcgcgggt 17580
cgccgcacgt ccccattcga acgcgttcgc tgccttttcc tccgcagttg ccactgggtc 17640
ctaaacacac tcatgttcat ggtgcacgta aaaccgttcg acgacgagtt cgtcctgccc 17700
cactggtaca tggcccggta cctgctggcc aacaacccgc cccccgttct ctcggccctg 17760
ttctgtgcca ccccgacaag ctcctcattc cggctgccgg ggccgccccc ccgctccgac 17820
tgcgtggcct ataaccccgc cgggatcatg gggagctgct gggcgtcgga ggaggtgcgc 17880
gcgcctctgg tctattggtg gctttcggag accccaaaac gacagacgtc gtcgctgttt 17940
tatcagtttt gttgaatttt aggaaataaa cccggttttg tttctgtggc ctcccgacgg 18000
atgcgcgtgt ccttactccg tcttggtggg tgggtggctg tgtatggcgt cccatctgtg 18060
cggggagggg ggcaagtcgg cacgtattcg gacagactca agcacacacg ggggagcgct 18120
cttgtctcag ggcaatgttt ttattggtca aactcaggca aacagaaacg acatcttgtc 18180
gtcaaaggga tacacaaact tcccccccctc gccccatact cccgccagca ccccggtaaa 18240
caccaactca atctcgcgca ggatttcgcg caggtgatga gcgcagtcca cgggggggag 18300
cacaaggggc cgcgggtata gatcgacggg gacgccgacc gactccccgc ctccgggaca 18360
gacacgcacg acgcgccgcc agtagtgctc tgcgtccagc aaggcgccgc cgcggaaggc 18420
agtgggggc aaggggtcgc tggcctcaaa gggggacacc cgaacgctcc agtactccgc 18480
gtccaaccgt ttattaaacg cgtccaagat aaggcggtcg caggcgtcct ccataaggcc 18540
ccgggccgtg agtgcgtcct cctccggcac gcctgccgtt gtcaggccca ggacccgtcg 18600
cagcgtgtcg cgtacgaccc cggccgccgt ggtgtacgcg ggcccgcgga gaggaaatcc 18660
cccaagatgg tcagtgttgt cgcgggagtt ccagaaccac actcccgcct ggctccaggc 18720
gactgcgtgg gtgtagacgc cctcgagggc caagcacagt gggtgccgca gccggaggcc 18780
gttggcccta agcacggctc ccacggccgt ctcgatggcc cgccgggcgt cctcgatcac 18840
cccggaagcc gcatccgcgt cttgggggtc cacgttaaag acaccccaga acgcaccccc 18900
atcgcccccg cagaccgcga acttcaccga gctggccgtc tcctcgatct gcaggcagac 18960
ggcggccatt accccaccca ggagctgccg cagcgcaggg caggcgttgc acgtgtccgg 19020
gaccaggcgc tccaagacgg ccccggccca gggctctgag ggagcggcca ccaccagcgc 19080
gtccagtctt gctaggcccg tccggccgtg ggggtccgcc agcccgctcc ccccgaggtc 19140
ggccagggcc gccaggagct gggcgcgaag tccggggaag caaaaccgcg ccgtccagac 19200
gggcccgacg gccgcgggcg ggtctaacag ttggatgatt ttagtggcgg gatgccaccg 19260
cgccaccgcc tcccgcactg cgggcaggag gcatccggct gccgccgagg ccacgccggg 19320
ccaggctcgc ggggggagga cgaccctgac ccccaccgcg ggccaggccc ccaggagcgc 19380
ggcgtaagcg gccgcggccc cgcgcaccag gtcccgtgcc gactcggccg tggccggcac 19440
ggtgaacgtg ggccaacccg gaaaccccag gacggcaaag tacgggacgg gtcccccccg 19500
gacctcaaac tcgggcccca gaaaggcaaa gacgggggcc agggccccgg gggcggcgtg 19560
gaccgtggta tgccactgcc ggaaaagggc gacgagcgcc ggcgcggaga acttctcgcc 19620
ggcgcttaca aagtagtcgt aatcgcgggg cagcagcacc cgtgccgtga ctcgttgtgg 19680
gtgcccgcgt ggccgcaggc ccacctcgca cacctcgacc aggtccccga acgcgccctc 19740
cttcttgatc ggcggaaacg caagagtctg gtattcgcgc gcaaatagcg cggttccggt 19800
ggtgatgtta acggtcagcg aagcggtgga cgcgcactgg ggggtgtcgc gaatggccgc 19860
caggcgcgcc cacgccagcc gcgcgtcggg atgctcggca acgcgcgccg ccagggccat 19920
agggtcgatg tcaatgttgg cctccgcgac caggagagcg gcgcgagggg cggcgggcgg 19980
gccccacgac gctctctcaa ctttcaccac cagtcccgtg cgtgggtccg agccgatacg 20040
cagcggggcg aacagggcca ccggcccggt ctggcgctcc agggccgcca ggacgcacgc 20100
gtacagcgcc cgccacagag tcgggttctc caggggctcc agcggggagg cggccggcgt 20160
cgtcgcggcg cgggcggccg ccacgacggc ctggacggag acgtccgcgg agccgtagaa 20220
atcccgcagc tccgtcgcgg tgacggagac ctccgcaaag cgcgcgcgac cctcccctgc 20280
ggcgttgcga catacaaaat acaccagggc gtggaagtac tcgcgagcgc ggggggggcag 20340
ccataccgcg taaagggtaa tggcgctgac gctctcctcc acccacacga tatctgcggt 20400
gtccatcgca cggcccctaa ggatcacggg cggtctgtgg gtcccatgct gccgtgcctg 20460
gccgggcccg gtgggttgcg gaaaccggtg acgggggggg gggcggtttt tggggttggg 20520
gtgggaaacg gcccgggtcc gggggccaac ttggcccctc ggtgcgttcc ggcaacagcg 20580
ccgccggtcc gcggacgacc acgtaccgaa cgagtgcggt cccgagactt atagggtgct 20640
aaagttcacc gccccctgca tcatgggcca ggcctcggtg gggagctccg acagcgccgc 20700
ctccaggatg atgtcagcgt tggggttggc gctggatgag tgcgtgcgca aacagcgccc 20760
ccacgcgggc acgcgtagct tgaagcgcgc gcccgcaaac tcccgcttgt gggccataag 20820
cagggcgtac agctgcctgt gggtccggca ggcgctgtgg tcgatgtggt gggcgtccaa 20880
caaccccacg attgtctgtt tggtgaggtt tttaacgcgc cccgccccgg gaaacgtctg 20940
cgtgcttttg gccatctgca cgccaaacag ttcgccccag attatcttga acagcgccac 21000
cgcgtggtcc gtctcactaa cggaccgcgc gggggacagc cgcttagggc gtcggcgacg 21060
cgcttgacgg cttcctccga gagcagaagt ccgtcggtta cgttacagtg gcccagttcg 21120
aacaccagct gcatgtagcg gtcgtagtgg ggggtcagca ggtccagcac gtcatcgggg 21180
ccgaaggtcc tcccagatcc cccggccgcc gagtcccaat gcaggcgcgc ggccatggtg 21240
ctgcacaggc acaacagctc ccagacaggg gttacgttca gggtgggggg cagggccacg 21300
agctccagct ctccggtgac gttgatcgtg gggatgacgc ccgtggcgta gtggtcatag 21360
atccgccgaa atatggcgct gctgcgggtg gccatgggaa cgcggagaca ggcctccagc 21420
aacgccaggt aaataaaccg cgtgcgtccc atcaggctgt tgaggttgcg catgagcgcg 21480
acaatttccg ccggcgcgac atcggaccgg aggtattttt cgacgaaaag acccacctcc 21540
tccgtctcgg cggcctgggc cggcagcgac gcctcgggat cccggcaccg cagctcccgt 21600
agatcgcgct gggccctgag ggcgtcgaaa tgtacgcccc gcaaaaaacag acagaagtcc 21660
tttggggtca gggtatcgtc gtgtccccag aagcgcacgc gtatgcagtt tagggtcagc 21720
agcatgtgaa ggatgttaag gctgtccgag agacacgcca gcgtgcatct ctcaaagtag 21780
tgtttgtaac ggaatttgtt gtagatgcgc gacccccgcc ccagcgacgt gtcgcatgcc 21840

-continued gacgcgtcac agcgcccctt gaaccggcga cacagcaggt ttgtgacctg ggagaactgc 21900
gcgggccact ggccgcagga actgaccacg tggttcagga gcatgggcgt aaagacgggc 21960
tccgagcgcg ccccggagcc gtccatgtaa atcagtagct ccccccttgcg gagggtgcgc 22020 acccgtccca gggactggta cacggacacc atgtccggtc cgtagttcat gggtttcacg 22080
taggcgaaca tgccatcaaa gtgcagggga tcgaagctga ggcccacggt tacgaccgtc 22140
gtgtatataa ccacgcggta ttggccccac gtggtcacgt ccccgagggg ggtgagcgag 22200
tgaagcaaca gcacgcggtc cgtaaactga cggcagaacc gggccacgat ctccgcgaag 22260
gagaccgtcg acgaaaaaat gcagatgtta tcgcccccgc caaggcgcgc ttccagctcc 22320
ccaaagaacg tggccccccg ggcgtccgga gaggcgtccg gagacgggcc gctcggcggc 22380
ccgggcgggc gcagggcagc ctgcaggagc tcggtcccca gacgcgggag aaacaggcac 22440
cggcgcgccg aaaacccggg catggcgtac tcgccgacca ccacatgcac gttttttttcg 22500 ccccggagac cgcacaggaa gtccaccaac tgcgcgttgg cggttgcgtc catggcgatg 22560
atccgaggac atgtgcgcag caggcgtagc attaacgcat ccacgcggcc cagttgctgc 22620
atcgttggcg aatagagctg gcccagcgtc gacataacct cgtccagaac gaggacgtcg 22680
tagttgttca gaaggttggg gcccacgcga tgaaggcttt ccacctggac gataagtcgg 22740
tggaaggggc ggtcgttcat aatgtaattg gtggatgaga agtaggtgac aaagtcgacc 22800
aggcctgact cagcgaaccg cgtcgccagg gtctgggtaa aactccgacg acaggagacg 22860
acgagcacac tcgtgtccgg agagtggatc gcttcccgca gccagcggat cagcgcggta 22920
gtttttcccg accccattgg cgcgcggacc acagtcacgc acctggccgt cggggcgctc 22980
gcgttgggga aggtgacggg tccgtgctgc tgccgctcga tcgttgtttt cgggtgaacc 23040
cggggcaccc attcggccaa atcccccccg tataacatcc gcgctagcga tacgctcgac 23100
gtgtactgtt cgcactcgtc gtccccaatg ggacgcccgg cccccagagg atcccccgac 23160
tccgcgcccc ccacgaaagg catgaccggg gcgcggacgg cgtggtgggt ctggtgtgtg 23220
caggtggcga cgtttgtggt ctctgcggtc tgcgtcacgg ggctcctcgt cctggcctct 23280
gtgttccggg cacggtttcc ctgcttttac gccacggcga gctcttatgc cggggttaac 23340
tccacggccg aggtgcgcgg gggtgtagcc gtgcccctca ggttggacac gcagagcctt 23400
gtgggcactt atgtaatcac ggccgtattg ttgttggccg cggccgtgta tgccgtggtc 23460
ggcgccgtga cctcccgcta cgaccgcgcc ctggacgcgg gccgccgtct ggctgcggcc 23520
cgcatggcca tgccgcacgc cacgctgatc gccggaaacg tctgctcttg gttgctgcag 23580
atcaccgtcc tgctgctggc ccatcgcatc agccagctgg cccacctggt ttacgtcctg 23640
cactttgcgt gtctggtgta ttttgcggcc catttttgca ccaggggggt cctgagcggg 23700
acgtatctgc gtcaggtgca cggcctgatg gagctggccc cgacccatca tcgcgtcgtc 23760
ggcccggctc gcgccgtgct gacaaacgcc ttgctgttgg gcgtcttcct gtgcacggcc 23820
gacgccgcgg tatccctgaa taccatcgcc gcgttcaact ttaatttttc ggccccgggc 23880
atgctcatct gcctgaccgt gctgttcgcc attctcgtcg tatcgctgtt gttggtggtc 23940
gagggggtgt tgtgtcacta cgtgcgcgtg ttggtgggcc cccacctggg ggccgttgcc 24000
gccacgggca tcgtcggcct ggcctgcgag cactattaca ccaacggcta ctacgtggtg 24060
gagacgcagt ggccgggggc acagacggga gtgcgcgtcg ccctcgccct ggtcgccgcc 24120
tttgccctcg gcatggccgt gctccgctgc acccgcgcct atctgtatca caggcggcac 24180
cacaccaaat tttttatgcg catgcgcgac acgcgacacc gcgcacattc cgccctcaag 24240
cgcgtacgca gttccatgcg cggatcgcga gacggccgcc acaggcccgc gcccggcagc 24300
ccgcccggga ttcccgaata tgcggaagac ccctacgcga tctcatacgg cggccagctc 24360
gaccggtacg gagattccga cggggagccg atttacgacg aggtggcgga cgaccaaacc 24420
gacgtattgt acgccaagat acaacacccg cggcacctgc ccgacgacga gcccatctat 24480
gacaccgttg gggggtacga ccccgagccc gccgaggacc ccgtgtacag caccgtccgc 24540
cgttggtagc tgtttggttc cgttttaata aaccgtttgt gtttaacccg accgtggtgt 24600
atgtctggtg tgtggcgtcc gatcccgtta ctatcaccgt cccccccct caaccccggc 24660 gattgtgggt tttttaaaaa cgacacgcgt gcgaccgtat acagaacatt attttggttt 24720
ttattcgcta tcggacatgg ggggtggaaa ctgggtggcg gggcaggcgc ctccgggggt 24780
ccgccggtga gtgtggcgcg agggggggtc cgacgaacgc aggcgcggtc tccccggggc 24840
ccgcgtaacc acgcgcatat ccgggggcac gtagaaatta ccttcctctt cggactcgat 24900
atccacgacg tcaaagtcgt gggcggtcag cgagacgacc tccccgtcgt cggtgatgag 24960
gacgttgttt cggcagcagc agggccgggc cccggagaac gagaggccca tagctcggcg 25020
agcgtgtcgt cgaacgccag gcggctgctt cgctggatgg ccttatagat ctccggatcg 25080
atgcggacgg gggtaatgat cagggcgatc ggaacggcct ggttcgggag aatggacgcc 25140
ttgctgggtc ctgcggcccc gagagccccg gcgccgtcct ccaggcggaa cgttacgccc 25200
tcctccgcgc tggtgcggtg cctgccgata aacgtcacca gatgcgggtg gggggggcag 25260
tcggggaagt ggctgtcgag cacgtagccc tgcaccaaga tctgcttaaa gttcgggtgg 25320
cgggggttcg cgaagacggg ctcgcggcgg accagatccc cggagctcca ggacacgggg 25380
gagatggtgt ggcgtccgag gtcgggggcg ccaaacagaa gcacctccga gacaacgccg 25440
ctatttaact ccaccaaggc ccgatccgcg gcggagcacc gcctttttttc gcccgaggcg 25500 tgggcctctg accaggcctg gtcttgcgtg acgagagcct cctccgggcc ggggacgcgc 25560
ccgggcgcga agtatcgcac gctgggcttc gggatcgacc ggataaatgc ccggaacgcc 25620
tccggggacc ggtgtgccat caagtcctcg tacgcggagg ccgtggggtc gctggggtcc 25680
atggggtcga aagcgtactt ggcccggcat ttgacctcgt aaaaggccag gggggtcttg 25740
gggactgggg ccaggtagcc gtgaatgtcc cgaggacaga cgagaatatc cagggacgcc 25800
ccgaccatcc ccgtgtgacc gtccatgagg accccacacg tatgcacgtt ctcttcggcg 25860
aggtcgctgg gttcgtggaa gataaagcgc cgcgtgtcgg cgccggcctc gccgccgtcg 25920
tccgcgcggc ccacgcagta gcgaaacagc aggcttcggg ccgtcggctc gttcacccgc 25980
ccgaacatca ccgccgaaga ctgtacatcc ggtcgcaggc tggcgttgtg cttcagccac 26040
tggggcgaga aacacggacc ctgggggccc cagcggaggg tggatgcggt cgtgaggccc 26100
cgccggagca gggcccatag ctggcagtcg gcctggtttt gcgtggccgc ctcgtaaaac 26160
cccatgaggg gccggggcgc cacggcgtcc gcggcggccg ggggggcgcg gcgcgtcagg 26220
cgccataggt gccggccgag tccgcggtcc accatacccg cctcctcgag gaccacggcc 26280
agggaacaca gataatccag gcgggcccag aggggaccga tggccagagg ggcgcggacg 26340
ccgcgcagca acccgcgcag gtggcgctcg aacgtctcgg ctagtatatg ggagggcagc 26400
gcgttgggga tcaccgacgc cgaccacata gagtcaaggt ccggggagtc gggatcggcg 26460
tccgggtcgc gggcgtgggt gcccccagga gatagcggaa tgtccggggt cggaggcccg 26520
gaggcgtcag aaagtgccgg cgacgcggcc cggggctttt cgtctgcggt gtcggtggcg 26580

```
tgctgatcac gtgggggggtt atcgggcgaa tgggagctcg ggtccacagc tgacgtcgtc  26640
tggggtgggg ggggcagggg acggaaggtg gttgtcagcg gaagactgtt agggcggggg  26700
cgcttggggg ggctgtcggg gccacgaggg gtgtcctcgg ccagggccca gggacgctta  26760
gtcacggtgc gtcccggcgg acatgctggg cctaccgtgg actccatttc cgagacgacg  26820
tggggggagc ggtggttgag cgcgccgccg ggtgaacgct gattctcacg acagcgcgtg  26880
ccgcgcgcac gggttggtgt gatacaggcg ggacaccagc accaggagag gcttaagctc  26940
gggaggcagc gccaccgacg acagtatcgc cttgtgtgtg tgctggtaat ttatacaccg  27000
atccgtaaac gcgcgccgaa tcttgggatt gcggaggtgg cgccggatgc cctctgggac  27060
gtcatacgcc aggccgtggg tgttggtctc ggccgagttg acaaacaggg ctgggtgcag  27120
cacgcagcga taggcgagca gggccagggc gaagtccggc gacagctggt tgttgaaata  27180
ctggtaaccg ggaaaccggg tcacgggtac gcccaggctc ggggcgacgt acacgctaac  27240
caccaactcc agcagcgtct ggcccagggc gtacaggtca accgctagcc cgacgtcgtg  27300
cttcaggcgg tggttggtaa attcggcccg ttcgttgtta aggtatttca ccaacagctc  27360
cgggggctgg ttatacccgt gacccaccag ggtgtgaaag ttggctgtgg ttagggcggt  27420
gggcatgcca aacatccggg gggacttgag gtccggctcc tggaggcaaa actgcccccg  27480
ggcgatcgtg gagttggagt tgagggtgac gaggctaaag tcggcgagga cggcccgccg  27540
gagcgagacg gcgtccgacc gcagcatgac gaggatgttg gcgcacttga tatccaggtg  27600
gctgatcccg caggtggtgt ttaaaaacac aacggcacgg gccagctccg tgaagcactg  27660
gtggagggcc gtcgagaccg aggggtttgt tgtgcgcagg gacgccagtt ggccgatata  27720
cttaccgagg tccatgtcgt acgcggggaa cactatctgt cgttgttgca gcgagaaccc  27780
gaggggcgcg atgaagccgc ggatgttgtg ggtgcggccg gcgcgtagag cgcactcccc  27840
gaccaacagg gtcgcgatga gctcaacggc aaaccactcc ttttccttta tggtcttaac  27900
ggcaagctta tgttcgcgaa tcagttggac ttcgccgtat cccccagacc ccccgaagct  27960
tcgggccccg gggatctcga gggtcgtgta gtgtagggcg gggttgatgg cgaacacggg  28020
gctgcatagc ttgcggatgc gcgtgagggt gaggatgtgc gagggggacg aggggggtgc  28080
ggttaacgcc gcctgggatc tgcgcagggg cgggcggttc agtttggccg ccgtaccggg  28140
cgcctcgggg gacgcgcggc gatgagacga gcggctcatt cgccatcggg atagtcccgc  28200
gcgaagccgc tcgcggaggc cggatcggtg gcggcacccg tgggaggagc gggagacggc  28260
ggcgttctgg agagaggggc cgctggggcg cccggaggcc ccatgggggt tggagtgtat  28320
gtaggatgcg agccaatcct tgaaggaccg ttggcgtgca ccttgggggc tgaggttagc  28380
tgccacatga ccagcaggtc gctgtctgcg ggactcatcc atccttcggc caggtcgccg  28440
tctccccaca gagaagcgtt ggtcgctgcc tcctcgagtt gctcctcctg gtccgcaaga  28500
cgatcgtcca cggcgtccag gcgctcacca agcgccggat cgaggtaccg tcggtgtgcg  28560
gttagaaagt cacgacgcgc cgcttgctcc tccacgcgaa ttttaacaca ggtcgcgcgc  28620
tgtcgcatca tctctaagcg cgcgcgggac tttagccgcg cctccaattc caagtgggcc  28680
gcctttgcag ccataaaggc gccaacaaac cgaggatctt gggtgctgac gccctcccgg  28740
tgcagctgca gggtctggtc cttgtaaatc tcggctcgga ggtgcgtctc ggccaggcgt  28800
cggcgcaggg ccgcgtgggc ggcatctcgg tccattccgc caccctgcgg gcgacccggg  28860
ggtgctctga tagtctcgcg tgcccaaggc ccgtgatcgg ggtacttcgc cgccgcgacc  28920
```

```
cgccacccgg tgtgcgcgat gtttggtcag cagctggcgt ccgacgtcca gcagtacctg  28980
gagcgcctcg agaaacagag gcaacttaag gtgggcgcgg acgaggcgtc ggcgggcctc  29040
acaatgggcg gcgatgccct acgagtgccc tttttagatt tcgcgaccgc gacccccaag  29100
cgccaccaga ccgtggtccc gggcgtcggg acgctccacg actgctgcga gcactcgccg  29160
ctcttctcgg ccgtggcgcg gcggctgctg tttaatagcc tggtgccggc gcaactaaag  29220
gggcgtgatt tcgggggcga ccacacggcc aagctggaat tcctggcccc cgagttggta  29280
cgggcggtgg cgcgactgcg gtttaaggag tgcgcgccgg cggacgtggt gcctcagcgt  29340
aacgcctact atagcgttct gaacacgttt caggccctcc accgctccga agcctttcgc  29400
cagctggtgc actttgtgcg ggactttgcc cagctgctta aaacctcctt ccgggcctcc  29460
agcctcacgg agaccacggg cccccccaaa aaacgggcca aggtggacgt ggccacccac  29520
ggccggacgt acggcacgct ggagctgttc caaaaaatga tccttatgca cgccacctac  29580
tttctggccg ccgtgctcct cggggaccac gcggagcagg tcaacacgtt cctgcgtctc  29640
gtgtttgaga tcccccctgtt tagcgacgcg gccgtgcgcc acttccgcca gcgcgccacc  29700
gtgtttctcg tcccccggcg ccacggcaag acctggtttc tggtgcccct catcgcgctg  29760
tcgctggcct cctttcgggg gatcaagatc ggctacacgg cgcacatccg caaggcgacc  29820
gagccggtgt ttgaggagat cgacgcctgc ctgcggggct ggttcggttc ggcccgagtg  29880
gaccacgtta aggggaaac catctccttc tcgtttccgg acgggtcgcg cagtaccatc  29940
gtgtttgcct ccagccacaa cacaaacgta agtcctcttt tctttcgcat ggctctccca  30000
aggggccccg ggtcgacccg acccacaccc acccacccac atacacacac aaccagacgc  30060
gggaggaaag tctgccccgt gggcactgat ttttattcgg gatcgcttga ggaggcccgg  30120
gcaacggccc gggcaacggt ggggcaactc gtagcaaata ggcgactgat gtacgaagag  30180
aagacacaca ggcgccaccc ggcgctggtc ggggggatgt tgtccgcgcc gcaccgtccc  30240
ccgacgacct cttgcagacg gtccgtgatg caaggacggc ggggggcctg cagcagggtg  30300
accgtatcca cgggatggcc aaagagaagc ggacacaggc tagcatcccc ctggaccgcc  30360
agggtacact gggccatctt ggcccacaga cacggggcga cgcagggaca ggactccgtt  30420
acgacggagg agagccacag tgcgttggcg gaatcgatgt ggggcggcgg ggcgcaggac  30480
tcgcagcccc ccgggtggtt agtgatcctg gccaggagcc atcccagatg gcgggccctg  30540
cttcccggtg gacagagcga ccccaggtcg ctgtccatgg cccagcagta gatctggccg  30600
ctggggaggt gccaccaggc ccccgggccc aaggcgcagc acgcgcccgg ctccgggggg  30660
gtcttcgcgg ggaccagata cgcgccatcc agctcgccga ccactggctc ctccgcgagc  30720
tgttcggtgg ttgggtcggg ggtttcctcc gggggggtgg ccgcccgtat gcgggcgaac  30780
gtgagggtgc acaggagcgg ggtcaggggg tgcgtcacgc tccggaggtg gacgatcgcg  30840
cagtagcggc gctcgcggtt aaagaaaaag agggcaaaga aggtgttcgg gggcaaccgc  30900
agcgccttgg ggcgcgtcag atacagaaaa atctcgcaga agagggcgcg cccggggtct  30960
gggttaggaa gggccacctg acacagaggc tcggtgagga ccgttagaca ccgaaagatc  31020
ttgagccgct cgtccgcccg aacgacgcgc cacacaaaga cggagttgac aatgcgcgcg  31080
atagagtcga cgtccgtccc caggtcgtcg actctgtcgc gcgtgccgcg agctccggcc  31140
cgggaatccg gccggggcaa ggtccccggg ggaccaggcg gcgccagggg ccgccggggt  31200
cccagctgcg ccatgccggg ggcgggggga gggcaaaccc cagaggcggg ggccaacggc  31260
gcggggagga gtggatgggc gaggtggccg gggaaggcg cccgctagcg agaacggccg  31320
```

```
ttcccggacg acaccttgcg acaaaaccta aggacagcgg cccgcgcgac ggggtccgag  31380
aggctaaggt aggccgcgat gttaatggtg aacgcaaagc cgccgggaaa gacaactatg  31440
ccacagaggc ggcgattaaa ccccaggcag aggtaggcgt agctttcccc gggcaggtat  31500
tgctcgcaga ccctgcgtgg ggctgtggag gggacggcct ccatgaagcg acatttactc  31560
tgctcgcgtt tactgacgtc accatccatc gccacggcga ttggacgatt gttaagccgc  31620
agcgtgtctc cgcttgtgct gtagtagtca aaaacgtaat ggccgtcgga gtcggcaaag  31680
cgggccggga ggtcgtcgcc gagcgggacg acccgccgcc cccgaccgcc ccgtcccccc  31740
aggtgtgcca ggacggccag ggcatacgcg gtgtgaaaaa aggcgtcggg ggcggtcccc  31800
tcgacggcgc gcatcaggtt ctcgaggaga atggggaagc gcctggtcac ctcccccagc  31860
cacgcgcgtt ggtcggggcc aaagtcatag cgcaggcgct gtgagattcg cgggccgccc  31920
tgaagcgcgg cccggatggc ctggcccagg gcccggaggc acgccagatg tatgcgcgcg  31980
gtaaaggcga cctcggcggc gatgtcaaag ggcggcagga cggggcgcgg gtggcgcagg  32040
ggcacctcga gcgcgggaaa gcggagcagc agctccgcct gcccagcggg agacagctgg  32100
tgggggcgca cgacgcgttc tgcggcgcag gcctcggtca gggccgtggc cagcgccgag  32160
gacagcagcg gagggcgggc gcgtcgcccg ccccacgcca ctgagttctc gtaggagacg  32220
acgacgaagc gctgcttggt tccgtagtgg tggcgcagga ccacggagat agaacgacgg  32280
ctccacagcc agtccggccg gtcgccgccg gccagggctt cccatccgcg atccaaccac  32340
tcgaccagcg accgcggctt tgtggtacca ggggtaaggg ttagaacgtc gttcaggatg  32400
tcctcgcccc cgggcccgtg gggcgctggg gccacaaagc ggcccccgcc ggggggctcc  32460
agacccgcca gcaccgcatc tgcgtcagcc gcccccatgg cgccccccgct gacggcctgg  32520
tgaaccaggg cgccctggcg gagccccgat gcaacgccac aggccgcacg cccggtccga  32580
gcgcggaccg ggtggcggcg ggtgacgtcc tgcactgccc gctgaaccaa cgcgaggatc  32640
tcctcgttct cctgtgcgat ggacacgtcc tgggccgcgg tcgtgtcgcc gccgggggcc  32700
gtcagctgct cctccgggga gatggggggg tcggacgccc cgacgatggg cgggtctgcg  32760
ggcgcccccg cgtggggccg ggccaagggc tgcggacgcg gggacgcgct ttcccccaga  32820
cccatggaca ggtgggccgc ggcctccttc gcggccggcg gggcggcggc gccaagcaga  32880
gcgacgtagc ggcacaaatg ccgacagacg cgcatgatgc gcgtgctgtc ggccgcgtag  32940
cgcgtgttgg gggggacgag ctcgtcgtaa ctaaacagaa tcacgcgggc acagctcgcc  33000
cccgagcccc acgcgaggcg cagcgccgcc acggcgtacg ggtcatagac gccctgcgcg  33060
tcacacacca cgggcaggga gacgaacaac cccccggcgc tggacgcacg cggaaggagg  33120
ccagggtgtg ccggcacgac gggggccaga agctccccca ccgcatccgc gggcacgtag  33180
gcggcaaacg ccgtgcacca cggggtacag tcgccggtgg catgagcccg agtctggatt  33240
tcgacctgga agtttgcggc cgtcccgagt ccggggcggc cgcgcatcag ggcggccaga  33300
gggattcccg cggccgccag gcactcgctg gatatgatga cgtgaaccaa agacgagggc  33360
cgacccgggc cgtggccgag atcgtactgg acctcgttgg ccaagtgcgc gttcatggtt  33420
cggggtgggt gtgggtgtgt aggcgatgcg ggtcccccga gtccgcggga agggcgtggg  33480
tttggcgcgc gtatgcgtat tcgccaacgg aggcgtgcgt gcttatgcgc ggcgcgtttc  33540
ttctgtctcc agggaatccg aggccaggac tttaacctgc tctttgtcga cgaggccaac  33600
tttattcgcc cggatgcggt ccagacgatt atgggctttc tcaaccaggc caactgcaag  33660
```

attatcttcg tgtcgtccac caacaccggg aaggccagta cgagcttttt gtacaacctc 33720
cgcggggccg ccgacgagct tctcaacgtg gtgacctata tatgcgatga tcacatgccg 33780
agggtggtga cgcacacaaa cgccacggcc tgttcttgtt atatcctcaa caagcccgtt 33840
ttcatcacga tggacggggc ggttcgccgg accgccgatt tgtttctggc cgattccttc 33900
atgcaggaga tcatcggggg ccaggccagg gagaccggcg acgaccggcc cgttctgacc 33960
aagtctgcgg gggagcggtt tctgttgtac cgcccctcga ccaccaccaa cagcggcctc 34020
atggcccccg atttgtacgt gtacgtggat cccgcgttca cggccaacac ccgagcctcc 34080
gggaccggcg tcgctgtcgt cgggcggtac cgcgacgatt atatcatctt tgccctggag 34140
cacttttttc tccgcgcgct cacgggctcg gcccccgccg acatcgcccg ctgcgtcgtc 34200
cacagtctga cgcaggtcct ggccctgcat cccggggcgt ttcgcggcgt ccgggtggcg 34260
gtcgagggaa atagcagcca ggactcggcc gtcgccatcg ccacgcacgt gcacacagag 34320
atgcaccgcc tactggcctc ggaggggggcc gacgcgggct cgggccccga gcttctcttc 34380
taccactgcg agcctcccgg gagcgcggtg ctgtacccct ttttcctgct caacaaacag 34440
aagacgcccg cctttgaaca ctttattaaa aagtttaact ccgggggcgt catggcctcc 34500
caggagatcg tttccgcgac ggtgcgcctg cagaccgacc cggtcgagta tctgctcgag 34560
cagctgaata acctcaccga aaccgtctcc cccaacactg acgtccgtac gtattccgga 34620
aaacggaacg gcgcctcgga tgaccttatg gtcgccgtca ttatggccat ctaccttgcg 34680
gcccaggccg gacctccgca cacattcgct cccatcacac gcgtttcgtg agcgcccaat 34740
aaacacaccc aggtatgcta cgcacgacca cggtgtcgcc tgttaagggg ggggaagggg 34800
gtgttggcgg gaagcgtggg aacacggggg attctctcac gaccggcacc agtaccaccc 34860
ccctgtgaac acagaaaccc aacccaaatc ccataaacat acgacacaca ggcatatttt 34920
ggaatttctt gggtttttat ttatttaggt atgctggggt ttctccctgg atgcccaccc 34980
cccacccccc cccgtgggtc tagccgggcc ttagggatag cgtataacgg gggccatgtc 35040
tccggaccgc acaacggccg cgccgtcaaa ggtgcacacc cgaaccacgg gagccagggc 35100
caaggtgtct cctagttggc ccgcgtgggt cagccaggcg acgagcgcct cgtaaagcgg 35160
cagccttcgc tctccatcct gcaccagggc cggggcttcg gggtgaatga gctgggcggc 35220
ctcccgcgtg acactctgca tctgcaggag agcgttcacg tacccgtcct gggcacttag 35280
cgcaaagagc cgggggatta gcgtaaggat gatggtggtt ccctccgtga tcgagtaaac 35340
catgttaagg accagcgatc gcagctcggc gtttacggga ccgagttgtt ggacgtccgc 35400
cagcagcgag aggcgactcc cgttgtagta cagcacgttg aggtctggca gccctccggg 35460
gtttctgggg ctggggttca ggtcccggat gcccctggcc acgagccgcg ccacgatttc 35520
gcgcgccagg ggcgatggaa gcggaacggg aaaccgcaac gtgaggtcca gcgaatccag 35580
gcgcacgtcc gtcgcttggc cctcgaacac gggcgggacg aggctgatgg ggtccccgtt 35640
acagagatct acgggggagg tgttgcgaag gttaacggtg ccggcgtggg tgaggcccac 35700
gtccaggggg caggcgacga ttcgcgtggg aagcacccgg gtgatgaccg cggggaagcg 35760
ccttcggtac gccagcaaca accccaacgt gtcgggactg acgcctccgg agacgaagga 35820
ttcgtgcgcc acgtcggcca gcgtcagttg ccggcggatg gtcggcagga ataccacccg 35880
cccttcgcag cgctgcagcg ccgccgcatc ggggcgcgag atgcccgagg gtatcgcgat 35940
gtcagtttca aagccgtccg ccagcatggc gccgatccac gcggcaggga gtgcagtggt 36000
ggttcgggtg gcgggaggag cgcggtgggg gtcagcggcg tagcagagac gggcgaccaa 36060
cctcgcatag gacgggggt gggtcttagg gggttgggag gcgacaggga ccccagagca 36120
tgcgcgggga ggtctgtcgg gcccagacgc accgagagcg aatccgtcca cggagtcccg 36180
gtctgggttt tatggggccc ggccctcgga atcgcggctt gtcggcgggg acaaaggggg 36240
cggggctagg gggcttgcgg aaacagaaga cgcgtgggat aaaagaatcg cactacccca 36300
aggaagggcg gggcggttta ttacagagcc agtcccttga gcggggatgc gtcatagacg 36360
agatactgcg cgaagtgggt ctcccgcgcg tgggcttccc cgttgcgggc gctgcggagg 36420
agggcggggt cgctggcgca ggtgagcggg taggcctcct gaaacaggcc acacgggtcc 36480
tccacgagtt cgcggcaccc cggggggcgc ttaaactgta cgtcgctggc ggcggtggcc 36540
gtggacaccg ccgaacccgt ctccacgatc aggcgctcca ggcagcgatg tttggcggcg 36600
atgtcggccg acgtaaagaa cttaaagcag gggctgagca ccggcgaggc cccgttgagg 36660
tggtaggccc cgttatagag caggtccccg tacgaaaatc gctgcgacgc ccacgggttg 36720
gccgtggccg caaaggcccg ggacgggtcg ctctggccgt ggtcgtacat gagggcggtg 36780
acatccccct ccttgtcccc cgcgtaaacg cccccggcgg cgcgtccccg ggggttgcag 36840
ggccggcgga agtagttgac gtcggtcgac acgggggtgg cgataaactc acacacggcg 36900
tcctggccgt ggtccatccc tgcgcgccgc ggcacctggg cgcacccgaa cacggggacg 36960
ggctgggccg gccccaggcg gtttcccgcc acgaccgcgt tccgcaggta cacggctgcc 37020
gcgttgtcca ggagaggggg agccccgcgg cccaggtaaa agttttgggg aaggttgccc 37080
atgtcggtga cggggttgcg gacggttgcc gtggccacga cggcggtgta gcccacgccc 37140
aggtccacgt tcccgcgcgg ctgggtgagc gtgaagttta cccccccgcc agtttcgtgc 37200
cgggccacct ggagctggcc caggaagtac gcctccgacg cgcgctccga gaacagcatg 37260
ttctcagtca caaagcggtc ctgtcggacg acggtgaacc caaacccggg atggaggccc 37320
gtcttgagct gatgatgcaa ggccacggga ctgatcttga agtaccccgc catgagcgcg 37380
taggtcagcg cgttctcccc ggccgcgctc tcgcggacgt gctgcacgac gggctgtcgg 37440
atcgacgaaa agtagttggc ccccagagcc ggggggacca gggggacctg ccgcgacagg 37500
tcgcgcaggg ccggggggaa attgggcgcg ttcgccacgt ggtcggcccc ggcgaacagc 37560
gcgttgacgg gaagggggta aaaatagtcg ccattttgga tggtatggtc cagatgctgg 37620
ggggccatca gcaggattcc ggcgtgcaac gccccgtcga atatgcgcat gttggtggtg 37680
gacgcggtgt tggcgcccgc gtcgggcgcc gccgagcaga gcagcgccgt tgtgcgttcg 37740
gccatgttgt gggccagcac ctgcagcgtg agcatggcgg gcccgtccac taccacgcgc 37800
ccgttgtgaa acatggcgtt gaccgtgttg gccaccagat tggccgggtg caggggggtgc 37860
gcggggtccg tcacggggtc gctggggcac tcctcgccgg gggcgatctc cgggaccacc 37920
atgttctgca gggtggcgta tacgcggtcg aagcgaaccc ccgcggtgca gcagcggccc 37980
cgcgagaagg cgggcaccat cacgtagtag taaatcttgt ggtgcacggt ccagtccgcc 38040
ccccggtgcg gccggtcatc cgcggcgtcc gcggctcggg cctgggtgtt gtgcagcagc 38100
tggccgtcgt tgcggttgaa gtccgcggtc gccacgttac atgccgccgc gtacacgggg 38160
tcgtggcccc ccgcgctaac ccggcagtcg cgatggcggt ccagggccgc gcgccgcatc 38220
agggcgtcac agtcccacac gaggggtggc agcagcgccg ggtctcgcat taggtgattc 38280
agctcggctt gcgcctgccc gcccagctcc gggccggtca gggtaaagtc atcaaccagc 38340
tgggccaggg cctcgacgtg cgccaccagg tcccggtaca cggccatgca ctcctcggga 38400

```
aggtctcccc cgaggtaggt cacgacgtac gagaccagcg agtagtcgtt cacgaacgcc  38460
gcgcaccgcg tgttgttcca gtagctggtg atgcactgga caacgagccg ggccagggcg  38520
cagaagacgt gctcgctgcc gtgtatggcg gcctgcagca ggtaaaacac cgccgggtag  38580
ttgcggtcgt cgaacgcccc gcgaacggcg gcgatggtgg cgggggccat ggcgtggcgt  38640
cccacccccca gctccaggcc ccgggcgtcc cggaacgccg ccggacatag cgccaggggc  38700
aagttgccgt tcaccacgcg ccaggtggcc tggatctccc ccgggccggc cgggggaacg  38760
tcccccccccg gcagctccac gtcggccacc cccacgaaga agtcgaacgc ggggtgcagc  38820
tcaagagcca ggttggcgtt gtcgggctgc ataaactgct ccggggtcat ctggccttcc  38880
gcgacccatc ggacccgccc gtgggccagg cgctgccccc aggcgttcaa aaacagctgc  38940
tgcatgtctg cggcggggcc ggccggggcc gccacgtacg ccccgtacgg attggcggct  39000
tcgacggggt cgcggttaag gcccccgacc gccgcgtcaa cgttcatcag cgaagggtgg  39060
cacacggtcc cgatcgcgtg ttccagagac aggcgcagca cctggcggtc cttcccccaa  39120
aaaaacagct ggcggggcgg gaaggcgcgg ggatccgggt ggccgggggc ggggactagg  39180
tccccggcgt gcgcggcaaa ccgttccatg accggattga acaggcccag gggcaggacg  39240
aacgtcaggt ccatggcgcc caccaggggg tagggaacgt tggtggcggc gtagatgcgc  39300
ttctccaggg cctccagaaa gaccagcttc tcgccgatgg acaccagatc cgcgcgcacg  39360
cgcgtcgtct ggggggcgct ctcgagctcg tccagcgtct gccggttcag gtcgagctgc  39420
tcctcctgca tctccagcag gtggcggccc acgtcgtcca gacttcgcac ggccttgccc  39480
atcacgagcg ccgtgaccag gttggccccg ttcaggacca tctcgccgta cgtcaccggc  39540
acgtcggctt cggtgtcctc cactttcagg aaggactgca ggaggcgctg tttgatcggg  39600
gctgtggtga ctagcacccc gtcgaccggc cgcccgcgcg tgtcggcatg cgtcagacgg  39660
ggcacggcca cggagggctg cgtggccgtg gtgaggtcca cgagccaggc ctcgacggcc  39720
tcccggcggt ggcccgcctt gcccaggaaa aagctcgtct cgcagaagct tcgctttagc  39780
tcggcgacca gggtcgcccg ggccaccctg gtggccaggc ggccgttgtc caggtatcgt  39840
tgcatcggca acaacaaagc caggggcggc gccttttcca gcagcacgtg cagcatctgg  39900
tcggccgtgc cgcgctcaaa cgccccgagg acggcctgga cgttgcgagc gagctgttgg  39960
atggcgcgca actggcgatg cgcgctgata cccgtcccgt ccagggcctc ccccgtgagc  40020
agggcgatgg cctcggtggc caggctgaag gcggcgttca gggcccggcg gtcgataatc  40080
ttggtcatgt aattgtgtgt gggttgctcg atggggtgcg ggccgtcgcg ggcaatcagc  40140
ggctggtgga cctcgaactg tacgcgcccc tcgttcatgt aggccagctc cggaaacttg  40200
gtacacacgc acgccaccga caacccgagc tccagaaagc gcacgagcga cagggtgttg  40260
caatacgacc ccagcagggc gtcgaactcg acgtcgtaca ggctgtttgc atcggagcgc  40320
acgcgggaaa aaaaatcgaa caggcgtcga tgcgacgcca cctcgatcgt gctaaggagg  40380
gacccggtcg gcaccatggc cgtggcatac cggtatcccg gagggtcgcg gttgggagcg  40440
gccatggggt cgcgtggaga tcggctgtct ctagcgatat tggcccgggg aggctaagat  40500
ccaccccaac gcccggccac ccgtgtacgt gcccgacggc ccaaggtcca ccgaaagaca  40560
cgacggaccc ggacccaaag aggcggggga tgctgtgtga gaggccgggt gtcggtcggg  40620
ggggaaaggc accgggagaa ggctgcggcc tcgttccagg agaacccagt gtccccaaca  40680
gacccgggga cgtgggatcc ccggccttat ataccccccc ccgcccccacc cccgttagaa  40740
cgcgacgggt gcattcaaga tggccctggt ccaaaagcgt gccaggaaga aattggcaga  40800
```

ggcggcaaag ctgtccgccg ccgccaccca catcgaggcc ccggccgcac aggctatccc 40860
cagggcccgt gtgcgcaggg gatcggtggg tggcagcatt tggttggtgg cgataaagtg 40920
gaaaagcccg tccggactga aggtctcgtg ggcggcggcg aacaaggcac acagggccgt 40980
gcctcccaaa aacacggaca tcccccaaaa cacgggcgcc gacaacggca gacgatccct 41040
cttgatgtta acgtacagga ggagcgcccg caccgcccac gtaacgtagt agccgacgat 41100
ggcggccagg atacaggccg gcgccaccac ccttccggtc agcccgtaat acatgcccgc 41160
tgccaccatc tccaacggct tcaggaccaa aaacgaccaa aggaacagaa tcacgcgctt 41220
tgaaaagacc ggctgggtat ggggcggaag acgcgagtat gccgaactga caaaaaaatc 41280
agaggtgccg tacgaggaca atgaaaactg ttcctccagc ggcagttctc cctcctccat 41340
ggtcatgggg tgtgcggtgg aggtggggag accgaaaccg caaagggtcg cttacgtcag 41400
caggatcccg agatcaaaga cacccgggtt cttgcacaaa caccacccgg gttgcatccg 41460
cggaggcgag tgttttgata aggccgttcc gcgccttgat ataacctttg atgttgacca 41520
caaaacccgg aatttacgcc tacgccccaa tgcccacgca agatgaggta ggtaaccccc 41580
ccgtgggtgt gacgttgcgt ttagttcatt ggaggccaag gggaaaaatg gggtggggag 41640
gaaacggaaa acccagtagg ccgtgtcggg aacacgcccg gggttgtcct caaaaggcag 41700
ggtccatact acggaagccg tcgttgtatt cgagacctgc ctgtgcgacg cacgtcgggg 41760
ttgcctgtgt ccggttcggc ccccaccgcg tgcggcacgc acgaggacga gtccgcgtgc 41820
tttattggcg ttccaagcgt tgccctccag tttctgttgt cggtgttccc ccatacccac 41880
gcccacatcc accgtagggg gcctctgggc cgtgttacgt cgccgcccgc gatggagctt 41940
agctacgcca ccaccatgca ctaccgggac gttgtgtttt acgtcacaac ggaccgaaac 42000
cgggcctact ttgtgtgcgg ggggtgtgtt tattccgtgg ggcggccgtg tgcctcgcag 42060
cccggggaga ttgccaagtt tggtctggtc gttcgaggga caggcccaga cgaccgcgtg 42120
gtcgccaact atgtacgaag cgaactccga caacgcggcc tgcaggacgt gcgtcccatt 42180
ggggaggacg aggtgtttct ggacagcgtg tgtcttctaa acccgaacgt gagctccgag 42240
ctggatgtga ttaacacgaa cgacgtggaa gtgctggacg aatgtctggc cgagtactgc 42300
acctcgctgc gaaccagccc gggtgtgcta atatccgggc tgcgcgtgcg ggcgcaagac 42360
agaatcatcg agttgtttga acacccaacg atagtcaacg tttcctcgca ctttgtgtat 42420
accccgtccc catacgtgtt cgccctggcc caggcgcacc tcccccggct cccgagctcg 42480
ctggaggccc tggtgagcgg cctgtttgac ggcatccccg ccccacgcca gccacttgac 42540
gcccacaacc cgcgcacgga tgtggttatc acgggccgcc gcgccccacg acccatcgcc 42600
gggtcggggg cggggtcggg gggcgcgggc gccaagcggg ccaccgtcag cgagttcgtg 42660
caagtcaaac acattgaccg cgtgggcccc gctggcgttt cgccggcgcc tccgccaaac 42720
aacaccgact cgagttccct ggtgcccggg gcccaggatt ccgcccccgcc cggccccacg 42780 ctaagggagc tgtggtgggt gttttatgcc gcagaccggg cgctggagga gccccgcgcc 42840
gactctggcc tcacccgcga ggaggtacgt gccgtacgtg ggttccggga gcaggcgtgg 42900
aaactgtttg gctccgcggg ggccccgcgg gcgtttatcg gggccgcgtt gggcctgagc 42960
cccctccaaa agctggccgt ttactactat atcatccacc gagagaggcg cctgtccccc 43020
ttccccgcgc tagtccggct cgtaggccgg tacacacagc gccacggcct gtacgtccct 43080
cggcccgacg acccagtctt ggccgatgcc atcaacgggc tggttcgcga cgcgctggcg 43140
gccggaacca cagccgagca gctcctcatg ttcgaccttc tccccccaaa ggacgtgccg 43200
gtgggaagcg acgtgcaggc cgacagcacc gctctgctgc gctttataga atcgcaacgt 43260
ctcgccgtcc ccggggggt gatctcccc gagcacgtcg cgtaccttgg tgcgttcctg 43320
agcgtgctgt acgctggccg cgggcgcatg tccgcagcaa cgcacaccgc gcggctgaca 43380
ggggtgacct ccctggtgct agcggtgggt gacgtggacc gtctttccgc gtttgaccgc 43440
ggagcggcgg gcgcggccag ccgcacgcgg gccgccgggt acctggatgt gcttctgacc 43500
gttcgtctcg ctcgctccaa acacggacag tctgtgtaac agaccccaat aaacgtatgt 43560
cgctaccaca cccttgtgtg tcaatggacg cctctccggg ggggaaggga aaacaaagag 43620
gggctggggg agcggcacca ctggggcctg aacaaacaaa caaaccacag acacggttac 43680
agtttattcg gtcgggcgga taaacggccg aagccacgcc ccctttattc gcgtctccaa 43740
aaaaacggga cacttgtccg gagaaccttt aggatgccag ccagggcggc ggtaatcata 43800
accacgccca gcgcagaggc ggccagaaac ccgggcgcaa ttgcggccac gggctgcgtg 43860
tcaaaggcta gcaaatgaat gacggttccg tttggaaata gcaacaaggc cgtggacggc 43920
acgtcgctcg aaaacacgct cggggcgccc tccgtcggcc cggcggcgat ttgctgctgt 43980
gtgttgtccg tatccaccag caacacagac atgacctccc cggctggggt gtagcgcata 44040
aacacggccc ccacgagccc caggtcgcgc tggttttggg tgcgcaccag ccgcttggac 44100
tcgatatccc gggtggagcc ttcgcatgtc gcggtgaggt aggttaggaa cagtgggcgt 44160
cggacgtcga cgccggtgag cttgtagccg atcccccggg gcagagggga gtgggtgacg 44220
acgtagctgg cgttgtgggt gatgggtacc aggatccgtg gctcgacgtt ggcagactgc 44280
cccccgcacc gatgtgaggc ctcagggacg aaggcgcgga tcagggcgtt gtagtgtgcc 44340
cagcgcgtca gggtcgaggc gaggccgtgg gtctgctggg ccaggacttc gaccggggtc 44400
tcggatcggg tggcttgagc cagcgcgtcc aggataaaca cgctctcgtc tagatcaaag 44460
cgcagggagg ccgcgcatgg cgaaaagtgg tccggaagcc aaaagagggt tttctggtgg 44520
tcggcccggg ccagcgcggt ccggaggtcg gcgttggtcg ctgcggcgac gtcggacgta 44580
cacagggccg atgctatcag aaggctccgg cgggcgcgtt cccgctgcac cgccgagggg 44640
acgcccgcca agaacggctg ccggaggaca gccgaggcgt aaaatagcgc ccggtggacg 44700
accggggtgg tcagcacgcg gcccccctaga aactcggcat acagggcgtc gatgagatgg 44760
gctgcgctgg gcgccactgc gtcgtacgcc gaggggctat ccagcacgaa ggccagctga 44820
tagcccagcg cgtgtaatgc caagctctgt tcgcgctcca gaatctcggc caccaggtgc 44880
tggagccgag cctctagctg caggcgggcc gtgggatcca agactgacac attaaaaaac 44940
acagaatccg cggcacagcc cgcggccccg cgggcggcca acccggcaag cgcgcgcgag 45000
tgggccaaaa agcctagcag gtcggagagg cagaccgcgc cgtttgcgtg ggcggcgttc 45060
acgaaagcaa aacccgacgt cgcgagcagc cccgttaggc gccagaagag aggggggcgc 45120
gggccctgct cggcgcccgc gtcccccgag aaaaactccg cgtatgcccg cgacaggaac 45180
tgggcgtagt tcgtgccctc ctccgggtag ccgcccacgc ggcggagggc gtccagcgcg 45240
gagccgttgt cggcccgcgt cagggaccct aggacaaaga cccgataccg ggggccgccc 45300
gggggcccgg gaagagcccc cgggggggttt tcgtccgcgg ggtccccgac ccgatctagc 45360
gtctggcccg cggggaccac catcacttcc accggagggc tgtcgtgcat ggatatcacg 45420
agccccatga attcccgccc gtagcgcgcg cgcaccagcg cggcatcgca cccgagcacc 45480
agctccccccg tcgtccagat gcccacgggc cacgtcgagg ccgacgggga gaaatacacg 45540
tacctacctg gggatctcaa caggccccgg gtggccaacc aggtcgtgga cgcgttgtgc 45600
aggtgcgtga tgtccagctc cgtcgtcggg tgccgccggg ccccaaccgg cggtcggggg 45660
ggcggtgtat cacgcggccc gcttgggtgg ctcgccgtcg ccacgttgtc tccccgcggg 45720
aacgtcaggg cctcggggtc agggacggcc gaaaacgtta cccaggcccg ggaacgcagc 45780
aacacggagg cgactggatt gtacaagaga cccttaaggg gggcgaccga ggggggaggc 45840
tgggcggtcg gctcgaccgt ggtgggggcg ggcaggctcg cgttcggggg ccggccgagc 45900
aggtaggtct tcgggatgta aagcagctgg ccggggtccc gcggaaactc ggccgtggtg 45960
accaatacaa aacaaaagcg ctcctcgtac cagcgaagaa ggggcagaga tgccgtagtc 46020
aggtttagtt cgtccggcgg cgccagaaat ccgcgcggtg gtttttgggg gtcgggggtg 46080
tttggcagcc acagacgccc ggtgttcgtg tcgcgccagt acatgcggtc catgcccagg 46140
ccatccaaaa accatgggtc tgtctgctca gtccagtcgt ggacctgacc ccacgcaacg 46200
cccaaaataa taaccccccac gaaccataaa ccattcccca tgggggaccc cgtccctaac 46260
ccacggggcc cgtggctatg gcagggcttg ccgccccgac gttggctgcg agccctgggc 46320
cttcacccga acttgggggg tggggtgggg aaaaggaaga aacgcgggcg tattggcccc 46380
aatggggtct cggtggggta tcgacagagt gccagccctg ggaccgaacc ccgcgtttat 46440
gaacaaacga cccaacaccc gtgcgtttta ttctgtcttt ttattgccgt catagcgcgg 46500
gttccttccg gtattgtctc cttccgtgtt tcagttagcc tcccccatct cccgggcaaa 46560
cgtgcgcgcc aggtcgcaga tcgtcggtat ggagccgggg gtggtgacgt gggtctggac 46620
catcccggag gtaagttgca gcagggcgtc ccggcagccg gcgggcgatt ggtcgtaatc 46680
caggataaag acgtgcatgg gacggaggcg tttggccaag acgtccaagg cccaggcaaa 46740
cacgttgtac aggtcgccgt tgggggccag caactcgggg gcccgaaaca gggtaaataa 46800
cgtgtccccg atatggggtc gtgggcccgc gttgctctgg ggctcggcac cctggggcgg 46860
cacggccgtc cccgaaagct gtccccaatc ctcccgccac gacccgccgc cctgcagata 46920
ccgcaccgta ttggcaagca gcccgtaaac gcggcgaatc gcggccagca tagccaggtc 46980
aagccgctcg ccggggcgct ggcgtttggc caggcggtcg atgtgtctgt cctccggaag 47040
ggcccccaac acgatgtttg tgccgggcaa ggtcggcggg atgagggcca cgaacgccag 47100
cacggcctgg ggggtcatgc tgcccataag gtatcgcgcg gccgggtagc acaggagggc 47160
ggcgatggga tggcggtcga agatgagggt gagggccggg ggcggggcat gtgagctccc 47220
agcctccccc ccgatatgag gagccagaac ggcgtcggtc acggcataag gcatgcccat 47280
tgttatctgg gcgcttgtca ttaccaccgc cgcgtccccg gccgatatct caccctggtc 47340
gaggcggtgt tgtgtggtgt agatgttcgc gattgtctcg gaagccccca gcacctgcca 47400
gtaagtcatc ggctcgggta cgtagacgat atcgtcgcgc gaacccaggg ccaccagcag 47460
ttgcgtggtg gtggttttcc ccatcccgtg aggaccctct atataaaccc gcagtagcgt 47520
gggcattttc tgctccaggc ggacttccgt ggcttcttgc tgccggcgag ggcgcaacgc 47580
cgtacgtcgg ttgctatggc cgcgagaacg cgcagcctgg tcgaacgcag acgcgtattg 47640
atggcagggg tacgaagcca tacgcgcttc tacaaggcgc ttgccgaaga ggtgcgggag 47700
tttcacgcca ccaagatctg cggcacgctg ttgacgctgt taagcgggtc gctgcagggt 47760
cgctcggtgt tcgaggccac acgcgtcacc ttaatatgcg aagtggacct gggaccgcgc 47820
cgccccgact gcatctgcgt gttcgaattc gtgaatgaca agacgctggg cggggtttgt 47880
gtcatcatag aactaaagac atgcaaatat atttcttccg gggacaccgc cagcaaacgc 47940
gagcaacggg ccacggggat gaagcagctg cgccactccc tgaagctcct gcagtccctc 48000
gcgcctccgg gtgacaagat agtgtacctg tgccccgtcc tggtgtttgt cgcccaacgg 48060
acgctccgcg tcagccgcgt gacccggctc gtcccgcaga aggtctccgg taatatcacc 48120
gcagtcgtgc ggatgctcca gagcctgtcc acgtatacgg tccccatgga gcctaggacc 48180
cagcgagccc gtcgccgccg cggcggcgcc gcccgggggt ctgcgagcag accgaaaagg 48240
tcacactctg gggcgcgcga cccgcccgag tcagcggccc gccagttacc acccgccgac 48300
caaacccccg cctccacgga gggcgggggg gtgcttaaga ggatcgcggc gctcttctgc 48360
gtgcccgtgg ccaccaagac caaaccccga gccgcctccg aatgagagtg tttcgttcct 48420
tcccccctccc cccgcgtcag acaaacccta accaccgctt aagcggcccc cgcgaggtcc 48480
gaagactcat ttggatccgg cgggagccac ccgacaacag cccccgggtt ttcccacgcc 48540
agacgccggt ccgctgtgcc atcgcgcccc ctcatcccac cccccatctt gtccccaaat 48600
aaaacaaggt ctggtagtta ggacaacgac cgcagttctc gtgtgttatt ttcgctctcc 48660
gcctctcgca gatggacccg tactgcccat ttgacgctct ggacgtctgg gaacacaggc 48720
gcttcatagt cgccgattcc cgaaacttca tcacccccga gttcccccgg gacttttgga 48780
tgtcgcccgt ctttaacctc ccccgggaga cggcggcgga gcaggtggtc gtcctacagg 48840
cccagcgcac agcggctgcc gctgccctgg agaacgccgc catgcaggcg gccgagctcc 48900
ccgtcgatat cgagcgccgg ttacgcccga tcgaacggaa cgtgcacaag atcgcaggcg 48960
ccctggaggc gctggagacg gcggcggccg ccgccgaaga ggcggatgcc gcgcgcgggg 49020
atgagccggc gggtgggggc gacggggggg cgcccccgag tctggccgtc gcggagatgg 49080
aggtccagat cgtgcgcaac gacccgccgc tacgatacga caccaacctc cccgtggatc 49140
tgctacacat ggtgtacgcg ggccgcgggg cgaccggatc gtcgggggtg gtgttcggga 49200
cctggtaccg cactatccag gaccgcacca tcacggactt tcccctgacc acccgcagtg 49260
ccgactttcg ggacggccgt atgtccaaga ccttcatgac ggcgctggta ctgtccctgc 49320
agtcgtgcgg ccggctgtat gtgggccagc gccactattc cgccttcgag tgcgccgtgt 49380
tgtgtctcta cctgctgtac cgaaacacgc acggggccgc cgacgatagc gaccgcgctc 49440
cggtcacgtt cggggatctg ctgggccggc tgccccgcta cctggcgtgc ctggccgcgg 49500
tgatcgggac cgagggcggc cggccacagt accgctaccg cgacgacaag ctccccaaga 49560
cgcagttcgc ggccggcggg ggccgctacg aacacggagc gctggcgtcg cacatcgtga 49620
tcgccacgct gatgcaccac ggggtgctcc cggcggcccc gggggacgtc ccccgggacg 49680
cgagcaccca cgttaacccc gacggcgtgg cgcaccacga cgacataaac cgcgccgccg 49740
ccgcgttcct cagccggggc cacaacctat tcctgtggga ggaccagact ctgctgcggg 49800
caaccgcgaa caccataacg gccctgggcg ttatccagcg gctcctcgcg aacggcaacg 49860
tgtacgcgga ccgcctcaac aaccgcctgc agctgggcat gctgatcccc ggagccgtcc 49920
cttcggaggc catcgcccgt ggggcctccg ggtccgactc gggggccatc aagagcggag 49980
acaacaatct ggaggcgcta tgtgccaatt acgtgcttcc gctgtaccgg gccgacccgg 50040
cggtcgagct gacccagctg tttcccggcc tggccgccct gtgtcttgac gcccaggcgg 50100
ggcggccggt cgggtcgacg cggcgggtgg tggatatgtc atcgggggcc cgccaggcgg 50160
cgctggtgcg cctcaccgcc ctggaactca tcaaccgcac ccgcacaaac cccacccccg 50220
tgggggaggt tatccacgcc cacgacgccc tggcgatcca atacgaacag gggcttggcc 50280

```
tgctggcgca gcaggcacgc attggcttgg gctccaacac caagcgtttc tccgcgttca  50340
acgttagcag cgactacgac atgttgtact ttttatgtct ggggttcatt ccacagtacc  50400
tgtcggcggt ttagtgggtg gtgggcgagg ggggaggggg cattagggag aaagaacaag  50460
agcctccgtt gggttttctt tgtgcctgta ctcaaaaggt catacccgt aaacggcggg  50520
ctccagtccc ggcccggcgg ttggcgtgaa cgcaacggcg ggagctgggt tagcgtttag  50580
tttagcattc gctctcgcct ttccgcccgc cccccgaccg ttgcgccttt ttttttttc  50640
gtccaccaaa gtctctgtgg gtgcgcgcat ggcagccgat gccccgggag accggatgga  50700
ggagcccctg ccagacaggg ccgtgcccat ttacgtggct gggtttttgg ccctgtatga  50760
cagcggggac tcgggcgagt tggcattgga tccggatacg gtgcgtgcgg ccctgcctcc  50820
ggataaccca ctcccgatta acgtggacca ccgcgctggc tgcgaggtgg ggcgggtgct  50880
ggccgtggtc gacgaccccc gcgggccgtt ttttgtggga ctgatcgcct gcgtgcaact  50940
ggagcgcgtc ctcgagacgg ccgccagcgc tgcgattttc gagcgccgcg ggccgccgct  51000
ctcccgggag gagcgcctgt tgtacctgat caccaactac ctgccctcgg tctccctggc  51060
cacaaaacgc ctggggggcg aggcgcaccc cgatcgcacg ctgttcgcgc acgtcgcgct  51120
gtgcgcgatc gggcggcgcc tcggcactat cgtcacctac gacaccggtc tcgacgccgc  51180
catcgcgccc tttcgccacc tgtcgccggc gtctcgcgag gggggcgcggc gactggccgc  51240
cgaggccgag ctcgcgctgt ccggacgcac ctgggcgccc ggcgtggagg cgctgaccca  51300
cacgctgctt tccaccgccg ttaacaacat gatgctgcgg gaccgctgga gcctggtggc  51360
cgagcggcgg cggcaggccg ggatcgccgg acacacctac ctccaggcga gcgaaaaatt  51420
caaaatgtgg ggggcggagc ctgtttccgc gccggcgcgc gggtataaga acggggcccc  51480
ggagtccacg gacataccgc ccggctcgat cgctgccgcg ccgcagggtg accggtgccc  51540
aatcgtccgt cagcgcgggg tcgcctcgcc cccggtactg ccccccatga accccgttcc  51600
ggcatcgggc accccggccc ccgcgccgcc cggcgacggg agctacctgt ggatcccggc  51660
ctcccattac aaccagctcg tcgccggcca cgccgcgccc caaccccagc cgcattccgc  51720
gtttggtttc ccggctgcgg cgggggccgt ggcctatggg cctcacggcg cgggtctttc  51780
ccagcattac cctccccacg tcgcccatca gtatcccggg gtgctgttct cgggacccag  51840
cccactcgag gcgcagatag ccgcgttggt gggggccata gccgcggacc gccaggcggg  51900
cggtcagacg gccgcgggag accctggggt ccgggggtcg ggaaagcgtc gccggtacga  51960
ggcggggccg tcggagtcct actgcgacca ggacgaaccg gacgcggact acccgtacta  52020
ccccggggag gctcgaggcg ggccgcgcgg ggtcgactct cggcgcgcgg cccgccagtc  52080
tcccgggacc aacgagacca tcacggcgct gatgggggcg gtgacgtctc tgcagcagga  52140
actggcgcac atgcgggctc ggaccagcgc cccctatgga atgtacacgc cggtggcgca  52200
ctatcgccct caggtggggg agccggaacc aacaacgacc cacccggccc tttgtccccc  52260
ggaggccgtg tatcgccccc caccacacag cgccccctac ggtcctcccc agggtccggc  52320
gtcccatgcc cccactcccc cgtatgcccc agctgcctgc ccgccaggcc cgccaccgcc  52380
cccatgtcct tccacccaga cgcgcgcccc tctaccgacg gagcccgcgt tcccccccgc  52440
cgccaccgga tcccaaccgg aggcatccaa cgcggaggcc ggggcccttg tcaacgccag  52500
cagcgcagca cacgtggacg ttgacacggc ccgcgccgcc gatttgttcg tctctcagat  52560
gatgggggcc cgctgattcg ccccggtctt tggtaccatg ggatgtctta ctgtatatct  52620
```

ttttaaataa accaggtaat accaaataag acccattggt gtatgttctt tttttattgg 52680
gaggcgcggg taggcgggta gctttacaat gcaaaagcct tcgacgtgga ggaaggcgtg 52740 ggggggaat cggcactgac caagggggtc cgttttgtca cgggaaagga aagaggaaac 52800
aggccgcgga cacccggggg agtttatgtg ttcccttttc tttcttccca cacacacaaa 52860
aggcgtacca aacaaacaaa ccaaaagatg cacatgcggt ttaacacccg tggtttttat 52920
ttacaacaaa ccccccgtca caggtcgtcc tcgtcggcgt caccgtcttt gttgggaact 52980
tgggtgtagt tggtgttgcg gcgcttgcgc atgaccatgt cggtgacctt ggcgctgagc 53040
agcgcgctcg tgcccttctt cttggccttg tgttccgtgc gctccatggc agacaccagg 53100
gccatgtacc gtatcatctc ccgggcctcg gctagcttgg cctcgtcaaa gtcgccgccc 53160
tcctcgccct ccccggacgc gtccgggttg gtggggttct tgagctcctt ggtggttagc 53220
gggtacaggg ccttcatggg gttgctctgc agccgcatga cgtagcgaaa ggcgaagaaa 53280
gccgccgcca ggccggccag gaccaacaga cccacggcca gcgccccaaa ggggttggac 53340
atgaaggagg acacgcccga cacggccgat accacgccgc ccacgatgcc catcaccacc 53400
ttgccgaccg cgcgccccag gtcgcccatc ccctcgaaga acgcgcccag gcccgcgaac 53460
atggcggcgt tggcgtcggc gtggatgacc gtgtcgatgt cggcgaagcg caggtcgtgc 53520
agctggttgc ggcgctggac ctccgtgtag tccagcaggc cgctgtcctt gatctcgtgt 53580
cgggtgtaca cctccagggg gacaaactcg tgatcctcca gcatggtgat gttgaggtcg 53640
atgaaggtgc tgacggtggt gatgtcggcg cggctcagct ggtgggagta cgcgtactcc 53700
tcgaagtaca cgtagccccc gccgaaggtg aagtagcgcc ggtgtcccac ggtgcacggc 53760
tcgatcgcat cgcgcgtcag ccgcagctcg ttgttctccc ccagctgccc ctcgaccaac 53820
gggccctggt cttcgtaccg aaagctgacc agggggcggc tgtagcaggc cccgggccgc 53880
gagctgatgc gcatcgagtt ttggacgatc acgttgtccg cggcgaccgg cacgcacgtg 53940
gagacggcca tcacgtcgcc gagcatccgc gcgctcaccc gccggcccac ggtggccgag 54000
gcgatggcgt tggggttcag cttgcgggcc tcgttccaca gggtcagctc gtgattctgc 54060
agctcgcacc acgcgatggc aacgcggccc aacatatcgt tgacatggcg ctgtatgtgg 54120
ttgtacgtaa actgcagccg ggcgaactcg atggaggagg tggtcttgat gcgctccacg 54180
gacgcgttgg cgctggcccc gggcggcggg ggcgtggggt ttgggggctt gcggctctgc 54240
tctcggaggt gttcccgcac gtacagctcc gcgagcgtgt tgctgagaag gggctggtac 54300
gcgatcagaa agcccccatt ggccaggtag tactgcggct ggcccacctt gatgtgcgtc 54360
gcgttgtacc tgcgggcgaa gatgcggtcc atggcgtcgc gggcgtcctt gccgatgcag 54420
tcccccaggt ccacgcgcga gagcgggtac tcggtcaggt tggtggtgaa ggtggtggat 54480
atggcgtcgg aggagaatcg gaaggagccg ccgtactcgg agcgcagcat ctcgtccacc 54540
tcctgccact tggtcatggt gcagaccgac gggcgctttg gcacccagtc ccaggccacg 54600
gtgaacttgg gggtcgtgag caggttccgg gtggtcggcg ccgtggcccg ggccttggtg 54660
gtgaggtcgc gcgcgtagaa gccgtcaacc tgcttgaagc ggtcggcggc gtagctggtg 54720
tgttcggtgt gcgacccctc ccggtagccg taaaacgggg acatgtacac aaagtcgcca 54780
gtcgccagca caaactcgtc gtacgggtac accgagcgcg cgtccacctc ctcgacgatg 54840
cagtttaccg tcgtcccgta ccggtggaac gcctccaccc gcgaggggtt gtacttgagg 54900
tcggtggtgt gccagccccg gctcgtgcgg gtcgcggcgt tggccggttt cagctccatg 54960
tcggtctcgt ggtcgtcccg gtgaaacgcg gtggtctcca ggttgttgcg cacgtacttg 55020
gccgtggacc gacagacccc cttggcgttg atcttgtcga tcacctcctc gaaggggacg 55080
ggggcgcggt cctcaaagat ccccataaac tgggagtagc ggtggccgaa ccacacctgc 55140
gaaacggtga cgtctttgta gtacatggtg gccttgaact tgtacggggc gatgttctcc 55200
ttgaagacca ccgcgatgcc ctccgtgtag ttctgaccct cgggccgggt cgggcagcgg 55260
cgcggctgct cgaactgcac caccgtggcg cccgtggggg gtgggcacac gtaaaagttt 55320
gcatcggtgt tctccgcctt gatgtcccgc aggtgctcgc gcagggtggc gtggcccgcg 55380
gcgacggtcg cgttgtcgcc ggcggggcgc ggcggcggtg ggtttttcgg tttttttgttc 55440
ttcttcggtt tcgtgtcccc cgttggggcg gggccagggg cgggcggcgc cggagtggca 55500
ggtcccccgt tcgccgcctg ggtcgcggcc gcgaccccag gcgtgccggg ggaactcgga 55560
gccgccgacg ccaccaggac ccccagcgtc aaccccaaga gcgcccatac gacgaaccac 55620
cggcaccccc gcgcgggggc gccctggcgc atggcgggac tacgggggcc cgtcgtgccc 55680
cccgtcaggt agcctggggg cgaggtgctg gaggaccgag tagaggatcg agaaaacgtc 55740
tcggtcgtag accacgaccg accgggggcc gatacagccg tcgggggcgc tctcgacgat 55800
ggccaccagc ggacagtcgg agtcgtacgt gagatatacg ccgggcgggt aacggtaacg 55860
accttcggag gtcgggcggc tgcagtccgg gcggcgcaac tcgagctccc cgcaccggta 55920
gaccgaggca aagagtgtgg tggcgataat cagctcgcga atatatcgcc aggcggcgcg 55980
ctgagtgggc gttattccgg aaatgccgtc aaaacagtaa aacctctgaa attcgctgac 56040
ggcccaatca gcacccgagc cccccgcccc catgatgaac cgggcgagct cctccttcag 56100
gtgcggcagg agccccacgt tctcgacgct gtaatacagc gcggtgttgg ggggctgggc 56160
gaagctgtgg gtggagtgat caaagagggg cccgttgacg agctcgaaga agcgatgggt 56220
gatgctgggg agcagggccg ggtccacctg gtgtcgcagg agagacgctc gcatgaaccg 56280
gtgcgcgtcg aacacgcccg gcgccgagcg gttgtcgatg accgtgcccg cgcccgccgt 56340
cagggcgcag aagcgcgcgc gcgccgcaaa gccgttggcg accgcggcga acgtcgcggg 56400
cagcacctcg ccgtggacgc tgacccgcag catcttctcg agctccccgc gctgctcgcg 56460
gacgcagcgc cccaggctgg ccaacgaccg cttcgtcagg cggtccgcgt acagccgccg 56520
tcgctcccgc acgtccgcgg ccgcttgcgt ggcgatgtcc ccccacgtct cgggcccctg 56580
ccccccgggc ccgcggcgac ggtcttcgtc ctcgcccccg cccccgggag ctcccaaccc 56640
ccgtgcccct tcctctacgg cgacacggtc cccgtcgtcg tcggggcccg cgccgccctt 56700
gggcgcgtcc gccgcgcccc ccgcccccat gcgcgccagc acgcgacgca gcgcctcctc 56760
gtcgcactgt tcggggctga cgaggcgccg caagagcggc gtcgtcaggt ggtggtcgta 56820
gcacgcgcgg atgagcgcct cgatctgatc gtcgggtgac gtggcctgac cgccgattat 56880
tagggcgtcc accatatcca gcgccgccag gtggctcccg aacgcgcgat cgaaatgctc 56940
cgcccgccgc ccgaacagcg ccagttccac ggccaccgcg gcggtctcct gctgcaactc 57000
gcgccgcgcc agcgcggtca ggttgctggc aaacgcgtcc atggtggtct ggccggcgcg 57060
gtcgccggac gcgagccaga atcgcaattc gctgatggcg tacaggccgg gcgtggtggc 57120
ctgaaacacg tcgtgcgcct ccagcagggc gtcggcctcc ttgcggaccg agtcgttctc 57180
gggcgacggg tggggctgcc cgtcgccccc cgcggtccgg gccagcgcat ggtccaacac 57240
ggagagcgcc cgcgcgcggt cggcgtccga cagcccggcg gcgtggggca ggtaccgccg 57300
cagctcgttg gcgtccagcc gcacctgcgc ctgctgggtg acgtggttac agatacggtc 57360
cgccaggcgg cgggcgatcg tcgccccctg gttcgccgtc acacacagtt cctcgaaaca 57420
gaccgcgcag gggtgggacg ggtcgctaag ctccgggggg acgataaggc ccgaccccac 57480
cgcccccacc ataaactccc gaacgcgctc cagcgcggcg gtggcgccgc gcgagggggt 57540
gatgaggtgg cagtagttta gctgctttag aaagttctcg acgtcgtgca ggaaacacag 57600
ctccatatgg acggtcccgc catacgtatc cagcctgacc cgttggtgat acggacaggg 57660
tcgggccagg cccatggtct ccgtgaaaaa caccgcgacg tctcccgcgg tcgcgaacgt 57720
ctccaggctg cccaggagcc gctcgccctc gcgccacgcg tactctagca gcaactccag 57780
ggtgaccgac agcggggtga gaaaggcccc ggcctgggcc tccaggcccg gcctcagacg 57840
acgccgcagc gcccgcacct gaagcgcgtt cagcttcagt tgggggagct tccccgtcc 57900
gatgtggggg tcgcaccgcc ggagcagctc tatctgaaac acataggtct gcacctgtcc 57960
gagcagggct aacaactttt gacgggccac ggtgggctcg gacaccgggg cggccatctc 58020
gcggcgccga tctgtaccgc ggccggagta tgcggtggac cgaggcggtc cgtacgctac 58080
ccggcgtctg gctgagcccc ggggtccccc tattcggggc ggcctcccgc gggcccgccg 58140
accggcaagc cgggagtcgg cggcgcgtgc gtttctgttc tattcccaga caccgcggag 58200
aggaatcacg gcccgcccag agatatagac acggaacaca aacaagcacg gatgtcgtag 58260
caataattta ttttacacac attccccgcc ccgccctagg ttcccccacc ccccaacccc 58320
tcacagcata tccaacgtca ggtctccctt tttgtcgggg ggcccctccc caaacgggtc 58380
atccccgtgg aacgcccgtt tgcggccggc aaatgccggt cccggggccc ccgggccgcc 58440
gaacggcgtc gcgttgtcgt cctcgcagcc aaaatcccca aagttaaaca cctccccggc 58500
gttgccgagt tggctgacta gggcctcggc ctcgtgcgcc acctccaggg ccgcgtccgt 58560
cgaccactcg ccgttgccgc gctccagggc acgtgcggtc agctccatca tctcctcgct 58620
taggtactcg tcctccagga gcgccagcca gtcctcgatc tgcagctgtt gggtgcgggg 58680
ccccaggctt ttcacggtcg ccacgaacac gctactggcg acggccgccc cgccctcgga 58740
gataatgccc cggagctgct cgcacagcga gctttcgtgc gctccgccgc cgaggctcga 58800
ggccgcgcac acaaacccgg cccggggaca ggccaggacg aacttgcggg tgcggtcaaa 58860
aataaggagc gggcacgcgt ttttgccgcc catcaggctg gcccagttcc cggcctgaaa 58920
cacacggtcg ttgccggcca tgccgtagta tttgctgatg ctcaacccca acacgaccat 58980
ggggcgtgcc gccatgacgg gccgcagcag gttgcagctg gcgaacatgg aggtccacgc 59040
gcccggatgc gcgtccacgg cgtccatcag cgcgcgggcc ccggcctcca ggcccgcccc 59100
gccctgcgcg gaccacgcgg ccgccgcctg cacgctgggg ggacggcggg accccgcgat 59160
gatggccgtg agggtgttga tgaagtacgt cgagtgatcg cagtaccgca gaatctggtt 59220
tgccatgtag tacatcgcca gctcgctcac gttgttgggg gccaggttaa taaagttgat 59280
cgcgccgtag tccagggaaa actttttaat gaacgcgatg gtctcgatgt cctcgcgcga 59340
caggagccgg gcgggaagct ggttgcgttg gagggccgtc cagaaccact gcgggttcgg 59400
ctggttggac cccgggggct tgccgttggg gaagatggcc gcgtggaact gcttcagcag 59460
aaagcccagc ggtccgagga ggatgtccac gcgcttgtcg ggcttctggt aggcgctctg 59520
gaggctggcg acccgcgcct tggcggcctc ggacgcgttg gcgctcgcgc ccgcgaacaa 59580
cacgcggctc ttgacgcgca gctccttggg aaaccccagg gtcacgcggg caacgtcgcc 59640
ctcgaagctg ctctcggcgg gggccgtctg gccggccgtc aggctggggg cgcagatagc 59700
cgcaccctcc gagagcgcga ccgtcagcgt tttggccgac agaaacccgt tgttaaacat 59760

-continued

```
gtccatcacg cgccgccgca gcaccggttg gaattgattg cgaaagttgc gcccctcgac  59820
cgactgcccg gcgaacaccc cgtggcactg gctcagggcc aggtcctggt acacggcgag  59880
gttggatcgc cgcccgagaa gctgaagcag ggggcacggc ccgcacgcgt acgggtccag  59940
cgtcagggac atggcgtggt tggcctcgcc cagaccgtcg cgaaacttga agttcctccc  60000
ctccaccagg ttgcgcatca gctgctccac ctcgcggtcc acgacctgcc tgacgttgtt  60060
caccaccgta tgcagggcct cgcggttggt gatgatggtc tccagccgcc ccatggccgt  60120
ggggaccgcc tggtccacgt actgcagggt ctcgagttcg gccatgacgc gctcggtcgc  60180
cgcgcggtac gtctcctgca tgatggtccg ggcggtctcg gatccgtccg cgcgcttcag  60240
ggccgagaag gcggcgtagt ttcccagcac gtcgcagtcg ctgtacatgc tgttcatggt  60300
cccgaagacg ccgatggctc cgcgggcggc gctggcgaac ttgggatggc gcgcccggag  60360
gcgcatgagc gtcgtgtgta cgcaggcgtg gcgcgtgtcg aaggtgcaca ggttacaggg  60420
cacgtcggtc tggttggagt ccgcgacgta tcgaaacacg tccatctcct ggcgcccgac  60480
gatcacgccg ccgtcgcagc gctccaggta aaacagcatc ttggccagca gcgccgggga  60540
aaacccacac agcatggcca ggtgctcgcc ggcaaattcc tgggttccgc cgacgagggg  60600
cgcggtgggc cgaccctcga acccgggcac cacgtgtccc tcgcggtcca cctgtgggtt  60660
ggccgccacg tgggtcccgg gcacgaggaa gaagcggtaa aaggagggtt tgctgtggtc  60720
ctttgggtcc gccgggccgg cgtcgtccac ctcggtgaga tggagggccg agttggtgct  60780
aaataccatg gcccccacga gtcccgcggc gcgcgccagg tacgccccga cggcgttggc  60840
gcgggccgcg gccgtgtcct ggccctcgaa cagcggccac gcggagatgt cggtgggcgg  60900
ctcgtcaaag acggccatcg acacgataga ctcgagggcc agggcggcgt ctccggccat  60960
gacggaggcc aggcgctgtt cgaacccgcc cgcagggccc ttgccgccgc cgtcgcgccc  61020
gccccgcggg gtcttaccct ggctggcttc gaaggccgtg aacgtaatgt cggcggggag  61080
ggcggcgccc tcgtggtttt cgtcaaacgc caggtgggcg gccgcgcggg ccacggcgtc  61140
cacgtttcgg catcgcagtg ccacggcggc gggtcccacg accgcctcga acaggaggcg  61200
gtggaggggg cggttaaaaa acggaagcgg gtaggtaaaa ttctccccga tcgatcggtg  61260
gttggcgttg aacggctctg cgatgacacg gctaaaatcc ggcatgaaca gctgcaacgg  61320
gtacacgggt atgcggtgca cctccgcccc gcctatggtt accttgtccg agcctcccag  61380
gtgcagaaag gtgttgttga tgcacacggc ctccttgaag ccctcggtaa cgaccagata  61440
caggagggcg cggtccgggt ccaggccgag gcgctcacac agcgcctccc ccgtcgtctc  61500
gtgtttgagg tcgccgggcc ggggggtgta gtccgaaaag ccaaaatggc ggcgtgcccg  61560
ctcgcagagt cgcgtcaggt tcggggcctg ggtgctgggg tccaggtgcc ggccgccgtg  61620
aaagacgtac acggacgagc tgtagtgcga gggcgtcagt ttcagggaca ccgcggtacc  61680
cccgagcccc gtcgtgcgag aacccacgac cacggccacg ttggcctcaa agccgctctc  61740
cacggtcagg cccacgacca ggggcgccac ggcgacgtcg gcatcgccgc tgcgcgccga  61800
cagtaacgcc agaagctcga tgccttcgga cggacacgcg cgagcgtaca cgtatcccag  61860
gggcccgggg gggaccttga tggtggttgc cgtcttgggc tttgtctcca tgtccttctg  61920
tcaatcggtc cgcgaacgga ggtaatcccg gcacgacgac ggacgcccga caaggtatgt  61980
ctcccgagcg tcaaaatccg gggggggggg cggcgacggt caaggggagg gttggagacc  62040
ggggttgggg aatgaatccc taccccttcac cgacaacccc ccgggtaatc acggggtgcc  62100
```

-continued gatgaacccc ggcggccggc aacgcggggt ccctgcgaga ggcacagatg cttacggtca 62160
ggtgctccgg gtcgggtgcg tctggtatgc ggttggtata tgtacacttt acctgggggc 62220
gtgcctggcc gccccagccc ctcccacgcc ctgcgcgtca tcagccggtg ggcgtggccg 62280
ctattataaa aaaagtgaga acgcgaagcg ttcgcacttt gtcctaataa tatatatatt 62340
attaggacaa agtgcgaacg cttcgcgttc tcactttttt tataatagcg gccacgccca 62400
ccggctacgt cacgctcctg tcggccgccg gcggtccata agcccggccg gccgggccga 62460
cgcgaataaa ccgggccgcc ggccggggcg ccgcgcagca gctcgccgcc cggatccgcc 62520
agacaaacaa ggcccttgca catgccggcc cgggcgagcc tgggggtccg gtaattttgc 62580
catcccaccc aagcggcttt ttgggttttt ctcttccccc ctccccacat ccccccctctt 62640 taggggttcg ggtggtaaca accgcgatgt tttccggtgg cggcggcccg ctgtccccccg 62700 gaggaaagtc ggcggccagg gcggcgtccg ggtttttttgc gcccgccggc cctcgcggag 62760
ccggccgggg acccccgcct tgcttgaggc aaaactttta caacccctac ctcgccccag 62820
tcgggacgca acagaagccg accgggccaa cccagcgcca tacgtactat agcgaatgcg 62880
atgaatttcg attcatcgcc ccgcgggtgc tggacgagga tgcccccccg gagaagcgcg 62940
ccggggtgca cgacggtcac ctcaagcgcg cccccaaggt gtactgcggg ggggacgagc 63000
gcgacgtcct ccgcgtcggg tcgggcggct tctggccgcg gcgctcgcgc ctgtggggcg 63060
gcgtggacca cgccccggcg gggttcaacc ccaccgtcac cgtctttcac gtgtacgaca 63120
tcctggagaa cgtggagcac gcgtacggca tgcgcgcggc ccagttccac gcgcggttta 63180
tggacgccat cacaccgacg gggaccgtca tcacgctcct gggcctgact ccggaaggcc 63240
accgggtggc cgttcacgtt tacggcacgc ggcagtactt ttacatgaac aaggaggagg 63300
tcgacaggca cctacaatgc cgcgccccac gagatctctg cgagcgcatg gccgcggccc 63360
tgcgcgagtc cccgggcgcg tcgttccgcg gcatttccgc ggaccacttc gaggcggagg 63420
tggtggagcg caccgacgtg tactactacg agacgcgccc cgctctgttt taccgcgtct 63480
acgtccgaag cgggcgcgtg ctgtcgtacc tgtgcgacaa cttctgcccg gccatcaaga 63540
agtacgaggg tggggtcgac gccaccaccc ggttcatcct ggacaacccc gggttcgtca 63600
ccttcggctg gtaccgtctc aaaccgggcc ggaacaacac gctagcccag ccgcgggccc 63660
cgatggcctt cgggacatcc agcgacgtcg agtttaactg tacggcggac aacctggcca 63720
tcgagggggg catgagcgac ctaccggcat acaagctcat gtgcttcgat atcgaatgca 63780
aggcgggggg ggaggacgag ctggcctttc cggtggccgg gcacccggag gacctggtca 63840
tccagatatc ctgtctgctc tacgacctgt ccaccaccgc cctggagcac gtcctcctgt 63900
tttcgctcgg ttcctgcgac ctccccgaat cccacctgaa cgagctggcg gccaggggcc 63960
tgcccacgcc cgtggttctg gaattcgaca gcgaattcga gatgctgttg gccttcatga 64020
cccttgtgaa acagtacggc cccgagttcg tgaccgggta caacatcatc aacttcgact 64080
ggcccttctt gctggccaag ctgacggaca tttacaaggt ccccctggac gggtacggcc 64140
gcatgaacgg ccggggcgtg tttcgcgtgt gggacatagg ccagagccac ttccagaagc 64200
gcagcaagat aaaggtgaac ggcatggtga acatcgacat gtacgggatt ataaccgaca 64260
agatcaagct ctcgagctac aagctcaacg ccgtggccga agccgtcctg aaggacaaga 64320
agaaggacct gagctatcgc gacatccccg cctactacgc cgccgggccc gcgcaacgcg 64380
gggtgatcgg cgagtactgc atacaggatt ccctgctggt gggccagctg ttttttaagt 64440
ttttgcccca tctggagctc tcggccgtcg cgcgcttggc gggtattaac atcacccgca 64500
ccatctacga cggccagcag atccgcgtct ttacgtgcct gctgcgcctg gccgaccaga 64560
agggctttat tctgccggac acccaggggc gatttagggg cgccgggggg gaggcgccca 64620
agcgtccggc cgcagcccgg gaggacgagg agcggccaga ggaggagggg gaggacgagg 64680
acgaacgcga ggagggcggg ggcgagcggg agccggaggg cgcgcgggag accgccggcc 64740
ggcacgtggg gtaccagggg gccagggtcc ttgaccccac ttccgggttt catgtgaacc 64800
ccgtggtggt gttcgacttt gccagcctgt accccagcat catccaggcc cacaacctgt 64860
gcttcagcac gctctccctg agggccgacg cagtggcgca cctggaggcg ggcaaggact 64920
acctggagat cgaggtgggg gggcgacggc tgttcttcgt caaggctcac gtgcgagaga 64980
gcctcctcag catcctcctg cgggactggc tcgccatgcg aaagcagatc cgctcgcgga 65040
ttccccagag cagccccgag gaggccgtgc tcctggacaa gcagcaggcc gccatcaagg 65100
tcgtgtgtaa ctcggtttac gggttcacgg gagtgcagca cggactcctg ccgtgcctgc 65160
acgttgccgc gacggtgacg accatcggcc gcgagatgct gctcgcgacc cgcgagtacg 65220
tccacgcgcg ctgggcggcc ttcgaacagc tcctggccga tttcccggag gcggccgaca 65280
tgcgcgcccc cgggccctat tccatgcgca tcatctacgg ggacacggac tccatctttg 65340
tgctgtgccg cggcctcacg gccgccgggc tgacggccgt gggcgacaag atggcgagcc 65400
acatctcgcg cgcgctgttt ctgtccccca tcaaactcga gtgcgaaaag acgttcacca 65460
agctgctgct gatcgccaag aaaaagtaca tcggcgtcat ctacgggggt aagatgctca 65520
tcaagggcgt ggatctggtg cgcaaaaaca actgcgcgtt tatcaaccgc acctccaggg 65580
ccctggtcga cctgctgttt tacgacgata ccgtatccgg agcggccgcc gcgttagccg 65640
agcgccccgc agaggagtgg ctggcgcgac ccctgcccga gggactgcag gcgttcgggg 65700
ccgtcctcgt agacgcccat cggcgcatca ccgacccgga gagggacatc caggactttg 65760
tcctcaccgc cgaactgagc agacacccgc gcgcgtacac caacaagcgc ctggcccacc 65820
tgacggtgta ttacaagctc atggcccgcc gcgcgcaggt cccgtccatc aaggaccgga 65880
tcccgtacgt gatcgtggcc cagacccgcg aggtagagga gacggtcgcg cggctggccg 65940
ccctccgcga gctcgacgcc gccgccccag gggacgagcc cgcccccccc gcggccctgc 66000
cctccccggc caagcgcccc cgggagacgc cgttgcatgc cgaccccccg ggaggcgcgt 66060
ccaagccccg caagctgctg gtgtccgagc tggccgagga tcccgcatac gccattgccc 66120
acggcgtcgc cctgaacacg gactattact tctcccacct gttgggggcg gcgtgcgtga 66180
cattcaaggc cctgtttggg aataacgcca agatcaccga gagtctgtta aaaaggttta 66240
ttcccgaagt gtggcacccc ccggacgacg tggccgcgcg gctccgggcc gcagggttcg 66300
gggcggtggg tgccggcgct acggcggagg aaactcgtcg aatgttgcat agagcctttg 66360
atactctagc atgagccccc cgtcgaagct gatgtccctc attttacaat aaatgtctgc 66420
ggccgacacg gtcggaatct ccgcgtccgt gggtttctct gcgttgcgcc ggaccacgag 66480
cacaaacgtg ctctgccaca cgtgggcgac gaaccggtac cccgggcacg cggtgagcat 66540
ccggtctatg agccggtagt gcaggtgggc ggacgtgccg ggaaagatga cgtacagcat 66600
gtggcccccg taagtggggt ccgggtaaaa caacagccgc gggtcgcacg ccccgcctcc 66660
gcgcaggatc gtgtggacga aaaaaagctc gggttggcca agaatcccgg ccaagaggtc 66720
ctggaggggg gcgttgtggc ggtcggccaa cacgaccaag gaggccagga aggcgcgatg 66780
ctcgaatatc gtgttgatct gctgcacgaa ggccaggatt agggcctcgc ggctggtggc 66840
ggcgaaccgc ccgtctcccg cgttgcacgc gggacagcaa cccccgatgc ctaggtagta 66900
gcccatcccg gagagggtca ggcagttgtc ggccacggtc tggtccagac agaagggcag 66960
cgagacggga gtggtcttca ccaggggcac cgagagcgag cgcacgatgg cgatctcctc 67020
ggagggcgtc tgggcgaggg cggcgaaaag gccccgatag cgctggcgct cgtgtaaaca 67080
cagctcctgt ttgcgggcgt gaggcggcag gctcttccgg gaggcccgac gcaccacgcc 67140
cagagtcccg ccggccgcag aggagcgcga ccgccggcgc tccttgccgt gatagggccc 67200
gggccgggag ccgcggcgat gggggtcggt gtcatacata ggtacacagg gtgtgctcca 67260
gggacaggag cgagatcgag tggcgtctaa gcagcgcgcc cgcctcacgg acaaatgtgg 67320
cgagcgcggt gggctttggt acaaatacct gatacgtctt gaaggtgtag atgagggcac 67380
gcaacgctat gcagacacgc ccctcgaact cgttcccgca ggccagcttg gccttgtgga 67440
gcagcagctc gtcgggatgg gtggcggggg gatggccgaa cagaacccag gggtcaacct 67500
ccatctccgt aatggcgcac atggggtcac agaacatgtg cttaaagatg gcctcgggcc 67560
ccgcggcccg aagcaggctc acaaaccggc ccccgtcccc gggctgcgtc tcggggtcag 67620
cctcgagctg gtcgacgacg ggtacgatac agtcgaagag gctcgtgttg ttttccgagt 67680
agcggaccac ggaggcccgg agtctgcgca gggccagcca gtaagcacgc accagtaaca 67740
ggttacacag caggcattct ccgccggtgc gcccgcgccc ccggccgtgt ttcagcacgg 67800
tggccatcag agggcccagg tcgaggtcgg gctgggcatc gggttcggta aactgcgcaa 67860
agcgcggagc cacgtcgcgc gtgcgtgccc cgcgatgcgc ttcccaggac tggcggaccg 67920
tggcgcgacg ggcctccgcg gcagcgcgca gctggggccc cgactcccag acggcggggg 67980
tgccggcgag gagcagcagg accagatccg cgtacgccca cgtatccggc gactcctccg 68040
gctcgcggtc cccggcgacc gtctcgaatt ccccgttgcg agcggcggcg cgcgtacagc 68100
agctgtcccc gcccccgcgc cgaccctccg tgcagtccag gagacgggcg caatccttcc 68160
agttcatcag cgcggtggtg agcgacggct gcgtgccgga tcccgccgac cccgcccccct 68220
cctcgccccc ggaggccaag gttccgatga gggcccgggt ggcagactgc gccaggaacg 68280
agtagttgga gtactgcacc ttggcggctc ccggggaggg cgagggcttg ggttgcttct 68340
gggcatgccg cccgggcacc ccgccgtcgg tacggaagca gcagtggaga aaaaagtgcc 68400
ggtggatgtc gtttatggtg agggcaaagc gtgcgaagga gccgaccagg gtcgccttct 68460
tggtgcgcag aaagtggcgg tccatgacgt acacaaactc gaacgcggcc acgaagatgc 68520
tagcggcgca gtggggcgcc cccaggcatt tggcacagag aaacgcgtaa tcggccaccc 68580
actgaggcga gaggcggtag gtttgcttgt acagctcgat ggtgcggcag accagacagg 68640
gccggtccag cgcgaaggtg tcgatggccg ccgcggaaaa gggcccggtg tccaaaagcc 68700
cctccccaca gggatccggg ggcgggttgc ggggtcctcc gcgcccgccc gaaccccctc 68760
cgtcgcccgc ccccccgcgg gcccttgagg gggcggtgac cacgtcggcg gcgacgtcct 68820
cgtcgagcgt accgacgggc ggcacaccta tcacgtgact ggccgtcagg agctcggcgc 68880
agagagcctc gttaagagcc aggaggctgg gatcgaaggc cacatacgcg cgctcgaacg 68940
cccccgcctt ccagctgctg ccgggggact cttcgcacac cgcgacgctc gccaggaccc 69000
cggggggcga agttgccatg gctgggcggg aggggcgcac gcgccagcga actttacggg 69060
acacaatccc cgactgcgcg ctgcggtccc agaccctgga gagtctagac gcgcgctacg 69120
tctcgcgaga cggcgcgcat gacgcggccg tctggttcga ggatatgacc cccgccgagc 69180
tggaggttgt cttcccgact acggacgcca agctgaacta cctgtcgcgg acgcagcggc 69240
tggcctccct cctgacgtac gccgggccta taaaagcgcc cgacgacgcc gccgccccgc 69300
agaccccgga caccgcgtgt gtgcacggcg agctgctcgc ccgcaagcgg gaaagattcg 69360
cggcggtcat taaccggttc ctggacctgc accagattct gcggggctga cgcgcgtgct 69420
gttgggcggg acggttcgcg aaccctttgg tgggtttacg cgggcacgca cgctcccatc 69480
gcgggcgcca tggcgggact gggcaagccc tacaccggcc acccaggtga cgccttcgag 69540
ggtctcgttc agcgaattcg gcttatcgtc ccatctacgt tgcggggcgg ggacggggag 69600
gcgggcccct actctccctc caacctcccc tccaggtgcg cctttcagtt tcatggccat 69660
gacgggtccg acgagtcgtt tcccatcgag tatgtactgc ggcttatgaa cgactgggcc 69720
gaggtcccgt gcaaccctta cctgcgcata cagaacaccg gcgtgtcggt gctgtttcag 69780
gggtttttc atcgcccaca caacgccccc gggggcgcga ttacgccaga gcggaccaat 69840
gtgatcctgg ggtccaccga gacgacgggg ttgtccctcg gcgacctgga caccatcaag 69900
gggcggctcg gcctggatgc ccggccgatg atggccagca tgtggatcag ctgctttgtg 69960
cgcatgcccc gcgtgcagct cgcgtttcgg ttcatgggcc ccgaagatgc cggacggacg 70020
agacggatcc tgtgccgcgc cgccgagcag gctattaccc gtcgccgccg aacccggcgg 70080
tcccgggagg cgtacggggc cgaggccggg ctgggggtgg ccggaacggg tttccgggcc 70140
agggggggacg gttttggccc gctccccttg ttaacccaag ggccctcccg cccgtggcac 70200
caggccctgc ggggtcttaa gcacctacgg attggccccc ccgcgctcgt tttggcggcg 70260
ggactcgtcc tgggggccgc tatttggtgg gtggttggtg ctggcgcgcg cctataaaaa 70320
aggacgcacc gccgccctaa tcgccagtgc gttccggacg ccttcgcccc acacagccct 70380
cccgaccgac acccccatat cgcttcccga cctccggtcc cgatggccgt cccgcaattt 70440
caccgcccca gcaccgttac caccgatagc gtccgggcgc ttggcatgcg cgggctcgtc 70500
ttggccacca ataactctca gtttatcatg gataacaacc acccacaccc ccagggcacc 70560
caaggggccg tgcgggagtt tctccgcggt caggcggcgg cactgacgga ccttggtctg 70620
gcccacgcaa acaacacgtt taccccgcag cctatgttcg cgggcgacgc accggccgcc 70680
tggttgcggc ccgcgtttgg cctgcggcgc acctattcac cttttgtcgt tcgagaacct 70740
tcgacgcccg ggaccccgtg aggcccaggg agttccttct ggggtgtttt aatcaataaa 70800
agaccacacc aacgcacgag ccttgcgttt aatgtcgtgt ttattcaagg gagtgggata 70860
gggttcgacg gttcgaaact taacacacca aataatcgag cgcgtctagc ccagtaacat 70920
gcgcacgtga tgtaggctgg tcagcacggc gtcgctgtga tgaagcagcg cccggcgggt 70980
ccgctgtaac tgctgttgta ggcggtaaca ggcgcggatc agcaccgcca gggcgctacg 71040
accggtgcgt tgcacgtagc gtcgcgacag aactgcgttt gccgatacgg gcggggggcc 71100
gaattgtaag cgcgtcacct cttgggagtc atcggcggat aacgcactga atggttcgtt 71160
ggttatgggg gagtgtggtt ccccagggag tgggtcgagc gcctcggcct cggaatccga 71220
gaggaacaac gaggtggcgt cggagtcttc gtcgtcagag acatacaggg tctgaagcag 71280
cgacacgggc ggggggtag cgtcgatgtg tagcgcgagg gaggatgccc acgaagacac 71340
cccagacaag gagctgcccg tgcgtggatt tgtggaagac gcggaagccg ggacggatgg 71400
gcggttttgc ggtgcccgga accgaaccgc cggatactcc ccgggtgcta catgcccgtt 71460
ttggggctgg ggttggggct ggggttgggg ctggggttgg ggctggggtt ggggctgggg 71520
ttggggctgg ggttggggtt ggggttgggg ctggggttgg ggttggggct ggggctgggg 71580

-continued

```
ctggggctgg ggctggggct ggggctgggg ctggggctgg ggctggggct ggggctgggg  71640
ctggggctgg ggctggggct ggggttgggg cgcggacagg cggctgacgg tcaaatgccc  71700
ccgggggcgc gcagatgtgg tgggcgtggc caccggctgc cgtgtagtgg ggcggcggga  71760
aaccgggcct ccgggcgtaa caccgccctc cagcgtcaag tatgtggggg gcgggcctga  71820
cgtcgggggc ggggtgacgg gttggaccgc gggaggcggg ggagagggac ctgcgggaga  71880
ggatgaggtc ggctcggccg ggttgcggcc taaaacaggg gccgtggggt cggcggggtc  71940
ccagggtgaa gggagggatt cccgcgattc ggacagcgac gcgacagcgg ggcgcgtaag  72000
gcgccgctgc ggcccgccta cgggaaccct gggggggggtt ggcgcgggac ccgaggttag  72060
cggggggcgg cggttttcgc ccccgggcaa aaccgtgccg gttgcgaccg ggggcggaac  72120
gggatcgata gggagagcgg gagaagcctg gccggcggac tggggaccga gcgggagggg  72180
cacaccagac accaaagcgt ggggcgctgg ctctgggggt ttgggagggg ccggggggcg  72240
cgcgaaatcg gtaaccgggg cgaccgtgtc ggggagggca ggcggccgcc aaccctgggt  72300
ggtcgcggaa gcctgggtgg cgcgcgccag ggagcgtgcc cggcggtgtc ggcgcgcgcg  72360
cgacccggac gaagaagcgg tagaagcgcg ggaggaggcg ggggggcggg gggcggtggc  72420
atcgggggc gccggggaac tttgggggga cggcaagcgc cggaagtcgt cgcgggggcc  72480
cacgggcgcc ggccgcgtgc tttcggccgg gacgcccggt cgtgcttcgc gagccgtgac  72540
tgccggccca gggggccgcg gtgcacactg ggacgtgggg acggactgat cggcggtggg  72600
cgaaaggggg tccggggcaa ggagggggcgc ggggccgccg gagtcgtcag acgcgagctc  72660
ctccaggccg tgaatccatg cccacatgcg aggggggacg ggctcgccgg gggtggcgtc  72720
ggtgaatagc gtgggggcca ggcttccggg ccccaacgag ccctccgccc caacaaggtc  72780
cgccgggccg ggggtcgggt tcgggaccga ggggctctgg tcgtcggggg cgcgctggta  72840
caccggatgc cccgggaata gctcccccga caggagggag gcgtcgaacg gccgcccgag  72900
gatagctcgc gcgaggaagg ggtcctcgtc ggtggcgctc gcggcgagga cgtcctcgcc  72960
gcccgccaca aacgggagct cctcggtggc ctcgctgcca acaaaccgca tgtcgggggg  73020
gccggggggg tccgggtttt cccacaacac cgcgaccggg gtcatggaga tgtccacgag  73080
caccaggcac ggcgggcccc gggcgagggg ccgctcggcg atgagcgcgg acaggcgcgg  73140
gagctgtgcc gccagacacg cgttttcgat cgggttaagg tcggcgtgca ggaggcggac  73200
ggcccacgtc tcgatgtcgg acgacacggc atcgcgcaag gcggcgtccg gcccgcgagc  73260
gcgtgagtca aacagcgtga ggcacagctc cagttccgac tcgcgggaaa aggccgtggt  73320
gttgcggagc gccacgacga cgggcgcgcc caggagcact gccgccagca ccaggtccat  73380
ggccgtaacg cgcgccgcgg gggtgcggtg ggtggcggcg gccggcacgg cgacgtgctg  73440
gcccgtgggc cggtagaggg cgttgggggg agcgggggggt gacgcctcgc gcccccccga  73500
ggggctcagc gtctgcccag attccagacg cgcggtcaga agggcgtcga aactgtcata  73560
ctctgtgtag tcgtccggaa acatgcaggt ccaaagagcg gccagcgcgg tgcttgggag  73620
acacatgcgc ccgaggacgc tcaccgccgc cagcgcctgg gcgggactca gctttcccag  73680
cgcggcgccg cgctcggttc ccagctcggg gaccgagcgc cagggcgcca gggggtcggt  73740
ttcggacaac ttgccgcggc gccagtctgc cagccgcgtg ccgaacatga ggccccgggt  73800
cggagggcct ccggccgaaa acgctggcag cacgcggatg cgggcgtctg gatgcggggt  73860
caggcgctgc acgaatagca tggaatctgc tgcgttctga aacgcacggg ggagggtgag  73920
atgcatgtac tcgtgttggc ggaccagatc caggcgccaa aaggtgtaaa tgtgttccgg  73980
```

```
ggagctggcc accagcgcca ccagcacgtc gttctcgtta aaggaaacgc ggtgcctagt  74040
ggagctctgg ggtccgagcg gcggccccgg ggccgccgcg tcacccccc attccagctg  74100
ggcccagcga cacccaaact cgcgcgtgag agtggtcgcg acgagggcga cgtagagctc  74160
ggccgccgca tccatcgagg ccccccatct cgcctggcgg tggcgcacaa agcgtccgaa  74220
gagctgaaag ttggcggcct gggcgtcgct gagggccagc tgaagccggt tgatgacggt  74280
gaggacgtac atggccgtga cggtcgaggc cgactccagg gtgtccgtcg gaagcggggg  74340
gcgaatgcat gccgcctcgg gacacatcag cagcgcgccg agcttgtcgg tcacggccgg  74400
gaagcagagc gcgtactgca gtggcgttcc atccgggacc aaaaagctgg gggcgaacgg  74460
cctatccagc gtactggtgg cctcgcgcag caccaggggc cccgggcctc cgctcactcg  74520
caggtacgcc tcgccccggc ggcgcagcat ctgcgggtcg gcctcttggc cgggtggggc  74580
ggacgcccgg gcgcgggcgt ctagggcgcg aagatccacg agcaggggcg cgggcgcggc  74640
cgccgcgccc gcgcccgtct ggcctgtggc cttggcgtac gcgctatata agcccatgcg  74700
gcgttggatg agctcccgcg cgccccggaa ctcctccacc gcccatgggg ccaggtcccc  74760
ggccaccgcg tccaattccg ccaacaggcc ccccagggtg tcaaagttca tctcccaggc  74820
caccccttggc accacctcgt cccgcagccg ggcgctcagg tcggcgtgtt gggccacgcg  74880
ccccccgagc tcctccacgg ccccggcccg ctcggcgctc ttggcgccca ggacgccctg  74940
gtacttggcg ggaaggcgct cgtagtcccg ctgggctcgc agccccgaca cagtgttggt  75000
ggtgtcctgc agggcgcgaa gctgctcgca tgccgcgcga aatccctcgg gcgatttcca  75060
ggcccccccg cgaacgcggc cgaagcgacc ccatacctcg tcccactccg cctcggcctc  75120
ctcgaaagac ctccgcaggg cctcgacgcg gcgacgggtg tcgaagagcg actgcaggcg  75180
cgcgccctgt cgcgtcagga ggcccgggcc gtcgccgctg gccgcgctta gcgggtgcgt  75240
ctcaaaggtg cgctgggcat gttccaacca ggcgaccgcc tgcacgtcga gctcgcgcgc  75300
cttctccgtc tggtccaaca gaatctcgac ctgatccgcg atctcctccg ccgagcgcgc  75360
ctggtccagc gtcttggcca cggtcgccgg gacggcaacc accttcagca gggtcttcag  75420
attggccaga ccctcggcct cgagctgggc ccggcgctcg cgcgcggcca gcacctcccg  75480
caaccccgcc gtgacccgct cggtggcttc ggcgcgctgc tgtttggcgc gcaccacggc  75540
gtccttggta tcggccaggt cctgtcgggt cacgaatgcg acgtagtcgg cgtacgccgt  75600
gtccttcacg gggctctggt ccacgcgctc cagcgccgcc acacacgcca ccagcgcgtc  75660
ctcgctcggg cagggcaggg tgacccctgc ccggacaagc tcggcggccg ccgccgggtc  75720
gttgcgcacc gcggatatct cctccgcggc ggcggccagg tccagcgcca cgcttccgat  75780
cgcgcgccgc gcgtcggccc ggagggcgtc caggcgatcg cggatatcca cgtactcggc  75840
gtagcccttt tgaaaaaacg gcacgtactg gcgcagggcc ggcacgcccc ccaagtcttc  75900
cgacaggtgt aggacggcct cgtggtagtc gataaacccg tcgttcgcct gggcccgctc  75960
cagcagcccc cccgcgagcc gcagaagccg cgccaggggc tcggtgtcca cccgaaacat  76020
gtcggcgtac gtgtcggccg cggccccgaa ggccgcgctc cagtcgatgc ggtgaatggc  76080
tgcgagcggg gggagcatgg ggtggcgctg gttctcgggg gtgtatgggt taaacgcaag  76140
ggccgtctcc agggcaaggg tcaccgcctt ggcgttggtt cccagcgcct gctcggcccg  76200
ctttcggaag tcccgggggt tgtagccgtg cgtgcccgcc agcgcctgca ggcgacggag  76260
ctcgaccacg tcaaactcgg caccgctttc cacgcggtcc agcacggcct ccacgtcggc  76320
```

-continued

```
ggcccagcgc tcgtggctac tgcgggcgcg ctgggccgcc atcttctctc tgaggtcggc  76380
ggtggcggcc tcaagttcgt cggcgcggcg tcgcgtggcg ccgatgacct ttcccagctc  76440
ctgcagggcg cgcccgctgg gggagtggtc cccggccgtc ccttcggcgt gcaacaggcc  76500
cccgaacctg ccctcgtggc ccgcgaggct ttcccgcgcg ccggtggtcg cgcgcgtcgc  76560
ggcctggatc agggaggcat gctctccctc cggttggttg gcggcccggc gcacctggac  76620
gacaaggtcg gcggcagccg accctaaggt cgtgagctgg gcgatggccc cccgcgcgtc  76680
cagggccaac cgagtcgcct tgacgtatcc cgcggcgctg tcggccatgg ccgctaggaa  76740
ggccaggggg gaggccgggt cgctggcggc cgcgcccagg gccgtcactg cgtcgaccag  76800
gacgcggtgc gcccgcacgg ccgcatccac cgtcgacgcg gggtctgccg tcgcgacggc  76860
ggcgctgccg gcgttgatgg cgttcgagac ggcgtgggct atgatcgggg cgtgatcggc  76920
gaagaactgc aagagaaacg gagtctcggg ggcgttggcg aacaggttct tcagcaccac  76980
cacgaagctg ggatgcaagc cggacagagc cgtcgccgtg tccggagtcg ggtgctccag  77040
ggcatctcgg tactgcccca gcagccccca catgtccgcc cgcagcgccg ccgtaacctc  77100
cgggggcgcc ccccgaacgg cctcggggag gtccgaccag cccgccggca gggaggcccg  77160
cagggtcgtc aggacggccg gacaggcctt tagccccaca aagtcaggga ggggccgcag  77220
gaccccctgg agtttgtgca agaacttctc ccgggcgtcg cgggccacct tcgcccgctc  77280
ccgcgctccc tcgagcattg cctccaggga gcgcgcgcgc tcccgcaaac gggcacgcgc  77340
atcgggggcg agctctgccg tcagcttggc ggcatccatg gcccgcgcct gccgcagcgc  77400
ttcctcggcc atgcgcgtgg cctctggcga cagcccgccg tcgtcggggt agggcgacgc  77460
gccgggcgca ggaacaaagg ccgcgtcgct gtccagctgc tggcccaggg ccgcatctag  77520
ggcgtcgaag cgccgcagct cggccagacc cgagctgcgg cgcgcctgct ggtcgttaat  77580
gtcgcggatg ctgcgcgcca gctcgtccag cggcttgcgt tctatcagcc cttggttggc  77640
ggcgtccgtc aggacggaga gccaggccgc caggtcctcg ggggcgtcca gcgtctggcc  77700
ccgctgtatc agatcccgca acaggatggc cgtggggctg gtcgcgatcg ggggcggggc  77760
gggaatggcg gcgctctgcg cgatgtcccg cgtgtgctgg tcgaagacag gcagggactc  77820
tagcagctgg accacgggca cgacggcggc cgaagccacg tgaaaccggc ggtcgttgtt  77880
gtcgctggcc tgcagagcct tggcgctgta tacggccccc cggtaaaagt actccttaac  77940
cgcgccctcg atcgcccgac gggcctgggt ccgcacctcc tccagccgaa cctgaacggc  78000
ctcggggccc aggggggggtg ggcgcggagc cccctgcggg gccgccccgg ccggggcggg  78060
cattacgccg aggggcccgg cgtgctgtga gaccgcgtcg accccgcgag cgagggcgtc  78120
gagggcctcg cgcatctggc gatcctccgc ctccaccccta atctcttcgc cacgggcaaa  78180
tttggccaga gcctggactc tatacagaag cggttctggg tgcgtcgggg tggcgggggc  78240
aaaaagggtg tccgggtggg cctgcgagcg ctccagaagc cactcgccga ggcgtgtata  78300
cagattggcc ggcggggccg cgcgaagctg cagctccagg tccgcgagtt ccccgtaaaa  78360
ggcgtccgtc tcccgaatga catccctagc cacaaggatc agcttcgcca gcgccaggcg  78420
accgatcaga gagttttcgt ccagcacgtg ctggacgagg ggcagatggg cggccacgtc  78480
ggccaggctc aggcgcgtgg aggccagaaa gtcccccacg gccgttttcc ggggcagcat  78540
gctcagggta aactccagca gggcggcggc cgggccggcc accccggcct gggtgtgcgt  78600
ccgggccccg ttctcgatga gaaaggcgag gacgcgttca aagaaaaaaa taacacagag  78660
ctccagcagc cccggagaag ccggatacgg cgaccgtaag gcgctgatgg tgagccgcga  78720
```

acacgcggcg acctcgcggg ccagggcggc ggagcacgcg gtgaacttaa ccgccgtggc 78780
ggccacgttt gggtgggcct cgaacagctg ggcaaggtct gcgcccgggg gctcgggtga 78840
gcggcgagtc ttcagcgcct cgagggcctg cgaggacgcc ggaaccgtgg gcccgtcgtc 78900
ctcgcccgcc tcggcgaccg gcggcccggc cgggtcgggg ggtgccgagg cgaggacagg 78960
ctccggaacg gaggcgggga ccgcggcccc gacgggggtt ttgcctttgg gggtggattt 79020
cttcttggtt ttggcagggg gggccgagcg tttcgttttc tcccccgaag tcaggtcttc 79080
gacgctggaa ggcggagtcc aggtgggtcg gcggcgcttg ggaaggccgg ccgagtagcg 79140
tgcccggtgc cgaccaaccg ggacgacgcc catctccagg acccgcatgt cgtcgtcatc 79200
ttcttcggcc gcctctgcgg cggggggctt gggggcggag ggaggcggtg gtgggatcgc 79260
ggagggtggg tcggcggagg ggggatccgt gggtggggta cccttcaggg ccaccgccca 79320
tacatcgtcg ggcgcccgat tcgggcgctt ggcctctggt tttgccgacg gaccggccgt 79380
cccccgggat gtctcggagg ccctgtcgtc gcgacgggcc cgggtcggtg gcggcgactg 79440
ggcggctgtg ggcgggtggg gccccgtgcc ccctaccccc tcccgggggc ccacgccgac 79500
gcagggctcc cccaggcccg cgatctcgcc ccgcaggggg tgcgtgatgg ccacgcgccg 79560
ttcgctgaac gcttcgtcct gcaggtaagt ctcgctggcc ccgtaaagat gcagagccgc 79620
ggccgtcaag tccgcaggag ccgcgggttc cgggcccgac ggcacgaaaa acaccatggc 79680
tcccgcccac cgtacgtccg ggcgatcgcg ggtgtaatac gtcaggtatg gatacatgtc 79740
ccccgcccgc actttggcga tgaacgcggg ggtgccctcc ggaaggccgt gcgggtcaaa 79800
aaggtatgcg gtgtcgccgt ccctgaacag ccccatccct agggggccaa tggttaggag 79860
cgtgtacgac agggggcgca gggcccacgg gccggcgaag aacgtgtgtg cggggcattg 79920
tgtctccagc aggcccgccg cgggctcccc gaagaagccc acctcgccgt atacgcgcga 79980
gaagacacag cgcagtccgc cgcgcgcccc tgggtactcg aggaagttgg ggagctcgac 80040
gatcgaacac atgcgcggcg gcccagggcc cgcggtcgcg cgcgtccact cgccccccctc 80100
gaccaaacaa ccctcgatgg cctccgcgga cagaacgtcg cgagggccca catcaaatat 80160
gaggctgaga aaggacagcg acgagcgcat gcacgatacc gacccccccg gctccaggtc 80220
gggcgcgaac tggttccgag caccggtgac cacgatgtcg cgatcccccc cgcgttccat 80280
cgtggagtgc ggtggggtgc ccgcgatcat atgtgcccta ctggccagag acccggcctg 80340
tttatggacc ggacccccgg ggttagtgtt gtttccgcca cccatgcccc cgtaccatgg 80400
ccccggttcc cctgattagg ctacgagtcg cggtgatcgc ttcccaaaaa ccgagctgcg 80460
tttgtctgtc ttgatctttc ccccccccgc ccgcccgccc gcccgcacac cataacaccg 80520
agaacaacac acgggggtgg gcgtaacata ataaagcttt attggtaact agttaacggc 80580
aagtccgtgg gtggcgcgac ggtgtcctcc gggctcatct cgtcgtcctc gacgggggtg 80640
ttggaatgag gcgccccctc gcggtccgcc tggcgtgggc cgtgcccata ggcctccggc 80700
ttctgtgcgt ccatgggcat aggcgcgggg agactgtttc cggcgtcgcg gacctccagg 80760
tccctgggag actccggtcc ggctaacgga cgaaacgcgg aagcgcgaaa cacgccgtcg 80820
gtgacccgca ggagctcgtt catcagtaac caatccatac tcagcgtaac ggccagcccc 80880
tggcgagaca gatccacgga gtccggaacc gcggtcgtct ggcccagggg gccgaggctg 80940
tagtcccccc aggcccctag gtcgcgacgg ctcgtaagca cgacgcggtc ggccgcgggg 81000
ctttgcgggg gggcgtcctc gggcgcatgc gccattacct ctcggatggc cgcggcgcgc 81060
tggtcggccg agctgaccaa gggcgccacg accacggcgc gctccgtctg caggcccttc 81120
cacgtgtcgt ggagttcctg gacaaactcg gccacgggct cgggtcccgc ggccgcgcgc 81180
gcggcttgat agcaggccga gagacgccgc cagcgcgcta gaaactgacc catgaagcaa 81240
aacccgggga cctggtctcc cgacagcagc ttcgacgccc gggcgtgaat gccggacacg 81300
acggacagaa acccgtgaat ttcgcgccgg accacggcca gcacgttgtc ctcgtgcgac 81360
acctgggccg ccagctcgtc acacaccccc aggtgcgccg tggtttcggt gatgacggaa 81420
cgcaggctcg cgagggacgc gaccagcgcg cgcttggcgt cgtgatacat gctgcagtac 81480
tgactcaccg cgtcccccat ggcctcgggg ggccagggcc ccaggcggtc gggcgtgtcc 81540
ccgaccaccg catacaggcg gcgcccgtcg ctctcgaacc gacactcgaa aaaggcggag 81600
agcgtgcgca tgtgcagccg cagcagcacg atggcgtcct ccagttggcg aatcaggggg 81660
tctgcgcgct cggcgaggtc ctgcagcacc ccccgggcgg ccagggcgta catgctaatc 81720
aacaggaggc tggtgcccac ctcgggggc ggggggggct gcagctggac caggggccgc 81780
agctgctcga cggcacccct ggagatcacg tacagctccc ggagcagctg ctctatgttg 81840
tcggccatct gcatagtggg gccgaggccg ccccgggcgg ccggttcgag gagggtaatc 81900
agcgcgccca gtttggtgcg atggccctcg accgtgggga gatagcccag cccaaaatcc 81960
cgggcccagg ccaacacacg cagggcgaac tcgaccgggc gtggaaggta ggccgcgcta 82020
cacgtggccc tcaacgcgtc cccgaccacc agggccagaa cgtaggggac gaagcccggg 82080
tcggcgagga cgttggggtg aatgccctcg agggcgggga agcggatctg ggtcgccgcg 82140
gccaggtgga cagagggggc gtggctgggc tgcccgacgg ggagaagcgc ggacagcggc 82200
gtggccgggg tggtgggggt gatgtcccag tgggtctgac catacacgtc gatccagatg 82260
agcgccgtct cgcggagaag gctgggttga ccggaactaa agcggcgctc ggccgtctca 82320
aactccccca cgagcgcccg ccgcaggctc gccagatgtt ccgtcggcac ggccggaccc 82380
atgatacgcg ccagcgtctg gctcagaacg ccccccgaca ggccgaccgc ctcgcagagc 82440
cgcccgtgcg tgtgctcgct ggcgccctgg acccgcctga aagtttttac gtagttggca 82500
tagtacccgt attcccgcgc cagaccaaac acgttcgacc ccgcgagggc aatgcaccca 82560
aagagctgct ggacttcgcc gagtccgtgg ccggcgggcg tccgcgcggg gacgcccgcc 82620
gccagaaacc cctccagggc cgaaaggtag tgcgtgcagt gcgagggcgt gaacccagcg 82680
tcgatcaggg tgttgatcac cacggagggc gaattggtat tctggatcaa cgtccacgtc 82740
tgctgcaaca gagccaacag ccgctgctgg gcgccggcgg agggctgctc cccgagctgc 82800
agcaggctgg agacggcagg ctggaagact gccagtgccg acgaactcag gaacggcacg 82860
tcgggatcaa acacggccac gtccgtccgc acgcgcgcca ttagcgtccc cgggggcgca 82920
caggccgagc gcgggctgac gcggctgagg gccgtcgaca cgcgcacctc ctcgcggctg 82980
cgaaccatct tgttggcctc cagtggcgga atcattatgg ccgggtcgat ctcccgcacg 83040
gtgtgctgaa actgcgccaa caggggcggc gggaccacag ccccccgctc gggggtcgtc 83100
aggtactcgt ccaccagggc caacgtaaag agggcccgtg tgaggggagt gagggtcgcg 83160
tcgtctatgc gctggaggtg cgccgagaac agcgtcaccc gattactcac cagggccaag 83220
aaccggaggc cctcttgcac gaacggggcg gggaagagca ggctgtacgc cggggtggta 83280
aggttcgcgc tgggctgccc caacgggacc ggcgccatct tgagcgacgt ctccccaagg 83340
gcctcgatgg aggtccgcgg gctcatggcc aagcagctct tggtgacggt ttgccagcgg 83400
tctatccact ccacggcgca ctggcggacg cggaccggcc ccagggccgc cgcggtgcgc 83460
aggccggcgg aatccagcgc atgggacgtg tcggagccgg tgaccgcgag gatggtgtcc 83520
ttgatgacct ccatctcccg gaaggcctgg tcgggggcct cggggagagc caccaccaag 83580
cggtgtacga gcaacccggg gaggttctcg gccaagagcg ccgtctccgg aagcccgtgg 83640
gcccggtgga gcgcgcacag gtgttccagc agcggccgcc agcatgcccg cgcgtctgcc 83700
ggggcgatgg ccgttcccga caacagaaac gccgccatgg cggcgcgcag cttggccgtg 83760
gccagaaacg ccgggtcgtc cgccccgttt gccgtctcgg ccgtgggggt tggcggttgg 83820
cgaaggccgg ctaggctcgc caataggcgc tgcataggtc cgtccgaggg cggaccggcg 83880
ggtgaggtcg tgacgacggg ggcctcggac gggagaccgc ggtctgccat gacgcccggc 83940
tcgcgtgggt gggggacagc gtagaccaac gacgagaccg ggcgggaatg actgtcgtgc 84000
gctgtaggga gcggcgaatt atcgatcccc tgcggccctc caggaacccc gcaggcgttg 84060
cgagtacccc gcgtcttcgc ggggtgttat acggccactt aagtcccggc atcccgttcg 84120
cggacccagg cccgggggat tgtccggatg tgcgggcagc ccggacggcg tgggttgcgg 84180
actttctgcg gggcggccca aatggccctt taaacgtgtg tatacggacg cgccgggcca 84240
gtcggccaac acaacccacc ggaggcggta gccgcgtttg gctgtggggt gggtggttcc 84300
gccttgcgtg agtgtccttt cgaccccccc ctcccccggg tcttgctagg tcgcgatctg 84360
tggtcgcaat gaagaccaat ccgctacccg caaccccttc cgtgtggggc gggagtaccg 84420
tggaactccc ccccaccaca cgcgataccg cggggcaggg cctgcttcgg cgcgtcctgc 84480
gcccccgat ctctcgccgc gacggcccag tgctccccag ggggtcggga ccccggaggg 84540
cggccagcac gctgtggttg cttggcctgg acggcacaga cgcgcccct ggggcgctga 84600
cccccaacga cgataccgaa caggccctgg acaagatcct gcggggcacc atgcgcgggg 84660
gggcggccct gatcggctcc ccgcgccatc atctaacccg ccaagtgatc ctgacggatc 84720
tgtgccaacc caacgcggat cgtgccggga cgctgcttct ggcgctgcgg caccccgccg 84780
acctgcctca cctggcccac cagcgcgccc cgccaggccg gcagaccgag cggctgggcg 84840
aggcctgggg ccagctgatg gaggcgaccg ccctggggtc ggggcgagcc gagagcgggt 84900
gcacgcgcgc gggcctcgtg tcgtttaact tcctggtggc ggcgtgtgcc gcctcgtacg 84960
acgcgcgcga cgccgccgat gcggtacggg cccacgtcac ggccaactac cgcgggacgc 85020
gggtgggggc gcgcctggat cgtttttccg agtgtctgcg cgccatggtt cacacgcacg 85080
tcttccccca cgaggtcatg cggtttttcg gggggctggt gtcgtgggtc acccaggacg 85140
agctagcgag cgtcaccgcc gtgtgcgccg ggccccagga ggcggcgcac accggccacc 85200
cgggccggcc ccgctcggcc gtgatcctcc cggcgtgtgc gttcgtggac ctggacgccg 85260
agctggggct ggggggcccg ggcgcggcgt ttctgtacct ggtattcact taccgccagc 85320
gccgggacca ggagctgtgt tgtgtgtacg tgatcaagag ccagctcccc ccgcgcgggt 85380
tggagccggc cctggagcgg ctgtttgggc gcctccggat caccaacacg attcacggca 85440
ccgaggacat gacgcccccg gccccaaacc gaaaccccga cttccccctc gcgggcctgg 85500
ccgccaatcc ccaaaccccg cgttgctcgg ctggccaggt cacgaacccc cagttcgccg 85560
acaggctgta ccgctggcag ccggaccttc gggggcgccc caccgcacgc acctgtacgt 85620
acgccgcctt tgcagagctc ggcatgatgc ccgaggatag tccccgctgc ctgcaccgca 85680
ccgagcgctt tggggcggtc agcgtccccg ttgttattct ggaaggcgtg gtgtggcgcc 85740
ccggcgagtg gcgggcatgc gcgtgagcgt agcaaacgcc ccgcccacac aacgctccgc 85800
ccccaacccc ttccccgctg tcactcgtgg ttcgttgacc cggacgtccg ccaaataaag 85860
ccactgaaac ccgaaacgcg agtgttgtaa cgtcctttgg gcgggaggaa gccacaaaat 85920
gcaaatggga tacatggaag gaacacaccc ccgtgactca ggacatcggc gtgtcctttt 85980
gggtttcact gaaactggcc cgcgccccac ccctgcgcga tgtggataaa aagccagcgc 86040
gggtggttta gggtaccaca ggtgggtgct ttggaaactt gtcggtcgcc gtgctcctgt 86100
gagcttgcgt ccctccccgg tttcctttgc gctcccgcct tccggacctg ctctcgccta 86160
tcttctttgg ctgtcggtgc gattcgtcag gcagcggcct tgtcgaatct cgaccccacc 86220
actcgccgga cccgccgacg tcccctctgg agcccgccga aacccgccgc gtctgttgaa 86280
atggccagcc gcccagccgc atcctctccc gtcgaagcgc gggcccoggt tgggggacag 86340
gaggccggcg gccccagcgc agccacccag ggggaggccg ccggggcccc tctcgcccac 86400
ggccaccacg tgtactgcca gcgagtcaat ggcgtgatgg tgctttccga caagacgccc 86460
gggtccgcgt cctaccgcat cagcgatagc aactttgtcc aatgtggttc caactgcacc 86520
atgattatcg acggagacgt ggtgcgcggg cgcccccagg acccgggggc cgcggcatcc 86580
cccgctccct tcgttgcggt gacaaacatc ggagccggca gcgacggcgg gaccgccgtc 86640
gttgcattcg gggggaaccc acgtcgctcg gcggggacgt ctaccggtac ccagacggcc 86700
gacgtcccag ccgaggccct tgggggcccc cctcctcctc cccgcttcac cctgggtggc 86760
ggctgttgct cctgtcgcga cacacggcgc cgctctgcgg tattcggggg ggagggggat 86820
cccgtcggcc ccgcggagtt cgtctcggac gaccggtcgt ccgattccga ctcggatgac 86880
tcggaggaca ccgactcgga gacgctgtca cacgcctcct cggacgtgtc cggcggggcc 86940
acgtacgacg acgcccttga ctccgattcg tcatcggatg actccctgca gatagatggc 87000
cccgtgtgtc gcccgtggag caatgacacc gcgcccctgg atgtttgccc cgggaccccc 87060
ggcccgggcg ccgacgccgg tggtccctca gcggtagacc cacacgcgcc gacgacaggg 87120
gccggcgctg gtcttgcggc cgatcccgcc gtggcccggg acgacgcgga ggggctttcg 87180
gacccccggc cacgtctggg aacgggcacg gcctaccccg tcccccctgga actcacgccc 87240
gagaacgcgg aggccgtggc gcgctttctg ggagatgccg tgaaccgcga acccgcgctc 87300
atgctggagt acttttgccg gtgcgcccgc gaggaaacca agcgtgtccc ccccaggaca 87360
ttctgcagcc cccctcgcct cacggaggac gactttgggc ttctcaacta cgcgctcgtg 87420
gagatgcagc gcctgtgtct ggacgttcct ccggtcccgc cgaacgcata catgccctat 87480
tatctcaggg agtatgtgac gcggctggtc aacgggttca agccgctggt gagccggtcc 87540
gctcgccttt accgcatcct gggggttctg gtgcacctgc ggatccggac ccgggaggcc 87600
tcctttgagg agtggctgcg atccaaggaa gtggccctgg actttggcct gacggaaagg 87660
cttcgcgagc acgaagccca gctggtgatc ctggcccagg ttctggacca ttacgactgt 87720
ctgatccaca gcacaccgca cacgctggtc gagcgggggc tgcaatcggc cctgaagtat 87780
gaggagtttt acctaaagcg ctttggcggg cactacatgg agtccgtctt ccagatgtac 87840
acccgcatcg ccggcttttt ggcctgccgg gccacgcgcg gcatgcgcca catcgccctg 87900
gggcgagagg ggtcgtggtg ggaaatgttc aagttctttt tccaccgcct ctacgaccac 87960
cagatcgtac cgtcgacccc cgccatgctg aacctgggga cccgcaacta ctacacctcc 88020
agctgctacc tggtaaaccc ccaggccacc acaaacaagg cgaccctgcg ggccatcacc 88080
agcaacgtca gtgccatcct cgcccgcaac gggggcatcg ggctatgcgt gcaggcgttt 88140
aacgactccg gccccgggac cgccagcgtc atgcccgccc tcaaggtcct cgactcgctg 88200
gtggcggcgc acaacaaaga gagcgcgcgt ccgaccggcg cgtgcgtgta cctggagccg 88260
tggcacaccg acgtgcgggc cgtgctccgg atgaaggggg tcctcgccgg cgaagaggcc 88320
cagcgctgcg acaatatctt cagcgccctc tggatgccag acctgttttt caagcgcctg 88380
attcgccacc tggacggcga gaagaacgtc acatggaccc tgttcgaccg ggacaccagc 88440
atgtcgctcg ccgactttca cggggaggag ttcgagaagc tctaccagca cctcgaggtc 88500
atggggttcg gcgagcagat acccatccag gagctggcct atggcattgt gcgcagtgcg 88560
gccacgaccg ggagcccctt cgtcatgttc aaagacgcgg tgaaccgcca ctacatctac 88620
gacacccagg gggcggccat cgccggctcc aacctctgca ccgagatcgt ccatccggcc 88680
tccaagcgat ccagtggggt ctgtaatctg ggaagcgtga atctggcccg atgcgtctcc 88740
aggcagacgt ttgactttgg gcggctccgc gacgccgtgc aggcgtgcgt gctgatggtg 88800
aacatcatga tcgacagcac gctacaaccc acgccccagt gcacccgcgg caacgacaac 88860
ctgcggtcca tgggaatcgg catgcagggc ctgcacacgg cctgcctgaa gctggggctg 88920
gatctggagt ctgccgaatt tcaggacctg aacaaacaca tcgccgaggt gatgctgctg 88980
tcggcgatga agaccagcaa cgcgctgtgc gttcgcgggg cccgtccctt caaccacttt 89040
aagcgcagca tgtatcgcgc cggccgcttt cactgggagc gctttccgga cgcccggccg 89100
cggtacgagg gcgagtggga gatgctacgc cagagcatga tgaaacacgg cctgcgcaac 89160
agccagtttg tcgcgctgat gcccaccgcc gcctcggcgc agatctcgga cgtcagcgag 89220
ggctttgccc ccctgttcac caacctgttt agcaaggtga cccgggacgg cgagacgctg 89280
cgccccaaca cgctcctgct aaaggaactg gaacgcacgt ttagcgggaa gcgcctcctg 89340
gaggtgatgg acagtctcga cgccaagcag tggtccgtgg cgcaggcgct cccgtgcctg 89400
gagcccaccc acccccctcg gcgattcaag accgcgtttg actacgacca gaagttgctg 89460
atcgacctgt gtgcggaccg cgccccctac gtcgaccata gccaatccat gaccctgtat 89520
gtcacggaga aggcggacgg gaccctccca gcctccaccc tggtccgcct tctggtccac 89580
gcatataagc gcggactaaa aacagggatg tactactgca aggttcgcaa ggcgaccaac 89640
agcggggtct ttggcggcga cgacaacatt gtctgcacga gctgcgcgct gtgaccgaca 89700
aaccccctcc gcgccaggcc cgccgccact gtcgtcgccg tcccacgcgc tcccccgctg 89760
ccatggattc cgcggcccca gccctctccc ccgctctgac ggcccatacg ggccagagcg 89820
cgccggcgga cctggcgatc cagattccaa agtgccccga ccccgagagg tacttctaca 89880
cctcccagtg tcccgacatt aaccacctgc gctccctcag catccttaac cgctggctgg 89940
aaaccgagct tgttttcgtg ggggacgagg aggacgtctc caagctttcc gagggcgagc 90000
tcagctttta ccgcttcctc ttcgctttcc tgtcggccgc cgacgacctg gttacggaaa 90060
acctgggcgg cctctccggc ctgtttgagc agaaggacat tctccactac tacgtggagc 90120
aggaatgcat cgaagtcgta cactcgcgcg tgtacaacat catccagctg gtgctttttc 90180
acaacaacga ccaggcgcgc cgcgagtacg tggccggcac catcaaccac ccggccatcc 90240
gcgccaaggt ggactggttg gaagcgcggg tgcgggaatg cgcctccgtt ccggaaaagt 90300
tcattctcat gatcctcatc gagggcatct tttttgccgc ctcgtttgcc gccatcgcct 90360
accttcgcac caacaacctt ctgcgggtca cctgccagtc aaacgacctc atcagccggg 90420
acgaggccgt gcacacgacg gcctcgtgtt acatctacaa caactacctc ggcgggcacg 90480
ccaagccccc gcccgaccgc gtgtacgggc tgttccgcca ggcggtcgag atcgagatcg 90540

-continued

```
gatttatccg atcccaggcg ccgacggaca gccatatcct gagcccggcg gcgctggcgg  90600
ccatcgaaaa ctacgtgcga ttcagcgcgg atcgcctgtt gggccttatc cacatgaagc  90660
cactgttttc cgccccaccc cccgacgcca gctttccgct gagcctcatg tccaccgaca  90720
aacacaccaa ttttttcgag tgtcgcagca cctcctacgc cggggcggtc gtcaacgatc  90780
tgtgagggtc gcggcgcgct tctacccgtg tttgcccata ataaacctct gaaccaaact  90840
ttgggtctca ttgtgattct tgtcagggac gcgggggtgg gagaggataa aaggcggcgc  90900
aaaaagcagt aaccaggtcc ggccagattc tgagggcata ggataccata attttattgg  90960
tgggtcgttt gttcggggac aagcgcgctc gtctgacgtt tggctactc gtcccagaat  91020
ttggccagga cgtccttgta gaacgcgggt ggggggcct gggtccgcag ctgctccaga  91080
aacctgtcgg cgatatcagg ggccgtgata tgccgggtca cgatagatcg cgccaggttt  91140
tcgtcgcgga tgtcctggta gataggcagg cgtttcagaa gagtccacgg cccccgctcc  91200
ttggggccga taagcgatat gacgtactta atgtagcggt gttccaccag ctcggtgatg  91260
gtcatgggat cggggagcca gtccagggac tctggggcgt cgtggatgac gtggcgtcgc  91320
cggctggcca cataactgcg gtgctcttcc agcagctgcg cgttcgggac ctggacgagc  91380
tcgggcgggg tgagtatctc cgaggaggac gacctggggc cggggtggcc cccggtaacg  91440
tcccggggat ccagggggag gtcctcgtcg tcttcgtatc cgccggcgat ctgttgggtt  91500
agaatttcgg tccacgagac gcgcgtctcg gtgccgccgg tggccggcgg cagagggggc  91560
ctggtttccg tggagcgcga gctggtgtgt tcccggcgga tggcccgccg ggtctgagag  91620
cgactcgggg gggtccagtg acattcgcgc agcacatcct ccacggaggc gtaggtgtta  91680
ttgggatgga ggtcggtgtg gcagcggaca aagagggcca ggaactgggg gtagctcatc  91740
ttaaagtact tcagtatatc gcgacagttg atcgtgggaa tgtagcaggc gctaatatcc  91800
aacacaatat cgcagcccat caacaggagg tcagtgtccg tggtgtacac gtacgcgacc  91860
gtgttggtgt gatagaggtt ggcgcaggca tcgtccgcct ccagctgacc cgagttaatg  91920
taggcgtacc ccagggcccg gagaacgcga atacagaaca gatgcgccag acgcagggcc  91980
ggcttcgagg gcgcggcgga cggcagcgcg gctccggacc cggccgtccc ccgggtcccc  92040
gaggccagag aggtgccgcg tcggcgcatg ttggaaaagg cagagctggg tctggagtcg  92100
gtgatggggg aaggcggtgg agaggcgtcc acgtcactgg cctcctcgtc cgtccggcac  92160
tgggccgtcg tgcgggccag gatggccttg gctccaaaca caaccggctc catacaattg  92220
accccgcgat cggtaacgaa gatggggaaa agggactttt gggtaaacac ctttaataag  92280
cgacagaggc agtgtagcgt aatggcctcg cggtcgtaac tggggtatcg gcgctgatat  92340
ttgaccacca acgtgtacat gacgttccac aggtccacgg caatgggggt gaagtacccg  92400
gccggggccc caaggccccg gcgcttgacc agatggtgtg tgtgggcaaa cttcatcatc  92460
ccgaacaaac ccatgtcagg tcgattgtaa ctgcggatcg gcctaactaa ggcgtggttg  92520
gtgcgacggt ccgggacacc cgagcctgtc tctctgtgta tggtgaccca gacaacaaca  92580
ccgacacaag aggacaataa tccgttaggg gacgctcttt ataatttcga tggcccaact  92640
ccacgcggat tggtgcagca ccctgcatgc gccggtgcgg gccaaccttc cccccgctca  92700
ttgcctcttc caaaagggtg tggcctaacg agctgggggc gtatttaatc aggctagcgc  92760
ggcgggcctg ccgtagtttc tggctcggtg agcgacggtc cggttgcttg ggtcccctgg  92820
ctgccatcaa aaccccaccc tcgcagcggc atacgccccc tccgcgtccc gcacccgaga  92880
ccccggcccg gctgccctca ccaccgaagc ccacctcgtc actgtggggt gttcccagcc  92940
```

cgcgttggga tgacggattc ccctggcggt gtggcccccg cctcccacgt ggaggacgcg 93000
tcggacgcgt ccctcgggca gccggaggag ggggcgccct gccaggtggt cctgcagggc 93060
gccgagctta atggaatcct acaggcgttt gccccgctgc gcacgagcct tctggactcg 93120
cttctggtta tgggagaccg gggcatcctt atccataaca cgatctttgg ggagcaggtg 93180
ttcctgcccc tggaacactc gcaattcagt cggtatcgct ggcgcggacc cacggcggcg 93240
ttcctgtctc tcgtggacca gaagcgctcc ctcctgagcg tgtttcgcgc caaccagtac 93300
ccggacctac gtcgggtgga gttggcgatc acgggccagg ccccgtttcg cacgctggtt 93360
cagcgcatat ggacgacgac gtccgacggc gaggccgttg agctagccag cgagacgctg 93420
atgaagcgcg aactgacgag ctttgtggtg ctggttcccc agggaacccc cgacgttcag 93480
ttgcgcctga cgaggccgca gctcaccaag gtccttaacg cgaccggggc cgatagtgcc 93540
acgcccacca cgttcgagct cggggttaac ggcaaatttt ccgtgttcac cacgagtacc 93600
tgcgtcacat ttgctgcccg cgaggagggc gtgtcgtcca gcaccagcac ccaggtccag 93660
atcctgtcca acgcgctcac caaggcgggc caggcggccg ccaacgccaa gacggtgtac 93720
ggggaaaata cccatcgtac cttctctgtg gtcgtcgacg attgcagcat gcgggcggtg 93780
ctccggcgac tgcaggtcgc cgggggcacc ctcaagttct tcctcacgac ccccgtcccc 93840
agtctgtgcg tcaccgccac cggtcccaac gcggtatcgg cggtatttct cctgaaaccc 93900
cagaagattt gcctggactg gctgggtcat agccaggggt ctccttccgc cgggagctcg 93960
gcctcccggg cctctgggag cgagccaaca gacagccagg actccgcgtc ggacgcggtc 94020
agccacggcg atccggaaga cctcgatggc gctgcccggg cgggagaggc gggggcctcg 94080
tacgcctgtc cgatgccgtc gtcgaccacg cgggtcactc ccacgaccaa gcgggggcgc 94140
tcgggggcg aggatgcgca cgcggacacg gccctaaaga aacctaagac ggggtcgccc 94200
accgcacccc cgcccgcaga tccagtcccc ctggacacgg aggacgactc cgatgcggcg 94260
gacgggacgg cggcccgtcc cgccgctcca gacgcccgaa gcggaagccg ttacgcgtgt 94320
tactttcgcg acctcccgac cggagaagca agccccggcg ccttctccgc cttccggggg 94380
ggcccccaaa ccccgtctgg ttttggattc ccctgacggg gcggggcctt agcggccgcc 94440
caaccctcgc aacatcccgg ggttaatgta aataaacttg gtattgccca acactctccc 94500
gcgtgtcgcg tgtggttcat gtgtgtgcct ggcgccccca ccctcgggtt cgtgtatttc 94560
ctttccctgt ccttataaaa gccgtatgtg gggcgctgac ggaaccaccc cgcgtgccat 94620
cacggccaag gcgcgggatg ctccgcaacg acagccaccg ggccgcgtcc ccggaggacg 94680
gccagggacg ggtcgacgac ggacggccac acctcgcgtg cgtgggggcc ctggcgcggg 94740
ggttcatgca tatctggctt caggccgcca cgctgggttt tgcgggatcg gtcgttatgt 94800
cgcgcgggcc gtacgcgaat gccgcgtctg ggcgttcgc cgtcgggtgc gccgtgctgg 94860
gctttatgcg cgcgcccct cccctcgcgc ggcccaccgc gcggatatac gcctggctca 94920
aactggcggc cggtggagcg gcccttgttc tgtggagtct cggggagccc ggcacgcagc 94980
cgggggccct ggccccgggc ccggccaccc agtgcctggc gctgggcgcc gcctatgcgg 95040
cgctcctggt gctcgccgat gacgtctatc cgctctttct cctcgccccg gggcccctgt 95100
tcgtcggcac cctggggatg gtcgtcggcg ggctgacgat cggaggcagc gcgcgctact 95160
ggtggatcgg tgggcccgcc gcggccgccc tggccgcggc ggtgttggcg ggcccggggg 95220
cgaccaccgc cagggactgc ttctccaggg cgtgccccga ccaccgccgc gtctgcgtca 95280

-continued

```
tcgtcgcagg cgagtctgtt tcccgccgcc ccccggagga cccagagcga cccggggacc  95340
cagggccacc gtcccccccg acaccccaac gatcccaggg gccgccggcc gatgaggtcg  95400
caccggccgg ggtagcgcgg cccgaaaacg tctgggtgcc cgtggtcacc tttctggggg  95460
ctggcgcgct cgccgtcaag acggtgcgag aacatgcccg gggaacgccg ggcccgggcc  95520
tgccgctgtg gccccaggtg tttctcggag gccatgtggc ggtggccctg acggagctgt  95580
gtcaggcgct tgcgccctgg gaccttacgg acccgctgct gtttgttcac gccggactgc  95640
aggtcatcaa cctcgggttg gtgtttcggt tttccgaggt tgtcgtgtat gcggcgctag  95700
ggggtgccgt gtggatttcg ttggcgcagg tgctggggct ccggcgtcgc ctgcacagga  95760
aggaccccgg ggacggggcc cggttggcgg cgacgcttcg gggcctcttc ttctccgtgt  95820
acgcgctggg gtttggggtg ggggcgctgc tgtgccctcc ggggtcaacg ggcgggcggt  95880
cgggcgattg atatattttt caataaaagg cattagtccc gaagaccgcc ggtgtgtgat  95940
gatttcgcca taacacccaa accccggatg gggcccgggt ataaattccg gaaggggaca  96000
cgggctacct tcactaccga gggcgcttgg tcgggaggcc gcatcgaacg cacaccccca  96060
tccggtggtc cgtgtggagg tcgtttttca gtgcccggtc tcgctttgcc gggaacgcta  96120
gccgatccct cgcgaggggg aggcgtcggg cggccagata tacgcgttga cattgattat  96180
tgactagtta ttaatagtaa tcaattacgg ggtcattagt tcatagccca tatatggagt  96240
tccgcgttac ataacttacg gtaaatggcc cgcctggctg accgcccaac gacccccgcc  96300
cattgacgtc aataatgacg tatgttccca tagtaacgcc aatagggact ttccattgac  96360
gtcaatgggt ggagtattta cggtaaactg cccacttggc agtacatcaa gtgtatcata  96420
tgccaagtac gccccctatt gacgtcaatg acggtaaatg gcccgcctgg cattatgccc  96480
agtacatgac cttatgggac tttcctactt ggcagtacat ctacgtatta gtcatcgcta  96540
ttaccatggt gatgcggttt tggcagtaca tcaatgggcg tggatagcgg tttgactcac  96600
ggggatttcc aagtctccac cccattgacg tcaatgggag tttgttttgg caccaaaatc  96660
aacgggactt tccaaaatgt cgtaacaact ccgccccatt gacgcaaatg ggcggtaggc  96720
gtgtacggtg ggaggtctat ataagcagag ctcgtttagt gaaccgtcag atcgcctgga  96780
gacgccatcc acgctgtttt gacctccata gaagacaccg ggaccgatcc agcctccgga  96840
ctctagagga tcgaaccctt gccaccatgg agggagccga agccggggca cgagccacct  96900
ttggcccttg ggattacggg gtgtttgcca ccatgttgct cgtcagtacc ggaatcggtt  96960
tgtgggtggg actcgctcgg ggcggtcaga ggtccgcaga tgatttcttt acaggaggaa  97020
ggcagctcgc cgcagtgcca gtagggttgt ctctcgctgc tagttttatg tctgcagtcc  97080
aagtcctggg tgtaccagcc gaagctgccc gatacggcct taaattcctt tggatgtgcg  97140
tagggcaact cttgaatagt ttgcttactg ccctgctttt tttgccaatc ttttacagac  97200
ttggtctgac aagtacctac caatatttgg agctgagatt ttctcgggca gtaaggcttt  97260
gcgggactct tcagtatttg gtggccacta tgctctacac aggcatcgtc atctatgctc  97320
ccgcattgat tcttaatcag gtgaccggcc ttgacatctg ggccagcctt ctctccactg  97380
ggatcatttg cacactttat actacagttg gcggtatgaa agctgtggtg tggactgacg  97440
tttttcaagt ggtagttatg cttgtgggtt tctgggtaat acttgctagg ggggtaatgc  97500
tgatgggagg gccatggaac gtcctgagcc tggcccaaaa ccactcaaga attaacctga  97560
tggattttga tcccgaccca aggagccgat atacattttg gaccttcgtg gtcggcggtt  97620
ccttggtatg gctttcaatg tatggggtaa accaagctca agtccaacgc tatgtcgctt  97680
```

```
gccataccga gaggaaagct aaacttgcac ttcttgtgaa ccaacttggt ctctttctca  97740
tagtggcaag cgctgcatgt tgcggaattg ttatgtttgt ttattacaaa gattgtgacc  97800
ccttgcttac tggccggata gccgcccccg atcagtatat gccccttctc gtgcttgata  97860
tattcgagga cctccccggt gttcccggac tcttcctcgc atgtgcttac tcaggcaccc  97920
tttctaccgc ctcaacctct atcaatgcaa tggctgcagt caccgtggag gacctcatta  97980
aacctcgaat gccatccctg gccccaagga aactcgtgtt tatatccaag ggcttgtcct  98040
tcatatatgg aagcacctgt ctgacagtag cagcattgtc ttctttgttg ggcggcgggg  98100
tactgcaggg gtcttttaca gtgatgggtg taatctcagg ccccctttttg gggctttta  98160
ctctggggat gctcttgccc gcttgcaaca cacctggcgt actctcagga ctgactgccg  98220
ggttggctgt ttcactttgg gttgcagtag gcgccacact gtatccaccc ggcgagcaaa  98280
ccatgggtgt tctcccaacc tcagcagcag gatgcacaaa cgcctccgtt ctgccttctc  98340
cccctggggc cgcaaataca tcaaggggaa tccctagtag cggcatggat agtggaagac  98400
ccgcctttgc cgacacattc tacgcagtta gctacctgta ttacggcgcc ttggggactc  98460
tcaccactat gctctgcggg gctctgatta gttatttgac cggtcccacc aaacgatcca  98520
gcctcggtcc cggacttctg tggtgggact tggcaagaca aactgcttct gttgctccca  98580
aagaagacac aactaccttg gaagattcac ttgtcaaagg accagaggac atcccagcag  98640
ccactaaaaa gccaccaggt ttcaggcccg aagcagagac acaccctctg taccttggcc  98700
acgacgtaga aaccaacctg tgaaagggtt cgatccctac cggttagtaa tgagtttaaa  98760
cgggggaggc taactgaaac acggaaggag acaataccgg aaggaacccg cgctatgacg  98820
gcaataaaaa gacagaataa aacgcacggg tgttgggtcg tttgttcata aacgcggggt  98880
tcggtcccag ggctggcact ctgtcgatac cccaccgaga ccccattggg gccaatacgc  98940
ccgcgtttct tccttttccc caccccaccc cccaagttcg ggtgaaggcc cagggctcgc  99000
agccaacgtc ggggcggcag gccctgccat agcagatctg cgcagctgcg cgagaccccc  99060
ccgttacctt tttaatatct atatagtttg gtcccccctct atcccgccca ccgctgggcg  99120
ctataaagcc gccaccctct cttccctcag gtcatccttg gtcgatcccg aacgacacac  99180
ggcgtggagc aaaacgcctc cccctgagcc gctttcctac cagcgcaacg gcatgcctct  99240
gcgggcatcg gaacacgcct accggcccct gggccccggg acaccccccca tgcgggctcg  99300
gctccccgcc gcggcctggg ttggcgtcgg gaccatcatc gggggagttg tgatcattgc  99360
cgcgttggtc ctcgtgccct cgcgggcctc gtgggcactt tccccatgcg acagcggatg  99420
gcacgagttc aacctcgggt gcatatcctg ggatccgacc cccatggagc acgagcaggc  99480
ggtcggcggc tgtagcgccc cggcgaccct gatcccccgc gcggctgcca aacagctggc  99540
cgccgtcgca cgcgtccagt cggcaagatc ctcgggctac tggtgggtga gcggagacgg  99600
cattcgggcc tgcctgcggc tcgtcgacgg cgtcggcggt attgaccagt tttgcgagga  99660
gcccgccctt cgcatatgct actatccccg cagtcccggg ggctttgttc agtttgtaac  99720
ttcgacccgc aacgcgctgg ggctgccgtg aggcgcgtgt actgcggtct gtctcgtctc  99780
ctcttctccc cttccctccc cctccgcatc ccaggatcac accggccaac gagggttggg  99840
gggtccggca cggacccaaa ataataaaca cacaatcacg tgcgataaaa agaacacgcg  99900
gtcccctgtg gtgtttttgg ttattttat taaatctcgt cgtcaaacag ggggaaaggg  99960
gcgtggtcta gcgacggcag cacgggtgga ggcgttcacc ggctccggcg tccttcgcgt 100020
```

-continued ttaagcttgg tcaggagggc gctcagggcg gcgacgttgg tcgggccgtc gttggtcagg 100080
gcgttggctc gatggcgggc gaggacgggc gaggggctca acggcggggg cgggggcccg 100140
gtgcggcccg ggggggaaaa tagggcggat cccccccagt cgtacagggg atttccgcc 100200 tcaatgtacg gggaggccgg cgctgcattc gccgtgttcg cgcagacgtt ttcgtagacc 100260
cgcatccatg gtatttcctc gtagacacgc cccccgtcct cgctcacagt ctcgtatatt 100320
gactcgtcgt cctcgtaggg ggcgtgccgt tcgcgggccg aggcggcgtg ggtggctttg 100380
cggcgggcgt cgtcgtcgtc gtcggccgtc agatacgtgg cttccatctg gtcgggttct 100440
ccctccgggg cgggtcccca cccccgtggc cgatcgaggc tccccagaga cgcgcgccgg 100500
acgaggaggg ggcacgtcgc cgccggcggt cgcctgtcgg gtcccgcgac gttacgggcc 100560
gggaggcgcg ggggcacctc ccccatgtgc gtgtaatacg tggccggctg tgcggccgca 100620
gcggggggct cggcgaccgg gtcgtccgca tccggaagcg ggggcgccgc gccgtccgcg 100680
cggcgcctcc ggaaccgccg ggtggccgcg ggggtcgagt gtaggcgagg tcgggggagg 100740
ggcgggggct cgttgtcgcg ccgcgcccgc tgaatctttt cccgacaggt cccaccccc 100800 gcgcgatgcc cccccgggcc gcgggccatg tcgtccgggg gaggccccgc ggaccacgtc 100860
gtccggcgag acgccacgag ccgcaggatg gactcgtagt ggagcgacgg cgccccgctg 100920
cggagcagat ccgcggccag ggcggccccg aaccaagcct tgatgctcaa ctccatccgg 100980
gcccagctgg gggcggtcat cgtggggaac agggggggcgg tggtccgaca gaaacgctcc 101040
tggctgtcca ccgcggcccg cagatactcg ttgttcaggc tgtcggtggc ccagacgccg 101100
tacccggtga gggtcgcgtt gatgatatac tgggcgtggt gatggacgat cgacagaacc 101160
tccaccgtgg atacgacggt atccacggtc ccgtacgtac cgccgctccg cttgccggtc 101220
tgccacaggt tggctaggcg cgtcaggtgg cccaggacgt cgctgaccgc cgccctgagc 101280
gccatgcact gcatggagcc ggtcgtgccg ctgggacccc ggtccagatg gcgcgcgaac 101340
gtttccgcgg gcgcctccgg gctgccgccg agcgggagga accggcgatt ggagggactc 101400
agccggtggc atacgtgctt gtctgtcgtc cacagcatcc aggacgccca ccggtacagc 101460
acggagacgt aggccaggag ctcgttgagc cgcagtgcgg tgtcggtgct ggggcggctt 101520
gggtccgccg ggcgcataaa gaacatgtac tgctgaatcc gatggagggc gtcgcgcagg 101580
ccggccacgg tggcggcgta cttggccgcc gcggccccgc tcttgaacgg ggtgcgcgcc 101640
agcagctttg gcgccagggt gggccgcagc agcacgtgaa ggctggggtc gcagtcgccc 101700
acggggtcct cggggacgtc caggccgctg ggcaccaccg tctgcaggta cttccagtac 101760
tgcgtgagga tggcgcggct caactggccg ccggtgagct ccacctcgcc cagcgcctgg 101820
gtggcggccg aagcgtagtg ccggatgtac tcgtagtgcg ggtcgctggc gagcccgtcc 101880
acgatcaaac tctcgggaac cgtgttgtgt tgccgcgcgg ccaaccggac gctgcgatcg 101940
gtgcaggtca gaaacgccgg ctgcgcgtcg tcggagcgct gccgcaaggc gcccacggcc 102000
gcgctaagga gcccctccgg ggtggggagc agacacccgc cgaagatgcg ccgctcggga 102060
acgcccgcgt tgtcgccgcg gatcaggttg gcaggcgtca ggcaccgcgc cagccgcagg 102120
gagctcgcgc cgcgcgtccg gcgctgcatg gtgacgcccg ttcggtcggg acccgccggt 102180
cggagttatg ccgcgtccag ggccatcggg gcgcttttta tcgggaggag cttatgggcg 102240
tggcgggcct cccagcccgg tcgcgcgcct ccccgacacg tgcgcccgca gggcggcggc 102300
cccctcgtct cccatcagca gtttcctaaa ctgggacatg atgtccacca cgcggacccg 102360
cgggcccaac acggacccgc cgcttacggg ggcggggggg aagggctcca ggtccttgag 102420
aagaaaggcg gggtctgccg tcccggacac gggggcccgg ggcgctgagg aggcggggcg 102480
cagatccacg tgctccgcgg ccgcgcggac gtccgcccag aacttggcgg gggtggtgcg 102540
cgcgtacagg ggctgggtcg ctcggaggac gcacgcgtag cgcagggggg tgtacgtgcc 102600
cacctcgggg gccgtgaatc ccccgtcaaa cgcggccagt gtcacgcacg ccaccacggt 102660
gtcggcaaag cccagcagcc gctgcaggac gagcccggcg gccagaatgg cgcgcgtggc 102720
cgccgcgtcg tcccggcgcc ggtgcgcgtc cccgcacgcc cgggcgtact ttaaggtcac 102780
ggtcgccagg gccgtgtgca gcgcgtacac cgcagcgccc agcacggcgt tgagcccgct 102840
gttggcgagc agccggcgcg ctgcggtgtc gcccagcgcc tcgtgctcgg cccccacgac 102900
cgcggggctt cccaggggca gggcgcgaaa cagctcctcc cgcgccacgt ccgcaaaggc 102960
ggggtggtgc acgtgcgggt gcaggcgcgc ccccacgacc accgagagcc actggaccgt 103020
ctgctccgcc atcaccgcca gcacatccag cacgcgcccc aggaaggcgg cctcccgcgt 103080
caaaacgcac cggacggcgt cgggattgaa gcgggcgagc agggccccgg tggccaggta 103140
cgtcatgcgg ccggcatagc gggcggccac gcgacagtcg cggtccagca gcgcgcgcac 103200
cccgggccag tacagcaggg accccagcga gctgcgaaac accgcggcgt cggggccgga 103260
ttggggggac actaaccccc ccgcgctcag taacggcacg gccgcggccc cgacgggacg 103320
caacgccgtg aggctcgcga actgccgcct cagctcggca gccctgtcgt ccaggtccga 103380
cccgcgcgcc tctgcgtgaa ggcgcgtccc gcacacccac ccgttgatgg ccagccgcac 103440
gacggcatcc gccaaaaagc tcatcgcctg ggcggggctg gtttttgttc gacgatccgt 103500
caggtcaaga atcccatcgc ccgtgatata ccaggccaac gcctcgccct gctgcagggt 103560
ttggcggaaa aacaccgcgg ggttgtcggg ggaggcgaag tgcatgaccc ccacgcgcga 103620
taacccgaac gcgctatccg gacacgggta aaacccggcc ggatgcccca gggctagggc 103680
ggagcgcacg gactcgtccc acacggcaac ctgaggggcc agtcgatcca acgggaatgc 103740 cgccccggagc tccgggcccg gcacgcgtcc ctccagaacc tccaccttgg gcggggaacg 103800
ggccccgccg ccgtcctccg gcccgacgtc ttccgggtag tcgtcctcct cgtactgcag 103860
ctcctctagg aacagcggcg acggcgccac ccgcgaaccg ccgacccgcc ccaaaatagc 103920
ccgcgcgtcg acgggaccca ggtatccccc ctgccgggcc tgcggaggac cgcggggaac 103980
ctcatcatca tcgtccaggc gaccgcgcac cgactggcta cgggccgcat cgggcccggg 104040
gcgctgccgg gacgctcggc gatgggatgt gggcggggct tccgacgcgc gccgtcgtcg 104100
ggctcgcggg ccttcccgtc gacggcgcac gggcggctcg tcgcccgcca tctcctccag 104160
agcctctagc tcgctgtcgt catccccgcg gaacaccgca cgcaggtacc ccatgaaccc 104220
caccccatcg cccgctggct cgtccgccac gggcgaggcg cgggggcggg tggatgcgcg 104280
cctcctacgc cccgcgggtt cgcgagccga catggtggcg atagacgcgg gttatcggat 104340
gtccgctacc ccccaaaaaa gaaaaagacc ccacagcgcg gatggaggcc ggggtaggtg 104400
ccgccggacc ccctcgcgat gggaatggac gggagcgacg gggccggcgc aaaaaacgca 104460
gtatctcccg cgaaggctac ccgccgcccc agcccccggc caaatgcgga aacggtcccg 104520
cgctctcgcc tttatacgcg ggccgccctg cgacacaatc acccgtccgt ggtttcgaat 104580
ctacacgaca ggcccgcaga cgcggctaac acacacgccg gcaacccaga ccccagtggg 104640
ttggttgcgc ggtcccgtct cctggctagt tcttttcccc accaccaaat aatcagacga 104700
caaccgcagg tttttgtaat gtatgtgctc gtgtttattg tggatacgaa ccggggacgg 104760
gaggggaaaa cccagacggg ggatgcgggt ccggtcgcgc cccctaccca ccgtactcgt 104820
caattccaag ggcatcggta aacatctgct caaactcgaa gtcggccata tccagagcgc 104880
cgtagggggc ggagtcgtgg ggggtaaatc ccggacccgg ggaatccccg tcccccaaca 104940
tgtccagatc gaaatcgtct agcgcgtcgg catgcgccat cgccacgtcc tcgccgtcta 105000
agtggagctc gtcccccagg ctgacatcgg tcgggggggc cgtcgacagt ctgcgcgtgt 105060
gtcccgcggg gagaaaggac aggcgcggag ccgccagccc cgcctcttcg gggcgtcgt 105120 cgtccgggag atcgagcagg ccctcgatgg tagacccgta attgtttttc gtacgcgcgc 105180
ggctgtacgc gtgttcccgc atgaccgcct cggagggcga ggtcgtgaag ctggaatacg 105240
agtccaactt cgcccgaatc aacaccataa atgcgggcct ggttgccatg cagggtggga 105300
ggggtcgtca acggcgcccc tggctcctcc gtagccgcgc tgcgcaccag cgggaggtta 105360
aggtgctcgc gaatgtggtt tagctcccgc agccggcggg cctcgattgg cactccccgg 105420
acggtgagcg ctccgttgac gaacatgaag ggctggaaca gacccgccaa ctgacgccag 105480
ctctccaggt cgcaacagag gcagtcaaac aggtcgggcc gcatcatctg ctcggcgtac 105540
gcggcccata ggatctcgcg ggtcaaaaat agatacaaat gcaaaaacag aacacgcgcc 105600
agacgagcgg tctctcggta gtacctgtcc gcgatcgtgg cgcgcagcat ttctcccagg 105660
tcgcgatcgc gtccgcgcat gtgcgcctgg cggtgcagct gccggacgct ggcgcgcagg 105720
taccggtaca gggccgagca gaagttggcc aacacggttc gatagctctc ctcccgcgcc 105780
cgtagctcgg cgtggaagaa acgagagagc gcttcgtagt agagcccgag gccgtcgcgg 105840
gtggccggaa gcgtcgggaa ggccacgtcg ccgtgggcgc gaatgtcgat ttgggcgcgt 105900
tcggggacgt acgcgtcccc ccattccacc acatcgctgg gcagcgttga taggaattta 105960
cactcccggt acaggtcggc gttggtcggt aacgccgaaa acaaatcctc gttccaggta 106020
tcgagcatgg tacatagcgc ggggcccgcg ctaaagccca agtcgtcgag gagacggtta 106080
aagagggcgg cggggggggac gggcatgggc ggggagggca tgagctgggc ctggctcagg 106140
cgccccgttg cgtacagcgg aggggccgcc ggggtgtttt tgggaccccc ggccgggcgg 106200
gggggtggtg gcgaagcgcc gtccgcgtcc atgtcggcaa acagctcgtc gaccaagagg 106260
tccattgggt ggggttgata cgggaaagac gatatcgggc ttttgatgcg atcgtccccg 106320
cccgcccaga gagtgtggga cgcccgacgg cgcgggaaga gaaaaacccc caaacgcgtt 106380
agaggaccgg acggacctta tggggggaag tgggcagcgg gaaccccgtc cgttcccgag 106440
gaatgacagc ccgtggtcgc caccccgcat ttaagcaacc cgcacgggcc gccccgtacc 106500
tcgtgacttc cccccacatt ggctcctgtc acgtgaaggc gaaccgaggg cggctgtcca 106560
acccaccccc cgccacccag tcacggtccc cgtcggattg ggaaacaaag gcacgcaacg 106620
ccaacaccga atgaacccct gttggtgctt tattgtctgg gtacggaagt ttttcactcg 106680
acgggccgtc tggggcgaga agcggagcgg gctggggctc gaggtcgctc ggtggggcgc 106740
gacgccgcag aacgccctcg agtcgccgtg gccgcgtcga cgtcctgcac cacgtctgga 106800
ttcaccaact cgttggcgcg ctgaagcagg tttttgccct cgcagaccgt cacgcggatg 106860
gtggtgatgc caaggagttc gttgaggtct tcgtctgtgc gcggacgcga catgtcccag 106920
agctggaccg ccgccatccg ggcatgcatg gccgccaggc gcccgaccgc ggcgcagaag 106980
acgcgcttgt taaagccggc cacccggggg gtccatggcg cgtcggggtt tggggggcg 107040 gtgctaaagt gcagctttct ggccagcccc tgcgcgggtg tcttggatcg ggttggcgcc 107100
gtcgacgcgg gggcgtctgg gagtgcggcg gattctggct gggccgattt cctgccgcgg 107160
gtggtctccg ccgccggggc cgcgggggcc ttagtcgcca cccgctgggt tcgggggccc 107220
cgggggcgg tggtgggtgt gcgtccggcc cctccggacc cagcgggcgg cggaggcgcc 107280
cgcgcaggcc ccgggccgga caaaaccgcc ccggaaacgg gacgccgcgt ccgggggacc 107340
tccgggtgtt cgtcgtcttc ggatgacgag cccccgtaga gggcataatc cgactcgtcg 107400
tactggacga aacggacctc gcccctcggg cgcgcgcgtg tctgtagggc gccacggcgg 107460
gaggtggcag gcggactatc gggactcgcc atacatgaag acggggtgta gtacagatcc 107520
tcgtactcat cgcgcggaac ctcccgcgga cccgacttca cggagcggcg agaggtcatg 107580
gttccacgaa cacgctaggg tcggatgcgc ggacaattag gcctgggttc ggacggcggg 107640
gggtggtgca ggtgtggaga ggtcgagcga taggggcggc ccgggagaga agagagggtc 107700
cgcaaaaccc actggggatg cgtgagtggc cctctgtggg cggtggggga gagtcttata 107760
ggaagtgcat ataaccacaa cccatgggtc taaccaatcc ccaggggcca agaaacagac 107820
acgccccaaa cggtctcggt ttccgcgaag aaggggaagt cctgggacac cctccacccc 107880
cacccctcac cccacacagg gcgggttcag gcgtgcccgg cagccagtag cctctggcag 107940
atctgacaga cgtgtgcgat aatacacacg cccatcgagg ccatgcctac ataaaagggc 108000
accagggccc ccggggcaga catttggcca gcgttttggg tctcgcaccg cgcgcccccg 108060
atcccatcgc gcccgccctc ctcgccgggc ggctccccgt gcgggcccgc gtctcccgcc 108120
gctaaggcga cgagcaagac aaacaacagg cccgcccgac agacccttct ggggggcccc 108180
atcgtcccta acaggaagat gagtcagtgg ggatccgggg cgatccttgt ccagccggac 108240
agcttgggtc gggggtacga tggcgactgg cacacggccg tcgctactcg cgggggcgga 108300
gtcgtgcaac tgaacctggt caacaggcgc gcggtggctt ttatgccgaa ggtcagcggg 108360
gactccggat gggccgtcgg gcgcgtctct ctggacctgc gaatggctat gccggctgac 108420
ttttgtgcga ttattcacgc ccccgcgcta tccagcccag ggcaccacgt aatactgggt 108480
cttatcgact cggggtaccg cggaaccgtt atggccgtgg tcgtagcgcc taaaaggacg 108540
cgggaatttg cccccgggac cctgcgggtc gacgtgacgt tcctggacat cctggcgacc 108600
cccccggccc tcaccaagcc gatttccctg cggcagttcc cgcaactggc gcccccccct 108660
ccaaccgggg ccgggatacg cgcagatcct tggttggagg gggcgctcgg ggacccaagc 108720
gtgactccgg ccctaccggc gcgacgccga gggcggtccc tcgtctatgc cggcgagctg 108780
acgccggttc agacggaaca cggggacggc gtacgagaag ccatcgcctt ccttccaaaa 108840
cgcgaggagg atgccggttt cgacattgtc gtccgtcgcc cggtcaccgt cccggcaaac 108900
ggcaccacgg tcgtgcagcc atccctccgc atgctccacg cggacgccgg gcccgcggcc 108960
tgttatgtgt tggggcggtc gtcgctcaac gcccgcggcc tcctggtcgt tcctacgcgc 109020
tggctccccg ggcacgtatg tgcgtttgtt gtttacaacc ttacgggggt tcctgtgacc 109080
ctcgaggccg gcgccaaggt cgcccagctc ctggttgcgg gggcggacgc tcttccttgg 109140
atccccccgg acaactttca cgggaccaaa gcgcttcgaa actaccccag gggtgttccg 109200
gactcaaccg ccgaacccag gaacccgccg ctcttggtgt ttacgaacga gtttgacgcg 109260
gaggcccccc cgagcgagcg cgggaccggg ggttttggct ctaccggtat ttagcccata 109320
gcttggggtt cgttccgggc aataaaaaac gtttgtatct catctttcct gtgtgtagtt 109380
gtttctgttg gaggcctgtg ggtctatcac acccgcccct ccatcccaca aacacagaac 109440
acacgggttg gatgaaaaca cgcatttatt gacccaaaac acacggagct gctcgagatg 109500

-continued ggccagggcg aggtgcggtt ggggaggctg taggtctggg aacggacacg cggggacacg 109560
attccggttt ggggtccggg agggcgtcgc cgtttcgggc ggcaggcgcc agcgtaacct 109620
ccgggggcgg cgtgtggggg tgccccaagg agggcgcctc ggtcacccca agcccccccca 109680 agcgggttcc cccggcaacc ccgaaggcgg agaggccaag ggcccgttcg gcgatggcca 109740
catcctccat gaccacgtcg ctctcggcca tgctccgaat agcctgggag acgagcacat 109800
ccgcggactt gtcagccgcc cccacggaca tgtacatctg caggatggtg gccatacacg 109860
tgtccgccag gcgccgcatc ttgtcctgat gggccgccac ggccccgtcg atcgtggggg 109920
cctcgagccc ggggtggtgg cgcgccagtc gttctaggtt caccatgcag gcgtggtacg 109980
tgcgggccaa ggcgcgggcc ttcacgaggc gtcgggtgtc gtccagggac cccagggcgt 110040
catcgagcgt gatgggggcg ggaagtagcg cgttaacgac caccagggcc tcctgcagcc 110100
gcggctccgc ctccgagggc ggaacggccg cgcggatcat ctcatattgt tcctcggggc 110160
gcgctcccca gccacatata gccccgagaa gagaagccat cgcgggcggg tactggccct 110220
tgggcgcgcg gacgcaatgg ggcaggaaga cgggaaccgc ggggagaggc gggcggccgg 110280
gactcccgtg gaggtgaccg cgctttatgc taccgacggg tgcgttatta cctcttcgat 110340
cgccctcctc acaaactctc tactgggggc cgagccggtt tatatattca gctacgacgc 110400
atacacgcac gatggccgtg ccgacgggcc cacggagcaa gacaggttcg aagagagtcg 110460
ggcgctctac caagcgtcgg gcgggctaaa tggcgactcc ttccgagtaa ccttttgttt 110520
attggggacg gaagtgggtg ggacccacca ggcccgcggg cgaacccgac ccatgttcgt 110580
ctgtcgcttc gagcgagcgg acgacgtcgc cgcgctacag gacgccctgg cgcacgggac 110640
cccgctacaa ccggaccaca tcgccgccac cctggacgcg gaggccacgt tcgcgctgca 110700
tgcgaacatg atcctggctc tcaccgtggc catcaacaac gccagccccc gcaccggacg 110760
cgacgccgcc gcggcgcagt atgatcaggg cgcgtcccta cgctcgctcg tggggcgcac 110820
gtccctggga caacgcggcc ttaccacgct atacgtccac cacgaggcgc gcgtgctggc 110880
cgcgtaccgc agggcgtatt atggaagcgc gcagagtccc ttctggtttc ttagcaaatt 110940
cgggccggac gaaaaaagcc tggtgctcac cactcggtac tacctgcttc aggcccagcg 111000 tctgggggc gcgggggcca cgtacgacct gcaggccatc aaggacatct gcgccaccta 111060
cgcgattccc cacgcccccc gccccgacac cgtcagcgcc gcgtccctga cctcgtttgc 111120
cgccatcacg cggttctgtt gcacgagcca gtacgcccgc ggggccgcgg cggccgggtt 111180
tccgctttac gtggagcgcc gtattgcggc cgacgtccgc gagaccagtg cgctggagaa 111240
gttcataacc cacgatcgca gttgcctgcg cgtgtccgac cgtgaattca ttacgtacat 111300
ttacctggcc cattttgagt gtttcagccc cccgcgccta gccacgcatc ttcgggccgt 111360
gacgacccac gaccccaacc ccgcggccaa cacggagcag ccctcgcccc tgggcaggga 111420
ggccgtggaa caattttttt gccacgtgcg cgcccaactg aatatcgggg agtacgtcaa 111480
acacaacgtg accccccggg agaccgtcct ggatggcgat acggccaagg cctacctgcg 111540
cgctcgcacg tacgcgcccg gggccctgac gcccgccccc gcgtattgcg gggccgtgga 111600
ctccgccacc aaaatgatgg ggcgtttggc ggacgccgaa aagctcctgg tcccccgcgg 111660
gtggcccgcg tttgcgcccg ccagtcccgg ggaggatacg gcgggcggca cgccgccccc 111720
acagacctgc ggaatcgtca agcgcctcct gagactggcc gccacggaac aacaggacac 111780
cacgcccccg gcgatcgcgg cgcttatccg taatgcggcg gtgcagactc ccctgcccgt 111840
ctaccggata tccatggtcc ccacgggaca ggcatttgcc gcgctggcct gggacgactg 111900
ggcccgcata acgcgggacg ctcgcctggc cgaagcggtc gtgtccgccg aagcggcggc 111960
gcaccccgac cacggcgcgc tgggcaggcg gctcacggat cgcatccgcg cccagggccc 112020
cgtgatgccc cctggcggcc tggatgccgg ggggcagatg tacgtgaatc gcaacgagat 112080
attcaacggc gcgctggcaa tcacaaacat catcctggat ctcgacatcg ccctgaagga 112140
gcccgtcccc tttcgccggc tccacgaggc cctgggccac tttaggcgcg gggctctggc 112200
tgcggttcag ctcctgtttc ccgcggcccg cgtggacccc gacgcatatc cctgttattt 112260
tttcaaaagc gcatgtcggc ccggcccggc gtccgtgggt tccggcagcg gactcggcga 112320
cgacggggac tggtttccct gctacgacga cgccggtgat gaggagtggg cggaggaccc 112380
gggcgccatg gacacatccc acgatccccc ggacgacgag gttgcctact ttgacctgtg 112440
ccacgaagtc ggccccacgg cggaacctcg cgaaacggat tcgcccgtgt gttcctgcac 112500
cgacaagatc ggactgcggg tgtgcatgcc cgtccccgcc ccgtacgtcg tccacggttc 112560
tctaacgatg cggggggtgg cacgggtcat ccagcaggcg gtgctgttgg accgagattt 112620
tgtggaggcc atcgggagct acgtaaaaaa cttcctgttg atcgatacgg gggtgtacgc 112680
ccacggccac agcctgcgct tgccgtattt tgccaaaatc gcccccgacg ggcctgcgtg 112740
cggaaggctg ctgccagtgt ttgtgatccc ccccgcctgc aaagacgttc cggcgtttgt 112800
cgccgcgcac gccgacccgc ggcgcttcca ttttcacgcc ccgcccacct atctcgcttc 112860
cccccgggag atccgtgtcc tgcacagcct gggtggggac tatgtgagct tctttgaaag 112920
gaaggcgtcc cgcaacgcgc tggaacactt tgggcgacgc gagaccctga cggaggtcct 112980
gggtcggtac aacgtacagc cggatgcggg ggggaccgtc gaggggttcg catcggaact 113040
gctggggcgg atagtcgcgt gcatcgaaac ccactttccc gaacacgccg gcgaatatca 113100
ggccgtatcc gtccggcggg ccgtcagtaa ggacgactgg gtcctcctac agctagtccc 113160
cgttcgcggt accctgcagc aaagcctgtc gtgtctgcgc tttaagcacg gccgggcgag 113220
tcgcgccacg gcgcggacat tcgtcgcgct gagcgtcggg gccaacaacc gcctgtgcgt 113280
gtccttgtgt cagcagtgct ttgccgccaa atgcgacagc aaccgcctgc acacgctgtt 113340
taccattgac gccggtacgc catgctcgcc gtccgttccc tgcagcacct ctcaaccgtc 113400
gtcttgataa cggcgtacgg cctcgtgctc gtgtggtaca ccgtcttcgg tcaccccccc 113460
aacgggggct ggcgcaacca cgcccatatc tgctacgcca atcttatcgc gggtagggtc 113520
gtgcccttcc aggtcccacc cgacgccatg aatcgtcgga tcatgaacgt ccacgaggca 113580
gttaactgtc tggagaccct atggtacaca cgggtgcgtc tggtggtcgt agggtggttc 113640
ctgtatctgg cgttcgtcgc cctccaccaa cgccgatgta tgtttggtgt cgtgagtccc 113700
gcccacaaga tggtggcccc ggccacctac ctcttgaact acgcaggccg catcgtatcg 113760
agcgtgttcc tgcagtaccc ctacacgaaa attacccgcc tgctctgcga gctgtcggtc 113820
cagcggcaaa acctggttca gttgtttgag acggacccgg tcaccttctt gtaccaccgc 113880
cccgccatcg gggtcatcgt aggctgcgag ttgatgctac gctttgtggc cgtgggtctc 113940
atcgtcggca ccgctttcat atcccggggg gcatgtgcaa tcacataccc cctgtttctg 114000
accatcacca cctggtgttt tgtctccacc atcggcctga cagagctgta ttgtattctg 114060
cggcggggcc cggcccccaa gaacgcagac aaggccgccg ccccggggcg atccaagggg 114120
ctgtcgggcg tctgcgggcg ctgctgttcc atcatcctct cgggcatcgc agtgcgattg 114180
tgttatatcg ccgtggtggc cggggtggtg ctcgtggcgc ttcactacga gcaggagatc 114240
cagaggcgcc tgtttgatgt atgacgtcac atccaggccg gcggaaaccg gaacggcata 114300
tgcaaattgg aaactgtcct gtcttggggc ccacccaccc gacgcgtcat atgcaaatga 114360
aaatcggtcc cccgaggcca cgtgtagcct ggatcccaac gaccccgccc atgggtccca 114420
attggccgtc ccgttaccaa gaccaaccca gccagcatat ccaccccgc ccgggtcccc 114480
gcggaagcgg aacggtgtat gtgatatgct aattaaatac atgccacgta cttatggtgt 114540
ctgattggtc cttgtctgtg ccggaggtgg ggcgggggcc ccgcccgggg ggcggaacga 114600
ggaggggttt gggagagccg gccccggcac cacgggtata aggacatcca ccacccggcc 114660
ggtggtggtg tgcagccgtg ttccaaccac ggtcacgctt cggtgcctct ccccgattcg 114720
ggcccggtcg ctcgctaccg gtgcgccacc accagaggcc atatccgaca ccccagcccc 114780
gacggcagcc gacagcccgg tcatggcgac tgacattgat atgctaattg acctcggcct 114840
ggacctctcc gacagcgatc tggacgagga cccacccgag ccggcggaga gccgccgcga 114900
cgacctggaa tcggacagca gcggggagtg ttcctcgtcg gacgaggaca tggaagaccc 114960
ccacggagag gacggaccgg agccgatact cgacgccgct cgcccggcgg tccgcccgtc 115020
tcgtccagaa gaccccggcg tacccagcac ccagacgcct cgtccgacgg agcggcaggg 115080
ccccaacgat cctcaaccag cgccccacag tgtgtggtcg cgcctcgggg cccggcgacc 115140
gtcttgctcc cccgagcagc acgggggcaa ggtggcccgc ctccaacccc caccgaccaa 115200
agcccagcct gcccgcggcg gacgccgcgg gcgtcgcagg ggtcggggtc gcggtggtcc 115260
cggggccgcc gatggtttgt cggacccccg ccggcgtgcc cccagaacca atcgcaaccc 115320
ggggggaccc cgccccgggg cggggtggac ggacggcccc ggcgcccccc atggcgaggc 115380
gtggcgcgga agtgagcagc ccgacccacc cggaggcccg cggacacggg gcgtgcgcca 115440
agcacccccc ccgctaatga cgctggcgat tgcccccccg cccgcggacc cccgcgcccc 115500
ggccccggag cgaaaggcgc ccgccgccga caccatcgac gccaccacgc ggttggtcct 115560
gcgctccatc tccgagcgcg cggcggtcga ccgcatcagc gagagctttg gccgcagcgc 115620
acaggtcatg cacgacccct ttggggggca gccgtttccc gccgcgaata gcccctgggc 115680
cccggtgttg gcgggccaag gagggccctt tgacgccgag accagacggg tctcctggga 115740
aaccttggtc gcccacggcc cgagcctcta tcgcactttt gccggcaatc ctcgggccgc 115800
atcgaccgcc aaggccatgc gcgactgcgt gctgcgccaa gaaaatttca tcgaggcgct 115860
ggcctccgcc gacgagacgc tggcgtggtg caagatgtgc atccaccaca acctgccgct 115920
gcgcccccag gaccccatta tcgggacggc cgcggctgtg ctggataacc tcgccacgcg 115980
cctgcggccc tttctccagt gctacctgaa ggcgcgaggc ctgtgcggcc tggacgaact 116040
gtgttcgcgg cggcgtctgg cggacattaa ggacattgca tccttcgtgt ttgtcattct 116100
ggccaggctc gccaaccgcg tcgagcgtgg cgtcgcggag atcgactacg cgacccttgg 116160
tgtcggggtc ggagagaaga tgcatttcta cctccccggg gcctgcatgg cgggcctgat 116220
cgaaatccta gacacacacc gccaggagtg ttcgagtcgt gtctgcgagt tgacggccag 116280
tcacatcgtc gcccccccgt acgtgcacgg caaatatttt tattgcaact ccctgtttta 116340
ggtacaataa aaacaaaaca tttcaaacaa atcgccccac gtgttgtcct tctttgctca 116400
tggccggcgg ggcgtgggtc acggcagatg gcgggggtgg gcccggcgta cggcctgggt 116460
gggcggaggg aactaaccca acgtataaat ccgtccccgc tccaaggccg gtgtcatagt 116520
gcccttagga gcttcccgcc cgggcgcatc ccccctttg cactatgaca gcgacccccc 116580
tcaccaacct gttcttacgg gccccggaca taacccacgt ggcccccccct tactgcctca 116640 acgccacctg gcaggccgaa acggccatac acaccagcaa aacggactcc gcttgcgtgg 116700
ccgtgcggag ttacctggtc cgcgcctcct gtgagaccag cggcacaatc cactgctttt 116760
tctttgcggt atacaaggac acccaccaca cccctccgct gattaccgag ctccgcaact 116820
ttgcggacct ggttaaccac ccgccggtcc tacgcgaact ggaggataag cgcggggtgc 116880
ggctgcggtg tgcgcggccg tttagcgtcg ggacgattaa ggacgtctct gggtccggcg 116940
cgtcctcggc gggagagtac acgataaacg ggatcgtgta ccactgccac tgtcggtatc 117000
cgttctcaaa aacatgctgg atgggggcct ccgcggccct acagcacctg cgctccatca 117060
gctccagcgg catggccgcc cgcgcggcag agcatcgacg cgtcaagatt aaaattaagg 117120
cgtgatctcc aacccccca tgaatgtgtg taacccccca aaaaaataaa cagccgtaac 117180
ccaatcaaac caggcgtggt gtgagtttgt ggacccaaag ccctcagaga caacgcgaca 117240
ggccagtatg gaccgtgata cttttattta ttaactcaca ggggcgctta ccgccacagg 117300
aataccagaa taatgaccac cactatcgcg accaccccaa atacagcatg gcgccccacc 117360
acgccacaac agccctgtcg ccggtatggg gcatgatcag acgagccgcg agccgcgcgt 117420
tgggccctgt acagctcgcg cgaattgacc ctaggaggcc gccacgcgcc cgagttttgc 117480
gttcgtcgct ggtcgtcggg cgccaaagcc ccggacggct gttcggtcga acgaacggcc 117540
acgacagtgg cataggttgg ggggtggtcc gacatagcct cggtgtacgt cgggaggccc 117600
gacaagaggt cccttgagat gtcgggtggg gccacaagcc tggtttccgg aagaaacagg 117660
ggggttgcca ataacccgcc agggccaaaa ctccggcgct gcgcacgtcg ttcggcgcgg 117720
cgccgggcgc gccgagcggc tcgctgggcg gcttggcgtg agcggccccg ctccgacgcc 117780
tcgccctctc cggaggaggt tggcggaatt ggcacggacg acaggggccc agcagagtac 117840
ggtggaggtg ggtccgtggg ggtgtccaga tcaataacga caaacggccc ctcgttccta 117900
ccagacaagc tatcgtaggg gggcggggga tcagcaaacg cgttccccgc gctccataga 117960
cccgcgtcgg gttgcgccgc ctccgaagcc atggatgcgc cccaaagcca cgactcccgc 118020
gcgctaggtc cttggggtaa gggaaaaggc cctactcccc atccaagcca gccaagttaa 118080
cgggctacgc cttcggggat gggactggca ccccggcgga ttttgttggg ctggtacgcg 118140
ttgcccaacc gagggccgcg tccacgggac gcgcctttta taaccccggg ggtcattccc 118200
aacgatcaca tgcaatctaa ctggctcccc tctccccccc tctcccctct cccccctct 118260
cccctctccc cccctctccc ctctcccccc ctctcccctc tccccccctc tcccctctcc 118320
ccccctctcc cctctcccc cctctcccct ctcccccccct ctcccctctc cccccctctc 118380
ccctctcccc ccctctcccc tctccccccc tgctctttcc ccgtgacacc cgacgctggg 118440
gggcgtggct gccgggaggg gccgcggatg ggcggggcct actcggtctc ccgcccccgc 118500
ccccgaaccg ccccgccggc cttgcccccc tttgatcccc tgctaccccc aacccgtgct 118560
cgtggtgcgg gttgggtggg gggggggagt gtgggcgggg gtgtgcggga ggtgtcggtg 118620
gtggtggtgg tggtaggaat ggtggtgagg gggggggcg ctggttggtc aaaaaaggga 118680
gggacggggg ccggcagacc gacggcgaca acgctccccg gcggccgggt cgcggctctt 118740
acgagcggcc cggcccgcgc tcccaccccc cgggccgtgt ccttgctttc cccccgtctc 118800
cccccccctc cttctcctcc tcctcctcct cgtttttcca aaccccgccc acccggcccg 118860
gcccggcccg gccaccgccg cccacccacc cacctcggga gacccagccc cggtcccccg 118920
ttccccgggg gccgttatct ccagcgcccc gtccggcgcg ccgccccccg ccgctaaacc 118980
ccatcccgcc cccgggaccc cacatataag cccccagcca cacgcaagaa cagacacgca 119040
gaacggctgt gtttatttaa ataaaccgat gtcggaataa acaaacacaa acacccgcga 119100
cggggggacg gagggagggg ggtgacgggg gacgggaaca gccacaaaaa acacccacaa 119160
aaaaaaacag ccaccccega caccccccc cacccccagt ctcttcgcct tttccccccc 119220
accccacgcc cccactgagc ccggtcgatc gacgagcacc cccgccccccg cccctgcccc 119280 ggcgaccccc ggcccgcacg atcccgacaa caataacaac cccaacggaa agcggcgggg 119340
tgtggggggg ggcgaggaac aaccgagggg aacgggggat ggaaggacgg gaagtggaag 119400
tcctgatacc catcctacac ccccctgcct tccaccctcc ggcccccgc gagtccaccc 119460 gccggccggc taccgagacc gaacacggcg gccgccgcag ccgccgcagc cgccgccgac 119520
accgcagagc cggcgcgcgc acacacaagc ggcagaggca gaaaggccca gagtcattgt 119580
ttatgtggcc gcgggccagc agacggcccg cgacaccccc cccccgcccc gtgtgggtat 119640
ccggcccccc gccccgcgcc ggtccattaa gggcgcgcgt gcccgcgaga tatcaatccg 119700
ttaagtgctc tgcagacagg ggcaccgcgc ccggaaatcc attaggccgc agacgaggaa 119760
aataaaatta catcacctac ccacgtggtg ctgtggcctg tttttgctgc gtcatctgag 119820
cctttataaa agcgggggcg cggccgtgcc gatcgcgggt ggtgcgaaag actttccggg 119880
cgcgtccggg tgccgcggct ctccgggccc ccctgcagcc ggggcggcca aggggcgtcg 119940
gcgacatcct ccccctaagc gccggccggc cgctggtctg ttttttgttt tccccgtttc 120000
gggggtgggg ggggttgcgg tttctgtttc tttaacccgt ctggggtgtt tttcgttccg 120060
tcgccggaat gtttcgttcg tctgtcccct cacggggcga aggccgcgta cggcccggga 120120
cgagggggcc cccgaccgcg gcggtccggg ccccgtccgg gcccgctcgc cggcacgcga 120180
cgcgaaaaag gccccccgga ggcttttccg ggttcccggc ccggggcctg agataaacaa 120240
tcggggttac cgccaacggc cggccccccgt ggcggcccgg cccggggccc cggcggaccc 120300
aaggggcccc ggcccggggc cccacaacgg cccggcgcat gcgctgtggt ttttttttct 120360
cggtgttttg tcgggctccg tcgcctttcc tgttctcgct tctccccccc ccccttctt 120420 cacccccagt accctcctcc ctcccttcct cccccgttat cccactcgtc aagggcgccc 120480
cggtgtggtt caacaaagac gccgcgtttc caggtaggtt agacacctgc ttctccccaa 120540
tagagggggg ggacccaaac gacagggggc gccccagagg ctaaggtcgg ccacgccact 120600
cgcgggtggg ctcgtgttac agcacaccag cccgttcttt tccccccctc ccacccttag 120660
tcagactctg ttacttaccc gtccgaccac caactgcccc cttatctaag ggccggctgg 120720
aagaccgcca gggggtcggc cggtgtcgct gtaacccccc acgccaatga cccacgtact 120780
ccaagaaggc atgtgtccca ccccgcctgt gtttttgtgc ctggctctct atgcttgggt 120840
cttactgccg gggggggggg agtgcggggg aggggggggtg tggaaggaaa tgcacggcgc 120900
gtgtgtaccc cccctaaagt tgttcctaaa gcgaggatat ggaggagtgg cgggtgccgg 120960
gggaccgggg tgatctctgg cacgcggggg tgggaagggt cgggggaggg gggatggggt 121020
accggcccac ctggccgacg cgggtgcgcg tgcctctgca caccaacccc acgtcccccg 121080
gcggtctcta agaagcaccg cccccccctcc ttcataccac cgagcatgcc tgggtgtggg 121140
ttggtaacca acacgcccat cccctcgtct cctgtgattc tctggctgca ccgcattctt 121200
gttttctaac tatgttcctg tttctgtctc cccccccacc cctccgcccc accccccaac 121260
acccacgtct gtggtgtggc cgaccccctt ttgggcgccc cgtcccgccc cgccacccct 121320
cccgtccttt gttgccctat agtgtagtta acccccccccc gccctttgtg gcggccagag 121380
gccaggtcag tccgggcggg caggcgctcg cggaaactta acacccacac ccaacccact 121440
gtggttctgg ctccatgcca gtggcaggat gctttcgggg atcggtggtc aggcagcccg 121500
ggccgcggct ctgtggttaa caccagagcc tgcccaacat ggcacccccca ctcccacgca 121560
cccccactcc cacgcacccc cactcccacg cacccccact cccacgcacc cccactccca 121620
cgcaccccca ctcccacgca cccccactcc cacgcacccc cactcccacg cacccccact 121680
cccacgcacc cccgagatcc atccaacaca gacagggaaa agatacaaaa gtaaaccttt 121740
atttcccaat agacagcaaa aatcccctga gttttttatt agggccaaca ctaaagaccc 121800
gctggtgtgt ggtgcccgtg tctttcactt ttcccctccc cgacacggat tggctggtgt 121860
agtgggcgcg gccagagacc acccagcgcc cgaccccccc ctccccacaa acacgggggg 121920
cgtcccttat tgttttccct cgtcccgggt cgacgccccc tgctccccgg accacgggtg 121980
ccgagaccgc aggctgcgga agtccagggc gcccactagg gtgccctggt cgaacagcat 122040
gttccccacg gggtcatcc agaggctgtt ccactccgac gcgggggccg tcgggtactc 122100
ggggggcatc acgtggttac ccgcggtctc ggggagcagg gtgcggcggc tccagccggg 122160
gaccgcggcc cgcagccggg tcgccatgtt tcccgtctgg tccaccagga ccacgtacgc 122220
cccgatgttc cccgtctcca tgtccaggat gggcaggcag tcccccgtga tcgtcttgtt 122280
cacgtaaggc gacagggcga ccacgctaga gacccccgag atgggcaggt agcgcgtgag 122340
gccgcccgcg ggggcggccc cggaagtctc cgcgtggcgc gtcttccggg cacacttcct 122400
cggcccccgc ggcccagaag cagcgcgggg gccgagggag gtttcctctt gtctccctcc 122460
cagggcaccg acggccccgc ccgaggaggc ggaagcggag gaggacgcgg ccccggcggc 122520
ggaagaggcg gcccccgcgg gagtcggggc cgaggaggaa gaggcagagg aggaagaggc 122580
ggaggccgcc gaggacgtca ggggggtccc gggcccaccc tggccgcgcc cccccggccc 122640
tgagtcggag ggggggtgcg tcgccgccct cttggcccct gccggcgcga ggggggggacg 122700
cgtggactgg ggggaggggt tttcctggcc cgacccgcgc ctcttcctcg gacgcaccgc 122760
cgcctcctgc tcgacagagg cggcggaggg gagcgggggg gcgccggagg gggcggcgcc 122820
gcgggagggc ccgtgtccac cctccacgcc cggccccccc gagccgcgcg ccaccgtcgc 122880
acgcgcccgg cacagactct gttcttggtt cgcggcctga gccagggacg agtgcgactg 122940
gggcacacgg cgcgcgtccg cgggggccgg ggcgcggggg ccgggccccg gaggcggcgc 123000
tcgcacgcac ggggccacgg ccgcgcgggg gcgcgcgggt cccgacgcgg ccgaggacgc 123060
ggtgggcccg gggcgggggg cggagcctgg catgggcgcc gcggggggcc tgtggggaga 123120
ggccgggggg gagtcgctga tcactatggg gtctctgttg tttgcaaggg gggcgggtct 123180
gttgacaagg gggcccgtcc ggcccctcgg ccgccccgcc tccgcttcaa caaccccaac 123240
cccaacccca acccccccgg aggggccaga cgcccccgc ggcgccgcgg ctcgcgactg 123300
gcgggagccg ccgccgccgc cgctgctgtt ggtggtggtg ttggtgttac tgctgccgtg 123360
tggcccgatg ggcgccgagg ggggcgctgt ccgagccgcg gccggctggg gggctgcgtg 123420
agacgccccg cccgtcacgg ggggcgcggc ggcgcctctg cgtggggggg cgcggggcgt 123480
ccggcggggg gcgggcggta cgtagtctgc tgcaagagac aacggggggc gcgatcaggt 123540
tacgcccccct cccaggccct ccctttccgc gcccgccctt tcctcgcccc cccgcccgcc 123600
tattcctccc tccccctcc tcctcctcct cccccagggt cctcgccgcc cccccgcctc 123660
accgtcgtcc aggtcgtcgt catcctcgtc cgtggtgggc tcagggtggg tgggcgacag 123720
ggccctcacc gtgtgccccc ccagggtcag gtaccgcggg gcgaaccgct gattgcccgt 123780
ccagataaag tccacggccg tgcccgccct gacggcctcc tcggcctcca tgcgggtctg 123840
ggggtcgttc acgatcggga tggtgctgaa cgacccgctg ggcgtcacgc ccactatcag 123900
gtacaccagc ttggcgttgc acagcgggca ggtgttgcgc aattgcatcc aggttttcat 123960
gcacgggatg cagaagcggt gcatgcacgg gaaggtgtcg cagcgcaggt ggggcgcgat 124020
ctcatccgtg cacacggcgc acacgtcgcc ctcgtcgctc cccccgtcct ctcgaggggg 124080
ggcgcccccg caactgccgg ggtcttcctc gcgggggggg ctcccccccg agaccgcccc 124140
cccatccacg ccctgcggcc ccagcagccc cgtctcgaac agttccgtgt ccgtgctgtc 124200
cgcctcggag gcggagtcgt cgtcatggtg gtcggcgtcc ccccgccccc ccacttcggt 124260
ctccgcctca gagtcgctgc tgtccggcag gtctcggtcg cagggaaaca cccagacatc 124320
cggggcgggc taaggggaaa aaaagggggg cgggtaagaa tggggggatt tcccgcgtca 124380
atcagcgccc acgagttccc cctctccccc cccccgcctc acaaagtcct gccccccctgc 124440
tggcctcgga agagggggga gaaaggggtc tgcaaccaaa ggtggtctgg gtccgtcctt 124500
tggatcccga cccctcttct tccctcttct cccgccctcc agacgcaccg gagtcggggg 124560
tcccacggcg tcccccaaat atggcgggcg gctcctcccc accccccctag atgcgtgtga 124620
gtaagggggc cctgcgtatg agtcagtggg gaccacgccc cctaacacgg cgaccccggt 124680
ccctgtgtgt ttgttgtggg ggcgtgtctc tgtgtatgag tcagggggtc ccacggcgac 124740
cccgggccct gcgtctgagt caaaggggcc atgtgtatgt gttgggggt ctgtatatat 124800
aaagtcaggg ggtcacatgg cgacccccaa cagggcgacc ccggtccctg tatatatagg 124860
gtcagggggt tccgcgcccc ctaacatggc gccccccggtc cctgtatata tagtgtcacg 124920
gggttccacg ccccctaaca tggcgcccgg ctcccgtgta tgagtggggg tcccccaaca 124980
tggcggccgg ttccagtgta agggtcgggg gtcccccaac atggcgcccc ccaatatggc 125040
gcccccaat atggcgcccc agacatggcg cccggcccct cacctcgcgc tgggggcggc 125100
cctcaggccg gcgggtactc gctccggggc ggggctccat gggggtcgta tgcggttgga 125160
gggtcgcgga cggagggtcc ctgggggtcg caacgtaggc ggggcttctg tggtgatgcg 125220
gagagggggc ggcccgagtc tgcctggctg ctgcgtctcg ctccgagtgc cgaggtgcaa 125280
atgcgaccag actgtcgggc cagggctaac ttataccccca cgcctttccc ctccccaaag 125340
gggcggcagt gacgattccc ccaatggccg cgcgtcccag gggaggcagg cccaccgcgg 125400
ggcggccccg tccccgggga ccaacccggc gcccccaaag aatatcatta gcatgcacgg 125460
cccggccccc gatttggggg accaacccgg tgtcccccaa agaaccccat tagcatgccc 125520
ctcccaccga cgcaacaggg gcttggcctg cgtcggtgcc ccggggcttc ccgccttccc 125580
gaagaaactc attaccatac ccggaacccc aggggaccaa tgcgggttca ttgagcgacc 125640
cgcgggccaa tgcgcgaggg gccgtgtgtt ccgccaaaaa agcaattagc ataacccgga 125700
accccagggg agtggttacg cgcggcgcgg gaggcgggga ataccggggt tgcccattaa 125760
gggccgcggg aattgccgga agcgggaagg gcggccgggg ccgcccatta atgagtttct 125820
aattaccata ccgggaagcg gaacaaggcc tcttgtaagt ttttaattac cataccggga 125880
agtgggcggc ccggcccact gggcggtaac tcccgcccag tgggccgggc cccgaagact 125940
cggcggacgc tggttggccg ggccccgccg cgctggcggc cgccgattgg ccagtcccgc 126000
cctccgaggg cgggcccgcc tcgggggcgg gccggctccc agcgtatata tgcgcggctc 126060
ctgccatcgt ctctccggag agcggcttgg tgcggagctc ccgggagctc cgcggaagac 126120
ccaggccgcc tcgggtgtaa cgttagaccg agttcgccgg gccggctccg cgggccaggg 126180
cccgggcacg ggcctcgggc cccaggcacg gcccgatgac cgcctcggcc tccgccaccc 126240
ggcgccggaa ccgagcccgg tcggcccgct cgcgggccca cgagccgcgg cgcgccaggc 126300
gggcggccga ggcccagacc accaggtggc gcacccggac gtggggcgag aagcgcaccc 126360
gcgcgggggt cgcgggggtc gcgggggtcg cgggggtcgc gggggtcgcg gggggctccg 126420
gcgccccctc cccgcccgcg cgtcgcaggc gcaggcgcgc caggtgctct gcggtgacgc 126480
gcaggcggag ggcgaggcgc ggcggaaggc ggaaggggcg tgaggggggg tgggaggggt 126540
tagccccgcc ccccgggccc gcgccgggcg gtggggaccg ggggcggggg gcggcggcgg 126600
tgggccgggc ctctggcgcc ggctcgggcg gggggctgtc cggccagtcg tcgtcatcgt 126660
cgtcgtcgga cgcggactcg ggaacgtgga gccactggcg cagcagcagc gaacaagaag 126720
gcgggggccc actggcgggg ggcggcggcg gggcggccgc gggcgcgctc ctgaccgcgg 126780
gttccgagtt gggcgtggag gttacctggg actgtgcggt tgggacggcg cccgtgggcc 126840
cgggcggccg gggcggcggg gggccgcgat ggcggcggcg gcgggccatg gagacagaga 126900
gcgtgccggg gtggtagagt ttgacaggca agcatgtgcg tgcagaggcg agtagtgctt 126960
gcctgtctaa ctcgctcgtc tcggccgcgg ggggcccggg ctgcgccgcc gcgctttaaa 127020
gggccgcgcg cgaccccccgg ggggtgtgtt tcgggggggg cccgttttcc gctcctcccc 127080
ccgctcctcc ccccgctcct ccccccgctc ctccccccgc tcctcccccc gctcctcccc 127140
ccgctcctcc ccccgctcct ccccccgctc ctccccccgc tcctcccccc gctcctcccc 127200
ccgctcctcc ccccgctcct ccccccgctc ctccccccgc tcctcccccc gctcctcccc 127260
ccgctcctcc ccccgctcct ccccccgctc cccaacgccc gccgcgcgcg cgcacgccgc 127320
ccggaccgcc gcccgccttt tttgcgcgcc gccccgcccg cggggggccc gggctgccac 127380
aggtgtaaca acaccaacag aacaccaaca gcacggcgca ccggcgactc cggttcctca 127440
tccacacgtc acacgtcacg tcatccacca cacctgccca ccaacacaac tcacagcgac 127500
aactcaccgc gcaacaactc ctgttcctca tccacacgtc accgcgcacc ccccgctcct 127560
ccagacgtcc cccagcgcaa cacgccgctc ctgtcacaca ccaccgcccc agccctcccc 127620
agccccagcc ctccccagcc ccagccctcc ccggccccag ccctccccgg ccccagccct 127680
ccccggcccc agccctcccc ggccccagcc ctccccggcc ccagccctcc ccggccccag 127740
ccctccccgg ccgcgtcccg cgctccctcg ggggggttcg ggcatctcta cctcagtgcc 127800
gccaatctca ggtcagagat ccaaaccctc cgggggcgcc cgcgcaccac caccgcccct 127860
cgccccctcc cgcccctcgc cccctcccgc ccctcgcccc ctcccgcccc tcgccccctc 127920
ccgcccctcg cccccctcccg cccctcgccc cctcccgccc ctcgcccct cccgcccctc 127980 gccccctccc gcccctcgcc ccctcccgcc cctcgccccc tcccgcccct cgccccctcc 128040
cgcccctcgc cccctcccgc ccctcgcccc ctcccgcccc tcgccccctc ccgcccctcg 128100
ccccctcccg cccctcgccc cctcccgccc ctcgcccct cccgcccctc gccccctccc 128160
gcccctcgcc ccctcccgcc cctcgaaata aacaacgcta ctgcaaaact aaatcaggtc 128220
gttgtcgttt attgcgtctt cgggtttcgc aagcgccccg ccccgtcccg gcccgttaca 128280
gcaccccgtc cccctcgaac gcgccgccgt cgtcgtcgtc ccaggcgcct tcccagtcca 128340
caacttcccg tcgcgggggc gtggccaagc ccgcctccgc ccccagcacc tccacggccc 128400
ccgccgccgc cagcacggtg ccgctgcggc ccgtggccga ggcccagcga atcccgggca 128460
acgccggcgg cagggccccc gggccgtcgt cgtcgtcgtc gccgccgcgc agcaccagcg 128520
ggggggcgtc gtcgtcgggc tccagcaggg cgcgggcgca aaagtccctc cgcggcccgc 128580
gccaccgggc cgggccggcg cgcaccgcct cgcgccccag cgccacgtac acgggccgca 128640
gcggcgcgcc caggccccag cgcgcgcagg cgcggtgcga gtgggcctcc tcctcgcaga 128700
agtccggcgc gccgggcgcc atggcgtcgg tggtccccga ggccgccgcc cggccgtcca 128760
gcgccggcag cacggcccgg cggtactcgc gcggggacat gggcaccggc gtgtccgggc 128820
cgaagcgcgt gcgcacgcgg tagcgcacgt tgccgccgcg gcacaggcgc agcggcggcg 128880
cgtcggggta caggcgcgcg tgcgcggcct ccacgcgcgc gaagaccccc gggccgaaca 128940
cgcggcccgg ggccagcacc gtgcggcgca ggtcccgcgc cgccggccag cgcacggcgc 129000
actgcacggc gggcagcagg tcgcacgcca ggtaggcgtg ctgccgcgac accgcgggcc 129060
cgtcggcggg ccagtcgcag gcgcgcacgg tgttgaccac gatgagccgc cggtcgccgg 129120
cgctggcgag cagccccaga aactccacgg ccccggcgaa ggccaggtcc cgcgtggaca 129180
gcagcagcac gccctgcgcg cccagcgccg acacgtcggg ggcgccggtc cagttgcccg 129240
cccaggcggc cgtgtccggc ccgcacagcc ggttggccag ggccgccagc aggcaggaca 129300
gcccgccgcg ctcggcggac cactccggcg gccccccccga ggccccgccg ccggccaggt 129360
cctcgcccgg cagcggcgag tacagcacca ccacgcgcac gtcctcgggg tcggggatct 129420
ggcgcatcca ggccgccatg cggcgcagcg ggcccgaggc gcgcaggggg ccaaagaggc 129480
ggcccccggc ggccccgtgg gggtgggggt tatcgtcgtc gtcgccgccg ccgcacgcgg 129540
cctgggcggc ggcggcgggc ccggcgcacc gcgcggcgat cgaggccagg gcccgcgggt 129600
caaacatgag ggccggtcgc caggggacgg ggaacagcgg gtggtccgtg agctcggcca 129660
cggcgcgcgg ggagcagtag gcctccaggg cggcggccgc gggcgccgcc gtgtggctgg 129720
gccccggggg ctgccgccgc cagccgccca gggggtcggg gccctcggcg ggccggcgcg 129780
acagcgccac ggggcgcggg cgggcctgcg ccgcggcggc ccggggcgcc gcgggctggg 129840
cgggggcggg ctcgggcccc gggggcgtgg agggggggcgc ggggaggggg gcgcgggcgt 129900
ccgagccggg ggcgtccgcg ccgctcttct tcgtcttcgg gggtcgcggg ccgccgcctc 129960
cgggcggccg ggccgggccg ggactcttgc gcttgcgccc ctcccgcggc gcggcggagg 130020
cggcggcggc cgccagcgcg tcggcggcgt ccggtgcgct ggcggccgcc gccagcaggg 130080
ggcgcaggct ctggttctca aacagcaggt ccgcggcggc ggcggccgcg gagctcggca 130140
ggcgcgggtc ccgcggcagc gcggggccca gggccccggc gaccaggctc acggcgcgca 130200
cggcggccac ggcggcctcg ctgccgccgg ccacgcgcag gtccccgcgc aggcgcatga 130260
gcaccagcgc gtcgcgcacg aaccgcagct cgcgcagcca cgcgcgcagg cggggcgcgt 130320
cggcgtgcgg cggcggcggg gaagcggggc ccgcgggtcc ctccggccgc ggggggctgg 130380
cgggccgggc cccggccagc cccgggacgg ccgccaggtc gccgtcgaag ccctcggcca 130440
gcgcctccag gatcccgcgg caggcggcca ggcactccac ggccacgcgg ccggcctggg 130500
cgcggcgccc ggcgtcgtcg tcggcgtcgg cgtggcgggc ggcgtcgggg tcgtcgcccc 130560
ccgcggggga ggcgggcgcg gcggacagcc gccccagggc ggcgaggatc cccgcggcgc 130620
cgtacccggc gggcaccgcg cgctcgcccg gtgcggcggc ggcggcgacg acggcggcgg 130680
cgaccccctc gtcatctgcg ccggcgccgg ggctccccgc ggcccccgtc agcgccgcgt 130740
tctcgcgcgc caacaggggc gcgtaggcgc ggcgcaggct ggtcagcagg aagcccttct 130800
gcgcgcggtc gtatcggcgg ctcatggcca cggcggccgc cgcgtgcgcc aggccccagc 130860
cgaagcggcc ggccgccatg gcgtagccca ggtggggcac ggcccgcgcc acgctgccgg 130920
tgatgaagga gctgctgttg cgcgcggcgc ccgagatccg gaagcaggcc tggtccagcg 130980
ccacgtcccc ggggaccacg cgcgggttct ggagccaccc catggcctcc gcgtccgggg 131040
tgtacagcag ccgcgtgatc agggcgtact gctgcgcggc gtcgcccagc tcgggcgccc 131100
acacggccgc cggggcgccc gaggcctcga accggcgtcg cgcctcctcc gcctcgggcg 131160
ccccccagag gcccgggcgg ctgtcgccca ggccgccgta cagcacccgc cccgggggcg 131220
ggggcccggc gccgggccac ggctccccgc tgacgtaccc gtcgcgatag cgcgcgtaga 131280
aggcgccgga ggccgcgtcg gcgtccagct cgacccgccg gggctgcccg gccgtgaagc 131340
ggcccgtggc gtcgcggccg gccaccgccg cgcgggcccg gcggcgctcg atgcggcccg 131400
cggaggccgc gggggtcctc gccgccgccc ggggcttggg cgcggcctcg gagagggggg 131460
gtggcccggg cgggggcggc gtccgcccgg gggcttccgg cgccgcgctc gacggacccc 131520
gcccgacggc ccgcgcctcg cgtgcgcggt cggccgcgtc gttgccgtcg tcgtcctcgt 131580
cctcgtcgga cgacgaggac gaagaggatg cggacgacga ggacgaggac ccggagtccg 131640
acgaggtcga tgacgccgat ggccgccgcc ggccgtgacg acgtctccgc ggcggctggg 131700
ccggcgggcg cggcgacagg cggtccgtgg ggtccggata cgcgccgcgt agcggggcct 131760
cccgtgcgcg gccccgggcc ggggcccggt cgccggcggc gtcggctgcg tcgtcgtact 131820
cgtccccgtc atcgtcgtcg gctcgaaagg cgggggtccg gggcggcgag gccgcggggt 131880
cgggcgtcgg gatcgtccgg acggcctcct ctaccatgga ggccagcagg gccagctgtc 131940
gcggcgagac ggcgtccccg gcgtcctcgc cggcgtcggt gcccgccgcg ggggccctcc 132000
cgtcccgccg ggcgtcgtcg aggtcgtggg ggtggtcggg gtcgtggtcg gggtcgtccc 132060
cgccctcctc cgtctccgcg ccccacccga gggcccccg ctcgtcgcgg tctgggctcg 132120
gggtgggcgg cggcccgtcg gtggggcccg gggagccggg gcgctgcttg ttctccgacg 132180
ccatcgccga tgcggggcga tcctccgggg atacggctgc gacggcggac gtagcacggt 132240
aggtcaccta cggactctcg atggggaggg ggcgagaccc acggaccccg acgacccccg 132300
ccgtcgacgc ggaactagcg cggaccggtc gatgcttggg tgggaaaaag gacagggacg 132360
gccgatcccc ctcccgcgct tcgtccgcgt atcggcgtcc cggcgcggcg agcgtctgac 132420
ggtctgtctc tggcggtccc gcgtcgggtc gtggatccgt gtcggcagcc gcgctccgtg 132480
tggacgatcg gggcgtcctc gggctcatat agtcccaggg gccggcggga aggaggagca 132540
gcggaggccg ccggccccc gccccccagg cgggcccgcc ccgaacggaa ttccattatg 132600
cacgaccccg ccccgacgcc ggcacgccgg gggcccgtgg ccgcggcccg ttggtcgaac 132660
ccccggcccc gcccatccgc gccatctgcc atgggcgggg cgcgagggcg ggtgggcccg 132720
cgccccgccc cgcatggcat ctcattaccg cccgatccgg tggtttccgc ttccgttccg 132780
catgctaacg aggaacgggc cgggggcggg gcccgggccc cgacttcccg gttcggcggt 132840
aatgagatac gagccccgcg cgcccgttgg ccgtccccgg gcccccggtc ccgcccgccg 132900
gacgttggga ccaacgggac ggcgggcggc ccaagggccg cccgccttgc cgccccccca 132960
ttggccggcg ggcgggaccg ccccaagggg gcggggccgc cgggtaaaag aagtgagaac 133020
gcgaagcgtt cgcacttcgt cccaatatat atatattatt agggcgaagt gcgagcactg 133080
gcgccgtgcc cgactccgcg ccggccccgg gggcgggccc gggcggcggg gggcgggtct 133140
ctccggcgca cataaaggcc cggcgcgacc gacgcccgca gacggcgccg gccacgaacg 133200
acgggagcgg ctgcggagca cgcggaccgg gagcgggact cgcagagggc cgtcggagcg 133260
gacggcgtcg gcatcgcgac gccccggctc gggatcggga tcgcatcgga aagggacacg 133320
cggaaagacc cacccacccc acccacgaaa cacaggggac gcaccccggg ggcctccgac 133380
gacagaaacc caccggtccg cctttgtgca cgggtaagca ccttgggtgg gcggaggagg 133440
gggggacgcg ggggcggagg aggggggacg cgggggcgga ggagggggga cgcgggggcg 133500
gaggaggggg gacgcggggg cggaggaggg gggacgcggg ggcggaggag ggggctcacc 133560
cgcgttcgtg ccttcccgca ggaggaacgt cctcgtcggg gcgaccggcg gcgaccgttg 133620
cgtggaccgc ttcctgctcg tcgggcgggg ggaagccact gtggtcctcc gggacgtttt 133680
ctggatggcc gacatttccc caggcgcttt tgcgccttgt gtaaaagcgc ggcgtcccgc 133740
tctccgatcc ccgcccctgg gcacgcgcaa gcgcaagcgc ccttcccgcc ccctctcatc 133800
ggagtctgag gtagaatccg atacagcctt ggagtctgag gtcgaatccg agacagcatc 133860
ggattcgacc gagtctgggg accaggatga agccccccgc atcggtggcc gtagggcccc 133920
ccggaggctt ggggggcggt tttttctgga catgtcggcg gaatccacca cggggacgga 133980
aacggatgcg tcggtgtcgg acgaccccga cgacacgtcc gactggtctt atgacgacat 134040
tcccccacga cccaagcggg cccgggtaaa cctgcggctc acgagctctc ccgatcggcg 134100
ggatggggtt atttttccta agatggggcg ggtccggtct acccgggaaa cgcagccccg 134160
ggcccccacc ccgtcggccc caagcccaaa tgcaatgcta cggcgctcgg tgcgccaggc 134220
ccagaggcgg agcagcgcac gatggacccc cgacctgggc tacatgcgcc agtgtatcaa 134280
tcagctgttt cgggtcctgc gggtcgcccg ggacccccac ggcagtgcca accgcctgcg 134340
ccacctgata cgcgactgtt acctgatggg atactgccga gcccgtctgg ccccgcgcac 134400
gtggtgccgt ttgctgcagg tgtccggcgg aacctggggc atgcacctgc gcaacaccat 134460
acgggaggtg gaggctcgat tcgacgccac cgcggaaccc gtgtgcaagc ttccttgttt 134520
ggagaccaga cggtacggcc cggagtgtga tcttagtaat ctcgagattc atctcagcgc 134580
gacaagcgat gatgaaatct ccgatgccac cgatctggag gccgccggtt cggaccacac 134640
gctcgcgtcc cagtccgaca cggaggatgc cccctccccc gttacgctgg aaaccccaga 134700
accccgcggg tccctcgctg tgcgtctgga ggatgagttt ggggagtttg actggacccc 134760
ccaggagggc tcccagccct ggctgtctgc ggtcgtggcc gataccagct ccgtggaacg 134820
cccgggccca tccgattctg ggcgggtcg cgccgcagaa gaccgcaagt gtctggacgg 134880
ctgccggaaa atgcgcttct ccaccgcctg ccccta tccg tgcagcgaca cgtttctccg 134940
gccgtgagtc cggtcgcccc gaccccccttg tatgtcccca aataaaagac caaaatcaaa 135000
gcgtttgtcc cagcgtctta atggcgggaa gggcggagag aaacagacca cgcgtacatg 135060
gggggtgttt gggggtttat tgacatcggg gctacagggt ggtaaccgga tagcagatgt 135120
gaggaagtct gggccgttcg ccgcgaacgg cgatcagagg gtccgtttct tgcggaccac 135180
ggcccggtga tgtgggttgc tcgtctggga tctcgggcat gcccatacac gcacaacacg 135240
gacgccgcac cggatgggac gtcgtaaggg ggcctggggt agctgggtgg ggtttgtgca 135300
gagcaatcag ggaccgcagc cagcgcatac aatcgcgctc ccgtccgttt gtcccgggca 135360
gtaccacgcc gtactggtat tcgtaccggc tgagcagggt ctccaggggg tggttggggg 135420
ccgcggggaa cggggtccac gccacggtcc actcgggcaa aaaccgagtc ggcacggccc 135480
acggttctcc cacccacgcg tctggggtct tgatggcgat aaatcttacc ccgagccgga 135540
ttttttgggc gtattcgaga aacggcacac acagatccgc cgcgcctacc acccacaagt 135600

-continued ggtagaggcg aggggggctg ggttggtctc ggtgcagcag tcggaagcac gccacggcgt 135660
ccacgacctc ggtgctctcc aaggggctgt cctccgcaaa caggcccgtg gtggtgtttg 135720
gggggcagcg acaggaccta gtgcgcacga tcgggcgggt gggtttgggt aagtccatca 135780
gcggctcggc caaccgtcga aggttggccg gacgaacgac gaccggggta cccaggggtt 135840
ctgatgccaa aatgcggcac tgcctaaaca ggaagctcca cagggccggg cttgcgtcga 135900
cggaagtccg gggcagggcg ttgttctggt caaggagggt cattacgttg acgacaacaa 135960
cgcccatgtt ggtatattac aggcccgtgt ccgatttggg gcacttgcag atttgtaagg 136020
ccacgcacgg cggggagaca ggccgacgcg ggggctgctc taaaaattta agggccctac 136080
ggtccacaga cccgccttcc cggggggggcc cttggagcga ccggcagcgg aggcgtccgg 136140
gggaggggag ggtgatttac gggggggtag gtcagggggt gggtcgtcaa actgccgctc 136200
cttaaaaccc cggggcccgt cgttcggggt gctcgttggt tggcactcac ggtgcggcga 136260
atggcctgtc gtaagttttg tcgcgtttac gggggacagg gcaggaggaa ggaggaggcc 136320
gtcccgccgg agacaaagcc gtcccgggtg tttcctcatg gccccttttta taccccagcc 136380
gaggacgcgt gcctggactc cccgcccccg gagaccccca aaccttccca caccacacca 136440
cccggcgatg ccgagcgcct gtgtcatctg caggagatcc tggcccagat gtacggaaac 136500
caggactacc ccatagagga cgaccccagc gcggatgccg cggacgatgt cgacgaggac 136560
gccccggacg acgtggccta tccggaggaa tacgcagagg agctttttct gcccggggac 136620
gcgcccggtc cccttatcgg ggccaacgac cacatccctc ccccgtgtgg cgcatctccc 136680
cccggtatac gacgacgcag ccgggatgag attggggcca cgggatttac cgcggaagaa 136740
ctggacgcca tggacaggga ggcggctcga gccatcagcc gcggcggcaa gccccccctcg 136800
accatggcca agctggtgac tggcatgggc tttacgatcc acggagcgct caccccagga 136860
tcggaggggt gtgtctttga cagcagccac ccagattacc cccaacgggt aatcgtgaag 136920
gcggggtggt acacgagcac gagccacgag gcgcgactgc tgaggcgact ggaccacccc 136980
gcgatcctgc ccctcctgga cctgcatgtc gtctccgggg tcacgtgtct ggtcctcccc 137040
aagtaccagg ccgacctgta tacctatctg agtaggcgcc tgaacccgct gggacgcccg 137100
cagatcgcag cggtctcccg gcagctccta agcgccgttg actacattca ccgccagggc 137160
attatccacc gcgacattaa gaccgaaaat atttttatta acacccccga ggacatttgc 137220
ctgggggact ttggtgccgc gtgcttcgtg cagggttccc gatcaagccc cttcccctac 137280
ggaatcgccg gaaccatcga caccaacgcc cccgaggtcc tggccgggga tccgtatacc 137340
accaccgtcg acatttggag cgccggtctg gtgatcttcg agactgccgt ccacaacgcg 137400
tccttgttct cggccccccg cggccccaaa aggggcccgt gcgacagtca gatcacccgc 137460
atcatccgac aggcccaggt ccacgttgac gagttttccc cgcatccaga atcgcgcctc 137520
acctcgcgct accgctcccg cgcggccggg aacaatcgcc cgccgtacac ccgaccggcc 137580
tggacccgct actacaagat ggacatagac gtcgaatatc tggtttgcaa agccctcacc 137640
ttcgacggcg cgcttcgccc cagcgccgca gagctgcttt gtttgccgct gtttcaacag 137700
aaatgaccgc ccccaggggg cggtgctgtt tgcgggttgg cacaaaaaga ccccgacccg 137760
cgtctgtggt gtttttggca tcatgtcgcc gggcgccatg cgtgccgttg ttcccattat 137820
cccattcctt ttggttcttg tcggtgtatc gggggttccc accaacgtct cctccaccac 137880
ccaaccccaa ctccagacca ccggtcgtcc ctcgcatgaa gcccccaaca tgacccagac 137940

-continued cggcaccacc gactctccca ccgccatcag ccttaccacg cccgaccaca caccccccat 138000
gccaagtatc ggactggagg aggaggaaga ggaggagggg gccggggacg gcgaacatct 138060
tgagggggga gatgggaccc gtgacaccct accccagtcc ccgggcccag ccttcccgtt 138120
ggctgaggac gtcgagaagg acaaacccaa ccgtcccgta gtcccatccc ccgatcccaa 138180
caactccccc gcgcgccccg agaccagtcg cccgaagaca ccccccacca ttatcgggcc 138240
gctggcaact cgccccacga cccgactcac ctcaaaggga cgacccttgg ttccgacgcc 138300
tcaacatacc ccgctgttct cgttcctcac tgcctccccc gccctggaca ccctcttcgt 138360
cgtcagcacc gtcatccaca ccttatcgtt tttgtgtatt ggtgcgatgg cgacacacct 138420
gtgtggcggt tggtccagac gcgggcgacg cacacaccct agcgtgcgtt acgtgtgcct 138480
gccgtccgaa cgcgggtagg gtatggggcg ggggatgggg agagcccaca cgcggaaagc 138540
aagaacaata aaggcggtgg tatctagttg atatgcatct ctgggtgttt ttggggtgtg 138600
gcggacgcgg ggcggtcatt ggacggggtg cagttaaata catgcccggg acccatgaag 138660
catgcgcgac ttccgggcct cggaacccac ccgaaacggc caacggacgt ctgagccagg 138720
cctggctatc cggagaaaca gcacacgact tggcgttctg tgtgtcgcga tgtctctgcg 138780
cgcagtctgg catctggggc ttttgggaag cctcgtgggg gctgttcttg ccgccaccca 138840
tcggggacct gcggccaaca caacggaccc cttaacgcac gccccagtgt cccctcaccc 138900
cagccccctg gggggctttg ccgtccccct cgtagtcggt gggctgtgcg ccgtagtcct 138960
gggggcggcg tgtctgcttg agctcctgcg tcgtacgtgc cgcgggtggg ggcgttacca 139020
tccctacatg gacccagttg tcgtataatt tccccccccc ccccccttct ccgcatgggt 139080
gatgtcgggt ccaaactccc gacaccacca gctggcatgg tataaatcac cggtgcgccc 139140
cccaaaccat gtccggcagg gggatggggg ggcgaatgcg gagggcaccc aacaacaccg 139200
ggctaaccag gaaatccgtg gccccggccc ccaataaaga tcgcggtagc ccggccgtgt 139260
gacactatcg tccataccga ccacaccgac gaatccccta agggggaggg gccattttac 139320
gaggaggagg ggtataacaa agtctgtctt taaaaagcag gggttaggga gttgttcggt 139380
cataagcttc agcgcgaacg accaactacc ccgatcatca gttatcctta aggtctcttt 139440
tgtgtggtgc gttccggtat ggggggggct gccgccaggt tgggggccgt gattttgttt 139500
gtcgtcatag tgggcctcca tggggtccgc ggcaaatatg ccttggcgga tgcctctctc 139560
aagatggccg accccaatcg ctttcgcggc aaagaccttc cggtcctgga ccagctgacc 139620
gaccctccgg gggtccggcg cgtgtaccac atccaggcgg gcctaccgga cccgttccag 139680
ccccccagcc tcccgatcac ggtttactac gccgtgttgg agcgcgcctg ccgcagcgtg 139740
ctcctaaacg caccgtcgga ggccccccag attgtccgcg gggcctccga agacgtccgg 139800
aaacaaccct acaacctgac catcgcttgg tttcggatgg gaggcaactg tgctatcccc 139860
atcacggtca tggagtacac cgaatgctcc tacaacaagt ctctgggggc ctgtcccatc 139920
cgaacgcagc cccgctggaa ctactatgac agcttcagcg ccgtcagcga ggataacctg 139980
gggttcctga tgcacgcccc cgcgtttgag accgccggca cgtacctgcg gctcgtgaag 140040
ataaacgact ggacggagat tacacagttt atcctggagc accgagccaa gggctcctgt 140100
aagtacgccc tcccgctgcg catccccccg tcagcctgcc tgtcccccca ggcctaccag 140160
cagggggtga cggtggacag catcgggatg ctgccccgct tcatccccga gaaccagcgc 140220
accgtcgccg tatacagctt gaagatcgcc gggtggcacg ggcccaaggc cccatacacg 140280
agcaccctgc tgcccccgga gctgtccgag acccccaacg ccacgcagcc agaactcgcc 140340
ccggaagacc ccgaggattc ggccctcttg gaggaccccg tggggacggt ggcgccgcaa 140400
atcccaccaa actggcacat accgtcgatc caggacgccg cgacgcctta ccatccccccg 140460 gccaccccga acaacatggg cctgatcgcc ggcgcggtgg gcggcagtct cctggcagcc 140520
ctggtcattt gcggaattgt gtactggatg cgccgccgca ctcaaaaagc cccaaagcgc 140580
atacgcctcc cccacatccg ggaagacgac cagccgtcct cgcaccagcc cttgttttac 140640 tagataccccc cccttaatgg gtgcgggggg gtcaggtctg cggggttggg atgggacctt 140700
aactccatat aaagcgagtc tggaaggggg gaaaggcgga cagtcgataa gtcggtagcg 140760
ggggacgcgc acctgttccg cctgtcgcac ccacagcttt ttttgcgaac cgtcccgttc 140820
cgggatgccg tgccgcccgt tgcagggcct ggtgctcgtg ggcctctggg tctgtgccac 140880
cagcctggtt gtccgtggcc ccacggtcag tctggtatca aactcatttg tggacgccgg 140940
ggccttgggg cccgacggcg tagtggagga agacctgctt attctcgggg agcttcgctt 141000
tgtgggggac caggtccccc acaccaccta ctacgatggg gtcgtagagc tgtggcacta 141060
ccccatggga cacaaatgcc cacgggtcgt gcatgtcgtc acggtgaccg cgtgcccacg 141120
tcgccccgcc gtggctttcg ccctgtgtcg cgcgaccgac agcactcaca gccccgcata 141180
tcccaccctg gagctgaatc tggcccaaca gccgcttttg cgggtccgga gggcgacgcg 141240
tgactatgcc ggggtgtacg tgttacgcgt atgggtcggg gacgcaccaa acgccagcct 141300
gtttgtcctg gggatggcca tagccgccga agggactctg gcgtacaacg gctcggccca 141360
tggctcctgc gacccgaaac tgcttccgta ttcggccccg cgtctggccc cggcgagcgt 141420
ataccaaccc gcccctaacc cggcctccac cccctcgacc accacctcca ccccctcgac 141480
caccacctcc accccctcga ccaccatccc cgctccccaa gcatcgacca caccccttccc 141540 cacgggagac ccaaaacccc aacctcacgg ggtcaaccac gaacccccat cgaatgccac 141600
gcgagcgacc cgcgactcgc gatacgcgct aacggtgacc cagataatcc agatagccat 141660
ccccgcgtcc attatagccc tggtgtttct ggggagctgt atttgcttta tacacagatg 141720
tcaacgccgc taccgacgct cccgccgccc gatttacaac ccccagatac ccactggcat 141780
ctcatgcgcg gtgaacgaag cggccatggc ccgcctcgga gccgagctca aatcgcatcc 141840
gagcaccccc cccaaatccc ggcgccggtc gtcacgcaca ccaatgccct ccctgacggc 141900
catcgccgaa gagtcggagc ccgcgggggc ggctgggctt ccgacgcccc ccgtggaccc 141960
cacgacatcc accccaacgc ctcccctgtt ggtataggtc cacggccact ggccgggggc 142020
accacataac cgaccgcagt cactgagttg ggaataaacc ggtattattt acctatatac 142080
gtgtatgtcc atttcttccc cccccccccc ggaaaccaaa gaaggaaaca aagaatggat 142140
gggaggagtt caggaagccg gggagagggc ccgcggcgca tttaaggcgt tgttgtgttg 142200
actttggctc ttctggcggg ttggtgcggt gctgtttgtt gggctcccat tttacccgaa 142260
gatcggctgc tatccccggg acatggatcg cggggcggtg gtggggtttc ttctcggtgt 142320
ttgtgttgta tcgtgcttgg cgggaacgcc caaaacgtcc tggagacggg tgagtgtcgg 142380
cgaggacgtt tcgttgcttc cagctccggg gcctacgggg cgcggcccga cccagaaact 142440
actatgggcc gtggaacccc tggatgggtg cggcccctta cacccgtcgt gggtctcgct 142500
gatgcccccc aagcaggtgc ccgagacggt cgtggatgcg gcgtgcatgc gcgctccggt 142560
cccgctggcg atggcgtacg cccccccggc cccatctgcg accgggggtc tacggacgga 142620
cttcgtgtgg caggagcgcg cggccgtggt taaccggagt ctggttattt acggggtccg 142680
agagacggac agcggcctgt ataccctgtc tgtgggcgac ataaaggacc cggctcgcca 142740
agtggcctcg gtggtcctgg tggtgcaacc ggccccagtt ccgaccccac ccccgacccc 142800
agccgattac gacgaggatg acaatgacga gggcgagggc gaggacgaaa gtctagccgg 142860
cactcccgcc agcgggaccc cccggctccc gcctcccccc gcccccccga ggtcttggcc 142920
cagcgccccc gaagtctcac acgtgcgtgg ggtgaccgtg cgtatggaga ctccggaagc 142980
tatcctgttt tcccccgggg aggcgtttag cacgaacgtc tccatccatg ccatcgccca 143040
cgacgaccag acctacacca tggacgtcgt ctggttgagg ttcgacgtgc cgacctcgtg 143100
tgccgagatg cgaatatacg aatcgtgtct gtatcacccg cagctcccag agtgtctgtc 143160
cccggccgac gctccgtgcg ccgcgagtac gtggacgtct cgcctggccg tccgcagcta 143220
cgcggggtgt tccagaacaa acccccgcc gcgctgttcg gccgaggctc acatggagcc 143280
cttcccgggg ctggcgtggc aggcggcctc cgtcaatctg gagttccggg acgcgtcccc 143340
acaacactcc ggcctgtatc tgtgcgtggt gtacgtcaac gaccatattc acgcatgggg 143400
ccacattacc atcagcaccg cggcgcagta ccggaacgcg gtggtggaac agcccctccc 143460
acagcgcggc gcggatttgg ccgagcccac ccacccgcac gtcggggccc ctccccacgc 143520
gcccccaacc cacggcgccc tgcggttagg ggcggtgatg gggccgccc tgctgctgtc 143580 tgcgctgggg ttgtcggtgt gggcgtgtat gacctgttgg cgcaggcgtg cctggcgggc 143640
ggttaaaagc agggcctcgg gtaaggggcc cacgtacatt cgcgtggccg acagcgagct 143700
gtacgcggac tggagctcgg acagcgaggg agaacgcgac caggtcccgt ggctggcccc 143760
cccggagaga cccgactctc cctccaccaa tggatccggc tttgagatct tatcaccaac 143820
ggctccgtct gtatacccc gtagcgatgg gcatcaatct cgccgccagc tcacaacctt 143880
tggatccgga aggcccgatc gccgttactc ccaggcctcc gattcgtccg tcttctggta 143940
aggcgcccca tcccgaggcc ccacgtcggt cgccgaactg ggcgaccgcc ggcgaggtgg 144000
acgtcggaga cgagctaatc gcgatttccg acgaacgcgg accccccga catgaccgcc 144060 cgcccctcgc cacgtcgacc gcgccctcgc cacacccgcg acccccgggc tacacggccg 144120
ttgtctcccc gatggccctc caggctgtcg acgcccctc cctgtttgtc gcctggctgg 144180
ccgctcggtg gctccggggg gcttccggcc tgggggccgt cctgtgtggg attgcgtggt 144240
atgtgacgtc aattgcccga ggcgcataaa gggccggtgg tccgcctagc cgcagcaaat 144300
taaaaatcgt gagtcactgc gaccgcaact tcccacccgg agctttcttc cggcctcgat 144360
gacgtcccgg ctctccgatc ccaactcctc agcgcgatcc gacatgtccg tgccgcttta 144420
tcccacggcc tcgccagttt cggtcgaagc ctactactcg gaaagcgaag acgaggcggc 144480
caacgacttc ctcgtacgca tggccgcca acagtcggta ttaaggcgtc gacgcagacg 144540
cacccgctgc gtcggcatgg tgatcgcctg tctcctcgtg gccgttctgt cgggcggatt 144600
tggggcgctc ctgatgtggc tgctccgcta aaagaccgca tcgacacgcg cgtccttctt 144660
gtcgtctctc ttccccccca tcaccccgca atttgcaccc agcctttaac tacattaaat 144720
tgggttcgat tggcaatgtt gtctcccggt tgatttttgg gtgggtgggg agtgggtggg 144780
tggggagtgg gtgggtgggg agtgggtggg tggggagtgg gtgggtgggg agtgggtggg 144840
tggggagtgg gtgggtgggg agtgggtggg tggggagtgg gtgggtgggg agtgggtggg 144900
tggggagtgg caaggaagaa acaagcccga ccaccagaca gaaaatgtaa ccatacccaa 144960
accgactctg gggctgttt gtggggtcgg aaccatagga tgaacaaacc accccgtacc 145020
tcccgcaccc ttgggtgcgg gtggctcatc ggcatctgtc cggtatgggt tgttccccac 145080
ccacttgcgt tcggacgtct tagaatcatg gcggttttct atgccgacat cggttttctc 145140
ccccgcaata agacacgatg cgataaaatc tgtttgtgaa atttattaag ggtacaaatt 145200
gccctagcac aggggtgggg ttagggccgg gtccccacac ccaaacgcac caaacagatg 145260
caggcagtgg gtcgagtaca gccccgcgta cgaacacgtc gatgcgtgtg tcagacagca 145320
ccagaaagca caggccatca acaggtcgtg catatgtcgg tgggtttgga cgcggggggc 145380
catggtggtg ataaagttaa tggccgccgt ccgccagggc cacaggggcg acgtctcttg 145440
gttggcccgg agccactggg tgtggaccag ccgcgcgtgg cggcccaaca tggcccctgt 145500
agccgggggc gggggatcgc gcacgtttgc agcgcacatg cgagacacct cgaccacggt 145560
tcggaagaag gcccggtggt ccgcgggcaa catcaccagg tgcgcaagcg cccgggcgtc 145620
cagagggtag agccctgagt catccgaggt tggctcatcg cccgggtcat gccgcaagtg 145680
cgtgtgggtt gggcttccgg tgggcgggac gcgaaccgcg gtgtggagcc ctacgcgggc 145740
ccgagcgtac gctccatctt gtggggagaa ggggtctggg ctcgccaggg gggcatactt 145800
gcccgggcta tacagacccg cgagccgtac gtggttcgcg gggggtgcgt ggggtccggg 145860
gctcccgggg aggccggggc tcccggggtt gtcgtggatc cctggggtca cgcggtaccc 145920
tggggtctct gggagctcgc ggtactctgg gttccctagg ttctcggggt ggtcgcggaa 145980
cccggggctc ccggggaaca cgcggtgtcc tggggattgt tggcggtcgg acggcttcag 146040
atggcttcga gatcgtagtg tccgcaccga ctcgtagtag acccgaatct ccacattgcc 146100
ccgccgcttg atcattatca ccccgttgcg gggtccgga gatcatgcgc gggtgtcctc 146160
gaggtgcgtg aacacctctg gggtgcatgc cggcggacgg cacgcctttt aagtaaacat 146220
ctgggtcgcc cggcccaact ggggccgggg gttgggtctg gctcatctcg agagccacgg 146280
ggggaaccac cctccgccca gaaacttggg cgatggtcgt acccgggact caacgggtta 146340
ccggattacg gggactgtcg gtcacggtcc cgccggttct tcgatgtgcc acacccaagg 146400
atgcgttggg ggcgattttg ggcagcagcc cgggagagcg cagcagagga cgctccgggt 146460
cgtgcacggc ggttttggcc gcctcccggt cctcacgccc ccttttattg atctcatcgc 146520
gtacgtcggc gtacgtcctg ggcccaaccc gcatgttgtc caggaaggtg tccgccattt 146580
ccagggccca cgacatgctc ccccgcccga cgagcaggaa gcggtccacg caacggtcgc 146640
cgccggtcgc cccgacgagc aggaagcggt ccacgcaacg gtcgccgccg gtcgcctcga 146700
cgaggacgtt cctcctgcgg gaaggcacga acgcgggtga gccccctcct ccgcccccgc 146760 gtccccccctc ctccgccccc gcgtcccccc tcctccgccc ccgcgtcccc cctcctccgc 146820
ccccgcgtcc cccctcctcc gcccccgcgt ccccccctcct ccgcccccgc gtccccccctc 146880 ctccaccccc gcgtcccccc ctcctccgcc cacccaaggt gcttacccgt gcacaaaggc 146940
ggaccggtgg gtttctgtcg tcggaggccc ccggggtgcg tcccctgtgt ttcgtgggtg 147000
gggtgggtgg gtctttccgc gtgtcccttt ccgatgcgat cccgatcccg agccggggcg 147060
tcgcgatgcc gacgccgtcc gctccgacgg ccctctgcga gtcccgctcc cggtccgcgt 147120
gctccgcagc cgctcccgtc gttcgtggcc ggcgccgtct gcgggcgtcg gtcgcgccgg 147180
gcctttatgt gcgccggaga gacccgcccc ccgccgcccg ggcccgcccc cggggccggc 147240
gcggagtcgg gcacggcgcc agtgctcgca cttcgcccta ataatatata tatattggga 147300
cgaagtgcga acgcttcgcg ttctcacttc ttttacccgg cggccccgcc cccttggggc 147360
ggtcccgccc gccggccaat ggggggcgg caaggcgggc ggcccttggg ccgcccgccg 147420

-continued tcccgttggt cccaacgtcc ggcgggcggg accgggggcc cggggacggc caacgggcgc 147480
gcggggctcg tatctcatta ccgccgaacc gggaagtcgg ggcccgggcc ccgcccccgg 147540
cccgttcctc gttagcatgc ggaacggaag cggaaaccac cggatcgggc ggtaatgaga 147600
tgccatgcgg ggcggggcgc gggcccaccc gccctcgcgc cccgcccatg gcagatggcg 147660
cggatgggcg gggccggggg ttcgaccaac gggccgcggc cacgggcccc cggcgtgccg 147720
gcgtcggggc ggggtcgtgc ataatggaat tccgttcggg gcgggcccgc ctgggggcg 147780 gggggccggc ggcctccgct gctcctcctt cccgccggcc cctgggacta tatgagcccg 147840
aggacgcccc gatcgtccac acggagcgcg gctgccgaca cggatccacg acccgacgcg 147900
ggaccgccag agacagaccg tcagacgctc gccgcgccgg gacgccgata cgcggacgaa 147960
gcgcgggagg gggatcggcc gtccctgtcc tttttcccac ccaagcatcg accggtccgc 148020
gctagttccg cgtcgacggc gggggtcgtc ggggtccgtg ggtctcgccc cctccccatc 148080
gagagtccgt aggtgaccta ccgtgctacg tccgccgtcg cagccgtatc cccggaggat 148140
cgccccgcat cggcgatggc gtcggagaac aagcagcgcc ccggctcccc gggccccacc 148200
gacgggccgc cgcccacccc gagcccagac cgcgacgagc ggggggccct cgggtggggc 148260
gcggagacgg aggagggcgg ggacgacccc gaccacgacc ccgaccaccc ccacgacctc 148320
gacgacgccc ggcgggacgg gagggccccc gcggcgggca ccgacgccgg cgaggacgcc 148380
ggggacgccg tctcgccgcg acagctggcc ctgctggcct ccatggtaga ggaggccgtc 148440
cggacgatcc cgacgcccga ccccgcggcc tcgccgcccc ggacccccgc ctttcgagcc 148500
gacgacgatg acggggacga gtacgacgac gcagccgacg ccgccggcga ccgggccccg 148560
gcccggggcc gcgcacggga ggccccgcta cgcggcgcgt atccggaccc cacggaccgc 148620
ctgtcgccgc gcccgccggc ccagccgccg cggagacgtc gtcacggccg gcggcggcca 148680
tcggcgtcat cgacctcgtc ggactccggg tcctcgtcct cgtcgtccgc atcctcttcg 148740
tcctcgtcgt ccgacgagga cgaggacgac gacggcaacg acgcggccga ccgcgcacgc 148800
gaggcgcggg ccgtcgggcg gggtccgtcg agcgcggcgc cggaagcccc cgggcggacg 148860
ccgcccccgc ccgggccacc ccccctctcc gaggccgcgc ccaagccccg ggcggcggcg 148920
aggacccccg cggcctccgc gggccgcatc gagcgccgcc gggcccgcgc ggcggtggcc 148980
ggccgcgacg ccacgggccg cttcacggcc gggcagcccc ggcgggtcga gctggacgcc 149040
gacgcggcct ccggcgcctt ctacgcgcgc tatcgcgacg ggtacgtcag cggggagccg 149100
tggcccggcg ccgggccccc gcccccgggg cgggtgctgt acggcggcct gggcgacagc 149160
cgcccgggcc tctgggggc gcccgaggcg gaggaggcgc gacgccggtt cgaggcctcg 149220
ggcgccccgg cggccgtgtg ggcgcccgag ctgggcgacg ccgcgcagca gtacgccctg 149280
atcacgcggc tgctgtacac cccggacgcg gaggccatgg ggtggctcca gaacccgcgc 149340
gtggtccccg gggacgtggc gctggaccag gcctgcttcc ggatctcggg cgccgcgcgc 149400
aacagcagct ccttcatcac cggcagcgtg gcgcgggccg tgccccacct gggctacgcc 149460
atggcggccg gccgcttcgg ctggggcctg gcgcacgcgg cggccgccgt ggccatgagc 149520
cgccgatacg accgcgcgca gaagggcttc ctgctgacca gcctgcgccg cgcctacgcg 149580
cccctgttgg cgcgcgagaa cgcggcgctg acgggggccg cggggagccc cggcgccggc 149640
gcagatgacg agggggtcgc cgccgccgtc gtcgccgccg ccgccgcacc gggcgagcgc 149700
gcggtgcccg ccgggtacgg cgccgcgggg atcctcgccg ccctggggcg gctgtccgcc 149760
gcgcccgcct cccccgcggg gggcgacgac cccgacgccg cccgccacgc cgacgccgac 149820

-continued gacgacgccg ggcgccgcgc ccaggccggc cgcgtggccg tggagtgcct ggccgcctgc 149880
cgcgggatcc tggaggcgct ggccgagggc ttcgacggcg acctggcggc cgtcccgggg 149940
ctggccgggg cccggcccgc cagccccccg cggccggagg gacccgcggg ccccgcttcc 150000
ccgccgccgc cgcacgccga cgcgccccgc ctgcgcgcgt ggctgcgcga gctgcggttc 150060
gtgcgcgacg cgctggtgct catgcgcctg cgcggggacc tgcgcgtggc cggcggcagc 150120
gaggccgccg tggccgccgt gcgcgccgtg agcctggtcg ccggggccct gggccccgcg 150180
ctgccgcggg acccgcgcct gccgagctcc gcggccgccg ccgccgcgga cctgctgttt 150240
gagaaccaga gcctgcgccc cctgctggcg gcggccgcca gcgcaccgga cgccgccgac 150300
gcgctggcgg ccgccgccgc ctccgccgcg ccgcgggagg ggcgcaagcg caagagtccc 150360
ggcccggccc ggccgcccgg aggcggcggc ccgcgacccc cgaagacgaa gaagagcggc 150420
gcggacgccc ccggctcgga cgcccgcgcc cccctccccg cgcccccctc cacgcccccg 150480
gggcccgagc ccgcccccgc ccagcccgcg gcgccccggg ccgccgcggc gcaggcccgc 150540
ccgcgccccg tggcgctgtc gcgccggccc gccgagggcc ccgacccccct gggcggctgg 150600
cggcggcagc ccccggggcc cagccacacg gcggcgcccg cggccgccgc cctggaggcc 150660
tactgctccc cgcgcgccgt ggccgagctc acggaccacc cgctgttccc cgtcccctgg 150720
cgaccggccc tcatgtttga cccgcgggcc ctggcctcga tcgccgcgcg gtgcgccggg 150780
cccgccgccg ccgcccaggc cgcgtgcggc ggcggcgacg acgacgataa cccccacccc 150840
cacggggccg ccgggggccg cctctttggc cccctgcgcg cctcgggccc gctgcgccgc 150900
atggcggcct ggatgcgcca gatccccgac cccgaggacg tgcgcgtggt ggtgctgtac 150960
tcgccgctgc cgggcgagga cctggccggc ggcggggcct cggggggggcc gccggagtgg 151020
tccgccgagc gcggcgggct gtcctgcctg ctggcggccc tggccaaccg gctgtgcggg 151080
ccggacacgg ccgcctgggc gggcaactgg accggcgccc ccgacgtgtc ggcgctgggc 151140
gcgcagggcg tgctgctgct gtccacgcgg gacctggcct tcgccggggc cgtggagttt 151200
ctggggctgc tcgccagcgc cggcgaccgg cggctcatcg tggtcaacac cgtgcgcgcc 151260
tgcgactggc ccgccgacgg gcccgcggtg tcgcggcagc acgcctacct ggcgtgcgac 151320
ctgctgcccg ccgtgcagtg cgccgtgcgc tggccggcgg cgcgggacct gcgccgcacg 151380
gtgctggccc cgggccgcgt gttcggcccg ggggtcttcg cgcgcgtgga ggccgcgcac 151440
gcgcgcctgt accccgacgc gccgccgctg cgcctgtgcc gcggcggcaa cgtgcgctac 151500
cgcgtgcgca cgcgcttcgg cccggacacg ccggtgccca tgtccccgcg cgagtaccgc 151560
cgggccgtgc tgccggcgct ggacggccgg gcggcggcct cggggaccac cgacgccatg 151620
gcgcccggcg cgccggactt ctgcgaggag gaggcccact cgcaccgcgc ctgcgcgcgc 151680
tggggcctgg gcgcgccgct gcggcccgtg tacgtggcgc tggggcgcga ggcggtgcgc 151740
gccggcccgg cccggtggcg cgggccgcgg agggactttt gcgcccgcgc cctgctggag 151800
cccgacgacg acgccccccc gctggtgctg cgcggcggcg acgacgacga cgacggcccg 151860
ggggccctgc cgccggcgtt gcccgggatt cgctgggcct cggccacggg ccgcagcggc 151920
accgtgctgg cggcggcggg ggccgtggag gtgctggggg cggaggcggg cttggccacg 151980
cccccgcgac gggaagttgt ggactgggaa ggcgcctggg acgacgacga cggcggcgcg 152040
ttcgaggggg acggggtgct gtaacgggcc gggacggggc ggggcgcttg cgaaacccga 152100
agacgcaata aacgacaacg acctgattta gttttgcagt agcgttgttt atttcgaggg 152160
gcgggagggg gcgaggggcg ggagggggcg aggggcggga gggggcgagg ggcgggaggg 152220
ggcgaggggc gggaggggc gaggggcggg agggggcgag gggcgggagg gggcgagggg 152280
cgggaggggg cgaggggcgg gagggggcga ggggcgggag ggggcgaggg gcgggagggg 152340
gcgaggggcg ggagggggcg aggggcggga gggggcgagg ggcgggaggg ggcgaggggc 152400 gggaggggc gaggggcggg agggggcgag gggcgggagg gggcgagggg cgggaggggg 152460
cgaggggcgg gagggggcga ggggcggtgg tggtgcgcgg gcgcccccgg agggtttgga 152520
tctctgacct gagattggcg gcactgaggt agagatgccc gaaccccccc gagggagcgc 152580
gggacgcggc cggggagggc tggggccggg gagggctggg gccggggagg gctggggccg 152640
gggagggctg gggccgggga gggctggggc cggggagggc tggggccggg gagggctggg 152700
gctggggagg gctggggctg gggagggctg gggcggtggt gtgtgacagg agcggcgtgt 152760
tgcgctgggg gacgtctgga ggagcggggg gtgcgcggtg acgtgtggat gaggaacagg 152820
agttgttgcg cggtgagttg tcgctgtgag ttgtgttggt gggcaggtgt ggtggatgac 152880
gtgacgtgtg acgtgtggat gaggaaccgg agtcgccggt gcgccgtgct gttggtgttc 152940
tgttggtgtt gttacacctg tggcagcccg ggccccccgc gggcggggcg gcgcgcaaaa 153000
aaggcgggcg gcggtccggg cggcgtgcgc gcgcgcggcg ggcgttgggg gagcgggggg 153060
aggagcgggg ggaggagcgg ggggaggagc ggggggagga gcgggggag gagcgggggg 153120 aggagcgggg ggaggagcgg ggggaggagc ggggggagga gcggggggag gagcgggggg 153180
aggagcgggg ggaggagcgg ggggaggagc ggggggagga gcggggggag gagcgggggg 153240
aggagcgggg ggaggagcgg ggggaggagc ggaaaacggg cccccccga aacacacccc 153300 ccgggggtcg cgcgcggccc tttaaagcg 153329

<210> SEQ ID NO 8
<211> LENGTH: 1863
<212> TYPE: DNA
<213> ORGANISM: Mus musculus

<400> SEQUENCE: 8
gccaccatgg agggagccga agccggggca cgagccacct ttggcccttg ggattacggg 60
gtgtttgcca ccatgttgct cgtcagtacc ggaatcggtt tgtgggtggg actcgctcgg 120
ggcggtcaga ggtccgcaga tgatttcttt acaggaggaa ggcagctcgc cgcagtgcca 180
gtagggttgt ctctcgctgc tagttttatg tctgcagtcc aagtcctggg tgtaccagcc 240
gaagctgccc gatacggcct taaattcctt tggatgtgcg tagggcaact cttgaatagt 300
ttgcttactg ccctgctttt tttgccaatc ttttacagac ttggtctgac aagtacctac 360
caatatttgg agctgagatt ttctcgggca gtaaggcttt gcgggactct tcagtatttg 420
gtggccacta tgctctacac aggcatcgtc atctatgctc ccgcattgat tcttaatcag 480
gtgaccggcc ttgacatctg ggccagcctt ctctccactg ggatcatttg cacactttat 540
actacagttg gcggtatgaa agctgtggtg tggactgacg tttttcaagt ggtagttatg 600
cttgtgggtt tctgggtaat acttgctagg ggggtaatgc tgatgggagg gccatggaac 660
gtcctgagcc tggcccaaaa ccactcaaga attaacctga tggattttga tcccgaccca 720
aggagccgat atacattttg gaccttcgtg gtcggcggtt ccttggtatg gctttcaatg 780
tatggggtaa accaagctca agtccaacgc tatgtcgctt gccataccga gaggaaagct 840
aaacttgcac ttcttgtgaa ccaacttggt ctctttctca tagtggcaag cgctgcatgt 900
tgcggaattg ttatgtttgt ttattacaaa gattgtgacc ccttgcttac tggccggata 960
gccgcccccg atcagtatat gccccttctc gtgcttgata tattcgagga cctccccggt 1020
gttcccggac tcttcctcgc atgtgcttac tcaggcaccc tttctaccgc ctcaacctct 1080
atcaatgcaa tggctgcagt caccgtggag gacctcatta aacctcgaat gccatccctg 1140
gccccaagga aactcgtgtt tatatccaag ggcttgtcct tcatatatgg aagcacctgt 1200
ctgacagtag cagcattgtc ttctttgttg ggcggcgggg tactgcaggg gtcttttaca 1260
gtgatgggtg taatctcagg cccccttttg ggggctttta ctctggggat gctcttgccc 1320
gcttgcaaca cacctggcgt actctcagga ctgactgccg ggttggctgt ttcactttgg 1380
gttgcagtag gcgccacact gtatccaccc ggcgagcaaa ccatgggtgt tctcccaacc 1440
tcagcagcag gatgcacaaa cgcctccgtt ctgccttctc cccctggggc cgcaaataca 1500
tcaaggggaa tccctagtag cggcatggat agtggaagac ccgcctttgc cgacacattc 1560
tacgcagtta gctacctgta ttacggcgcc ttggggactc tcaccactat gctctgcggg 1620
gctctgatta gttatttgac cggtcccacc aaacgatcca gcctcggtcc cggacttctg 1680
tggtgggact tggcaagaca aactgcttct gttgctccca aagaagacac aactaccttg 1740
gaagattcac ttgtcaaagg accagaggac atcccagcag ccactaaaaa gccaccaggt 1800
ttcaggcccg aagcagagac acaccctctg taccttggcc acgacgtaga aaccaacctg 1860
tga 1863

<210> SEQ ID NO 9
<211> LENGTH: 1854
<212> TYPE: DNA
<213> ORGANISM: Mus musculus

<400> SEQUENCE: 9
atggagggag ccgaagccgg ggcacgagcc acctttggcc cttgggatta cggggtgttt 60
gccaccatgt tgctcgtcag taccggaatc ggtttgtggg tgggactcgc tcggggcggt 120
cagaggtccg cagatgattt ctttacagga ggaaggcagc tcgccgcagt gccagtaggg 180
ttgtctctcg ctgctagttt tatgtctgca gtccaagtcc tgggtgtacc agccgaagct 240
gcccgatacg gccttaaatt cctttggatg tgcgtagggc aactcttgaa tagtttgctt 300
actgccctgc ttttttgcc aatcttttac agacttggtc tgacaagtac ctaccaatat 360
ttggagctga gattttctcg ggcagtaagg ctttgcggga ctcttcagta tttggtggcc 420
actatgctct acacaggcat cgtcatctat gctcccgcat tgattcttaa tcaggtgacc 480
ggccttgaca tctgggccag ccttctctcc actgggatca tttgcacact ttatactaca 540
gttggcggta tgaaagctgt ggtgtggact gacgtttttc aagtggtagt tatgcttgtg 600
ggtttctggg taatacttgc tagggggta atgctgatgg gagggccatg gaacgtcctg 660
agcctggccc aaaaccactc aagaattaac ctgatggatt ttgatcccga cccaaggagc 720
cgatatacat tttggacctt cgtggtcggc ggttccttgg tatggctttc aatgtatggg 780
gtaaaccaag ctcaagtcca acgctatgtc gcttgccata ccgagaggaa agctaaactt 840
gcacttcttg tgaaccaact tggtctcttt ctcatagtgg caagcgctgc atgttgcgga 900
attgttatgt ttgtttatta caaagattgt gaccccttgc ttactggccg gatagccgcc 960
cccgatcagt atatgcccct tctcgtgctt gatatattcg aggacctccc cggtgttccc 1020
ggactcttcc tcgcatgtgc ttactcaggc accctttcta ccgcctcaac ctctatcaat 1080
gcaatggctg cagtcaccgt ggaggacctc attaaacctc gaatgccatc cctggcccca 1140

-continued aggaaactcg tgtttatatc caagggcttg tccttcatat atggaagcac ctgtctgaca 1200
gtagcagcat tgtcttcttt gttgggcggc ggggtactgc aggggtcttt tacagtgatg 1260
ggtgtaatct caggccccct tttgggggct tttactctgg ggatgctctt gcccgcttgc 1320
aacacacctg gcgtactctc aggactgact gccgggttgg ctgtttcact ttgggttgca 1380
gtaggcgcca cactgtatcc acccggcgag caaaccatgg gtgttctccc aacctcagca 1440
gcaggatgca caaacgcctc cgttctgcct tctccccctg gggccgcaaa tacatcaagg 1500
ggaatcccta gtagcggcat ggatagtgga agacccgcct ttgccgacac attctacgca 1560
gttagctacc tgtattacgg cgccttgggg actctcacca ctatgctctg cggggctctg 1620
attagttatt tgaccggtcc caccaaacga tccagcctcg gtcccggact tctgtggtgg 1680
gacttggcaa gacaaactgc ttctgttgct cccaaagaag acacaactac cttggaagat 1740
tcacttgtca aaggaccaga ggacatccca gcagccacta aaaagccacc aggtttcagg 1800
cccgaagcag agacacaccc tctgtacctt ggccacgacg tagaaaccaa cctg 1854

<210> SEQ ID NO 10
<211> LENGTH: 618
<212> TYPE: PRT
<213> ORGANISM: Mus musculus

<400> SEQUENCE: 10

Met Glu Gly Ala Glu Ala Gly Ala Arg Ala Thr Phe Gly Pro Trp Asp
1 5 10 15

Tyr Gly Val Phe Ala Thr Met Leu Leu Val Ser Thr Gly Ile Gly Leu
20 25 30

Trp Val Gly Leu Ala Arg Gly Gly Gln Arg Ser Ala Asp Asp Phe Phe
35 40 45

Thr Gly Gly Arg Gln Leu Ala Ala Val Pro Val Gly Leu Ser Leu Ala
50 55 60

Ala Ser Phe Met Ser Ala Val Gln Val Leu Gly Val Pro Ala Glu Ala
65 70 75 80

Ala Arg Tyr Gly Leu Lys Phe Leu Trp Met Cys Val Gly Gln Leu Leu
85 90 95

Asn Ser Leu Leu Thr Ala Leu Leu Phe Leu Pro Ile Phe Tyr Arg Leu
100 105 110

Gly Leu Thr Ser Thr Tyr Gln Tyr Leu Glu Leu Arg Phe Ser Arg Ala
115 120 125

Val Arg Leu Cys Gly Thr Leu Gln Tyr Leu Val Ala Thr Met Leu Tyr
130 135 140

Thr Gly Ile Val Ile Tyr Ala Pro Ala Leu Ile Leu Asn Gln Val Thr
145 150 155 160

Gly Leu Asp Ile Trp Ala Ser Leu Leu Ser Thr Gly Ile Ile Cys Thr
165 170 175

Leu Tyr Thr Thr Val Gly Gly Met Lys Ala Val Val Trp Thr Asp Val
180 185 190

Phe Gln Val Val Val Met Leu Val Gly Phe Trp Val Ile Leu Ala Arg
195 200 205

Gly Val Met Leu Met Gly Gly Pro Trp Asn Val Leu Ser Leu Ala Gln
210 215 220

Asn His Ser Arg Ile Asn Leu Met Asp Phe Asp Pro Asp Pro Arg Ser
225 230 235 240

Arg Tyr Thr Phe Trp Thr Phe Val Val Gly Gly Ser Leu Val Trp Leu
245 250 255

```
Ser Met Tyr Gly Val Asn Gln Ala Gln Val Gln Arg Tyr Val Ala Cys
            260                 265                 270

His Thr Glu Arg Lys Ala Lys Leu Ala Leu Leu Val Asn Gln Leu Gly
        275                 280                 285

Leu Phe Leu Ile Val Ala Ser Ala Ala Cys Cys Gly Ile Val Met Phe
    290                 295                 300

Val Tyr Tyr Lys Asp Cys Asp Pro Leu Leu Thr Gly Arg Ile Ala Ala
305                 310                 315                 320

Pro Asp Gln Tyr Met Pro Leu Leu Val Leu Asp Ile Phe Glu Asp Leu
                325                 330                 335

Pro Gly Val Pro Gly Leu Phe Leu Ala Cys Ala Tyr Ser Gly Thr Leu
            340                 345                 350

Ser Thr Ala Ser Thr Ser Ile Asn Ala Met Ala Ala Val Thr Val Glu
        355                 360                 365

Asp Leu Ile Lys Pro Arg Met Pro Ser Leu Ala Pro Arg Lys Leu Val
    370                 375                 380

Phe Ile Ser Lys Gly Leu Ser Phe Ile Tyr Gly Ser Thr Cys Leu Thr
385                 390                 395                 400

Val Ala Ala Leu Ser Ser Leu Leu Gly Gly Gly Val Leu Gln Gly Ser
                405                 410                 415

Phe Thr Val Met Gly Val Ile Ser Gly Pro Leu Leu Gly Ala Phe Thr
            420                 425                 430

Leu Gly Met Leu Leu Pro Ala Cys Asn Thr Pro Gly Val Leu Ser Gly
        435                 440                 445

Leu Thr Ala Gly Leu Ala Val Ser Leu Trp Val Ala Val Gly Ala Thr
    450                 455                 460

Leu Tyr Pro Pro Gly Glu Gln Thr Met Gly Val Leu Pro Thr Ser Ala
465                 470                 475                 480

Ala Gly Cys Thr Asn Ala Ser Val Leu Pro Ser Pro Pro Gly Ala Ala
                485                 490                 495

Asn Thr Ser Arg Gly Ile Pro Ser Ser Gly Met Asp Ser Gly Arg Pro
            500                 505                 510

Ala Phe Ala Asp Thr Phe Tyr Ala Val Ser Tyr Leu Tyr Tyr Gly Ala
        515                 520                 525

Leu Gly Thr Leu Thr Thr Met Leu Cys Gly Ala Leu Ile Ser Tyr Leu
    530                 535                 540

Thr Gly Pro Thr Lys Arg Ser Ser Leu Gly Pro Gly Leu Leu Trp Trp
545                 550                 555                 560

Asp Leu Ala Arg Gln Thr Ala Ser Val Ala Pro Lys Glu Asp Thr Thr
                565                 570                 575

Thr Leu Glu Asp Ser Leu Val Lys Gly Pro Glu Asp Ile Pro Ala Ala
            580                 585                 590

Thr Lys Lys Pro Pro Gly Phe Arg Pro Glu Ala Glu Thr His Pro Leu
        595                 600                 605

Tyr Leu Gly His Asp Val Glu Thr Asn Leu
    610                 615
```

<210> SEQ ID NO 11
<211> LENGTH: 2897
<212> TYPE: DNA
<213> ORGANISM: Artificial sequence
<220> FEATURE:
<223> OTHER INFORMATION: expression cassette

<400> SEQUENCE: 11

-continued

```
ggccagatat acgcgttgac attgattatt gactagttat taatagtaat caattacggg     60
gtcattagtt catagcccat atatggagtt ccgcgttaca taacttacgg taaatggccc    120
gcctggctga ccgcccaacg acccccgccc attgacgtca ataatgacgt atgttcccat    180
agtaacgcca atagggactt tccattgacg tcaatgggtg gagtatttac ggtaaactgc    240
ccacttggca gtacatcaag tgtatcatat gccaagtacg ccccctattg acgtcaatga    300
cggtaaatgg cccgcctggc attatgccca gtacatgacc ttatgggact ttcctacttg    360
gcagtacatc tacgtattag tcatcgctat taccatggtg atgcggtttt ggcagtacat    420
caatgggcgt ggatagcggt ttgactcacg gggatttcca agtctccacc ccattgacgt    480
caatgggagt ttgttttggc accaaaatca acgggacttt ccaaaatgtc gtaacaactc    540
cgccccattg acgcaaatgg gcggtaggcg tgtacggtgg gaggtctata taagcagagc    600
tcgtttagtg aaccgtcaga tcgcctggag acgccatcca cgctgttttg acctccatag    660
aagacaccgg gaccgatcca gcctccggac tctagaggat cgaacccttg ccaccatgga    720
gggagccgaa gccggggcac gagccacctt tggcccttgg gattacgggg tgtttgccac    780
catgttgctc gtcagtaccg gaatcggttt gtgggtggga ctcgctcggg gcggtcagag    840
gtccgcagat gatttcttta caggaggaag gcagctcgcc gcagtgccag tagggttgtc    900
tctcgctgct agttttatgt ctgcagtcca agtcctgggt gtaccagccg aagctgcccg    960
atacggcctt aaattccttt ggatgtgcgt agggcaactc ttgaatagtt tgcttactgc   1020
cctgcttttt ttgccaatct tttacagact tggtctgaca agtacctacc aatatttgga   1080
gctgagattt tctcgggcag taaggctttg cgggactctt cagtatttgg tggccactat   1140
gctctacaca ggcatcgtca tctatgctcc cgcattgatt cttaatcagg tgaccggcct   1200
tgacatctgg gccagccttc tctccactgg gatcatttgc acactttata ctacagttgg   1260
cggtatgaaa gctgtggtgt ggactgacgt ttttcaagtg gtagttatgc ttgtgggttt   1320
ctgggtaata cttgctaggg ggtaatgct gatgggaggg ccatggaacg tcctgagcct   1380
ggcccaaaac cactcaagaa ttaacctgat ggattttgat cccgacccaa ggagccgata   1440
tacattttgg accttcgtgg tcggcggttc cttggtatgg ctttcaatgt atggggtaaa   1500
ccaagctcaa gtccaacgct atgtcgcttg ccataccgag aggaaagcta aacttgcact   1560
tcttgtgaac caacttggtc tctttctcat agtggcaagc gctgcatgtt gcggaattgt   1620
tatgtttgtt tattacaaag attgtgaccc cttgcttact ggccggatag ccgcccccga   1680
tcagtatatg ccccttctcg tgcttgatat attcgaggac ctccccggtg ttcccggact   1740
cttcctcgca tgtgcttact caggcaccct ttctaccgcc tcaacctcta tcaatgcaat   1800
ggctgcagtc accgtggagg acctcattaa acctcgaatg ccatccctgg ccccaaggaa   1860
actcgtgttt atatccaagg gcttgtcctt catatatgga agcacctgtc tgacagtagc   1920
agcattgtct tctttgttgg gcggcggggt actgcagggg tcttttacag tgatgggtgt   1980
aatctcaggc cccctttttgg gggcttttac tctggggatg ctcttgcccg cttgcaacac   2040
acctggcgta ctctcaggac tgactgccgg gttggctgtt tcactttggg ttgcagtagg   2100
cgccacactg tatccacccg gcgagcaaac catgggtgtt ctcccaacct cagcagcagg   2160
atgcacaaac gcctccgttc tgccttctcc ccctggggcc gcaaatacat caaggggaat   2220
ccctagtagc ggcatggata gtggaagacc cgcctttgcc gacacattct acgcagttag   2280
ctacctgtat tacggcgcct tggggactct caccactatg ctctgcgggg ctctgattag   2340
```

```
ttatttgacc ggtcccacca aacgatccag cctcggtccc ggacttctgt ggtgggactt   2400

ggcaagacaa actgcttctg ttgctcccaa agaagacaca actaccttgg aagattcact   2460

tgtcaaagga ccagaggaca tcccagcagc cactaaaaag ccaccaggtt tcaggcccga   2520

agcagagaca caccctctgt accttggcca cgacgtagaa accaacctgt gaaagggttc   2580

gatccctacc ggttagtaat gagtttaaac gggggaggct aactgaaaca cggaaggaga   2640

caataccgga aggaacccgc gctatgacgg caataaaaag acagaataaa acgcacgggt   2700

gttgggtcgt ttgttcataa acgcggggtt cggtcccagg gctggcactc tgtcgatacc   2760

ccaccgagac cccattgggg ccaatacgcc cgcgtttctt ccttttcccc accccacccc   2820

ccaagttcgg gtgaaggccc agggctcgca gccaacgtcg ggcggcaggc ccctgccata   2880

gcagatctgc gcagctg                                                   2897


<210> SEQ ID NO 12
<211> LENGTH: 643
<212> TYPE: PRT
<213> ORGANISM: Homo sapiens

<400> SEQUENCE: 12

Met Glu Ala Val Glu Thr Gly Glu Arg Pro Thr Phe Gly Ala Trp Asp
1               5                   10                  15

Tyr Gly Val Phe Ala Leu Met Leu Leu Val Ser Thr Gly Ile Gly Leu
            20                  25                  30

Trp Val Gly Leu Ala Arg Gly Gly Gln Arg Ser Ala Glu Asp Phe Phe
        35                  40                  45

Thr Gly Gly Arg Arg Leu Ala Ala Leu Pro Val Gly Leu Ser Leu Ser
    50                  55                  60

Ala Ser Phe Met Ser Ala Val Gln Val Leu Gly Val Pro Ser Glu Ala
65                  70                  75                  80

Tyr Arg Tyr Gly Leu Lys Phe Leu Trp Met Cys Leu Gly Gln Leu Leu
                85                  90                  95

Asn Ser Val Leu Thr Ala Leu Leu Phe Met Pro Val Phe Tyr Arg Leu
            100                 105                 110

Gly Leu Thr Ser Thr Tyr Glu Tyr Leu Glu Met Arg Phe Ser Arg Ala
        115                 120                 125

Val Arg Leu Cys Gly Thr Leu Gln Tyr Ile Val Ala Thr Met Leu Tyr
    130                 135                 140

Thr Gly Ile Val Ile Tyr Ala Pro Ala Leu Ile Leu Asn Gln Val Thr
145                 150                 155                 160

Gly Leu Asp Ile Trp Ala Ser Leu Leu Ser Thr Gly Ile Ile Cys Thr
                165                 170                 175

Phe Tyr Thr Ala Val Gly Gly Met Lys Ala Val Val Trp Thr Asp Val
            180                 185                 190

Phe Gln Val Val Val Met Leu Ser Gly Phe Trp Val Val Leu Ala Arg
        195                 200                 205

Gly Val Met Leu Val Gly Gly Pro Arg Gln Val Leu Thr Leu Ala Gln
    210                 215                 220

Asn His Ser Arg Ile Asn Leu Met Asp Phe Asn Pro Asp Pro Arg Ser
225                 230                 235                 240

Arg Tyr Thr Phe Trp Thr Phe Val Val Gly Gly Thr Leu Val Trp Leu
                245                 250                 255

Ser Met Tyr Gly Val Asn Gln Ala Gln Val Gln Arg Tyr Val Ala Cys
            260                 265                 270
```

```
Arg Thr Glu Lys Gln Ala Lys Leu Ala Leu Leu Ile Asn Gln Val Gly
        275                 280                 285

Leu Phe Leu Ile Val Ser Ser Ala Ala Cys Cys Gly Ile Val Met Phe
    290                 295                 300

Val Phe Tyr Thr Asp Cys Asp Pro Leu Leu Leu Gly Arg Ile Ser Ala
305                 310                 315                 320

Pro Asp Gln Tyr Met Pro Leu Leu Val Leu Asp Ile Phe Glu Asp Leu
                325                 330                 335

Pro Gly Val Pro Gly Leu Phe Leu Ala Cys Ala Tyr Ser Gly Thr Leu
            340                 345                 350

Ser Thr Ala Ser Thr Ser Ile Asn Ala Met Ala Ala Val Thr Val Glu
        355                 360                 365

Asp Leu Ile Lys Pro Arg Leu Arg Ser Leu Ala Pro Arg Lys Leu Val
    370                 375                 380

Ile Ile Ser Lys Gly Leu Ser Leu Ile Tyr Gly Ser Ala Cys Leu Thr
385                 390                 395                 400

Val Ala Ala Leu Ser Ser Leu Leu Gly Gly Gly Val Leu Gln Gly Ser
                405                 410                 415

Phe Thr Val Met Gly Val Ile Ser Gly Pro Leu Leu Gly Ala Phe Ile
            420                 425                 430

Leu Gly Met Phe Leu Pro Ala Cys Asn Thr Pro Gly Val Leu Ala Gly
        435                 440                 445

Leu Gly Ala Gly Leu Ala Leu Ser Leu Trp Val Ala Leu Gly Ala Thr
    450                 455                 460

Leu Tyr Pro Pro Ser Glu Gln Thr Met Arg Val Leu Pro Ser Ser Ala
465                 470                 475                 480

Ala Arg Cys Val Ala Leu Ser Val Asn Ala Ser Gly Leu Leu Asp Pro
                485                 490                 495

Ala Leu Leu Pro Ala Asn Asp Ser Ser Arg Ala Pro Ser Ser Gly Met
            500                 505                 510

Asp Ala Ser Arg Pro Ala Leu Ala Asp Ser Phe Tyr Ala Ile Ser Tyr
        515                 520                 525

Leu Tyr Tyr Gly Ala Leu Gly Thr Leu Thr Thr Val Leu Cys Gly Ala
    530                 535                 540

Leu Ile Ser Cys Leu Thr Gly Pro Thr Lys Arg Ser Thr Leu Ala Pro
545                 550                 555                 560

Gly Leu Leu Trp Trp Asp Leu Ala Arg Gln Thr Ala Ser Val Ala Pro
                565                 570                 575

Lys Glu Glu Val Ala Ile Leu Asp Asp Asn Leu Val Lys Gly Pro Glu
            580                 585                 590

Glu Leu Pro Thr Gly Asn Lys Lys Pro Pro Gly Phe Leu Pro Thr Asn
        595                 600                 605

Glu Asp Arg Leu Phe Phe Leu Gly Gln Lys Glu Leu Glu Gly Ala Gly
    610                 615                 620

Ser Trp Thr Pro Cys Val Gly His Asp Gly Gly Arg Asp Gln Gln Glu
625                 630                 635                 640

Thr Asn Leu
```

<210> SEQ ID NO 13
<211> LENGTH: 9
<212> TYPE: PRT
<213> ORGANISM: Homo sapiens

<400> SEQUENCE: 13

```
Glu Ala Asp Pro Thr Gly His Ser Tyr
1               5


<210> SEQ ID NO 14
<211> LENGTH: 15
<212> TYPE: PRT
<213> ORGANISM: Homo sapiens

<400> SEQUENCE: 14

Thr Ser Cys Ile Leu Glu Ser Leu Phe Arg Ala Val Ile Thr Lys
1               5                   10                  15


<210> SEQ ID NO 15
<211> LENGTH: 12
<212> TYPE: PRT
<213> ORGANISM: Homo sapiens

<400> SEQUENCE: 15

Glu Tyr Val Ile Lys Val Ser Ala Arg Val Arg Phe
1               5                   10


<210> SEQ ID NO 16
<211> LENGTH: 9
<212> TYPE: PRT
<213> ORGANISM: Homo sapiens

<400> SEQUENCE: 16

Glu Val Asp Pro Ile Gly His Leu Tyr
1               5


<210> SEQ ID NO 17
<211> LENGTH: 9
<212> TYPE: PRT
<213> ORGANISM: Homo sapiens

<400> SEQUENCE: 17

Phe Leu Trp Gly Pro Arg Ala Leu Val
1               5


<210> SEQ ID NO 18
<211> LENGTH: 12
<212> TYPE: PRT
<213> ORGANISM: Homo sapiens

<400> SEQUENCE: 18

Val Ile Phe Ser Lys Ala Ser Ser Ser Leu Gln Leu
1               5                   10


<210> SEQ ID NO 19
<211> LENGTH: 9
<212> TYPE: PRT
<213> ORGANISM: Homo sapiens

<400> SEQUENCE: 19

Ser Leu Leu Met Trp Ile Thr Gln Cys
1               5


<210> SEQ ID NO 20
<211> LENGTH: 9
<212> TYPE: PRT
<213> ORGANISM: Homo sapiens

<400> SEQUENCE: 20

Met Pro Phe Ala Thr Pro Met Glu Ala
1               5
```

<210> SEQ ID NO 21
<211> LENGTH: 12
<212> TYPE: PRT
<213> ORGANISM: Homo sapiens

<400> SEQUENCE: 21

Glu Phe Tyr Leu Ala Met Pro Phe Ala Thr Pro Met
1 5 10

<210> SEQ ID NO 22
<211> LENGTH: 10
<212> TYPE: PRT
<213> ORGANISM: Homo sapiens

<400> SEQUENCE: 22

Glu Ala Ala Gly Ile Gly Ile Leu Thr Val
1 5 10

<210> SEQ ID NO 23
<211> LENGTH: 10
<212> TYPE: PRT
<213> ORGANISM: Homo sapiens

<400> SEQUENCE: 23

Glu Ala Ala Gly Ile Gly Ile Leu Thr Val
1 5 10

<210> SEQ ID NO 24
<211> LENGTH: 9
<212> TYPE: PRT
<213> ORGANISM: Homo sapiens

<400> SEQUENCE: 24

Ile Leu Thr Val Ile Leu Gly Val Leu
1 5

<210> SEQ ID NO 25
<211> LENGTH: 14
<212> TYPE: PRT
<213> ORGANISM: Homo sapiens

<400> SEQUENCE: 25

Ala Ala Gly Ile Gly Ile Leu Thr Val Ile Leu Gly Val Leu
1 5 10

<210> SEQ ID NO 26
<211> LENGTH: 9
<212> TYPE: PRT
<213> ORGANISM: Homo sapiens

<400> SEQUENCE: 26

Met Leu Leu Ala Val Leu Tyr Cys Leu
1 5

<210> SEQ ID NO 27
<211> LENGTH: 11
<212> TYPE: PRT
<213> ORGANISM: Homo sapiens

<400> SEQUENCE: 27

Ser Ser Asp Tyr Val Ile Pro Ile Gly Thr Tyr
1 5 10

<210> SEQ ID NO 28
<211> LENGTH: 13
<212> TYPE: PRT
<213> ORGANISM: Homo sapiens

<400> SEQUENCE: 28

Ser Tyr Leu Gln Asp Ser Asp Pro Asp Ser Phe Gln Asp
1               5                   10

<210> SEQ ID NO 29
<211> LENGTH: 9
<212> TYPE: PRT
<213> ORGANISM: Homo sapiens

<400> SEQUENCE: 29

Lys Thr Trp Gly Gln Tyr Trp Gln Val
1               5

<210> SEQ ID NO 30
<211> LENGTH: 9
<212> TYPE: PRT
<213> ORGANISM: Homo sapiens

<400> SEQUENCE: 30

Leu Ile Tyr Arg Arg Arg Leu Met Lys
1               5

<210> SEQ ID NO 31
<211> LENGTH: 15
<212> TYPE: PRT
<213> ORGANISM: Homo sapiens

<400> SEQUENCE: 31

Gly Arg Ala Met Leu Gly Thr His Thr Met Glu Val Thr Val Tyr
1               5                   10                  15

<210> SEQ ID NO 32
<211> LENGTH: 10
<212> TYPE: PRT
<213> ORGANISM: Homo sapiens

<400> SEQUENCE: 32

Ala Cys Asp Pro His Ser Gly His Phe Val
1               5                   10

<210> SEQ ID NO 33
<211> LENGTH: 9
<212> TYPE: PRT
<213> ORGANISM: Homo sapiens

<400> SEQUENCE: 33

Ser Tyr Leu Asp Ser Gly Ile His Phe
1               5

<210> SEQ ID NO 34
<211> LENGTH: 10
<212> TYPE: PRT
<213> ORGANISM: Homo sapiens

<400> SEQUENCE: 34

Ile Leu Asp Thr Ala Gly Arg Glu Glu Tyr
1               5                   10

COMPOSITIONS COMPRISING HERPES SIMPLEX VIRUS-I FOR USE IN METHODS OF TREATING AND PREVENTING CANCER

CROSS REFERENCE TO RELATED APPLICATIONS

This application is the U.S. National Stage of International Application PCT/US2019/044749, filed Aug. 1, 2019, which designates the U.S. and was published by the International Bureau in English on Feb. 6, 2020, and which claims the benefit of U.S. Provisional Application Nos. 62/713,183 and 62/713,269, both filed Aug. 1, 2018; all of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070114-0016SEQLST.TXT, created on Jul. 31, 2019, and having a size of 609 kilobytes, and is filed concurrently with the specification. The sequence listing contained in this ASCII formatted document is part of the specification and is herein incorporated by reference in its entirety.

FIELD OF THE INVENTION

The present invention relates to the field of oncology, particularly to compositions and methods for treating or preventing cancer.

BACKGROUND OF THE INVENTION

Viruses that preferentially lyse cancer cells are described as being "oncolytic" or tumor-lysing. Oncolytic virotherapy works by directly killing tumor cells and stimulating an immune response. Viruses used for this method fall into three major categories: wild type animal viruses that do not normally infect human cells but are cytotoxic to human cancer cells, attenuated mutants of human viruses in which genes important for virus replication that are not needed for growth in cancer cells have been mutated or deleted, and viruses that have been attenuated by serial passage in culture like most live virus vaccines. The idea to use viruses as cancer therapy originated in the early 1900's when it was observed that occasionally viral infections would result in remission in some cancer patients (Dock (1904) *Am. J. Med. Sci.* 127(4):563). Many different live viruses have been tested as potential therapy for cancer in the last century, beginning as early as 1910, when a live-attenuated Rabies vaccine was observed to result in regression of cervical cancer in a patient (Sinkovics & Horvath (2008) *Arch. Immunol. Ther. Exp.* 56 Suppl 1:3s-59s). Other viruses known to infect humans including Epstein-Barre, adenovirus, and hepatitis virus were investigated with variable results in efficacy in the mid-1900's (Hoster et al. (1949) *Cancer Res.* 9:473-480; Taylor (1953) *Br. Med. J.* 1:589-593; Huebner et al. (1956) *Cancer* 9:1211-1218). Studies on the use of viruses in the treatment of carcinoma of the cervix (Hoster et al. (1949) *Cancer Res.* 9:473-480; Taylor (1953) *Br. Med. J.* 1:589-593; Huebner et al. (1956) *Cancer* 9:1211-1218). Safety concerns regarding using live viruses in cancer patients markedly limited the field of oncolytic virotherapy until the development of molecular tools enabling genetic engineering in the 1990's (Kelly & Russell (2007) *Mol. Ther.* 15:651-659). The field has now expanded to include many different viruses and has become increasingly sophisticated as molecular tools to create purposeful viral genetic mutations that enhance cancer-killing abilities and safety have become more widely available.

Some viruses have a natural lytic phase in their life cycle and have a natural affinity for rapidly dividing cells (e.g. herpes simplex virus type-1 and parvoviruses). The affinity for rapidly dividing cells can be enhanced through careful, selective genetic engineering; further, cellular tropism can be similarly altered to retarget viral infections to limit them to transformed cells, thereby sparing normal tissues. Non-essential genes associated with virulence can also be deleted for enhanced safety while maintaining the ability to replicate.

In addition to direct lysis, oncolytic viruses may also cause cell death indirectly through immunogenic cell death (ICD) where ER stress results in expression of danger associated molecular patterns (DAMPs) as has been shown with adenoviruses (Diaconu et al. (2012) *Cancer Res.* 72:2327-2338), coxsackie B3 virus (Miyamoto et al. (2012) *Cancer Res.* 72:2609-2621), and measles (Donnelly et al. (2013) *Gene Ther.* 20:7-15). Adaptive immune responses have been demonstrated for reoviruses (Prestwich et al. (2008) *Clin. Cancer Res.* 14:7358-7366), herpes simplex virus (HSV) (Toda et al. (1998) *J. Immunol.* 160:4457-4464; Toda et al. (1999) *Hum. Gene Ther.* 10:385-393), and vaccinia (Thorne & Contag (2008) *Gene Ther.* 15:753-758). Selective destruction of tumor-supporting components of the tumor microenvironment including tumor-associated vasculature has been shown for vesicular stomatitis virus (VSV), vaccinia virus, and herpes simplex virus type 1 (HSV-1), which can all infect endothelial cells (Breitbach et al. (2013) *Cancer Res.* 73:1265-1275; Breitbach et al. (2011) *Mol. Ther.* 19:886-894; Benencia et al. (2005) *Hum. Gene Ther.* 16:765-778). Some viruses may inhibit tumor growth due to direct disruption of tumor-associated vasculature through infection of endothelial cells in this mechanism. In some instances, infection of endothelial cells by certain viruses is dependent on expression of high levels of VEGF and FGF which are often present in the tumor microenvironments.

The ability of replication competent viruses to act as a self-sustaining intralesional therapeutic is an advantage. Systemic administration of cancer therapeutics can result in significant toxicity and local administration of many therapeutics may be quickly cleared. While intralesional oncolytic virotherapy is practical for easy-to-access tumors like melanoma or squamous cell carcinoma, administration for internal or widely disseminated cancers has been less practical, largely due to the fact that safe and efficacious systemic viral delivery presents inherent challenges. One is that intravenous delivery poses the risk of systemic infection and complications. Retargeting the virus via genetic manipulation could be one solution; however, as mentioned, efficacy would be expected to be limited in a strict target-dependent strategy due to heterogeneity of expression of targets within and between patients. Further, high doses may be necessary in order to achieve an efficacious systemic dose since a percentage of injected virus is likely to be sequestered in the liver after intravenous injection and since patients may already have, or may develop during therapy, circulating neutralizing antibodies in the serum which may result in rapid elimination of virus before it can reach the tumor (Fountzilas et al. (2017) *Oncotarget* 8:102617-102639; Alemany et al. (2000) *J. Gen. Virol.* 81:2605-2609; Dubin et al.

(1992) *Curr. Top. Microbiol. Immunol.* 179:111-120). In general, it is thought that the majority of virus injected intravenously is cleared within about 2 minutes (Willmon et al. (2009) *Mol. Ther.* 17:1667-1676). It is estimated that 50-80% of humans possess neutralizing antibodies to HSV (Fountzilas et al. (2017) *Oncotarget* 8:102617-102639; Fields et al. (1996) "*Fields Virology,*" 3rd ed, Lippincott-Raven Publishers, Philadelphia). Efforts to reduce elimination of oncolytic viruses after systemic delivery have included pretreatment with cyclophosphamide/cobra venom to exhaust complement and IgM in mouse models (Sanchala et al. (2017) *Front. Pharmacol.* 8:270; Ikeda et al. (1999) *Nat. Med.* 5:881-887; Ikeda et al. (2000) *J. Virol.* 74:4765-4775; Wakimoto et al. (2002) *Mol. Ther.* 5:275-282). However, cancer patients already have suppressed systemic immunity. Further suppressing the immune system could result in severe off-target distribution leading to disseminated infection and a marked increase in adverse events/toxicity. Development of improved systemic delivery strategies are underway. One potential method that has been explored is copper chelation intended to increase stability of oncolytic HSV (oHSV) in the serum (Yoo et al. (2012) *Clin. Cancer Res.* 18:4931-4941). Another general strategy is retargeting of the virus which can be accomplished in a number of ways including: 1.) altering the viral envelope to contain single chain antibodies (scFv) or peptide ligands specific for a desired receptor (Gatta et al. (2015) *PLoS Pathog.* 11:e1004907; Leoni et al. (2015) *Oncotarget* 6:34774-34787; Zhou & Roizman (2006) *PNAS* 103:5508-5513; Uchida et al. (2013) *Mol. Ther.* 21:561-569; Shibata et al. (2016) *Gene Ther.* 23:479-488); 2.) adapters/soluble receptors that recognize tumor and virus to facilitate binding (Kwon et al. (2006) *J. Virol.* 80:138-148; Nakano et al. (2005) *Mol. Ther.* 11:617-626; Baek et al. (2011) *Mol Ther.* 19:507-514); 3.) inserting glycoproteins with a receptor from other viruses (Sanchala et al. (2017) *Front. Pharmacol.* 8:270; Lander et al. (2001) *Nature* 409:860-921; Anderson et al. (2000) *J. Virol.* 74:2481-2487) and 4.) use of carrier cells (Willmon et al. (2009) *Mol. Ther.* 17:1667-1676).

Currently, intratumoral delivery is considered to be the most viable delivery strategy, and the most reliable method to deliver oHSV-1 (Sanchala et al. (2017) *Front. Pharmacol.* 8:270; Shintani et al. (2011) *Virol. J.* 8:446). The ability of a live attenuated virus to create a replication niche in the tumor and microenvironment and to even amplify its presence and effect through replication and lysis prevents the need for frequent injections. Some oncolytic viruses even develop a syncytial phenotype which can facilitate rapid spread throughout the tumor and could be helpful when entry receptor expression is low in some instances. A major challenge to utilizing HSV-1 in oncolytic virotherapy is infection efficiency of tumor cells (Sanchala et al. (2017) *Front. Pharmacol.* 8:270; Shintani et al. (2011) *Virol. J.* 8:446). Strategies to improve viral spread after intratumoral injection are necessary. Such strategies have so far included injecting multiple tumors or injecting a single tumor in multiple sites; it is advised that doses be given as 3-5 injections or, when given as a single injection, that the volume compose 10-100% of the tumor volume (Sanchala et al. (2017) *Front. Pharmacol.* 8:270; U.S. Pat. App. Pub. No. 2002/0061298 A1). Improvement in intratumoral delivery has been investigated through the use of ultrasound for cell membrane permeabilization and sonoporation and co-injection of collagenase for improved intratumoral distribution as examples (Shintani et al. (2011) *Virol. J.* 8:446; McKee et al. (2006) *Cancer Res.* 66:2509-2513). Chemically sensitizing tumors using small molecules such as histone deacetylase inhibitors to limit IFN activity to improve viral spread has also been explored (Otsuki et al. (2008) *Mol. Ther.* 16:1546-1555).

There are advantages and disadvantages to all candidate oncolytic viruses. In many regards, treating tumors with virus is a form of targeted therapy since the lytic effect often depends on the ability of the virus to enter through specific receptors, replicate, and lyse cells. Viral entry receptor expression by tumor cells can vary and may represent a significant challenge. As tumor cells evolve in the tumor microenvironment and new, increasingly malignant subclones emerge, cells that would normally express an entry receptor, may lose expression or expression may become extremely heterogeneous within the tumor. These challenges can potentially be overcome by using viruses that can enter through multiple receptors, such as HSV-1, which can enter through nectin-1, HVEM, or other receptors. Other strategies include retargeting viral tropism through genetic engineering; however, mutations may reduce replication efficiency; additionally, even after retargeting to another receptor type, the same challenge may exist in that receptor expression may be heterogeneous.

Another challenge is limiting replication to tumor cells, which can present a safety issue. In some instances, intrinsic properties of some tumors naturally allow more efficient replication in comparison to non-transformed, normal cells, such as reovirus's exploitation of cancer cell RAS pathway activation (Alain et al. (2007) *Mol. Ther.* 15:1512-1521; Marcato et al. (2007) *Mol. Ther.* 15:1522-1530; Strong et al. (1998) *EMBO J.* 17:3351-3362). Alternatively, genetic modifications can limit replication by knocking out a factor necessary for replication that is made in excess in rapidly dividing cancer cells. For example, thymidine kinase (TK) is an enzyme known to have increased expression in dividing cells in the G1 phase of the cell cycle and is also necessary for HSV-1 replication since it is critical for DNA synthesis and repair (Gasparri et al. (2009) *Eur. J. Cell. Biol.* 88:779-785). Deletion of thymidine kinase in HSV-1 therefore prevents replication in cells that are not dividing, greatly reducing the virus's ability to replicate in normal tissue (Whitley & Roizman (2001) *Lancet* 357:1513-1518; Field & Wildy (1978) *J. Hyg.* (Load) 81:267-277; Jamieson A T, Gentry & Subak-Sharpe (1974) *J. Gen. Virol.* 24:465-480).

A safe and effective replication competent HSV-1 virus will be important to the development of oncolytic virotherapies involving an oHSV expressing an oncolytic protein and cancer vaccines comprising an HSV engineered to express a tumor antigen. HSV has many non-essential genes and can stably carry large fragments of foreign DNA. This genetic flexibility is ideal for the expression of foreign proteins such as, for example, candidate oncolytic proteins and tumor antigens (Murphy et al. (2000) *J. Virol* 74:7745-7754; Watanabe et al. (2007) *Virology* 357:186-198). Already recombinant HSV-expressing granulocyte monocyte colony stimulating factor (GM-CSF), a potent chemokine functioning in the maturation of macrophages, is being used in combination with other chemotherapeutics for the treatment of squamous cell cancer of the head and neck with promising phase I/II results (Harrington et al. (2010) *Clin. Cancer Res.* 16:4005-4015). FDA approval for this particular HSV virotherapy for melanoma is expected to pave the way for the use of live-attenuated HSV-based vectors in new methods for treating or preventing cancer. See also, U.S. Pat. App. Pub. Nos. 2013/0202639 and 2010/0297085.

BRIEF SUMMARY OF THE INVENTION

The present invention provides compositions and methods for treating of preventing cancer. The compositions comprise recombinant herpes simplex virus (HSV) genomes. The HSV genomes of the present invention are nucleic acid molecules comprising a modified UL53 gene comprising a deletion corresponding to the region of the UL53 gene that encodes amino acids 31-68 of wild-type glycoprotein K (gK) and a modified UL20 gene comprising a deletion corresponding to the region of the UL20 gene that encodes amino acids 4-22 of wild-type UL20 protein and that further comprises a nucleic acid construct encoding an oncolytic protein or tumor antigen of interest. An HSV comprising a recombinant HSV genome of the present invention is capable of replication in a host cell of interest but is incapable of entry into axonal compartments of neurons, and capable of expressing in the host cell of interest the nucleic acid construct encoding the oncolytic protein or tumor antigen of interest. Preferred host cells are tumor cells, particularly human tumor cells.

In a preferred embodiment, the present invention provides a recombinant HSV genome that is referred to herein as VC2-ΔgC-NIS and that comprises the nucleotide sequence set forth in SEQ ID NO: 7. VC2-ΔgC-NIS comprises the modifications to the UL53 and UL20 genes described above and further comprises the replacement of the HSV gene (UL44) encoding glycoprotein C (gC) with an expression cassette comprising a nucleotide sequence encoding the *Mus musculus* sodium iodide symporter (NIS) having the amino acid sequence set forth in SEQ ID NO: 10.

In addition to the recombinant HSV genomes, the present invention provides herpes simplex viruses (HSVs) comprising a recombinant HSV genome of the present invention, and compositions comprising such HSVs including, but not limited to, compositions for treating or preventing cancer and cancer vaccines.

The present invention further provides methods for treating or preventing cancer comprising administering to the patient, particularly a human patient, a therapeutically effective amount vaccine of the present invention of a composition comprising an HSV or cancer vaccine of the present invention.

Additionally provided are methods for producing vaccines, compositions, and viruses comprising a recombinant HSV genome of the present invention.

SEQUENCE LISTING

Figure 1A:
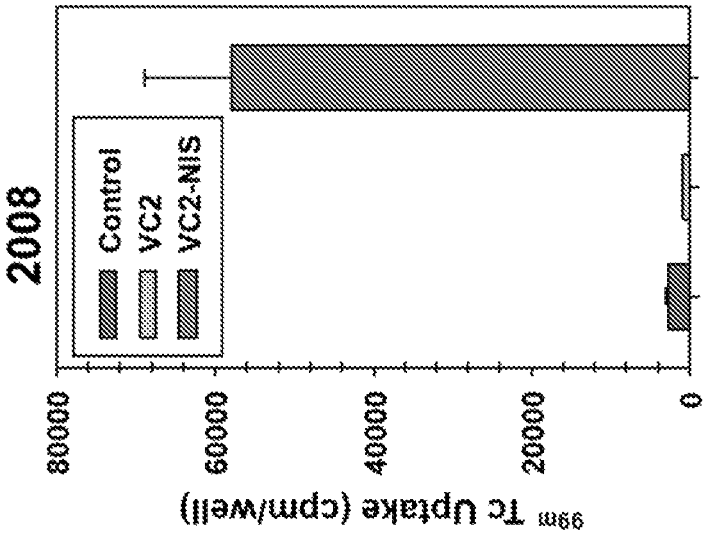
FIGS. 1A-1G. Radioactive uptake in different ovarian cancer cell lines. Analysis of radioactive uptake of $^{99m}$Tc in seven different cell lines (FIGS. 1A-1G). Cell lines 2008, IG-10-pLuc, HM3-pLuc, and SKOV-3-luc (FIGS. 1A, 1C, 1F, and 1G respectively) infected with VC2-NIS showed significantly more uptake compared with the uninfected and those infected with the VC2 virus.
Figure 1B:
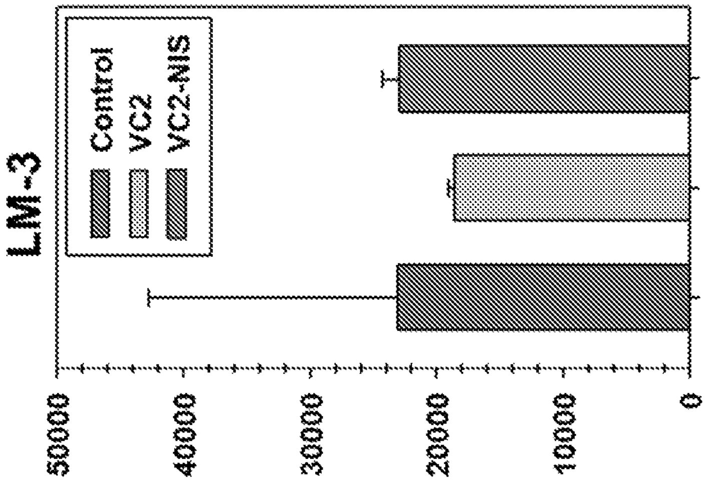
Figure 1C:
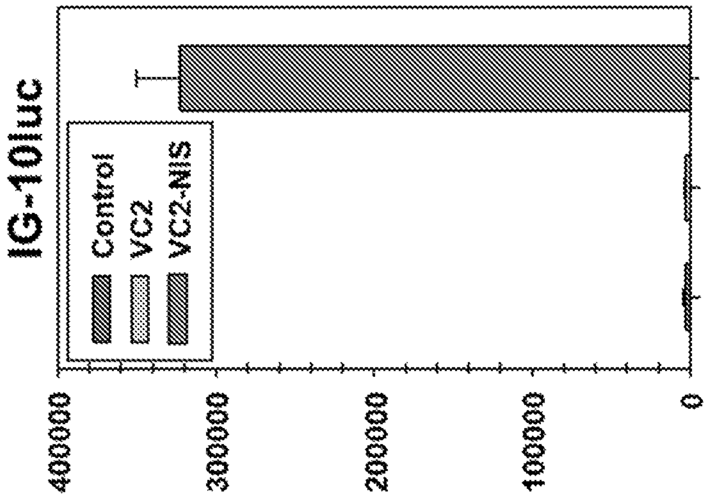
Figure 1D:
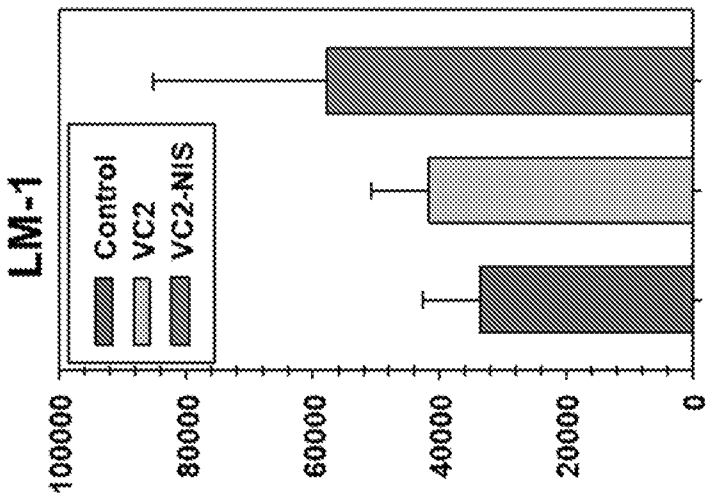
Figure 1F:
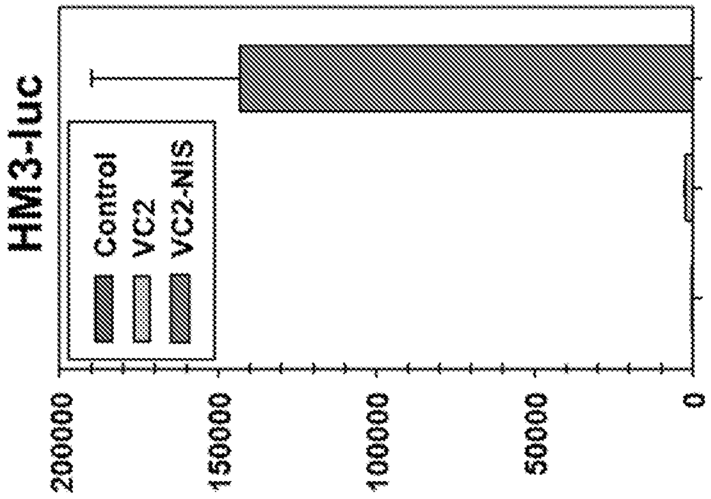
Figure 1E:
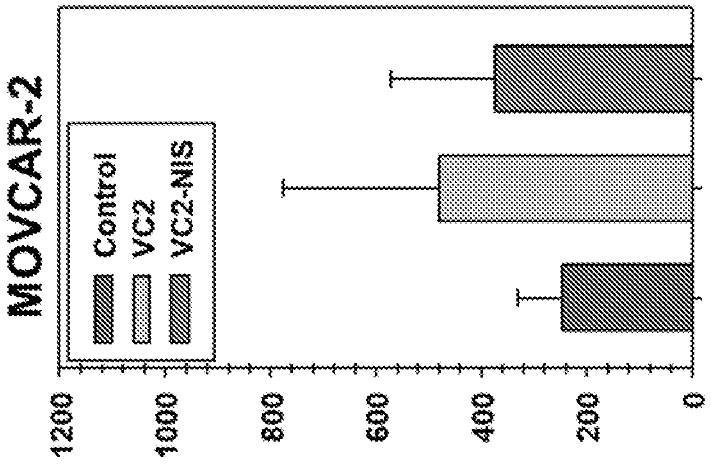
Figure 1G:
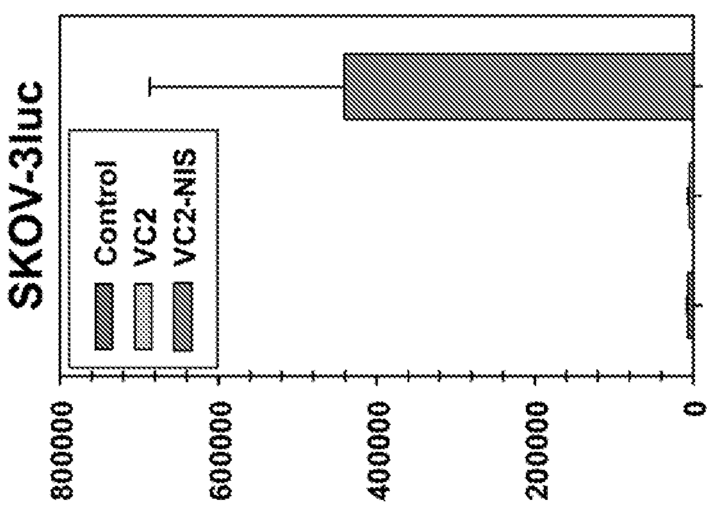
Figure 2A:
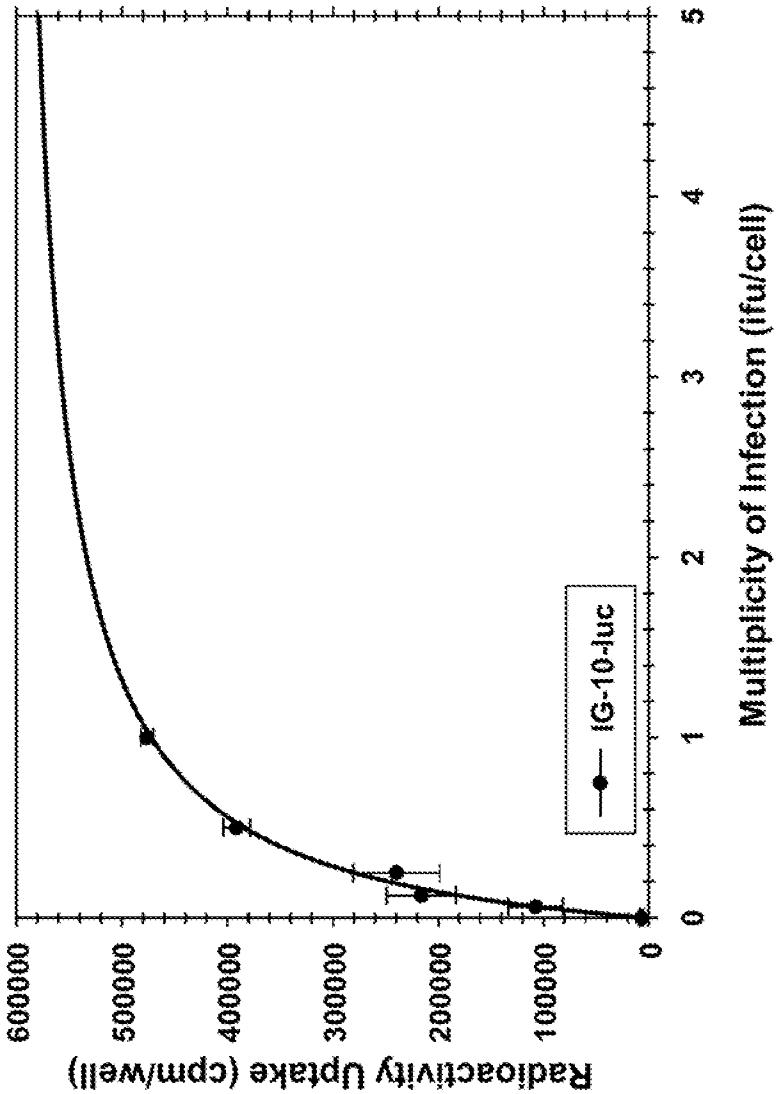
FIGS. 2A-2B. Dose Effect of VC2-NIS Infection. IG-10-pLuc cells were infected with increasing MOI of VC2-NIS and radioactive uptake of $^{99m}$Tc was determined after 24 h. Shown is a standard dose curve (FIG. 2A). A 50% effective dose (ED50) of 0.27 infections units (ifu)/cell was determined using a log curve as shown in FIG. 2B.
Figure 2B:
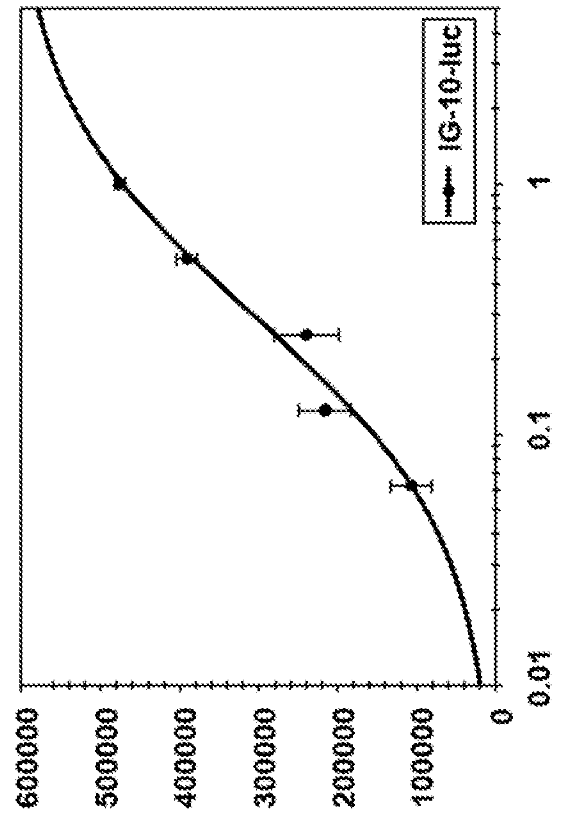

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the genome of VC2 which is a modified form of the human herpes simplex virus 1, strain F ("HSV-1(F)") deletions in the UL20 and UL53 genes. The nucleotide sequence of the genome of HSV-1(F) is publicly available as GenBank Accession No. GU734771.1. The GenBank database can be accessed on the World Wide Web at ncbi.nlm.nih.gov/genbank.

SEQ ID NO: 2 sets forth the nucleotide sequence of the modified UL20 gene of VC2.

SEQ ID NO: 3 sets forth the amino acid sequence of the modified UL20 protein that is encoded by the modified UL20 gene of VC2.

SEQ ID NO: 4 sets forth the nucleotide sequence of the modified UL53 gene of VC2.

SEQ ID NO: 5 sets forth the amino acid sequence of the modified glycoprotein K (gK) that is encoded by modified UL53 gene of VC2.

SEQ ID NO: 6 sets forth the nucleotide sequence of VC2-ΔgC, a modified form of the VC2 genome (SEQ ID NO: 1) comprising the deletion of the gene (UL44) encoding glycoprotein C (gC).

SEQ ID NO: 7 sets forth the nucleotide sequence of the VC2-ΔgC-NIS, a recombinant HSV genome that is a modified form of the VC2 genome (SEQ ID NO: 1) further comprising the replacement of the gene (UL44) encoding glycoprotein C (gC) with an expression cassette comprising a nucleotide sequence encoding the *Mus musculus* sodium iodide symporter (NIS).

SEQ ID NO: 8 sets forth the nucleotide sequence encoding the *Mus musculus* sodium iodide symporter (NIS) that is contained in SEQ ID NO: 7.

SEQ ID NO: 9 sets forth the coding region of the nucleotide encoding NIS that is set forth in SEQ ID NO: 8. If desired, a stop codon (e.g. TAA, TAG, or TGA) can be operably linked to the 3' end of a nucleic acid molecule comprising SEQ ID NO: 9. It is noted that the native stop codon of NIS is TGA.

SEQ ID NO: 10 sets forth the amino acid sequence of NIS.

SEQ ID NO: 11 sets forth the nucleotide sequence of the expression cassette that is contained in the nucleotide sequence of VC2-ΔgC-NIS provided in SEQ ID NO: 7. The expression cassette comprises in operable linkage the CMV promoter, the nucleotide sequence of the *Mus musculus* NIS (SEQ ID NO: 7) and the TK poly A signal derived from the pcDNA 3.3 TOPO plasmid (Thermo Fisher Scientific Inc., Waltham, MA, USA).

SEQ ID NO: 12 sets forth the amino acid sequence of the *Homo sapiens* sodium iodide cotransporter (NCBI Reference Sequence NP_000444.1).

SEQ ID NO: 13-34 set forth the amino acid sequences of peptides shown in Table 1 below.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

The present invention relates to genetically engineered viruses, particularly herpes simplex viruses (HSVs), that find use in methods for treating and preventing cancer. A herpes simplex virus (HSV) of the present invention comprises a recombinant HSV genome that has been genetically engineered to be incapable of replication in a host cell but incapable of entry into axonal compartments of neurons. An example of an HSV comprising such a recombinant HSV genome is VC2, a genetically engineered HSV-1 that is derived from HSV-1 strain F. See WO 2015/172033, herein incorporated by reference. The recombinant HSV genomes of the present invention have addition been modified to be capable of expressing in a host cell of interest, preferably a human cancer or tumor cell of interest, a nucleic acid construct encoding oncolytic protein or a tumor antigen of interest.

Definitions

In the context of this disclosure, a number of terms are used. The following definitions are provided immediately below. Other definitions can be found throughout the disclosure. It is understood that the definitions provided herein are the preferred definitions for the purposes of describing the present invention, unless it is stated otherwise herein or apparent form the context of usage.

"Oncolytic virotherapy" is intended to mean a treatment using an oncolytic virus (a virus that infects and breaks down cancer cells but not normal cells). Oncolytic virotherapy may make it easier to kill tumor cells with chemotherapy and radiation therapy. It is a type of targeted therapy. Also called "oncolytic virus therapy", "viral therapy", and "virotherapy".

"Oncolysis" is the lysis (breakdown) of cancer cells that can be caused, for example, by chemical or physical means (for example, strong detergents or high-energy sound waves) or by infection with a strain of virus that can lyse cancer cells.

An "oncolytic virus" is a type of virus that is capable of infecting and lysing cancer cells but preferably, does not infect normal cells. Oncolytic viruses can occur naturally or can be made in the laboratory by genetically modifying a naturally occurring viruses. The oncolytic viruses of the present invention are non-naturally occurring viruses comprising a genetically engineered genome.

An "oncolytic composition" is a composition of the present invention comprising an oncolytic virus of the present invention, the genome of which has been modified to express an oncolytic protein. Preferably, the oncolytic virus is a modified HSV-1, more preferably a modified VC2 or variant thereof.

An "oncolytic protein" that is expressed by an oncolytic virus of the present invention and is capable of promoting or enhancing oncolysis when expressed from a recombinant HSV genome in a cancer cell.

A "vaccine" is substance or group of substances meant to cause the immune system to respond to a tumor or to microorganisms, such as bacteria or viruses. A vaccine can, for example, help a human body recognize and destroy cancer cells, viruses, or microorganisms.

A "cancer vaccine" is a vaccine, when administered to a patient, that can be used to treat existing cancer or to prevent the development of a cancer. Vaccines that treat existing cancer are known as "therapeutic cancer vaccines". Vaccines that prevent the development of a cancer are known as "preventative cancer vaccines".

A "tumor antigen" is an antigenic substance produced in tumor cells. Tumor antigens are broadly classified into two groups: tumor-specific antigens, which are present only on tumor cells and not on any other cell; and tumor-associated antigens (TAA), which are present on some tumor cells and also some normal cells.

Description

The present invention provides compositions and methods for treating or preventing cancer. Thus, the compositions and methods of the present invention find use in treating or preventing cancer, particularly cancers that are known to afflict humans. While the examples described hereinbelow relate to specific cancers, the compositions and methods are not limited to any particular cancer but are widely adaptable for use in treating or preventing any cancer of interest in a patient. Such cancers of interest include, but are not limited to, acute lymphoblastic leukemia (ALL), acute myeloid leukemia (AML), adrenocortical carcinoma, AIDS-related cancers (e.g. Kaposi sarcoma, aids-related lymphoma, primary CNS), anal cancer, appendix cancer, astrocytomas, atypical teratoid/rhabdoid tumor, central nervous system (brain cancer), basal cell carcinoma of the skin, bladder cancer, bone cancer (e.g. Ewing sarcoma, osteosarcoma, malignant fibrous histiocytoma), brain tumors, breast cancer, bronchial tumors, Burkitt lymphoma, carcinoid tumor (gastrointestinal), carcinoma, cardiac (heart) tumors, atypical teratoid/rhabdoid tumor (brain cancer), embryonal tumors, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors (brain cancer), endometrial cancer (uterine cancer), ependymoma, esophageal cancer, esthesioneuroblastoma (head and neck cancer), extragonadal germ cell tumor, eye cancer (e.g. intraocular melanoma, retinoblastoma), fallopian tube cancer, gallbladder cancer, gastric (stomach) cancer, gastrointestinal carcinoid tumor, gastrointestinal stromal tumors (GIST), germ cell tumors (e.g. childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, hepatocellular (liver) cancer, histiocytosis, Langerhans cell, Hodgkin lymphoma, hypopharyngeal cancer (head and neck cancer), intraocular melanoma, pancreatic cancer, Kaposi sarcoma (soft tissue sarcoma), kidney (renal cell) cancer, Langerhans cell histiocytosis, laryngeal cancer (head and neck cancer), leukemia, lip and oral cavity cancer, liver cancer, lung cancer, lymphoma, male breast cancer, malignant fibrous histiocytoma of bone and osteosarcoma, melanoma, Merkel cell carcinoma, mesothelioma, midline tract carcinoma, mouth cancer, multiple endocrine neoplasia syndromes, multiple myeloma/plasma cell neoplasms, myelodysplastic syndromes, myeloproliferative neoplasms, myelodysplastic/myeloproliferative neoplasms, nasal cavity and paranasal sinus cancer, nasopharyngeal cancer, neuroblastoma, non-Hodgkin lymphoma, non-small cell lung cancer, oral cancer, lip and oral cavity cancer, oropharyngeal cancer, ovarian cancer, pancreatic cancer, pancreatic neuroendocrine tumors (islet cell tumors), paraganglioma, paranasal sinus and nasal cavity cancer (head and neck cancer), parathyroid cancer, penile cancer, pharyngeal cancer, pheochromocytoma, pituitary tumor, plasma cell neoplasm/multiple myeloma, primary central nervous system (CNS) lymphoma, primary peritoneal cancer, prostate cancer, rectal cancer, recurrent cancer, renal cell (kidney) cancer, retinoblastoma, salivary gland cancer, sarcoma (e.g. Ewing sarcoma, Kaposi sarcoma, osteosarcoma, soft tissue sarcoma, uterine sarcoma), Sezary syndrome, skin cancer, small cell lung cancer, small intestine cancer, soft tissue sarcoma, squamous cell carcinoma of the skin, testicular cancer, throat cancer (nasopharyngeal cancer, oropharyngeal cancer, hypopharyngeal cancer), thymoma and thymic carcinoma, thyroid cancer, transitional cell cancer of the renal pelvis and ureter, urethral cancer, uterine cancer (e.g. endometrial cancer, uterine sarcoma), vaginal cancer, and, vulvar cancer.

In some preferred embodiments of the invention, the cancer of interest is selected from the group consisting of melanoma, lung cancer, prostate cancer, pancreatic cancer, breast cancer, colorectal cancer, kidney cancer, bladder cancer, non-Hodgkin's lymphoma, thyroid cancer, endometrial cancer, ovarian cancer, leukemia, and liver cancer. In other preferred embodiments, the cancer of interest is melanoma. In still other preferred embodiments, the cancer of interest is ovarian cancer.

The present invention provides recombinant HSV genomes and HSVs comprising such recombinant HSV genomes, and other compositions comprising such HSVs, including, for example, cancer vaccines. The recombinant HSV genomes of the present invention comprise: (a) a modified UL53 gene comprising a deletion corresponding to the region of the UL53 gene that encodes amino acids 31-68 of wild-type gK; (b) a modified UL20 gene comprising a deletion corresponding to the region of the UL20 gene that encodes amino acids 4-22 of wild-type UL20 protein; and (c) a nucleic acid construct encoding an oncolytic protein or tumor antigen. An HSV comprising such a recombinant HSV genome is capable of replication in a host cell but incapable of entry into axonal compartments of neurons.

The recombinant HSV genomes of the present invention can be constructed, for example, from a wild-type HSV-1 or HSV-2 genome using standard genetic engineering methods disclosed elsewhere herein or otherwise known. An example of a wild-type HSV-1 genome is the genome of HSV-1 strain F (GenBank Accession No. GU734771.1; available on the World Wide Web at ncbi.nlm.nih.gov/genbank). An example of a wild-type HSV-2 genome is the genome of HSV-2 strain HG52 (GenBank Accession No. JN561323.2; available on the World Wide Web at ncbi.nlm.nih.gov/genbank).

In preferred embodiments of the present invention, the genome of VC2 is used to produce the recombinant HSV genomes of the present invention because the VC2 genome already comprises (a) a modified UL53 gene comprising a deletion corresponding to the region of the UL53 gene that encodes amino acids 31-68 of wild-type gK; (b) a modified UL20 gene comprising a deletion corresponding to the region of the UL20 gene that encodes amino acids 4-22 of wild-type UL20 protein. Thus, only the further modification of the VC2 genome to comprise (c) a nucleic acid construct encoding an oncolytic protein or tumor antigen.

VC2 or other HSV genome can be further modified to comprise the nucleic acid construct encoding an oncolytic protein or tumor antigen by replacing a non-essential HSV gene with the nucleic acid construct encoding an oncolytic protein or tumor antigen or by inserting the nucleic acid construct in an intergenic, non-coding region without affecting virus replication, as long as adjacent genes are not affected. Examples of some non-essential genes include, but are not limited to, UL1, UL5, UL8, UL 27, UL30, UL44, and UL52. For a comprehensive list of essential and non-essential HSV genes, see "The function of herpes simplex virus genes: A primer for genetic engineering of novel vectors," National Academy of Sciences, 1996, (*NAS Colloquium*) *Genetic Engineering of Viruses and Viral Vectors*, Washington, DC: The National Academies Press.

In one embodiment of the invention, the nucleic acid construct encoding an oncolytic protein or tumor antigen is inserted into or replaces all or at least a portion of UL23, whereby the recombinant HSV genome no longer encodes a functional thymidine kinase. It is recognized that HSV requires thymidine kinase activity to replicate. It is further recognized that actively dividing host cells that are cancer cells comprise thymidine kinase activity that can support HSV replication but non-dividing host cells lack thymidine kinase activity. Thus, in this embodiment of the invention, HSV replication can be limited to actively dividing host cells, particularly cancer cells.

The nucleic acid construct encoding an oncolytic protein or tumor antigen can encode any oncolytic protein or tumor antigen for any particular cancer of interest. Examples of some oncolytic proteins for ovarian cancer include, for example, *Mus musculus* sodium iodide symporter (NIS) (SEQ ID NO: 10) and the *Homo sapiens* sodium iodide cotransporter (SEQ ID NO: 10). Example of some tumor antigens for melanoma are provided below in Table 1 and set forth in SEQ ID NOS: 13-34.

TABLE 1

Examples of melanoma-associated antigens, peptides, and MHC molecules presenting those peptides

| Proteins | Peptides | SEQ ID NO | Presenting MHC |
|---|---|---|---|
| MAGE-A1[a] | EADPTGHSY | 13 | HLA-A1 & B37 |
| MAGE-A1[a] | TSCILESLFRAVITK | 14 | HLA-DP4 |
| MAGE-A1[a] | EYVIKVSARVRF | 15 | HLA-DR15 |
| MAGE-A3[a] | EVDPIGHLY | 16 | HLA-A1 |
| MAGE-A3[a] | FLWGPRALV | 17 | HLA-A2 |
| MAGE-A3[a] | VIFSKASSSLQL | 18 | HLA-DR4 |
| NY-ESO-1[a] | SLLMWITQC | 19 | HLA-A2 |
| NY-ESO-1[a] | MPFATPMEA | 20 | HLA-B51 |
| NY-ESO-1[a] | EFYLAMPFATPM | 21 | HLA-DR1 |
| Melan-A/MART-1[b] | (E)AAGIGILTV | 22 | HLA-A2 |
| Melan-A/MART-1[b] | EAAGIGILTV | 23 | HLAB35 |
| Melan-A/MART-1[b] | ILTVILGVL | 24 | HLA-A2 |
| Melan-A/MART-1[b] | AAGIGILTVILGVL | 25 | HLA-DR1 |
| Tyrosinase[b] | MLLAVLYCL | 26 | HLA-A2 |
| Tyrosinase[b] | SSDYVIPIGTY | 27 | HLA-A1 |
| Tyrosinase[b] | SYLQDSDPDSFQD | 28 | HLA-DR4 |
| gp100/pmel17[b] | KTWGQYWQV | 29 | HLA-A2 |
| gp100/pmel17[b] | LIYRRRLMK | 30 | HLA-A3 |
| gp100/pmel17[b] | GRAMLGTHTMEVTVY | 31 | HLA-DQ6 |
| CDK4[c] | ACDPHSGHFV | 32 | HLA-A2 |
| beta-catenin[c] | SYLDSGIHF | 33 | HLA-A24 |
| N-ras[c] | ILDTAGREEY | 34 | HLA-A1 |

While the tumor antigen can be a tumor-specific antigen or a tumor-associated antigen, the tumor antigen is a tumor-specific antigen in preferred embodiments of the invention.

Typically, the nucleic acid construct encoding an oncolytic protein or tumor antigen will be in the form of an expression cassette comprising a promoter operably linked to a coding sequence for the oncolytic protein or tumor antigen. Preferably, the promoter is capable of driving the expression of an operably linked nucleotide sequence (e.g. a coding sequence) in a host cell of interest, particularly a mammalian cell, more particularly a human cell, most particularly a human cancer cell. Examples of some promoters that can be used in the present invention are CMV, EF1a, SV40, PGK1, Ubc, human beta actin, and CAG promoters. If desired, the expression cassette can further comprise one or more additional 5' and/or 3' regulatory components such as, example an enhancer and a polyadenylation signal.

The present invention further provides compositions comprising a recombinant HSV genome of the present invention. Such compositions include, for example, HSVs comprising a recombinant HSV genome of the present invention and cancer vaccines and other compositions comprising such an HSV. The vaccines and compositions can further comprise one or more pharmaceutically acceptable components including, but not limited to, a carrier, an excipient, a stabilizing agent, a preservative, an immunostimulant, and an adjuvant. Each of the pharmaceutically acceptable components is present in the vaccines and immunogenic compositions in a pharmaceutically acceptable amount. Such a pharmaceutically acceptable amount is an amount that is sufficient to produce the desired result (e.g. the amount of stabilizer sufficient to stabilize the vaccine after making and until administration) but is considered safe for administration to an animal, particularly a human.

The cancer vaccines and other compositions of the present invention can comprise a live HSV and/or an inactivated HSV. Preferably, the vaccines of the present invention comprise a live, attenuated HSV comprising a recombinant HSV genome of the present invention.

The present invention further provides methods for treating or preventing cancer comprising the step of administering to the patient a therapeutically effective amount of a cancer vaccine of other composition of the present invention. Preferably, the patient is an animal. More preferably, the patient is a human.

A "therapeutically effective amount" as used herein refers to that amount which provides a therapeutic effect for a given condition and administration regimen. In particular aspects of the invention, a "therapeutically effective amount" refers to an amount of a cancer vaccine or other immunogenic composition of the invention that, when administered to an animal, brings about a positive therapeutic response with respect to the prevention or treatment of the animal for a cancer of interest. A positive therapeutic response with respect to preventing cancer includes, for example, the production of antibodies against the tumor antigen by the animal in a quantity sufficient to protect against development of the cancer. Similarly, a positive therapeutic response in regard to treating a patient for cancer includes curing or ameliorating the symptoms of the cancer such as, example lysing cancer cells. The phrase "therapeutically effective amount" is used herein to mean an amount sufficient to cause an improvement in a clinically significant condition in an animal, particularly a human.

In some embodiments of the methods of the invention, the therapeutically effective amount of a cancer vaccine or composition of the invention is administered to the patient in a single dose. In other embodiments, the cancer vaccine or composition is administered to the patient in multiple doses. It is recognized that the therapeutically effective amount of a cancer vaccine or composition of the invention can vary depending on the dosing regimen and can even vary from one administration to the next in multiple dosing regimens.

The present invention additionally provides methods for producing an HSV comprising a recombinant genome of the present invention. The methods comprising transfecting a host cell with the recombinant HSV genome of the present invention and incubating the transfected host cell under conditions favorable for the formation of an HSV virus comprising the recombinant HSV genome, whereby the HSV is produced. Preferably, the host cell is an animal cell and can be either a host cell contained in an animal or an in-vitro-cultured animal cell including, for example, an in-vitro cultured human cell. The conditions under which the transfected host cell is incubated will depend on a number of factors including, but not limited to, the particular host cell, the amount of the recombinant HSV genome that is transfected into the host cell, and the particular HSV that is produced from the recombinant HSV genome. It is recognized that those of skill in the art can determine empirically the optimal conditions for producing a recombinant HSV of the present invention in a transfected host cell by methods described elsewhere herein or otherwise known in the art. The methods can further comprise the optional step of purifying the recombinant HSV virus by separating the recombinant HSV from the cellular components of the host cell using standard methods that are known in the art.

In a preferred embodiment, the HSV comprises a recombinant HSV genome comprising the deletion of nucleotides 41339 to 41395 and 112160 to 112274 from the genome of HSV-1(F) (GenBank Accession No. GU734771.1) and further comprise a nucleotide sequence encoding an oncolytic protein or tumor antigen. Such a recombinant HSV genome encodes both a modified gK in which amino acids 31 to 68 in the amino terminal region of gK from HSV-1(F) have been deleted and a modified UL20 protein in which amino acids 4-22 in the amino terminal region of the UL20 protein from HSV-1(F) have been deleted. The amino acid sequences of the modified UL20 protein and the modified gK are set forth in SEQ ID NOS: 3 and 5, respectively. Examples of nucleotide sequences encoding the modified UL20 protein and the modified gK are set forth in SEQ ID NOS: 2 and 4, respectively. The VC2 genome of the invention comprises the nucleotide sequences of the modified UL20 and UL53 genes set forth in SEQ ID NOS: 2 and 4, respectively.

An example of a recombinant HSV genome of the present invention is provided in SEQ ID NO: 7. This recombinant HSV genome is a modified VC2 genome comprising the replacement of the gene (UL44) encoding glycoprotein C (gC) with an expression cassette comprising a nucleotide sequence encoding the *Mus musculus* sodium iodide symporter (NIS). The nucleotide sequence of the expression cassette is provided in SEQ ID NO: 11.

Further provided are methods for producing a composition for treating or preventing cancer or a cancer vaccine. The methods involve producing the HSV comprising the recombinant genome essentially as described above. In particular, the methods for producing a composition for treating or preventing cancer or a cancer vaccine comprise transfecting a host cell with the recombinant HSV genome of the invention, incubating the transfected host cell under conditions favorable for the formation of a HSV virus comprising the recombinant HSV genome, purifying the HSV virus comprising the recombinant HSV genome, and optionally, combining the purified HSV virus with at least one pharmaceutically acceptable component.

A composition for treating or preventing cancer or a cancer vaccine of the present invention can comprise one or more pharmaceutically acceptable components including, but not limited to, a carrier, an excipient, a stabilizing agent, a preservative, an immunostimulant, and an adjuvant. In general, a pharmaceutically acceptable component does not itself induce the production of an immune response in the animal receiving the component and can be administered without undue toxicity in composition of the present invention. As used herein, the term "pharmaceutically acceptable" means being approved by a regulatory agency of the Federal or a state government or listed in the U.S. Pharmacopia, European Pharmacopia or other generally recognized pharmacopia for use in vertebrates, and more particularly in humans. These compositions can be useful as a vaccine and/or antigenic compositions for inducing a protective immune response in a vertebrate.

Carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition), herein incorporated in its entirety by reference. The formulation should suit the mode of administration. In a preferred embodiment, the formulation is suitable for administration to humans, preferably is sterile, non-particulate and/or non-pyrogenic.

Examples of stabilizing agents, immunostimulants, and adjuvants include alum, incomplete Freud's adjuvant, MR-59 (Chiron), muramyl tripeptide phosphatidylethanolamide, and mono-phosphoryl Lipid A. Preservatives include, for example, thimerosal, benzyl alcohol, and parabens. Such stabilizing agents, adjuvants, immune stimulants, and preservatives are well known in the art and can be used singly or in combination.

Pharmaceutically acceptable components can include, for example, minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, and the like.

Certain methods of the invention involve administering a therapeutically effective amount of a composition for treating or preventing cancer or a cancer vaccine to a patient. The methods of the present invention do not depend on a particular method of administering the composition for treating or preventing cancer or the cancer vaccine to the patient. For example, the composition for treating or preventing cancer or the cancer vaccine can be administered orally, intratumorally, intradermally, intranasally, intramuscularly, intraperitoneally, intravenously, or subcutaneously using routine methods known in the art or disclosed elsewhere herein. In preferred embodiments of the invention, the composition for treating or preventing cancer and the cancer vaccine are administered intratumorally.

The recombinant HSV genomes of the present invention comprise nucleotide sequences which are modified by methods disclosed herein or otherwise known in the art so as to produce a recombinant HSV genome. A virus comprising the recombinant HSV genome of the present invention is capable of replication in a host cell and incapable of entry into axonal compartments of neurons. Variant recombinant HSV genomes encompassed by the present invention have at least about 80%, 85%, 90%, 91%, 92%, 93%, 94%, 95%, 96%, 97%, 98%, 99% or more sequence identity to the full-length nucleotide sequences set forth in SEQ ID NO: 11, respectively. Viruses comprising such variant recombinant HSV genomes are capable of replication in a host cell and incapable of entry into axonal compartments of neurons.

The present invention additionally encompasses variant recombinant HSV genomes that comprise variant forms of any one or more of the individual genes within a recombinant HSV genome, but not limited to UL53, UL20, and the oncolytic protein or tumor antigen of interest. For example, VC2-ΔgC-NIS (SEQ ID NO: 7) can comprise a variant nucleotide sequence encoding a NIS protein this identical to the amino acid sequence forth in SEQ ID NO: 10 or a variant NIS protein that comprises sodium-iodide transporter activity when expressed in a host cell. It is recognized that sodium-iodide transporter activity can be assayed by methods disclosed elsewhere herein or otherwise known in the art.

A gene or nucleotide sequence encoding a variant oncolytic protein or tumor antigen in the recombinant HSV genomes encompassed by the present invention has at least about 80%, 85%, 90%, 91%, 92%, 93%, 94%, 95%, 96%, 97%, 98%, 99% or more sequence identity to the corresponding full-length nucleotide sequence of that gene or nucleotide sequence in a recombinant HSV genome disclosed herein or encode a protein having at least about 80%, 85%, 90%, 91%, 92%, 93%, 94%, 95%, 96%, 97%, 98%, 99% or more sequence identity to the corresponding full-length amino acid sequence of the corresponding non-variant protein.

The present invention provides compositions and methods for treating of preventing cancer. The compositions comprise recombinant herpes simplex virus (HSV) genomes. The HSV genomes of the present invention are nucleic acid molecules comprising a modified UL53 gene comprising a deletion corresponding to the region of the UL53 gene that encodes amino acids 31-68 of wild-type glycoprotein K (gK) and a modified UL20 gene comprising a deletion corresponding to the region of the UL20 gene that encodes amino acids 4-22 of wild-type UL20 protein and that further comprises a nucleic acid construct encoding an oncolytic protein or tumor antigen of interest.

The present invention encompasses isolated or substantially purified polynucleotide (also referred to herein as "nucleic acid molecule", "nucleic acid" and the like) or protein (also referred to herein as "polypeptide") compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular recombinant HSV genome of the invention will have at least about 80%, 85%, 90%, 91%, 92%, 93%, 94%, 95%, 96%, 97%, 98%, 99% or more sequence identity to the recombinant HSV genome as determined by sequence alignment "Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of a protein will have at least about 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, and insertions. Methods for such manipulations are generally known in the art. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The deletions, insertions, and substitutions of the protein sequences encompassed herein are not expected to produce radical changes in the characteristics of the protein except for those changes that are disclosed herein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed hereinbelow.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *PNAS* 94:4504-4509; Crameri et al. (1998) *Nature* 391:288-291; and U.S. Pat. Nos. 5,605,793 and 5,837,458.

PCR amplification methods can be used in making the recombinant HSV genomes of the present invention. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

It is recognized that the recombinant HSV genomes of the present invention encompass other nucleic acid molecules comprising a nucleotide sequence that is sufficiently identical to a nucleotide sequence disclosed herein. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 80% identity, preferably or 85% identity, more preferably 90% or 95% identity, most preferably 96%, 97%, 98% or 99% identity, are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. LAST, Gapped BLAST, and PSI-Blast, XBLAST and NBLAST are available on the World Wide Web at ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention using BLAST with the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by BLAST using default parameters.

As used herein, the term "operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame.

As used herein unless stated otherwise or apparent from the context of usage, a host cell is an animal cell, preferably a mammalian cell, more preferably a human cell. Similarly, a host or host organism is an animal, preferably a mammal, more preferably a human.

The following examples are offered by way of illustration and not by way of limitation.

Example 1

HSV-1-Mediated Oncolytic Virotherapy for Treating Ovarian Cancer

Ovarian cancer has the fifth highest mortality rate of cancer deaths amongst women and accounts for the most deaths of all other female reproductive cancers. To date, there are limited therapeutic options for advanced disease. Oncolytic virotherapy uses viruses that are derived or engineered from naturally occurring viruses to target and specifically kill cancer cells, leaving normal cells unaffected. Oncolytic herpes simplex viruses (oHSVs) have shown promise in cancer therapy and have received FDA approval in treating melanoma. Our aim was to determine the efficacy of an attenuated oHSV-1 vector, constructed to express the sodium iodide symporter (NIS) gene (VC2-NIS) for monitoring infection and spread in tumors.

As disclosed hereinbelow, an expression comprising the NIS reporter gene, when inserted into the parental VC2 oncolytic HSV-1 vector, can be used to kill ovarian cancer cells and to monitor infection and spread using radioactive technetium.

Methods

- Step 1: Identify which human (2008, SKOV3-luc) and mouse (IG-10-pLuc, HM3-pLuc, LM1, LM3, MOVCAR-2) ovarian cancer cell lines are capable of infection by the virus (VC2-NIS).
  - Radioactive $^{99m}$Tc uptake was used as a surrogate to monitor NIS reporter activity in cells infected for 24 h with VC2-NIS, and uptake in cells infected with a control virus (VC2) was compared to uptake in uninfected cells.
- Step 2: Identify the dose effect of VC2-NIS infection on the cell lines.
  - The amount (MOI) of virus used to infect cells was varied and the impact on NIS reporter expression was determined by assessing $^{99m}$Tc uptake. NIS expression in VC2-NIS infected cells was monitored by Western blot and flow cytometry analyses.
- Step 3: Quantify the amount of cells killed by the VC2-NIS virus.
  - A luciferase assay was used to measure cell viability after VC2-NIS infection in luciferase-expressing cell lines, and activity in cells infected with a control virus (VC2) compared was compared to activity in uninfected cells.
- Step 4: Monitor $^{99m}$Tc uptake in cells infected with VC2-NIS in vitro by single photon emission computed tomography (SPECT) imaging.
  - The IG-10-pLuc, HM3-pLuc, and SKOV-3-luc cell lines were plated in 35 mm tissue culture dishes and infected for 24 h with VC2-NIS. Uptake of $^{99m}$Tc was compared to cells infected with a control virus (VC2) or to uninfected cells. SPECT imaging was used to monitor $^{99m}$Tc after a 1 h. A CT scan was also obtained to provide localization of the SPECT signal.

Discussion

Figure 3A:
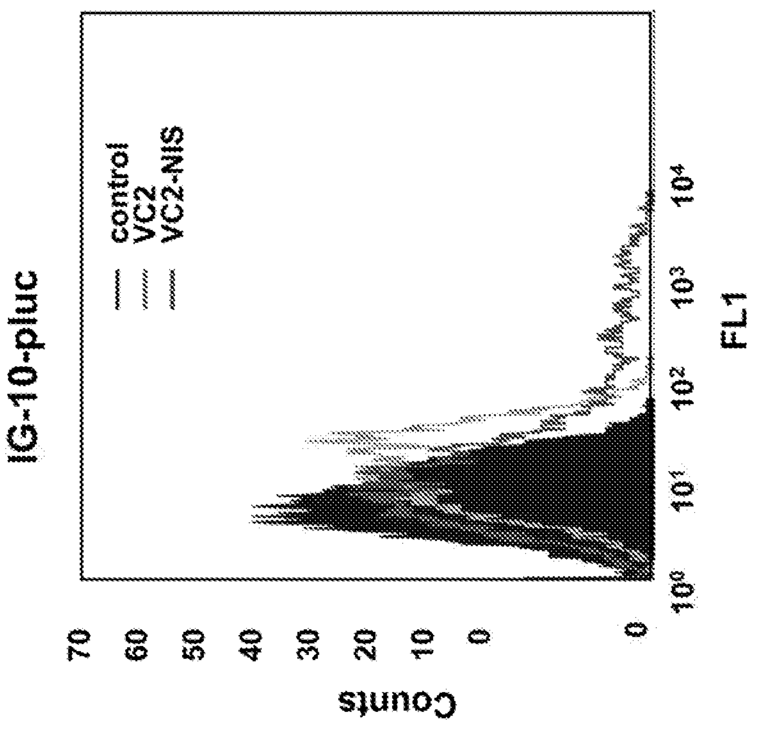
FIGS. 3A-3B. Flow Cytometry Analysis. IG-10-pLuc (FIG. 3A) and SKOV-3-luc (FIG. 3B) cells were analyzed for NIS expression after 24 h infection. VC2-NIS infected cells exhibited an increased fluorescence intensity compared with VC2 infected cells or uninfected control cells.
Figure 3B:
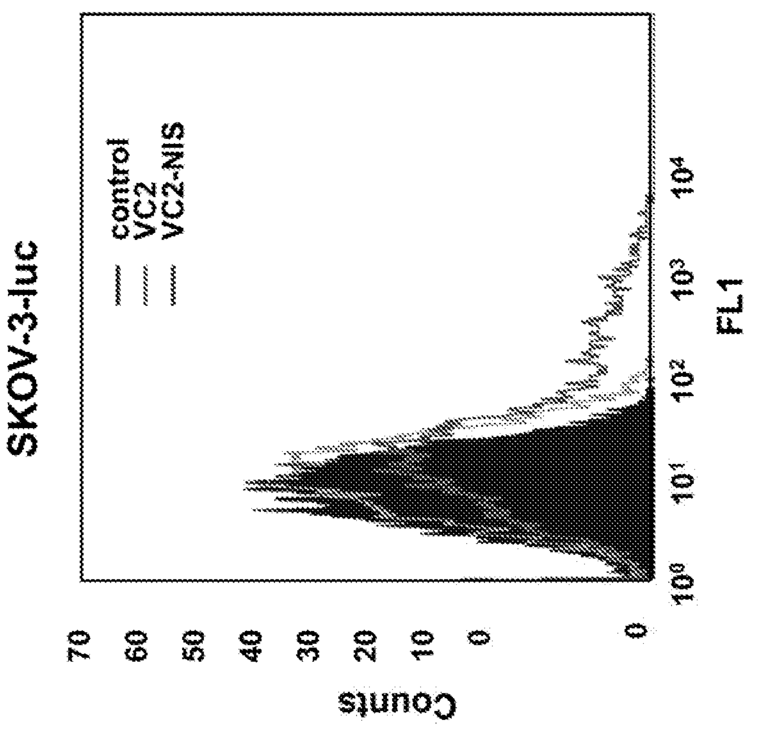
Figure 4A:
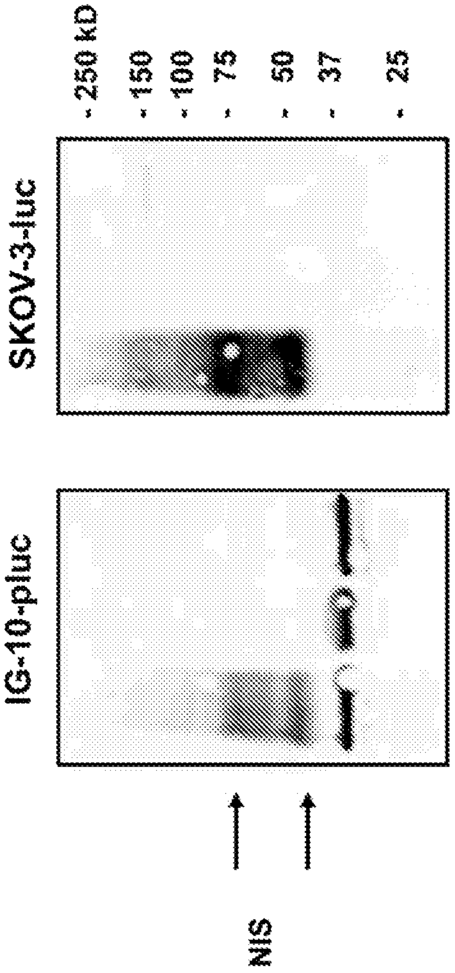
FIGS. 4A-4B. Western blot analysis. NIS expression was identified in IG-10-pLuc and SKOV-3-luc cell lines infected with VC2-NIS (FIG. 4A). Arrows show hyper- and hypoglycoslyated bands. Actin expression (FIG. 4B) was used as a loading control for the samples FIGS. 5A-5C. Quantification of Cell Killing Activity. Luciferase activity was determined in HM3-pLuc (FIG. 5A), IG-10-pLuc (FIG. 5B), and SKOV-3-luc (FIG. 5C) cells after infection with VC2-NIS compared with VC2 infected cells or uninfected control cells. Cells infected with VC2 or VC2-NIS showed a transient increase in luciferase activity until 24 hours followed by a decrease in activity indicative of cell death due to oHSV cytolytic activity. The transient increase observed may be due to activation of the CMV promoter driving the luciferase reporter gene stably transfected into the cell lines.
Figure 4B:
Figure 6B:
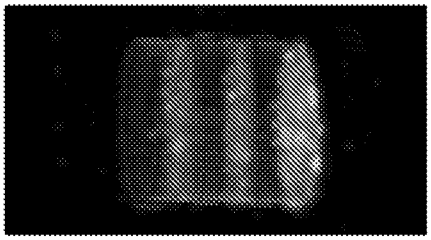
FIGS. 6A-6B. SPECT/CT Image analysis of VC2-NIS and VC2 infected cells. Shown are (FIG. 6A) transverse and (FIG. 6B) frontal planar images of 35 mm dishes after 24 h infection and 1 h uptake of $^{99m}$Tc. The IG-10-pLuc cell line infected with VC2-NIS demonstrated the highest amount of radioactive uptake compared with the SKOV-3-luc and HM3-pLuc cell lines. Cells infected with VC2 showed only background uptake.
Figure 6A:
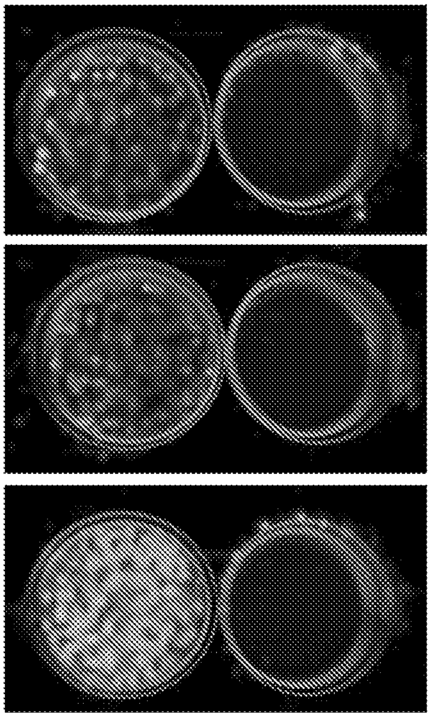

Infection of ovarian cancer cells with VC2-NIS resulted in robust NIS expression detected in 2008, HM3-pLuc, IG-10-pLuc, and SKOV-3-luc cells as determined by $^{99m}$Tc uptake (FIGS. 1A-1G and 2A-2B), flow cytometry analysis (FIGS. 3A-3B) western blot analysis (FIGS. 4A-4B), and SPECT/CT imaging (FIGS. 6A-6B).

An increase in $^{99m}$Tc uptake was not observed in LM1 (FIG. 1D), LM3 (FIG. 1B), and MOVCAR-2 cells (FIG. 1E), possibly due to high endogenous levels of NIS gene expression.

Figure 5A:
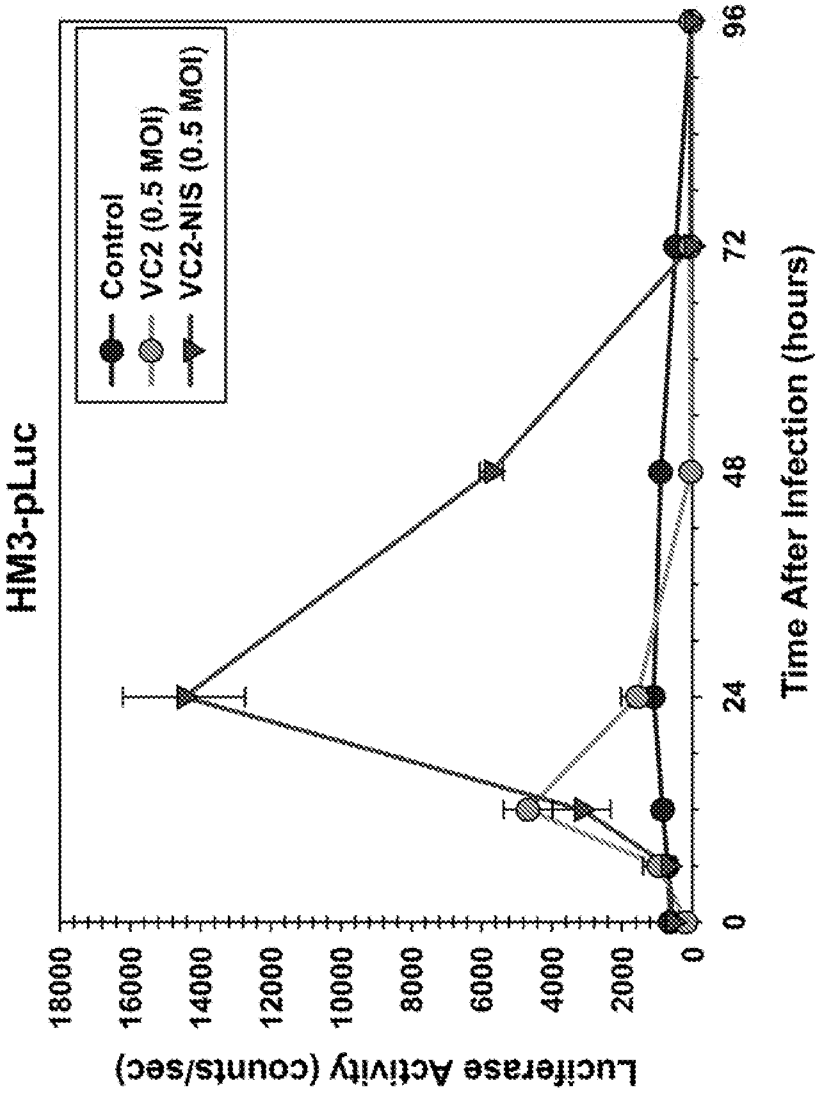
Figure 5B:
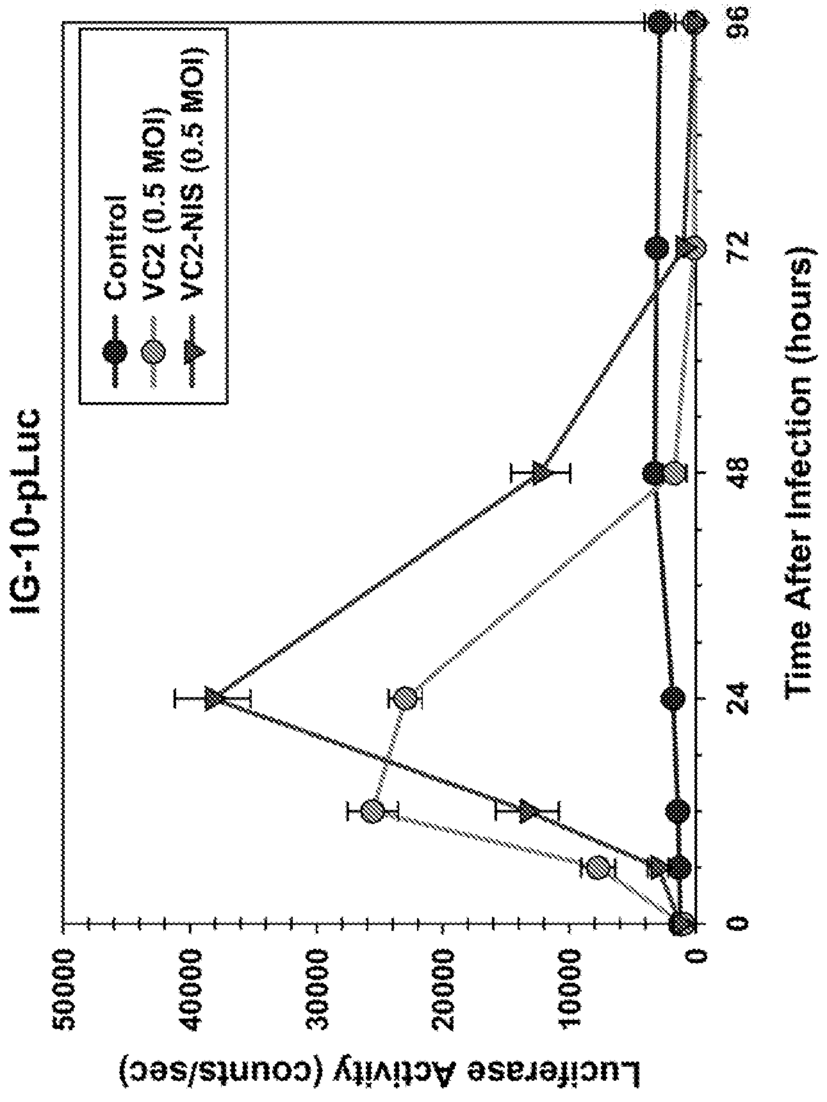
Figure 5C:
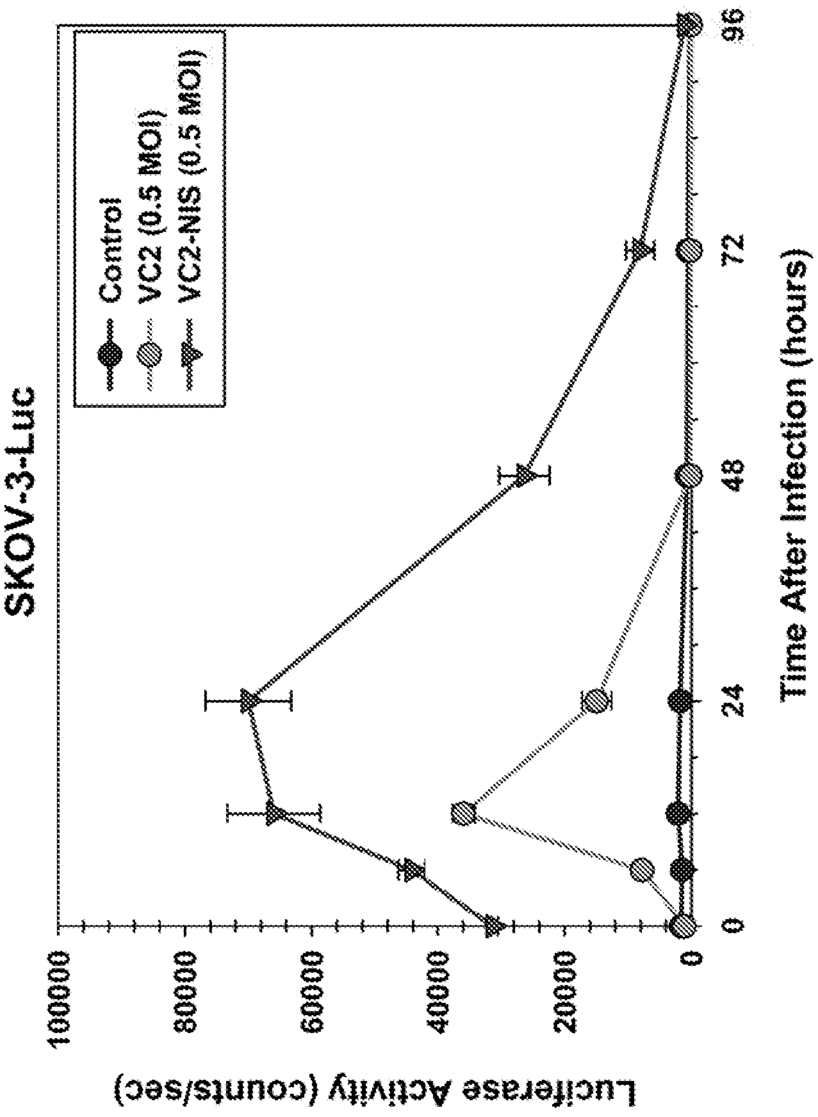

In FIGS. 5A-5C, the transient increase in luciferase activity we observed was unexpected. The luciferase expressing cell lines were produced by stable transfection of plasmids in which the luciferase reporter was driven by a cytomegalovirus (CMV) promoter. This result led to the hypothesis that VC2-NIS infection was activating the CMV promoter. This result was confirmed by infecting cells with the VC2 virus. A similar pattern of transient luciferase increase was found, supporting oHSV viral activation of luciferase activity after infection.

Conclusions

These studies demonstrate that VC2-NIS oHSV (SEQ ID NO: 7) has the capability for tracking and killing ovarian cancer cells in vitro. Moreover, oncolytic virotherapy methods for treating cancer comprising the administration of both VC2-NIS oHSV can be combined with radiotherapy methods involving the administration of a radioisotope, such as, for example, $^{131}$I. Finally, the oncolytic virotherapy approaches disclosed hereinabove can also be combined with cancer immunotherapy using immune checkpoint inhibitors.

Example 2

Development of a Murine Melanoma Model for Testing Immunomodulatory and Oncolytic Herpes Simplex Virus-1

Summary

Viruses that preferentially lyse cancer cells are described as being "oncolytic" or "tumor-lysing". Many different viruses have been tested as potential therapy for cancer. Herpes Simplex Virus type-1 (HSV-1) has long been hailed as a promising virus for the development of oncolytic virotherapy, and the first virus to receive FDA approval is an engineered HSV-1, Talimogene Laherperavec/T-VEC/Imlygic. Despite promising preclinical data in mouse models, T-VEC has shown variable efficacy in clinical trials involving human patients with metastatic melanoma. The exact mechanism for lack of response in the majority of human patients is unknown, but more efficacious and safe treatment strategies are needed. We previously demonstrated strong protective cell-mediated and humoral immune responses in VC2-vaccinated mice challenged with HSV-1 and HSV-2 after a single intramuscular vaccination. We hypothesized that the strong immunogenicity of VC2 could induce anti-tumor immune responses when injected into melanoma tumors in mice. VC2 has a significant safety advantage in that it contains specific deletions that make it unable to enter ganglionic axons and establish latency but replicates efficiently in other permissible cell types. We developed an immunocompetent, syngeneic murine melanoma model double-labeled with firefly luciferase and enhanced green fluorescent protein (B16F10-fLuc-eGFP) to test VC2 for anti-tumor effects. We additionally created a stably transfected cell line expressing human nectin-1 (B16F10-fLuc-eGFP-nectin-1) and observed enhanced cytolysis and viral replication in vitro. However, in vitro cytotoxicity assays cannot account for immune-mediated anti-tumor effects and immunogenic cell death. In fact, it has been reported that, regarding oncolytic HSV, in vitro cytotoxicity and viral persistence in vivo do not correlate with anti-tumor efficacy; it has instead been shown that expression of markers of immunogenic cell death, increased antigen presenting cells, and T cell responses may be more likely associated with HSV-associated therapeutic benefits (Workenhe et al. (2014) *Mol. Ther.* 22:123-131). We therefore utilized the B16F10-fLuc-eGFP model system developed in our laboratory to test VC2 for anti-tumor effects. The lack of nectin-1 receptors and poor immunogenicity of B16F10 murine melanoma may make it a good model for human melanoma patients that are unresponsive to current oncolytic HSV-1 therapy and other immune-modulating strategies. We found that, even in this difficult to treat model, VC2-treated mice had a median survival time (MST) almost twice that of mock-treated controls. Survival times were significantly negatively correlated with tumor size at the initiation of VC2 therapy, a dose-dependent effect. Further, there was significant infiltration of macrophages and T cells in the tumor microenvironment of VC2-treated mice owing to the remarkable immunogenicity of the virus. We demonstrated utility of the model in assessing response to therapy with increased sensitivity using bioluminescent imaging in the face of tumor pseudoprogression which may cause response to treatment to be underestimated in preclinical mouse studies involving immunotherapy development. Results of VC2 testing in our novel murine melanoma model system suggest the strong immunogenicity of VC2 make it a good candidate for viral vector development using a variety of oncolytic virotherapy and vectored tumor vaccine strategies. Future directions involve modeling dosing and combinatorial strategies which more accurately account for the variable sensitivity to oncolytic HSV-1 in human melanoma patients. Development of safe and efficacious dosing strategies based on tumor sensitivity aims to improve predictive value of preclinical testing in preparation for clinical trials.

Introduction

Viruses that preferentially lyse cancer cells are described as being "oncolytic" or tumor-lysing. Many different viruses have been tested as potential therapy for cancer in the last century, beginning as early as 1910, when a live-attenuated Rabies vaccine was observed to result in regression of cervical cancer in a patient (Sinkovics & Horvath (2008) *Arch. Immunol. Ther. Exp.* 56 Suppl 1:3s-59s). The field has expanded to include many different viruses and has become increasingly sophisticated as molecular tools to create purposeful viral genetic mutations that enhance cancer-killing abilities and safety have become more widely available. Some viruses have a natural lytic phase in their life cycle and have a natural affinity for rapidly dividing cells (e.g. herpes simplex virus type-1 and parvoviruses).

Herpes Simplex Virus type-1 (HSV-1) has long been hailed as a promising virus for the development of oncolytic virotherapy. The reasons cited are many. HSV-1 has a large genome with a number of non-essential genes that can be deleted to reduce pathogenicity or for insertion of therapeutic transgenes. Additionally, antiviral drugs exist which can control acute infection in the event of viral dissemination and/or adverse events. In the 1990's, the prospect of using viruses to treat tumors using an attenuated TK-negative HSV mutant showed promise in treating gliomas in a xenogenic mouse model after intratumoral injection (Martuza et al. (1991) *Science* 252:854-856). Twenty-five years later, the first ever oncolytic virotherapy was approved by the FDA for the treatment of metastatic melanoma in people, a mutated HSV-1 virus referred to as Talimogene Laherperavec (T-VEC) or Imlygic. T-VEC is a mutated oncolytic HSV-1 based virus with mutations in infectious cell protein (ICP) 34.5 and ICP47, while expressing US11 and human granulocyte macrophage-colony stimulating factor (GM-CSF). Viral expression of human GM-CSF was intended to improve antitumor immune responses and has demonstrated efficacy in some murine tumor models (Toda et al. (2000) *Mol. Ther.* 2:324-329). Tumor growth inhibition and/or regression was observed in xenogenic mouse models and in the syngeneic A20 B cell lymphoma model. While the aforementioned preclinical studies showed impressive results in murine models, efficacy in human clinical trials has shown more variability with only a small subset of patients having durable responses. Further, adverse effects including herpetic oral lesions, viral dissemination, and herpetic keratitis have reportedly been associated with treatment in some patients. The reason that only a small subset of patients responds and yet others experience adverse effects is unknown, but more widely efficacious and safe treatment strategies are needed for melanoma patients.

Some preclinical studies involving oncolytic HSV-1 mutants have shown that rapid infection and spread in vitro predicts better in vivo response; however, such studies have been most often performed in xenogeneic models and account only for direct lysis secondary to viral replication but do not account for host immune responses (Wollmann et al. (2005) *J. Virol.* 79:6005-6022; Bennett et al. (2002) *Cancer Gene Ther.* 9:935-945). The efficiency with which HSV-1 infects, spreads, replicates and directly lyses cells may depend on both virus and host-specific factors. Viral factors include the presence or absence of ICP34.5, for example; in its absence, protein shutoff by the host is permanent and the virus fails to efficiently replicate, limiting spread and replicative lysis of the cell. This is a common deletion in oncolytic HSV-1 mutants tested in clinical trials since it is a neurovirulence factor and inhibits the virus's ability to grow in non-neoplastic cells; however, the reduced ability of the virus to replicate may also reduce potency in inducing anti-tumor effects. Host factors may include the presence or absence of HSV-1 entry receptors such as nectin-1 and HVEM. In fact, nectin-1 expression has been identified as a marker of sensitivity to oncolytic HSV-1 in a xenogeneic squamous cell carcinoma mouse model; there was no correlation between therapeutic responses and HVEM expression (Yu et al. (2007) Mol. Ther. 15:103-113). It is difficult to know, however, if this result would translate to human patients with intact immune systems.

There is disagreement among researchers working in oncolytic virotherapy development on the importance of tumor cell lysis versus stimulation of immune response by the virus. Some would argue that spread, persistence and continued replication within the tumor and/or microenvironment are less important than immunogenicity of the virus and the immune response in the early stages of viral infection 119. In fact, it has been reported that, regarding oncolytic HSV, in vitro cytotoxicity and viral persistence in vivo do not correlate with anti-tumor efficacy; it has instead been shown that expression of markers of immunogenic cell death, such as heat shock protein 70 and elevated levels of serum high mobility group box 1 (HMGB1), increased antigen presenting cells, and CD8+ T cell responses may be more likely associated with HSV-associated therapeutic benefits (Workenhe et al. (2014) *Mol. Ther.* 22:123-131).

Based on these observations in the literature which highlight the importance of immunogenicity over direct cytotoxicity in oncolytic HSV-1 virotherapy, we aimed to test the ability of VC2, a highly immunogenic HSV-1 live-attenuated virus genetically engineered in our laboratory, to generate an anti-tumor response in absence of robust replicative cell lysis. We previously reported that a single, intramuscular vaccination with VC2, an HSV-1 live-attenuated vaccine strain generated in our laboratory, resulted in protective, strong cell-mediated and humoral immune responses against lethal challenge with HSV-1 and HSV-2 in mice (Stanfield et al. (2014) PLoS One 9:e109890). We hypothesized that VC2 could generate a therapeutic immune response in the TME in the poorly immunogenic B16F10 syngeneic murine melanoma model. We also previously showed that VC2 replicates as efficiently as the parental F strain but cannot enter ganglionic axons due to a specific mutation in UL20 and glycoprotein K (gK) due to its inability to enter by fusion. This confers a significant safety advantage by preventing the establishment of latency, while still allowing efficient replication in permissible cells. As mentioned, oncolytic HSV-1 mutants developed for clinical trials typically include a deletion in late gene γ 34.5 as a safety feature because of its association with neurovirulence, but this mutation significantly dampens viral replication, which may limit therapeutic effect. VC2 overcomes this problem by allowing efficient replication in permissible cells without compromising overall safety.

Safety and efficacy studies in immune-oncology are generally performed in GEM or syngeneic models since an intact immune system is necessary for evaluating efficacy in immune-stimulating therapeutics and for assessing for immunotoxic effects (Li et al. (2017) *Pharmacol. Ther.* 173:34-46). We chose the syngeneic, immunocompetent B16F10 murine melanoma model over a xenogeneic model in order to evaluate immune response to VC2 virotherapy rather than direct cytotoxic/lytic effects of the virus. The B16F10 model is a notoriously difficult tumor model in which to elicit a therapeutic response due to its aggressively growing nature. Based on the lack of HSV-1 entry receptors and the known poor immunogenicity of the B16F10 cell line (reference), we consider the syngeneic B16F10 murine melanoma model to be a good model for human melanoma patients which respond poorly to current oncolytic virotherapy and other immune modulating cancer therapies, which represent the majority of patients in clinical trials to date. These are the patients with the greatest need for more efficacious and safe therapies and therefore are our target population.

We have further enhanced the model by utilizing B16F10 cells expressing enhanced green fluorescent protein (eGFP) and firefly luciferase (fLuc) for advanced fluorescent microscopy and in vivo tumor monitoring capabilities (B16F10-fLuc-eGFP), respectively. Bioluminescence is the most sensitive method for monitoring tumor progression in vivo. Most often, luciferase-expressing cancer cells are used in models where tumor cells are implanted internally or in experimental metastasis models where the tumor cells are injected directly into the vascular system. In our model system, tumor cells are orthotopically engrafted intradermally in the poorly haired region of the pinna for the ease of visual monitoring and measuring tumors with microcalipers. However, response to therapies intended to stimulate an immune response against tumors are difficult to monitor by traditional microcaliper measurements due to pseudoprogression. Pseudoprogression is the appearance of disease progression clinically or via diagnostic imaging that is occasionally seen in cancer patients receiving immunotherapy treatment. The precise mechanism is poorly defined, but it is hypothesized that pseudoprogression is the result of tumor enlargement secondary to acute inflammation and necrosis, which represent the intended effects of stimulating an immune response against the tumor, rather than true proliferation of the tumor cells. This phenomenon has been observed in melanoma patients being treated with immune checkpoint inhibitors including nivolumab and ipilimumab who show a discrepancy between overall survival time and progression-free interval; patients may appear to acutely progress in response to treatment but ultimately show response manifested as improved overall survival down the road. In most transplantable murine melanoma models, the time frame for generating a therapeutic response with a candidate drug is short. The course of in vivo experiments is limited by outgrowth of the primary tumor since the tumors grow rapidly and often ulcerate quickly after a tumor has become macroscopically visible necessitating euthanasia. When the time course for evaluation of therapeutic response may be as short as one week, sensitive assessment of early response to drugs is critical. As pseudoprogression may result in premature discontinuation of drugs in human patients in clinical trials, it may also lead to premature discontinuation of testing of promising therapeutic in preclinical trials with mouse models. In clinical trials with human patients, treatment may be discontinued, and overall therapeutic efficacy may still be observed as improved overall survival times in some cases. However, in preclinical testing, mice may be euthanized prematurely due to the appearance of rapid tumor growth in response to immune modulating drugs and effect the overall survival times and ultimately the outcome of whether or not to continue the drug development strategy. We aimed to develop an immunocompetent murine melanoma model that allows sensitive observation of tumor growth during immunomodulatory therapy with the highly immunogenic HSV-1 vaccine strain developed in our laboratory, VC2. We developed a model that can detect acute responses using in vivo imaging with greater sensitivity than traditional microcaliper measurement. This model system will be invaluable in evaluating acute response to treatment and testing dosing and combinatorial strategies with higher sensitivity and greater efficiency that traditional microcaliper measurement.

Tumor heterogeneity is also a significant challenge in treating tumors in human patients with targeted therapies including oncolytic viruses and immunotherapies. Nectin-1 expression has been found to be a factor in sensitivity to oncolytic HSV-1 in a xenogeneic immunodeficient murine squamous cell carcinoma model. Therefore, we further created a stably transformed B16F10-fLuc-eGFP murine melanoma cell line that expresses human nectin-1. Modeling patient factors that determine efficacy and safety is critical to developing efficacious and safe dosing regimens in the age of precision medicine. The ability to test dosing strategies on mice with nectin-1 positive versus nectin-1 negative melanoma tumors may be helpful for developing dosing strategies based on patient tumor receptor expression.

Herein, we describe our modeling strategy and results of preliminary efficacy and safety testing of VC2 in a syngeneic, immunocompetent murine melanoma model. Due to potential advantages in replication and safety over the currently available oncolytic virotherapy, and due to the previously demonstrated remarkable immunogenicity of VC2, we aimed to test for efficacy in inhibiting tumor growth and extending survival times in our double-labeled B16F10 syngeneic murine melanoma model in absence of nectin-1 expression and direct, replicative cell lysis. We further aimed to screen for safety and evaluate direct effects on tumor cell proliferation and immune cell infiltration in the TME.

Methods

Cells

B16F10 cells expressing enhanced green fluorescent protein (eGFP) and firefly luciferase (fLuc) were utilized in all experiments. Firefly luciferase detection is the most sensitive method of monitoring tumor growth and progression (reference); this is particularly important in preclinical testing of therapies which involve stimulating an immune response since swelling associated with inflammation often results in "pseudoprogression" and makes response to therapy difficult to evaluate. Fluorescent protein expression enhances sensitivity of detection of metastases at necropsy and also allows for fluorescent microscopy of tumors. B16F10-fLuc-eGFP murine melanoma cells were maintained under sterile conditions at 37° C. with 5% $CO_2$ and propagated as adherent monolayers in T75 flasks containing Dulbecco's Modified Eagle Medium (DMEM) supplemented with 10% filtered, heat inactivated fetal bovine serum (FBS) and 100 ug/ml Primocin. Prior to use, cells were trypsinized, centrifuged, counted using a hemocytometer, and resuspended to the desired concentration in sterile phosphate-buffered saline. Trypan blue exclusion was performed to evaluate cell viability during counting; cell viability was at least 90% for all experiments.

Human Nectin-1 Stable Transfection

In order to confirm that the lack of cytolysis was due to an entry receptor deficiency in B16F10 cells and not a defect in another segment of the replication cycle, we created a stably transfected B16F10-eGFP-fLuc cell line expressing human nectin-1 using an SV40 lentiviral particle packaged vector under the control of a CMV promoter; nectin-1 is tagged with the red fluorescent protein mCherry at the C-terminus.

In Vitro Growth Curve B16F10 and B16F10-fLuc-eGFP.

Prior to engraftment in mice, in vitro growth was evaluated to compare inherent proliferative capacity of B16F10-eGFP-fLuc cells to the parent B16F10 cell line. Cells were seeded at a density of 20,000/well in three 6-well plates. Cells from three wells were collected and counted using a hemocytometer once every 24 hours for 5 days. A growth curve was similarly generated to compare B16F10-fLuc-eGFP and B16F10-fLuc-eGFP-nectin-1 but the initial seeding cell density was 50,000 cells/well.

VC2 Viral Stock Preparation

VC2 stocks were prepared in baby hamster kidney (BHK) cells. T-150 flasks inoculated with virus were maintained under sterile conditions at 37° C. with 5% $CO_2$ for 24-48 hours until cells were rounded up but still adherent. Cells were scraped using a cell scraper and flask contents including cells and spent media were poured into 50 ml tubes. Tubes were centrifuged at, supernatant decanted, pellet submerged in liquid nitrogen until frozen, thawed in a 36 degree? warm water bath, and resuspended in 2 ml of supernatant. Centrifuge and freeze-thaw cycles were repeated 2 more times to free intracellular virions. The pellet was discarded, and the viral stock solution was ultracentrifuged using at 27,000 RPM for 2 hours until a viral pellet was visible. Viral pellet was resuspended in 1 ml of sterile PBS. Concentrated viral stock was titrated on African green monkey kidney (vero) cells; concentration was determined to be $10^9$ plaque forming units (PFU)/ml. Stock was aliquoted into individual doses of $10^6$ PFU in 100 ul of PBS in Eppendorf tubes and stored at −80 degrees.

Tumor Induction and Monitoring

Twenty, 6-8-week-old, female C57BL/6J mice were anesthetized with 2-3% isoflurane and engrafted with 600,000 B16F10-fLuc-eGFP cells suspended in 100 μL of sterile PBS intradermally in the left pinna with a 27-gauge needle on a 1 mL syringe after disinfection with 70% isopropyl alcohol. Tumors were imaged using a Spectra Ami In Vivo Imaging System (IVIS) 10 minutes after intraperitoneal injection of 100 ul of d-luciferin potassium (Biogold) in the week before, during, and after treatment. Tumors were additionally measured every other day using digital micro-calipers; volumes were calculated using the formula for an ellipsoid ($V=(\pi/6)\times L\times W\times H$). Mice were euthanized when tumors averaged 500 $mm^3$. Tumor specific growth rates (SGR) were calculated as the percent change in tumor volume per day from two measured time points ($SGR=\ln(V_2/V_1)/(t_2-t_1)$). At necropsy, tumors were removed with the pinna and weighed using a digital gram scale. Tumor volumes were compared statistically between the control and treatment groups at the time treatment was initiated and at the time of euthanasia for experimental validation; there was no significant difference in tumor volumes or variance in the control and treatment groups at the time treatment or mock-treatment was initiated (student's t test, unpaired, two-tailed P=0.6457; F test, P=0.4727) or at the time of euthanasia (student's t test, unpaired, two-tailed P=0.2781; F test, P=0.4010).

Intratumoral Injections

Intratumoral injection is currently considered the most reliable method to deliver oncolytic HSV-1 (Sanchala et al. (2017) *Front. Pharmacol.* 8:270; Shintani et al. (2011) *Virol. J.* 8:446). A major challenge to utilizing HSV-1 in oncolytic virotherapy, however, is infection efficiency of tumor cells. Id. Strategies to improve intratumoral viral spread have so far included injecting multiple tumors or injection a single tumor in multiple sites; it is advised that doses be given as 3-5 injections or, when given as a single injection, that the volume compose 10-100% of the tumor volume (Sanchala et al. (2017) *Front. Pharmacol.* 8:270; U.S. Pat. App. Pub. No. 2002/0061298 A1). For this reason, we chose to deliver VC2 in up to 4 doses of $10^6$ PFU in volumes of 100 ul when tumors averaged 100 $mm^3$.

Histopathology

Tumors and additional tissues (liver, spleen, lung, kidney, brain, thymus) were fixed in 10% neutral buffered formalin, paraffin embedded, sectioned at 4 μm with a microtome, mounted on glass slides, and stained routinely with hematoxylin and eosino (H&E). Slides were evaluated by a board-certified veterinary pathologist.

Digital Image Analysis of Oncolysis

Whole slides containing H&E-stained sections of tumor were digitally scanned using a Hamamatsu Nanozoomer slide scanner. To objectively evaluate and compare the amount of tumor lysis in VC2-treated and control tumors, Nanozoomer viewing software was used to measure the area ($mm^2$) of tumor and the area of necrosis and results were expressed as % necrosis within histologic section (necrosis $mm^2$/tumor $mm^2\times100\%$). Measurements were made at 1× magnification.

Immunohistochemistry and Semiquantification

Ki-67 proliferation index. Immunohistochemistry for Ki-67 was performed to compare the percentage of cells actively cycling in VC2-treated and mock-treated groups and a Ki-67 proliferation index was determined. Within a 40× high power field, 100 cells were designated as either positive or negative for nuclear immunoreactivity for Ki-67; counting was done using digitally scanned virtual slides and cells were marked with a circle when counted so as not to count any cell more than once in the analysis. Ki-67 proliferation index was expressed as a percentage of positive cells (number of positive cells/100×100%).

Immune infiltration. Immunohistochemistry was performed for immunophenotyping of immune cell infiltrates in the TME. Specifically, staining was performed for CD3 (pan-T cell marker) and IBA-1 (pan-macrophage marker). Because of the prominence of macrophages in the tumor microenvironment, additional characterization included staining for arginase-1, a marker of the M2 phenotype. Slides were evaluated by a board-certified veterinary pathologist and semiquantification was performed; areas of infiltration at the tumor-stroma interface were evaluated and immunoreactive cells were counted in ten 40× high power fields and recorded.

Microvasular density (MVD). Immunohistochemistry for CD31 was performed to highlight vascular profiles within the tumor. MVD was determined by counting vascular profiles in a 20× field (Weidner's method).

Safety Assessments

Mice were observed and body weight recorded daily. Body temperature was also assessed daily using IPT-300 temperature sensing transponders implanted subcutaneously in the subcutis of the interscapular area. Necropsy was performed and vital organs (liver, spleen, lung, kidneys) weighed. Tissues were collected, fixed in 10% neutral buffered formalin, processed routinely, paraffin-embedded, sectioned at 4 μm with a microtome, and stained with hematoxylin and eosin (H&E).

Results

B16F10-fLuc-eGFP and B16F10-fLuc-eGFP-Nectin-1 Melanoma Model Development

Figure 7:
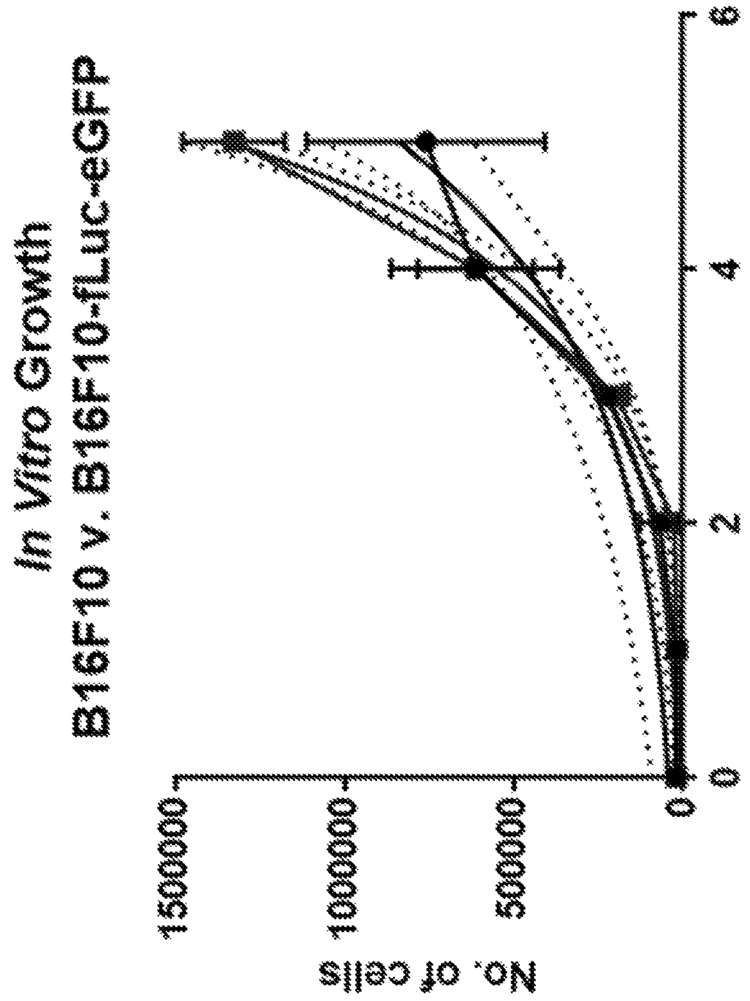
FIG. 7. B16F10 v. B16F10-fLuc-eGFP In Vitro Growth Curve. No significant differences in growth were observed in vitro. Growth fit an exponential growth curve.

In vitro growth curve B16F10 and B16F10-fLuc-eGFP. Prior to engraftment in mice, in vitro growth was evaluated to compare proliferative capacity of B16F10-eGFP-fLuc cells to the parent B16F10 cell line. Cells were seeded at a density of 20,000/well in three 6-well plates. Cells from three wells were collected and counted using a hemocytometer once every 24 hours for 5 days. There was no significant difference in growth between B16F10-eGFP-fLuc cells and the B16F10 parent line (FIG. 7). Growth pattern best fit an exponential growth curve for both B16F10 ($R^2$=0.7687) and B16F10-fLuc-eGFP ($R^2$=0.9645) and doubling times were 1.165 and 0.7732 days, respectively.

Figure 8:
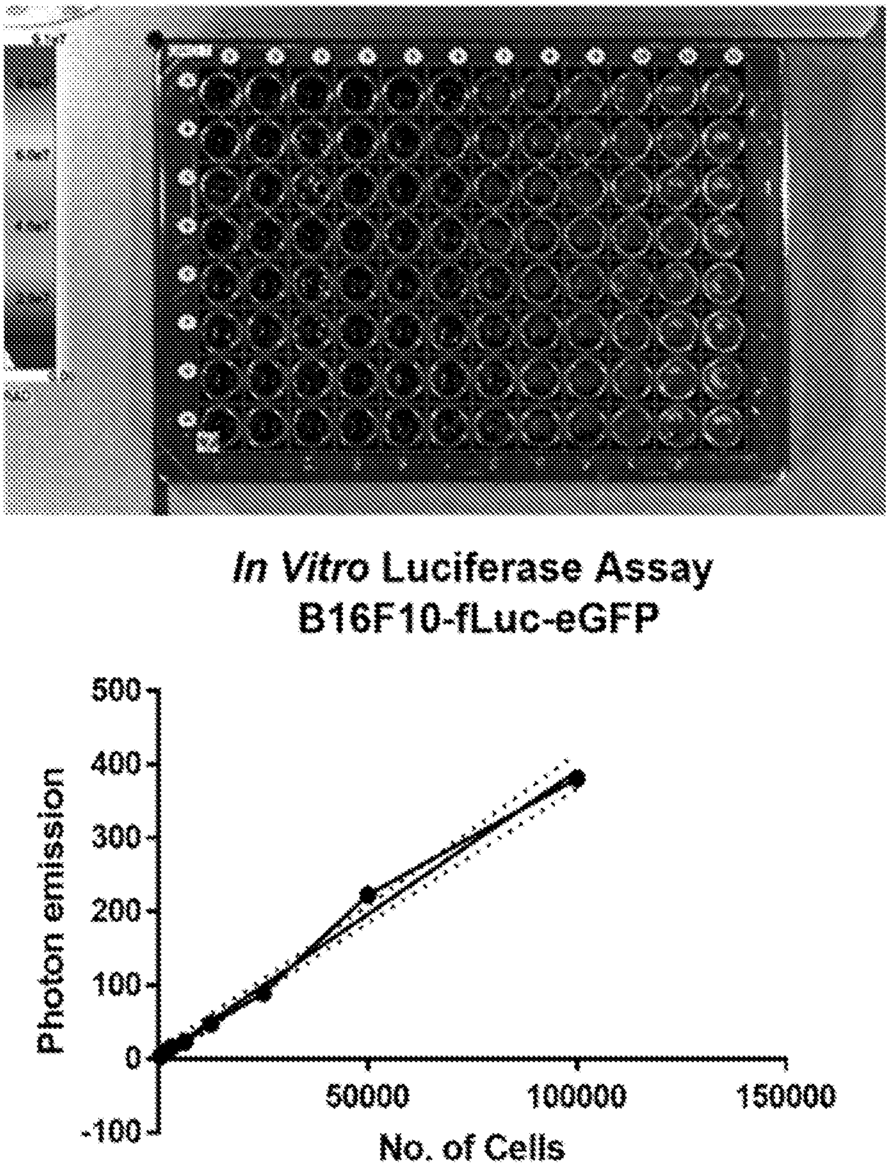
FIG. 8. In Vitro Luciferase Assay. Photon emission significantly correlates with cell number in vitro.

In Vitro Luciferase Assay. B16F10-fLuc-eGFP cells were titrated on a 96-well plate and evaluated using the Spectra Ami imaging system within 10 minutes of applying luciferin substrate. There was strong correlation between the number of cells inoculated per well and photon emission in vitro (FIG. 8) (Pearson r=0.9966; P<0.0001****).

Figure 9:
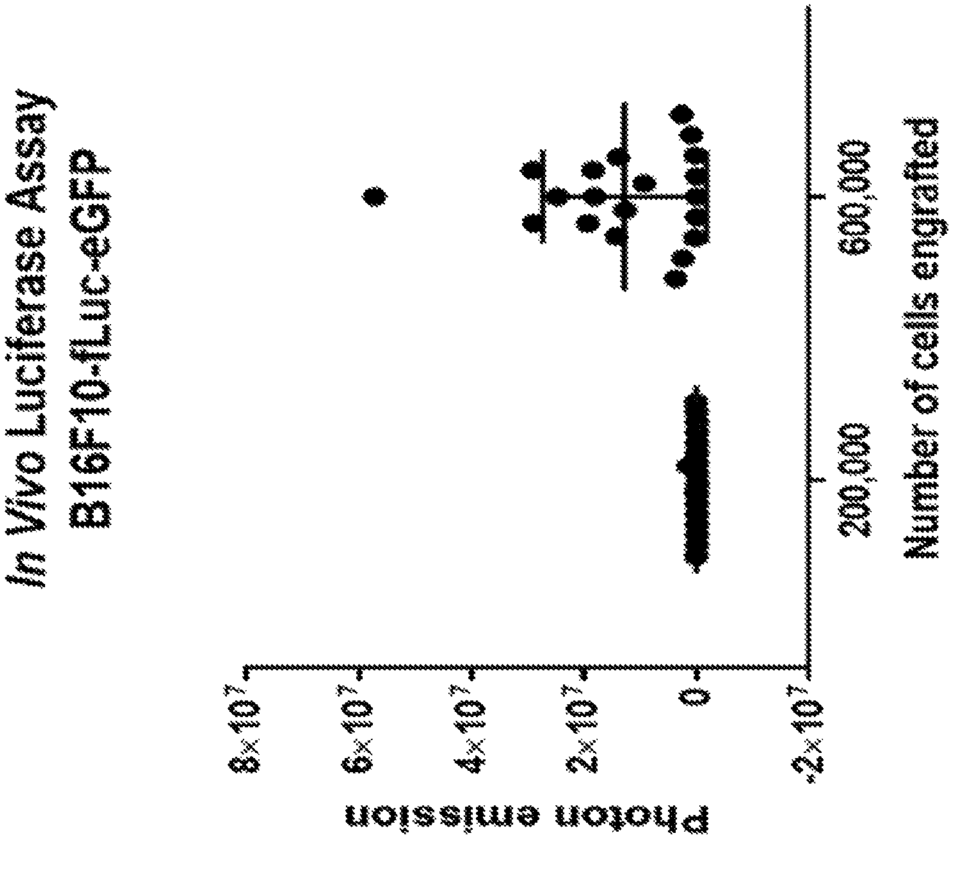
FIG. 9. In Vivo Luciferase Assay. There was significant correlation with engrafted number of cells and photon emission in vivo. More variation resulted when a higher number of cells are engrafted. $2\times10^5$ cells was the lower limit of detection in vivo.

In Vivo Luciferase Assay. In order to determine whether luciferase expression correlated with cell number in vivo, mice were engrafted with $2\times10^5$ or $6\times10^5$ cells in each pinna (FIG. 9). Mice were imaged within an hour of engraftment approximately 10 minutes after intraperitoneal administration of luciferin. Significant correlation between the number of cells engrafted and bioluminescence was detected (Pearson r=0.5268; P=0.0007*). Engraftment technique was evaluated statistically using an unpaired, two-tailed student's t test. As would be expected, photon emission was significantly higher in mice engrafted with $6\times10^5$ cells versus $2\times10^5$ cells (P=0.0007*); however, variance in photon emission was also significantly higher in mice engrafted with $6\times10^5$ cells (P<0.0001****).

In Vivo Enhanced Green Fluorescent Protein (eGFP) Expression. B16F10-fLuc-eGFP melanoma tumors expressed eGFP in vivo. Fluorescence microscopy aids in detection of micrometastases in the sentinel lymph nodes at postmortem examination. Expression of fluorescent proteins is the only technique to achieve single cell resolution in a whole tumor ex vivo or using intravital microscopy.

Stable transfection of B16F10-fLuc-eGFP murine melanoma cells with human nectin-1. B16F10 murine melanoma cells have typically been regarded as non-permissible to HSV-1 infection. However, after in vitro infection with VC2, virus can be detected in the cytoplasm via immunofluorescent microscopy, but significant cytolysis was not observed (not shown). In cells which lack entry receptors, HSV-1 enters via atypical endocytosis/phagocytosis but replication may not occur. Nectin-1 receptor expression has been shown to be a marker of sensitivity to oncolytic herpesvirus treatment in another common skin cancer, squamous cell carcinoma. In order to evaluate whether lack of cytolysis was due to an entry receptor deficiency in B16F10 cells, we created a stably transfected B16F10-fLuc-eGFP cell line with human nectin-1; nectin-1 was tagged with the red fluorescent protein mCherry fused to the C-terminus to create the B16F10-fLuc-eGFP-nectin-1 line. Transfected cells strongly, diffusely expressed red fluorescent protein on the plasma membrane and emitted a yellow color after merging due to co-localization with the eGFP expressing cell line (not shown).

Figure 10:
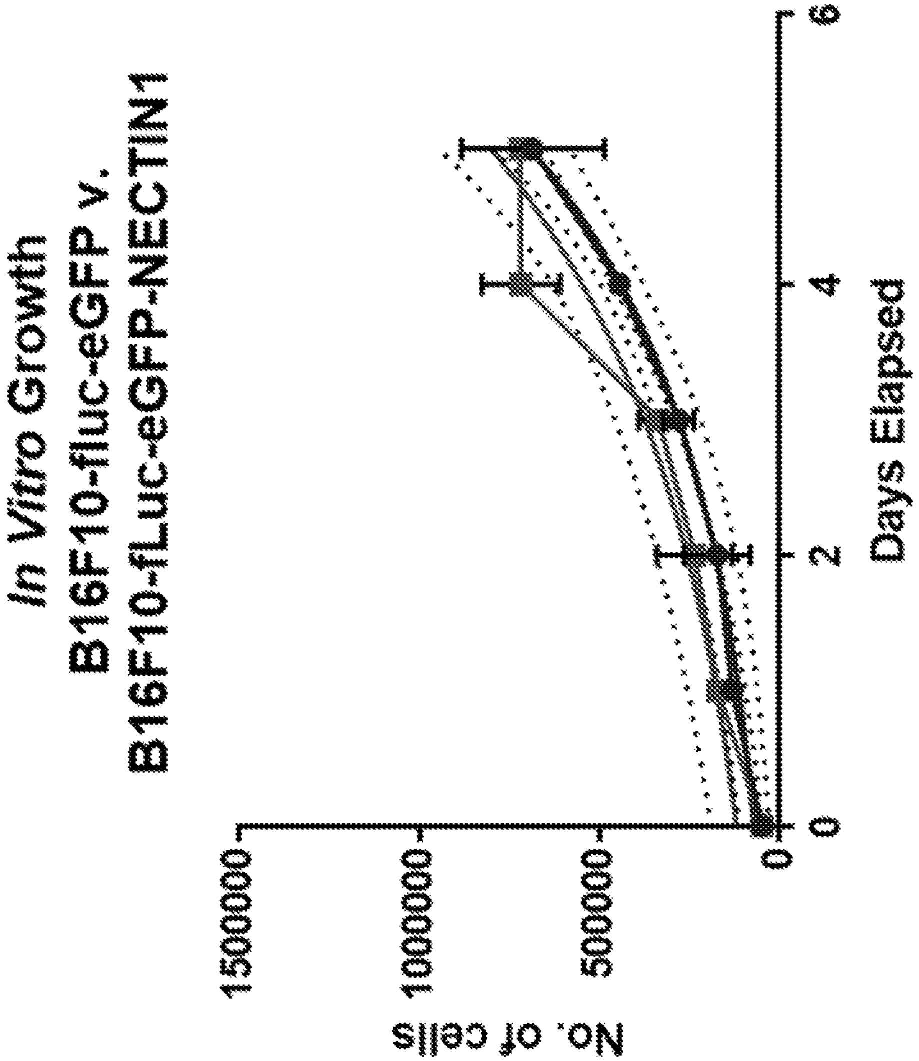
FIG. 10. B16F10-fLuc-eGFP and B16F10-fLuc-eGFP-nectin-1 In Vitro Growth Curve.

In Vitro Growth Curve B16F10-fLuc-eGFP and B16F10-fLuc-eGFP-nectin-1. We evaluated in vitro growth of the nectin-1 expressing line in comparison to the parental line, B16F10-fLuc-eGFP (FIG. 10). There was no significant difference between cell lines at any time point over the course of five days. The B16F10-fLuc-eGFP and B16F10-fLuc-eGFP-nectin-1 cell lines had doubling times of 1.544 and 1.839 days, respectively. An exponential growth curve fit both B16F10-fLuc-eGFP ($R^2$=0.9129) and B16F10-fLuc-eGFP-nectin-1 ($R^2$=0.8685) cell lines.

Figure 11A:
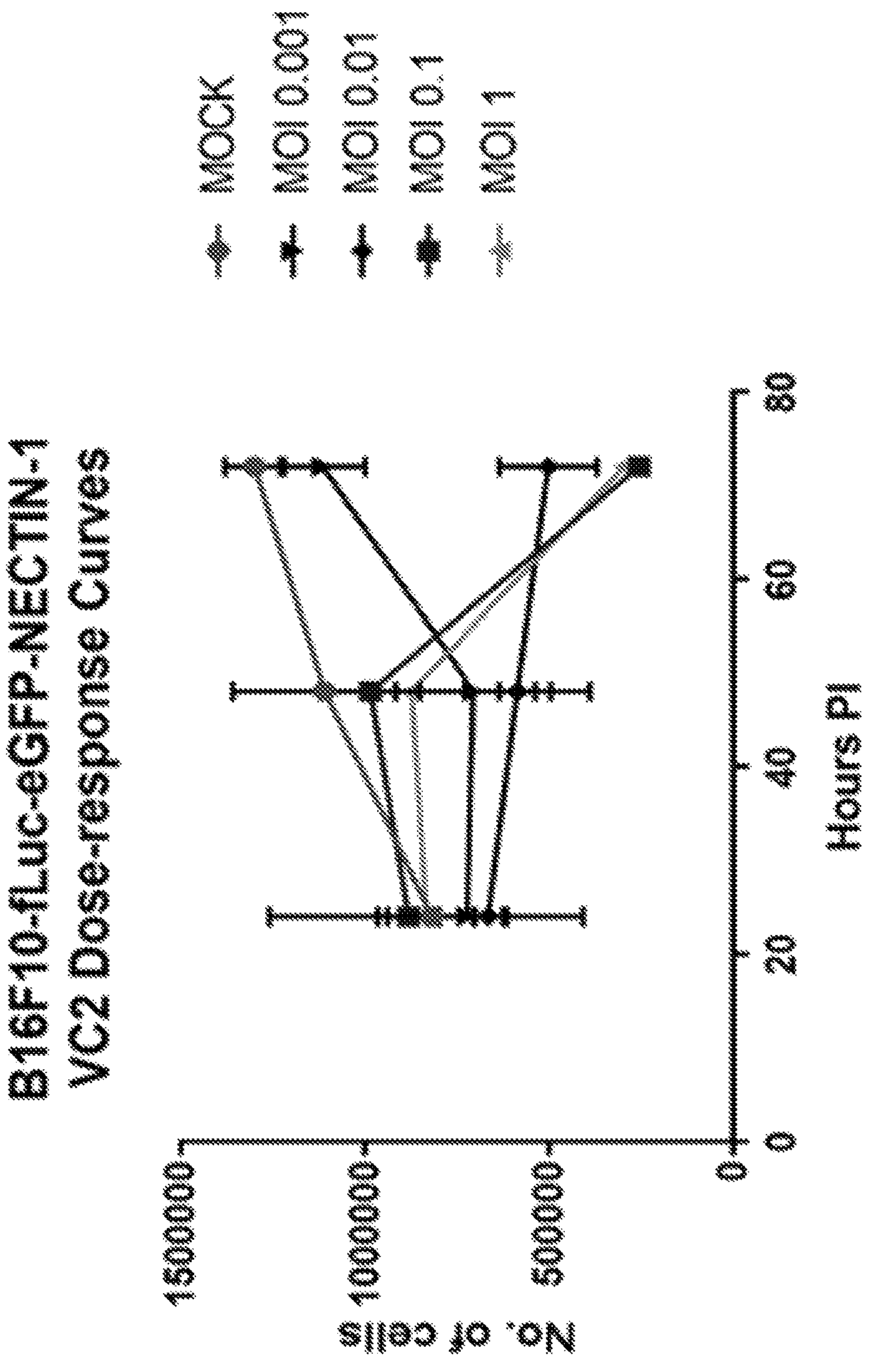
FIGS. 11A-11-C. In Vitro VC2 Dose-response Curves for B16F10-fLuc-eGFP-nectin-1 (FIG. 11A), B16F10-fLuc-eGFP (FIG. 11B), and Composite (FIG. 11C).
Figure 11B:
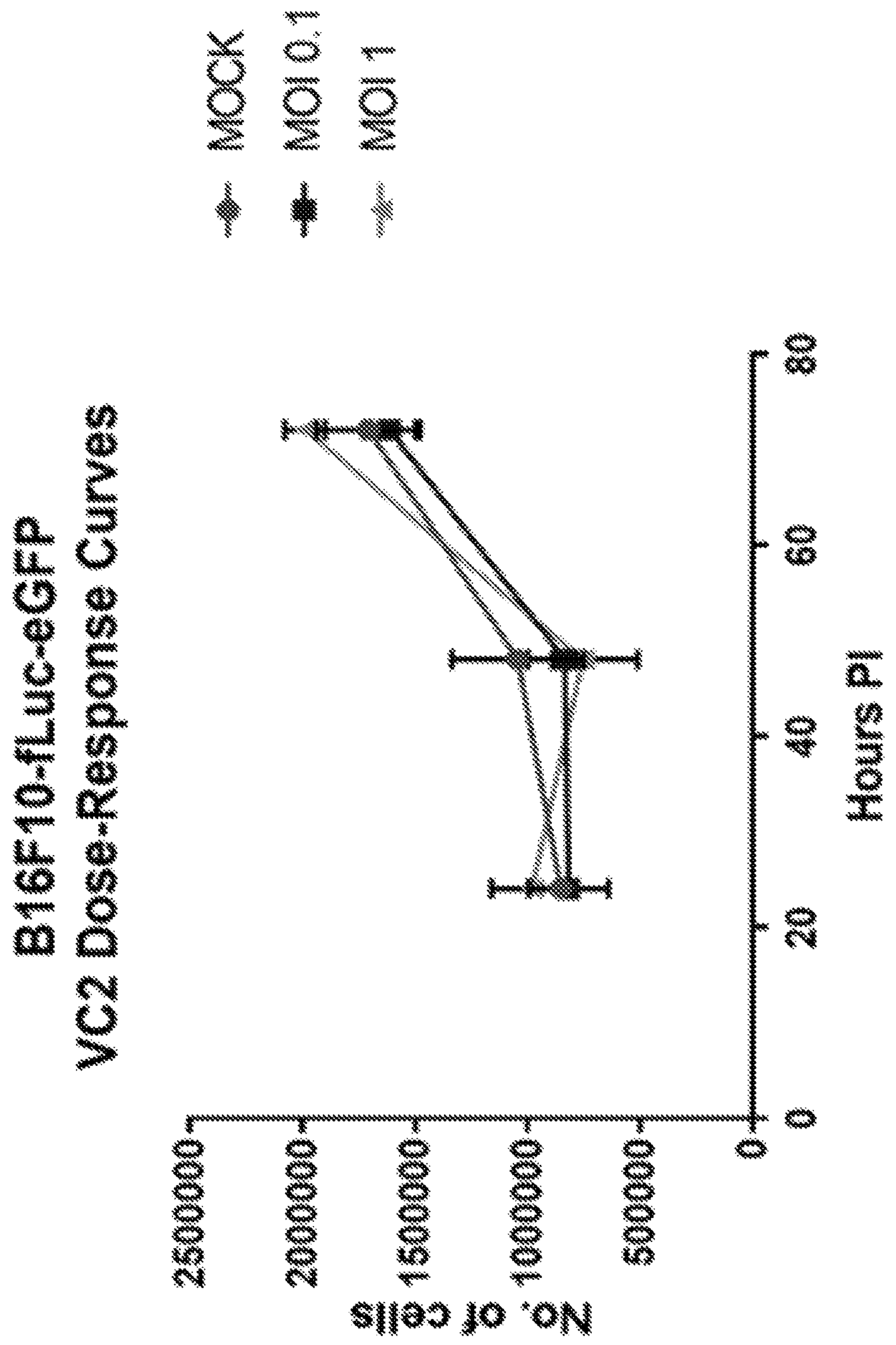
Figure 11C:
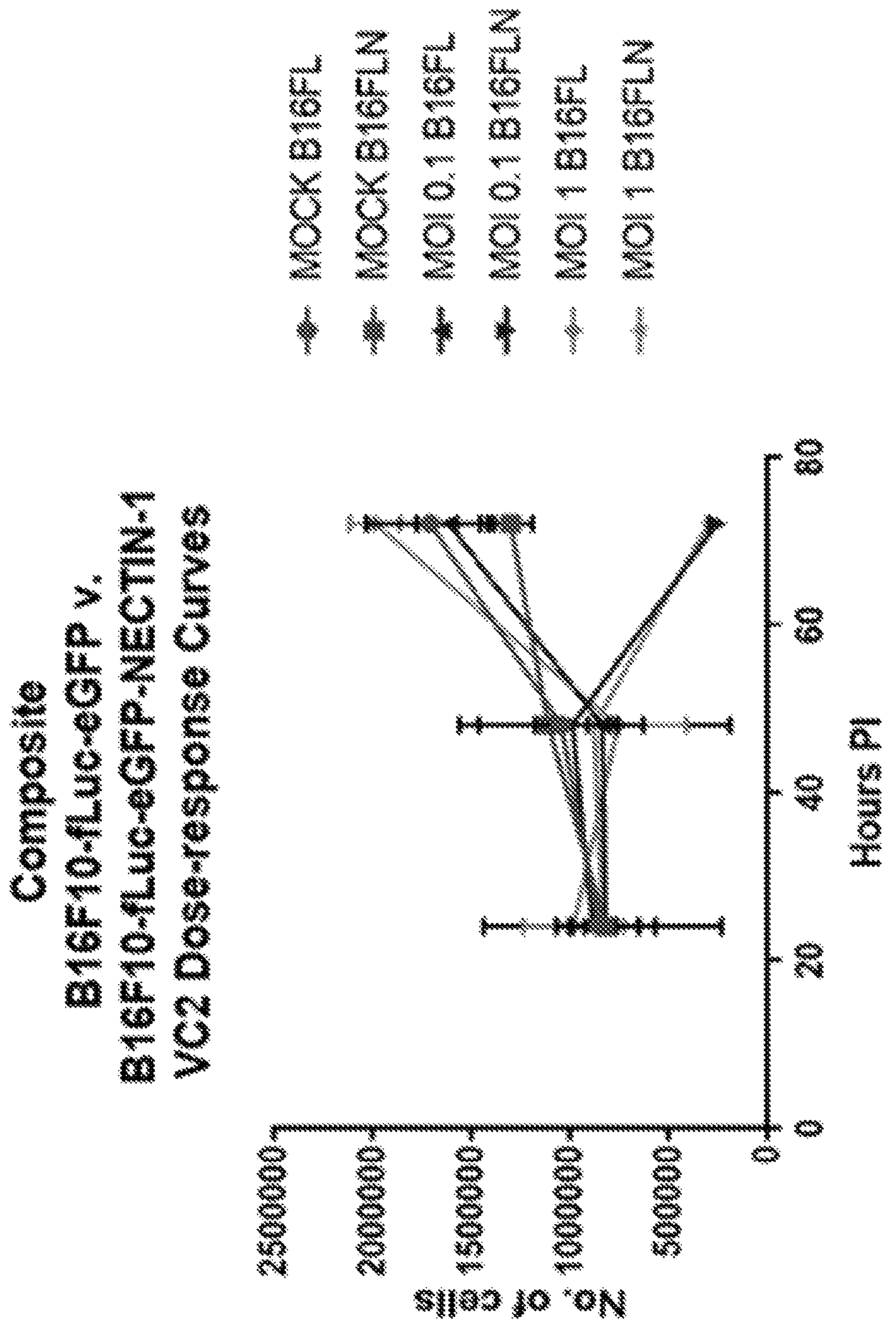

In vitro VC2 infections in B16F10-fLuc-eGFP and B16F10-fLuc-eGFP-nectin-1 cells. B16F10-fLuc-eGFP-nectin-1 cells were infected with VC2 at an MOI of 0.001, 0.01, 0.1, and 1.0 and cells were examined using fluorescent microscopy prior to trypsinization and counting of live cells using trypan blue exclusion assay once every 24 hours for 3 days post infection (FIGS. 11A-11C). There was no significant growth inhibition of B16F10-fLuc-eGFP-nectin-1 cells at 24 and 48 hours at any MOI evaluated in comparison to mock-infected cells. At 72 hours, there was no difference between MOI 0.001 and mock-infected cells, but there was significant decrease in live cells at MOI 0.1 (P=0.0119*) and 1.0 (P=0.0158*); cells infected with an MOI of 0.01 approached significant growth inhibition (P=0.0668). In comparison, B16F10-fLuc-eGFP cells were not significantly decreased at any time point over the full 72 hours at an MOI of 0.01, 0.1, or 1.0 in comparison to mock-treated control wells. Cytolytic effect was increased in nectin-1 receptor containing cells in a dose and time-dependent manner.

Figure 12:
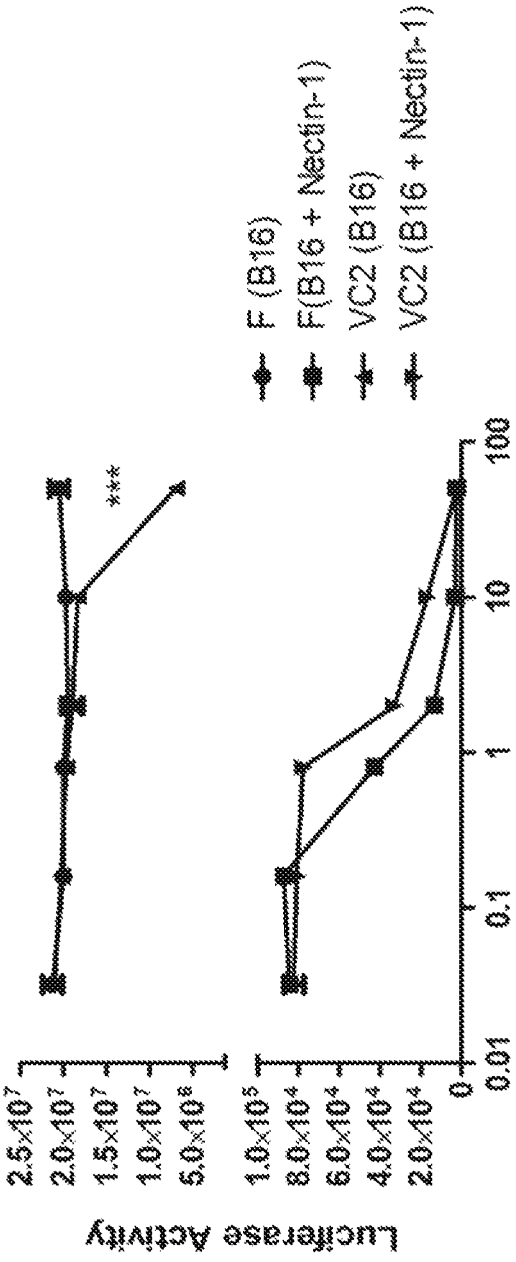
FIG. 12. In vitro Bioluminescence Cytotoxicity Assay B16F10-fLuc-eGFP and B16F10-fLuc-eGFP-nectin-1.

Bioluminescence cytotoxicity assay. The ability to detect cell death related to VC2 infection via bioluminescence was assessed. Cells were infected at an MOI of 0.1, 1.0, 10, and 100. Results of the bioluminescence cytotoxicity assay were similar to that found from trypan blue exclusion assay (FIG. 12). Significant cytotoxicity and reduction of bioluminescent signal was not observed with VC2 infection of B16F10-fLuc-eGFP except at MOI 100, but cell viability and bioluminescence were significantly decreased when B16F10-fLuc-eGFP cells expressing human nectin-1 were infected.

Figure 13:
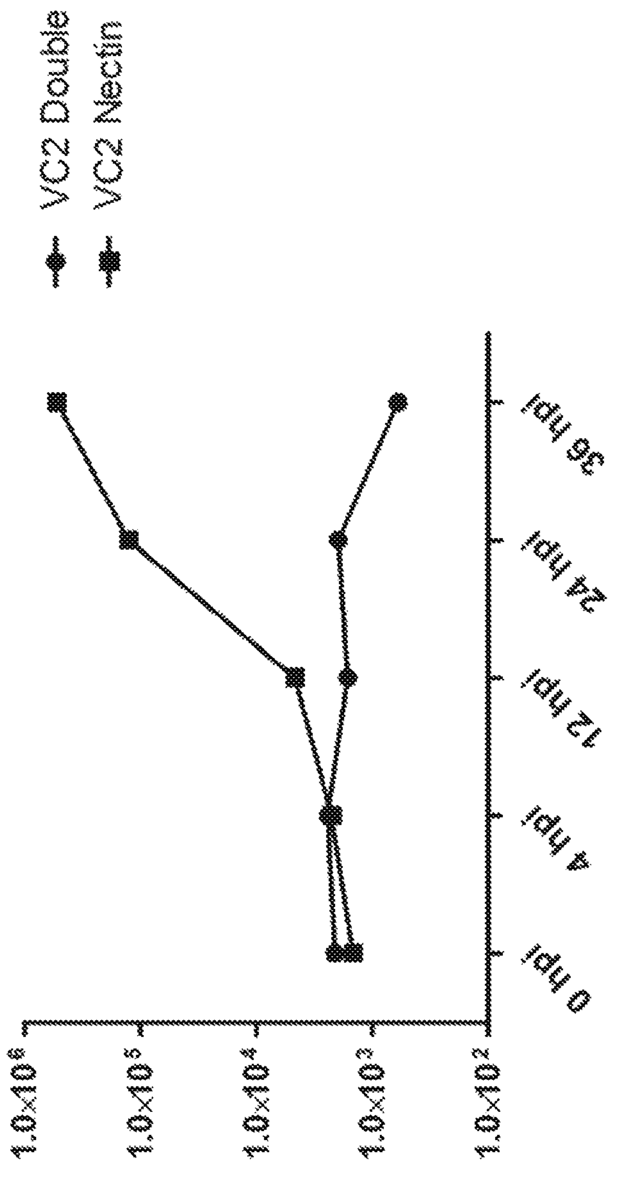
FIG. 13. In Vitro VC2 replication curves B16F10-fLuc-eGFP and B16F10-fLuc-eGFP-nectin-1.

VC2 replication in B16F10-fLuc-eGFP versus B16F10-fLuc-eGFP-nectin-1. Additionally, VC2 grew to higher titers in B16F10-fLuc-eGFP-nectin-1 cells than in the B16F10-fLuc-eGFP cells lacking nectin-1 expression (FIG. 13).

In Vivo B16F10-fLuc-eGFP and B16F10-fLuc-eGFP-nectin-1 Engraftment Efficiency. Engraftment rate was evaluated using a cell density inoculum of $2\times10^5$ cells and $6\times10^5$ cells. When mice were engrafted with the higher cell density, ⅘ or 80% developed a macroscopic tumor (not shown), while only ⅗ or 60% developed a tumor when engrafted with $2\times10^5$ cells (not shown). B16F10-fLuc-eGFP cells expressing human nectin-1 formed tumors in immunocompetent mice; however engraftment efficiency was reduced in comparison to the nectin-1-negative cell line when $6\times10^5$ were similarly engrafted in the pinna with only ⅗ or 60% of animals forming a macroscopic tumor within a two to three week time frame. Nectin-1 expression was observed within tumors via fluorescent microscopy demonstrating red fluorescence. Nectin-1 receptors also appeared to be functional within tumors since immunohistochemical staining for HSV-1 showed strong immunoreactivity in necrotic areas at 72 hours post-infection. Nectin-1-expressing tumors had extensive areas of intratumoral necrosis in comparison with nectin-1 negative tumors even in uninfected controls. Comparison of necrosis in VC2 treated nectin-1 positive and nectin-1 negative cells after infection is therefore not possible due to the phenotype difference induced by nectin-1 expression.

To summarize our findings during development of the B16F10-fLuc-eGFP/nectin-1 syngeneic murine melanoma model, we found that expression of luciferase and enhanced green fluorescent protein had no effect on tumor cell growth in comparison to the parental B16F10 cell line in vitro. Further, stable transfection of the human nectin-1 receptor also had no negative impact on in vitro cell tumor cell growth. We showed that bioluminescence correlates with cell number in vitro and in vivo after engraftment in mice. We determined that nectin-1 expression is an important factor in tumor cell lysis in the B16F10-fLuc-eGFP murine melanoma cell line in response to VC2 infection in vitro and that lysis occurs in a dose-dependent manner. In vivo, we found that B16F10-fLuc-eGFP cells express the luciferase and eGFP reporter genes well and form tumors in immunocompetent mice with acceptable tumor induction rates; B16F10-fLuc-eGFP-nectin-1 cells also form tumors but with reduced engraftment efficiency. B16F10-fLuc-eGFP-nectin-1 tumors express nectin-1 receptors in vivo which are functional for VC2 entry based on immunohistochemical staining for HSV-1 within tumors.

VC2 Efficacy Assessment in the B16F10-fLuc-eGFP Model.

During model development, we found that VC2 only resulted in significant cytotoxicity of tumor cells in the presence of nectin-1 receptors in vitro. However, in vitro cytotoxicity testing cannot account for host immune responses and immunogenic cell death, which have been shown to be important in generating effective, durable anti-tumor immune responses. We aimed to test the ability of our model to evaluate therapeutic response to the highly immunogenic VC2 HSV-1 live attenuated vaccine strain administered intratumorally in absence of a direct cytolytic effect. We hypothesized that immunogenicity of the virus alone could have a strong adjuvant effect in stimulating anti-tumor immune responses and have a therapeutic immune-modulating effects in the tumor microenvironment. We also hypothesized that bioluminescence would be more sensitive for detection of therapeutic response than tumor volume in the face of an inflamed tumor microenvironment, an intended effect of immunogenic, immune-modulating VC2 virotherapy. Improved overall survival was the desired endpoint.

Twenty 8-10-week-old female C57BL/6 mice with B16F10-fLuc-eGFP melanoma tumors on the pinna were divided into two groups, a control group consisting of nine mice and a treatment group consisting of 11 mice. Tumors averaged approximately 100 $mm^3$ when VC2 or mock treatment with PBS was initiated and animals were euthanized when tumors had grown significantly (P=0.0001***) averaging 500 $mm^3$; no significant differences were found in tumor volume between the two groups prior to the initiation of therapy or at the time of postmortem examination.

Up to four doses of $1\times10^6$ PFU of VC2 in 100 ul were administered intratumorally to the treated group within a week's time, while mock-treated mice received the same volume and dosing frequency of PBS. All 20 animals were monitored for tumor growth using measurement with digital microcalipers during the course of treatment to monitor progression of the primary tumor. Four mock-treated control mice and eight VC2-treated mice were also monitored using in vivo imaging to detect tumor bioluminescence during the week of treatment with VC2 virotherapy to assess the utility of bioluminescent imaging to detect acute response to intratumoral virotherapy treatment in comparison to traditional microcaliper measurement.

Figure 14A:
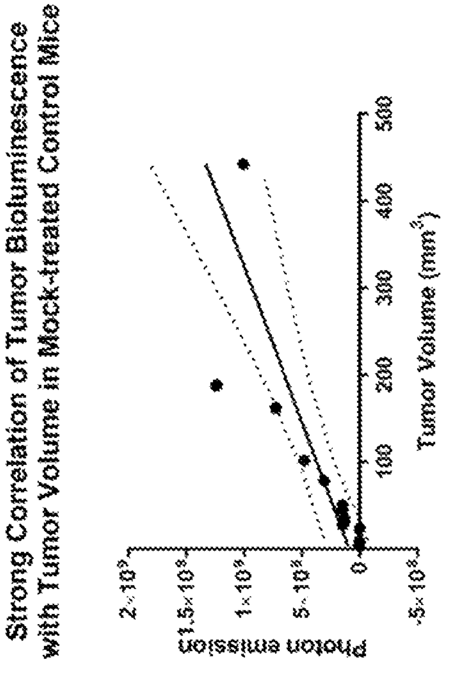
FIGS. 14A-14B. Correlation of bioluminescence and tumor volume in mock-treated (FIG. 14A) and VC2-treated mice (FIG. 14B) during the week of treatment.
Figure 14B:
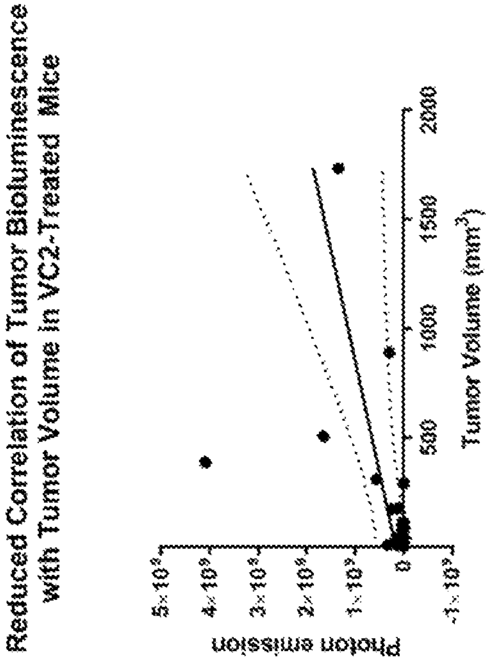

Prior to initiation of VC2 virotherapy or mock treatment with PBS, there was highly significant correlation between tumor volume and photon emission from tumors during bioluminescent in vivo imaging (Pearson r correlation coefficient=0.8549, P=0.0004***). However, when paired tumor volume and tumor bioluminescence values were compared during the week of treatment, there was reduced correlation in the VC2-treated group (Pearson r correlation coefficient=0.4225; P=0.0354*) in comparison to the mock-treated control group, in which tumor volume and bioluminescence correlated strongly (Pearson r correlation coefficient=0.8258; P=0.0009*) (FIGS. 14A-14B**).

When growth curves were produced and superimposed on each other for individual animals based on tumor volume and tumor bioluminescence, we found that the tumor growth trends generally paralleled each other for the control group, but growth curves frequently showed differing trends in the VC2 treated group depending on whether tumor volume or bioluminescence was assessed (not shown). Tumor bioluminescence was often decreasing in the VC2-treated group despite the appearance of increasing tumor volume. Based on the highly immunogenic nature of the VC2 vaccine, we hypothesized that the discrepancy could be due to acute necrosis and inflammation associated with acute immune response to the virus. We suspected that the immune-stimulating effects in the tumor microenvironment resulted in tumor swelling or "pseudoprogression" rather than true tumor cell proliferation and progression. We therefore aimed to evaluate and compare tumor necrosis and inflammation within the tumor microenvironment in the VC2 and mock-treated control groups.

Tumor Necrosis (Oncolysis)

HSV-1 is regarded as having a lytic life cycle, since death of the host cell is the ultimate outcome of productive infection. We aimed to evaluate the amount of tumor lysis we could detect on histopathology from tumors treated with VC2 versus mock-injected tumors. In order to objectively quantify the amount of lysis present, we used digital image analysis to outline and quantify the area ($mm^2$) of the tumor section and the area of necrosis and express the value as percent necrosis within the tissue section We found that there was a trend towards increased tumor lysis in sections from VC2-treated tumors, although differences were not statistically significant (unpaired, two-tailed, student t test; P=0.3890). However, as survival was our endpoint, animals were euthanized at varying time periods based on perceived clinical disease progression. Therefore, we thought it was possible that the amount of necrosis could vary with regard to the amount of time that passed before euthanasia occurred. In the VC2-treated group, larger areas of necrosis were observed when sections of the tumor were examined with more proximity to the time of the last VC2 injection (Pearson r correlation coefficient=−0.7833; P=0.0125*). In order to ensure this correlation was not a mechanical effect resulting from injection, we also evaluated the control group separately and found no significant correlation between the amount of necrosis on histopathology and the time elapsed post-injection of PBS (Pearson r (correlation coefficient)=−0.503; P=0.3073). Although there were no significant differences in size of tumors between the VC2 and mock-treated groups at the time of necropsy, we wanted to rule out the possibility that increased necrosis may be related to the size of the tumor rather than the time elapsed after injection of virus. No correlation was found for size and degree of necrosis for the control (Pearson r (correlation coefficient)= −0.2902; P=0.5769) or VC2-treated groups (Pearson r (correlation coefficient)=−0.05462; P=0.8890). Our interpretation is that increased necrosis/tumor lysis may be more evident at earlier time points after VC2 treatment based on our analysis showing increased tumor necrosis when less time elapsed between VC2 treatment and examination of tumor tissue. We also performed immunohistochemistry for HSV-1 on a tumor that was inoculated with VC2 6 days prior. We found marked cytoplasmic immunoreactivity in the cytoplasm, which was more intense in cells adjacent to areas of intratumoral lysis (not shown). Although VC2 likely replicates in stroma and other cells in the tumor microenvironment more efficiently than the B16F10-fLuc-eGFP tumor cells lacking nectin-1, immunofluorescent staining showed VC2 co-localized to the cytoplasm and cell membrane in some areas of the tumor (not shown).

Response to VC2 in the Tumor Microenvironment

We hypothesized that the highly immunogenic VC2 vaccine would stimulate an immune response in the tumor microenvironment. We observed that although there was no statistical difference in tumor volumes at necropsy between VC2 and control groups (P=0.2781), tumor mass at necropsy was increased for VC2 treated animals (P=0.0287). We suspected this increase in tumor mass could be related to increased infiltration by immune cells. We also suspected the previously mentioned discrepancy in correlation between tumor bioluminescence and tumor volume during VC2 treatment could have been the result of increased inflammation in the tumor microenvironment in VC2-treated mice, which resulted in increasing tumor volumes and the clinical perception of tumor progression although bioluminescent imaging suggested tumors were regressing. We therefore aimed to evaluate whether mice treated with VC2 had evidence of enhanced immune responses in the tumor microenvironment compared to mock-treated control mice using immunohistochemistry.

We found that in VC2-treated mice, macrophages were significantly increased in the tumor microenvironment (unpaired, two-tailed t test; P=0.0033); importantly, we also found that arginase-1 expression, a typical marker of the anti-inflammatory, protumorigenic M2 macrophage phenotype in mice, was decreased (unpaired, two-tailed t test, P=0.0003) in comparison to mock-treated controls. The increase in macrophages was also accompanied by an increase in CD3+ T cells in the tumor microenvironment (unpaired, two-tailed t test; P=0.0458). Infiltration by T cells is a positive prognostic indicator in human patients with melanoma and is frequently observed in biopsies of patients with regressing lesions.

Microvascular Density

Although B16F10 cells themselves support only non-productive infection with VC2, other cell types in the tumor microenvironment would be expected to be able to support robust replication including fibroblasts and endothelial cells. B16F10-fLuc-eGFP tumors are markedly vascular, containing tortuous tumor-associated vessels (not shown). We hypothesized that VC2-treated tumors may have reduced vascularity due to destruction via viral replication, destruction via inflammation as a bystander response, or as a result of decreased numbers of M2 macrophages which produce abundant vasculogenic VEGF. Microvascular density was slightly reduced in VC2-treated mice and approached statistical significance (unpaired t test, P=0.0617).

Overall Survival

Figure 15:
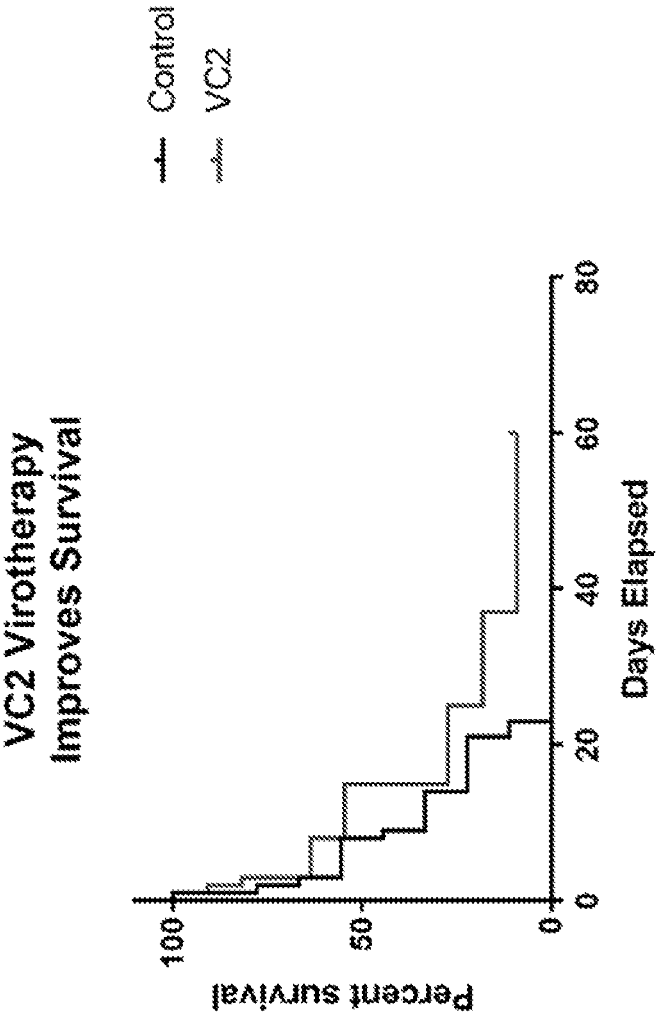
FIG. 15. Kaplan Meier Survival Curve.

VC2-treated mice trended towards increased survival times in comparison with mock-treated animals. Mice that received VC2 treatment had a median survival time of 15 days, almost twice that of control mice which was 8 days, although the difference in survival was not found to be significant when a Kaplan Meier curve and log-rank test were generated (P=0.153) (FIG. 15); notably, one VC2-treated mouse had a complete response with no sign of disease more than 180 days after treatment.

Figure 16:
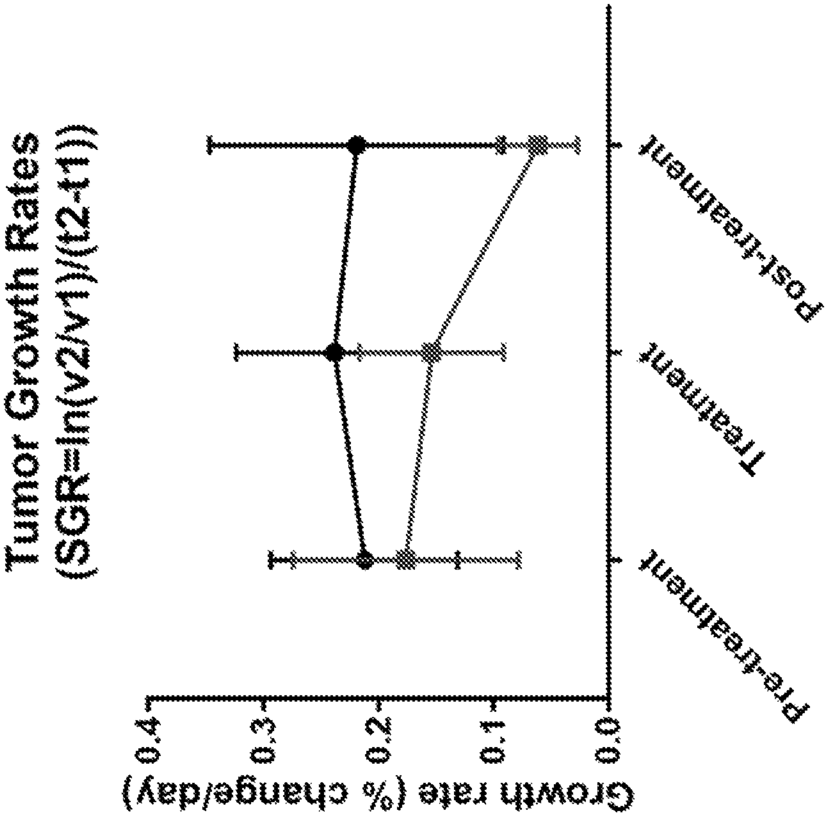
FIG. 16. Decreased growth rates in VC2 treated mice in the week during and after treatment.
Figure 17A:
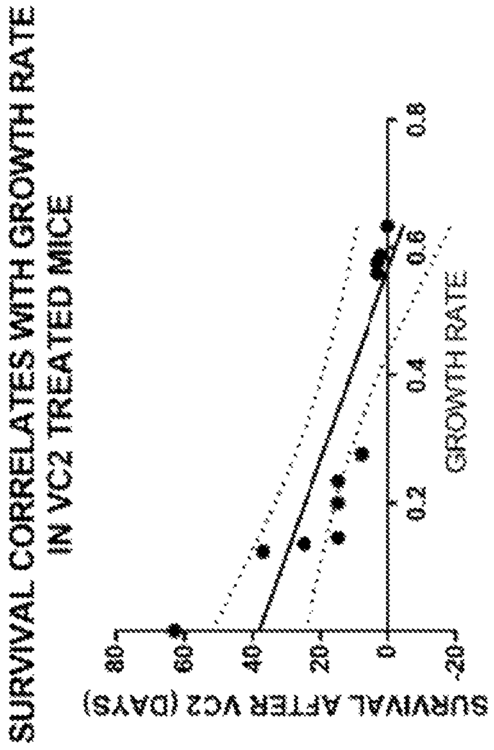
FIGS. 17A-17D. Survival is significantly correlated with tumor growth rates and initial tumor volume at the time treatment was initiated in VC2-treated but not mock-treated mice.
Figure 17B:
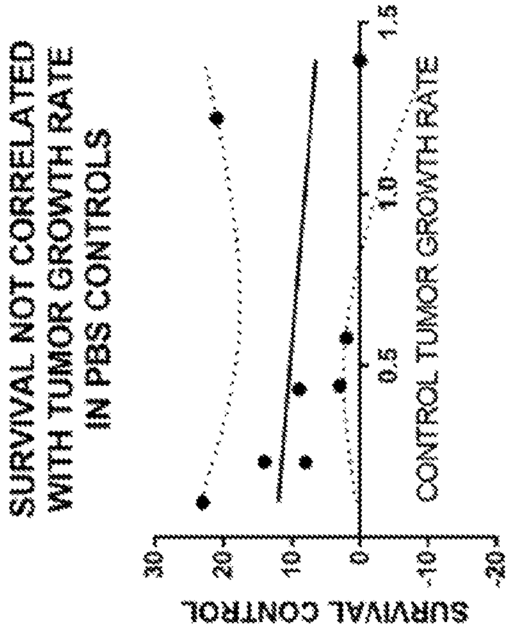
Figure 17D:
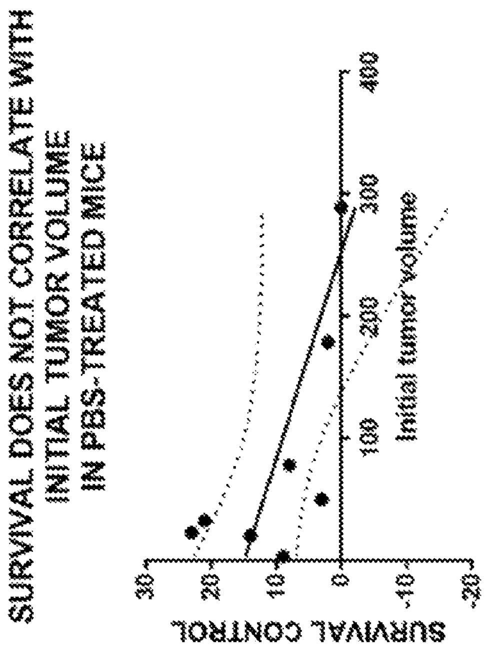
Figure 17C:
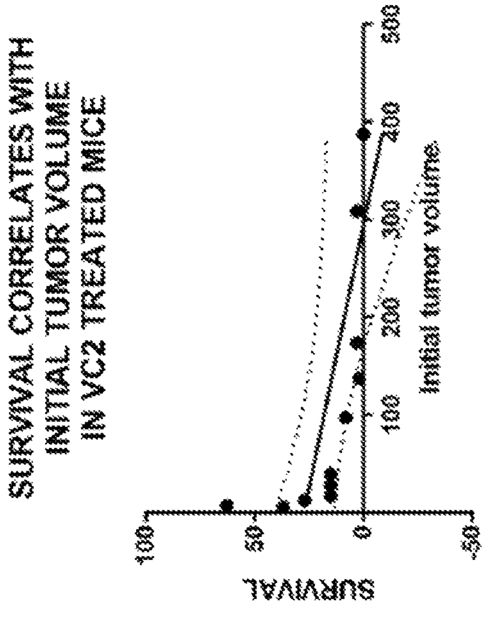

Primary tumor growth is the major limiting factor in survival in most transplantable murine tumor models. For this reason, we wanted to evaluate what effect, if any, VC2 had on tumor growth rates. Tumor specific growth rate (SGR) is calculated using tumor volumes over time. Growth rates were evaluated for control and VC2-treated animals the week before treatment, the week during treatment, and the week following treatment using the formula, $SGR=\ln(V_2/V_1)/(t_2-t_1)$, which calculates the percent change in tumor volume per day from two measured time points. VC2-treated mice trended towards decreasing growth rates during treatment in comparison to mock-treated controls, but differences between the two groups were not statistically significant (FIG. 16). The reduction in tumor growth rates may be underestimated since the formula is based on tumor volumes rather than bioluminescence which detects responses with greater sensitivity. When overall growth rates were calculated and compared with regard to survival time, we found differences in the impact of overall specific growth rate on overall survival between mock-treated and VC2-treated mice. There was no correlation in growth rate and overall survival in mock-treated mice ((Pearson r (correlation coefficient)=−0.2379; P=0.5705) (FIGS. 17B, 17D), while VC2-treated mice showed a significant, negative correlation ((Pearson r (correlation coefficient)=−0.8159; P=0.0022) (FIGS. 17A, 17C). In the treated group, animals with slower growth rates lived longer. Our interpretation is that mock treatment had no effect on growth rates, and therefore no relationship could be established when evaluated for correlation with survival.

Response to immune modulating cancer therapies, and oncolytic virotherapy specifically, varies markedly in human patients as previously mentioned. Additionally, high variability in response within treatment groups is typical in immuno-oncology studies involving preclinical testing of immunotherapies in mice in comparison to more traditional pharmacology studies (Li et al. (2017) *Pharmacol. Ther.* 173:34-46). We therefore desired to identify any factor that could have led to improved responses, i.e. longer survival times, in some animals treated with VC2 as compared to other animals within the treatment group. We found that tumor volume at the time treatment was initiated correlated significantly with overall survival in the VC2 treated group, but not the control group. Although tumor volumes averaged 100 $mm^3$ at the start of treatment, some variation in individual tumor volumes between mice at the time treatment was noted; however, as was demonstrated in FIG. 14B there was no statistical difference in tumor volumes between VC2 and control groups prior to experimental manipulation (unpaired t test, P=0.6457) and variance between the two groups was also insignificant (F test, P=0.4727). Nonetheless, there was a significant, direct, negative correlation between the tumor volume at the start of initiation of treatment and overall survival (Pearson r (correlation coefficient)=−0.6397; P=0.0340) (FIGS. 17A, 17C). Put simply, animals treated with VC2 lived longer when treatment was initiated when the tumors were smaller. This is in concordance with a survey of preclinical immuno-oncology studies which showed that only small tumors typically responded well, and only resulted in delayed tumor growth (Li et al. (2017) *Pharmacol. Ther.* 173:34-46; Wen et al. (2012) *Oncoimmunology* 1:172-178). There was no significant correlation between initial tumor volume and survival times for the control group (Pearson r (correlation coefficient)=−0.0559; P=0.8954) (FIGS. 17B, 17D). We wondered if smaller tumors simply grew more slowly and may not be a result of treatment. This was not the case. When we looked for a relationship between tumor size and growth rate, control mice showed no significant correlation (Pearson r (correlation coefficient)=−0.6146; P=0.1049), while there appeared to be a strongly significant relationship between starting tumor size and growth rate in the VC2-treated mice (Pearson r (correlation coefficient)=−0.8772; P=0.0005). Mice that received VC2 treatment had slower overall growth rates than mice that received mock treatment, and slower growth rates correlated significantly with smaller tumors at the time therapy was initiated. Since all animals received a dose of $1\times10^6$ PFU per injection, tumors that were slightly smaller, in essence, received a higher dose. The finding that mice treated with tumors which were smaller had reduced tumor growth rates and that those reduced growth rates correlated with longer survival times, suggest that VC2 may reduce tumor growth rates and extend overall survival in a dose-dependent manner even in absence of the entry receptor, nectin-1. We hypothesized that reduced cell cycling could be another mechanism by which VC2 exerts effects in controlling and slowing tumor growth.

Cell Cycling—Tumor Ki-67 Index.

Figure 18:
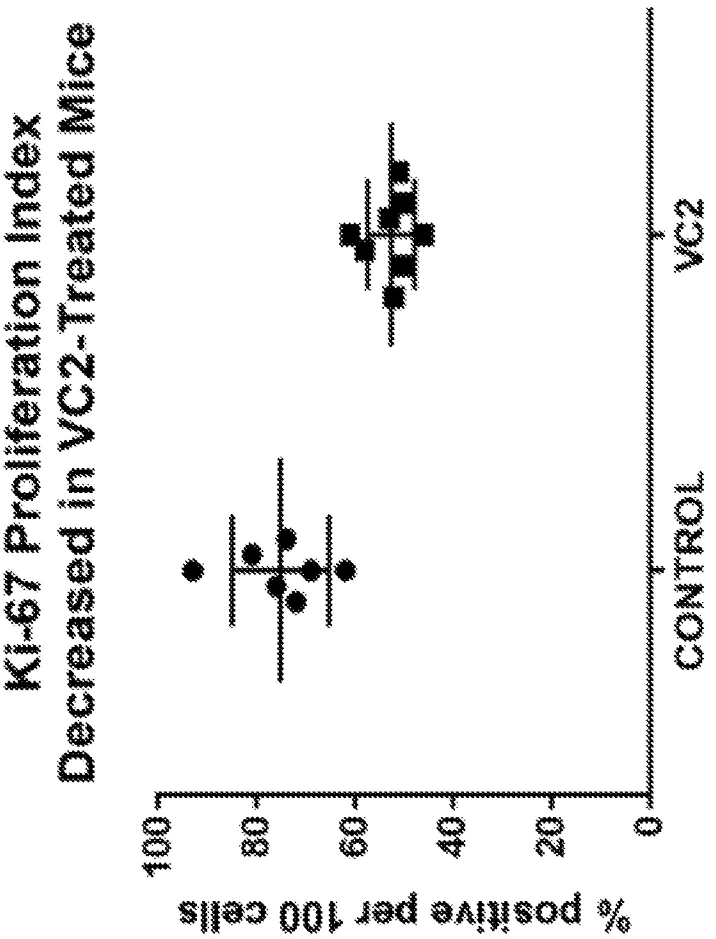
FIG. 18. Ki-67 proliferation index is markedly significantly decreased in VC2-treated animals.

Tumor cell proliferation is characteristic of melanoma progression and Ki-67 is a common biomarker used in melanoma and other cancers; Ki-67 index holds independent prognostic value in melanoma patients (Gimotty et al. (2005) *J. Clin. Oncol.* 23:8048-8056). We evaluated Ki-67 expression to determine if VC2 virotherapy had any effect on cell cycling. Ki-67 is a more sensitive indicator of cell cycling than mitotic index since it is a marker for cells in all stages of the cell cycle, while mitotic index only gives an indication of cells in M phase. Tumors from mice treated with VC2 had markedly significantly reduced Ki-67 expression (P<0.0001) in comparison to mock-treated controls (FIG. 18). This finding suggests that a modulation of the cell cycle may be one mechanism in which VC2 reduces tumor growth rates and prolongs survival in tumor bearing mice.

Safety

Figure 19:
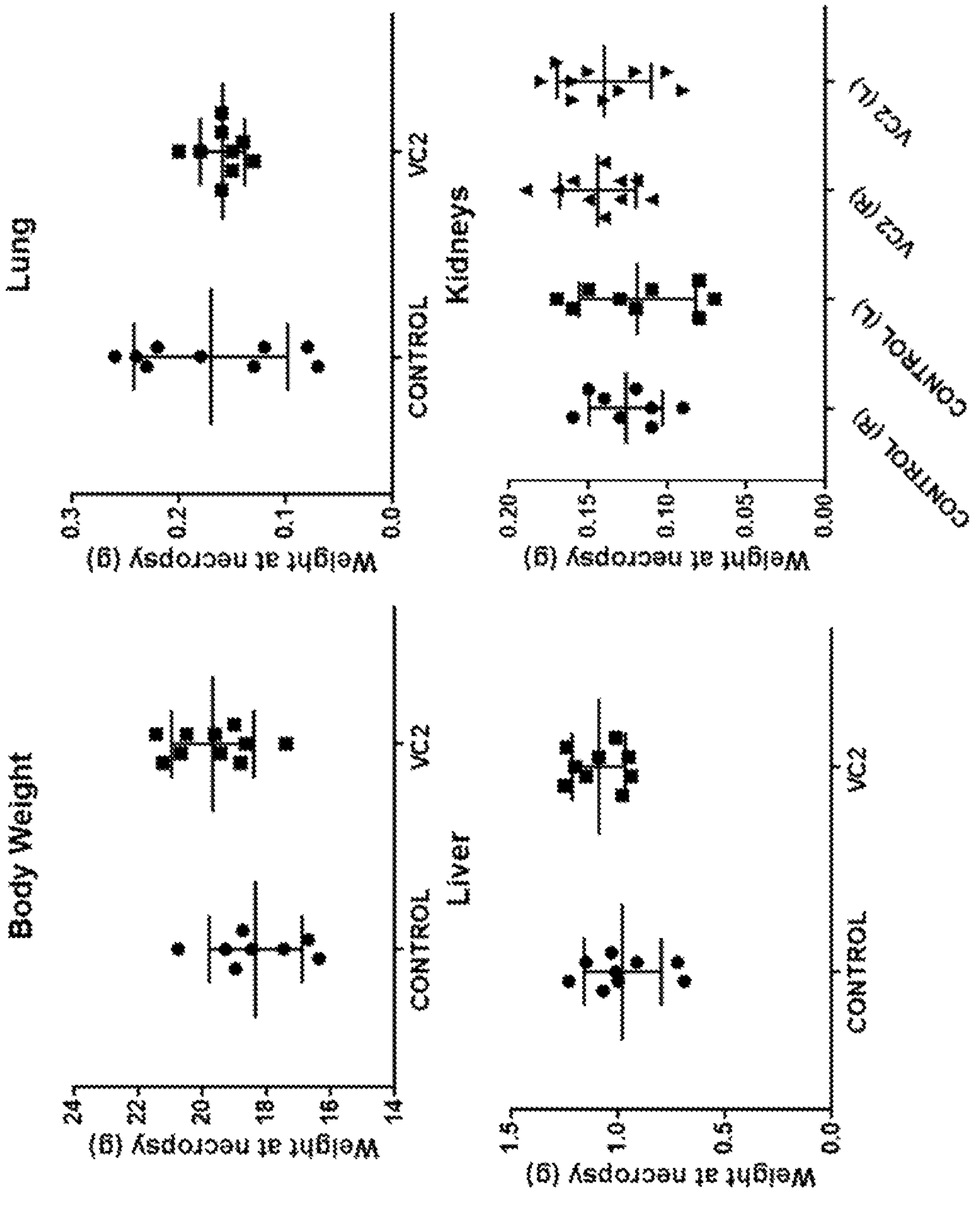
FIG. 19. VC2 had increased body weight in comparison to control mice at necropsy and approached significance (P=0.0542).
Figure 20:
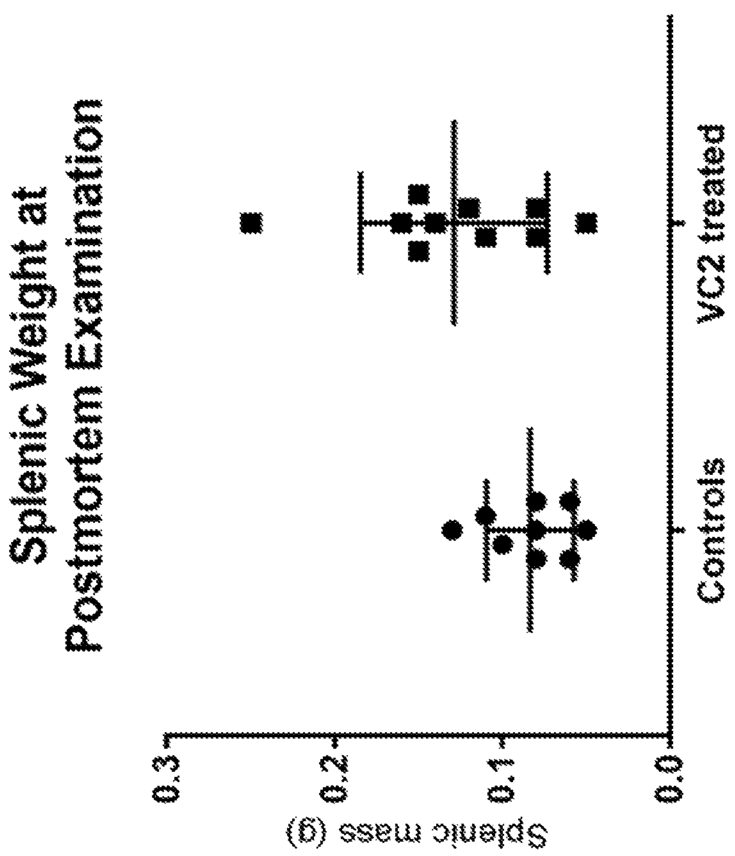
FIG. 20. Splenic mass is increased in VC2-treated mice at postmortem examination.
Figure 21:
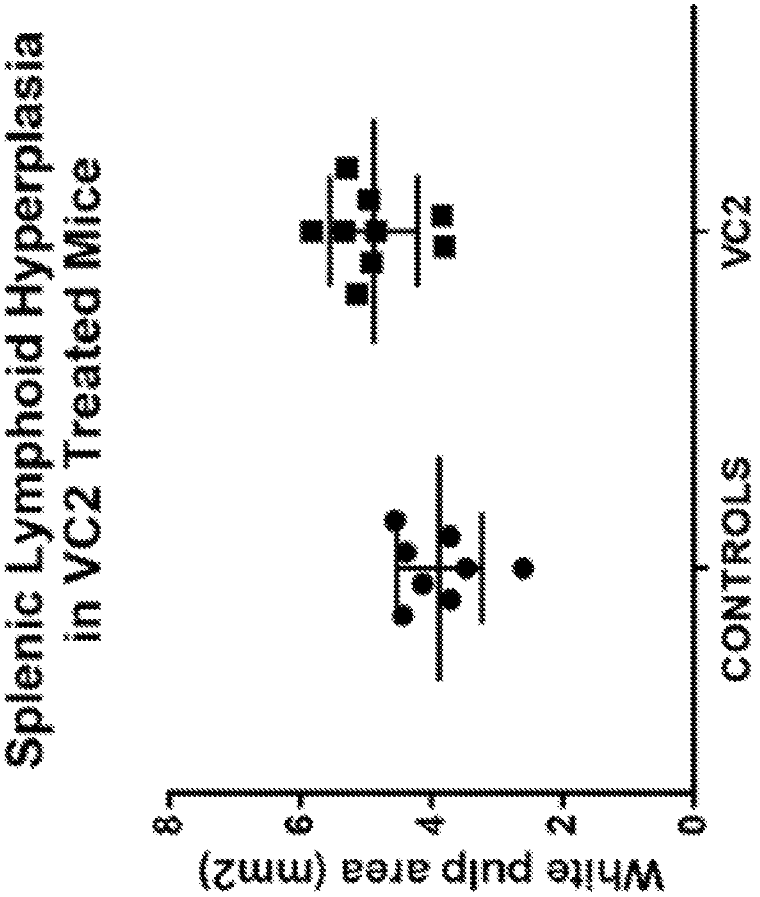
FIG. 21. Lymphoid hyperplasia was demonstrated in the spleens of VC2-treated mice using morphometric digital image analysis.

Safety assessments of mice receiving VC2 virotherapy showed that treatment was well-tolerated. Treated animals maintained their body condition as well or better than mock-treated mice. At the time of postmortem examination, VC2-treated mice weighed more on average although the difference was not significant (P=0.0542) (FIG. 19). Body temperature was monitored via subcutaneously implanted, temperature sensing transponders. No clinically significant pyrexia was observed in treated animals at any time. Vital organs were weighed at postmortem exam and splenomegaly was the only significant abnormality observed in VC2 treated mice (P=0.0388) (FIG. 20); morphometric digital image analysis showed that VC2 treated mice had significant lymphoid hyperplasia in comparison to mock treated controls (P=0.0068) (FIG. 21). Splenomegaly and lymphoid hyperplasia in VC2 treated animals suggests a systemic immune response to virotherapy, although it is undetermined if this response is tumor specific.

Discussion

Melanoma is a notoriously difficult cancer to treat in human patients and is resistant to most traditional cancer therapies including chemotherapy and radiation. Novel therapies which stimulate anti-tumor immune responses have shown promise, including oncolytic virotherapy; however, preclinical testing in murine tumor models have often not been predictive of response in human patients. Response to the FDA-approved oncolytic herpesvirus T-VEC has shown limited efficacy in a subset of patients in clinical trials despite robust responses in mice and some human patients have experienced adverse effects. The mechanisms of variability in response are not well-understood. We aimed to create a murine melanoma model for testing immune-modulating therapeutic effects of novel, genetically engineered herpesviruses.

In our early work, we observed poor infection efficiency of B16F10-fLuc-eGFP murine melanoma cells with oncolytic herpesviruses and poor sensitivity to cell killing although VC2 could be detected in the cytoplasm of B16F10-fLuc-eGFP cells at 12 hours via immunofluorescent microscopy. We hypothesized that decreased in vitro sensitivity to HSV-1 mutants may be related to lack of nectin-1 receptors which have been shown to be predictive of oncolytic HSV-1 sensitivity in a murine squamous cell carcinoma model. We therefore created a stably transfected murine melanoma cell line expressing human nectin-1 and demonstrated improved viral replication and cytolysis in vitro.

The detection of virus in the cytoplasm B16F10-fLuc-eGFP cells after in vitro infection but lack of significant cytopathic effect suggests the virus may enter but not replicate and lyse the tumor cells in absence of nectin-1. Cells may become infected with HSV-1 through gD receptor binding to HVEM, nectin-1, or 3-O-sulfate HS and fusion or via receptor independent atypical endocytosis/phagocytosis. When entry receptors are present, virions may enter via fusion or endocytosis. However, when appropriate receptors are not present, HSV-1 must enter via endocytosis only and occurs rapidly. In fact, it has been shown that Chinese hamster ovary cells (CHO), which are known to lack HSV-1 entry receptors and are widely considered to be non-permissible, are able to be efficiently infected with HSV-1 at a rate similar to vero cells and CHO cells transduced to express nectin-1 (Nicola & Straus (2004) *J. Virol.* 78:7508-7517). Therefore, entry via the endocytic pathway appears to be independent of viral entry receptor expression. However, infection of cells lacking entry receptors via the endocytic pathway does not result in a productive infection and release of infectious viral progeny. Id. Infection of such cells is considered to be non-productive since infectious progeny are not produced and enveloped virions are degraded via fusion of the endocytic membrane with lysosome.

While this would markedly limit the spread and pathogenicity of a virus in tumor cells lacking entry receptors in vitro, the complexity of the tumor microenvironment (TME) would include a host of cells which may better support productive infection such as cancer associated fibroblasts (CAF), immune cells, and endothelial cells of tumor-associated vasculature. These cell-types, and others in the TME, supply a replication niche for virus to persist and allow waves of infection of even poorly permissible tumor cells lacking entry receptors via endocytosis. Productive infection in stroma and tumor-associated vasculature could have multiple direct and indirect therapeutic anti-tumor benefits. Induction of ICD associated with efficient viral replication in these cells may release DAMPs such as ATP and HMGB1 to enhance the innate immune response in the tumor microenvironment. On the other hand, direct effects could include directly eliminating a portion of cancer-associated fibroblasts (CAF) and disrupting tumor-associated vasculature, creating a microenvironment that is less supportive of tumor growth. The ability of a live attenuated virus to create a replication niche in the tumor microenvironment and amplify its presence and effect through replication could decrease the need for frequent injections by supplying a continuous supply of virus for infection of tumor cells. We detected intratumoral VC2 at 6 days post infection in association with necrotic areas despite the lack of nectin-1 receptors. Even in the absence of direct lysis in the B16F10-fLuc-eGFP cell line lacking nectin-1, cell death may still occur via immunogenic cell death secondary to indirect ER stress, a factor impossible to account for in vitro.

Another factor impossible to account for in vitro is host immune response. Some studies have shown that rapid infection and spread in vitro predicts better in vivo response; however, such studies have been performed in xenogenic models and therefore do not account for immune responses (Wollmann et al. (2005) *J. Virol.* 79:6005-6022; Bennett et al. (2002) *Cancer Gene Ther.* 9:935-945). Some would argue that spread, persistence and continued replication within the tumor and/or microenvironment are less important than immunogenicity of the virus and immune response in the early stages of viral infection. In fact, it has been reported that, regarding oncolytic HSV, in vitro cytotoxicity and viral persistence in vivo do not correlate with anti-tumor efficacy. It has instead been shown that expression of markers of immunogenic cell death, such as heat shock protein 70 and elevated levels of serum high mobility group box 1 (HMGB1), increased antigen presenting cells, and CD8+ T cell responses may be more likely associated with HSV-associated therapeutic benefits (Workenhe et al. (2014) *Mol. Ther.* 22:123-131).

We therefore aimed to test the ability of the highly immunogenic HSV-1 live attenuated vaccine strain, VC2, in stimulating a therapeutic immune response against melanoma tumors in mice. In comparison to cancer drug discovery that focuses cytotoxic and/or targeted approaches, relevant models for immuno-oncology approaches are more limited and are urgently needed (Li et al. (2017) *Pharmacol. Ther.* 173:34-46). Models are specifically needed which can answer questions regarding why only certain subsets of patients respond, how to predict responders, and how to extend or improve responses in resistant or only partially responsive patients. Id. Syngeneic murine tumor models are commonly used in preclinical immuno-oncology studies but there are many challenges including a short window for evaluating response before tumors ulcerate or reach a size requiring euthanasia based on IACUC standards. Id. We utilized B16F10-fLuc-eGFP murine melanoma cells lacking nectin-1 receptors in order to demonstrate the immunogenicity of the virus alone in absence of robust replication and direct lysis and destruction of tumor cells. We additionally demonstrated that monitoring bioluminescence improved sensitivity in detecting acute responses to virotherapy over traditional microcaliper measurement. Mice may be prematurely euthanized when clinical assessment of tumor progression is based on tumor volume alone since immune-stimulating therapies result in acute necrosis, inflammation, and swelling of the tumor, a phenomenon referred to as pseudoprogression. More sensitive evaluation of response to therapy should improve development of effective therapeutic strategies since acute responses will be more apparent and direct dosing strategies in subsequent studies. We hypothesized that the discrepancy between correlation of tumor volumes and tumor bioluminescence during VC2 treatment could indeed be related to acute necrosis and inflammation during the early stages of virotherapy. In the VC2-treated group, larger areas of necrosis were observed when sections of the tumor were examined when less time had elapsed since the last VC2 injection. Early responses may be undetected or underestimated since necrosis may be a more prominent histologic change in the early stages of VC2 virotherapy and differences in virus-treated and control groups may be less apparent when tumors are examined at later time points.

There are a number of pathways that the cell can utilize to trigger death and result in tumor lysis in response to HSV-1 infection including apoptosis and necroptosis, and the mechanism of cell death has an influence on the immune response. Cancer cells may have mutations that make these cell death pathways ineffective. Further, HSV-1 has evolved mechanisms of evading these pathways in order to keep the cell alive to buy time for replication. However, even if these pathways are initially skirted by the virus, cells will ultimately still die as a result of ER stress either directly or indirectly, in a process referred to as immunogenic cell death. Immunogenic cell death is recognized as an important factor in eliciting antitumor immune responses through traditional cancer therapies such as chemotherapy and radiation as well as oncolytic virotherapy using HSV-1-based viruses.

Cell death may also occur even in a nonproductive infection, related to ICP0 expression by HSV-1, which is a tegument protein referred to as an “apoptoxin”. ICP0 can activate caspase-3 and trigger apoptosis without the need for viral replication to occur; it is possible that at a high enough dose of virus, significant amounts of ICP0 may be able to induce apoptosis even in absence of replication in cells that do not support productive infection. However, in cells that permit viral replication, transcription of early and late genes may inhibit apoptotic pathways; this extends the life of the cell to allow time for replication. When HSV-1 is successful in preventing apoptosis, necroptosis is another pathway by which the cell can trigger its own death to limit viral spread and replication (Yu & He (2016) *Virol. J.* 13:77). In humans, HSV-1 has evolved mechanisms to also evade this pathway of cell death. R1 prevents necroptosis in human cells, but not in mouse cells, where RIP3 is efficiently activated by ICP6 after HSV-1 infection in a manner independent of TNFR, TLR3, or DAI (Wang et al. (2014) *PNAS* 111:15438-15443; Huang et al. (2015) *Cell Host Microbe* 17:229-242). This is one factor responsible for limiting viral replication in mouse cells in general, a non-natural host. Therefore, it is expected that in permissive human cells infected with wild-type HSV-1, virus would replicate to much higher titers than in mouse cells. Further, the outcome of the infection and mechanism of cell death may be different based on dose of virus, species, and cell type. This is important to keep in mind when performing preclinical mouse studies where a wide variety of tumor modeling strategies and tumor cell types are used. Since B16F10 murine melanoma cells do not support productive infections with HSV-1, direct cytotoxicity is likely minimal at the doses of VC2 we used in our in vivo experiments, although some apoptosis secondary to ICP0 is possible. Necroptosis is unlikely to occur to much degree since ICP6 is involved in triggering this pathway in HSV-1 infections and requires initiation of replication in order to be expressed. Type I immunogenic cell death is considered likely to be a predominating mechanism of cell death in tumor cells lacking entry receptors required for efficient replication in oncolytic HSV-1 virotherapy.

Effective anti-tumor immune responses require functional innate and adaptive systems. The initial step in mounting adaptive immunity is efficient recognition and presentation of antigens by antigen presenting cells of the innate immune system including macrophages and dendritic cells. M1 type macrophages, or "classically activated" macrophages are effective at antigen presentation, produce pro-inflammatory cytokines, and have anti-tumorigenic effects overall. M2 type or "alternatively activated" macrophages are ineffective antigen-presenters, produce immunosuppressive cytokines, and play many roles in supporting tumor growth and progression. We detected reduced expression of arginase-1 by macrophages, a canonical marker of the M2 phenotype in mice, in the TME of VC2-treated tumors although macrophages overall were generally increased suggesting repolarization to an M1 phenotype. We also detected increased numbers of CD3+ T cells in the TME in VC2-treated mice. T cells are important in generating adaptive anti-tumor immunity and have been observed in the TME of regressing tumors in human melanoma patients.

In addition to increased tumor lysis and inflammation associated with VC2 treatment, we also found reduced Ki-67 expression in VC2-treated tumors indicating a lower proportion of cells actively proliferating in the cell cycle. Evidence suggests that HSV-1 has evolved a complex and sophisticated ability to modulate the cell cycle in order to infect and replicate (Flemington (2001) *J. Virol.* 75:4475-4481). Soon after entry, HSV-1 is known to elicit a cell cycle block to limit host protein production in order to use cellular machinery for early stages of viral replication; subsequently, HSV-1 reverses the cell cycle block through expression of late gene γ34.5 in order to replicate with maximum efficiency. Since HSV-1 can enter cells lacking entry receptors through endocytosis, we hypothesized that VC2 entry of B16F10-fLuc-eGFP may elicit cell cycle block, since this effect is known to occur without replication even in the presence of non-replicating HSV-1 L particles. The finding that Ki-67 proliferation index was significantly decreased in VC2-treated tumors was compatible with our hypothesis that VC2 may initiate a cell-cycle block as one mechanism of slowing tumor growth.

In summary, we have developed an immunocompetent murine melanoma model for testing oncolytic and immunomodulatory HSV-1 viruses. We demonstrated utility of the model in assessing response to therapy with increased sensitivity using bioluminescent imaging. We demonstrated strong immune responses in the tumor microenvironment in VC2-treated mice. The apparent remarkable immunogenicity of VC2 makes it a promising candidate for further development as a viral vector for immune modulating cancer therapy. Studies are underway to further evaluate efficacy and safety in the model and develop the ideal dosing and/or combinatorial drug strategies in preparation for clinical trials.

Example 3

VC2 for the Treatment of Melanoma

Melanoma is the most aggressive and lethal malignancy of the skin and accounts for 90% of skin cancer-related deaths. The most common site for first metastasis is sentinel lymph nodes (SLN). Subsequently, disease spreads to the liver, lungs, and brain in patients with stage IV melanoma. Treatment options for metastatic melanoma in people is severely limited. Greater than 90% of cancer deaths overall are related to metastatic disease.

Melanoma is considered to be an immunogenic tumor type. Occasionally, regressing melanoma lesions have been associated with infiltration of T cells which have been shown to recognize autologous melanoma antigens in human patients. Circulating antibodies to melanoma antigens have also been detected in the serum of patients. These observations have spurred interest in development of immunotherapies for the treatment of metastatic melanoma. Oncolytic virotherapy, has been widely investigated for oncolytic and immunomodulating effects. The first ever oncolytic virotherapy to receive FDA-approval is an HSV-1-based virus (Talimogene Laherperavec (T-Vec) or Imlygic) containing a transgene for human GM-CSF to enhance an anti-tumor immune response after intratumoral injection. Durable response rate in human patients was only 16% despite impressive efficacy in anti-tumor effects in vitro and in murine tumor models. Novel viruses with enhanced immune-stimulating properties and improved efficacy and safety profiles are needed. Further, the lack of concordance of preclinical murine studies with results in human clinical trials highlights the need for improved murine tumor modeling strategies for testing oncolytic and immune-modulating viruses for anti-tumor effects.

The development of a live-attenuated HSV-1 vaccine, VC2, which has shown efficacy in protection against lethal HSV-1 and HSV-2 challenge after a single intramuscular injection has been previously reported (see WO 2015/172033). VC2 has a deletion in gK which prevents entry into ganglionic axons but replicates efficiently in permissive cells. Further, VC2 is highly immunogenic generating strong cell-mediated and humoral immune responses.

An immunocompetent double-labeled murine melanoma model for testing the immune-modulating and adjuvant effects of oncolytic herpesviruses was developed (see Example 2). Intratumoral virotherapy using VC2 resulted in significant reduction in Ki-67 proliferation indices in comparison to mock treated controls. Further, there were significant increases in CD3+ T cells and IBA-1+ macrophages in the tumor microenvironment, but reduced expression of arginase-1, a marker of the M2, pro-tumorigenic macrophage phenotype in mice. Median survival times (MST) of VC2 treated mice were nearly twice that of mock-treated controls and one out of eleven VC2-treated mice had a complete response with no evidence of disease at greater than 180 days. The utility of bioluminescence in monitoring primary tumor growth during efficacy testing of immune-stimulating therapy with VC2 was evaluated, and it is was found that bioluminescence allows for more sensitive assessment of anti-tumor responses during the acute inflammatory phase of treatment during which pseudo-progression can result in misleading increases in tumor volumes using traditional microcaliper measurements. These findings suggest that the remarkable immunogenicity of VC2 makes it a good candidate as a vector for tumor vaccine development and our immunocompetent bioluminescent model allows for sensitive assessment of response to therapy in the face of marked acute inflammation and pseudo-progression. These findings represent significant progress in viral vector development for cancer therapy and significant improvement in modeling strategies that aim to test immune-stimulating anti-cancer therapies in immuno-oncology studies.

The article “a” and “an” are used herein to refer to one or more than one (i.e., to at least one) of the grammatical object of the article. By way of example, “an element” means one or more element.

Throughout the specification the word “comprising,” or variations such as “comprises” or “comprising,” will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant herpes simplex virus (HSV) genome, wherein the recombinant HSV genome comprises:

(a) a modified UL53 gene comprising a deletion corresponding to the region of the UL53 gene that encodes amino acids 31-68 of wild-type gK;

(b) a modified UL20 gene comprising a deletion corresponding to the region of the UL20 gene that encodes amino acids 4-22 of wild-type UL20 protein; and (c) a nucleic acid construct encoding a sodium iodide symporter (NIS);

wherein an HSV comprising the recombinant HSV genome is capable of replication in a host cell and incapable of entry into axonal compartments of neurons.

2. The recombinant HSV genome of claim 1, wherein the recombinant HSV genome is derived from the genome of HSV-1 or HSV-2.

3. The recombinant HSV genome of claim 2, wherein HSV-1 is HSV-1 strain F.

4. The recombinant HSV genome of claim 2, wherein the recombinant HSV genome comprises the nucleotide sequence set forth in SEQ ID NO: 7.

5. The recombinant HSV genome of claim 1, wherein the NIS is encoded by a nucleotide sequence selected from the group consisting of:

i. the nucleotide sequence set forth in SEQ ID NO: 8, 9, or 11;

ii. a nucleotide sequence encoding a protein comprising the amino acid sequence set forth in SEQ ID NO: 10 or 12; and iii. a nucleotide sequence encoding a NIS protein comprising at least 90% amino acid sequence identity to at least one of SEQ ID NO: 10 and 12, wherein the NIS protein comprises NIS activity when expressed in a host cell.

6. A herpes simplex virus (HSV) comprising the recombinant HSV genome of claim 1.

7. A composition for treating cancer comprising the HSV of claim 6.

8. The composition of claim 7, further comprising a pharmaceutically acceptable component selected from the group consisting of a carrier, an excipient, a stabilizing agent, a preservative, an immunostimulant, and an adjuvant.

9. The recombinant HSV genome of claim 5, wherein the nucleic acid construct comprises a nucleotide sequence encoding a NIS protein comprising at least 95% amino acid sequence identity to at least one of SEQ ID NO: 10 and 12, and wherein the NIS protein comprises NIS activity when expressed in a host cell.

10. The recombinant HSV genome of claim 5, wherein the nucleic acid construct comprises a nucleotide sequence selected from the group consisting of the nucleotide sequences set forth in SEQ ID NO: 8, 9, and 11 and a nucleotide sequence encoding a protein comprising the amino acid sequence set forth in SEQ ID NO: 10 or 12.

11. A method for treating cancer, the method comprising administering to a patient a therapeutically effective amount of a composition comprising the recombinant HSV genome of claim 1.

12. The method for claim 11, wherein the cancer is selected from the group consisting of melanoma, lung cancer, prostate cancer, pancreatic cancer, breast cancer, colorectal cancer, kidney cancer, bladder cancer, non-Hodgkin's lymphoma, thyroid cancer, endometrial cancer, ovarian cancer, leukemia, and liver cancer.

13. The method of claim 11, wherein the patient is administered a therapeutically effective amount of a composition comprising an HSV, the HSV comprising a recombinant HSV genome which comprises a nucleic acid construct encoding a *Mus musculus* sodium iodide symporter or a *Homo sapiens* sodium iodide cotransporter.

14. The method of claim 11, wherein the nucleic acid construct comprises a nucleotide sequence selected from the group consisting of:

the nucleotide sequence set forth in SEQ ID NO: 8, 9, or 11;

a nucleotide sequence encoding a protein comprising the amino acid sequence set forth in SEQ ID NO: 10 or 12; and a nucleotide sequence encoding a NIS protein comprising at least 90% amino acid sequence identity to at least one of SEQ ID NO: 10 and 12, wherein the NIS protein comprises NIS activity when expressed in a host cell.

15. The method of claim 11, further comprising administering to the patient a therapeutically effective amount of $^{131}I$ before, at the same time as, and/or after the composition comprising the HSV is administered.

16. The method of claim 11, wherein the nucleic acid construct comprises a nucleotide sequence encoding a NIS protein comprising at least 95% amino acid sequence identity to at least one of SEQ ID NO: 10 and 12, and wherein the NIS protein comprises NIS activity when expressed in a host cell.

17. The method of claim 11, wherein the nucleic acid construct comprises a nucleotide sequence selected from the group consisting of the nucleotide sequences set forth in SEQ ID NO: 8, 9, and 11 and a nucleotide sequence encoding a protein comprising the amino acid sequence set forth in SEQ ID NO: 10 or 12.

18. A method for producing a composition for treating cancer, the method comprising:

(a) transfecting a host cell with the recombinant HSV genome of claim 1;

(b) incubating the transfected host cell under conditions favorable for the formation of an HSV comprising the recombinant HSV genome;

(c) purifying the HSV comprising the recombinant HSV genome; and optionally (d) combining the purified HSV with at least one pharmaceutically acceptable component.

19. A method for producing an HSV, the method comprising:

(a) transfecting a host cell with the recombinant HSV genome of claim 1; and (b) incubating the transfected host cell under conditions favorable for the formation of an HSV virus comprising the recombinant HSV genome, whereby an HSV comprising the recombinant HSV genome is produced.

20. The method of claim 19, further comprising purifying the recombinant HSV virus produced in (b).

* * * * *